US012601744B2

(12) United States Patent
Hickok et al.

(10) Patent No.: US 12,601,744 B2
(45) Date of Patent: *Apr. 14, 2026

(54) BIOMARKERS AND METHODS FOR PREDICTING PRETERM BIRTH

(71) Applicant: Sera Prognostics, Inc., Salt Lake City, UT (US)

(72) Inventors: Durlin Edward Hickok, Seattle, WA (US); John Jay Boniface, Salt Lake City, UT (US); Gregory Charles Critchfield, Holladay, UT (US); Tracey Cristine Fleischer, Sandy, UT (US)

(73) Assignee: Sera Prognostics, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/352,898

(22) Filed: Jun. 21, 2021

(65) Prior Publication Data

US 2022/0178938 A1 Jun. 9, 2022

Related U.S. Application Data

(63) Continuation of application No. 16/255,757, filed on Jan. 23, 2019, now abandoned, which is a continuation of application No. 15/286,486, filed on Oct. 5, 2016, now abandoned, which is a continuation of application No. 14/213,861, filed on Mar. 14, 2014, now abandoned.

(60) Provisional application No. 61/919,586, filed on Dec. 20, 2013, provisional application No. 61/798,504, filed on Mar. 15, 2013.

(51) Int. Cl.
G01N 33/68 (2006.01)
C07K 4/12 (2006.01)

(52) U.S. Cl.
CPC ............. G01N 33/689 (2013.01); C07K 4/12 (2013.01); G01N 2800/368 (2013.01); G01N 2800/60 (2013.01)

(58) Field of Classification Search
None
See application file for complete search history.

(56) References Cited

U.S. PATENT DOCUMENTS

| | | | |
|---|---|---|---|
| 7,790,463 B2 | 9/2010 | Mor et al. | |
| 2002/0137086 A1 | 9/2002 | Olek et al. | |
| 2004/0203023 A1 | 10/2004 | Chandrasiri-Herath | |
| 2006/0134654 A1* | 6/2006 | Wewer ................. | G01N 33/689 435/6.12 |
| 2007/0141055 A1 | 6/2007 | Kajander et al. | |
| 2010/0017143 A1 | 1/2010 | Nagalla et al. | |
| 2010/0173317 A1 | 7/2010 | Nakamura et al. | |
| 2010/0173786 A1 | 7/2010 | Brun et al. | |
| 2011/0165554 A1 | 7/2011 | Levin et al. | |
| 2011/0171645 A1 | 7/2011 | McManus et al. | |
| 2011/0195478 A1 | 8/2011 | Chen et al. | |
| 2012/0077209 A1 | 3/2012 | Chance et al. | |
| 2012/0142559 A1* | 6/2012 | Tuytten ................ | G01N 33/689 435/6.12 |
| 2012/0214685 A1* | 8/2012 | Speicher ............ | G01N 33/6893 435/7.4 |
| 2012/0315630 A1 | 12/2012 | Gong et al. | |
| 2013/0040844 A1 | 2/2013 | Wyss-Coray | |
| 2013/0045889 A1 | 2/2013 | Kas et al. | |
| 2013/0137595 A1 | 5/2013 | Zangar et al. | |
| 2014/0287948 A1 | 9/2014 | Boniface et al. | |
| 2014/0287950 A1 | 9/2014 | Hickok et al. | |
| 2016/0154003 A1 | 6/2016 | Boniface et al. | |
| 2017/0146548 A1 | 5/2017 | Hickok et al. | |
| 2018/0172696 A1 | 6/2018 | Boniface et al. | |
| 2019/0317107 A1 | 10/2019 | Boniface et al. | |
| 2019/0376978 A1 | 12/2019 | Hickok et al. | |

FOREIGN PATENT DOCUMENTS

| | | |
|---|---|---|
| CN | 101437959 A | 5/2009 |
| CN | 102460176 A | 5/2012 |
| JP | 2007-506979 A | 3/2007 |

(Continued)

OTHER PUBLICATIONS

Poon et al., Obstet Gynecol 2008;112:1082-90 (Year: 2008).*
Law et al., Int. J. Mol. Sci. 2015, 16, 10952-10985; doi:10.3390/ijms160510952 (Year: 2015).*
Goetzinger et al., Prenatal Diagnosis 2012, 32, 1002-1007 (Year: 2012).*
Piche-Nicholas et al., MAbs. 2018; 10: 81-94. doi: 10.1080/19420862.2017.1389355 (Year: 2018).*
Déglon et al., Anal Bioanal Chem (2012) 402:2485-2498; published online: Jun. 25, 2011 (Year: 2011).*

(Continued)

*Primary Examiner* — Christina M Borgeest
(74) *Attorney, Agent, or Firm* — Greenberg Traurig, LLP

(57) ABSTRACT

The disclosure provides biomarker panels, methods and kits for determining the probability for preterm birth in a pregnant female. The present disclosure is based, in part, on the discovery that certain proteins and peptides in biological samples obtained from a pregnant female are differentially expressed in pregnant females that have an increased risk of developing in the future or presently suffering from preterm birth relative to matched controls. The present disclosure is further based, in part, on the unexpected discovery that panels combining one or more of these proteins and peptides can be utilized in methods of determining the probability for preterm birth in a pregnant female with relatively high sensitivity and specificity. These proteins and peptides disclosed herein serve as biomarkers for classifying test samples, predicting a probability of preterm birth, monitoring of progress of preterm birth in a pregnant female, either individually or in a panel of biomarkers.

8 Claims, 2 Drawing Sheets

Specification includes a Sequence Listing.

(56) References Cited

FOREIGN PATENT DOCUMENTS

| | | | |
|---|---|---|---|
| JP | 2011-501133 A | 1/2011 | |
| WO | WO 2005/014635 A2 | 2/2005 | |
| WO | WO 2005/031364 A1 | 4/2005 | |
| WO | WO 2006/029838 A2 | 3/2006 | |
| WO | WO 2006/034427 A2 | 3/2006 | |
| WO | WO 2006/074360 A2 | 7/2006 | |
| WO | WO 2008/054764 A2 | 5/2008 | |
| WO | WO 2008/063369 A2 | 5/2008 | |
| WO | WO 2009/014987 A2 | 1/2009 | |
| WO | WO 2009/049189 A2 | 4/2009 | |
| WO | WO 2009/097579 * | 8/2009 | G01N 33/68 |
| WO | WO 2009/097579 A1 | 8/2009 | |
| WO | WO 2010/017201 A1 | 2/2010 | |
| WO | WO 2010/133173 A1 | 11/2010 | |
| WO | WO 2011/077129 A1 | 6/2011 | |
| WO | WO 2011/100792 A1 | 8/2011 | |
| WO | WO 2012/040073 A2 | 3/2012 | |
| WO | WO 2013/096862 * | 6/2013 | G01N 33/68 |
| WO | WO 2014/144129 A2 | 9/2014 | |
| WO | WO 2016/205723 A2 | 12/2016 | |
| WO | WO 2019/036032 A1 | 2/2019 | |

OTHER PUBLICATIONS

The abstract by Goetzinger et al., American Journal of Obstetrics and Gynecology, (Jan. 2012) vol. 206, No. 1, Suppl. S, pp. S7 (Year: 2012).*

Anderson et al., "Quantitative mass spectrometric multiple reaction monitoring assays for major plasma proteins," Mol. Cell. Proteomics, 5(4):573-588 (2006).

Behrman et al. eds., "Preterm Birth: Causes, Consequences, and Prevention," Institute of Medicine (US) Committee on Understanding Premature Birth and Assuring Healthy Outcomes, National Academies Press, Washington DC, 791 pages (2007).

Biemann, "Sequencing of peptides by tandem mass spectrometry and high-energy collision-induced dissociation," Methods Enzymol., 193:455-479 (1990).

Blencowe et al., "National, regional and worldwide estimates of preterm birth." Lancet, 9; 379(9832):2162-2172 (2012).

Box et al., "An analysis of transformations," Royal Stat. Soc. Series B, 26:211-246 (1964).

Breiman, "Random Forests," Mach. Learn., 45:5-32 (2001).

Brody et al., "Life's simple measures: unlocking the proteome," J. Mol. Biol., 422(5):595-606 (2012).

Cocksedge et al., "Does free androgen index predict subsequent pregnancy outcome in women with recurrent miscarriage?," Hum. Reprod., 23(4):797-802 (2008).

Craig et al., "TANDEM: matching proteins with tandem mass Spectra," Bioinformatics, 20:1466-1467 (2004).

Eastaugh et al., "Comparison of Neural Networks and Statistical Models to Predict Gestational Age at Birth," Neural Comput. Applic., 6(3):158-164 (1997).

Efron et al., "Least angle regression," Annals Statistics, 32:407-451 (2004).

Eng et al., "An Approach to Correlate Tandem Mass Spectral Data of Peptides with Amino Acid Sequences in a Protein Database," J. Am. Soc. Mass Spectrom, 5:976-989 (1994).

Erez et al., "High Tissue Factor Activity and Low Tissue Factor Pathway Inhibitor Concentrations in Patients with Preterm Labor," J. Matern. Fetal Neonatal Med., 23(1):23-33 (2010).

Flick et al., "Mechanistic insights from serum proteomic biomarkers predictive of spontaneous preterm birth," Am. J. Obstet. Gynecol., Abstract No. 253, S148-S149 (2016).

Gadsden et al., "Serum alpha-fetoprotein: I. Evaluation of quantitative assays adapted to automated immunoassay systems," Ann. Clin. Lab Sci., 21(4):246-253 (1991).

Haefliger et al., "Structural and Functional Characterization of Complement C8γ, A Member of the Lipocalin Protein Family," Mol. Immunol., 28(1-2):123-131 (1991).

Hao et al., "Expression and clinical significance of IGFBP-1 in early spontaneous abortion patients with polycystic ovary syndrome," Hebei Yiyao, 35:3525-3527 (2013). (English translation of abstract only).

Hao et al., "Expression of glycodelin level in patients with polycystic ovary syndrome during early spontaneous abortion and clinical significance," Jiefangjun Yiyao Zazhi, 25:63-66 (2013). (English trabslation of abstract only).

Haviland et al., "Complete cDNA sequence of human complement pro-C5. Evidence of truncated transcripts derived from a single copy gene," J. Immunol., 146(1):362-368 (1991).

Howson et al. eds., "Born too soon: The Global Action Report on Preterm Birth," World Health Organization, Geneva, 126 pages (2012).

Huang et al., "Tree-structured supervised learning and the genetics of hypertension," Proc. Nat. Acad. Sci. U.S.A., 101:10529-10534 (2004).

Keller et al., "Empirical Stat istical Model To Estimate the Accuracy of Peptide Identificat ions Made by MS/MS and Database Search," Anal. Chem, 74:5383-5392 (2002).

Kim et al., "ITI-H4, as a biomarker in the serum of recurrent pregnancy loss (RPL) patients," Mol. Biosyst., 7(5):1430-1440 (2011).

Klee et al., "Strategy for the development of a mass spectrometry assay for measuring sex hormone binding globulin (SHBG) in human serum," Clinical Chemistry, Poster B-103, 58(S10):A77 (2012).

Kuhn et al., "Quantification of C-reactive protein in the serum of patients with rheumatoid arthritis using multiple reaction monitoring mass spectrometry and 13C-labeled peptide standards," Proteomics, 4:1175-1186 (2004).

Ling et al. "Multiplexing molecular diagnostics and immunoassays using emerging microarray technologies" Expert Rev. Mol. Diagn., 7:87-98 (2007).

Liu et al., "Recent developments in protein and cell-targeted aptamer selection and applications," Curr. Med. Chem., 18(27):4117-4125 (2011).

McLean et al., "Effect of Collision Energy Optimization on the Measurement of Peptides by Selected Reaction Monitoring (SRM) Mass Spectrometry," Anal. Chem., 82(24):10116-10124 (2010).

McLean et al., "Skyline: an open source document editor for creating and analyzing targeted proteomics experiments," Bioinformatics, 26(7):966-968 (2010).

Nielsen et al., "Multiplexed sandwich assays in microarray format," J. Immunol. Methods, 290:107-120 (2004).

Okon et al., "Serum androgen levels in women who have recurrent miscarriages and their correlation with markers of endometrial function," Fertil. Steril., 69(4):682-690 (1998).

Oliveira et al., "Primary Structure of Human C-reactive Protein," J. Biol. Chem., 254(2):489-502 (1979).

Petersen et al., "Characterization of the gene for human plasminogen, a key proenzyme in the fibrinolytic system," J. Biol. Chem., 265(11):6104-6111 (1990).

Polpitiya et al., "DAnTE: a statistical tool for quantitative analysis of -omics data," Bioinformatics, 24:1556-1558 (2008).

Reid, "Complete Amino Acid Sequences of the Three Collagen-Like Regions present in Subcomponent Clq of the First Component of Human Complement," Biochem. J., 179(2):367-371 (1979).

Romero et al., "A genetic association study of maternal and fetal candidate genes that predispose to preterm prelabor rupture of membranes (PROM)," Am. J. Obstet. Gynecol., 203(4):361.e1-361.e30 (2010).

Ruczinski et al., "Logic Regression," J. Comput. Graph. Stat., 12(3):475-511 (2003).

Saade et al., "Development and validation of a spontaneous preterm delivery predictor in asymptomatic women," Am. J. Obstet. Gynecol., 214(5): 633.e1-633.e24 (2016).

Schumann et al., "Structure and Function of Lipopolysaccharide Binding Protein," Science, 249(4975):1429-1431 (1990).

Selby et al., "Analysis of a Major Human Chorionic Somatomammotropin Gene," J. Biol. Chem., 259(21):13131-13138 (1984).

Self et al., "Advances in immunoassay technology" Curr. Opin. Biotechnol., 7:60-65 (1996).

(56)                    References Cited

OTHER PUBLICATIONS

Shi et al., "IgY14 and SuperMix immunoaffinity separations coupled with liquid chromatography-mass spectrometry for human plasma proteomics biomarker discovery," *Methods*, 56(2):246-253 (2012).

Spencer et al., "First trimester sex hormone-binding globulin and subsequent development of preeclampsia or other adverse pregnancy outcomes," *Hypertens. Pregnancy*, 24(3):303-311 (2005).

Stella et al., "Preterm labor biomarker discovery in serum using 3 proteomic profiling methodologies," *Am. J. Obstet. Gynecol.*, 387:e1-e13 (2009).

Suh et al., "Comparative profiling of plasma proteome from breast cancer patients reveals thrombospondin-1 and BRWD3 as serological biomarkers," *Exp. Mol. Med.*, 44(1):36-44, Supplemental Data (2012).

Tibshirani et al., "Diagnosis of multiple cancer types by shrunken centroids of gene expression," *Proc. Natl. Acad. Sci. USA*, 99:6567-6572 (2002).

Tusher et al., "Significance analysis of microarrays applied to the ionizing radiation response," *Proc. Natl. Acad. Sci. USA*, 98:5116-5121 (2001).

Underwood et al., "The association of the angiotensinogen gene with insulin sensitivity in humans: a tagging single nucleotide polymorphism and haplotype approach," *Metabolism*, 60(8):1150-1157 (2011).

Villanueva et al., "Automated serum peptide profiling," *Nat. Protoc.*, 1(2):880-891 (2006).

Walz et al., "Amino acid sequence of human prothrombin fragments 1 and 2," *Proc. Natl. Acad. Sci. U.S.A.*, 74(5):1969-1972 (1977).

Watt et al., "Amino Acid Sequence of the β Chain of Human Fibrinogen," *Biochemistry*, 18(1):68-76 (1979).

Williams et al., "Low birth weight and preterm delivery in relation to early-gestation vaginal bleeding and elevated maternal serum alpha-fetoprotein," *Obstet. Gynecol.*, 80(5):745-749 (1992).

Wolter et al., "A proteome signature for intrauterine growth restriction derived from multifactorial analysis of mass spectrometry-based cord blood serum profiling," *Electrophoresis*, 33:1881-1893 (2012).

Yocum et al., "Current affairs in quantitative targeted proteomics: multiple reaction monitoring-mass spectrometry," *Brief Funct. Genomic Proteomic.*, 8(2):145-157 (2009).

"Enzyme Entry: EC 3.4.21.26" Prolyl Ologipeptidase, Enzyme. expasy.org (Expasy). Retrieved from the internet: https://enzyme.expasy.org.

"Enzyme Entry: EC 3.4.21.37" for Leukocyte Elastase, Enzyme. expasy.org (Expasy). Retrieved from the internet: https://enzyme.expasy.org.

Ananth et al., "Impact of Pregnancy-induced Hypertension on Stillbirth and Neonatal Mortality," *Epidemiology*, 21(1):118-123 (2010).

Anderson, "Sex-hormone-binding globulin," *Clin. Endocrinol. (Oxf)*, 3(1):69-96 (1974).

Bach et al., "Bolasso: Model Consistent Lasso Estimation through the Bootstrap," *Proceedings of the 25th International Conference on Machine Learning*, Helsinki, Finland, 2008, pp. 1-8.

Bocchinfuso et al., "Selective removal of glycosylation sites from sex hormone-binding globulin by site-directed mutagenesis," *Endocrinology*, 131(5):2331-2336 (1992).

Burchard, Expert Declaration from Chinese Patent No. ZL201480028164.3, pp. 1-3, Sep. 27, 2022.

Centers for Disease Control and Prevention, "Premature Birth," Nov. 1, 2021, pp. 1-2.

Ding et al., "Investigation of Correlation Between SHBG IR and Pathogenesis of Pregnant Hypertension," *Hebei Medical Journal*, Mar. 2008. 30(3):284-285 (2008). English translation of abstract only.

Garite et al., "A multicenter prospective study of neonatal outcomes at less than 32 weeks associated with indications for maternal admission and delivery," *Am. J. Obstet. Gynecol.*, 217(1):72e1-72e9 (2017).

Hillenkamp et al., "Matrix-assisted laser desorption/ionization mass spectrometry of biopolymers," *Anal. Chem.* 63(24):1193A-1203A (1991).

Jin et al., "Sex hormone-binding globulin of gestational diabetes mellitus pregnant women with well-controlled glucose and pregnancy outcomes," *Chin J Obstet Gynecol*, 46(6):422-426 (2011). English translation of abstract only.

March of Dimes, "Preterm Labor and Premature Birth: Are You at Risk?," Mar. 2018, pp. 1-7.

Medline Plus, "SHBG Blood Test," *National Library of Medicine (US)*, Bethesda, MD; pp. 1-5 (2020). Retrieved from the internet: https://medlineplus.gov/lab-tests/shbg-blood-test/.

National Center for Biotechnology Information (NCBI), "8mer_1," Bethesda, MD, National Library of Medicine (US), accessed Sep. 16, 2022. Retrieved from the internet: https://blast.ncbi.nlm.nih.gov/Blast.cgi.

National Center for Biotechnology Information (NCBI), "8mer_2," Bethesda, MD, National Library of Medicine (US), accessed Sep. 16, 2022. Retrieved from the internet: https://blast.ncbi.nlm.nih.gov/Blast.cgi.

National Center for Biotechnology Information (NCBI), "8mer_3," Bethesda, MD, National Library of Medicine (US), accessed Sep. 16, 2022. Retrieved from the internet: https://blast.ncbi.nlm.nih.gov/Blast.cgi.

National Center for Biotechnology Information (NCBI), "8mer_4," Bethesda, MD, National Library of Medicine (US), accessed Sep. 16, 2022. Retrieved from the internet: https://blast.ncbi.nlm.nih.gov/Blast.cgi.

National Center for Biotechnology Information (NCBI), "8mer_5," Bethesda, MD, National Library of Medicine (US), accessed Sep. 16, 2022. Retrieved from the internet: https://blast.ncbi.nlm.nih.gov/Blast.cgi.

National Center for Biotechnology Information (NCBI), "8mer_6," Bethesda, MD, National Library of Medicine (US), accessed Sep. 16, 2022. Retrieved from the internet: https://blast.ncbi.nlm.nih.gov/Blast.cgi.

National Center for Biotechnology Information (NCBI), "8mer_7," Bethesda, MD, National Library of Medicine (US), accessed Sep. 16, 2022. Retrieved from the internet: https://blast.ncbi.nlm.nih.gov/Blast.cgi.

Pietrangelo, "What Does It Mean to Have Low Sex Hormone-Binding Globulin (SHBG) Levels?" *HealthLine*, pp. 1-8 (2019).

Rolnik et al., "ASPRE trial: performance of screening for preterm pre-eclampsia," *Ultrasound Obstet. Gynecol.*, 50:492-495 (2017).

Romero, "Preterm labor: One syndrome, many causes," *Science*, 345(6198):760-765 (2014).

Sibai et al., "Preterm delivery in women with pregestational diabetes mellitus or chronic hypertension relative to women with uncomplicated pregnancies," *Am. J. Obstet. Gynecol.*, 183(6):1520-1524 (2000).

Thadhani et al., "First-trimester sex hormone binding globulin and subsequent gestational diabetes mellitus," *Am J Obstet Gynecol.*, 189(1):171-176 (2003).

Weissgerber et al., "Preeclampsia and Diabetes," *Curr. Diab. Rep.*, 15:9, pp. 1-10 (2015).

World Health Organization, "Preterm Birth," Feb. 19, 2018, pp. 1-5.

Xu et al., "Sparse Algorithms Are Not Stable: A No. Free-Lunch Theorem," *IEEE Transactions On Pattern Analysis and Machine Intelligence*, 34(1):187-193 (2012).

Pereira et al. "Insights into 1,3,4, INV. the multifactorial nature of preterm birth: proteomic profiling of the maternal serum glycoproteome and maternal serum peptidome among women in preterm labor," *Am. J. Obstet. Gynecol.*, 202(6):555e1-555e10 (2010).

Moawad et al., "The Preterm 1-15 Prediction Study: The value of serum alkaline phosphatase, [alpha]-fetoprotein, plasma corticotropin-releasing hormone, and other serum markers for the prediction of spontaneous preterm birth," *Am. J. Obstet. Gynecol.*, 186(5):990-996 (2002).

\* cited by examiner

Predicted GAB vs. Actual Category

BIOMARKERS AND METHODS FOR PREDICTING PRETERM BIRTH

This application is a continuation of application Ser. No. 16/255,757 filed Jan. 23, 2019, which is a continuation of Ser. No. 15/286,486, filed Oct. 5, 2016, which is a continuation of application Ser. No. 14/213,861, filed Mar. 14, 2014, which claims the benefit of U.S. provisional patent application No. 61/919,586, filed Dec. 20, 2013, and U.S. provisional application No. 61/798,504, filed Mar. 15, 2013, each of which is incorporated herein by reference in its entirety.

This application incorporates by reference a Sequence Listing submitted herewith as an ASCII text file entitled 203123-011030_US_SL.txt created on Sep. 21, 2023, and having a size of 344,958 bytes.

The invention relates generally to the field of personalized medicine and, more specifically to compositions and methods for determining the probability for preterm birth in a pregnant female.

BACKGROUND

According to the World Health Organization, an estimated 15 million babies are born preterm (before 37 completed weeks of gestation) every year. In almost all countries with reliable data, preterm birth rates are increasing. See, World Health Organization; March of Dimes; The Partnership for Maternal, Newborn & Child Health; Save the Children, Born too soon: the global action report on preterm birth, ISBN 9789241503433 (2012). An estimated 1 million babies die annually from preterm birth complications. Globally, preterm birth is the leading cause of newborn deaths (babies in the first four weeks of life) and the second leading cause of death after pneumonia in children under five years. Many survivors face a lifetime of disability, including learning disabilities and visual and hearing problems.

Across 184 countries with reliable data, the rate of preterm birth ranges from 5% to 18% of babies born. Blencowe et al., "National, regional and worldwide estimates of preterm birth." The Lancet, 9; 379 (9832): 2162-72 (2012). While over 60% of preterm births occur in Africa and south Asia, preterm birth is nevertheless a global problem. Countries with the highest numbers include Brazil, India, Nigeria and the United States of America. Of the 11 countries with preterm birth rates over 15%, all but two are in sub-Saharan Africa. In the poorest countries, on average, 12% of babies are born too soon compared with 9% in higher-income countries. Within countries, poorer families are at higher risk. More than three-quarters of premature babies can be saved with feasible, cost-effective care, for example, antenatal steroid injections given to pregnant women at risk of preterm labour to strengthen the babies' lungs.

Infants born preterm are at greater risk than infants born at term for mortality and a variety of health and developmental problems. Complications include acute respiratory, gastrointestinal, immunologic, central nervous system, hearing, and vision problems, as well as longer-term motor, cognitive, visual, hearing, behavioral, social-emotional, health, and growth problems. The birth of a preterm infant can also bring considerable emotional and economic costs to families and have implications for public-sector services, such as health insurance, educational, and other social support systems. The greatest risk of mortality and morbidity is for those infants born at the earliest gestational ages. However, those infants born nearer to term represent the greatest number of infants born preterm and also experience more complications than infants born at term.

To prevent preterm birth in women who are less than 24 weeks pregnant with an ultrasound showing cervical opening, a surgical procedure known as cervical cerclage can be employed in which the cervix is stitched closed with strong sutures. For women less than 34 weeks pregnant and in active preterm labor, hospitalization may be necessary as well as the administration of medications to temporarily halt preterm labor and/or promote the fetal lung development. If a pregnant women is determined to be at risk for preterm birth, health care providers can implement various clinical strategies that may include preventive medications, for example, hydroxyprogesterone caproate (Makena) injections and/or vaginal progesterone gel, cervical pessaries, restrictions on sexual activity and/or other physical activities, and alterations of treatments for chronic conditions, such as diabetes and high blood pressure, that increase the risk of preterm labor.

There is a great need to identify and provide women at risk for preterm birth with proper antenatal care. Women identified as high-risk can be scheduled for more intensive antenatal surveillance and prophylactic interventions. Current strategies for risk assessment are based on the obstetric and medical history and clinical examination, but these strategies are only able to identify a small percentage of women who are at risk for preterm delivery. Reliable early identification of risk for preterm birth would enable planning appropriate monitoring and clinical management to prevent preterm delivery. Such monitoring and management might include: more frequent prenatal care visits, serial cervical length measurements, enhanced education regarding signs and symptoms of early preterm labor, lifestyle interventions for modifiable risk behaviors, cervical pessaries and progesterone treatment. Finally, reliable antenatal identification of risk for preterm birth also is crucial to cost-effective allocation of monitoring resources.

The present invention addresses this need by providing compositions and methods for determining whether a pregnant woman is at risk for preterm birth. Related advantages are provided as well.

SUMMARY

The present invention provides compositions and methods for predicting the probability of preterm birth in a pregnant female.

In one aspect, the invention provides a panel of isolated biomarkers comprising N of the biomarkers listed in Tables 1 through 63. In some embodiments, N is a number selected from the group consisting of 2 to 24. In additional embodiments, the biomarker panel comprises at least two of the isolated biomarkers selected from the group consisting of AFTECCVVASQLR (SEQ ID NO: 1), ELLESYIDGR (SEQ ID NO: 2), and ITLPDFTGDLR (SEQ ID NO: 3). In additional embodiments, the biomarker panel comprises at least two of the isolated biomarkers selected from the group consisting of FLNWIK (SEQ ID NO: 4), FGFGGSTDSG-PIR (SEQ ID NO: 5), LLELTGPK (SEQ ID NO: 6), VEHSDLSFSK (SEQ ID NO: 7), IEGNLIFDPNNYLPK (SEQ ID NO: 8), ALVLELAK (SEQ ID NO: 9), TQILE-WAAER (SEQ ID NO: 10), DVLLL-VHNLPQNLPGYFWYK (SEQ ID NO: 11), SEP-RPGVLLR (SEQ ID NO: 12), ITQDAQLK (SEQ ID NO: 13), ALDLSLK (SEQ ID NO: 14), WWGGQPLWITATK (SEQ ID NO: 15), and LSETNR (SEQ ID NO: 16)

In further embodiments, the biomarker panel comprises at least two of the isolated biomarkers selected from the group consisting of the biomarkers set forth in Table 50 and the biomarkers set forth in Table 52.

In a further aspect, the invention provides a panel of isolated biomarkers comprising N of the biomarkers listed in Tables 1 through 63. In some embodiments, N is a number selected from the group consisting of 2 to 24. In additional embodiments, the biomarker panel comprises at least two of the isolated biomarkers selected from the group consisting of the biomarkers set forth in Table 50 and the biomarkers set forth in Table 52.

In some embodiments, the invention provides a biomarker panel comprising at least two of the isolated biomarkers selected from the group consisting of lipopolysaccharide-binding protein (LBP), prothrombin (THRB), complement component C5 (C5 or CO5), plasminogen (PLMN), and complement component C8 gamma chain (C8G or CO8G).

In some embodiments, the invention provides a biomarker panel comprising at least two of the isolated biomarkers selected from the group consisting of Alpha-1B-glycopro-tein (A1BG), Disintegrin and metalloproteinase domain-containing protein 12 (ADA12), Apolipoprotein B-100 (APOB), Beta-2-microglobulin (B2MG), CCAAT/en-hancer-binding protein alpha/beta (HP8 Peptide), Corticos-teroid-binding globulin (CBG), Complement component C6, Endoglin (EGLN), Ectonucleotide pyrophosphatase/phosphodiesterase family member 2 (ENPP2), Coagulation factor VII (FA7), Hyaluronan-binding protein 2 (HABP2), Pregnancy-specific beta-1-glycoprotein 9 (PSG9), Inhibin beta E chain (INHBE).

In other embodiments, the invention provides a biomarker panel comprising lipopolysaccharide-binding protein (LBP), prothrombin (THRB), complement component C5 (C5 or CO5), plasminogen (PLMN), complement component C8 gamma chain (C8G or CO8G), complement component 1, q subcomponent, B chain (C1QB), fibrinogen beta chain (FIBB or FIB), C-reactive protein (CRP), inter-alpha-trypsin inhibitor heavy chain H4 (ITIH4), chorionic somatomam-motropin hormone (CSH), and angiotensinogen (ANG or ANGT).

In other embodiments, the invention provides a biomarker panel comprising Alpha-1B-glycoprotein (A1BG), Disinte-grin and metalloproteinase domain-containing protein 12 (ADA12), Apolipoprotein B-100 (APOB), Beta-2-micro-globulin (B2MG), CCAAT/enhancer-binding protein alpha/beta (HP8 Peptide), Corticosteroid-binding globulin (CBG), Complement component C6, Endoglin (EGLN), Ectonucle-otide pyrophosphatase/phosphodiesterase family member 2 (ENPP2), Coagulation factor VII (FA7), Hyaluronan-bind-ing protein 2 (HABP2), Pregnancy-specific beta-1-glyco-protein 9 (PSG9), Inhibin beta E chain (INHBE).

In additional embodiments, the invention provides a bio-marker panel comprising at least two of the isolated bio-markers selected from the group consisting of the biomark-ers set forth in Table 51 and the biomarkers set forth in Table 53.

Also provided by the invention is a method of determin-ing probability for preterm birth in a pregnant female comprising detecting a measurable feature of each of N biomarkers selected from the biomarkers listed in Tables 1 through 63 in a biological sample obtained from the preg-nant female, and analyzing the measurable feature to deter-mine the probability for preterm birth in the pregnant female. In some embodiments, the invention provides a method of predicting GAB, the method encompassing detecting a measurable feature of each of N biomarkers selected from the biomarkers listed in Tables 1 through 63 in a biological sample obtained from a pregnant female, and analyzing said measurable feature to predict GAB.

In some embodiments, a measurable feature comprises fragments or derivatives of each of the N biomarkers selected from the biomarkers listed in Tables 1 through 63. In some embodiments of the disclosed methods detecting a measurable feature comprises quantifying an amount of each of N biomarkers selected from the biomarkers listed in Tables 1 through 63, combinations or portions and/or deriva-tives thereof in a biological sample obtained from the pregnant female. In additional embodiments, the disclosed methods of determining probability for preterm birth in a pregnant female further encompass detecting a measurable feature for one or more risk indicia associated with preterm birth.

In some embodiments, the disclosed methods of deter-mining probability for preterm birth in a pregnant female and related methods disclosed herein comprise detecting a measurable feature of each of N biomarkers, wherein N is selected from the group consisting of 2 to 24. In further embodiments, the disclosed methods of determining prob-ability for preterm birth in a pregnant female and related methods disclosed herein comprise detecting a measurable feature of each of at least two isolated biomarkers selected from the group consisting of AFTECCVVASQLR (SEQ ID NO: 1), ELLESYIDGR (SEQ ID NO: 2), and ITLPDFTGDLR (SEQ ID NO: 3). In further embodiments, the disclosed methods of determining probability for pre-term birth in a pregnant female and related methods dis-closed herein comprise detecting a measurable feature of each of at least two isolated biomarkers selected from the group consisting of FLNWIK (SEQ ID NO: 4), FGFGG-STDSGPIR (SEQ ID NO: 5), LLELTGPK (SEQ ID NO: 6), VEHSDLSFSK (SEQ ID NO: 7), IEGNLIFDPNNYLPK (SEQ ID NO: 8), ALVLELAK (SEQ ID NO: 9), TQILE-WAAER (SEQ ID NO: 10), DVLLL-VHNLPQNLPGYFWYK (SEQ ID NO: 11), SEP-RPGVLLR (SEQ ID NO: 12), ITQDAQLK (SEQ ID NO: 13), ALDLSLK (SEQ ID NO: 14), WWGGQPLWITATK (SEQ ID NO: 15), and LSETNR (SEQ ID NO: 16). In further embodiments, the disclosed methods of determining probability for preterm birth in a pregnant female and related methods disclosed herein comprise detecting a measurable feature of each of at least two isolated biomarkers selected from the group consisting of the biomarkers set forth in Table 50 and the biomarkers set forth in Table 52.

In other embodiments, the disclosed methods of deter-mining probability for preterm birth in a pregnant female comprise detecting a measurable feature of each of at least two isolated biomarkers selected from the group consisting of lipopolysaccharide-binding protein (LBP), prothrombin (THRB), complement component C5 (C5 or CO5), plasmi-nogen (PLMN), and complement component C8 gamma chain (C8G or CO8G).

In other embodiments, the disclosed methods of deter-mining probability for preterm birth in a pregnant female comprise detecting a measurable feature of each of at least two isolated biomarkers selected from the group consisting of Alpha-1B-glycoprotein (A1BG), Disintegrin and metal-loproteinase domain-containing protein 12 (ADA12), Apo-lipoprotein B-100 (APOB), Beta-2-microglobulin (B2MG), CCAAT/enhancer-binding protein alpha/beta (HP8 Peptide), Corticosteroid-binding globulin (CBG), Complement com-ponent C6, Endoglin (EGLN), Ectonucleotide pyrophos-phatase/phosphodiesterase family member 2 (ENPP2), Coagulation factor VII (FA7), Hyaluronan-binding protein 2

(HABP2), Pregnancy-specific beta-1-glycoprotein 9 (PSG9), Inhibin beta E chain (INHBE).

In further embodiments, the disclosed methods of determining probability for preterm birth in a pregnant female comprise detecting a measurable feature of each of at least two isolated biomarkers selected from the group consisting of lipopolysaccharide-binding protein (LBP), prothrombin (THRB), complement component C5 (C5 or CO5), plasminogen (PLMN), complement component C8 gamma chain (C8G or CO8G), complement component 1, q subcomponent, B chain (C1QB), fibrinogen beta chain (FIBB or FIB), C-reactive protein (CRP), inter-alpha-trypsin inhibitor heavy chain H4 (ITIH4), chorionic somatomammotropin hormone (CSH), and angiotensinogen (ANG or ANGT).

In further embodiments, the disclosed methods of determining probability for preterm birth in a pregnant female comprise detecting a measurable feature of each of at least two isolated biomarkers selected from the group consisting of the biomarkers set forth in Table 51 and the biomarkers set forth in Table 53.

In some embodiments of the methods of determining probability for preterm birth in a pregnant female, the probability for preterm birth in the pregnant female is calculated based on the quantified amount of each of N biomarkers selected from the biomarkers listed in Tables 1 through 63. In some embodiments, the disclosed methods for determining the probability of preterm birth encompass detecting and/or quantifying one or more biomarkers using mass spectrometry, a capture agent or a combination thereof.

In some embodiments, the disclosed methods of determining probability for preterm birth in a pregnant female encompass an initial step of providing a biomarker panel comprising N of the biomarkers listed in Tables 1 through 63. In additional embodiments, the disclosed methods of determining probability for preterm birth in a pregnant female encompass an initial step of providing a biological sample from the pregnant female.

In some embodiments, the disclosed methods of determining probability for preterm birth in a pregnant female encompass communicating the probability to a health care provider. In additional embodiments, the communication informs a subsequent treatment decision for the pregnant female. In further embodiments, the treatment decision of one or more selected from the group of consisting of more frequent prenatal care visits, serial cervical length measurements, enhanced education regarding signs and symptoms of early preterm labor, lifestyle interventions for modifiable risk behaviors and progesterone treatment.

In further embodiments, the disclosed methods of determining probability for preterm birth in a pregnant female encompass analyzing the measurable feature of one or more isolated biomarkers using a predictive model. In some embodiments of the disclosed methods, a measurable feature of one or more isolated biomarkers is compared with a reference feature.

In additional embodiments, the disclosed methods of determining probability for preterm birth in a pregnant female encompass using one or more analyses selected from a linear discriminant analysis model, a support vector machine classification algorithm, a recursive feature elimination model, a prediction analysis of microarray model, a logistic regression model, a CART algorithm, a flex tree algorithm, a LART algorithm, a random forest algorithm, a MART algorithm, a machine learning algorithm, a penalized regression method, and a combination thereof. In one embodiment, the disclosed methods of determining probability for preterm birth in a pregnant female encompass logistic regression.

In some embodiments, the invention provides a method of determining probability for preterm birth in a pregnant female, the method encompassing quantifying in a biological sample obtained from the pregnant female an amount of each of N biomarkers selected from the biomarkers listed in Tables 1 through 63; multiplying the amount by a predetermined coefficient, and determining the probability for preterm birth in the pregnant female comprising adding the individual products to obtain a total risk score that corresponds to the probability In additional embodiments, the invention provides a method of predicting GAB, the method comprising: (a) quantifying in a biological sample obtained from said pregnant female an amount of each of N biomarkers selected from the biomarkers listed in Tables 1 through 63; (b) multiplying or thresholding said amount by a predetermined coefficient, (c) determining the predicted GAB birth in said pregnant female comprising adding said individual products to obtain a total risk score that corresponds to said predicted GAB.

In further embodiments, the invention provides a method of predicting time to birth in a pregnant female, the method comprising: (a) obtaining a biological sample from said pregnant female; (b) quantifying an amount of each of N biomarkers selected from the biomarkers listed in Tables 1 through 63 in said biological sample; (c) multiplying or thresholding said amount by a predetermined coefficient, (d) determining predicted GAB in said pregnant female comprising adding said individual products to obtain a total risk score that corresponds to said predicted GAB; and (e) subtracting the estimated gestational age (GA) at time biological sample was obtained from the predicted GAB to predict time to birth in said pregnant female.

Other features and advantages of the invention will be apparent from the detailed description, and from the claims.

DETAILED DESCRIPTION

Figure 1:
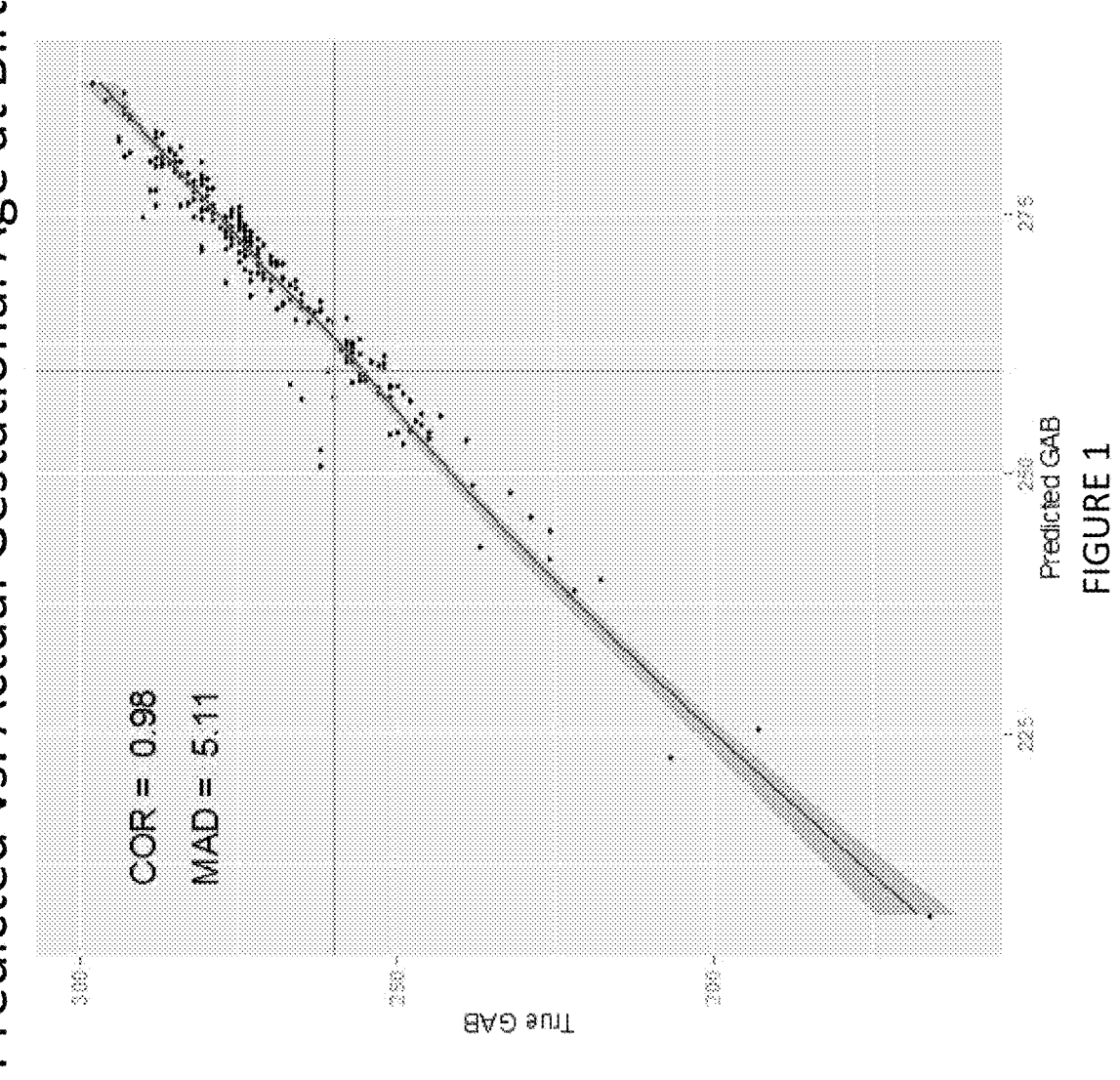
FIG. 1. Scatterplot of actual gestational age at birth versus predicted gestational age from random forest regression model.

The present disclosure is based, in part, on the discovery that certain proteins and peptides in biological samples obtained from a pregnant female are differentially expressed in pregnant females that have an increased risk of preterm birth relative to controls. The present disclosure is further based, in part, on the unexpected discovery that panels combining one or more of these proteins and peptides can be utilized in methods of determining the probability for preterm birth in a pregnant female with high sensitivity and specificity. These proteins and peptides disclosed herein serve as biomarkers for classifying test samples, predicting probability of preterm birth, predicting probability of term birth, predicting gestational age at birth (GAB), predicting time to birth and/or monitoring of progress of preventative therapy in a pregnant female, either individually or in a panel of biomarkers.

The disclosure provides biomarker panels, methods and kits for determining the probability for preterm birth in a pregnant female. One major advantage of the present disclosure is that risk of developing preterm birth can be assessed early during pregnancy so that appropriate monitoring and clinical management to prevent preterm delivery can be initiated in a timely fashion. The present invention is of particular benefit to females lacking any risk factors for preterm birth and who would not otherwise be identified and treated.

By way of example, the present disclosure includes methods for generating a result useful in determining probability for preterm birth in a pregnant female by obtaining a dataset associated with a sample, where the dataset at least includes quantitative data about biomarkers and panels of biomarkers that have been identified as predictive of preterm birth, and inputting the dataset into an analytic process that uses the dataset to generate a result useful in determining probability for preterm birth in a pregnant female. As described further below, this quantitative data can include amino acids, peptides, polypeptides, proteins, nucleotides, nucleic acids, nucleosides, sugars, fatty acids, steroids, metabolites, carbohydrates, lipids, hormones, antibodies, regions of interest that serve as surrogates for biological macromolecules and combinations thereof.

In addition to the specific biomarkers identified in this disclosure, for example, by accession number in a public database, sequence, or reference, the invention also contemplates use of biomarker variants that are at least 90% or at least 95% or at least 97% identical to the exemplified sequences and that are now known or later discovered and that have utility for the methods of the invention. These variants may represent polymorphisms, splice variants, mutations, and the like. In this regard, the instant specification discloses multiple art-known proteins in the context of the invention and provides exemplary accession numbers associated with one or more public databases as well as exemplary references to published journal articles relating to these art-known proteins. However, those skilled in the art appreciate that additional accession numbers and journal articles can easily be identified that can provide additional characteristics of the disclosed biomarkers and that the exemplified references are in no way limiting with regard to the disclosed biomarkers. As described herein, various techniques and reagents find use in the methods of the present invention. Suitable samples in the context of the present invention include, for example, blood, plasma, serum, amniotic fluid, vaginal secretions, saliva, and urine. In some embodiments, the biological sample is selected from the group consisting of whole blood, plasma, and serum. In a particular embodiment, the biological sample is serum. As described herein, biomarkers can be detected through a variety of assays and techniques known in the art. As further described herein, such assays include, without limitation, mass spectrometry (MS)-based assays, antibody-based assays as well as assays that combine aspects of the two.

Protein biomarkers associated with the probability for preterm birth in a pregnant female include, but are not limited to, one or more of the isolated biomarkers listed in Tables 1 through 63. In addition to the specific biomarkers, the disclosure further includes biomarker variants that are about 90%, about 95%, or about 97% identical to the exemplified sequences. Variants, as used herein, include polymorphisms, splice variants, mutations, and the like.

Additional markers can be selected from one or more risk indicia, including but not limited to, maternal characteristics, medical history, past pregnancy history, and obstetrical history. Such additional markers can include, for example, previous low birth weight or preterm delivery, multiple 2nd trimester spontaneous abortions, prior first trimester induced abortion, familial and intergenerational factors, history of infertility, nulliparity, placental abnormalities, cervical and uterine anomalies, short cervical length measurements, gestational bleeding, intrauterine growth restriction, in utero diethylstilbestrol exposure, multiple gestations, infant sex, short stature, low prepregnancy weight, low or high body mass index, diabetes, hypertension, urogenital infections (i.e. urinary tract infection), asthma, anxiety and depression, asthma, hypertension, hypothyroidism. Demographic risk indicia for preterm birth can include, for example, maternal age, race/ethnicity, single marital status, low socioeconomic status, maternal age, employment-related physical activity, occupational exposures and environment exposures and stress. Further risk indicia can include, inadequate prenatal care, cigarette smoking, use of marijuana and other illicit drugs, cocaine use, alcohol consumption, caffeine intake, maternal weight gain, dietary intake, sexual activity during late pregnancy and leisure-time physical activities. (Preterm Birth: Causes, Consequences, and Prevention, Institute of Medicine (US) Committee on Understanding Premature Birth and Assuring Healthy Outcomes; Behrman RE, Butler AS, editors. Washington (DC): National Academies Press (US); 2007). Additional risk indicia useful for as markers can be identified using learning algorithms known in the art, such as linear discriminant analysis, support vector machine classification, recursive feature elimination, prediction analysis of microarray, logistic regression, CART, FlexTree, LART, random forest, MART, and/or survival analysis regression, which are known to those of skill in the art and are further described herein.

Provided herein are panels of isolated biomarkers comprising N of the biomarkers selected from the group listed in Tables 1 through 63. In the disclosed panels of biomarkers N can be a number selected from the group consisting of 2 to 24. In the disclosed methods, the number of biomarkers that are detected and whose levels are determined, can be 1, or more than 1, such as 2, 3, 4, 5, 6, 7, 8, 9, 10, 11, 12, 12, 14, 15, 16, 17, 18, 19, 20, 21, 22, 23, 24, 25 or more. In certain embodiments, the number of biomarkers that are detected, and whose levels are determined, can be 1, or more than 1, such as 2, 3, 4, 5, 6, 7, 8, 9, 10, or more. The methods of this disclosure are useful for determining the probability for preterm birth in a pregnant female.

While certain of the biomarkers listed in Tables 1 through 63 are useful alone for determining the probability for preterm birth in a pregnant female, methods are also described herein for the grouping of multiple subsets of the biomarkers that are each useful as a panel of three or more biomarkers. In some embodiments, the invention provides panels comprising N biomarkers, wherein N is at least three biomarkers. In other embodiments, N is selected to be any number from 3-23 biomarkers.

In yet other embodiments, N is selected to be any number from 2-5, 2-10, 2-15, 2-20, or 2-23. In other embodiments, N is selected to be any number from 3-5, 3-10, 3-15, 3-20, or 3-23. In other embodiments, N is selected to be any number from 4-5, 4-10, 4-15, 4-20, or 4-23. In other embodiments, N is selected to be any number from 5-10, 5-15, 5-20, or 5-23. In other embodiments, N is selected to be any number from 6-10, 6-15, 6-20, or 6-23. In other embodiments, N is selected to be any number from 7-10, 7-15, 7-20, or 7-23. In other embodiments, N is selected to be any number from 8-10, 8-15, 8-20, or 8-23. In other embodiments, N is selected to be any number from 9-10, 9-15, 9-20, or 9-23. In other embodiments, N is selected to be any number from 10-15, 10-20, or 10-23. It will be appreciated that N can be selected to encompass similar, but higher order, ranges.

In certain embodiments, the panel of isolated biomarkers comprises one or more, two or more, three or more, four or more, or five isolated biomarkers comprising an amino acid sequence selected from AFTECCVVASQLR (SEQ ID NO: 1), ELLESYIDGR (SEQ ID NO: 2), ITLPDFTGDLR (SEQ ID NO: 3), TDAPDLPEENQAR (SEQ ID NO: 17) and SFRPFVPR (SEQ ID NO: 18). In some embodiments, the panel of isolated biomarkers comprises one or more, two or more, three or more, four or more, or five isolated biomarkers comprising an amino acid sequence selected from FLNWIK (SEQ ID NO: 4), FGFGGSTDSGPIR (SEQ ID NO: 5), LLELTGPK (SEQ ID NO: 6), VEHSDLSFSK (SEQ ID NO: 7), IEGNLIFDPNNYLPK (SEQ ID NO: 8), ALVLELAK (SEQ ID NO: 9), TQILEWAAER (SEQ ID NO: 10), DVLLLVHNLPQNLPGYFWYK (SEQ ID NO: 11), SEPRPGVLLR (SEQ ID NO: 12), ITQDAQLK (SEQ ID NO: 13), ALDLSLK (SEQ ID NO: 14), WWGGQPLWI-TATK (SEQ ID NO: 15), and LSETNR (SEQ ID NO: 16).

In some embodiments, the panel of isolated biomarkers comprises one or more, two or more, or three of the isolated biomarkers consisting of an amino acid sequence selected from AFTECCVVASQLR (SEQ ID NO: 1), ELLESYIDGR (SEQ ID NO: 2), and ITLPDFTGDLR (SEQ ID NO: 3). In some embodiments, the panel of isolated biomarkers comprises one or more, two or more, or three of the isolated biomarkers consisting of an amino acid sequence selected from FLNWIK (SEQ ID NO: 4), FGFGGSTDSGPIR (SEQ ID NO: 5), LLELTGPK (SEQ ID NO: 6), VEHSDLSFSK (SEQ ID NO: 7), IEGNLIFDPNNYLPK (SEQ ID NO: 8), ALVLELAK (SEQ ID NO: 9), TQILEWAAER (SEQ ID NO: 10), DVLLLVHNLPQNLPGYFWYK (SEQ ID NO: 11), SEPRPGVLLR (SEQ ID NO: 12), ITQDAQLK (SEQ ID NO: 13), ALDLSLK (SEQ ID NO: 14), WWGGQPLWI-TATK (SEQ ID NO: 15), and LSETNR (SEQ ID NO: 16).

In some embodiments, the panel of isolated biomarkers comprises one or more, two or more, or three of the isolated biomarkers consisting of an amino acid sequence selected from the biomarkers set forth in Table 50 and the biomarkers set forth in Table 52.

In some embodiments, the panel of isolated biomarkers comprises one or more peptides comprising a fragment from lipopolysaccharide-binding protein (LBP), Schumann et al., *Science* 249 (4975), 1429-1431 (1990) (UniProtKB/Swiss-Prot: P18428.3); prothrombin (THRB), Walz et al., *Proc. Natl. Acad. Sci. U.S.A.* 74 (5), 1969-1972 (1977) (NCBI Reference Sequence: NP_000497.1); complement component C5 (C5 or CO5) Haviland, *J. Immunol.* 146 (1), 362-368 (1991) (GenBank: AAA51925.1); plasminogen (PLMN) Petersen et al., *J. Biol. Chem.* 265 (11), 6104-6111 (1990) (NCBI Reference Sequences: NP_000292.1 NP_001161810.1); and complement component C8 gamma chain (C8G or CO8G), Haefliger et al., *Mol. Immunol.* 28 (1-2), 123-131 (1991) (NCBI Reference Sequence: NP_000597.2).

In some embodiments, the panel of isolated biomarkers comprises one or more peptides comprising a fragment from cell adhesion molecule with homology to complement component 1, q subcomponent, B chain (C1QB), Reid, *Biochem. J.* 179 (2), 367-371 (1979) (NCBI Reference Sequence: NP_000482.3); fibrinogen beta chain (FIBB or FIB); Watt et al., *Biochemistry* 18 (1), 68-76 (1979) (NCBI Reference Sequences: NP_001171670.1 and NP_005132.2); C-reactive protein (CRP), Oliveira et al., *J. Biol. Chem.* 254 (2), 489-502 (1979) (*NCBI Reference Sequence*: NP_000558.2); inter-alpha-trypsin inhibitor heavy chain H4 (ITIH4) Kim et al., *Mol. Biosyst.* 7 (5), 1430-1440 (2011) (NCBI Reference Sequences: NP 001159921.1 and NP_002209.2); chorionic somatomammotropin hormone (CSH) Selby et al., *J. Biol. Chem.* 259 (21), 13131-13138 (1984) (NCBI Reference Sequence: NP_001308.1); and angiotensinogen (ANG or ANGT) Underwood et al., *Metabolism* 60 (8): 1150-7 (2011) (NCBI Reference Sequence: NP_000020.1).

In additional embodiments, the invention provides a panel of isolated biomarkers comprising N of the biomarkers listed in Tables 1 through 63. In some embodiments, N is a number selected from the group consisting of 2 to 24. In additional embodiments, the biomarker panel comprises at least two of the isolated biomarkers selected from the group consisting of AFTECCVVASQLR (SEQ ID NO: 1), ELLESYIDGR (SEQ ID NO: 2), and ITLPDFTGDLR (SEQ ID NO: 3). In additional embodiments, the biomarker panel comprises at least two of the isolated biomarkers selected from the group consisting of AFTECCVVASQLR (SEQ ID NO: 1), ELLESYIDGR (SEQ ID NO: 2), ITLPDFTGDLR (SEQ ID NO: 3), TDAPDLPEENQAR (SEQ ID NO: 17) and SFRPFVPR (SEQ ID NO: 18). In additional embodiments, the biomarker panel comprises at least two of the isolated biomarkers selected from the group consisting of FLNWIK (SEQ ID NO: 4), FGFGGSTDSGPIR (SEQ ID NO: 5), LLELTGPK (SEQ ID NO: 6), VEHSDLSFSK (SEQ ID NO: 7), IEGNLIFDPNNYLPK (SEQ ID NO: 8), ALVLELAK (SEQ ID NO: 9), TQILEWAAER (SEQ ID NO: 10), DVLLLVHNLPQNLPGYFWYK (SEQ ID NO: 11), SEPRPGVLLR (SEQ ID NO: 12), ITQDAQLK (SEQ ID NO: 13), ALDLSLK (SEQ ID NO: 14), WWGGQPLWITATK (SEQ ID NO: 15), and LSETNR (SEQ ID NO: 16).

In additional embodiments, the biomarker panel comprises at least two of the isolated biomarkers selected from the group consisting of the biomarkers set forth in Table 50 and the biomarkers set forth in Table 52.

In further embodiments, the biomarker panel comprises at least two of the isolated biomarkers selected from the group consisting of lipopolysaccharide-binding protein (LBP), prothrombin (THRB), complement component C5 (C5 or CO5), plasminogen (PLMN), and complement component C8 gamma chain (C8G or CO8G). In another embodiment, the invention provides a biomarker panel comprising at least three isolated biomarkers selected from the group consisting of lipopolysaccharide-binding protein (LBP), prothrombin (THRB), complement component C5 (C5 or CO5), plasminogen (PLMN), and complement component C8 gamma chain (C8G or CO8G).

In further embodiments, the biomarker panel comprises at least two of the isolated biomarkers selected from the group consisting of Alpha-1B-glycoprotein (A1BG), Disintegrin and metalloproteinase domain-containing protein 12 (ADA12), Apolipoprotein B-100 (APOB), Beta-2-microglobulin (B2MG), CCAAT/enhancer-binding protein alpha/beta (HP8 Peptide), Corticosteroid-binding globulin (CBG), Complement component C6, Endoglin (EGLN), Ectonucleotide pyrophosphatase/phosphodiesterase family member 2 (ENPP2), Coagulation factor VII (FA7), Hyaluronan-binding protein 2 (HABP2), Pregnancy-specific beta-1-glycoprotein 9 (PSG9), Inhibin beta E chain (INHBE).

In some embodiments, the invention provides a biomarker panel comprising lipopolysaccharide-binding protein (LBP), prothrombin (THRB), complement component C5 (C5 or CO5), plasminogen (PLMN), complement component C8 gamma chain (C8G or CO8G), complement component 1, q subcomponent, B chain (CIQB), fibrinogen beta chain (FIBB or FIB), C-reactive protein (CRP), inter-alpha-trypsin inhibitor heavy chain H4 (ITIH4), chorionic somatomam-motropin hormone (CSH), and angiotensinogen (ANG or ANGT). In some embodiments, the invention provides a biomarker panel comprising Alpha-1B-glycoprotein (A1BG), Disintegrin and metalloproteinase domain-contain-ing protein 12 (ADA12), Apolipoprotein B-100 (APOB), Beta-2-microglobulin (B2MG), CCAAT/enhancer-binding protein alpha/beta (HP8 Peptide), Corticosteroid-binding globulin (CBG), Complement component C6, Endoglin (EGLN), Ectonucleotide pyrophosphatase/phosphodies-terase family member 2 (ENPP2), Coagulation factor VII (FA7), Hyaluronan-binding protein 2 (HABP2), Pregnancy-specific beta-1-glycoprotein 9 (PSG9), Inhibin beta E chain (INHBE).

In another aspect, the invention provides a biomarker panel comprising at least two isolated biomarkers selected from the group consisting of lipopolysaccharide-binding protein (LBP), prothrombin (THRB), complement compo-nent C5 (C5 or CO5), plasminogen (PLMN), complement component C8 gamma chain (C8G or CO8G), complement component 1, q subcomponent, B chain (C1QB), fibrinogen beta chain (FIBB or FIB), C-reactive protein (CRP), inter-alpha-trypsin inhibitor heavy chain H4 (ITIH4), chorionic somatomammotropin hormone (CSH), and angiotensinogen (ANG or ANGT) and the biomarkers set forth in Tables 51 and 53.

In another aspect, the invention provides a biomarker panel comprising at least two isolated biomarkers selected from the group consisting of Alpha-1B-glycoprotein (A1BG), Disintegrin and metalloproteinase domain-contain-ing protein 12 (ADA12), Apolipoprotein B-100 (APOB), Beta-2-microglobulin (B2MG), CCAAT/enhancer-binding protein alpha/beta (HP8 Peptide), Corticosteroid-binding globulin (CBG), Complement component C6, Endoglin (EGLN), Ectonucleotide pyrophosphatase/phosphodies-terase family member 2 (ENPP2), Coagulation factor VII (FA7), Hyaluronan-binding protein 2 (HABP2), Pregnancy-specific beta-1-glycoprotein 9 (PSG9), Inhibin beta E chain (INHBE).

It must be noted that, as used in this specification and the appended claims, the singular forms "a", "an" and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or con-tains an element or list of elements does not include only those elements but can include other elements not expressly listed or inherent to such process, method, product-by-process, or composition of matter.

As used herein, the term "panel" refers to a composition, such as an array or a collection, comprising one or more biomarkers. The term can also refer to a profile or index of expression patterns of one or more biomarkers described herein. The number of biomarkers useful for a biomarker panel is based on the sensitivity and specificity value for the particular combination of biomarker values.

As used herein, and unless otherwise specified, the terms "isolated" and "purified" generally describes a composition of matter that has been removed from its native environment (e.g., the natural environment if it is naturally occurring), and thus is altered by the hand of man from its natural state. An isolated protein or nucleic acid is distinct from the way it exists in nature.

The term "biomarker" refers to a biological molecule, or a fragment of a biological molecule, the change and/or the detection of which can be correlated with a particular physical condition or state. The terms "marker" and "bio-marker" are used interchangeably throughout the disclosure. For example, the biomarkers of the present invention are correlated with an increased likelihood of preterm birth. Such biomarkers include, but are not limited to, biological molecules comprising nucleotides, nucleic acids, nucleo-sides, amino acids, sugars, fatty acids, steroids, metabolites, peptides, polypeptides, proteins, carbohydrates, lipids, hor-mones, antibodies, regions of interest that serve as surro-gates for biological macromolecules and combinations thereof (e.g., glycoproteins, ribonucleoproteins, lipopro-teins). The term also encompasses portions or fragments of a biological molecule, for example, peptide fragment of a protein or polypeptide that comprises at least 5 consecutive amino acid residues, at least 6 consecutive amino acid residues, at least 7 consecutive amino acid residues, at least 8 consecutive amino acid residues, at least 9 consecutive amino acid residues, at least 10 consecutive amino acid residues, at least 11 consecutive amino acid residues, at least 12 consecutive amino acid residues, at least 13 consecutive amino acid residues, at least 14 consecutive amino acid residues, at least 15 consecutive amino acid residues, at least 5 consecutive amino acid residues, at least 16 consecutive amino acid residues, at least 17 consecutive amino acid residues, at least 18 consecutive amino acid residues, at least 19 consecutive amino acid residues, at least 20 consecutive amino acid residues, at least 21 consecutive amino acid residues, at least 22 consecutive amino acid residues, at least 23 consecutive amino acid residues, at least 24 consecutive amino acid residues, at least 25 consecutive amino acid residues, or more consecutive amino acid residues.

The invention also provides a method of determining probability for preterm birth in a pregnant female, the method comprising detecting a measurable feature of each of N biomarkers selected from the biomarkers listed in Tables 1 through 63 in a biological sample obtained from the pregnant female, and analyzing the measurable feature to determine the probability for preterm birth in the pregnant female. As disclosed herein, a measurable feature comprises fragments or derivatives of each of said N biomarkers selected from the biomarkers listed in Tables 1 through 63. In some embodiments of the disclosed methods detecting a measurable feature comprises quantifying an amount of each of N biomarkers selected from the biomarkers listed in Tables 1 through 63, combinations or portions and/or deriva-tives thereof in a biological sample obtained from said pregnant female.

The invention further provides a method of predicting GAB, the method encompassing detecting a measurable feature of each of N biomarkers selected from the biomark-ers listed in Tables 1 through 63 in a biological sample obtained from a pregnant female, and analyzing the measurable feature to predict GAB.

The invention also provides a method of predicting GAB, the method comprising: (a) quantifying in a biological sample obtained from the pregnant female an amount of each of N biomarkers selected from the biomarkers listed in Tables 1 through 63; (b) multiplying or thresholding the amount by a predetermined coefficient, (c) determining the predicted GAB birth in the pregnant female comprising adding the individual products to obtain a total risk score that corresponds to the predicted GAB.

The invention further provides a method of predicting time to birth in a pregnant female, the method comprising: (a) obtaining a biological sample from the pregnant female; (b) quantifying an amount of each of N biomarkers selected from the biomarkers listed in Tables 1 through 63 in the biological sample; (c) multiplying or thresholding the amount by a predetermined coefficient, (d) determining predicted GAB in the pregnant female comprising adding the individual products to obtain a total risk score that corresponds to the predicted GAB; and (e) subtracting the estimated gestational age (GA) at time biological sample was obtained from the predicted GAB to predict time to birth in said pregnant female. For methods directed to predicting time to birth, it is understood that "birth" means birth following spontaneous onset of labor, with or without rupture of membranes.

Although described and exemplified with reference to methods of determining probability for preterm birth in a pregnant female, the present disclosure is similarly applicable to the methods of predicting GAB, the methods for predicting term birth, methods for determining the probability of term birth in a pregnant female as well methods of predicting time to birth in a pregnant female. It will be apparent to one skilled in the art that each of the aforementioned methods has specific and substantial utilities and benefits with regard maternal-fetal health considerations.

In some embodiments, the method of determining probability for preterm birth in a pregnant female and related methods disclosed herein comprise detecting a measurable feature of each of N biomarkers, wherein N is selected from the group consisting of 2 to 24. In further embodiments, the disclosed methods of determining probability for preterm birth in a pregnant female and related methods disclosed herein comprise detecting a measurable feature of each of at least two isolated biomarkers selected from the group consisting of AFTECCVVASQLR (SEQ ID NO: 1), ELLESYIDGR (SEQ ID NO: 2), and ITLPDFTGDLR (SEQ ID NO: 3). In further embodiments, the disclosed methods of determining probability for preterm birth in a pregnant female and related methods disclosed herein comprise detecting a measurable feature of each of at least two isolated biomarkers selected from the group consisting of FLNWIK (SEQ ID NO: 4), FGFGGSTDSGPIR (SEQ ID NO: 5), LLELTGPK (SEQ ID NO: 6), VEHSDLSFSK (SEQ ID NO: 7), IEGNLIFDPNNYLPK (SEQ ID NO: 8), ALVLELAK (SEQ ID NO: 9), TQILEWAAER (SEQ ID NO: 10), DVLLLVHNLPQNLPGYFWYK (SEQ ID NO: 11), SEPRPGVLLR (SEQ ID NO: 12), ITQDAQLK (SEQ ID NO: 13), ALDLSLK (SEQ ID NO: 14), WWGGQPLWITATK (SEQ ID NO: 15), and LSETNR (SEQ ID NO: 16).

In additional embodiments, the disclosed methods of determining probability for preterm birth in a pregnant female and related methods disclosed herein comprise detecting a measurable feature of each of at least two isolated biomarkers selected from the group consisting of the biomarkers set forth in Table 50 and the biomarkers set forth in Table 52.

In additional embodiments, the method of determining probability for preterm birth in a pregnant female and related methods disclosed herein comprise detecting a measurable feature of each of at least two isolated biomarkers selected from the group consisting of lipopolysaccharide-binding protein (LBP), prothrombin (THRB), complement component C5 (C5 or CO5), plasminogen (PLMN), and complement component C8 gamma chain (C8G or CO8G).

In additional embodiments, the method of determining probability for preterm birth in a pregnant female and related methods disclosed herein comprise detecting a measurable feature of each of at least two isolated biomarkers selected from the group consisting of Alpha-1B-glycoprotein (A1BG), Disintegrin and metalloproteinase domain-containing protein 12 (ADA12), Apolipoprotein B-100 (APOB), Beta-2-microglobulin (B2MG), CCAAT/enhancer-binding protein alpha/beta (HP8 Peptide), Corticosteroid-binding globulin (CBG), Complement component C6, Endoglin (EGLN), Ectonucleotide pyrophosphatase/phosphodiesterase family member 2 (ENPP2), Coagulation factor VII (FA7), Hyaluronan-binding protein 2 (HABP2), Pregnancy-specific beta-1-glycoprotein 9 (PSG9), Inhibin beta E chain (INHBE).

In further embodiments, the disclosed method of determining probability for preterm birth in a pregnant female and related methods disclosed herein comprise detecting a measurable feature of each of at least two isolated biomarkers selected from the group consisting of lipopolysaccharide-binding protein (LBP), prothrombin (THRB), complement component C5 (C5 or CO5), plasminogen (PLMN), complement component C8 gamma chain (C8G or CO8G), complement component 1, q subcomponent, B chain (C1QB), fibrinogen beta chain (FIBB or FIB), C-reactive protein (CRP), inter-alpha-trypsin inhibitor heavy chain H4 (ITIH4), chorionic somatomammotropin hormone (CSH), and angiotensinogen (ANG or ANGT).

In further embodiments, the disclosed method of determining probability for preterm birth in a pregnant female and related methods disclosed herein comprise detecting a measurable feature of each of at least two isolated biomarkers selected from the group consisting of Alpha-1B-glycoprotein (A1BG), Disintegrin and metalloproteinase domain-containing protein 12 (ADA12), Apolipoprotein B-100 (APOB), Beta-2-microglobulin (B2MG), CCAAT/enhancer-binding protein alpha/beta (HP8 Peptide), Corticosteroid-binding globulin (CBG), Complement component C6, Endoglin (EGLN), Ectonucleotide pyrophosphatase/phosphodiesterase family member 2 (ENPP2), Coagulation factor VII (FA7), Hyaluronan-binding protein 2 (HABP2), Pregnancy-specific beta-1-glycoprotein 9 (PSG9), Inhibin beta E chain (INHBE).

In further embodiments, the disclosed method of determining probability for preterm birth in a pregnant female and related methods disclosed herein comprise detecting a measurable feature of each of at least two isolated biomarkers selected from the group consisting of Alpha-1B-glycoprotein (A1BG), Disintegrin and metalloproteinase domain-containing protein 12 (ADA12), Apolipoprotein B-100 (APOB), Beta-2-microglobulin (B2MG), CCAAT/enhancer-binding protein alpha/beta (HP8 Peptide), Corticosteroid-binding globulin (CBG), Complement component C6, Endoglin (EGLN), Ectonucleotide pyrophosphatase/phosphodiesterase family member 2 (ENPP2), Coagulation factor VII (FA7), Hyaluronan-binding protein 2 (HABP2), Pregnancy-specific beta-1-glycoprotein 9 (PSG9), Inhibin beta E chain (INHBE).

In further embodiments, the disclosed method of determining probability for preterm birth in a pregnant female and related methods disclosed herein comprise detecting a measurable feature of each of at least two isolated biomarkers selected from the group consisting of the biomarkers set forth in Table 51 and the biomarkers set forth in Table 53.

In additional embodiments, the methods of determining probability for preterm birth in a pregnant female further encompass detecting a measurable feature for one or more risk indicia associated with preterm birth. In additional embodiments the risk indicia are selected form the group consisting of previous low birth weight or preterm delivery, multiple 2nd trimester spontaneous abortions, prior first trimester induced abortion, familial and intergenerational factors, history of infertility, nulliparity, placental abnormalities, cervical and uterine anomalies, gestational bleeding, intrauterine growth restriction, in utero diethylstilbestrol exposure, multiple gestations, infant sex, short stature, low prepregnancy weight, low or high body mass index, diabetes, hypertension, and urogenital infections.

A "measurable feature" is any property, characteristic or aspect that can be determined and correlated with the probability for preterm birth in a subject. The term further encompasses any property, characteristic or aspect that can be determined and correlated in connection with a prediction of GAB, a prediction of term birth, or a prediction of time to birth in a pregnant female. For a biomarker, such a measurable feature can include, for example, the presence, absence, or concentration of the biomarker, or a fragment thereof, in the biological sample, an altered structure, such as, for example, the presence or amount of a post-translational modification, such as oxidation at one or more positions on the amino acid sequence of the biomarker or, for example, the presence of an altered conformation in comparison to the conformation of the biomarker in normal control subjects, and/or the presence, amount, or altered structure of the biomarker as a part of a profile of more than one biomarker. In addition to biomarkers, measurable features can further include risk indicia including, for example, maternal characteristics, age, race, ethnicity, medical history, past pregnancy history, obstetrical history. For a risk indicium, a measurable feature can include, for example, previous low birth weight or preterm delivery, multiple 2nd trimester spontaneous abortions, prior first trimester induced abortion, familial and intergenerational factors, history of infertility, nulliparity, placental abnormalities, cervical and uterine anomalies, short cervical length measurements, gestational bleeding, intrauterine growth restriction, in utero diethylstilbestrol exposure, multiple gestations, infant sex, short stature, low prepregnancy weight/low body mass index, diabetes, hypertension, urogenital infections, hypothyroidism, asthma, low educational attainment, cigarette smoking, drug use and alcohol consumption.

In some embodiments of the disclosed methods of determining probability for preterm birth in a pregnant female, the probability for preterm birth in the pregnant female is calculated based on the quantified amount of each of N biomarkers selected from the biomarkers listed in Tables 1 through 63. In some embodiments, the disclosed methods for determining the probability of preterm birth encompass detecting and/or quantifying one or more biomarkers using mass spectrometry, a capture agent or a combination thereof.

In some embodiments, the disclosed methods of determining probability for preterm birth in a pregnant female encompass an initial step of providing a biomarker panel comprising N of the biomarkers listed in Tables 1 through 63. In additional embodiments, the disclosed methods of determining probability for preterm birth in a pregnant female encompass an initial step of providing a biological sample from the pregnant female.

In some embodiments, the disclosed methods of determining probability for preterm birth in a pregnant female encompass communicating the probability to a health care provider. The disclosed of predicting GAB, the methods for predicting term birth, methods for determining the probability of term birth in a pregnant female as well methods of predicting time to birth in a pregnant female similarly encompass communicating the probability to a health care provider. As stated above, although described and exemplified with reference to determining probability for preterm birth in a pregnant female, all embodiments described throughout this disclosure are similarly applicable to the methods of predicting GAB, the methods for predicting term birth, methods for determining the probability of term birth in a pregnant female as well methods of predicting time to birth in a pregnant female. Specifically, he biomarkers and panels recited throughout this application with express reference to methods for preterm birth can also be used in methods for predicting GAB, the methods for predicting term birth, methods for determining the probability of term birth in a pregnant female as well methods of predicting time to birth in a pregnant female. It will be apparent to one skilled in the art that each of the aforementioned methods have specific and substantial utilities and benefits with regard maternal-fetal health considerations.

In additional embodiments, the communication informs a subsequent treatment decision for the pregnant female. In some embodiments, the method of determining probability for preterm birth in a pregnant female encompasses the additional feature of expressing the probability as a risk score.

As used herein, the term "risk score" refers to a score that can be assigned based on comparing the amount of one or more biomarkers in a biological sample obtained from a pregnant female to a standard or reference score that represents an average amount of the one or more biomarkers calculated from biological samples obtained from a random pool of pregnant females. Because the level of a biomarker may not be static throughout pregnancy, a standard or reference score has to have been obtained for the gestational time point that corresponds to that of the pregnant female at the time the sample was taken. The standard or reference score can be predetermined and built into a predictor model such that the comparison is indirect rather than actually performed every time the probability is determined for a subject. A risk score can be a standard (e.g., a number) or a threshold (e.g., a line on a graph). The value of the risk score correlates to the deviation, upwards or downwards, from the average amount of the one or more biomarkers calculated from biological samples obtained from a random pool of pregnant females. In certain embodiments, if a risk score is greater than a standard or reference risk score, the pregnant female can have an increased likelihood of preterm birth. In some embodiments, the magnitude of a pregnant female's risk score, or the amount by which it exceeds a reference risk score, can be indicative of or correlated to that pregnant female's level of risk.

In the context of the present invention, the term "biological sample," encompasses any sample that is taken from pregnant female and contains one or more of the biomarkers listed in Tables 1 through 63. Suitable samples in the context of the present invention include, for example, blood, plasma, serum, amniotic fluid, vaginal secretions, saliva, and urine. In some embodiments, the biological sample is selected from the group consisting of whole blood, plasma, and serum. In a particular embodiment, the biological sample is serum. As will be appreciated by those skilled in the art, a biological sample can include any fraction or component of blood, without limitation, T cells, monocytes, neutrophils, erythrocytes, platelets and microvesicles such as exosomes and exosome-like vesicles. In a particular embodiment, the biological sample is serum.

Preterm birth refers to delivery or birth at a gestational age less than 37 completed weeks. Other commonly used sub-categories of preterm birth have been established and delineate moderately preterm (birth at 33 to 36 weeks of gestation), very preterm (birth at <33 weeks of gestation), and extremely preterm (birth at ≤28 weeks of gestation). With regard to the methods disclosed herein, those skilled in the art understand that the cut-offs that delineate preterm birth and term birth as well as the cut-offs that delineate subcat-egories of preterm birth can be adjusted in practicing the methods disclosed herein, for example, to maximize a particular health benefit. It is further understood that such adjustments are well within the skill set of individuals considered skilled in the art and encompassed within the scope of the inventions disclosed herein. Gestational age is a proxy for the extent of fetal development and the fetus's readiness for birth. Gestational age has typically been defined as the length of time from the date of the last normal menses to the date of birth. However, obstetric measures and ultrasound estimates also can aid in estimating gestational age. Preterm births have generally been classified into two separate subgroups. One, spontaneous preterm births are those occurring subsequent to spontaneous onset of preterm labor or preterm premature rupture of membranes regardless of subsequent labor augmentation or cesarean delivery. Two, indicated preterm births are those occurring following induction or cesarean section for one or more conditions that the woman's caregiver determines to threaten the health or life of the mother and/or fetus. In some embodiments, the methods disclosed herein are directed to determining the probability for spontaneous preterm birth. In additional embodiments, the methods disclosed herein are directed to predicting gestational birth.

As used herein, the term "estimated gestational age" or "estimated GA" refers to the GA determined based on the date of the last normal menses and additional obstetric measures, ultrasound estimates or other clinical parameters including, without limitation, those described in the preceding paragraph. In contrast the term "predicted gestational age at birth" or "predicted GAB" refers to the GAB determined based on the methods of the invention as disclosed herein. As used herein, "term birth" refers to birth at a gestational age equal or more than 37 completed weeks.

In some embodiments, the pregnant female is between 17 and 28 weeks of gestation at the time the biological sample is collected. In other embodiments, the pregnant female is between 16 and 29 weeks, between 17 and 28 weeks, between 18 and 27 weeks, between 19 and 26 weeks, between 20 and 25 weeks, between 21 and 24 weeks, or between 22 and 23 weeks of gestation at the time the biological sample is collected. In further embodiments, the pregnant female is between about 17 and 22 weeks, between about 16 and 22 weeks between about 22 and 25 weeks, between about 13 and 25 weeks, between about 26 and 28, or between about 26 and 29 weeks of gestation at the time the biological sample is collected. Accordingly, the gestational age of a pregnant female at the time the biological sample is collected can be 15, 16, 17, 18, 19, 20, 21, 22, 23, 24, 25, 26, 27, 28, 29 or 30 weeks.

In some embodiments of the claimed methods the measurable feature comprises fragments or derivatives of each of the N biomarkers selected from the biomarkers listed in Tables 1 through 63. In additional embodiments of the claimed methods, detecting a measurable feature comprises quantifying an amount of each of N biomarkers selected from the biomarkers listed in Tables 1 through 63, combinations or portions and/or derivatives thereof in a biological sample obtained from said pregnant female.

The term "amount" or "level" as used herein refers to a quantity of a biomarker that is detectable or measurable in a biological sample and/or control. The quantity of a biomarker can be, for example, a quantity of polypeptide, the quantity of nucleic acid, or the quantity of a fragment or surrogate. The term can alternatively include combinations thereof. The term "amount" or "level" of a biomarker is a measurable feature of that biomarker.

In some embodiments, calculating the probability for preterm birth in a pregnant female is based on the quantified amount of each of N biomarkers selected from the biomarkers listed in Tables 1 through 63. Any existing, available or conventional separation, detection and quantification methods can be used herein to measure the presence or absence (e.g., readout being present vs. absent; or detectable amount vs. undetectable amount) and/or quantity (e.g., readout being an absolute or relative quantity, such as, for example, absolute or relative concentration) of biomarkers, peptides, polypeptides, proteins and/or fragments thereof and optionally of the one or more other biomarkers or fragments thereof in samples. In some embodiments, detection and/or quantification of one or more biomarkers comprises an assay that utilizes a capture agent. In further embodiments, the capture agent is an antibody, antibody fragment, nucleic acid-based protein binding reagent, small molecule or variant thereof. In additional embodiments, the assay is an enzyme immunoassay (EIA), enzyme-linked immunosorbent assay (ELISA), and radioimmunoassay (RIA). In some embodiments, detection and/or quantification of one or more biomarkers further comprises mass spectrometry (MS). In yet further embodiments, the mass spectrometry is co-immunoprecipitation-mass spectrometry (co-IP MS), where coimmunoprecipitation, a technique suitable for the isolation of whole protein complexes is followed by mass spectrometric analysis.

As used herein, the term "mass spectrometer" refers to a device able to volatilize/ionize analytes to form gas-phase ions and determine their absolute or relative molecular masses. Suitable methods of volatilization/ionization are matrix-assisted laser desorption ionization (MALDI), electrospray, laser/light, thermal, electrical, atomized/sprayed and the like, or combinations thereof. Suitable forms of mass spectrometry include, but are not limited to, ion trap instruments, quadrupole instruments, electrostatic and magnetic sector instruments, time of flight instruments, time of flight tandem mass spectrometer (TOF MS/MS), Fourier-transform mass spectrometers, Orbitraps and hybrid instruments composed of various combinations of these types of mass analyzers. These instruments can, in turn, be interfaced with a variety of other instruments that fractionate the samples (for example, liquid chromatography or solid-phase adsorption techniques based on chemical, or biological properties) and that ionize the samples for introduction into the mass spectrometer, including matrix-assisted laser desorption (MALDI), electrospray, or nanospray ionization (ESI) or combinations thereof.

Generally, any mass spectrometric (MS) technique that can provide precise information on the mass of peptides, and preferably also on fragmentation and/or (partial) amino acid sequence of selected peptides (e.g., in tandem mass spectrometry, MS/MS; or in post source decay, TOF MS), can be used in the methods disclosed herein. Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000; Biemann 1990. Methods Enzymol 193:455-79; or Methods in Enzymology, vol. 402: "Biological Mass Spectrometry", by Burlingame, ed., Academic Press 2005) and can be used in practicing the methods disclosed herein. Accordingly, in some embodiments, the disclosed methods comprise performing quantitative MS to measure one or more biomarkers. Such quantitative methods can be performed in an automated (Villanueva, et al., Nature Protocols (2006) 1 (2): 880-891) or semi-automated format. In particular embodiments, MS can be operably linked to a liquid chromatography device (LC-MS/MS or LC-MS) or gas chromatography device (GC-MS or GC-MS/MS). Other methods useful in this context include isotope-coded affinity tag (ICAT), tandem mass tags (TMT), or stable isotope labeling by amino acids in cell culture (SILAC), followed by chromatography and MS/MS.

As used herein, the terms "multiple reaction monitoring (MRM)" or "selected reaction monitoring (SRM)" refer to an MS-based quantification method that is particularly useful for quantifying analytes that are in low abundance. In an SRM experiment, a predefined precursor ion and one or more of its fragments are selected by the two mass filters of a triple quadrupole instrument and monitored over time for precise quantification. Multiple SRM precursor and fragment ion pairs can be measured within the same experiment on the chromatographic time scale by rapidly toggling between the different precursor/fragment pairs to perform an MRM experiment. A series of transitions (precursor/fragment ion pairs) in combination with the retention time of the targeted analyte (e.g., peptide or small molecule such as chemical entity, steroid, hormone) can constitute a definitive assay. A large number of analytes can be quantified during a single LC-MS experiment. The term "scheduled," or "dynamic" in reference to MRM or SRM, refers to a variation of the assay wherein the transitions for a particular analyte are only acquired in a time window around the expected retention time, significantly increasing the number of analytes that can be detected and quantified in a single LC-MS experiment and contributing to the selectivity of the test, as retention time is a property dependent on the physical nature of the analyte. A single analyte can also be monitored with more than one transition. Finally, included in the assay can be standards that correspond to the analytes of interest (e.g., same amino acid sequence), but differ by the inclusion of stable isotopes. Stable isotopic standards (SIS) can be incorporated into the assay at precise levels and used to quantify the corresponding unknown analyte. An additional level of specificity is contributed by the co-elution of the unknown analyte and its corresponding SIS and properties of their transitions (e.g., the similarity in the ratio of the level of two transitions of the unknown and the ratio of the two transitions of its corresponding SIS).

Mass spectrometry assays, instruments and systems suitable for biomarker peptide analysis can include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$_n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$_n$; ion mobility spectrometry (IMS); inductively coupled plasma mass spectrometry (ICP-MS) atmospheric pressure photoionization mass spectrometry (APPI-MS); APPI-MS/MS; and APPI-(MS)$_n$. Peptide ion fragmentation in tandem MS (MS/MS) arrangements can be achieved using manners established in the art, such as, e.g., collision induced dissociation (CID). As described herein, detection and quantification of biomarkers by mass spectrometry can involve multiple reaction monitoring (MRM), such as described among others by Kuhn et al. Proteomics 4:1175-86 (2004). Scheduled multiple-reaction-monitoring (Scheduled MRM) mode acquisition during LC-MS/MS analysis enhances the sensitivity and accuracy of peptide quantitation. Anderson and Hunter, Molecular and Cellular Proteomics 5 (4): 573 (2006). As described herein, mass spectrometry-based assays can be advantageously combined with upstream peptide or protein separation or fractionation methods, such as for example with the chromatographic and other methods described herein below. As further described herein, shotgun quantitative proteomics can be combined with SRM/MRM-based assays for high-throughput identification and verification of prognostic biomarkers of preterm birth.

A person skilled in the art will appreciate that a number of methods can be used to determine the amount of a biomarker, including mass spectrometry approaches, such as MS/MS, LC-MS/MS, multiple reaction monitoring (MRM) or SRM and product-ion monitoring (PIM) and also including antibody based methods such as immunoassays such as Western blots, enzyme-linked immunosorbant assay (ELISA), immunoprecipitation, immunohistochemistry, immunofluorescence, radioimmunoassay, dot blotting, and FACS. Accordingly, in some embodiments, determining the level of the at least one biomarker comprises using an immunoassay and/or mass spectrometric methods. In additional embodiments, the mass spectrometric methods are selected from MS, MS/MS, LC-MS/MS, SRM, PIM, and other such methods that are known in the art. In other embodiments, LC-MS/MS further comprises 1D LC-MS/MS, 2D LC-MS/MS or 3D LC-MS/MS. Immunoassay techniques and protocols are generally known to those skilled in the art (Price and Newman, Principles and Practice of Immunoassay, 2nd Edition, Grove's Dictionaries, 1997; and Gosling, Immunoassays: A Practical Approach, Oxford University Press, 2000.) A variety of immunoassay techniques, including competitive and non-competitive immunoassays, can be used (Self et al., Curr. Opin. Biotechnol., 7:60-65 (1996).

In further embodiments, the immunoassay is selected from Western blot, ELISA, immunoprecipitation, immunohistochemistry, immunofluorescence, radioimmunoassay (RIA), dot blotting, and FACS. In certain embodiments, the immunoassay is an ELISA. In yet a further embodiment, the ELISA is direct ELISA (enzyme-linked immunosorbent assay), indirect ELISA, sandwich ELISA, competitive ELISA, multiplex ELISA, ELISPOT technologies, and other similar techniques known in the art. Principles of these immunoassay methods are known in the art, for example John R. Crowther, The ELISA Guidebook, 1st ed., Humana Press 2000, ISBN 0896037282. Typically ELISAs are performed with antibodies but they can be performed with any capture agents that bind specifically to one or more biomarkers of the invention and that can be detected. Multiplex ELISA allows simultaneous detection of two or more analytes within a single compartment (e.g., microplate well) usually at a plurality of array addresses (Nielsen and Geierstanger 2004. *J Immunol Methods* 290:107-20 (2004) and Ling et al. 2007. *Expert Rev Mol Diagn* 7:87-98 (2007)).

In some embodiments, Radioimmunoassay (RIA) can be used to detect one or more biomarkers in the methods of the invention. RIA is a competition-based assay that is well known in the art and involves mixing known quantities of radioactively-labelled (e.g., $^{125}$I or $^{131}$I-labelled) target analyte with antibody specific for the analyte, then adding non-labelled analyte from a sample and measuring the amount of labelled analyte that is displaced (see, e.g., *An Introduction to Radioimmunoassay and Related Techniques*, by Chard T, ed., Elsevier Science 1995, ISBN 0444821198 for guidance).

A detectable label can be used in the assays described herein for direct or indirect detection of the biomarkers in the methods of the invention. A wide variety of detectable labels can be used, with the choice of label depending on the sensitivity required, ease of conjugation with the antibody, stability requirements, and available instrumentation and disposal provisions. Those skilled in the art are familiar with selection of a suitable detectable label based on the assay detection of the biomarkers in the methods of the invention. Suitable detectable labels include, but are not limited to, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), enzymes (e.g., luciferase, horseradish peroxidase, alkaline phosphatase, etc.), nanoparticles, biotin, digoxigenin, metals, and the like.

For mass-spectrometry based analysis, differential tagging with isotopic reagents, e.g., isotope-coded affinity tags (ICAT) or the more recent variation that uses isobaric tagging reagents, iTRAQ (Applied Biosystems, Foster City, Calif.), or tandem mass tags, TMT, (Thermo Scientific, Rockford, IL), followed by multidimensional liquid chromatography (LC) and tandem mass spectrometry (MS/MS) analysis can provide a further methodology in practicing the methods of the invention.

A chemiluminescence assay using a chemiluminescent antibody can be used for sensitive, non-radioactive detection of protein levels. An antibody labeled with fluorochrome also can be suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), beta-galactosidase, urease, and the like. Detection systems using suitable substrates for horseradish-peroxidase, alkaline phosphatase, beta-galactosidase are well known in the art.

A signal from the direct or indirect label can be analyzed, for example, using a spectrophotometer to detect color from a chromogenic substrate; a radiation counter to detect radiation such as a gamma counter for detection of 1251; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, assays used to practice the invention can be automated or performed robotically, and the signal from multiple samples can be detected simultaneously.

In some embodiments, the methods described herein encompass quantification of the biomarkers using mass spectrometry (MS). In further embodiments, the mass spectrometry can be liquid chromatography-mass spectrometry (LC-MS), multiple reaction monitoring (MRM) or selected reaction monitoring (SRM). In additional embodiments, the MRM or SRM can further encompass scheduled MRM or scheduled SRM.

As described above, chromatography can also be used in practicing the methods of the invention. Chromatography encompasses methods for separating chemical substances and generally involves a process in which a mixture of analytes is carried by a moving stream of liquid or gas ("mobile phase") and separated into components as a result of differential distribution of the analytes as they flow around or over a stationary liquid or solid phase ("stationary phase"), between the mobile phase and said stationary phase. The stationary phase can be usually a finely divided solid, a sheet of filter material, or a thin film of a liquid on the surface of a solid, or the like. Chromatography is well understood by those skilled in the art as a technique applicable for the separation of chemical compounds of biological origin, such as, e.g., amino acids, proteins, fragments of proteins or peptides, etc.

Chromatography can be columnar (i.e., wherein the stationary phase is deposited or packed in a column), preferably liquid chromatography, and yet more preferably high-performance liquid chromatography (HPLC), or ultra high performance/pressure liquid chromatography (UHPLC). Particulars of chromatography are well known in the art (Bidlingmeyer, *Practical HPLC Methodology and Applications*, John Wiley & Sons Inc., 1993). Exemplary types of chromatography include, without limitation, high-performance liquid chromatography (HPLC), UHPLC, normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilised metal affinity chromatography, and the like. Chromatography, including single-, two- or more-dimensional chromatography, can be used as a peptide fractionation method in conjunction with a further peptide analysis method, such as for example, with a downstream mass spectrometry analysis as described elsewhere in this specification.

Further peptide or polypeptide separation, identification or quantification methods can be used, optionally in conjunction with any of the above described analysis methods, for measuring biomarkers in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In the context of the invention, the term "capture agent" refers to a compound that can specifically bind to a target, in particular a biomarker. The term includes antibodies, antibody fragments, nucleic acid-based protein binding reagents (e.g. aptamers, Slow Off-rate Modified Aptamers (SOMAmer™)), protein-capture agents, natural ligands (i.e. a hormone for its receptor or vice versa), small molecules or variants thereof.

Capture agents can be configured to specifically bind to a target, in particular a biomarker. Capture agents can include but are not limited to organic molecules, such as polypeptides, polynucleotides and other non polymeric molecules that are identifiable to a skilled person. In the embodiments disclosed herein, capture agents include any agent that can be used to detect, purify, isolate, or enrich a target, in particular a biomarker. Any art-known affinity capture technologies can be used to selectively isolate and enrich/concentrate biomarkers that are components of complex mixtures of biological media for use in the disclosed methods.

Antibody capture agents that specifically bind to a biomarker can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986). Antibody capture agents can be any immunoglobulin or derivative thereof, whether natural or wholly or partially synthetically produced. All derivatives thereof which maintain specific binding ability are also included in the term. Antibody capture agents have a binding domain that is homologous or largely homologous to an immunoglobulin binding domain and can be derived from natural sources, or partly or wholly synthetically produced. Antibody capture agents can be monoclonal or polyclonal antibodies. In some embodiments, an antibody is a single chain antibody. Those of ordinary skill in the art will appreciate that antibodies can be provided in any of a variety of forms including, for example, humanized, partially humanized, chimeric, chimeric humanized, etc. Antibody capture agents can be antibody fragments including, but not limited to, Fab, Fab', F(ab')2, scFv, Fv, dsFv diabody, and Fd fragments. An antibody capture agent can be produced by any means. For example, an antibody capture agent can be enzymatically or chemically produced by fragmentation of an intact antibody and/or it can be recombinantly produced from a gene encoding the partial antibody sequence. An antibody capture agent can comprise a single chain antibody fragment. Alternatively or additionally, antibody capture agent can comprise multiple chains which are linked together, for example, by disulfide linkages; and, any functional fragments obtained from such molecules, wherein such fragments retain specific-binding properties of the parent antibody molecule. Because of their smaller size as functional components of the whole molecule, antibody fragments can offer advantages over intact antibodies for use in certain immunochemical techniques and experimental applications.

Suitable capture agents useful for practicing the invention also include aptamers. Aptamers are oligonucleotide sequences that can bind to their targets specifically via unique three dimensional (3-D) structures. An aptamer can include any suitable number of nucleotides and different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Use of an aptamer capture agent can include the use of two or more aptamers that specifically bind the same biomarker. An aptamer can include a tag. An aptamer can be identified using any known method, including the SELEX (systematic evolution of ligands by exponential enrichment), process. Once identified, an aptamer can be prepared or synthesized in accordance with any known method, including chemical synthetic methods and enzymatic synthetic methods and used in a variety of applications for biomarker detection. Liu et al., *Curr Med Chem.* 18 (27): 4117-25 (2011). Capture agents useful in practicing the methods of the invention also include SOMAmers (Slow Off-Rate Modified Aptamers) known in the art to have improved off-rate characteristics. Brody et al., *J Mol Biol.* 422 (5): 595-606 (2012). SOMAmers can be generated using any known method, including the SELEX method.

It is understood by those skilled in the art that biomarkers can be modified prior to analysis to improve their resolution or to determine their identity. For example, the biomarkers can be subject to proteolytic digestion before analysis. Any protease can be used. Proteases, such as trypsin, that are likely to cleave the biomarkers into a discrete number of fragments are particularly useful. The fragments that result from digestion function as a fingerprint for the biomarkers, thereby enabling their detection indirectly. This is particularly useful where there are biomarkers with similar molecular masses that might be confused for the biomarker in question. Also, proteolytic fragmentation is useful for high molecular weight biomarkers because smaller biomarkers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the biomarkers can be modified by the attachment of a tag of particular molecular weight that specifically binds to molecular biomarkers, further distinguishing them. Optionally, after detecting such modified biomarkers, the identity of the biomarkers can be further determined by matching the physical and chemical characteristics of the modified biomarkers in a protein database (e.g., SwissProt).

It is further appreciated in the art that biomarkers in a sample can be captured on a substrate for detection. Traditional substrates include antibody-coated 96-well plates or nitrocellulose membranes that are subsequently probed for the presence of the proteins. Alternatively, protein-binding molecules attached to microspheres, microparticles, microbeads, beads, or other particles can be used for capture and detection of biomarkers. The protein-binding molecules can be antibodies, peptides, peptoids, aptamers, small molecule ligands or other protein-binding capture agents attached to the surface of particles. Each protein-binding molecule can include unique detectable label that is coded such that it can be distinguished from other detectable labels attached to other protein-binding molecules to allow detection of biomarkers in multiplex assays. Examples include, but are not limited to, color-coded microspheres with known fluorescent light intensities (see e.g., microspheres with xMAP technology produced by Luminex (Austin, Tex.); microspheres containing quantum dot nanocrystals, for example, having different ratios and combinations of quantum dot colors (e.g., Qdot nanocrystals produced by Life Technologies (Carlsbad, Calif.); glass coated metal nanoparticles (see e.g., SERS nanotags produced by Nanoplex Technologies, Inc. (Mountain View, Calif.); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., Cy Vera microbeads produced by Illumina (San Diego, Calif.); chemiluminescent dyes, combinations of dye compounds; and beads of detectably different sizes.

In another aspect, biochips can be used for capture and detection of the biomarkers of the invention. Many protein biochips are known in the art. These include, for example, protein biochips produced by Packard BioScience Company (Meriden Conn.), Zyomyx (Hayward, Calif.) and Phylos (Lexington, Mass.). In general, protein biochips comprise a substrate having a surface. A capture reagent or adsorbent is attached to the surface of the substrate. Frequently, the surface comprises a plurality of addressable locations, each of which location has the capture agent bound there. The capture agent can be a biological molecule, such as a polypeptide or a nucleic acid, which captures other biomarkers in a specific manner. Alternatively, the capture agent can be a chromatographic material, such as an anion exchange material or a hydrophilic material. Examples of protein biochips are well known in the art.

Measuring mRNA in a biological sample can be used as a surrogate for detection of the level of the corresponding protein biomarker in a biological sample. Thus, any of the biomarkers or biomarker panels described herein can also be detected by detecting the appropriate RNA. Levels of mRNA can measured by reverse transcription quantitative polymerase chain reaction (RT-PCR followed with qPCR). RT-PCR is used to create a cDNA from the mRNA. The cDNA can be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See *Gene Expression Profiling: Methods and Protocols*, Richard A. Shimkets, editor, Humana Press, 2004.

Some embodiments disclosed herein relate to diagnostic and prognostic methods of determining the probability for preterm birth in a pregnant female. The detection of the level of expression of one or more biomarkers and/or the determination of a ratio of biomarkers can be used to determine the probability for preterm birth in a pregnant female.

Such detection methods can be used, for example, for early diagnosis of the condition, to determine whether a subject is predisposed to preterm birth, to monitor the progress of preterm birth or the progress of treatment protocols, to assess the severity of preterm birth, to forecast the outcome of preterm birth and/or prospects of recovery or birth at full term, or to aid in the determination of a suitable treatment for preterm birth.

The quantitation of biomarkers in a biological sample can be determined, without limitation, by the methods described above as well as any other method known in the art. The quantitative data thus obtained is then subjected to an analytic classification process. In such a process, the raw data is manipulated according to an algorithm, where the algorithm has been pre-defined by a training set of data, for example as described in the examples provided herein. An algorithm can utilize the training set of data provided herein, or can utilize the guidelines provided herein to generate an algorithm with a different set of data.

In some embodiments, analyzing a measurable feature to determine the probability for preterm birth in a pregnant female encompasses the use of a predictive model. In further embodiments, analyzing a measurable feature to determine the probability for preterm birth in a pregnant female encompasses comparing said measurable feature with a reference feature. As those skilled in the art can appreciate, such comparison can be a direct comparison to the reference feature or an indirect comparison where the reference feature has been incorporated into the predictive model. In further embodiments, analyzing a measurable feature to determine the probability for preterm birth in a pregnant female encompasses one or more of a linear discriminant analysis model, a support vector machine classification algorithm, a recursive feature elimination model, a prediction analysis of microarray model, a logistic regression model, a CART algorithm, a flex tree algorithm, a LART algorithm, a random forest algorithm, a MART algorithm, a machine learning algorithm, a penalized regression method, or a combination thereof. In particular embodiments, the analysis comprises logistic regression.

An analytic classification process can use any one of a variety of statistical analytic methods to manipulate the quantitative data and provide for classification of the sample. Examples of useful methods include linear discriminant analysis, recursive feature elimination, a prediction analysis of microarray, a logistic regression, a CART algorithm, a FlexTree algorithm, a LART algorithm, a random forest algorithm, a MART algorithm, machine learning algorithms; etc.

For creation of a random forest for prediction of GAB one skilled in the art can consider a set of k subjects (pregnant women) for whom the gestational age at birth (GAB) is known, and for whom N analytes (transitions) have been measured in a blood specimen taken several weeks prior to birth. A regression tree begins with a root node that contains all the subjects. The average GAB for all subjects can be calculated in the root node. The variance of the GAB within the root node will be high, because there is a mixture of women with different GAB's. The root node is then divided (partitioned) into two branches, so that each branch contains women with a similar GAB. The average GAB for subjects in each branch is again calculated. The variance of the GAB within each branch will be lower than in the root node, because the subset of women within each branch has relatively more similar GAB's than those in the root node. The two branches are created by selecting an analyte and a threshold value for the analyte that creates branches with similar GAB. The analyte and threshold value are chosen from among the set of all analytes and threshold values, usually with a random subset of the analytes at each node. The procedure continues recursively producing branches to create leaves (terminal nodes) in which the subjects have very similar GAB's. The predicted GAB in each terminal node is the average GAB for subjects in that terminal node. This procedure creates a single regression tree. A random forest can consist of several hundred or several thousand such trees.

Classification can be made according to predictive modeling methods that set a threshold for determining the probability that a sample belongs to a given class. The probability preferably is at least 50%, or at least 60%, or at least 70%, or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. AUROC (area under the ROC curve) or accuracy, of a particular value, or range of values. Area under the curve measures are useful for comparing the accuracy of a classifier across the complete data range. Classifiers with a greater AUC have a greater capacity to classify unknowns correctly between two groups of interest. In some embodiments, a desired quality threshold is a predictive model that will classify a sample with an accuracy of at least about 0.5, at least about 0.55, at least about 0.6, at least about 0.7, at least about 0.75, at least about 0.8, at least about 0.85, at least about 0.9, at least about 0.95, or higher. As an alternative measure, a desired quality threshold can refer to a predictive model that will classify a sample with an AUC of at least about 0.7, at least about 0.75, at least about 0.8, at least about 0.85, at least about 0.9, or higher.

As is known in the art, the relative sensitivity and specificity of a predictive model can be adjusted to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about 0.7, at least about 0.75, at least about 0.8, at least about 0.85, at least about 0.9, or higher.

The raw data can be initially analyzed by measuring the values for each biomarker, usually in triplicate or in multiple triplicates. The data can be manipulated, for example, raw data can be transformed using standard curves, and the average of triplicate measurements used to calculate the average and standard deviation for each patient. These values can be transformed before being used in the models, e.g. log-transformed, Box-Cox transformed (Box and Cox, *Royal Stat. Soc.*, Series B, 26:211-246 (1964). The data are then input into a predictive model, which will classify the sample according to the state. The resulting information can be communicated to a patient or health care provider.

To generate a predictive model for preterm birth, a robust data set, comprising known control samples and samples corresponding to the preterm birth classification of interest is used in a training set. A sample size can be selected using generally accepted criteria. As discussed above, different statistical methods can be used to obtain a highly accurate predictive model. Examples of such analysis are provided in Example 2.

In one embodiment, hierarchical clustering is performed in the derivation of a predictive model, where the Pearson correlation is employed as the clustering metric. One approach is to consider a preterm birth dataset as a "learning sample" in a problem of "supervised learning." CART is a standard in applications to medicine (Singer, Recursive Partitioning in the Health Sciences, Springer (1999)) and can be modified by transforming any qualitative features to quantitative features; sorting them by attained significance levels, evaluated by sample reuse methods for Hotelling's T2 statistic; and suitable application of the lasso method. Problems in prediction are turned into problems in regression without losing sight of prediction, indeed by making suitable use of the Gini criterion for classification in evaluating the quality of regressions.

This approach led to what is termed FlexTree (Huang, *Proc. Nat. Acad. Sci. U.S.A* 101:10529-10534 (2004)). FlexTree performs very well in simulations and when applied to multiple forms of data and is useful for practicing the claimed methods. Software automating FlexTree has been developed. Alternatively, LARTree or LART can be used (Turnbull (2005) *Classification Trees with Subset Analysis Selection by the Lasso*, Stanford University). The name reflects binary trees, as in CART and FlexTree; the lasso, as has been noted; and the implementation of the lasso through what is termed LARS by Efron et al. (2004) *Annals of Statistics* 32:407-451 (2004). See, also, Huang et al., *Proc. Natl. Acad. Sci. USA.* 101 (29): 10529-34 (2004). Other methods of analysis that can be used include logic regression. One method of logic regression Ruczinski, *Journal of Computational and Graphical Statistics* 12:475-512 (2003). Logic regression resembles CART in that its classifier can be displayed as a binary tree. It is different in that each node has Boolean statements about features that are more general than the simple "and" statements produced by CART.

Another approach is that of nearest shrunken centroids (Tibshirani, *Proc. Natl. Acad. Sci. U.S.A* 99:6567-72 (2002)). The technology is k-means-like, but has the advantage that by shrinking cluster centers, one automatically selects features, as is the case in the lasso, to focus attention on small numbers of those that are informative. The approach is available as PAM software and is widely used. Two further sets of algorithms that can be used are random forests (Breiman, *Machine Learning* 45:5-32 (2001)) and MART (Hastie, *The Elements of Statistical Learning*, Springer (2001)). These two methods are known in the art as "committee methods," that involve predictors that "vote" on outcome.

To provide significance ordering, the false discovery rate (FDR) can be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (Tusher et al., *Proc. Natl. Acad. Sci. U.S.A* 98, 5116-21 (2001)). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value can be applied to the correlations between experimental profiles. Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pair wise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

In an alternative analytical approach, variables chosen in the cross-sectional analysis are separately employed as predictors in a time-to-event analysis (survival analysis), where the event is the occurrence of preterm birth, and subjects with no event are considered censored at the time of giving birth. Given the specific pregnancy outcome (preterm birth event or no event), the random lengths of time each patient will be observed, and selection of proteomic and other features, a parametric approach to analyzing survival can be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and corresponding functions are available with this model.

In addition the Cox models can be used, especially since reductions of numbers of covariates to manageable size with the lasso will significantly simplify the analysis, allowing the possibility of a nonparametric or semi-parametric approach to prediction of time to preterm birth. These statistical tools are known in the art and applicable to all manner of proteomic data. A set of biomarker, clinical and genetic data that can be easily determined, and that is highly informative regarding the probability for preterm birth and predicted time to a preterm birth event in said pregnant female is provided. Also, algorithms provide information regarding the probability for preterm birth in the pregnant female.

Accordingly, one skilled in the art understands that the probability for preterm birth according to the invention can be determined using either a quantitative or a categorical variable. For example, in practicing the methods of the invention the measurable feature of each of N biomarkers can be subjected to categorical data analysis to determine the probability for preterm birth as a binary categorical outcome. Alternatively, the methods of the invention may analyze the measurable feature of each of N biomarkers by initially calculating quantitative variables, in particular, predicted gestational age at birth. The predicted gestational age at birth can subsequently be used as a basis to predict risk of preterm birth. By initially using a quantitative variable and subsequently converting the quantitative variable into a categorical variable the methods of the invention take into account the continuum of measurements detected for the measurable features. For example, by predicting the gestational age at birth rather than making a binary prediction of preterm birth versus term birth, it is possible to tailor the treatment for the pregnant female. For example, an earlier predicted gestational age at birth will result in more intensive prenatal intervention, i.e. monitoring and treatment, than a predicted gestational age that approaches full term.

Among women with a predicted GAB of j days plus or minus k days, p (PTB) can be estimated as the proportion of women in the PAPR clinical trial (see Example 1) with a predicted GAB of j days plus or minus k days who actually deliver before 37 weeks gestational age. More generally, for women with a predicted GAB of j days plus or minus k days, the probability that the actual gestational age at birth will be less than a specified gestational age, p (actual GAB<specified GAB), was estimated as the proportion of women in the PAPR clinical trial with a predicted GAB of j days plus or minus k days who actually deliver before the specified gestational age.

In the development of a predictive model, it can be desirable to select a subset of markers, i.e. at least 3, at least 4, at least 5, at least 6, up to the complete set of markers. Usually a subset of markers will be chosen that provides for the needs of the quantitative sample analysis, e.g. availability of reagents, convenience of quantitation, etc., while maintaining a highly accurate predictive model. The selection of a number of informative markers for building classification models requires the definition of a performance metric and a user-defined threshold for producing a model with useful predictive ability based on this metric. For example, the performance metric can be the AUC, the sensitivity and/or specificity of the prediction as well as the overall accuracy of the prediction model.

As will be understood by those skilled in the art, an analytic classification process can use any one of a variety of statistical analytic methods to manipulate the quantitative data and provide for classification of the sample. Examples of useful methods include, without limitation, linear discriminant analysis, recursive feature elimination, a prediction analysis of microarray, a logistic regression, a CART algorithm, a FlexTree algorithm, a LART algorithm, a random forest algorithm, a MART algorithm, and machine learning algorithms.

As described in Example 2, various methods are used in a training model. The selection of a subset of markers can be for a forward selection or a backward selection of a marker subset. The number of markers can be selected that will optimize the performance of a model without the use of all the markers. One way to define the optimum number of terms is to choose the number of terms that produce a model with desired predictive ability (e.g. an AUC>0.75, or equivalent measures of sensitivity/specificity) that lies no more than one standard error from the maximum value obtained for this metric using any combination and number of terms used for the given algorithm.

TABLE 1

| Transitions with p-values less than 0.05 in univariate Cox Proportional Hazards analyses to predict Gestational Age at Birth | | | |
| --- | --- | --- | --- |
| Transition | Peptide disclosed in adjacemt column | Protein | p-value Cox uni-variate |
| ITLPDFTGDLR_624.34_920.4 | (SEQ ID NO: 3) | LBP_HUMAN | 0.006 |
| ELLESYIDGR_597.8_710.3 | (SEQ ID NO: 2) | THRB_HUMAN | 0.006 |

TABLE 1-continued

Transitions with p-values less than 0.05 in
univariate Cox Proportional Hazards
analyses to predict Gestational Age at Birth

| Transition | Peptide disclosed in adjacemt column | Protein | p-value Cox univariate |
|---|---|---|---|
| TDAPDLPEENQAR_728.34_613.3 | (SEQ ID NO: 17) | CO5_HUMAN | 0.007 |
| AFTECCVVASQLR_770.87_574.3 | (SEQ ID NO: 1) | CO5_HUMAN | 0.009 |
| SFRPFVPR_335.86_272.2 | (SEQ ID NO: 18) | LBP_HUMAN | 0.011 |
| ITLPDFTGDLR_624.34_288.2 | (SEQ ID NO: 3) | LBP_HUMAN | 0.012 |
| SFRPFVPR_335.86_635.3 | (SEQ ID NO: 18) | LBP_HUMAN | 0.015 |
| ELLESYIDGR_597.8_839.4 | (SEQ ID NO: 2) | THRB_HUMAN | 0.018 |
| LEQGENVFLQATDK_796.4_822.4 | (SEQ ID NO: 19) | C1QB_HUMAN | 0.019 |
| ETAASLLQAGYK_626.33_679.4 | (SEQ ID NO: 20) | THRB_HUMAN | 0.021 |
| VTGWGNLK_437.74_617.3 | (SEQ ID NO: 21) | THRB_HUMAN | 0.021 |
| EAQLPVIENK_570.82_699.4 | (SEQ ID NO: 22) | PLMN_HUMAN | 0.023 |
| EAQLPVIENK_570.82_329.1 | (SEQ ID NO: 22) | PLMN_HUMAN | 0.023 |
| FLQEQGHR_338.84_497.3 | (SEQ ID NO: 23) | CO8G_HUMAN | 0.025 |
| IRPFFPQQ_516.79_661.4 | (SEQ ID NO: 24) | FIBB_HUMAN | 0.028 |
| ETAASLLQAGYK_626.33_879.5 | (SEQ ID NO: 20) | THRB_HUMAN | 0.029 |
| AFTECCVVASQLR_770.87_673.4 | (SEQ ID NO: 1) | CO5_HUMAN | 0.030 |
| TLLPVSKPEIR_418.26_288.2 | (SEQ ID NO: 25) | CO5_HUMAN | 0.030 |
| LSSPAVITDK_515.79_743.4 | (SEQ ID NO: 26) | PLMN_HUMAN | 0.033 |
| YEVQGEVFTKPQLWP_910.96_392.2 | (SEQ ID NO: 27) | CRP_HUMAN | 0.036 |
| LQGTLPVEAR_542.31_571.3 | (SEQ ID NO: 28) | CO5_HUMAN | 0.036 |
| VRPQQLVK_484.31_609.3 | (SEQ ID NO: 29) | ITIH4_HUMAN | 0.036 |
| IEEIAAK_387.22_531.3 | (SEQ ID NO: 30) | CO5_HUMAN | 0.041 |
| TLLPVSKPEIR_418.26_514.3 | (SEQ ID NO: 25) | CO5_HUMAN | 0.042 |
| VQEAHLTEDQI-FYFPK_655.66_701.4 | (SEQ ID NO: 31) | CO8G_HUMAN | 0.047 |
| ISLLLIESWLEPVR_834.49_371.2 | (SEQ ID NO: 32) | CSH_HUMAN | 0.048 |
| ALQDQLVLVAAK_634.88_289.2 | (SEQ ID NO: 33) | ANGT_HUMAN | 0.048 |
| YEFLNGR_449.72_293.1 | (SEQ ID NO: 34) | PLMN_HUMAN | 0.049 |

TABLE 2

Transitions selected by the Cox stepwise AIC analysis

| Transition | Peptide disclosed in adjacemt column | coef | exp(coef) | se(coef) | z | Pr(>\|z\|) |
|---|---|---|---|---|---|---|
| Collection.Window.GA.in.Days | | 1.28E-01 | 1.14E+00 | 2.44E-02 | 5.26 | 1.40E-07 |
| ITLPDFTGDLR_624.34_920.4 | (SEQ ID NO: 3) | 2.02E+00 | 7.52E+00 | 1.14E+00 | 1.77 | 0.07667 |

TABLE 2-continued

Transitions selected by the Cox stepwise AIC analysis

| Transition | Peptide disclosed in adjacemt column | coef | exp(coef) | se(coef) | z | Pr(>\|z\|) |
|---|---|---|---|---|---|---|
| TPSAAYLWVGTGASEAEK_919.45_849.4 | (SEQ ID NO: 35) | 2.85E+01 | 2.44E+12 | 3.06E+00 | 9.31 | <2e-16 |
| TATSEYQTFFNPR_781.37_386.2 | (SEQ ID NO: 36) | 5.14E+00 | 1.70E+02 | 6.26E-01 | 8.21 | 2.20E-16 |
| TASDFITK_441.73_781.4 | (SEQ ID NO: 37) | -1.25E+00 | 2.86E-01 | 1.58E+00 | -0.79 | 0.42856 |
| IITGLLEFEVYLEYLQNR_738.4_530.3 | (SEQ ID NO: 38) | 1.30E+01 | 4.49E+05 | 1.45E+00 | 9 | <2e-16 |
| IIGGSDADIK_494.77_762.4 | (SEQ ID NO: 39) | -6.43E+01 | 1.16E-28 | 6.64E+00 | -9.68 | <2e-16 |
| YTTEIIK_434.25_603.4 | (SEQ ID NO: 40) | 6.96E+01 | 1.75E+30 | 7.06E+00 | 9.86 | <2e-16 |
| EDTPNSVWEPAK_686.82_315.2 | (SEQ ID NO: 41) | 7.91E+00 | 2.73E+03 | 2.66E+00 | 2.98 | 0.00293 |
| LYYGDDEK_501.72_726.3 | (SEQ ID NO: 42) | 8.74E+00 | 6.23E+03 | 1.57E+00 | 5.57 | 2.50E-08 |
| VRPQQLVK_484.31_609.3 | (SEQ ID NO: 29) | 4.64E+01 | 1.36E+20 | 3.97E+00 | 11.66 | <2e-16 |
| GGEIEGFR_432.71_379.2 | (SEQ ID NO: 43) | -3.33E+00 | 3.57E-02 | 2.19E+00 | -1.52 | 0.12792 |
| DGSPDVTTADIGANTPDATK_973.45_844.4 | (SEQ ID NO: 44) | -1.52E+01 | 2.51E-07 | 1.41E+00 | -10.8 | <2e-16 |
| VQEAHLTEDQIFYFPK_655.66_391.2 | (SEQ ID NO: 31) | -2.02E+01 | 1.77E-09 | 2.45E+00 | -8.22 | 2.20E-16 |
| VEIDTK_352.7_476.3 | (SEQ ID NO: 45) | 7.06E+00 | 1.17E+03 | 1.45E+00 | 4.86 | 1.20E-06 |
| AVLTIDEK_444.76_605.3 | (SEQ ID NO: 46) | 7.85E+00 | 2.56E+03 | 9.46E-01 | 8.29 | <2e-16 |
| FSVVYAK_407.23_579.4 | (SEQ ID NO: 47) | -2.44E+01 | 2.42E-11 | 3.08E+00 | -7.93 | 2.20E-15 |
| YYLQGAK_421.72_516.3 | (SEQ ID NO: 48) | -1.82E+01 | 1.22E-08 | 2.45E+00 | -7.44 | 1.00E-13 |
| EENFYVDETTVVK_786.88_259.1 | (SEQ ID NO: 49) | -1.90E+01 | 5.36E-09 | 2.71E+00 | -7.03 | 2.00E-12 |
| YGFYTHVFR_397.2_421.3 | (SEQ ID NO: 50) | 1.90E+01 | 1.71E+08 | 2.73E+00 | 6.93 | 4.20E-12 |
| HTLNQIDEVK_598.82_951.5 | (SEQ ID NO: 51) | 1.03E+01 | 3.04E+04 | 2.11E+00 | 4.89 | 9.90E-07 |
| AFIQLWAFDAVK_704.89_836.4 | (SEQ ID NO: 52) | 1.08E+01 | 4.72E+04 | 2.59E+00 | 4.16 | 3.20E-05 |
| SGFSFGFK_438.72_585.3 | (SEQ ID NO: 53) | 1.35E+01 | 7.32E+05 | 2.56E+00 | 5.27 | 1.40E-07 |
| GWVTDGFSSLK_598.8_854.4 | (SEQ ID NO: 54) | -3.12E+00 | 4.42E-02 | 9.16E-01 | -3.4 | 0.00066 |
| ITENDIQIALDDAK_779.9_632.3 | (SEQ ID NO: 55) | 1.91E+00 | 6.78E+00 | 1.36E+00 | 1.4 | 0.16036 |

TABLE 3

Transitions selected by Cox lasso model

| Transition | Peptide disclosed in adjacemt column | coef | exp(coef) | se(coef) | z | Pr(>\|z\|) |
|---|---|---|---|---|---|---|
| Collection.Window.GA.in.Days | | 0.0233 | 1.02357 | 0.00928 | 2.51 | 0.012 |
| AFTECCVVASQLR_770.87_574.3 | (SEQ ID NO: 1) | 1.07568 | 2.93198 | 0.84554 | 1.27 | 0.203 |
| ELLESYIDGR_597.8_710.3 | (SEQ ID NO: 2) | 1.3847 | 3.99365 | 0.70784 | 1.96 | 0.05 |
| ITLPDFTGDLR_624.34_920.4 | (SEQ ID NO: 3) | 0.814 | 2.25691 | 0.40652 | 2 | 0.045 |

TABLE 4

Area under the ROC (AUROC) curve for individual
analytes to discriminate pre-term birth subjects
from non-pre-term birth subjects. The 77
transitions with the highest AUROC area are shown.

| Transition | Peptide disclosed in adjacemt column | AUROC |
|---|---|---|
| ELLESYIDGR_597.8_710.3 | (SEQ ID NO: 2) | 0.71 |
| AFTECCVVASQLR_770.87_574.3 | (SEQ ID NO: 1) | 0.70 |
| ITLPDFTGDLR_624.34_920.4 | (SEQ ID NO: 3) | 0.70 |
| IRPFFPQQ_516.79_661.4 | (SEQ ID NO: 24) | 0.68 |
| TDAPDLPEENQAR_728.34_613.3 | (SEQ ID NO: 17) | 0.67 |
| ITLPDFTGDLR_624.34_288.2 | (SEQ ID NO: 3) | 0.67 |
| ELLESYIDGR_597.8_839.4 | (SEQ ID NO: 2) | 0.67 |
| SFRPFVPR_335.86_635.3 | (SEQ ID NO: 18) | 0.67 |
| ETAASLLQAGYK_626.33_879.5 | (SEQ ID NO: 20) | 0.67 |
| TLLPVSKPEIR_418.26_288.2 | (SEQ ID NO: 25) | 0.66 |
| ETAASLLQAGYK_626.33_679.4 | (SEQ ID NO: 20) | 0.66 |
| SFRPFVPR_335.86_272.2 | (SEQ ID NO: 18) | 0.66 |
| LQGTLPVEAR_542.31_571.3 | (SEQ ID NO: 28) | 0.66 |
| VEPLYELVTATDFAYSSTVR_754.38_712.4 | (SEQ ID NO: 56) | 0.66 |
| DPDQTDGLGLSYLSSHIANVER_796.39_328.1 | (SEQ ID NO: 57) | 0.66 |
| VTGWGNLK_437.74_617.3 | (SEQ ID NO: 21) | 0.65 |
| ALQDQLVLVAAK_634.88_289.2 | (SEQ ID NO: 33) | 0.65 |
| EAQLPVIENK_570.82_329.1 | (SEQ ID NO: 22) | 0.65 |
| VRPQQLVK_484.31_609.3 | (SEQ ID NO: 29) | 0.65 |
| AFTECCVVASQLR_770.87_673.4 | (SEQ ID NO: 1) | 0.65 |
| YEFLNGR_449.72_293.1 | (SEQ ID NO: 34) | 0.65 |
| VGEYSLYIGR_578.8_871.5 | (SEQ ID NO: 58) | 0.64 |
| EAQLPVIENK_570.82_699.4 | (SEQ ID NO: 22) | 0.64 |
| TLLPVSKPEIR_418.26_514.3 | (SEQ ID NO: 25) | 0.64 |
| IEEIAAK_387.22_531.3 | (SEQ ID NO: 30) | 0.64 |
| LEQGENVFLQATDK_796.4_822.4 | (SEQ ID NO: 19) | 0.64 |
| LQGTLPVEAR_542.31_842.5 | (SEQ ID NO: 28) | 0.64 |
| FLQEQGHR_338.84_497.3 | (SEQ ID NO: 23) | 0.63 |
| ISLLLIESWLEPVR_834.49_371.2 | (SEQ ID NO: 32) | 0.63 |
| IITGLLEFEVYLEYLQNR_738.4_530.3 | (SEQ ID NO: 38) | 0.63 |
| LSSPAVITDK_515.79_743.4 | (SEQ ID NO: 26) | 0.63 |
| VRPQQLVK_484.31_722.4 | (SEQ ID NO: 29) | 0.63 |
| SLPVSDSVLSGFEQR_810.92_723.3 | (SEQ ID NO: 59) | 0.63 |
| VQEAHLTEDQIFYFPK_655.66_701.4 | (SEQ ID NO: 31) | 0.63 |
| NADYSYSVWK_616.78_333.2 | (SEQ ID NO: 60) | 0.63 |

TABLE 4-continued

Area under the ROC (AUROC) curve for individual
analytes to discriminate pre-term birth subjects
from non-pre-term birth subjects. The 77
transitions with the highest AUROC area are shown.

| Transition | Peptide disclosed in adjacemt column | AUROC |
|---|---|---|
| DAQYAPGYDK_564.25_813.4 | (SEQ ID NO: 61) | 0.62 |
| FQLPGQK_409.23_276.1 | (SEQ ID NO: 62) | 0.62 |
| TASDFITK_441.73_781.4 | (SEQ ID NO: 37) | 0.62 |
| YGLVTYATYPK_638.33_334.2 | (SEQ ID NO: 63) | 0.62 |
| GSFALSFPVESDVAPIAR_931.99_363.2 | (SEQ ID NO: 64) | 0.62 |
| TLLIANETLR_572.34_703.4 | (SEQ ID NO: 65) | 0.62 |
| VILGAHQEVNLEPHVQEIEVSR_832.78_860.4 | (SEQ ID NO: 66) | 0.62 |
| TATSEYQTFFNPR_781.37_386.2 | (SEQ ID NO: 36) | 0.62 |
| YEVQGEVFTKPQLWP_910.96_392.2 | (SEQ ID NO: 27) | 0.62 |
| DISEVVTPR_508.27_472.3 | (SEQ ID NO: 67) | 0.62 |
| GSFALSFPVESDVAPIAR_931.99_456.3 | (SEQ ID NO: 64) | 0.62 |
| YGFYTHVFR_397.2_421.3 | (SEQ ID NO: 50) | 0.62 |
| TLEAQLTPR_514.79_685.4 | (SEQ ID NO: 68) | 0.62 |
| YGFYTHVFR_397.2_659.4 | (SEQ ID NO: 50) | 0.62 |
| AVGYLITGYQR_620.84_737.4 | (SEQ ID NO: 69) | 0.61 |
| DPDQTDGLGLSYLSSHIANVER_796.39_456.2 | (SEQ ID NO: 57) | 0.61 |
| FNAVLTNPQGDYDTSTGK_964.46_262.1 | (SEQ ID NO: 70) | 0.61 |
| SPEQQETVLDGNLIIR_906.48_685.4 | (SEQ ID NO: 71) | 0.61 |
| ALNHLPLEYNSALYSR_620.99_538.3 | (SEQ ID NO: 72) | 0.61 |
| GGEIEGFR_432.71_508.3 | (SEQ ID NO: 43) | 0.61 |
| GIVEECCFR_585.26_900.3 | (SEQ ID NO: 74) | 0.61 |
| DAQYAPGYDK_564.25_315.1 | (SEQ ID NO: 61) | 0.61 |
| FAFNLYR_465.75_712.4 | (SEQ ID NO: 75) | 0.61 |
| YTTEIIK_434.25_603.4 | (SEQ ID NO: 40) | 0.61 |
| AVLTIDEK_444.76_605.3 | (SEQ ID NO: 46) | 0.61 |
| AITPPHPASQANIIFDITEGNLR_825.77_459.3 | (SEQ ID NO: 76) | 0.60 |
| EPGLCTWQSLR_673.83_790.4 | (SEQ ID NO: 77) | 0.60 |
| AVYEAVLR_460.76_587.4 | (SEQ ID NO: 78) | 0.60 |
| ALQDQLVLVAAK_634.88_956.6 | (SEQ ID NO: 33) | 0.60 |
| AWVAWR_394.71_531.3 | (SEQ ID NO: 79) | 0.60 |
| TNLESILSYPK_632.84_807.5 | (SEQ ID NO: 80) | 0.60 |
| HLSLLTTLSNR_418.91_376.2 | (SEQ ID NO: 81) | 0.60 |
| FTFTLHLETPKPSISSSNLNPR_829.44_787.4 | (SEQ ID NO: 82) | 0.60 |
| AVGYLITGYQR_620.84_523.3 | (SEQ ID NO: 69) | 0.60 |

TABLE 4-continued

Area under the ROC (AUROC) curve for individual
analytes to discriminate pre-term birth subjects
from non-pre-term birth subjects. The 77
transitions with the highest AUROC area are shown.

| Transition | Peptide disclosed in adjacemt column | AUROC |
|---|---|---|
| FQLPGQK_409.23_429.2 | (SEQ ID NO: 62) | 0.60 |
| YGLVTYATYPK_638.33_843.4 | (SEQ ID NO: 63) | 0.60 |
| TELRPGETLNVNFLLR_624.68_662.4 | (SEQ ID NO: 83) | 0.60 |
| LSSPAVITDK_515.79_830.5 | (SEQ ID NO: 26) | 0.60 |
| TATSEYQTFFNPR_781.37_272.2 | (SEQ ID NO: 36) | 0.60 |
| LPTAVVPLR_483.31_385.3 | (SEQ ID NO: 84) | 0.60 |
| APLTKPLK_289.86_260.2 | (SEQ ID NO: 85) | 0.60 |

TABLE 5

AUROCs for random forest, boosting, lasso,
and logistic regression models for a specific
number of transitions permitted in the model,
as estimated by 100 rounds of bootstrap
resampling.

| Number of transitions | rf | boosting | logit | lasso |
|---|---|---|---|---|
| 1 | 0.59 | 0.67 | 0.64 | 0.69 |
| 2 | 0.66 | 0.70 | 0.63 | 0.68 |
| 3 | 0.69 | 0.70 | 0.58 | 0.71 |
| 4 | 0.68 | 0.72 | 0.58 | 0.71 |
| 5 | 0.73 | 0.71 | 0.58 | 0.68 |
| 6 | 0.72 | 0.72 | 0.56 | 0.68 |
| 7 | 0.74 | 0.70 | 0.60 | 0.67 |
| 8 | 0.73 | 0.72 | 0.62 | 0.67 |

TABLE 5-continued

AUROCs for random forest, boosting, lasso,
and logistic regression models for a specific
number of transitions permitted in the model,
as estimated by 100 rounds of bootstrap
resampling.

| Number of transitions | rf | boosting | logit | lasso |
|---|---|---|---|---|
| 9 | 0.72 | 0.72 | 0.60 | 0.67 |
| 10 | 0.74 | 0.71 | 0.62 | 0.66 |
| 11 | 0.73 | 0.69 | 0.58 | 0.67 |
| 12 | 0.73 | 0.69 | 0.59 | 0.66 |
| 13 | 0.74 | 0.71 | 0.57 | 0.66 |
| 14 | 0.73 | 0.70 | 0.57 | 0.65 |
| 15 | 0.72 | 0.70 | 0.55 | 0.64 |

TABLE 6

Top 15 transitions selected by each multivariate method, ranked by
importance for that method.

| | rf | Peptide disclosed in adjacent column | boosting | Peptide disclosed in adjacent column |
|---|---|---|---|---|
| 1 | ELLESYIDGR_597.8_710.3 | 2 | AFTECCVVASQLR_770.87_574.3 | 1 |
| 2 | TATSEYQTFFNPR_781.37_386.2 | 36 | DPDQTDGLGLSYLSSHIANVER_796.39_328.1 | 57 |
| 3 | ITLPDFTGDLR_624.34_920.4 | 3 | ELLESYIDGR_597.8_710.3 | 2 |
| 4 | AFTECCVVASQLR_770.87_574.3 | 1 | TATSEYQTFFNPR_781.37_386.2 | 36 |
| 5 | VEPLYELVTATDFAYSSTVR_754.38_712.4 | 56 | ITLPDFTGDLR_624.34_920.4 | 3 |
| 6 | GSFALSFPVESDVAPIAR_931.99_363.2 | 64 | GGEIEGFR_432.71_379.2 | 43 |
| 7 | VGEYSLYIGR_578.8_871.5 | 58 | ALQDQLVLVAAK_634.88_289.2 | 33 |
| 8 | SFRPFVPR_335.86_635.3 | 18 | VGEYSLYIGR_578.8_871.5 | 58 |
| 9 | ALQDQLVLVAAK_634.88_289.2 | 33 | VEPLYELVTATDFAYSSTVR_754.38_712.4 | 56 |
| 10 | EDTPNSVWEPAK_686.82_315.2 | 41 | SPEQQETVLDGNLIIR_906.48_685.4 | 71 |

TABLE 6-continued

Top 15 transitions selected by each multivariate method, ranked by
importance for that method.

| 11 | YGFYTHVFR_397.2_421.3 | 50 | YEFLNGR_449.72_293.1 | 34 |
| 12 | DPDQTDGLGLSYLSSHIANVER_796.39_328.1 | 57 | LEQGENVFLQATDK_796.4_822.4 | 19 |
| 13 | LEQGENVFLQATDK_796.4_822.4 | 19 | LQGTLPVEAR_542.31_571.3 | 28 |
| 14 | LQGTLPVEAR_542.31_571.3 | 28 | ISLLLIESWLEPVR_834.49_371.2 | 32 |
| 15 | SFRPFVPR_335.86_272.2 | 18 | TASDFITK_441.73_781.4 | 37 |

| | lasso | Peptide disclosed in adjacent column | logit | Peptide disclosed in adjacent column |
|---|---|---|---|---|
| 1 | AFTECCVVASQLR_770.87_574.3 | 1 | ALQDQLVLVAAK_634.88_289.2 | 33 |
| 2 | ISLLLIESWLEPVR_834.49_371.2 | 32 | AVLTIDEK_444.76_605.3 | 46 |
| 3 | LPTAVVPLR_483.31_385.3 | 84 | Collection.Window.GA.in.Days | |
| 4 | ALQDQLVLVAAK_634.88_289.2 | 33 | AHYDLR_387.7_566.3 | 88 |
| 5 | ETAASLLQAGYK_626.33_679.4 | 20 | AEAQAQYSAAVAK_654.33_908.5 | 89 |
| 6 | IITGLLEFEVYLEYLQNR_738.4_530.3 | 38 | AEAQAQYSAAVAK_654.33_709.4 | 89 |
| 7 | ADSQAQLLLSTVVGVFTAPGLHLK_822.46_983.6 | 86 | ADSQAQLLLSTVVGVFTAPGLHLK_822.46_983.6 | 86 |
| 8 | SLPVSDSVLSGFEQR_810.92_723.3 | 59 | AITPPHPASQANIIFDITEGNLR_825.77_459.3 | 76 |
| 9 | SFRPFVPR_335.86_272.2 | 18 | ADSQAQLLLSTVVGVFTAPGLHLK_822.46_664.4 | 86 |
| 10 | IIGGSDADIK_494.77_260.2 | 39 | AYSDLSR_406.2_375.2 | 90 |
| 11 | NADYSYSVWK_616.78_333.2 | 60 | DALSSVQESQVAQQAR_572.96_672.4 | 91 |
| 12 | GSFALSFPVESDVAPIAR_931.99_456.3 | 64 | ANRPFLVFIR_411.58_435.3 | 92 |
| 13 | LSSPAVITDK_515.79_743.4 | 26 | DALSSVQESQVAQQAR_572.96_502.3 | 91 |
| 14 | ELPEHTVK_476.76_347.2 | 87 | ALEQDLPVNIK_620.35_570.4 | 93 |
| 15 | EAQLPVIENK_570.82_699.4 | 22 | AVLTIDEK_444.76_718.4 | 46 |

In yet another aspect, the invention provides kits for determining probability of preterm birth, wherein the kits can be used to detect N of the isolated biomarkers listed in Tables 1 through 63. For example, the kits can be used to detect one or more, two or more, or three of the isolated biomarkers selected from the group consisting of AFTECCVVASQLR (SEQ ID NO: 1), ELLESYIDGR (SEQ ID NO: 2), and ITLPDFTGDLR (SEQ ID NO: 3). For example, the kits can be used to detect one or more, two or more, or three of the isolated biomarkers selected from the group consisting of FLNWIK (SEQ ID NO: 4), FGFGG-STDSGPIR (SEQ ID NO: 5), LLELTGPK (SEQ ID NO: 6), VEHSDLSFSK (SEQ ID NO: 7), IEGNLIFDPNNYLPK (SEQ ID NO: 8), ALVLELAK (SEQ ID NO: 9), TQILE-WAAER (SEQ ID NO: 10), DVLLL-VHNLPQNLPGYFWYK (SEQ ID NO: 11), SEP-RPGVLLR (SEQ ID NO: 12), ITQDAQLK (SEQ ID NO: 13), ALDLSLK (SEQ ID NO: 14), WWGGQPLWITATK (SEQ ID NO: 15), and LSETNR (SEQ ID NO: 16).

In another aspect, the kits can be used to detect one or more, two or more, three or more, four or more, five or more, six or more, seven or more, or eight of the isolated bio-markers selected from the group consisting of lipopolysac-charide-binding protein (LBP), prothrombin (THRB), complement component C5 (C5 or CO5), plasminogen (PLMN), and complement component C8 gamma chain (C8G or CO8G).

In another aspect, the kits can be used to detect one or more, two or more, three or more, four or more, five or more, six or more, seven or more, or eight of the isolated bio-markers selected from the group consisting of Alpha-1B-glycoprotein (A1BG), Disintegrin and metalloproteinase domain-containing protein 12 (ADA12), Apolipoprotein B-100 (APOB), Beta-2-microglobulin (B2MG), CCAAT/enhancer-binding protein alpha/beta (HP8 Peptide), Corti-costeroid-binding globulin (CBG), Complement component C6, Endoglin (EGLN), Ectonucleotide pyrophosphatase/phosphodiesterase family member 2 (ENPP2), Coagulation factor VII (FA7), Hyaluronan-binding protein 2 (HABP2), Pregnancy-specific beta-1-glycoprotein 9 (PSG9), Inhibin beta E chain (INHBE).

The kit can include one or more agents for detection of biomarkers, a container for holding a biological sample isolated from a pregnant female; and printed instructions for reacting agents with the biological sample or a portion of the biological sample to detect the presence or amount of the isolated biomarkers in the biological sample. The agents can be packaged in separate containers. The kit can further comprise one or more control reference samples and reagents for performing an immunoassay.

In one embodiment, the kit comprises agents for measuring the levels of at least N of the isolated biomarkers listed in Tables 1 through 63. The kit can include antibodies that specifically bind to these biomarkers, for example, the kit can contain at least one of an antibody that specifically binds to lipopolysaccharide-binding protein (LBP), an antibody that specifically binds to prothrombin (THRB), an antibody that specifically binds to complement component C5 (C5 or CO5), an antibody that specifically binds to plasminogen (PLMN), and an antibody that specifically binds to complement component C8 gamma chain (C8G or CO8G).

In one embodiment, the kit comprises agents for measuring the levels of at least N of the isolated biomarkers listed in Tables 1 through 63. The kit can include antibodies that specifically bind to these biomarkers, for example, the kit can contain at least one of an antibody that specifically binds to Alpha-1B-glycoprotein (A1BG), Disintegrin and metalloproteinase domain-containing protein 12 (ADA12), Apolipoprotein B-100 (APOB), Beta-2-microglobulin (B2MG), CCAAT/enhancer-binding protein alpha/beta (HP8 Peptide), Corticosteroid-binding globulin (CBG), Complement component C6, Endoglin (EGLN), Ectonucleotide pyrophosphatase/phosphodiesterase family member 2 (ENPP2), Coagulation factor VII (FA7), Hyaluronan-binding protein 2 (HABP2), Pregnancy-specific beta-1-glycoprotein 9 (PSG9), Inhibin beta E chain (INHBE).

The kit can comprise one or more containers for compositions contained in the kit. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for methods of determining probability of preterm birth.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

EXAMPLES

Example 1. Development of Sample Set for Discovery and Validation of Biomarkers for Preterm Birth A standard protocol was developed governing conduct of the Proteomic Assessment of Preterm Risk (PAPR) clinical study. This protocol also specified that the samples and clinical information could be used to study other pregnancy complications for some of the subjects. Specimens were obtained from women at 11 Internal Review Board (IRB)

approved sites across the United States. After providing informed consent, serum and plasma samples were obtained, as well as pertinent information regarding the patient's demographic characteristics, past medical and pregnancy history, current pregnancy history and concurrent medications. Following delivery, data were collected relating to maternal and infant conditions and complications. Serum and plasma samples were processed according to a protocol that requires standardized refrigerated centrifugation, aliquoting of the samples into 0.5 ml 2-D bar-coded cryovials and subsequent freezing at −80° C.

Following delivery, preterm birth cases were individually reviewed to determine their status as either a spontaneous preterm birth or a medically indicated preterm birth. Only spontaneous preterm birth cases were used for this analysis. For discovery of biomarkers of preterm birth, 80 samples were analyzed in two gestational age groups: a) a late window composed of samples from 23-28 weeks of gestation which included 13 cases, 13 term controls matched within one week of sample collection and 14 term random controls, and, b) an early window composed of samples from 17-22 weeks of gestation included 15 cases, 15 term controls matched within one week of sample collection and 10 random term controls.

The samples were subsequently depleted of high abundance proteins using the Human 14 Multiple Affinity Removal System (MARS 14), which removes 14 of the most abundant proteins that are treated as uninformative with regard to the identification for disease-relevant changes in the serum proteome. To this end, equal volumes of each clinical or a pooled human serum sample (HGS) sample were diluted with column buffer and filtered to remove precipitates. Filtered samples were depleted using a MARS-14 column (4.6×100 mm, Cat. #5188-6558, Agilent Technologies). Samples were chilled to 4° C. in the autosampler, the depletion column was run at room temperature, and collected fractions were kept at 4° C. until further analysis. The unbound fractions were collected for further analysis.

A second aliquot of each clinical serum sample and of each HGS was diluted into ammonium bicarbonate buffer and depleted of the 14 high and approximately 60 additional moderately abundant proteins using an IgY14-SuperMix (Sigma) hand-packed column, comprised of 10 mL of bulk material (50% slurry, Sigma). Shi et al., *Methods,* 56 (2): 246-53 (2012). Samples were chilled to 4° C. in the autosampler, the depletion column was run at room temperature, and collected fractions were kept at 4° C. until further analysis. The unbound fractions were collected for further analysis.

Depleted serum samples were denatured with trifluorethanol, reduced with dithiotreitol, alkylated using iodoacetamide, and then digested with trypsin at a 1:10 trypsin: protein ratio. Following trypsin digestion, samples were desalted on a C18 column, and the eluate lyophilized to dryness. The desalted samples were resolubilized in a reconstitution solution containing five internal standard peptides.

Depleted and trypsin digested samples were analyzed using a scheduled Multiple Reaction Monitoring method (sMRM). The peptides were separated on a 150 mm×0.32 mm Bio-Basic C18 column (ThermoFisher) at a flow rate of 5 μl/min using a Waters Nano Acquity UPLC and eluted using an acetonitrile gradient into a AB SCIEX QTRAP 5500 with a Turbo V source (AB SCIEX, Framingham, MA). The sMRM assay measured 1708 transitions that correspond to 854 peptides and 236 proteins. Chromatographic peaks were integrated using Rosetta Elucidator software (*Ceiba* Solutions).

Transitions were excluded from analysis, if their intensity area counts were less than 10000 and if they were missing in more than three samples per batch. Intensity area counts were log transformed and Mass Spectrometry run order trends and depletion batch effects were minimized using a regression analysis.

Example 2. Analysis I of Transitions to Identify Preterm Birth Biomarkers

The objective of these analyses was to examine the data collected in Example 1 to identify transitions and proteins that predict preterm birth. The specific analyses employed were (i) Cox time-to-event analyses and (ii) models with preterm birth as a binary categorical dependent variable. The dependent variable for all the Cox analyses was Gestational Age of time to event (where event is preterm birth). For the purpose of the Cox analyses, preterm birth subjects have the event on the day of birth. Term subjects are censored on the day of birth. Gestational age on the day of specimen collection is a covariate in all Cox analyses.

The assay data were previously adjusted for run order and depletion batch, and log transformed. Values for gestational age at time of sample collection were adjusted as follows. Transition values were regressed on gestational age at time of sample collection using only controls (non-pre-term subjects). The residuals from the regression were designated as adjusted values. The adjusted values were used in the models with pre-term birth as a binary categorical dependent variable. Unadjusted values were used in the Cox analyses.
Univariate Cox Proportional Hazards Analyses Univariate Cox Proportional Hazards analyses was performed to predict Gestational Age at Birth, including Gestational age on the day of specimen collection as a covariate. Table 1 shows the transitions with p-values less than 0.05. Five proteins have multiple transitions among those with p-value less than 0.05: lipopolysaccharide-binding protein (LBP), prothrombin (THRB), complement component C5 (C5 or CO5), plasminogen (PLMN), and complement component C8 gamma chain (C8G or CO8G).
Multivariate Cox Proportional Hazards Analyses: Stepwise AIC Selection Cox Proportional Hazards analyses was performed to predict Gestational Age at Birth, including Gestational age on the day of specimen collection as a covariate, using stepwise and lasso models for variable selection. These analyses include a total of n=80 subjects, with number of PTB events=28. The stepwise variable selection analysis used the Akaike Information Criterion (AIC) as the stopping criterion. Table 2 shows the transitions selected by the stepwise AIC analysis. The coefficient of determination (R2) for the stepwise AIC model is 0.86 (not corrected for multiple comparisons).
Multivariate Cox Proportional Hazards Analyses: Lasso Selection Lasso variable selection was used as the second method of multivariate Cox Proportional Hazards analyses to predict Gestational Age at Birth, including Gestational age on the day of specimen collection as a covariate. This analysis uses a lambda penalty for lasso estimated by cross validation. Table 3 shows the results. The lasso variable selection method is considerably more stringent than the stepwise AIC, and selects only 3 transitions for the final model, representing 3 different proteins. These 3 proteins give the top 4 transitions from the univariate analysis; 2 of the top 4 univariate are from the same protein, and hence are not both selected by the lasso method. Lasso tends to select a relatively small number of variables with low mutual correlation. The coefficient of determination (R2) for the lasso model is 0.21 (not corrected for multiple comparisons).
Univariate AUROC Analysis of Preterm Birth as a Binary Categorical Dependent Variable Univariate analyses was performed to discriminate pre-term subjects from non-pre-term subjects (pre-term as a binary categorical variable) as estimated by area under the receiver operating characteristic (AUROC) curve. These analyses use transition values adjusted for gestational age at time of sample collection, as described above. Table 4 shows the AUROC curve for the 77 transitions with the highest AUROC area of 0.6 or greater.
Multivariate Analysis of Preterm Birth as a Binary Categorical Dependent Variable Multivariate analyses was performed to predict preterm birth as a binary categorical dependent variable, using random forest, boosting, lasso, and logistic regression models. Random forest and boosting models grow many classification trees. The trees vote on the assignment of each subject to one of the possible classes. The forest chooses the class with the most votes over all the trees.

For each of the four methods (random forest, boosting, lasso, and logistic regression) each method was allowed to select and rank its own best 15 transitions. We then built models with 1 to 15 transitions. Each method sequentially reduces the number of nodes from 15 to 1 independently. A recursive option was used to reduce the number of nodes at each step: To determine which node to remove, the nodes were ranked at each step based on their importance from a nested cross-validation procedure. The least important node was eliminated. The importance measures for lasso and logistic regression are z-values. For random forest and boosting, the variable importance was calculated from permuting out-of-bag data: for each tree, the classification error rate on the out-of-bag portion of the data was recorded; the error rate was then recalculated after permuting the values of each variable (i.e., transition); if the transition was in fact important, there would have been be a big difference between the two error rates; the difference between the two error rates were then averaged over all trees, and normalized by the standard deviation of the differences. The AUCs for these models are shown in Table 5, as estimated by 100 rounds of bootstrap resampling. Table 6 shows the top 15 transitions selected by each multivariate method, ranked by importance for that method. These multivariate analyses suggest that models that combine 3 or more transitions give AUC greater than 0.7, as estimated by bootstrap.

In multivariate models, random forest (rf), boosting, and lasso models gave the best area under the AUROC curve. The following transitions were selected by these models, as significant in Cox univariate models, and/or having high univariate ROC's:

AFTECCVVASQLR_770.87_574.3 ("AFTECCVVASQLR" is disclosed as SEQ ID NO: 1)

ELLESYIDGR_597.8_710.3 ("ELLESYIDGR" is disclosed as SEQ ID NO: 2)

ITLPDFTGDLR_624.34_920.4 ("ITLPDFTGDLR" is disclosed as SEQ ID NO: 3)

TDAPDLPEENQAR_728.34_613.3 ("TDAPDLPEENQAR" is disclosed as SEQ ID NO: 17)

SFRPFVPR_335.86_635.3 ("SFRPFVPR" is disclosed as SEQ ID NO: 18)

In summary, univariate and multivariate Cox analyses was performed using transitions to predict Gestational Age at Birth (GAB), including Gestational age on the day of specimen collection as a covariate. In the univariate Cox analysis, five proteins were identified that have multiple transitions among those with p-value less than 0.05: lipopolysaccharide-binding protein (LBP), prothrombin (THRB), complement component C5 (C5 or CO5), plasminogen (PLMN), and complement component C8 gamma chain (C8G or CO8G).

In multivariate Cox analyses, stepwise AIC variable analysis selects 24 transitions, while the lasso model selects 3 transitions, which include the 3 top proteins in the univariate analysis. Univariate (AUROC) and multivariate (random forest, boosting, lasso, and logistic regression) analyses were performed to predict pre-term birth as a binary categorical variable. Univariate analyses identified 63 analytes with AUROC of 0.6 or greater. Multivariate analyses suggest that models that combine 3 or more transitions give AUC greater than 0.7, as estimated by bootstrap.

Example 3. Study II to Identify and Confirm Preterm Birth Biomarkers

A further study was performed using essentially the same methods described in the preceding Examples unless noted below. In this study, 2 gestational aged matched controls were used for each case of 28 cases and 56 matched controls, all from the early gestational window only (17-22 weeks).

The samples were processed in 4 batches with each batch composed of 7 cases, 14 matched controls and 3 HGS controls. Serum samples were depleted of the 14 most abundant serum samples by MARS14 as described in Example 1. Depleted serum was then reduced with dithiothreitol, alkylated with iodacetamide, and then digested with trypsin at a 1:20 trypsin to protein ratio overnight at 37° C. Following trypsin digestion, the samples were desalted on an Empore C18 96-well Solid Phase Extraction Plate (3M Company) and lyophilized to dryness. The desalted samples were resolubilized in a reconstitution solution containing five internal standard peptides.

The LC-MS/MS analysis was performed with an Agilent Poroshell 120 EC-C18 column (2.1×50 mm, 2.7 μm) and eluted with an acetonitrile gradient into a Agilent 6490 Triple Quadrapole mass spectrometer.

Data analysis included the use of conditional logistic regression where each matching triplet (case and 2 matched controls) was a stratum. The p-value reported in the table indicates whether there is a significant difference between cases and matched controls.

TABLE 7

Results of Study II

| Transition | SEQ ID NO: | Protein | Annotation | p-value |
|---|---|---|---|---|
| DFHINLFQVLPWLK | 94 | CFAB_HUMAN | Complement factor B | 0.006729512 |
| ITLPDFTGDLR | 3 | LBP_HUMAN | Lipopolysaccharide-binding protein | 0.012907017 |
| WWGGQPLWITATK | 15 | ENPP2_HUMAN | Ectonucleotide pyrophosphatase/ phosphodiesterase family member 2 | 0.013346 |
| TASDFITK | 37 | GELS_HUMAN | Gelsolin | 0.013841221 |
| AGLLRPDYALLGHR | 95 | PGRP2_HUMAN | N-acetylmuramoyl-L-alanine amidase | 0.014241979 |
| FLQEQGHR | 23 | CO8G_HUMAN | Complement component C8 gamma chain | 0.014339596 |
| FLNWIK | 4 | HABP2_HUMAN | Hyaluronan-binding protein 2 | 0.014790418 |
| EKPAGGIPVLGSLVNTVLK | 96 | BPIB1_HUMAN | BPI fold-containing family B member 1 | 0.019027746 |
| ITGFLKPGK | 97 | LBP_HUMAN | Lipopolysaccharide-binding protein | 0.019836986 |
| YGLVTYATYPK | 63 | CFAB_HUMAN | Complement factor B | 0.019927774 |
| SLLQPNK | 98 | CO8A_HUMAN | Complement component C8 alpha chain | 0.020930939 |
| DISEVVTPR | 67 | CFAB_HUMAN | Complement factor B | 0.021738046 |
| VQEAHLTEDQIFYFPK | 31 | CO8G_HUMAN | Complement component C8 gamma chain | 0.021924548 |

TABLE 7-continued

Results of Study II

| Transition | SEQ ID NO: | Protein | Annotation | p-value |
|---|---|---|---|---|
| SPELQAEAK | 99 | APOA2_HUMAN | Apolipoprotein A-II | 0.025944285 |
| TYLHTYESEI | 100 | ENPP2_HUMAN | Ectonucleotide pyrophosphatase/ phosphodiesterase family member 2 | 0.026150038 |
| DSPSVWAAVPGK | 101 | PROF1_HUMAN | Profilin-1 | 0.026607371 |
| HYINLITR | 102 | NPY_HUMAN | Pro-neuropeptide Y | 0.027432804 |
| SLPVSDSVLSGFE QR | 59 | CO8G_HUMAN | Complement component C8 gamma chain | 0.029647857 |
| IPGIFELGISSQSD R | 103 | CO8B_HUMAN | Complement component C8 beta chain | 0.030430996 |
| IQTHSTTYR | 104 | F13B_HUMAN | Coagulation factor XIII B chain | 0.031667664 |
| DGSPDVTTADIGA NTPDATK | 44 | PGRP2_HUMAN | N-acetylmuramoyl-L-alanine amidase | 0.034738338 |
| QLGLPGPPDVPDH AAYHPF | 105 | ITIH4_HUMAN | Inter-alpha-trypsin inhibitor heavy chain H4 | 0.043130591 |
| FPLGSYTIQNIVA GSTYLFSTK | 106 | LCAP_HUMAN | Leucyl-cystinyl aminopeptidase | 0.044698045 |
| AHYDLR | 88 | FETUA_HUMAN | Alpha-2-HS-glycoprotein | 0.046259201 |
| SFRPFVPR | 18 | LBP_HUMAN | Lipopolysaccharide-binding protein | 0.047948847 |

Example 4. Study III Shotgun Identification of Preterm Birth Biomarkers

A further study used a hypothesis-independent shotgun approach to identify and quantify additional biomarkers not present on our multiplexed hypothesis dependent MRM assay. Samples were processed as described in the preceding Examples unless noted below.

Tryptic digests of MARS depleted patient (preterm birth cases and term controls) samples were fractionated by two-dimensional liquid chromatography and analyzed by tandem mass spectrometry. Aliquots of the samples, equivalent to 3-4 μl of serum, were injected onto a 6 cm×75 μm self-packed strong cation exchange (Luna SCX, Phenomenex) column. Peptides were eluded from the SCX column with salt (15, 30, 50, 70, and 100% B, where B=250 mM ammonium acetate, 2% acetonitrile, 0.1% formic acid in water) and consecutively for each salt elution, were bound to a 0.5 μl C18 packed stem trap (Optimize Technologies, Inc.) and further fractionated on a 10 cm×75 μm reversed phase ProteoPep II PicoFrit column (New Objective). Peptides were eluted from the reversed phase column with an acetonitrile gradient containing 0.1% formic acid and directly ionized on an LTQ-Orbitrap (ThermoFisher). For each scan, peptide parent ion masses were obtained in the Orbitrap at 60K resolution and the top seven most abundant ions were fragmented in the LTQ to obtain peptide sequence information.

Parent and fragment ion data were used to search the Human RefSeq database using the Sequest (Eng et al., J. Am. Soc. Mass Spectrom 1994; 5:976-989) and X!Tandem (Craig and Beavis, Bioinformatics 2004; 20:1466-1467) algorithms. For Sequest, data was searched with a 20 ppm tolerance for the parent ion and 1 AMU for the fragment ion. Two missed trypsin cleavages were allowed, and modifications included static cysteine carboxyamidomethylation and methionine oxidation. After searching the data was filtered by charge state vs. Xcorr scores (charge $+1\geq1.5$ Xcorr, charge $+2\geq2.0$, charge $+3\geq2.5$). Similar search parameters were used for X!tandem, except the mass tolerance for the fragment ion was 0.8 AMU and there is no Xcorr filtering. Instead, the PeptideProphet algorithm (Keller et al., Anal. Chem 2002; 74:5383-5392) was used to validate each X!Tandem peptide-spectrum assignment and Protein assignments were validated using ProteinProphet algorithm (Nesvizhskii et al., Anal. Chem 2002; 74:5383-5392). Data was filtered to include only the peptide-spectrum matches that had PeptideProphet probability of 0.9 or more. After compiling peptide and protein identifications, spectral count data for each peptide were imported into DAnTE software (Polpitiya et al., Bioinformatics. 2008; 24:1556-1558). Log transformed data was mean centered and missing values were filtered, by requiring that a peptide had to be identified in at least 4 cases and 4 controls. To determine the significance of an analyte, Receiver Operating Characteristic (ROC) curves for each analyte were created where the true positive rate (Sensitivity) is plotted as a function of the false positive rate (1-Specificity) for different thresholds that separate the SPTB and Term groups. The area under the ROC curve (AUC) is equal to the probability that a classifier will rank a randomly chosen positive instance higher than a randomly chosen negative one. Peptides with AUC greater than or equal to 0.6 found uniquely by Sequest or Xtandem are found in Tables 8 and 9, respectively, and those identified by both approaches are found in Table 10.

TABLE 8

| | | | Full peptide SEQ ID NO: | Core peptide SEQ ID NO: | S_AUC |
|---|---|---|---|---|---|
| | | Significant peptides (AUC>0.6) for Sequest only | | | |
| Protein Description | Uniprot ID (name) | Peptide | | | |
| 5'-AMP-activated protein kinase subunit gamma-3 | Q9UGI9 (AAKG3_HUMAN) | K.LVIFDTM*LEIK.K | 107 | 1070 | 0.78 |
| afamin precursor | P43652 (AFAM_HUMAN) | K.FIEDNIEYITIIAFAQYVQEATFEEMEK.L | 108 | 1071 | 0.79 |
| afamin precursor | P43652 (AFAM_HUMAN) | K.IAPQLSTEELVSLGEK.M | 109 | 832 | 0.71 |
| afamin precursor | P43652 (AFAM_HUMAN) | K.LKHELTDEELQSLFTNFANVVDK.C | 110 | 1072 | 0.60 |
| afamin precursor | P43652 (AFAM_HUMAN) | K.LPNNVLQEK.I | 111 | 814 | 0.60 |
| afamin precursor | P43652 (AFAM_HUMAN) | K.SDVGFLPPFPTLDPEEK.C | 112 | 1073 | 0.71 |
| afamin precursor | P43652 (AFAM_HUMAN) | K.VMNHICSK.Q | 113 | 1074 | 0.68 |
| afamin precursor | P43652 (AFAM_HUMAN) | R.ESLLNHFLYEVAR.R | 114 | 1075 | 0.69 |
| afamin precursor | P43652 (AFAM_HUMAN) | R.LCFFYNKK.S | 115 | 1076 | 0.69 |
| alpha-1-antichymotrypsin precursor | P01011 (AACT_HUMAN) | K.AVLDVFEEGTEASAATAVK.I | 116 | 1077 | 0.72 |
| alpha-1-antichymotrypsin precursor | P01011 (AACT_HUMAN) | K.EQLSLLDR.F | 117 | 1078 | 0.65 |
| alpha-1-antichymotrypsin precursor | P01011 (AACT_HUMAN) | K.EQLSLLDRFTEDAK.R | 118 | 1079 | 0.64 |
| alpha-1-antichymotrypsin precursor | P01011 (AACT_HUMAN) | K.EQLSLLDRFTEDAKR.L | 119 | 1080 | 0.60 |
| alpha-1-antichymotrypsin precursor | P01011 (AACT_HUMAN) | K.ITDLIKDLDSQTMM*VLVNYIFFK.A | 120 | 1081 | 0.65 |
| alpha-1-antichymotrypsin precursor | P01011 (AACT_HUMAN) | K.ITLLSALVETR.T | 121 | 1082 | 0.62 |
| alpha-1-antichymotrypsin precursor | P01011 (AACT_HUMAN) | K.RLYGSEAFATDFQDSAAAK.K | 122 | 1083 | 0.62 |
| alpha-1-antichymotrypsin precursor | P01011 (AACT_HUMAN) | R.EIGELYLPK.F | 123 | 895 | 0.65 |
| alpha-1B-glycoprotein precursor | P04217 (A1BG_HUMAN) | R.CEGPIPDVTFELLR.E | 124 | 1084 | 0.67 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| alpha-1B-glycoprotein precursor | P04217 (A1BG_HUMAN) | R.FALVR.E | 125 | 1085 | 0.79 |
| alpha-2-antiplasmin isoform a precursor | P08697 (A2AP_HUMAN) | K.SPPGVCSR.D | 126 | 1086 | 0.81 |
| alpha-2-antiplasmin isoform a precursor | P08697 (A2AP_HUMAN) | R.DSFHLDEQFTVPVEMMQAR.T | 127 | 1087 | 0.69 |
| alpha-2-HS-glycoprotein preproprotein | P02765 (FETUA_HUMAN) | K.CNLLAEK.Q | 128 | 1088 | 0.67 |
| alpha-2-HS-glycoprotein preproprotein | P02765 (FETUA_HUMAN) | K.EHAVEGDCDFQLLK.L | 129 | 1089 | 0.67 |
| alpha-2-HS-glycoprotein preproprotein | P02765 (FETUA_HUMAN) | K.HTLNQIDEVKVWPQQPSGELFE IEIDTLETTCHVLDPTPVAR.C | 130 | 1090 | 0.64 |
| alpha-2-macroglobulin precursor | P01023 (A2MG_HUMAN) | K.MVSGFIPLKPTVK.M | 131 | 1091 | 0.73 |
| alpha-2-macroglobulin precursor | P01023 (A2MG_HUMAN) | R.AFQPFFVELTM*PYSVIR.G | 132 | 1092 | 0.68 |
| alpha-2-macroglobulin precursor | P01023 (A2MG_HUMAN) | R.AFQPFFVELTMPYSVIR.G | 132 | 1092 | 0.62 |
| alpha-2-macroglobulin precursor | P01023 (A2MG_HUMAN) | R.NQGNTWLTAFVLK.T | 133 | 1093 | 0.73 |
| angiotensinogen preproprotein | P01019 (ANGT_HUMAN) | K.IDRFMQAVTGWK.T | 134 | 1094 | 0.81 |
| angiotensinogen preproprotein | P01019 (ANGT_HUMAN) | K.LDTEDKLR.A | 135 | 1095 | 0.72 |
| angiotensinogen preproprotein | P01019 (ANGT_HUMAN) | K.TGCSLMGASVDSTLAFNTYVHF QGK.M | 136 | 1096 | 0.64 |
| angiotensinogen preproprotein | P01019 (ANGT_HUMAN) | R.AAMVGMLANFLGFR.I | 137 | 1097 | 0.62 |
| antithrombin-III precursor | P01008 (ANT3_HUMAN) | K.NDNDNIFLSPLSISTAFAMTK.L | 138 | 1098 | 0.64 |
| antithrombin-III precursor | P01008 (ANT3_HUMAN) | K.SKLPGIVAEGRDDLYVSDAFHK. A | 139 | 1099 | 0.81 |
| antithrombin-III precursor | P01008 (ANT3_HUMAN) | R.EVPLNTIIFMGR.V | 140 | 1100 | 0.61 |
| antithrombin-III precursor | P01008 (ANT3_HUMAN) | R.FATTFYQHLADSKNDNDNIFLS PLSISTAFAMTK.L | 141 | 1101 | 0.66 |
| antithrombin-Ill precursor | P01008 (ANT3_HUMAN) | R.ITDVIPSEAINELTVLVLVNTIYFK G | 142 | 1102 | 0.60 |
| antithrombin-III precursor | P01008 (ANT3_HUMAN) | R.RVWELSK.A | 143 | 1103 | 0.63 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| antithrombin-III precursor | P01008 (ANT3_HUMAN) | R.VAEGTQVLELPFKGDDITM*VLI LPKPEK.S | 144 | 1104 | 0.62 |
| antithrombin-III precursor | P01008 (ANT3_HUMAN) | R.VAEGTQVLELPFKGDDITMVLIL PKPEK.S | 144 | 1104 | 0.62 |
| apolipoprotein A-II preproprotein | P02652 (APOA2_HUMAN) | K.AGTELVNFLSYFVELGTQPATQ.- | 145 | 1105 | 0.61 |
| apolipoprotein A-II preproprotein | P02652 (APOA2_HUMAN) | K.EPCVESLVSQYFQTVTDYGK.D | 146 | 1106 | 0.63 |
| apolipoprotein A-IV precursor | P06727 (APOA4_HUMAN) | K.ALVQQMEQLR.Q | 147 | 1107 | 0.61 |
| apolipoprotein A-IV precursor | P06727 (APOA4_HUMAN) | K.LGPHAGDVEGHLSFLEK.D | 148 | 1108 | 0.61 |
| apolipoprotein A-IV precursor | P06727 (APOA4_HUMAN) | K.SELTQQLNALFQDK.L | 149 | 1109 | 0.71 |
| apolipoprotein A-IV precursor | P06727 (APOA4_HUMAN) | K.SLAELGGHLDQQVEEFRR.R | 150 | 1110 | 0.61 |
| apolipoprotein A-IV precursor | P06727 (APOA4_HUMAN) | K.VKIDQTVEELRR.S | 15 | 1111 | 0.75 |
| apolipoprotein A-IV precursor | P06727 (APOA4_HUMAN) | K.VNSFFSTFK.E | 152 | 1112 | 0.63 |
| apolipoprotein B-100 precursor | P04114 (APOB_HUMAN) | K.ATFQTPDFIVPLTDLR.I | 153 | 1113 | 0.65 |
| apolipoprotein B-100 precursor | P04114 (APOB_HUMAN) | K.AVSM*PSFSILGSDVR.V | 154 | 1114 | 0.65 |
| apolipoprotein B-100 precursor | P04114 (APOB_HUMAN) | K.AVSMPSFSILGSDVR.V | 154 | 1114 | 0.67 |
| apolipoprotein B-100 precursor | P04114 (APOB_HUMAN) | K.EQHLFLPFSYK.N | 155 | 1115 | 0.65 |
| apolipoprotein B-100 precursor | P04114 (APOB_HUMAN) | K.KIISDYHQQFR.Y | 156 | 1116 | 0.63 |
| apolipoprotein B-100 precursor | P04114 (APOB_HUMAN) | K.QVFLYPEKDEPTYILNIK.R | 157 | 1117 | 0.64 |
| apolipoprotein B-100 precursor | P04114 (APOB_HUMAN) | K.SPAFTDLHLR.Y | 158 | 1118 | 0.69 |
| apolipoprotein B-100 precursor | P04114 (APOB_HUMAN) | K.TILGTMPAFEVSLQALQK.A | 159 | 1119 | 0.62 |
| apolipoprotein B-100 precursor | P04114 (APOB_HUMAN) | K.VLADKFIIPGLK.L | 160 | 1120 | 0.72 |
| apolipoprotein B-100 precursor | P04114 (APOB_HUMAN) | K.YSQPEDSLIPFFEITVPESQLTVS QFTLPK.S | 161 | 1121 | 0.61 |
| apolipoprotein B-100 precursor | P04114 (APOB_HUMAN) | R.DLKVEDIPLAR.I | 162 | 1122 | 0.64 |
| apolipoprotein B-100 precursor | P04114 (APOB_HUMAN) | R.GIISALLVPPETEEAK.Q | 163 | 1123 | 0.81 |
| apolipoprotein B-100 precursor | P04114 (APOB_HUMAN) | R.ILGEELGFASLHDLQLLGK.L | 164 | 1124 | 0.62 |
| apolipoprotein B-100 precursor | P04114 (APOB_HUMAN) | R.LELELRPTGEIEQYSVSATYELQR .E | 165 | 1125 | 0.60 |

TABLE 8-continued

| Protein Description | Uniprot ID (name) | Peptide | Full peptide SEQ ID NO: | Core peptide SEQ ID NO: | S_AUC |
|---|---|---|---|---|---|
| apolipoprotein B-100 precursor | P04114 (APOB_HUMAN) | R.NIQEYLSILTDPDGK.G | 166 | 1126 | 0.68 |
| apolipoprotein B-100 precursor | P04114 (APOB_HUMAN) | R.TFQIPGYTVPVVNVEVSPFTIEM SAFGYVFPK.A | 167 | 1127 | 0.75 |
| apolipoprotein B-100 precursor | P04114 (APOB_HUMAN) | R.TIDQMLNSELQWPVPDIYLR.D | 168 | 1128 | 0.70 |
| apolipoprotein C-I precursor | P02654 (APOC1_HUMAN) | K.MREWFSETFQK.V | 169 | 1129 | 0.61 |
| apolipoprotein C-II precursor | P02655 (APOC2_HUMAN) | K.STAAMSTYTGIFTDQVLSVLKGE E.- | 170 | 1130 | 0.61 |
| apolipoprotein C-III precursor | P02656 (APOC3_HUMAN) | R.GWVTDGFSSLK.D | 171 | 54 | 0.62 |
| apolipoprotein E precursor | P02649 (APOE_HUMAN) | R.AATVGSLAGQPLQER.A | 172 | 1131 | 0.61 |
| apolipoprotein E precursor | P02649 (APOE_HUMAN) | R.LKSWFEPLVEDMQR.Q | 173 | 1132 | 0.65 |
| apolipoprotein E precursor | P02649 (APOE_HUMAN) | R.WVQTLSEQVQEELLSSQVTQEL R.A | 174 | 1133 | 0.64 |
| ATP-binding cassette sub-family D member 4 | 014678 (ABCD4_HUMAN) | K.LCGGGRWELM*R.I | 175 | 1134 | 0.60 |
| ATP-binding cassette sub-family F member 3 | Q9NUQ8 (ABCF3_HUMAN) | K.LPGLLK.R | 176 | 1135 | 0.73 |
| beta-2-glycoprotein 1 precursor | P02749 (APOH_HUMAN) | K.EHSSLAFWK.T | 177 | 1034 | 0.64 |
| beta-2-glycoprotein 1 precursor | P02749 (APOH_HUMAN) | R.TCPKPDDLPFSTVVPLK.T | 178 | 1136 | 0.60 |
| beta-2-glycoprotein 1 precursor | P02749 (APOH_HUMAN) | R.VCPFAGILENGAVR.Y | 179 | 1137 | 0.68 |
| beta-Ala-His dipeptidase precursor | Q96KN2 (CNDP1_HUMAN) | K.LFAAFFLEMAQLH.- | 180 | 1138 | 0.68 |
| biotinidase precursor | P43251 (BTD_HUMAN) | K.SHLIIAQVAK.N | 181 | 1139 | 0.62 |
| carboxypeptidase B2 preproprotein | Q96IY4 (CBPB2_HUMAN) | K.NAIWIDCGIHAR.E | 182 | 1140 | 0.62 |
| carboxypeptidase N catalytic chain precursor | P15169 (CBPN_HUMAN) | R.EALIQFLEQVHQGIK.G | 183 | 1141 | 0.69 |
| carboxypeptidase N subunit 2 precursor | P22792 (CPN2_HUMAN) | R.LLNIQTYCAGPAYLK.G | 184 | 1142 | 0.62 |
| catalase | P04040 (CATA_HUMAN) | R.LCENIAGHLKDAQIFIQK.K | 185 | 1143 | 0.62 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| ceruloplasmin precursor | P00450 (CERU_HUMAN) | K.AETGDKVYVHLK.N | 186 | 1144 | 0.61 |
| ceruloplasmin precursor | P00450 (CERU_HUMAN) | K.AGLQAFFQVQECNK.S | 187 | 1145 | 0.62 |
| ceruloplasmin precursor | P00450 (CERU_HUMAN) | K.DIASGLIGPLIICK.K | 188 | 1146 | 0.63 |
| ceruloplasmin precursor | P00450 (CERU_HUMAN) | K.DIFTGLIGPM*K.I | 189 | 1147 | 0.63 |
| ceruloplasmin precursor | P00450 (CERU_HUMAN) | K.DIFTGLIGPMK.I | 189 | 1147 | 0.68 |
| ceruloplasmin precursor | P00450 (CERU_HUMAN) | K.M*YYSAVDPTKDIFTGLIGPMK. I | 190 | 1148 | 0.62 |
| ceruloplasmin precursor | P00450 (CERU_HUMAN) | K.MYYSAVDPTKDIFTGLIGPM*K. I | 190 | 1148 | 0.63 |
| ceruloplasmin precursor | P00450 (CERU_HUMAN) | K.PVWLGFLGPIIK.A | 191 | 1149 | 0.63 |
| ceruloplasmin precursor | P00450 (CERU_HUMAN) | R.ADDKVYPGEQYTYMLLATEEQS PGEGDGNCVTR.I | 192 | 1150 | 0.64 |
| ceruloplasmin precursor | P00450 (CERU_HUMAN) | R.DTANLFPQTSLTLHM*WPDTE GTFNVECLTTDHYTGGMK.Q | 193 | 1151 | 0.71 |
| ceruloplasmin precursor | P00450 (CERU_HUMAN) | R.DTANLFPQTSLTLHMWPDTEG TFNVECLTTDHYTGGMK.Q | 193 | 1151 | 0.68 |
| ceruloplasmin precursor | P00450 (CERU_HUMAN) | R.FNKNNEGTYYSPNYNPQSR.S | 194 | 1152 | 0.74 |
| ceruloplasmin precursor | P00450 (CERU_HUMAN) | R.IDTINLFPATLFDAYM*VAQNP GEWM*LSCQNLNHLK.A | 195 | 1153 | 0.75 |
| ceruloplasmin precursor | P00450 (CERU_HUMAN) | R.IDTINLFPATLFDAYM*VAQNP GEWMLSCQNLNHLK.A | 195 | 1153 | 0.86 |
| ceruloplasmin precursor | P00450 (CERU_HUMAN) | R.IDTINLFPATLFDAYMVAQNPG EWM*LSCQNLNHLK.A | 195 | 1153 | 0.60 |
| ceruloplasmin precursor | P00450 (CERU_HUMAN) | R.KAEEEHLGILGPQLHADVGDKV K.I | 196 | 1154 | 0.71 |
| ceruloplasmin precursor | P00450 (CERU_HUMAN) | R.TTIEKPVWLGFLGPIIK.A | 197 | 1026 | 0.63 |
| cholinesterase precursor | P06276 (CHLE_HUMAN) | R.FWTSFFPK.V | 198 | 1155 | 0.76 |
| clusterin preproprotein | P10909 (CLUS_HUMAN) | K.LFDSDPITVTVPVEVSR.K | 199 | 1156 | 0.78 |
| clusterin preproprotein | P10909 (CLUS_HUMAN) | R.ASSIIDELFQDR.F | 200 | 1157 | 0.68 |
| coagulation factor IX preproprotein | P00740 (FA9_HUMAN) | K.WIVTAAHCVETGVK.I | 201 | 1158 | 0.60 |
| coagulation factor VII isoform a preproprotein | P08709 (FA7_HUMAN) | R.FSLVSGWGQLLDR.G | 202 | 878 | 0.78 |
| coagulation factor X preproprotein | P00742 (FA10_HUMAN) | K.ETYDFDIAVLR.L | 203 | 1159 | 0.75 |

TABLE 8-continued

| | | | | | |
|---|---|---|---|---|---|
| | | | Significant peptides (AUC>0.6) for Sequest only | | |
| Protein Description | Uniprot ID (name) | Peptide | Full peptide SEQ ID NO: | Core peptide SEQ ID NO: | S_AUC |
| coiled-coil domain-containing protein 13 | Q8IYE1 (CCD13_HUMAN) | K.VRQLEMEIGQLNVHYLR.N | 204 | 1160 | 0.67 |
| complement C1q subcomponent subunit A precursor | P02745 (C1QA_HUMAN) | R.PAFSAIR.R | 205 | 1161 | 0.66 |
| complement C1q subcomponent subunit B precursor | P02746 (C1QB_HUMAN) | K.VVTFCDYAYNTFQVTTGGMVL K.L | 206 | 1162 | 0.63 |
| complement C1q subcomponent subunit C precursor | P02747 (C1QC_HUMAN) | K.FQSVFTVTR.Q | 207 | 862 | 0.63 |
| complement C1r subcomponent precursor | P00736 (C1R_HUMAN) | K.TLDEFTIIQNLQPQYQFR.D | 208 | 1163 | 0.62 |
| complement C1r subcomponent precursor | P00736 (C1R_HUMAN) | R.MDVFSQNMFCAGHPSLK.Q | 209 | 1164 | 0.68 |
| complement C1r subcomponent precursor | P00736 (C1R_HUMAN) | R.WILTAAHTLYPK.E | 210 | 886 | 0.74 |
| complement C1s subcomponent precursor | P09871 (C1S_HUMAN) | K.FYAAGLVSWGPQCGTYGLYTR. V | 211 | 1165 | 0.68 |
| complement C1s subcomponent precursor | P09871 (C1S_HUMAN) | K.GFQVVVTLR.R | 212 | 1166 | 0.63 |
| complement C2 isoform 3 | P06681 (CO2_HUMAN) | R.GALISDQWVLTAAHCFR.D | 213 | 1167 | 0.61 |
| complement C2 isoform 3 | P06681 (CO2_HUMAN) | R.PICLPCTMEANLALR.R | 214 | 1168 | 0.66 |
| complement C3 precursor | P01024 (CO3_HUMAN) | R.YYGGGYGSTQATFMVFQALAQ YQK.D | 215 | 1169 | 0.75 |
| complement C4-A isoform 1 | P0C0L4 (CO4A_HUMAN) | K.GLCVATPVQLR.V | 216 | 1170 | 0.74 |
| complement C4-A isoform 1 | P0C0L4 (CO4A_HUMAN) | K.M*RPSTDTITVM*VENSHGLR. V | 217 | 1171 | 0.83 |
| complement C4-A isoform 1 | P0C0L4 (CO4A_HUMAN) | K.MRPSTDTITVM*VENSHGLR.V | 217 | 1171 | 0.72 |
| complement C4-A isoform 1 | P0C0L4 (CO4A_HUMAN) | K.VGLSGM*AIADVTLLSGFHALR. A | 218 | 1172 | 0.71 |
| complement C4-A isoform 1 | P0C0L4 (CO4A_HUMAN) | K.VLSLAQEQVGGSPEK.L | 219 | 1173 | 0.63 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| complement C4-A isoform 1 | P0C0L4 (CO4A_HUMAN) | R.EMSGSPASGIPVK.V | 220 | 1174 | 0.65 |
| complement C4-A isoform 1 | P0C0L4 (CO4A_HUMAN) | R.GCGEQTM*IYLAPTLAASR.Y | 221 | 1175 | 0.75 |
| complement C4-A isoform 1 | P0C0L4 (CO4A_HUMAN) | R.GLQDEDGYR.M | 222 | 1176 | 0.75 |
| complement C4-A isoform 1 | P0C0L4 (CO4A_HUMAN) | R.GQIVFMNREPK.R | 223 | 1177 | 0.93 |
| complement C4-A isoform 1 | P0C0L4 (CO4A_HUMAN) | R.KKEVYM*PSSIFQDDFVIPDISE PGTWK.I | 224 | 1178 | 0.72 |
| complement C4-A isoform 1 | P0C0L4 (CO4A_HUMAN) | R.LPMSVR.R | 225 | 1179 | 0.78 |
| complement C4-A isoform 1 | P0C0L4 (CO4A_HUMAN) | R.LTVAAPPSGGPGFLSIER.P | 226 | 1180 | 0.84 |
| complement C4-A isoform 1 | P0C0L4 (CO4A_HUMAN) | R.NFLVR.A | 227 | 1181 | 0.75 |
| complement C4-A isoform 1 | P0C0L4 (CO4A_HUMAN) | R.NGESVKLHLETDSLALVALGALD TALYAAGSK.S | 228 | 1182 | 0.88 |
| complement C4-A isoform 1 | P0C0L4 (CO4A_HUMAN) | R.QGSFQGGFR.S | 229 | 1183 | 0.60 |
| complement C4-A isoform 1 | P0C0L4 (CO4A_HUMAN) | R.TLEIPGNSDPNMIPDGDFNSYV R.V | 230 | 1184 | 0.69 |
| complement C4-A isoform 1 | P0C0L4 (CO4A_HUMAN) | R.VTASDPLDTLGSEGALSPGGVA SLLR.L | 231 | 1185 | 0.63 |
| complement C4-A isoform 1 | P0C0L4 (CO4A_HUMAN) | R.YLDKTEQWSTLPPETK.D | 232 | 1186 | 0.67 |
| complement C5 preproprotein | P01031 (CO5_HUMAN) | K.ADNFLLENTLPAQSTFTLAISAY ALSLGDK.T | 233 | 1187 | 0.63 |
| complement C5 preproprotein | P01031 (CO5_HUMAN) | K.ALVEGVDQLFTDYQIK.D | 234 | 1188 | 0.63 |
| complement C5 preproprotein | P01031 (CO5_HUMAN) | K.DGHVILQLNSIPSSDFLCVR.F | 235 | 1189 | 0.62 |
| complement C5 preproprotein | P01031 (CO5_HUMAN) | K.DVFLEMNIPYSVVR.G | 236 | 1190 | 0.63 |
| complement C5 preproprotein | P01031 (CO5_HUMAN) | K.EFPYRIPLDLVPK.T | 237 | 1191 | 0.60 |
| complement C5 preproprotein | P01031 (CO5_HUMAN) | K.FQNSAILTIQPK.Q | 238 | 1192 | 0.67 |
| complement C5 preproprotein | P01031 (CO5_HUMAN) | K.VFKDVFLEMNIPYSVVR.G | 239 | 1193 | 0.63 |
| complement C5 preproprotein | P01031 (CO5_HUMAN) | R.VFQFLEK.S | 240 | 810 | 0.61 |
| complement component C6 precursor | P13671 (CO6_HUMAN) | K.DLHLSDVFLK.A | 241 | 856 | 0.60 |
| complement component C6 precursor | P13671 (CO6_HUMAN) | R.TECIKPVVQEVLTITPFQR.L | 242 | 1194 | 0.62 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| complement component C7 precursor | P10643 (CO7_HUMAN) | K.SSGWHFVVK.F | 243 | 1195 | 0.61 |
| complement component C7 precursor | P10643 (CO7_HUMAN) | R.ILPLTVCK.M | 244 | 1196 | 0.75 |
| complement component C8 alpha chain precursor | P07357 (CO8A_HUMAN) | R.ALDQYLMEFNACR.C | 245 | 1197 | 0.65 |
| complement component C8 gamma chain precursor | P07360 (CO8G_HUMAN) | K.YGFCEAADQFHVLDEVR.R | 246 | 1198 | 0.60 |
| complement component C9 precursor | P02748 (CO9_HUMAN) | R.AIEDYINEFSVRK.C | 247 | 1199 | 0.69 |
| complement component C9 precursor | P02748 (CO9_HUMAN) | R.TAGYGINILGMDPLSTPFDNEFYNGLCNR.D | 248 | 1200 | 0.69 |
| complement factor B preproprotein | P00751 (CFAB_HUMAN) | K.ALFVSEEEKK.L | 249 | 1201 | 0.64 |
| complement factor B preproprotein | P00751 (CFAB_HUMAN) | K.CLVNLIEK.V | 250 | 1202 | 0.70 |
| complement factor B preproprotein | P00751 (CFAB_HUMAN) | K.EAGIPEFYDYDVALIK.L | 251 | 1203 | 0.66 |
| complement factor B preproprotein | P00751 (CFAB_HUMAN) | K.VSEADSSNADWVTK.Q | 252 | 813 | 0.73 |
| complement factor B preproprotein | P00751 (CFAB_HUMAN) | K.YGQTIRPICLPCTEGTTR.A | 253 | 1204 | 0.67 |
| complement factor B preproprotein | P00751 (CFAB_HUMAN) | R.DLEIEVVLFHPNYNINGK.K | 254 | 1205 | 0.71 |
| complement factor B preproprotein | P00751 (CFAB_HUMAN) | R.FLCTGGVSPYADPNTCR.G | 255 | 1206 | 0.64 |
| complement factor H isoform a precursor | P08603 (CFAH_HUMAN) | K.DGWSAQPTCIK.S | 256 | 1207 | 0.80 |
| complement factor H isoform a precursor | P08603 (CFAH_HUMAN) | K.EGWIHTVCINGR.W | 257 | 1208 | 0.67 |
| complement factor H isoform a precursor | P08603 (CFAH_HUMAN) | K.TDCLSLPSFENAIPMGEK.K | 258 | 1209 | 0.61 |
| complement factor H isoform a precursor | P08603 (CFAH_HUMAN) | R.DTSCVNPPTVQNAYIVSR.Q | 259 | 1210 | 0.60 |
| complement factor H isoform b precursor | P08603 (CFAH_HUMAN) | K.CTSTGWIPAPR.C | 260 | 1211 | 0.68 |

TABLE 8-continued

| | | | Full peptide SEQ ID | Core peptide SEQ ID | |
| Protein Description | Uniprot ID (name) | Peptide | NO: | NO: | S_AUC |
| --- | --- | --- | --- | --- | --- |
| complement factor H isoform b precursor | P08603 (CFAH_HUMAN) | K.IIYKENER.F | 261 | 1212 | 0.76 |
| complement factor H isoform b precursor | P08603 (CFAH_HUMAN) | K.IVSSAM*EPDREYHFGQAVR.F | 262 | 1213 | 0.75 |
| complement factor H isoform b precursor | P08603 (CFAH_HUMAN) | K.IVSSAMEPDREYHFGQAVR.F | 262 | 1213 | 0.68 |
| complement factor H isoform b precursor | P08603 (CFAH_HUMAN) | R.CTLKPCDYPDIK.H | 263 | 1214 | 0.81 |
| complement factor H isoform b precursor | P08603 (CFAH_HUMAN) | R.KGEWVALNPLR.K | 264 | 1215 | 0.60 |
| complement factor H isoform b precursor | P08603 (CFAH_HUMAN) | R.KGEWVALNPLRK.C | 265 | 1216 | 0.69 |
| complement factor H isoform b precursor | P08603 (CFAH_HUMAN) | R.RPYFPVAVGK.Y | 266 | 1217 | 0.68 |
| complement factor H-related protein 1 precursor | Q03591 (FHR1_HUMAN) | R.EIMENYNIALR.W | 267 | 1218 | 0.64 |
| complement factor I preproprotein | P05156 (CFAI_HUMAN) | K.DASGITCGGIYIGGCWILTAAHC LR.A | 268 | 1219 | 0.71 |
| complement factor I preproprotein | P05156 (CFAI_HUMAN) | K.VANYFDWISYHVGR.P | 269 | 1220 | 0.72 |
| complement factor I preproprotein | P05156 (CFAI_HUMAN) | R.IIFHENYNAGTYQNDIALIEMK.K | 270 | 1221 | 0.63 |
| complement factor I preproprotein | P05156 (CFAI_HUMAN) | R.YQIWTTVVDWIHPDLK.R | 271 | 1222 | 0.63 |
| conserved oligomeric Golgi complex subunit 6 isoform | Q9Y2V7 (COG6_HUMAN) | K.ISNLLK.F | 272 | 1223 | 0.65 |
| corticosteroid-binding globulin precursor | P08185 (CBG_HUMAN) | R.WSAGLTSSQVDLYIPK.V | 273 | 916 | 0.62 |
| C-reactive protein precursor | P02741 (CRP_HUMAN) | K.YEVQGEVFTKPQLWP.- | 274 | 27 | 0.60 |
| dopamine beta-hydroxylase precursor | P09172 (DOPO_HUMAN) | R.HVLAAWALGAK.A | 275 | 1224 | 0.88 |
| double-stranded RNA-specific editase B2 | Q9NS39 (RED2_HUMAN) | R.AGLRYVCLAEPAER.R | 276 | 1225 | 0.75 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| dual oxidase 2 precursor | Q9NRD8 (DUOX2_HUMAN) | R.FTQLCVKGGGGGGNGIR.D | 277 | 1226 | 0.65 |
| FERM domain-containing protein 8 | Q9BZ67 (FRMD8_HUMAN) | R.VQLGPYQPGRPAACDLR.E | 278 | 1227 | 0.65 |
| fetuin-B precursor | Q9UGM5 (FETUB_HUMAN) | R.GGLGSLFYLTLDVLETDCHVLR.K | 279 | 1228 | 0.83 |
| ficolin-3 isoform 1 precursor | O75636 (FCN3_HUMAN) | R.ELLSQGATLSGWYHLCLPEGR.A | 280 | 1229 | 0.69 |
| gastric intrinsic factor precursor | P27352 (IF_HUMAN) | K.KTTDM*ILNEIKQGK.F | 281 | 1230 | 0.60 |
| gelsolin isoform d | P06396 (GELS_HUMAN) | K.NWRDPDQTDGLGLSYLSSHIANVER.V | 282 | 1231 | 0.72 |
| gelsolin isoform d | P06396 (GELS_HUMAN) | K.TPSAAYLWVGTGASEAEK.T | 283 | 35 | 0.80 |
| gelsolin isoform d | P06396 (GELS_HUMAN) | R.VEKFDLVPVPTNLYGDFFTGDAYVILK.T | 284 | 1232 | 0.60 |
| gelsolin isoform d | P06396 (GELS_HUMAN) | R.VPFDAATLHTSTAMAAQHGMDDDGTGQK.Q | 285 | 1233 | 0.67 |
| glutathione peroxidase 3 precursor | P22352 (GPX3_HUMAN) | K.FYTFLK.N | 286 | 1234 | 0.63 |
| hemopexin precursor | P02790 (HEMO_HUMAN) | K.GDKVWVYPPEKK.E | 287 | 1235 | 0.65 |
| hemopexin precursor | P02790 (HEMO_HUMAN) | K.LLQDEFPGIPSPLDAAVECHR.G | 288 | 1236 | 0.71 |
| hemopexin precursor | P02790 (HEMO_HUMAN) | K.SGAQATWTELPWPHEK.V | 289 | 888 | 0.64 |
| hemopexin precursor | P02790 (HEMO_HUMAN) | K.SGAQATWTELPWPHEKVDGALCMEK.S | 290 | 1237 | 0.61 |
| hemopexin precursor | P02790 (HEMO_HUMAN) | K.VDGALCMEK.S | 291 | 1238 | 0.66 |
| hemopexin precursor | P02790 (HEMO_HUMAN) | R.DYFMPCPGR.G | 292 | 1239 | 0.68 |
| hemopexin precursor | P02790 (HEMO_HUMAN) | R.EWFWDLATGTM*K.E | 293 | 1240 | 0.64 |
| hemopexin precursor | P02790 (HEMO_HUMAN) | R.QGHNSVFLIK.G | 294 | 830 | 0.71 |
| heparin cofactor 2 precursor | P05546 (HEP2_HUMAN) | K.HQGTITVNEEGTQATTVTTVGFMPLSTQVR.F | 295 | 1241 | 0.60 |
| heparin cofactor 2 precursor | P05546 (HEP2_HUMAN) | K.YEITTIHNLFR.K | 296 | 1242 | 0.62 |
| heparin cofactor 2 precursor | P05546 (HEP2_HUMAN) | R.LNILNAK.F | 297 | 1243 | 0.68 |
| heparin cofactor 2 precursor | P05546 (HEP2_HUMAN) | R.NFGYTLR.S | 298 | 1244 | 0.64 |

TABLE 8-continued

| Protein Description | Uniprot ID (name) | Peptide | Full peptide SEQ ID NO: | Core peptide SEQ ID NO: | S_AUC |
|---|---|---|---|---|---|
| heparin cofactor 2 precursor | P05546 (HEP2_HUMAN) | R.VLKDQVNTFDNIFIAPVGISTAM GM*ISLGLK.G | 1047 | 1245 | 0.63 |
| hepatocyte cell adhesion molecule precursor | Q14CZ8 (HECAM_HUMAN) | K.PLLNDSRMLLSPDQK.V | 1048 | 1246 | 0.61 |
| hepatocyte growth factor activator preproprotein | Q04756 (HGFA_HUMAN) | R.VQLSPDLLATLPEPASPGR.Q | 299 | 1247 | 0.82 |
| histidine-rich glycoprotein precursor | P04196 (HRG_HUMAN) | R.DGYLFQLLR.I | 300 | 1248 | 0.63 |
| hyaluronan-binding protein 2 isoform 1 preproprotein | Q14520 (HABP2_HUMAN) | K.FLNWIK.A | 301 | 4 | 0.82 |
| hyaluronan-binding protein 2 isoform 1 preproprotein | Q14520 (HABP2_HUMAN) | K.LKPVDGHCALESK.Y | 302 | 1249 | 0.61 |
| hyaluronan-binding protein 2 isoform 1 preproprotein | Q14520 (HABP2_HUMAN) | K.RPGVYTQVTK.F | 303 | 1250 | 0.74 |
| inactive caspase-12 | Q6UXS9 (CASPC_HUMAN) | K.AGADTHGRLLQGNICNDAVTK. A | 304 | 1251 | 0.74 |
| insulin-degrading enzyme isoform 1 | P14735 (IDE_HUMAN) | K.KIIEKM*ATFEIDEK.R | 305 | 1252 | 0.85 |
| insulin-like growth factor-binding protein complex acid labile subunit isoform 2 precursor | P35858 (ALS_HUMAN) | R.SFEGLGQLEVLTLDHNQLQEVK. A | 306 | 1253 | 0.62 |
| inter-alpha-trypsin inhibitor heavy chain H1 isoform a precursor | P19827 (ITIH1_HUMAN) | K.ELAAQTIKK.S | 307 | 1254 | 0.81 |
| inter-alpha-trypsin inhibitor heavy chain H1 isoform a precursor | P19827 (ITIH1_HUMAN) | K.GSLVQASEANLQAAQDFVR.G | 308 | 900 | 0.71 |
| inter-alpha-trypsin inhibitor heavy chain H1 isoform a precursor | P19827 (ITIH1_HUMAN) | K.QLVHHFEIDVDIFEPQGISK.L | 309 | 1255 | 0.70 |
| inter-alpha-trypsin inhibitor heavy chain H1 isoform a precursor | P19827 (ITIH1_HUMAN) | K.QYYEGSEIVVAGR.I | 310 | 1256 | 0.83 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| inter-alpha-trypsin inhibitor heavy chain H1 isoform a precursor | P19827 (ITIH1_HUMAN) | R.EVAFDLEIPKTAFISDFAVTADG NAFIGDIK.D | 311 | 1257 | 0.70 |
| inter-alpha-trypsin inhibitor heavy chain H1 isoform a precursor | P19827 (ITIH1_HUMAN) | R.GMADQDGLKPTIDKPSEDSPPL EM*LGPR.R | 312 | 1258 | 0.63 |
| inter-alpha-trypsin inhibitor heavy chain H1 isoform a precursor | P19827 (ITIH1_HUMAN) | R.GMADQDGLKPTIDKPSEDSPPL EMLGPR.R | 312 | 1258 | 0.60 |
| inter-alpha-trypsin inhibitor heavy chain H2 precursor | P19823 (ITIH2_HUMAN) | K.FDPAKLDQIESVITATSANTQLV LETLAQM*DDLQDFLSK.D | 313 | 1259 | 0.80 |
| inter-alpha-trypsin inhibitor heavy chain H2 precursor | P19823 (ITIH2_HUMAN) | K.KFYNQVSTPLLR.N | 314 | 1260 | 0.76 |
| inter-alpha-trypsin inhibitor heavy chain H2 precursor | P19823 (ITIH2_HUMAN) | K.NILFVIDVSGSM*WGVK.M | 315 | 1261 | 0.68 |
| inter-alpha-trypsin inhibitor heavy chain H2 precursor | P19823 (ITIH2_HUMAN) | K.NILFVIDVSGSMWGVK.M | 315 | 1261 | 0.62 |
| inter-alpha-trypsin inhibitor heavy chain H2 precursor | P19823 (ITIH2_HUMAN) | R.KLGSYEHR.I | 316 | 1262 | 0.72 |
| inter-alpha-trypsin inhibitor heavy chain H2 precursor | P19823 (ITIH2_HUMAN) | R.LSNENHGIAQR.I | 317 | 1024 | 0.66 |
| inter-alpha-trypsin inhibitor heavy chain H2 precursor | P19823 (ITIH2_HUMAN) | R.MATTMIQSK.V | 318 | 1263 | 0.60 |
| inter-alpha-trypsin inhibitor heavy chain H2 precursor | P19823 (ITIH2_HUMAN) | R.SILQM*SLDHHIVTPLTSLVIENE AGDER.M | 319 | 1264 | 0.63 |
| inter-alpha-trypsin inhibitor heavy chain H2 precursor | P19823 (ITIH2_HUMAN) | R.SILQMSLDHHIVTPLTSLVIENEA GDER.M | 319 | 1264 | 0.65 |
| inter-alpha-trypsin inhibitor heavy chain H2 precursor | P19823 (ITIH2_HUMAN) | R.TEVNVLPGAK.V | 320 | 1265 | 0.69 |
| inter-alpha-trypsin inhibitor heavy chain H4 isoform 1 precursor | Q14624 (ITIH4_HUMAN) | K.NVVFVIDK.S | 321 | 1266 | 0.68 |

TABLE 8-continued

| Protein Description | Uniprot ID (name) | Peptide | Full peptide SEQ ID NO: | Core peptide SEQ ID NO: | S_AUC |
|---|---|---|---|---|---|
| inter-alpha-trypsin inhibitor heavy chain H4 isoform 1 precursor | Q14624 (ITIH4_HUMAN) | K.WKETLFSVMPGLK.M | 322 | 1267 | 0.65 |
| inter-alpha-trypsin inhibitor heavy chain H4 isoform 1 precursor | Q14624 (ITIH4_HUMAN) | K.YIFHNFM*ER.L | 323 | 1268 | 0.67 |
| inter-alpha-trypsin inhibitor heavy chain H4 isoform 1 precursor | Q14624 (ITIH4_HUMAN) | R.FAHTVVTSR.V | 324 | 1269 | 0.63 |
| inter-alpha-trypsin inhibitor heavy chain H4 isoform 1 precursor | Q14624 (ITIH4_HUMAN) | R.FKPTLSQQQK.S | 325 | 1270 | 0.60 |
| inter-alpha-trypsin inhibitor heavy chain H4 isoform 1 precursor | Q14624 (ITIH4_HUMAN) | R.IHEDSDSALQLQDFYQEVANPL LTAVTFEYPSNAVEEVTQNNFR.L | 326 | 1271 | 0.64 |
| inter-alpha-trypsin inhibitor heavy chain H4 isoform 1 precursor | Q14624 (ITIH4_HUMAN) | R.MNFRPGVLSSR.Q | 327 | 1272 | 0.63 |
| inter-alpha-trypsin inhibitor heavy chain H4 isoform 1 precursor | Q14624 (ITIH4_HUMAN) | R.NVHSAGAAGSR.M | 328 | 1273 | 0.62 |
| inter-alpha-trypsin inhibitor heavy chain H4 isoform 1 precursor | Q14624 (ITIH4_HUMAN) | R.NVHSGSTFFK.Y | 329 | 1274 | 0.75 |
| inter-alpha-trypsin inhibitor heavy chain H4 isoform 1 precursor | Q14624 (ITIH4_HUMAN) | R.RLGVYELLLK.V | 330 | 1275 | 0.66 |
| kallistatin precursor | P29622 (KAIN_HUMAN) | K.KLELHLPK.F | 331 | 1276 | 0.78 |
| kallistatin precursor | P29622 (KAIN_HUMAN) | R.EIEEVLTPEMLMR.W | 332 | 1277 | 0.60 |
| kininogen-1 isoform 2 precursor | P01042 (KNG1_HUMAN) | K.AATGECTATVGKR.S | 333 | 1278 | 0.67 |
| kininogen-1 isoform 2 precursor | P01042 (KNG1_HUMAN) | K.LGQSLDCNAEVYVVPWEK.K | 334 | 1279 | 0.72 |
| kininogen-1 isoform 2 precursor | P01042 (KNG1_HUMAN) | K.YNSQNQSNNQFVLYR.I | 335 | 1280 | 0.62 |

Significant peptides (AUC>0.6) for Sequest only

TABLE 8-continued

| Protein Description | Uniprot ID (name) | Peptide | Full peptide SEQ ID NO: | Core peptide SEQ ID NO: | S_AUC |
|---|---|---|---|---|---|
| kininogen-1 isoform 2 precursor | P01042 (KNG1_HUMAN) | R.QVVAGLNFR.I | 336 | 1281 | 0.64 |
| leucine-rich alpha-2-glycoprotein precursor | P02750 (A2GL_HUMAN) | K.DLLLPQPDLR.Y | 337 | 1282 | 0.64 |
| leucine-rich alpha-2-glycoprotein precursor | P02750 (A2GL_HUMAN) | R.LHLEGNKLQVLGK.D | 338 | 1283 | 0.76 |
| leucine-rich alpha-2-glycoprotein precursor | P02750 (A2GL_HUMAN) | R.TLDLGENQLETLPPDLLR.G | 339 | 1284 | 0.61 |
| lipopolysaccharide-binding protein precursor | P18428 (LBP_HUMAN) | K.GLQYAAQEGLLALQSELLR.I | 340 | 818 | 0.82 |
| lipopolysaccharide-binding protein precursor | P18428 (LBP_HUMAN) | K.LAEGFPLPLLK.R | 341 | 1285 | 0.66 |
| lumican precursor | P51884 (LUM_HUMAN) | K.SLEYLDLSFNQIAR.L | 342 | 1286 | 0.65 |
| lumican precursor | P51884 (LUM_HUMAN) | R.LKEDAVSAAFK.G | 343 | 1287 | 0.74 |
| m7GpppX diphosphatase | Q96C86 (DCPS_HUMAN) | R.IVFENPDPSDGFVLIPDLK.W | 344 | 1288 | 0.62 |
| matrix metalloproteinase-19 isoform 1 preproprotein | Q99542 (MMP19_HUMAN) | R.VYFFK.G | 345 | 1289 | 0.63 |
| MBT domain-containing protein 1 | Q05BQ5 (MBTD1_HUMAN) | K.WFDYLR.E | 346 | 1290 | 0.65 |
| monocyte differentiation antigen CD14 precursor | P08571 (CD14_HUMAN) | R.LTVGAAQVPAQLLVGALR.V | 347 | 1291 | 0.66 |
| pappalysin-1 preproprotein | Q13219 (PAPP1_HUMAN) | R.VSFSSPLVAISGVALR.S | 348 | 1011 | 0.66 |
| phosphatidylinositol-glycan-specific phospholipase D precursor | P80108 (PHLD_HUMAN) | K.GIVAAFYSGPSLSDKEK.L | 349 | 1292 | 0.71 |
| phosphatidylinositol-glycan-specific phospholipase D precursor | P80108 (PHLD_HUMAN) | R.WYVPVKDLLGIYEK.L | 350 | 1293 | 0.71 |
| pigment epithelium-derived factor precursor | P36955 (PEDF_HUMAN) | K.LQSLFDSPDFSK.I | 351 | 1294 | 0.61 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| pigment epithelium-derived factor precursor | P36955 (PEDF_HUMAN) | R.ALYYDLISSPDIHGTYK.E | 352 | 1295 | 0.72 |
| plasma kallikrein preproprotein | P03952 (KLKB1_HUMAN) | R.CLLFSFLPASSINDMEKR.F | 353 | 1296 | 0.60 |
| plasma protease C1 inhibitor precursor | P05155 (IC1_HUMAN) | K.FQPTLLTLPR.I | 354 | 1018 | 0.70 |
| plasma protease C1 inhibitor precursor | P05155 (IC1_HUMAN) | K.GVTSVSQIFHSPDLAIR.D | 355 | 1016 | 0.66 |
| plasminogen isoform 1 precursor | P00747 (PLMN_HUMAN) | K.VIPACLPSPNYVVADR.T | 356 | 1297 | 0.63 |
| plasminogen isoform 1 precursor | P00747 (PLMN_HUMAN) | R.FVTWIEGVMR.N | 357 | 1298 | 0.60 |
| plasminogen isoform 1 precursor | P00747 (PLMN_HUMAN) | R.HSIFTPETNPR.A | 358 | 1299 | 0.63 |
| platelet basic protein preproprotein | P02775 (CXCL7_HUMAN) | K.GKEESLDSDLYAELR.C | 359 | 1300 | 0.70 |
| platelet glycoprotein V precursor | P40197 (GPV_HUMAN) | K.MVLLEQLFLDHNALR.G | 360 | 1301 | 0.66 |
| platelet glycoprotein V precursor | P40197 (GPV_HUMAN) | R.LVSLDSGLLNSLGALTELQFHR. N | 361 | 1302 | 0.88 |
| pregnancy zone protein precursor | P20742 (PZP_HUMAN) | K.ALLAYAFSLLGK.Q | 362 | 1303 | 0.66 |
| pregnancy zone protein precursor | P20742 (PZP_HUMAN) | K.DLFHCVSFTLPR.I | 363 | 1304 | 0.86 |
| pregnancy zone protein precursor | P20742 (PZP_HUMAN) | K.MLQITNTGFEMK.L | 364 | 1305 | 0.84 |
| pregnancy zone protein precursor | P20742 (PZP_HUMAN) | R.NELIPLIYLENPRR.N | 365 | 1306 | 0.65 |
| pregnancy zone protein precursor | P20742 (PZP_HUMAN) | R.SYIFIDEAHITQSLTWLSQMQK. D | 366 | 1307 | 0.68 |
| pregnancy-specific beta-1-glycoprotein 2 precursor | P11465 (PSG2_HUMAN) | R.SDPVTLNLLHGPDLPR.I | 367 | 1308 | 0.66 |
| pregnancy-specific beta-1-glycoprotein 3 precursor | Q16557 (PSG3_HUMAN) | R.TLFLFGVTK.Y | 368 | 1309 | 0.62 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| pregnancy-specific beta-1-glycoprotein 5 precursor | Q15238 (PSG5_HUMAN) | R.ILILPSVTR.N | 369 | 789 | 0.76 |
| pregnancy-specific beta-1-glycoprotein 6 isoform a | Q00889 (PSG6_HUMAN) | R.SDPVTLNLLPK.L | 370 | 1310 | 0.63 |
| progesterone-induced-blocking factor 1 | Q8WXW3 (PIBF1_HUMAN) | R.VLQLEK.Q | 371 | 1311 | 0.71 |
| protein AMBP preproprotein | P02760 (AMBP_HUMAN) | R.VVAQGVGIPEDSIFTMADR.G | 372 | 1312 | 0.60 |
| protein CBFA2T2 isoform MTGR1b | O43439 (MTG8R_HUMAN) | R.LTEREWADEWKHLDHALNCIM EMVEK.T | 373 | 1313 | 0.70 |
| protein FAM98C | Q17RN3 (FA98C_HUMAN) | R.ALCGGDGAAALREPGAGLR.L | 374 | 1314 | 0.75 |
| protein NLRC3 | Q7RTR2 (NLRC3_HUMAN) | K.ALM*DLLAGKGSQGSQAPQAL DR.T | 375 | 1315 | 0.92 |
| protein Z-dependent protease inhibitor precursor | Q9UK55 (ZPI_HUMAN) | K.MGDHLALEDYLTTDLVETWLR. N | 376 | 1316 | 0.60 |
| prothrombin preproprotein | P00734 (THRB_HUMAN) | K.SPQELLCGASLISDR.W | 377 | 1317 | 0.84 |
| prothrombin preproprotein | P00734 (THRB_HUMAN) | R.LAVTTHGLPCLAWASAQAK.A | 378 | 1318 | 0.62 |
| prothrombin preproprotein | P00734 (THRB_HUMAN) | R.SEGSSVNLSPPLEQCVPDR.G | 379 | 1319 | 0.70 |
| prothrombin preproprotein | P00734 (THRB_HUMAN) | R.SGIECQLWR.S | 380 | 1320 | 0.68 |
| prothrombin preproprotein | P00734 (THRB_HUMAN) | R.TATSEYQTFFNPR.T | 381 | 36 | 0.60 |
| prothrombin preproprotein | P00734 (THRB_HUMAN) | R.VTGWGNLKETWTANVGK.G | 382 | 1321 | 0.69 |
| putative hydroxypyruvate isomerase isoform 1 | Q5T013 (HYI_HUMAN) | R.IHLM*AGR.V | 383 | 1322 | 0.69 |
| putative hydroxypyruvate isomerase isoform 1 | Q5T013 (HYI_HUMAN) | R.IHLMAGR.V | 383 | 1322 | 0.66 |
| ras-like protein family member 10A precursor | Q92737 (RSLAA_HUMAN) | R.PAHPALR.L | 384 | 1323 | 0.71 |
| ras-related GTP-binding protein A | Q7L523 (RRAGA_HUMAN) | K.ISNIIK.Q | 385 | 1324 | 0.82 |

TABLE 8-continued

| Protein Description | Uniprot ID (name) | Peptide | Full peptide SEQ ID NO: | Core peptide SEQ ID NO: | S_AUC |
|---|---|---|---|---|---|
| retinol-binding protein 4 precursor | P02753 (RET4_HUMAN) | K.M*KYWGVASFLQK.G | 386 | 1325 | 0.73 |
| retinol-binding protein 4 precursor | P02753 (RET4_HUMAN) | R.FSGTWYAM*AK.K | 387 | 1326 | 0.63 |
| retinol-binding protein 4 precursor | P02753 (RET4_HUMAN) | R.LLNLDGTCADSYSFVFSR.D | 388 | 1327 | 0.79 |
| retinol-binding protein 4 precursor | P02753 (RET4_HUMAN) | R.LLNNWDVCADMVGTFTDTED PAKFK.M | 389 | 1328 | 0.77 |
| sex hormone-binding globulin isoform 1 precursor | P04278 (SHBG_HUMAN) | R.LFLGALPGEDSSTSFCLNGLWA QGQR.L | 390 | 1329 | 0.66 |
| sex hormone-binding globulin isoform 4 precursor | P04278 (SHBG_HUMAN) | K.DDWFMLGLR.D | 391 | 1330 | 0.60 |
| sex hormone-binding globulin isoform 4 precursor | P04278 (SHBG_HUMAN) | R.SCDVESNPGIFLPPGTQAEFNLR .G | 392 | 1331 | 0.64 |
| sex hormone-binding globulin isoform 4 precursor | P04278 (SHBG_HUMAN) | R.TWDPEGVIFYGDTNPKDDWF M*LGLR.D | 393 | 1332 | 0.65 |
| sex hormone-binding globulin isoform 4 precursor | P04278 (SHBG_HUMAN) | R.TWDPEGVIFYGDTNPKDDWF MLGLR.D | 393 | 1332 | 0.66 |
| signal transducer and activator of transcription 2 | P52630 (STAT2_HUMAN) | R.KFCRDIQDPTQLAEMIFNLLLEE K.R | 394 | 1333 | 0.73 |
| spectrin beta chain, non-erythrocytic 1 | Q13813 (SPTN1_HUMAN) | R.NELIRQEKLEQLAR.R | 395 | 1334 | 0.60 |
| stabilin-1 precursor | Q9NY15 (STAB1_HUMAN) | R.KNLSER.W | 396 | 1335 | 0.88 |
| succinate-semialdehyde dehydrogenase, mitochondrial | P51649 (SSDH_HUMAN) | R.KWYNLMIQNK.D | 397 | 1336 | 0.88 |
| tetranectin precursor | P05452 (TETN_HUMAN) | K.SRLDTLAQEVALLK.E | 398 | 1337 | 0.75 |
| THAP domain-containing protein 6 | Q8TBB0 (THAP6_HUMAN) | K.RLDVNAAGIWEPKK.G | 399 | 1338 | 0.69 |
| thyroxine-binding globulin precursor | P05543 (THBG_HUMAN) | R.SILFLGK.V | 400 | 881 | 0.79 |
| tripartite motif-containing protein 5 | Q9C035 (TRIM5_HUMAN) | R.ELISDLEHRLQGSVM*ELLQGV DGVIK.R | 401 | 1339 | 0.60 |

TABLE 8-continued

Significant peptides (AUC>0.6) for Sequest only

| Protein Description | Uniprot ID (name) | Peptide | Full peptide SEQ ID NO: | Core peptide SEQ ID NO: | S_AUC |
|---|---|---|---|---|---|
| vitamin D-binding protein isoform 1 precursor | P02774 (VTDB_HUMAN) | K.EDFTSLSLVLYSR.K | 1049 | 1340 | 0.66 |
| vitamin D-binding protein isoform 1 precursor | P02774 (VTDB_HUMAN) | K.ELSSFIDKGQELCADYSENTFTEY K.K | 402 | 1341 | 0.67 |
| vitamin D-binding protein isoform 1 precursor | P02774 (VTDB_HUMAN) | K.ELSSFIDKGQELCADYSENTFTEY KK.K | 403 | 1342 | 0.66 |
| vitamin D-binding protein isoform 1 precursor | P02774 (VTDB_HUMAN) | K.EVVSLTEACCAEGADPDCYDTR. T | 404 | 1343 | 0.65 |
| vitamin D-binding protein isoform 1 precursor | P02774 (VTDB_HUMAN) | K.TAMDVFVCTYFMPAAQLPELP DVELPTNKDVCDPGNTK.V | 405 | 1344 | 0.84 |
| vitamin D-binding protein isoform 1 precursor | P02774 (VTDB_HUMAN) | R.RTHLPEVFLSK.V | 406 | 1345 | 0.69 |
| vitamin D-binding protein isoform 1 precursor | P02774 (VTDB_HUMAN) | R.VCSQYAAYGEK.K | 407 | 1346 | 0.66 |
| vitronectin precursor | P04004 (VTNC_HUMAN) | K.LIRDVWGIEGPIDAAFTR.I | 408 | 1347 | 0.61 |
| vitronectin precursor | P04004 (VTNC_HUMAN) | R.DVWGIEGPIDAAFTR.I | 409 | 1348 | 0.63 |
| vitronectin precursor | P04004 (VTNC_HUMAN) | R.ERVYFFK.G | 410 | 1349 | 0.81 |
| vitronectin precursor | P04004 (VTNC_HUMAN) | R.FEDGVLDPDYPR.N | 411 | 1350 | 0.64 |
| vitronectin precursor | P04004 (VTNC_HUMAN) | R.IYISGM*APRPSLAK.K | 412 | 1351 | 0.75 |
| zinc finger protein 142 | P52746 (ZN142_HUMAN) | K.TRFLLR.T | 413 | 1352 | 0.66 |

TABLE 9

Significant peptides (AUC > 0.6) for for X!Tandem only

| Protein description | Uniprot ID (name) | Peptide | Full peptide SEQ ID NO: | Core peptide SEQ ID NO: | XT_AUC |
|---|---|---|---|---|---|
| afamin precursor | P43652 (AFAM_HUMAN) | K.HELTDEELQSLFTNFANVVDK.C | 414 | 823 | 0.65 |
| afamin precursor | P43652 (AFAM_HUMAN) | R.NPFVFAPTLLTVAVHFEEVAK.S | 415 | 1353 | 0.91 |
| alpha-1-antichymotrypsin precursor | P01011 (AACT_HUMAN) | K.ADLSGITGAR.N | 416 | 1354 | 0.67 |

TABLE 9-continued

| Protein description | Uniprot ID (name) | Peptide | Full peptide SEQ ID NO: | Core peptide SEQ ID NO: | XT_AUC |
|---|---|---|---|---|---|
| alpha-1-antichymotrypsin precursor | P01011 (AACT_HUMAN) | K.MEEVEAMLLPETLKR.W | 417 | 1355 | 0.60 |
| alpha-1-antichymotrypsin precursor | P01011 (AACT_HUMAN) | K.WEMPFDPQDTHQSR.F | 418 | 1356 | 0.64 |
| alpha-1-antichymotrypsin precursor | P01011 (AACT_HUMAN) | R.LYGSEAFATDFQDSAAAK.K | 419 | 1357 | 0.62 |
| alpha-1B-glycoprotein precursor | P04217 (A1BG_HUMAN) | K.HQFLLTGDTQGR.Y | 420 | 1358 | 0.72 |
| alpha-1B-glycoprotein precursor | P04217 (A1BG_HUMAN) | K.NGVAQEPVHLDSPAIK.H | 421 | 1359 | 0.63 |
| alpha-1B-glycoprotein precursor | P04217 (A1BG_HUMAN) | K.SLPAPWLSM*APVSWITPGLK.T | 422 | 1360 | 0.72 |
| alpha-1B-glycoprotein precursor | P04217 (A1BG_HUMAN) | K.VTLTCVAPLSGVDFQLRR.G | 423 | 1361 | 0.67 |
| alpha-1B-glycoprotein precursor | P04217 (A1BG_HUMAN) | R.C*EGPIPDVTFELLR.E | 124 | 1084 | 0.67 |
| alpha-1B-glycoprotein precursor | P04217 (A1BG_HUMAN) | R.C*LAPLEGAR.F | 424 | 1362 | 0.79 |
| alpha-1B-glycoprotein precursor | P04217 (A1BG_HUMAN) | R.CLAPLEGAR.F | 424 | 1362 | 0.63 |
| alpha-1B-glycoprotein precursor | P04217 (A1BG_HUMAN) | R.GVTFLLR.R | 425 | 1363 | 0.69 |
| alpha-1B-glycoprotein precursor | P04217 (A1BG_HUMAN) | R.LHDNQNGWSGDSAPVELILSDETL PAPEFSPEPESGR.A | 426 | 1364 | 0.60 |
| alpha-1B-glycoprotein precursor | P04217 (A1BG_HUMAN) | R.TPGAAANLELIFVGPQHAGNYR.C | 427 | 1365 | 0.62 |
| alpha-2-antiplasmin isoform a precursor | P08697 (A2AP_HUMAN) | K.HQM*DLVATLSQLGLQELFQAPDL R.G | 428 | 1366 | 0.61 |
| alpha-2-antiplasmin isoform a precursor | P08697 (A2AP_HUMAN) | R.LCQDLGPGAFR.L | 429 | 1367 | 0.68 |
| alpha-2-antiplasmin isoform a precursor | P08697 (A2AP_HUMAN) | R.WFLLEQPEIQVAHFPFK.N | 430 | 1368 | 0.60 |
| alpha-2-HS-glycoprotein preproprotein | P02765 (FETUA_HUMAN) | K.VWPQQPSGELFEIEIDTLETTCHVL DPTPVAR.C | 431 | 1369 | 0.61 |
| alpha-2-HS-glycoprotein preproprotein | P02765 (FETUA_HUMAN) | R.HTFMGVVSLGSPSGEVSHPR.K | 432 | 1370 | 0.68 |
| alpha-2-HS-glycoprotein preproprotein | P02765 (FETUA_HUMAN) | R.Q*PNCDDPETEEAALVAIDYINQNL PWGYK.H | 433 | 1371 | 0.69 |
| alpha-2-HS-glycoprotein preproprotein | P02765 (FETUA_HUMAN) | R.QPNCDDPETEEAALVAIDYINQNLP WGYK.H | 433 | 1371 | 0.64 |
| alpha-2-HS-glycoprotein preproprotein | P02765 (FETUA_HUMAN) | R.TVVQPSVGAAAGPVVPPCPGR.I | 434 | 1372 | 0.64 |

TABLE 9-continued

| Protein description | Uniprot ID (name) | Peptide | Full peptide SEQ ID NO: | Core peptide SEQ ID NO: | XT_AUC |
|---|---|---|---|---|---|
| angiotensinogen preproprotein | P01019 (ANGT_HUMAN) | K.QPFVQGLALYTPVVLPR.S | 435 | 1373 | 0.73 |
| angiotensinogen preproprotein | P01019 (ANGT_HUMAN) | R.AAM*VGM*LANFLGFR.I | 137 | 1097 | 0.62 |
| apolipoprotein A-IV precursor | P06727 (APOA4_HUMAN) | K.LVPFATELHER.L | 436 | 1374 | 0.64 |
| apolipoprotein A-IV precursor | P06727 (APOA4_HUMAN) | R.LLPHANEVSQK.I | 437 | 1375 | 0.61 |
| apolipoprotein A-IV precursor | P06727 (APOA4_HUMAN) | R.SLAPYAQDTQEKLNHQLEGLTFQM K.K | 438 | 1376 | 0.70 |
| apolipoprotein B-100 precursor | P04114 (APOB_HUMAN) | K.FPEVDVLTK.Y | 439 | 1377 | 0.61 |
| apolipoprotein B-100 precursor | P04114 (APOB_HUMAN) | K.HINIDQFVR.K | 440 | 1378 | 0.70 |
| apolipoprotein B-100 precursor | P04114 (APOB_HUMAN) | K.LLSGGNTLHLVSTTK.T | 441 | 1379 | 0.66 |
| apolipoprotein B-100 precursor | P04114 (APOB_HUMAN) | K.Q*VFLYPEKDEPTYILNIKR.G | 442 | 1380 | 0.81 |
| apolipoprotein B-100 precursor | P04114 (APOB_HUMAN) | K.QVFLYPEKDEPTYILNIKR.G | 442 | 1380 | 0.77 |
| apolipoprotein B-100 precursor | P04114 (APOB_HUMAN) | K.SLHMYANR.L | 443 | 1381 | 0.83 |
| apolipoprotein B-100 precursor | P04114 (APOB_HUMAN) | K.SVSDGIAALDLNAVANK.I | 444 | 1382 | 0.62 |
| apolipoprotein B-100 precursor | P04114 (APOB_HUMAN) | K.SVSLPSLDPASAKIEGNLIFDPNNYL PK.E | 445 | 1383 | 0.67 |
| apolipoprotein B-100 precursor | P04114 (APOB_HUMAN) | K.TEVIPPLIENR.Q | 446 | 1384 | 0.63 |
| apolipoprotein B-100 precursor | P04114 (APOB_HUMAN) | K.VLVDHFGYTK.D | 447 | 1385 | 0.76 |
| apolipoprotein B-100 precursor | P04114 (APOB_HUMAN) | R.TSSFALNLPTLPEVKFPEVDVLTK.Y | 448 | 1386 | 0.62 |
| apolipoprotein C-III precursor | P02656 (APOC3_HUMAN) | R.GWVTDGFSSLKDYWSTVK.D | 449 | 1387 | 0.66 |
| apolipoprotein E precursor | P02649 (APOE_HUMAN) | R.GEVQAMLGQSTEELR.V | 450 | 1388 | 0.81 |
| apolipoprotein E precursor | P02649 (APOE_HUMAN) | R.LAVYQAGAR.E | 451 | 1389 | 0.63 |
| apolipoprotein E precursor | P02649 (APOE_HUMAN) | R.LGPLVEQGR.V | 452 | 1390 | 0.69 |
| attractin isoform 2 preproprotein | O75882 (ATRN_HUMAN) | K.LTLTPWVGLR.K | 453 | 1391 | 0.69 |
| beta-2-glycoprotein 1 precursor | P02749 (APOH_HUMAN) | K.FICPLTGLWPINTLK.C | 454 | 1392 | 0.63 |
| beta-2-glycoprotein 1 precursor | P02749 (APOH_HUMAN) | K.TFYEPGEEITYSCKPGYVSR.G | 455 | 1393 | 0.62 |
| beta-Ala-His dipeptidase precursor | Q96KN2 (CNDP1_HUMAN) | K.MVVSMTLGLHPWIANIDDTQYLA AK.R | 456 | 1394 | 0.81 |

TABLE 9-continued

Significant peptides (AUC > 0.6) for for X!Tandem only

| Protein description | Uniprot ID (name) | Peptide | Full peptide SEQ ID NO: | Core peptide SEQ ID NO: | XT_AUC |
|---|---|---|---|---|---|
| beta-Ala-His dipeptidase precursor | Q96KN2 (CNDP1_HUMAN) | K.VFQYIDLHQDEFVQTLK.E | 457 | 961 | 0.65 |
| biotinidase precursor | P43251 (BTD_HUMAN) | R.TSIYPFLDFM*PSPQVVR.W | 458 | 1395 | 0.79 |
| carboxypeptidase N catalytic chain precursor | P15169 (CBPN_HUMAN) | R.ELMLQLSEFLCEEFR.N | 459 | 1396 | 0.61 |
| ceruloplasmin precursor | P00450 (CERU_HUMAN) | K.AEEEHLGILGPQLHADVGDKVK.I | 460 | 1397 | 0.73 |
| ceruloplasmin precursor | P00450 (CERU_HUMAN) | K.ALYLQYTDETFR.T | 461 | 1398 | 0.64 |
| ceruloplasmin precursor | P00450 (CERU_HUMAN) | K.DVDKEFYLFPTVFDENESLLLEDNIR.M | 462 | 1399 | 0.62 |
| ceruloplasmin precursor | P00450 (CERU_HUMAN) | K.HYYIGIIETTWDYASDHGEK.K | 463 | 1400 | 0.61 |
| ceruloplasmin precursor | P00450 (CERU_HUMAN) | R.EYTDASFTNRK.E | 464 | 1401 | 0.67 |
| ceruloplasmin precursor | P00450 (CERU_HUMAN) | R.HYYIAAEEIIWNYAPSGIDIFTK.E | 465 | 1402 | 0.63 |
| ceruloplasmin precursor | P00450 (CERU_HUMAN) | R.IYHSHIDAPK.D | 466 | 1403 | 0.62 |
| ceruloplasmin precursor | P00450 (CERU_HUMAN) | R.Q*KDVDKEFYLFPTVFDENESLLLEDNIR.M | 467 | 1404 | 0.74 |
| ceruloplasmin precursor | P00450 (CERU_HUMAN) | R.QKDVDKEFYLFPTVFDENESLLLEDNIR.M | 467 | 1404 | 0.65 |
| ceruloplasmin precursor | P00450 (CERU_HUMAN) | R.TYYIAAVEVEWDYSPQR.E | 468 | 1405 | 0.90 |
| coagulation factor IX preproprotein | P00740 (FA9_HUMAN) | R.SALVLQYLR.V | 469 | 1406 | 0.69 |
| coagulation factor V precursor | P12259 (FA5_HUMAN) | K.EFNPLVIVGLSK.D | 470 | 1407 | 0.61 |
| coagulation factor XII precursor | P00748 (FA12_HUMAN) | R.NPDNDIRPWCFVLNR.D | 471 | 1408 | 0.65 |
| coagulation factor XII precursor | P00748 (FA12_HUMAN) | R.VVGGLVALR.G | 472 | 944 | 0.61 |
| complement C1q subcomponent subunit B precursor | P02746 (C1QB_HUMAN) | K.NSLLGMEGANSIFSGFLLFPDMEA.- | 473 | 1409 | 0.64 |
| complement C1q subcomponent subunit B precursor | P02746 (C1QB_HUMAN) | K.VPGLYYFTYHASSR.G | 474 | 1060 | 0.63 |
| complement C1q subcomponent subunit C precursor | P02747 (C1QC_HUMAN) | R.Q*THQPPAPNSLIR.F | 475 | 1410 | 0.60 |
| complement C1r subcomponent precursor | P00736 (C1R_HUMAN) | R.LPVANPQACENWLR.G | 476 | 1411 | 0.72 |
| complement C2 isoform 3 | P06681 (CO2_HUMAN) | K.NQGILEFYGDDIALLK.L | 477 | 1412 | 0.74 |
| complement C2 isoform 3 | P06681 (CO2_HUMAN) | K.RNDYLDIYAIGVGK.L | 478 | 1413 | 0.61 |

TABLE 9-continued

Significant peptides (AUC > 0.6) for for X!Tandem only

| Protein description | Uniprot ID (name) | Peptide | Full peptide SEQ ID NO: | Core peptide SEQ ID NO: | XT_AUC |
|---|---|---|---|---|---|
| complement C2 isoform 3 | P06681 (CO2_HUMAN) | R.QPYSYDFPEDVAPALGTSFSHMLG ATNPTQK.T | 479 | 1414 | 0.78 |
| complement C3 precursor | P01024 (CO3_HUMAN) | R.IHWESASLLR.S | 480 | 1415 | 0.69 |
| complement C4-A isoform 1 | P0C0L4 (CO4A_HUMAN) | K.FACYYPR.V | 481 | 1416 | 0.64 |
| complement C4-A isoform 1 | P0C0L4 (CO4A_HUMAN) | K.LHLETDSLALVALGALDTALYAAGS K.S | 482 | 1417 | 0.74 |
| complement C4-A isoform 1 | P0C0L4 (CO4A_HUMAN) | K.LVNGQSHISLSK.A | 483 | 1418 | 0.64 |
| complement C4-A isoform 1 | P0C0L4 (CO4A_HUMAN) | K.M*RPSTDTITVMVENSHGLR.V | 217 | 1171 | 0.60 |
| complement C4-A isoform 1 | P0C0L4 (CO4A_HUMAN) | K.MRPSTDTITVMVENSHGLR.V | 217 | 1171 | 0.65 |
| complement C4-A isoform 1 | P0C0L4 (CO4A_HUMAN) | K.SCGLHQLLR.G | 484 | 1419 | 0.74 |
| complement C4-A isoform 1 | P0C0L4 (CO4A_HUMAN) | K.VGLSGMAIADVTLLSGFHALR.A | 218 | 1172 | 0.61 |
| complement C4-A isoform 1 | P0C0L4 (CO4A_HUMAN) | K.YVLPNFEVK.I | 485 | 1420 | 0.64 |
| complement C4-A isoform 1 | P0C0L4 (CO4A_HUMAN) | R.ALEILQEEDLIDEDDIPVR.S | 486 | 1421 | 0.64 |
| complement C4-A isoform 1 | P0C0L4 (CO4A_HUMAN) | R.ECVGFEAVQEVPVGLVQPASATLY DYYNPER.R | 487 | 1422 | 0.62 |
| complement C4-A isoform 1 | P0C0L4 (CO4A_HUMAN) | R.EELVYELNPLDHR.G | 488 | 1423 | 0.66 |
| complement C4-A isoform 1 | P0C0L4 (CO4A_HUMAN) | R.STQDTVIALDALSAYWIASHTTEER.G | 489 | 1424 | 0.70 |
| complement C4-A isoform 1 | P0C0L4 (CO4A_HUMAN) | R.VGDTLNLNLR.A | 490 | 1425 | 0.79 |
| complement C4-A isoform 1 | P0C0L4 (CO4A_HUMAN) | R.VHYTVCIWR.N | 491 | 1426 | 0.65 |
| complement C4-B-like preproprotein | P0C0L5 (CO4B_HUMAN) | K.GLCVATPVQLR.V | 216 | 1170 | 1.00 |
| complement C4-B-like preproprotein | P0C0L5 (CO4B_HUMAN) | K.KYVLPNFEVK.I | 492 | 1427 | 0.60 |
| complement C4-B-like preproprotein | P0C0L5 (CO4B_HUMAN) | K.VDFTLSSERDFALLSLQVPLKDAK.S | 493 | 1428 | 0.74 |
| complement C4-B-like preproprotein | P0C0L5 (CO4B_HUMAN) | R.EMSGSPASGIPVK.V | 220 | 1174 | 0.72 |
| complement C4-B-like preproprotein | P0C0L5 (CO4B_HUMAN) | R.GCGEQTM*IYLAPTLAASR.Y | 221 | 1175 | 0.75 |
| complement C4-B-like preproprotein | P0C0L5 (CO4B_HUMAN) | R.NGESVKLHLETDSLALVALGALDTA LYAAGSK.S | 228 | 1182 | 0.85 |
| complement C5 preproprotein | P01031 (CO5_HUMAN) | R.IPLDLVPK.T | 1043 | 1429 | 0.65 |
| complement C5 preproprotein | P01031 (CO5_HUMAN) | R.SYFPESWLWEVHLVPR.R | 494 | 4930 | 0.63 |

TABLE 9-continued

| | | | Full peptide | Core peptide | |
|---|---|---|---|---|---|
| Protein description | Uniprot ID (name) | Peptide | SEQ ID NO: | SEQ ID NO: | XT_AUC |
| complement C5 preproprotein | P01031 (CO5_HUMAN) | R.YGGGFYSTQDTINAIEGLTEYSLLVK.Q | 495 | 1431 | 0.62 |
| complement component C6 precursor | P13671 (CO6_HUMAN) | K.ENPAVIDFELAPIVDLVR.N | 1044 | 893 | 0.63 |
| complement component C8 alpha chain precursor | P07357 (CO8A_HUMAN) | K.YNPVVIDFEMQPIHEVLR.H | 1045 | 1432 | 0.61 |
| complement component C8 alpha chain precursor | P07357 (CO8A_HUMAN) | R.HTSLGPLEAK.R | 496 | 1433 | 0.65 |
| complement component C8 beta chain preproprotein | P07358 (CO8B_HUMAN) | K.C*QHEMDQYWGIGSLASGINLFTN SFEGPVLDHR.Y | 497 | 1434 | 0.61 |
| complement component C8 beta chain preproprotein | P07358 (CO8B_HUMAN) | K.SGFSFGFK.I | 498 | 53 | 0.64 |
| complement component C8 beta chain preproprotein | P07358 (CO8B_HUMAN) | R.DTMVEDLVVLVR.G | 499 | 1435 | 0.77 |
| complement component C8 gamma chain precursor | P07360 (CO8G_HUMAN) | K.ANFDAQQFAGTWLLVAVGSACR.F | 500 | 1436 | 0.63 |
| complement component C8 gamma chain precursor | P07360 (CO8G_HUMAN) | R.AEATTLHVAPQGTAMAVSTFR.K | 501 | 1437 | 0.61 |
| complement component C9 precursor | P02748 (CO9_HUMAN) | R.DVVLTTTFVDDIK.A | 502 | 1438 | 0.73 |
| complement component C9 precursor | P02748 (CO9_HUMAN) | R.RPWNVASLIYETK.G | 503 | 1439 | 0.66 |
| complement factor B preproprotein | P00751 (CFAB_HUMAN) | K.ISVIRPSK.G | 504 | 1440 | 0.70 |
| complement factor B preproprotein | P00751 (CFAB_HUMAN) | K.VASYGVKPR.Y | 505 | 1441 | 0.63 |
| complement factor B preproprotein | P00751 (CFAB_HUMAN) | R.DFHINLFQVLPWLK.E | 506 | 94 | 0.68 |
| complement factor B preproprotein | P00751 (CFAB_HUMAN) | R.DLLYIGK.D | 507 | 1442 | 0.63 |
| complement factor B preproprotein | P00751 (CFAB_HUMAN) | R.GDSGGPLIVHK.R | 1046 | 1443 | 0.63 |
| complement factor B preproprotein | P00751 (CFAB_HUMAN) | R.LEDSVTYHCSR.G | 508 | 1444 | 0.68 |
| complement factor B preproprotein | P00751 (CFAB_HUMAN) | R.LPPTTTCQQQK.E | 509 | 1445 | 0.68 |
| complement factor H isoform a precursor | P08603 (CFAH_HUMAN) | K.CLHPCVISR.E | 510 | 1446 | 0.62 |
| complement factor H isoform a precursor | P08603 (CFAH_HUMAN) | K.CTSTGWIPAPR.C | 260 | 1211 | 0.74 |
| complement factor H isoform a precursor | P08603 (CFAH_HUMAN) | K.IDVHLVPDR.K | 511 | 1447 | 0.66 |

TABLE 9-continued

Significant peptides (AUC > 0.6) for for X!Tandem only

| Protein description | Uniprot ID (name) | Peptide | Full peptide SEQ ID NO: | Core peptide SEQ ID NO: | XT_AUC |
|---|---|---|---|---|---|
| complement factor H isoform a precursor | P08603 (CFAH_HUMAN) | K.IVSSAMEPDREYHFGQAVR.F | 262 | 1213 | 0.67 |
| complement factor H isoform a precursor | P08603 (CFAH_HUMAN) | K.SIDVACHPGYALPK.A | 512 | 1488 | 0.67 |
| complement factor H isoform a precursor | P08603 (CFAH_HUMAN) | K.VSVLCQENYLIQEGEEITCKDGR.W | 513 | 1449 | 0.63 |
| complement factor H isoform a precursor | P08603 (CFAH_HUMAN) | K.WSSPPQCEGLPCK.S | 514 | 1450 | 0.60 |
| complement factor H isoform a precursor | P08603 (CFAH_HUMAN) | R.EIMENYNIALR.W | 267 | 1218 | 0.61 |
| complement factor H isoform a precursor | P08603 (CFAH_HUMAN) | R.RPYFPVAVGK.Y | 266 | 1217 | 0.83 |
| complement factor H isoform a precursor | P08603 (CFAH_HUMAN) | R.WQSIPLCVEK.I | 515 | 1451 | 0.63 |
| complement factor I preproprotein | P05156 (CFAI_HUMAN) | R.YQIWTTVVDWIHPDLKR.I | 516 | 1452 | 0.72 |
| corticosteroid-binding globulin precursor | P08185 (CBG_HUMAN) | K.AVLQLNEEGVDTAGSTGVTLNLTSK PIILR.F | 517 | 1453 | 0.61 |
| corticosteroid-binding globulin precursor | P08185 (CBG_HUMAN) | R.GLASANVDFAFSLYK.H | 518 | 1454 | 0.66 |
| fibrinogen alpha chain isoform alpha-E preproprotein | P02671 (FIBA_HUMAN) | K.TFPGFFSPMLGEFVSETESR.G | 519 | 1455 | 0.62 |
| gelsolin isoform b | P06396 (GELS_HUMAN) | K.FDLVPVPTNLYGDFFTGDAYVILK.T | 520 | 1456 | 0.66 |
| gelsolin isoform b | P06396 (GELS_HUMAN) | K.QTQVSVLPEGGETPLFK.Q | 521 | 1457 | 0.66 |
| gelsolin isoform b | P06396 (GELS_HUMAN) | K.TPSAAYLWVGTGASEAEK.T | 283 | 35 | 0.71 |
| gelsolin isoform b | P06396 (GELS_HUMAN) | R.AQPVQVAEGSEPDGFWEALGGK.A | 522 | 837 | 0.67 |
| gelsolin isoform b | P06396 (GELS_HUMAN) | R.IEGSNKVPVDPATYGQFYGGDSYIIL YNYR.H | 523 | 1458 | 0.60 |
| gelsolin isoform b | P06396 (GELS_HUMAN) | R.VEKFDLVPVPTNLYGDFFTGDAYVI LK.T | 284 | 1232 | 0.73 |
| gelsolin isoform b | P06396 (GELS_HUMAN) | R.VPFDAATLHTSTAMAAQHGMDD DGTGQK.Q | 285 | 1233 | 0.63 |
| glutathione peroxidase 3 precursor | P22352 (GPX3_HUMAN) | K.FLVGPDGIPIMR.W | 524 | 1459 | 0.60 |
| hemopexin precursor | P02790 (HEMO_HUMAN) | K.ALPQPQNVTSLLGCTH.- | 525 | 1460 | 0.63 |
| hemopexin precursor | P02790 (HEMO_HUMAN) | K.SLGPNSCSANGPGLYLIHGPNLYCY SDVEK.L | 526 | 1461 | 0.68 |
| hemopexin precursor | P02790 (HEMO_HUMAN) | R.DGWHSWPIAHQWPQGPSAVDAA FSWEEK.L | 527 | 1462 | 0.63 |
| hemopexin precursor | P02790 (HEMO_HUMAN) | R.GECQAEGVLFFQGDR.E | 528 | 1463 | 0.67 |
| hemopexin precursor | P02790 (HEMO_HUMAN) | R.GECQAEGVLFFQGDREWFWDLAT GTM*K.E | 529 | 1464 | 0.67 |

TABLE 9-continued

| Protein description | Uniprot ID (name) | Peptide | Full peptide SEQ ID NO: | Core peptide SEQ ID NO: | XT_AUC |
|---|---|---|---|---|---|
| hemopexin precursor | P02790 (HEMO_HUMAN) | R.LEKEVGTPHGIILDSVDAAFICPGSS R.L | 530 | 1465 | 0.75 |
| hemopexin precursor | P02790 (HEMO_HUMAN) | R.LWWLDLK.S | 531 | 1466 | 0.62 |
| hemopexin precursor | P02790 (HEMO_HUMAN) | R.WKNFPSPVDAAFR.Q | 532 | 1467 | 0.68 |
| heparin cofactor 2 precursor | P05546 (HEP2_HUMAN) | K.DQVNTFDNIFIAPVGISTAMGMISL GLK.G | 533 | 1468 | 0.60 |
| insulin-like growth factor-binding protein complex acid labile subunit isoform 2 precursor | P35858 (ALS_HUMAN) | K.ANVFVQLPR.L | 534 | 1469 | 0.71 |
| insulin-like growth factor-binding protein complex acid labile subunit isoform 2 precursor | P35858 (ALS_HUMAN) | R.LEALPNSLLAPLGR.L | 535 | 1470 | 0.61 |
| insulin-like growth factor-binding protein complex acid labile subunit isoform 2 precursor | P35858 (ALS_HUMAN) | R.LFQGLGK.L | 536 | 1471 | 0.68 |
| insulin-like growth factor-binding protein complex acid labile subunit isoform 2 precursor | P35858 (ALS_HUMAN) | R.NLIAAVAPGAFLGLK.A | 537 | 1472 | 0.76 |
| insulin-like growth factor-binding protein complex acid labile subunit isoform 2 precursor | P35858 (ALS_HUMAN) | R.TFTPQPPGLER.L | 538 | 1473 | 0.73 |
| inter-alpha-trypsin inhibitor heavy chain H1 isoform a precursor | P19827 (ITIH1_HUMAN) | K.Q*LVHHFEIDVDIFEPQGISK.L | 309 | 1255 | 0.69 |
| inter-alpha-trypsin inhibitor heavy chain H1 isoform a precursor | P19827 (ITIH1_HUMAN) | K.VTFQLTYEEVLK.R | 539 | 1474 | 0.61 |
| inter-alpha-trypsin inhibitor heavy chain H1 isoform a precursor | P19827 (ITIH1_HUMAN) | K.VTFQLTYEEVLKR.N | 540 | 1475 | 0.70 |
| inter-alpha-trypsin inhibitor heavy chain H1 isoform a precursor | P19827 (ITIH1_HUMAN) | R.GIEILNQVQESLPELSNHASILIMLT DGDPTEGVTDR.S | 541 | 1476 | 0.62 |
| inter-alpha-trypsin inhibitor heavy chain H1 isoform a precursor | P19827 (ITIH1_HUMAN) | R.GM*ADQDGLKPTIDKPSEDSPPLE M*LGPR.R | 312 | 1258 | 0.79 |
| inter-alpha-trypsin inhibitor heavy chain H1 isoform a precursor | P19827 (ITIH1_HUMAN) | R.KAAISGENAGLVR.A | 542 | 1477 | 0.78 |
| inter-alpha-trypsin inhibitor heavy chain H2 precursor | P19823 (ITIH2_HUMAN) | K.AGELEVFNGYFVHFFAPDNLDPIPK .N | 543 | 1478 | 0.64 |
| inter-alpha-trypsin inhibitor heavy chain H2 precursor | P19823 (ITIH2_HUMAN) | K.FYNQVSTPLLR.N | 544 | 1479 | 0.68 |

TABLE 9-continued

Significant peptides (AUC > 0.6) for for X!Tandem only

| Protein description | Uniprot ID (name) | Peptide | Full peptide SEQ ID NO: | Core peptide SEQ ID NO: | XT_AUC |
|---|---|---|---|---|---|
| inter-alpha-trypsin inhibitor heavy chain H2 precursor | P19823 (ITIH2_HUMAN) | K.VQFELHYQEVK.W | 545 | 1480 | 0.68 |
| inter-alpha-trypsin inhibitor heavy chain H2 precursor | P19823 (ITIH2_HUMAN) | R.ETAVDGELVVLYDVK.R | 546 | 1481 | 0.63 |
| inter-alpha-trypsin inhibitor heavy chain H2 precursor | P19823 (ITIH2_HUMAN) | R.IYLQPGR.L | 547 | 969 | 0.75 |
| inter-alpha-trypsin inhibitor heavy chain H3 preproprotein | Q06033 (ITIH3_HUMAN) | R.LWAYLTIEQLLEK.R | 548 | 1482 | 0.60 |
| inter-alpha-trypsin inhibitor heavy chain H4 isoform 1 precursor | Q14624 (ITIH4_HUMAN) | K.ITFELVYEELLK.R | 549 | 1483 | 0.60 |
| inter-alpha-trypsin inhibitor heavy chain H4 isoform 1 precursor | Q14624 (ITIH4_HUMAN) | K.LQDRGPDVLTATVSGK.L | 550 | 1484 | 0.67 |
| inter-alpha-trypsin inhibitor heavy chain H4 isoform 1 precursor | Q14624 (ITIH4_HUMAN) | K.TGLLLLSDPDKVTIGLLFWDGRGEG LR.L | 551 | 1485 | 0.63 |
| inter-alpha-trypsin inhibitor heavy chain H4 isoform 1 precursor | Q14624 (ITIH4_HUMAN) | K.WKETLFSVM*PGLK.M | 322 | 1267 | 0.79 |
| inter-alpha-trypsin inhibitor heavy chain H4 isoform 1 precursor | Q14624 (ITIH4_HUMAN) | R.AISGGSIQIENGYFVHYFAPEGLTT M*PK.N | 552 | 1486 | 0.60 |
| inter-alpha-trypsin inhibitor heavy chain H4 isoform 1 precursor | Q14624 (ITIH4_HUMAN) | R.AISGGSIQIENGYFVHYFAPEGLTT MPK.N | 552 | 1486 | 0.65 |
| inter-alpha-trypsin inhibitor heavy chain H4 isoform 1 precursor | Q14624 (ITIH4_HUMAN) | R.ANTVQEATFQMELPK.K | 553 | 1487 | 0.68 |
| inter-alpha-trypsin inhibitor heavy chain H4 isoform 1 precursor | Q14624 (ITIH4_HUMAN) | R.SFAAGIQALGGTNINDAMLMAVQ LLDSSNQEER.L | 554 | 1488 | 0.64 |
| inter-alpha-trypsin inhibitor heavy chain H4 isoform 1 precursor | Q14624 (ITIH4_HUMAN) | R.VQGNDHSATR.E | 555 | 1489 | 0.63 |
| inter-alpha-trypsin inhibitor heavy chain H4 isoform 2 precursor | Q14624 (ITIH4_HUMAN) | K.ITFELVYEELLKR.R | 556 | 1490 | 0.60 |
| inter-alpha-trypsin inhibitor heavy chain H4 isoform 2 precursor | Q14624 (ITIH4_HUMAN) | K.VTIGLLFWDGR.G | 557 | 1491 | 0.65 |
| inter-alpha-trypsin inhibitor heavy chain H4 isoform 2 precursor | Q14624 (ITIH4_HUMAN) | R.LWAYLTIQQLLEQTVSASDADQQA LR.N | 558 | 1492 | 0.68 |
| kallistatin precursor | P29622 (KAIN_HUMAN) | K.LFHTNFYDTVGTIQLINDHVK.K | 559 | 1493 | 0.73 |
| kininogen-1 isoform 2 precursor | P01042 (KNG1_HUMAN) | K.ENFLFLTPDCK.S | 560 | 1494 | 0.64 |
| kininogen-1 isoform 2 precursor | P01042 (KNG1_HUMAN) | K.IYPTVNCQPLGMISLMK.R | 561 | 1495 | 0.64 |

TABLE 9-continued

Significant peptides (AUC > 0.6) for for X!Tandem only

| Protein description | Uniprot ID (name) | Peptide | Full peptide SEQ ID NO: | Core peptide SEQ ID NO: | XT_AUC |
|---|---|---|---|---|---|
| kininogen-1 isoform 2 precursor | P01042 (KNG1_HUMAN) | K.KIYPTVNCQPLGMISLMK.R | 562 | 1496 | 0.78 |
| kininogen-1 isoform 2 precursor | P01042 (KNG1_HUMAN) | K.SLWNGDTGECTDNAYIDIQLR.I | 563 | 1497 | 0.67 |
| lumican precursor | P51884 (LUM_HUMAN) | K.ILGPLSYSK.I | 564 | 1498 | 0.60 |
| N-acetylmuramoyl-L-alanine amidase precursor | Q96PD5 (PGRP2_HUMAN) | K.EYGVVLAPDGSTVAVEPLLAGLEAG LQGR.R | 565 | 1499 | 0.61 |
| N-acetylmuramoyl-L-alanine amidase precursor | Q96PD5 (PGRP2_HUMAN) | R.EGKEYGVVLAPDGSTVAVEPLLAGL EAGLQGR.R | 566 | 1500 | 0.69 |
| N-acetylmuramoyl-L-alanine amidase precursor | Q96PD5 (PGRP2_HUMAN) | R.Q*NGAALTSASILAQQVWGTLVLL QR.L | 567 | 1501 | 0.60 |
| pigment epithelium-derived factor precursor | P36955 (PEDF_HUMAN) | K.IAQLPLTGSMSIIFFLPLK.V | 568 | 1502 | 0.65 |
| pigment epithelium-derived factor precursor | P36955 (PEDF_HUMAN) | R.SSTSPTTNVLLSPLSVATALSALSLG AEQR.T | 569 | 1503 | 0.79 |
| plasma kallikrein preproprotein | P03952 (KLKB1_HUMAN) | K.VAEYMDWILEK.T | 570 | 1504 | 0.62 |
| plasma kallikrein preproprotein | P03952 (KLKB1_HUMAN) | R.C*LLFSFLPASSINDMEKR.F | 353 | 1296 | 0.60 |
| plasma kallikrein preproprotein | P03952 (KLKB1_HUMAN) | R.C*QFFSYATQTFHK.A | 571 | 1505 | 0.60 |
| plasma kallikrein preproprotein | P03952 (KLKB1_HUMAN) | R.CLLFSFLPASSINDMEK.R | 572 | 1506 | 0.76 |
| plasma protease C1 inhibitor precursor | P05155 (IC1_HUMAN) | R.LVLLNAIYLSAK.W | 573 | 1507 | 0.96 |
| pregnancy zone protein precursor | P20742 (PZP_HUMAN) | R.NALFCLESAWNVAK.E | 574 | 1508 | 0.67 |
| pregnancy zone protein precursor | P20742 (PZP_HUMAN) | R.NQGNTWLTAFVLK.T | 133 | 1093 | 0.61 |
| pregnancy-specific beta-1-glycoprotein 9 precursor | Q00887 (PSG9_HUMAN) | R.SNPVILNVLYGPDLPR.I | 575 | 1509 | 0.62 |
| prenylcysteine oxidase 1 precursor | Q9UHG3 (PCYOX_HUMAN) | K.IAIIGAGIGGTSAAYYLR.Q | 576 | 1510 | 0.71 |
| protein AMBP preproprotein | P02760 (AMBP_HUMAN) | K.WYNLAIGSTCPWLK.K | 577 | 1511 | 0.77 |
| protein AMBP preproprotein | P02760 (AMBP_HUMAN) | R.TVAACNLPIVR.G | 578 | 1512 | 0.66 |
| prothrombin preproprotein | P00734 (THRB_HUMAN) | .R.IVEGSDAEIGMSPWQVMLFR.K | 579 | 1513 | 0.62 |
| prothrombin preproprotein | P00734 (THRB_HUMAN) | R.RQECSIPVCGQDQVTVAMTPR.S | 580 | 1514 | 0.69 |
| prothrombin preproprotein | P00734 (THRB_HUMAN) | R.TFGSGEADCGLRPLFEK.K | 581 | 1515 | 0.61 |

TABLE 9-continued

Significant peptides (AUC > 0.6) for for X!Tandem only

| Protein description | Uniprot ID (name) | Peptide | Full peptide SEQ ID NO: | Core peptide SEQ ID NO: | XT_AUC |
|---|---|---|---|---|---|
| retinol-binding protein 4 precursor | P02753 (RET4_HUMAN) | R.FSGTWYAMAK.K | 387 | 1326 | 0.60 |
| retinol-binding protein 4 precursor | P02753 (RET4_HUMAN) | R.LLNNWDVCADMVGTFTDTEDPAK .F | 582 | 1516 | 0.64 |
| serum amyloid P-component precursor | P02743 (SAMP_HUMAN) | R.GYVIIKPLVWV.- | 583 | 976 | 0.62 |
| sex hormone-binding globulin isoform 1 precursor | P04278 (SHBG_HUMAN) | K.VVLSSGSGPGLDLPLVLGLPLQLK.L | 584 | 946 | 0.60 |
| sex hormone-binding globulin isoform 1 precursor | P04278 (SHBG_HUMAN) | R.TWDPEGVIFYGDTNPKDDWFM*L GLR.D | 393 | 1332 | 0.75 |
| sex hormone-binding globulin isoform 1 precursor | P04278 (SHBG_HUMAN) | R.TWDPEGVIFYGDTNPKDDWFMLG LR.D | 393 | 1332 | 0.74 |
| thrombospondin-1 precursor | P07996 (TSP1_HUMAN) | K.GFLLLASLR.Q | 585 | 1517 | 0.70 |
| thyroxine-binding globulin precursor | P05543 (THBG_HUMAN) | K.AVLHIGEK.G | 586 | 817 | 0.85 |
| thyroxine-binding globulin precursor | P05543 (THBG_HUMAN) | K.FSISATYDLGATLLK.M | 587 | 1518 | 0.65 |
| thyroxine-binding globulin precursor | P05543 (THBG_HUMAN) | K.KELELQIGNALFIGK.H | 588 | 1519 | 0.61 |
| thyroxine-binding globulin precursor | P05543 (THBG_HUMAN) | K.MSSINADFAFNLYR.R | 589 | 1520 | 0.67 |
| transforming growth factor-beta-induced protein ig-h3 precursor | Q15582 (BGH3_HUMAN) | R.LTLLAPLNSVFK.D | 590 | 1041 | 0.65 |
| transthyretin precursor | P02766 (TTHY_HUMAN) | R.GSPAINVAVHVFR.K | 591 | 1521 | 0.67 |
| uncharacterized protein C3orf20 isoform 1 | Q8ND61 (CC020_HUMAN) | K.MPSHLMLAR.K | 592 | 1522 | 0.64 |
| vitamin D-binding protein isoform 1 precursor | P02774 (VTDB_HUMAN) | K.ELPEHTVK.L | 593 | 87 | 0.75 |
| vitamin D-binding protein isoform 1 precursor | P02774 (VTDB_HUMAN) | K.EYANQFMWEYSTNYGQAPLSLLVS YTK.S | 594 | 1523 | 0.69 |
| vitamin D-binding protein isoform 1 precursor | P02774 (VTDB_HUMAN) | K.HLSLLTTLSNR.V | 595 | 81 | 0.65 |
| vitamin D-binding protein isoform 1 precursor | P02774 (VTDB_HUMAN) | K.HQPQEFPTYVEPTNDEICEAFR.K | 596 | 1524 | 0.64 |
| vitamin D-binding protein isoform 1 precursor | P02774 (VTDB_HUMAN) | K.LAQKVPTADLEDVLPLAEDITNILSK.C | 597 | 1525 | 0.73 |
| vitamin D-binding protein isoform 1 precursor | P02774 (VTDB_HUMAN) | K.LCDNLSTK.N | 598 | 1526 | 0.70 |

TABLE 9-continued

Significant peptides (AUC > 0.6) for for X!Tandem only

| Protein description | Uniprot ID (name) | Peptide | Full peptide SEQ ID NO: | Core peptide SEQ ID NO: | XT_AUC |
|---|---|---|---|---|---|
| vitamin D-binding protein isoform 1 precursor | P02774 (VTDB_HUMAN) | K.LCMAALK.H | 599 | 1527 | 0.63 |
| vitamin D-binding protein isoform 1 precursor | P02774 (VTDB_HUMAN) | K.SCESNSPFPVHPGTAECCTK.E | 600 | 1528 | 0.63 |
| vitamin D-binding protein isoform 1 precursor | P02774 (VTDB_HUMAN) | K.SYLSMVGSCCTSASPTVCFLK.E | 601 | 1529 | 0.61 |
| vitamin D-binding protein isoform 1 precursor | P02774 (VTDB_HUMAN) | K.TAMDVFVCTYFM*PAAQLPELPDV ELPTNK.D | 602 | 1530 | 0.61 |
| vitamin D-binding protein isoform 1 precursor | P02774 (VTDB_HUMAN) | K.VLEPTLK.S | 603 | 920 | 0.69 |
| vitamin D-binding protein isoform 1 precursor | P02774 (VTDB_HUMAN) | R.KFPSGTFEQVSQLVK.E | 604 | 1531 | 0.66 |
| vitamin D-binding protein isoform 1 precursor | P02774 (VTDB_HUMAN) | R.THLPEVFLSK.V | 605 | 1532 | 0.62 |
| vitamin D-binding protein isoform 1 precursor | P02774 (VTDB_HUMAN) | R.TSALSAK.S | 606 | 1533 | 0.74 |
| vitronectin precursor | P04004 (VTNC_HUMAN) | R.GQYCYELDEK.A | 607 | 1534 | 0.73 |
| vitronectin precursor | P04004 (VTNC_HUMAN) | R.M*DWLVPATCEPIQSVFFFSGDK.Y | 608 | 1535 | 0.64 |
| vitronectin precursor | P04004 (VTNC_HUMAN) | R.Q*PQFISR.D | 609 | 1536 | 0.63 |

TABLE 10

Significant peptides (AUC > 0.6) for both X!Tandem and Sequest

| Protein description | Uniprot ID (name) | Peptide | Full peptide SEQ ID NO: | Full peptide SEQ ID NO: | XT_AUC | S_AUC |
|---|---|---|---|---|---|---|
| afamin precursor | P43652 (AFAM_HUMAN) | K.HFQNLGK.D | 610 | 831 | 0.74 | 0.61 |
| afamin precursor | P43652 (AFAM_HUMAN) | R.RHPDLSIPELL R.I | 611 | 1537 | 0.67 | 0.63 |
| afamin precursor | P43652 (AFAM_HUMAN) | R.TINPAVDHCC K.T | 612 | 1538 | 0.66 | 0.86 |
| alpha-1-antichymotrypsin precursor | P01011 (AACT_HUMAN) | K.ITDLIKDLDSQ TMMVLVNYIFF K.A | 120 | 1081 | 0.71 | 0.73 |
| alpha-1-antichymotrypsin precursor | P01011 (AACT_HUMAN) | R.DYNLNDILLQ LGIEEAFTSK.A | 613 | 1539 | 0.74 | 0.62 |
| alpha-1-antichymotrypsin precursor | P01011 (AACT_HUMAN) | R.GTHVDLGLAS ANVDFAFSLYK.Q | 614 | 1540 | 0.76 | 0.61 |

TABLE 10-continued

| Protein description | Uniprot ID (name) | Peptide | Full peptide SEQ ID NO: | Full peptide SEQ ID NO: | XT_AUC | S_AUC |
|---|---|---|---|---|---|---|
| alpha-1B-glycoprotein precursor | P04217 (A1BG_HUMAN) | K.SLPAPWLSMA PVSWITPGLK.T | 422 | 1360 | 0.71 | 0.65 |
| alpha-2-antiplasmin isoform a precursor | P08697 (A2AP_HUMAN) | K.GFPIKEDFLEQ SEQLFGAKPVSL TGK.Q | 615 | 1541 | 0.66 | 0.69 |
| alpha-2-antiplasmin isoform a precursor | P08697 (A2AP_HUMAN) | K.HQMDLVATL SQLGLQELFQAP DLR.G | 428 | 1366 | 0.67 | 0.60 |
| alpha-2-antiplasmin isoform a precursor | P08697 (A2AP_HUMAN) | R.QLTSGPNQEQ VSPLTLLK.L | 616 | 1542 | 0.66 | 0.61 |
| alpha-2-HS-glycoprotein preproprotein | P02765 (FETUA_HUMAN) | R.AQLVPLPPST YVEFTVSGTDC VAK.E | 617 | 1543 | 0.64 | 0.63 |
| angiotensinogen preproprotein | P01019 (ANGT_HUMAN) | K.DPTFIPAPIQA K.T | 618 | 857 | 0.69 | 0.69 |
| angiotensinogen preproprotein | P01019 (ANGT_HUMAN) | R.FM*QAVTGW K.T | 619 | 1544 | 0.65 | 0.65 |
| antithrombin-III precursor | P01008 (ANT3_HUMAN) | K.ANRPFLVFIR.E | 620 | 92 | 0.72 | 0.60 |
| antithrombin-III precursor | P01008 (ANT3_HUMAN) | K.GDDITMVLIL PKPEK.S | 621 | 1545 | 0.69 | 0.68 |
| antithrombin-III precursor | P01008 (ANT3_HUMAN) | R.DIPMNPMCIY R.S | 622 | 1546 | 0.63 | 0.78 |
| apolipoprotein A-IV precursor | P06727 (APOA4_HUMAN) | K.KLVPFATELH ER.L | 623 | 1547 | 0.65 | 0.77 |
| apolipoprotein A-IV precursor | P06727 (APOA4_HUMAN) | K.SLAELGGHLD QQVEEFR.R | 624 | 1548 | 0.60 | 0.75 |
| apolipoprotein B-100 precursor | P04114 (APOB_HUMAN) | K.ALYWVNGQV PDGVSK.V | 625 | 1549 | 0.61 | 0.63 |
| apolipoprotein B-100 precursor | P04114 (APOB_HUMAN) | K.FIIPGLK.L | 626 | 1550 | 0.64 | 0.68 |
| apolipoprotein B-100 precursor | P04114 (APOB_HUMAN) | K.FSVPAGIVIPS FQALTAR.F | 627 | 1551 | 0.63 | 0.63 |
| apolipoprotein B-100 precursor | P04114 (APOB_HUMAN) | K.IEGNLIFDPNN YLPK.E | 628 | 8 | 0.63 | 0.65 |
| apolipoprotein B-100 precursor | P04114 (APOB_HUMAN) | K.LNDLNSVLV MPTFHVPFTDL QVPSCK.L | 629 | 1522 | 0.91 | 0.88 |
| apolipoprotein B-100 precursor | P04114 (APOB_HUMAN) | K.VELEVPQLCS FILK.T | 630 | 1553 | 0.60 | 0.61 |
| apolipoprotein B-100 precursor | P04114 (APOB_HUMAN) | K.VNWEEEAAS GLLTSLK.D | 631 | 1554 | 0.60 | 0.73 |
| apolipoprotein B-100 precursor | P04114 (APOB_HUMAN) | R.ATLYALSHAV NNYHK.T | 632 | 1555 | 0.78 | 0.80 |
| apolipoprotein B-100 precursor | P04114 (APOB_HUMAN) | R.TGISPLALIK.G | 633 | 866 | 0.64 | 0.77 |
| apolipoprotein B-100 precursor | P04114 (APOB_HUMAN) | R.TLQGIPQMIG EVIR.K | 634 | 1556 | 0.65 | 0.66 |
| apolipoprotein C-III precursor | P02656 (APOC3_HUMAN) | K.DALSSVQESQ VAQQAR.G | 635 | 91 | 0.80 | 0.69 |

TABLE 10-continued

| | | | Full peptide SEQ ID NO: | Full peptide SEQ ID NO: | | |
|---|---|---|---|---|---|---|
| Protein description | Uniprot ID (name) | Peptide | | | XT_AUC | S_AUC |
| Significant peptides (AUC > 0.6) for both X!Tandem and Sequest | | | | | | |
| apolipoprotein C-IV precursor | P55056 (APOC4_HUMAN) | R.DGWQWFWSP STFR.G | 636 | 1557 | 0.63 | 0.67 |
| apolipoprotein E precursor | P02649 (APOE_HUMAN) | K.VQAAVGTSA APVPSDNH.- | 637 | 1558 | 0.70 | 0.72 |
| apolipoprotein E precursor | P02649 (APOE_HUMAN) | R.WELALGR.F | 638 | 1559 | 0.88 | 0.60 |
| beta-2-microglobulin precursor | P61769 (B2MG_HUMAN) | K.SNFLNCYVSG FHPSDIEVDLLK.N | 639 | 1560 | 0.60 | 0.70 |
| bone marrow proteoglycan isoform 1 preproprotein | P13727 (PRG2_HUMAN) | R.GGHCVALCT R.G | 640 | 1561 | 0.83 | 0.86 |
| carboxypeptidase B2 preproprotein | Q96IY4 (CBPB2_HUMAN) | R.LVDFYVMPV VNVDGYDYSW K.K | 641 | 1562 | 0.61 | 0.65 |
| carboxypeptidase B2 preproprotein | Q96IY4 (CBPB2_HUMAN) | R.YTHGHGSETL YLAPGGGDDWI YDLGIK.Y | 642 | 1563 | 0.60 | 0.68 |
| carboxypeptidase N subunit 2 precursor | P22792 (CPN2_HUMAN) | K.LSNNALSGLP QGVFGK.L | 643 | 1564 | 0.65 | 0.67 |
| carboxypeptidase N subunit 2 precursor | P22792 (CPN2_HUMAN) | K.TLNLAQNLLA QLPEELFHPLTS LQTLK.L | 644 | 1565 | 0.67 | 0.69 |
| carboxypeptidase N subunit 2 precursor | P22792 (CPN2_HUMAN) | R.WLNVQLSPR.Q | 645 | 1566 | 0.74 | 0.67 |
| ceruloplasmin precursor | P00450 (CERU_HUMAN) | K.GDSVVWYLF SAGNEADVHGI YFSGNTYLWR.G | 646 | 1567 | 0.90 | 0.72 |
| ceruloplasmin precursor | P00450 (CERU_HUMAN) | K.MYYSAVDPT K.D | 647 | 1568 | 0.70 | 0.82 |
| ceruloplasmin precursor | P00450 (CERU_HUMAN) | R.GPEEEHLGIL GPVIWAEVGDTI R.V | 648 | 1569 | 0.60 | 0.65 |
| ceruloplasmin precursor | P00450 (CERU_HUMAN) | R.IDTINLFPATL FDAYMVAQNP GEWMLSCQNL NHLK.A | 195 | 1153 | 0.66 | 0.70 |
| ceruloplasmin precursor | P00450 (CERU_HUMAN) | R.SGAGTEDSAC IPWAYYSTVDQ VKDLYSGLIGPL IVCR.R | 649 | 1570 | 0.88 | 0.92 |
| cholinesterase precursor | P06276 (CHLE_HUMAN) | K.IFFPGVSEFGK .E | 650 | 1571 | 0.70 | 0.63 |
| cholinesterase precursor | P06276 (CHLE_HUMAN) | R.AILQSGSFNAP WAVTSLYEAR.N | 651 | 1572 | 0.75 | 0.77 |
| chorionic gonadotropin, beta polypeptide 8 precursor | P01233 (CGHB_HUMAN) | R.VLQGVLPALP QVVCNYR.D | 652 | 1573 | 0.60 | 0.75 |
| chorionic somatomammotropin hormone 2 isoform 2 precursor | P01243 (CSH_HUMAN) | R.ISLLLIESWLE PVR.F | 653 | 32 | 0.83 | 0.63 |
| coagulation factor XII precursor | P00748 (FA12_HUMAN) | R.LHEAFSPVSY QHDLALLR.L | 654 | 940 | 0.60 | 0.66 |

TABLE 10-continued

Significant peptides (AUC > 0.6) for both X!Tandem and Sequest

| Protein description | Uniprot ID (name) | Peptide | Full peptide SEQ ID NO: | Full peptide SEQ ID NO: | XT_AUC | S_AUC |
|---|---|---|---|---|---|---|
| coagulation factor XII precursor | P00748 (FA12_HUMAN) | R.TTLSGAPCQP WASEATYR.N | 655 | 1574 | 0.69 | 0.82 |
| complement C1q subcomponent subunit A precursor | P02745 (C1QA_HUMAN) | K.GLFQVVSGG MVLQLQQGDQ VWVEKDPK.K | 656 | 1575 | 0.65 | 0.60 |
| complement C1r subcomponent precursor | P00736 (C1R_HUMAN) | K.VLNYVDWIK K.E | 657 | 1576 | 0.80 | 0.76 |
| complement C1s subcomponent precursor | P09871 (C1S_HUMAN) | K.SNALDIIFQTD LTGQK.K | 658 | 1577 | 0.62 | 0.77 |
| complement C4-A isoform 1 | P0C0L4 (CO4A_HUMAN) | K.EGAIHREELV YELNPLDHR.G | 659 | 1578 | 0.76 | 0.75 |
| complement C4-A isoform 1 | P0C0L4 (CO4A_HUMAN) | K.ITQVLHFTK.D | 660 | 1579 | 0.63 | 0.62 |
| complement C4-A isoform 1 | P0C0L4 (CO4A_HUMAN) | K.SHALQLNNR.Q | 661 | 1580 | 0.66 | 0.71 |
| complement C4-A isoform 1 | P0C0L4 (CO4A_HUMAN) | R.AVGSGATFSH YYYM*ILSR.G | 662 | 1581 | 0.65 | 0.60 |
| complement C4-A isoform 1 | P0C0L4 (CO4A_HUMAN) | R.EPFLSCCQFA ESLR.K | 663 | 1582 | 0.64 | 0.72 |
| complement C4-A isoform 1 | P0C0L4 (CO4A_HUMAN) | R.GHLFLQTDQP IYNPGQR.V | 664 | 1583 | 0.63 | 0.76 |
| complement C4-A isoform 1 | P0C0L4 (CO4A_HUMAN) | R.GLEEELQFSL GSK.I | 665 | 1584 | 0.68 | 0.68 |
| complement C4-A isoform 1 | P0C0L4 (CO4A_HUMAN) | R.GSFEFPVGDA VSK.V | 666 | 1585 | 0.67 | 0.70 |
| complement C4-A isoform 1 | P0C0L4 (CO4A_HUMAN) | R.LLATLCSAEV CQCAEGK.C | 667 | 1586 | 0.61 | 0.71 |
| complement C4-A isoform 1 | P0C0L4 (CO4A_HUMAN) | R.VQQPDCREPF LSCCQFAESLRK .K | 668 669 | 1587 1588 | 0.65 | 0.83 |
| complement C4-A isoform 1 | P0C0L4 (CO4A_HUMAN) | R.YIYGKPVQGV AYVR.F | | | 0.82 | 0.76 |
| complement C5 preproprotein | P01031 (CO5_HUMAN) | K.ITHYNYLILSK .G | 670 | 1589 | 0.66 | 0.69 |
| complement C5 preproprotein | P01031 (CO5_HUMAN) | R.ENSLYLTAFT VIGIR.K | 671 | 1590 | 0.60 | 0.68 |
| complement C5 preproprotein | P01031 (CO5_HUMAN) | R.KAFDICPLVK.I | 672 | 1591 | 0.77 | 0.65 |
| complement C5 preproprotein | P01031 (CO5_HUMAN) | R.VDDGVASFVL NLPSGVTVLEFN VK.T | 673 | 1592 | 0.68 | 0.61 |
| complement component C6 precursor | P13671 (CO6_HUMAN) | K.TFSEWLESVK ENPAVIDFELAP IVDLVR.N | 674 | 1593 | 0.94 | 0.64 |
| complement component C6 precursor | P13671 (CO6_HUMAN) | R.IFDDFGTHYF TSGSLGGVYDL LYQFSSEELK.N | 675 | 1594 | 0.78 | 0.75 |
| complement component C7 precursor | P10643 (CO7_HUMAN) | K.ELSHLPSLYD YSAYR.R | 676 | 1595 | 0.69 | 0.71 |

TABLE 10-continued

| | | | Full peptide SEQ ID | Full peptide SEQ ID | | |
|---|---|---|---|---|---|---|
| Protein description | Uniprot ID (name) | Peptide | NO: | NO: | XT_AUC | S_AUC |
| complement component C7 precursor | P10643 (CO7_HUMAN) | R.RYSAWAESV TNLPQVIK.Q | 677 | 1596 | 0.71 | 0.70 |
| complement component C8 alpha chain precursor | P07357 (CO8A_HUMAN) | K.YNPVVIDFEM *QPIHEVLR.H | 1045 | 1432 | 0.68 | 0.73 |
| complement component C8 beta chain preproprotein | P07358 (CO8B_HUMAN) | K.VEPLYELVTA TDFAYSSTVR.Q | 678 | 56 | 0.69 | 0.70 |
| complement component C8 beta chain preproprotein | P07358 (CO8B_HUMAN) | R.SLM*LHYEFL QR.V | 679 | 1597 | 0.61 | 0.65 |
| complement component C8 gamma chain precursor | P07360 (CO8G_HUMAN) | K.YGFCEAADQF HVLDEVRR.- | 46 | 1598 | 0.78 | 0.76 |
| complement component C8 gamma chain precursor | P07360 (CO8G_HUMAN) | R.FLQEQGHR.A | 681 | 23 | 0.63 | 0.69 |
| complement component C8 gamma chain precursor | P07360 (CO8G_HUMAN) | R.KLDGICWQV R.Q | 682 | 1599 | 0.75 | 0.70 |
| complement component C8 gamma chain precursor | P07360 (CO8G_HUMAN) | R.SLPVSDSVLS GFEQR.V | 683 | 59 | 0.70 | 0.60 |
| complement component C9 precursor | P02748 (CO9_HUMAN) | R.GTVIDVTDFV NWASSINDAPV LISQK.L | 684 | 1600 | 0.68 | 0.69 |
| complement factor B preproprotein | P00751 (CFAB_HUMAN) | K.NPREDYLDV YVFGVGPLVNQ VNINALASK.K | 685 | 1601 | 0.72 | 0.77 |
| complement factor B preproprotein | P00751 (CFAB_HUMAN) | R.GDSGGPLIVH KR.S | 686 | 1602 | 0.60 | 0.76 |
| complement factor B preproprotein | P00751 (CFAB_HUMAN) | R.HVIILMTDGL HNM*GGDPITVI DEIR.D | 687 | 1603 | 0.60 | 0.64 |
| complement factor B preproprotein | P00751 (CFAB_HUMAN) | R.KNPREDYLDV YVFGVGPLVNQ VNINALASK.K | 668 | 1604 | 0.63 | 0.63 |
| complement factor H isoform a precursor | P08603 (CFAH_HUMAN) | K.SCDIPVFMNA R.T | 689 | 1605 | 0.62 | 0.71 |
| complement factor H isoform a precursor | P08603 (CFAH_HUMAN) | K.SPPEISHGVV AHMSDSYQYGE EVTYK.C | 690 | 1606 | 0.88 | 0.88 |
| complement factor H isoform a precursor | P08603 (CFAH_HUMAN) | K.TDCLSLPSFE NAIPMGEKK.D | 691 | 1607 | 0.61 | 0.66 |
| complement factor I preproprotein | P05156 (CFAI_HUMAN) | K.RAQLGDLPW QVAIK.D | 692 | 1608 | 0.71 | 0.74 |
| complement factor I preproprotein | P05156 (CFAI_HUMAN) | K.SLECLHPGTK.F | 693 | 1609 | 0.64 | 0.81 |
| complement factor I preproprotein | P05156 (CFAI_HUMAN) | R.TMGYQDFAD VVCYTQK.A | 694 | 1610 | 0.73 | 0.75 |
| extracellular matrix protein 1 isoform 3 precursor | Q16610 (ECM1_HUMAN) | R.ELLALIQLER.E | 695 | 1611 | 0.69 | 0.65 |

TABLE 10-continued

| Protein description | Uniprot ID (name) | Peptide | Full peptide SEQ ID NO: | Full peptide SEQ ID NO: | XT_AUC | S_AUC |
|---|---|---|---|---|---|---|
| gelsolin isoform a precursor | P06396 (GELS_HUMAN) | R.VPEARPNSMV VEHPEFLK.A | 696 | 1612 | 0.76 | 0.62 |
| glutathione peroxidase 3 precursor | P22352 (GPX3_HUMAN) | R.LFWEPMK.V | 697 | 1613 | 0.69 | 0.67 |
| hemopexin precursor | P02790 (HEMO_HUMAN) | R.DVRDYFMPCP GR.G | 698 | 1614 | 0.70 | 0.72 |
| heparin cofactor 2 precursor | P05546 (HEP2_HUMAN) | K.DALENIDPAT QMMILNCIYFK.G | 699 | 1615 | 0.61 | 0.65 |
| heparin cofactor 2 precursor | P05546 (HEP2_HUMAN) | K.GLIKDALENI DPATQMMILNC IYFK.G | 700 | 1616 | 0.64 | 0.64 |
| heparin cofactor 2 precursor | P05546 (HEP2_HUMAN) | K.QFPILLDFK.T | 701 | 1617 | 0.61 | 0.69 |
| heparin cofactor 2 precursor | P05546 (HEP2_HUMAN) | R.VLKDQVNTF DNIFIAPVGISTA MGMISLGLK.G | 1047 | 1245 | 0.88 | 0.75 |
| insulin-like growth factor-binding protein complex acid labile subunit isoform 2 precursor | P35858 (ALS_HUMAN) | R.AFWLDVSHN R.L | 702 | 1618 | 0.61 | 0.82 |
| inter-alpha-trypsin inhibitor heavy chain H1 isoform a precursor | P19827 (ITIH1_HUMAN) | K.ADVQAHGEG QEFSITCLVDEE EMKK.L | 703 | 1619 | 0.61 | 0.74 |
| inter-alpha-trypsin inhibitor heavy chain H1 isoform a precursor | P19827 (ITIH1_HUMAN) | K.ILGDM*QPGD YFDLVLFGTR.V | 704 | 1620 | 0.71 | 0.63 |
| inter-alpha-trypsin inhibitor heavy chain H1 isoform a precursor | P19827 (ITIH1_HUMAN) | K.ILGDMQPGDY FDLVLFGTR.V | 704 | 1620 | 0.68 | 0.60 |
| inter-alpha-trypsin inhibitor heavy chain H1 isoform a precursor | P19827 (ITIH1_HUMAN) | K.NVVFVIDISGS MR.G | 705 | 1621 | 0.76 | 0.83 |
| inter-alpha-trypsin inhibitor heavy chain H1 isoform a precursor | P19827 (ITIH1_HUMAN) | K.TAFISDFAVT ADGNAFIGDIKD K.V | 706 | 1622 | 0.74 | 0.63 |
| inter-alpha-trypsin inhibitor heavy chain H1 isoform a precursor | P19827 (ITIH1_HUMAN) | R.GHMLENHVE R.L | 707 | 1623 | 0.78 | 0.80 |
| inter-alpha-trypsin inhibitor heavy chain H1 isoform a precursor | P19827 (ITIH1_HUMAN) | R.GM*ADQDGL KPTIDKPSEDSP PLEMLGPR.R | 312 | 1258 | 0.61 | 0.62 |
| inter-alpha-trypsin inhibitor heavy chain H1 isoform a precursor | P19827 (ITIH1_HUMAN) | R.LWAYLTIQEL LAK.R | 708 | 1052 | 0.68 | 0.62 |
| inter-alpha-trypsin inhibitor heavy chain H1 isoform a precursor | P19827 (ITIH1_HUMAN) | R.NHM*QYEIVI K.V | 709 | 1624 | 0.67 | 0.65 |
| inter-alpha-trypsin inhibitor heavy chain H2 precursor | P19823 (ITIH2_HUMAN) | K.AHVSFKPTVA QQR.I | 710 | 1625 | 0.75 | 0.61 |
| inter-alpha-trypsin inhibitor heavy chain H2 precursor | P19823 (ITIH2_HUMAN) | K.ENIQDNISLFS LGM*GFDVDYD FLKR.L | 711 | 1626 | 0.80 | 0.93 |

TABLE 10-continued

Significant peptides (AUC > 0.6) for both X!Tandem and Sequest

| Protein description | Uniprot ID (name) | Peptide | Full peptide SEQ ID NO: | Full peptide SEQ ID NO: | XT_AUC | S_AUC |
|---|---|---|---|---|---|---|
| inter-alpha-trypsin inhibitor heavy chain H2 precursor | P19823 (ITIH2_HUMAN) | K.ENIQDNISLFS LGMGFDVDYDF LKR.L | 711 | 1626 | 0.63 | 0.80 |
| inter-alpha-trypsin inhibitor heavy chain H2 precursor | P19823 (ITIH2_HUMAN) | K.HLEVDVWVIE PQGLR.F | 712 | 1627 | 0.61 | 0.61 |
| inter-alpha-trypsin inhibitor heavy chain H2 precursor | P19823 (ITIH2_HUMAN) | K.LWAYLTINQL LAER.S | 713 | 1628 | 0.69 | 0.62 |
| inter-alpha-trypsin inhibitor heavy chain H2 precursor | P19823 (ITIH2_HUMAN) | R.AEDHFSVIDF NQNIR.T | 714 | 1629 | 0.65 | 0.63 |
| inter-alpha-trypsin inhibitor heavy chain H2 precursor | P19823 (ITIH2_HUMAN) | R.FLHVPDTFEG HFDGVPVISK.G | 715 | 1630 | 0.66 | 0.62 |
| inter-alpha-trypsin inhibitor heavy chain H4 isoform 1 precursor | Q14624 (ITIH4_HUMAN) | K.ILDDLSPR.D | 716 | 852 | 0.67 | 0.65 |
| inter-alpha-trypsin inhibitor heavy chain H4 isoform 1 precursor | Q14624 (ITIH4_HUMAN) | K.IPKPEASFSPR.R | 717 | 928 | 0.69 | 0.77 |
| inter-alpha-trypsin inhibitor heavy chain H4 isoform 1 precursor | Q14624 (ITIH4_HUMAN) | K.SPEQQETVLD GNLIIR.Y | 718 | 71 | 0.63 | 0.69 |
| inter-alpha-trypsin inhibitor heavy chain H4 isoform 1 precursor | Q14624 (ITIH4_HUMAN) | K.YIFHNFMER.L | 323 | 1268 | 0.66 | 0.61 |
| inter-alpha-trypsin inhibitor heavy chain H4 isoform 1 precursor | Q14624 (ITIH4_HUMAN) | R.FSSHVGGTLG QFYQEVLWGSP AASDDGRR.T | 719 | 1631 | 0.69 | 0.71 |
| inter-alpha-trypsin inhibitor heavy chain H4 isoform 1 precursor | Q14624 (ITIH4_HUMAN) | R.GPDVLTATVS GK.L | 720 | 1632 | 0.63 | 0.82 |
| inter-alpha-trypsin inhibitor heavy chain H4 isoform 1 precursor | Q14624 (ITIH4_HUMAN) | R.NMEQFQVSVS VAPNAK.I | 721 | 1633 | 0.78 | 0.60 |
| inter-alpha-trypsin inhibitor heavy chain H4 isoform 1 precursor | Q14624 (ITIH4_HUMAN) | R.RLDYQEGPPG VEISCWSVEL.- | 722 | 1634 | 0.68 | 0.62 |
| kallistatin precursor | P29622 (KAIN_HUMAN) | K.IVDLVSELKK.D | 723 | 1635 | 0.75 | 0.67 |
| kallistatin precursor | P29622 (KAIN_HUMAN) | R.VGSALFLSHN LK.F | 724 | 1636 | 0.70 | 0.74 |
| kininogen-1 isoform 2 precursor | P01042 (KNG1_HUMAN) | K.IYPTVNCQPL GM*ISLM*K.R | 561 | 1495 | 0.89 | 0.62 |
| kininogen-1 isoform 2 precursor | P01042 (KNG1_HUMAN) | K.TVGSDTFYSF K.Y | 725 | 1637 | 0.61 | 0.68 |
| kininogen-1 isoform 2 precursor | P01042 (KNG1_HUMAN) | R.DIPTNSPELEE TLTHTITK.L | 726 | 1638 | 0.61 | 0.76 |
| kininogen-1 isoform 2 precursor | P01042 (KNG1_HUMAN) | R.VQVVAGK.K | 727 | 1639 | 0.67 | 0.71 |

TABLE 10-continued

| Protein description | Uniprot ID (name) | Peptide | Full peptide SEQ ID NO: | Full peptide SEQ ID NO: | XT_AUC | S_AUC |
|---|---|---|---|---|---|---|
| | | Significant peptides (AUC > 0.6) for both X!Tandem and Sequest | | | | |
| lumican precursor | P51884 (LUM_HUMAN) | R.FNALQYLR.L | 728 | 1640 | 0.68 | 0.76 |
| macrophage colony-stimulating factor 1 receptor precursor | P09603 (CSF1_HUMAN) | K.VIPGPPALTLV PAELVR.I | 729 | 1641 | 0.68 | 0.60 |
| monocyte differentiation antigen CD14 precursor | P08571 (CD14_HUMAN) | K.ITGTMPPLPLE ATGLALSSLR.L | 730 | 1642 | 0.80 | 0.67 |
| N-acetylmuramoyl-L-alanine amidase precursor | Q96PD5 (PGRP2_HUMAN) | K.EFTEAFLGCP AIHPR.C | 731 | 1643 | 0.62 | 0.64 |
| N-acetylmuramoyl-L-alanine amidase precursor | Q96PD5 (PGRP2_HUMAN) | R.RVINLPLDSM AAPWETGDTFP DVVAIAPDVR.A | 732 | 1644 | 0.63 | 0.62 |
| phosphatidylinositol-glycan-specific phospholipase D precursor | P80108 (PHLD_HUMAN) | R.GVFFSVNSWT PDSMSFIYK.A | 733 | 1645 | 0.67 | 0.78 |
| pigment epithelium-derived factor precursor | P36955 (PEDF_HUMAN) | K.EIPDEISILLLGVAHF K.G | 734 | 1646 | 0.63 | 0.61 |
| pigment epithelium-derived factor precursor | P36955 (PEDF_HUMAN) | K.IAQLPLTGSM*SIIF FLPLK.V | 568 | 1502 | 0.79 | 0.61 |
| pigment epithelium-derived factor precursor | P36955 (PEDF_HUMAN) | K.TVQAVLTVPK.L | 735 | 826 | 0.75 | 0.79 |
| pigment epithelium-derived factor precursor | P36955 (PEDF_HUMAN) | R.ALYYDLISSPDIHGT YKELLDTVTAPQK.N | 736 | 1647 | 0.60 | 0.73 |
| pigment epithelium-derived factor precursor | P36955 (PEDF_HUMAN) | R.DTDTGALLFIGK.I | 737 | 854 | 0.85 | 0.62 |
| plasminogen isoform 1 precursor | P00747 (PLMN_HUMAN) | R.ELRPWCFTTDPNK R.W | 738 | 1648 | 0.70 | 0.68 |
| plasminogen isoform 1 precursor | P00747 (PLMN_HUMAN) | R.TECFITGWGETQGT FGAGLLK.E | 739 | 1649 | 0.63 | 0.68 |
| platelet basic protein preproprotein | P02775 (CXCL7_HUMAN) | K.GTHCNQVEVIATLK .D | 740 | 1650 | 0.60 | 0.61 |
| pregnancy zone protein precursor | P20742 (PZP_HUMAN) | K.AVGYLITGYQR.Q | 741 | 69 | 0.87 | 0.73 |
| pregnancy zone protein precursor | P20742 (PZP_HUMAN) | R.AVDQSVLLM*KPE AELSVSSVYNLLTVK.D | 742 | 1651 | 0.64 | 0.62 |
| pregnancy zone protein precursor | P20742 (PZP_HUMAN) | R.IQHPFTVEEFVLPK.F | 743 | 934 | 0.66 | 0.74 |
| pregnancy zone protein precursor | P20742 (PZP_HUMAN) | R.NELIPLIYLENPR.R | 744 | 1652 | 0.61 | 0.61 |
| protein AMBP preproprotein | P02760 (AMBP_HUMAN) | R.AFIQLWAFDAVK.G | 745 | 52 | 0.72 | 0.67 |
| proteoglycan 4 isoform B precursor | Q92954 (PRG4_HUMAN) | K.GFGGLTGQIVAALS TAK.Y | 746 | 1653 | 0.70 | 0.72 |
| prothrombin preproprotein | P00734 (THRB_HUMAN) | K.YGFYTHVFR.L | 747 | 50 | 0.70 | 0.63 |
| prothrombin preproprotein | P00734 (THRB_HUMAN) | R.IVEGSDAEIGM*SP WQVMLFR.K | 579 | 1513 | 0.63 | 0.71 |

TABLE 10-continued

| | | | Full peptide SEQ ID | Full peptide SEQ ID | | |
|---|---|---|---|---|---|---|
| Protein description | Uniprot ID (name) | Peptide | NO: | NO: | XT_AUC | S_AUC |
| retinol-binding protein 4 precursor | P02753 (RET4_HUMAN) | K.KDPEGLFLQDNIVA EFSVDETGQMSATAK .G | 748 | 1654 | 0.67 | 0.67 |
| thyroxine-binding globulin precursor | P05543 (THBG_HUMAN) | K.AQWANPFDPSKTE DSSSFLIDK.T | 749 | 1655 | 0.67 | 0.80 |
| thyroxine-binding globulin precursor | P05543 (THBG_HUMAN) | K.GWVDLFVPK.F | 750 | 1656 | 0.67 | 0.64 |
| thyroxine-binding globulin precursor | P05543 (THBG_HUMAN) | R.SFM*LLILER.S | 751 | 1657 | 0.65 | 0.68 |
| thyroxine-binding globulin precursor | P05543 (THBG_HUMAN) | R.SFMLLILER.S | 751 | 1657 | 0.64 | 0.62 |
| vitamin D-binding protein isoform 1 precursor | P02774 (VTDB_HUMAN) | K.EFSHLGKEDFTSLSL VLYSR.K | 752 | 1658 | 0.74 | 0.61 |
| vitamin D-binding protein isoform 1 precursor | P02774 (VTDB_HUMAN) | K.EYANQFM*WEYST NYGQAPLSLLVSYTK.S | 594 | 1523 | 0.73 | 0.61 |
| vitamin D-binding protein isoform 1 precursor | P02774 (VTDB_HUMAN) | K.HQPQEFPTYVEPTN DEICEAFRK.D | 753 | 1659 | 0.67 | 0.69 |
| vitamin D-binding protein isoform 1 precursor | P02774 (VTDB_HUMAN) | K.SYLSM*VGSCCTSA SPTVCFLK.E | 601 | 1529 | 0.63 | 0.62 |
| vitamin D-binding protein isoform 1 precursor | P02774 (VTDB_HUMAN) | K.TAM*DVFVCTYFM PAAQLPELPDVELPT NK.D | 602 | 1530 | 0.63 | 0.60 |
| vitamin D-binding protein isoform 1 precursor | P02774 (VTDB_HUMAN) | K.VPTADLEDVLPLAE DITNILSK.C | 754 | 1660 | 0.70 | 0.71 |
| vitronectin precursor | P04004 (VTNC_HUMAN) | K.AVRPGYPK.L | 755 | 1661 | 0.68 | 0.77 |
| vitronectin precursor | P04004 (VTNC_HUMAN) | R.MDWLVPATCEPIQ SVFFFSGDK.Y | 608 | 1535 | 0.67 | 0.65 |
| zinc-alpha-2-glycoprotein precursor | P25311 (ZA2G_HUMAN) | K.EIPAWVPFDPAAQI TK.Q | 756 | 1662 | 0.63 | 0.67 |

The differentially expressed proteins identified by the hypothesis-independent strategy above, not already present in our MRM-MS assay, were candidates for incorporation into the MRM-MS assay. Two additional proteins (AFP, PGH1) of functional interest were also selected for MRM development. Candidates were prioritized by AUC and biological function, with preference give for new pathways. Sequences for each protein of interest, were imported into Skyline software which generated a list of tryptic peptides, m/z values for the parent ions and fragment ions, and an instrument-specific collision energy (McLean et al. Bioinformatics (2010) 26 (7): 966-968; McLean et al. Anal. Chem (2010) 82 (24): 10116-10124).

The list was refined by eliminating peptides containing cysteines and methionines, and by using the shotgun data to select the charge state(s) and a subset of potential fragment ions for each peptide that had already been observed on a mass spectrometer.

After prioritizing parent and fragment ions, a list of transitions was exported with a single predicted collision energy. Approximately 100 transitions were added to a single MRM run. For development, MRM data was collected on either a QTRAP 5500 (AB Sciex) or a 6490 QQQ (Agilent). Commercially available human female serum (from pregnant and non-pregnant donors), was depleted and processed to tryptic peptides, as described above, and used to "scan" for peptides of interest. In some cases, purified synthetic peptides were used for further optimization. For development, digested serum or purified synthetic peptides were separated with a 15 min acetonitrile gradient at 100 ul/min on a 2.1×50 mM Poroshell 120 EC-C18 column (Agilent) at 40° C.

The MS/MS data was imported back into Skyline, where all chromatograms for each peptide were overlayed and used to identify a consensus peak corresponding to the peptide of interest and the transitions with the highest intensities and the least noise. Table 11, contains a list of the most intensely observed candidate transitions and peptides for transfer to the MRM assay.

TABLE 11

Candidate peptides and transitions for transferring to the MRM assay

| Protein | Peptide | Full peptide SEQ ID NO: | Core peptide SEQ ID NO: | m/z, charge | fragment ion, m/z, charge, rank | area |
|---|---|---|---|---|---|---|
| alpha-1-antichymotrypsin | K.ADLSGITGAR.N | 416 | 1354 | 480.7591++ | S [y7] - 661.3628+[1] | 1437602 |
| | | | | | G [y6] - 574.3307+[2] | 637584 |
| | | | | | T [y4] - 404.2252+[3] | 350392 |
| | | | | | L [y8] - 774.4468+[4] | 191870 |
| | | | | | G [y3] - 303.1775+[5] | 150575 |
| | | | | | I [y5] - 517.3093+[6] | 97828 |
| alpha-1-antichymotrypsin | K.EQLSLLDR.F | 117 | 1078 | 487.2693++ | S [y5] - 603.3461+[1] | 345602 |
| | | | | | L [y6] - 716.4301+[2] | 230046 |
| | | | | | L [y4] - 516.3140+[3] | 143874 |
| | | | | | D [y2] - 290.1459+[4] | 113381 |
| | | | | | D [y2] - 290.1459+[5] | 113381 |
| | | | | | Q [b2] - 258.1084+[6] | 78157 |
| alpha-1-antichymotrypsin | K.ITLLSALVETR.T | 121 | 1082 | 608.3690++ | S [y7] - 775.4308+[1] | 1059034 |
| | | | | | L [y8] - 888.5149+[2] | 541969 |
| | | | | | T [b2] - 215.1390+[3] | 408819 |
| | | | | | L [y9] - 1001.5990+[4] | 438441 |
| | | | | | V [y4] - 504.2776+[5] | 311293 |
| | | | | | L [y5] - 617.3617+[6] | 262544 |
| | | | | | L [b3] - 328.2231+[7] | 197526 |
| | | | | | T [y2] - 276.1666+[8] | 212816 |
| | | | | | E [y3] - 405.2092+[9] | 207163 |
| alpha-1-antichymotrypsin | R.EIGELYLPK.F | 123 | 895 | 531.2975++ | G [y7] - 819.4611+[2] | 977307 |
| | | | | | L [y5] - 633.3970+[3] | 820582 |
| | | | | | Y [y4] - 520.3130+[4] | 400762 |
| | | | | | L [y3] - 357.2496+[5] | 498958 |
| | | | | | P [y2] - 244.1656+[1] | 1320591 |
| | | | | | I [b2] - 243.1339+[6] | 303268 |
| | | | | | G [b3] - 300.1554+[7] | 305120 |
| alpha-1-antichymotrypsin | R.GTHVDLGLASA NVDFAFSLYK.Q | 614 | 1540 | 742.3794+++ | D [y8] - 990.4931+[1] | 154927 |
| | | | | | L [b8] - 793.4203+[2] | 51068 |
| | | | | | D [b5] - 510.2307+[3] | 45310 |
| | | | | | F [y7] - 875.4662+[4] | 42630 |
| | | | | | A [b9] - 864.4574+[5] | 43355 |
| | | | | | S [y4] - 510.2922+[6] | 45310 |
| | | | | | F [y5] - 657.3606+[7] | 37330 |
| | | | | | V [y9] - 1089.5615+[8] | 32491 |
| | | | | | G [b7] - 680.3362+[9] | 38185 |
| | | | | | Y [y2] - 310.1761+[10] | 36336 |
| | | | | | N [b12] - 1136.5695+[11] | 16389 |
| | | | | | S [b10] - 951.4894+[12] | 16365 |
| | | | | | L [b6] - 623.3148+[13] | 13687 |
| | | | | | L [y3] - 423.2602+[14] | 17156 |
| | | | | | V [b4] - 395.2037+[15] | 10964 |
| alpha-1-antichymotrypsin | R.NLAVSQVVHK.A | 757 | 1663 | 547.8195++ | A [y8] - 867.5047+[1] | 266203 |
| | | | | | L [b2] - 228.1343+[2] | 314232 |
| | | | | | V [y7] - 796.4676+[3] | 165231 |
| | | | | | A [b3] - 299.1714+[4] | 173694 |
| | | | | | S [y6] - 697.3991+[5] | 158512 |
| | | | | | H [y2] - 284.1717+[6] | 136431 |
| | | | | | V [b4] - 398.2398+[7] | 36099 |
| | | | | | S [b5] - 485.2718+[8] | 23836 |
| | | | | 365.5487+++ | S [y6] - 697.3991+[1] | 223443 |
| | | | | | V [y3] - 383.2401+[2] | 112952 |
| | | | | | V [y4] - 482.3085+[3] | 84872 |
| | | | | | Q [y5] - 610.3671+[4] | 30835 |
| inter-alpha-trypsin inhibitor heavy chain H1 | K.AAISGENAGLVR .A | 758 | 1664 | 579.3173++ | S [y9] - 902.4690+[1] | 518001 |
| | | | | | G [y8] - 815.4370+[2] | 326256 |
| | | | | | N [y6] - 629.3729+[3] | 296670 |
| | | | | | S [b4] - 343.1976+[4] | 258172 |
| inter-alpha-trypsin inhibitor heavy chain H1 | K.GSLVQASEANL QAAQDFVR.G | 308 | 900 | 668.6763+++ | A [y7] - 806.4155+[1] | 304374 |
| | | | | | A [y6] - 735.3784+[2] | 193844 |
| | | | | | V [b4] - 357.2132+[3] | 294094 |
| | | | | | F [y3] - 421.2558+[4] | 167816 |
| | | | | | A [b6] - 556.3089+[5] | 149216 |
| | | | | | L [b11] - 535.7775++[6] | 156882 |

TABLE 11-continued

Candidate peptides and transitions for transferring to the MRM assay

| Protein | Peptide | Full peptide SEQ ID NO: | Core peptide SEQ ID NO: | m/z, charge | fragment ion, m/z, charge, rank | area |
|---|---|---|---|---|---|---|
| | | | | | A [b13] - 635.3253++[7] | 249287 |
| | | | | | A [y14] - 760.3786++[8] | 123723 |
| | | | | | F [b17] - 865.9208++[9] | 23057 |
| inter-alpha-trypsin inhibitor heavy chain H1 | K.TAFISDFAVTAD GNAFIGDIK.D | 759 | 1665 | 1087.0442++ | G [y4] - 432.2453+[1] | 22362 |
| | | | | | I [y5] - 545.3293+[2] | 8319 |
| | | | | | A [b8] - 853.4090+[3] | 7006 |
| | | | | | G [y9] - 934.4993+[4] | 6755 |
| | | | | | F [y6] - 692.3978+[5] | 6193 |
| | | | | | V [b9] - 952.4775+[6] | 9508 |
| inter-alpha-trypsin inhibitor heavy chain H1 | K.VTYDVSR.D | 760 | 1666 | 420.2165++ | Y [y5] - 639.3097+[1] | 609348 |
| | | | | | T [b2] - 201.1234+[2] | 792556 |
| | | | | | D [y4] - 476.2463+[3] | 169546 |
| | | | | | V [y3] - 361.2194+[4] | 256946 |
| | | | | | Y [y5] - 320.1585++[5] | 110608 |
| | | | | | S [y2] - 262.1510+[6] | 50268 |
| | | | | | Y [b3] - 182.5970++[7] | 10947 |
| | | | | | D [b4] - 479.2136+[8] | 13662 |
| inter-alpha-trypsin inhibitor heavy chain H1 | R.EVAFDLEIPK.T | 761 | 1667 | 580.8135++ | P [y2] - 244.1656+[1] | 2032509 |
| | | | | | D [y6] - 714.4032+[2] | 672749 |
| | | | | | A [y8] - 932.5088+[3] | 390837 |
| | | | | | L [y5] - 599.3763+[4] | 255527 |
| | | | | | F [y7] - 861.4716+[5] | 305087 |
| inter-alpha-trypsin inhibitor heavy chain H1 | R.LWAYLTIQELLA K.R | 708 | 1052 | 781.4531++ | W [b2] - 300.1707+[1] | 602601 |
| | | | | | A [b3] - 371.2078+[2] | 356967 |
| | | | | | T [y8] - 915.5510+[3] | 150419 |
| | | | | | Y [b4] - 534.2711+[4] | 103449 |
| | | | | | I [y7] - 814.5033+[5] | 72044 |
| | | | | | Q [y6] - 701.4192+[6] | 66989 |
| | | | | | L [b5] - 647.3552+[7] | 99820 |
| | | | | | E [y5] - 573.3606+[8] | 44843 |
| inter-alpha-trypsin inhibitor heavy chain H2 | K.FYNQVSTPLLR.N | 544 | 1479 | 669.3642++ | S [y6] - 686.4196+[1] | 367330 |
| | | | | | V [y7] - 785.4880+[2] | 182396 |
| | | | | | P [y4] - 498.3398+[3] | 103638 |
| | | | | | Y [b2] - 311.1390+[4] | 52172 |
| | | | | | Q [b4] - 553.2405+[5] | 54270 |
| | | | | | N [b3] - 425.1819+[6] | 34567 |
| inter-alpha-trypsin inhibitor heavy chain H2 | K.HLEVDVWVIEP QGLR.F | 712 | 1627 | 597.3247+++ | I [y7] - 812.4625+[1] | 206996 |
| | | | | | P [y5] - 570.3358+[2] | 303693 |
| | | | | | E [y6] - 699.3784+[3] | 126752 |
| | | | | | P [y5] - 285.6715++[4] | 79841 |
| inter-alpha-trypsin inhibitor heavy chain H2 | K.TAGLVR.S | 762 | 1668 | 308.6925++ | A [b2] - 173.0921+[1] | 460019 |
| | | | | | G [y4] - 444.2929+[2] | 789068 |
| | | | | | V [y2] - 274.1874+[3] | 34333 |
| | | | | | G [b3] - 230.1135+[4] | 15169 |
| | | | | | L [y3] - 387.2714+[5] | 29020 |
| inter-alpha-trypsin inhibitor heavy chain H2 | R.IYLQPGR.L | 547 | 969 | 423.7452++ | L [y5] - 570.3358+[1] | 638209 |
| | | | | | P [y3] - 329.1932+[2] | 235194 |
| | | | | | Y [b2] - 277.1547+[3] | 266889 |
| | | | | | Q [y4] - 457.2518+[4] | 171389 |
| inter-alpha-trypsin inhibitor heavy chain H2 | R.LSNENHGIAQR.I | 317 | 1024 | 413.5461+++ | N [y9] - 519.7574++[1] | 325409 |
| | | | | | N [y7] - 398.2146++[2] | 39521 |
| | | | | | G [y5] - 544.3202+[3] | 139598 |
| | | | | | S [b2] - 201.1234+[4] | 54786 |
| | | | | | E [y8] - 462.7359++[5] | 30623 |
| inter-alpha-trypsin inhibitor heavy chain H2 | R.SLAPTAAAKR.R | 763 | 1669 | 415.2425++ | A [y7] - 629.3617+[1] | 582421 |
| | | | | | L [b2] - 201.1234+[2] | 430584 |
| | | | | | P [y6] - 558.3246+[3] | 463815 |
| | | | | | A [b3] - 272.1605+[4] | 204183 |
| | | | | | T [y5] - 461.2718+[5] | 47301 |
| inter-alpha-trypsin inhibitor heavy chain H3 | K.EVSFDVELPK.T | 764 | 1670 | 581.8032++ | P [y2] - 244.1656+[1] | 132304 |
| | | | | | V [b2] - 229.1183+[2] | 48895 |
| | | | | | L [y3] - 357.2496+[3] | 20685 |

TABLE 11-continued

Candidate peptides and transitions for transferring to the MRM assay

| Protein | Peptide | Full peptide SEQ ID NO: | Core peptide SEQ ID NO: | m/z, charge | fragment ion, m/z, charge, rank | area |
|---|---|---|---|---|---|---|
| inter-alpha-trypsin inhibitor heavy chain H3 | K.IQENVR.N | 765 | 1671 | 379.7114++ | E [y4] - 517.2729+[1] | 190296 |
| | | | | | E [b3] - 371.1925+[2] | 51697 |
| | | | | | Q [b2] - 242.1499+[3] | 54241 |
| | | | | | N [y3] - 388.2303+[4] | 21156 |
| | | | | | V [y2] - 274.1874+[5] | 8309 |
| inter-alpha-trypsin inhibitor heavy chain H3 | R.ALDLSLK.Y | 766 | 14 | 380.2342++ | D [y5] - 575.3399+[1] | 687902 |
| | | | | | L [b2] - 185.1285+[2] | 241010 |
| | | | | | L [y2] - 260.1969+[3] | 29365 |
| inter-alpha-trypsin inhibitor heavy chain H3 | R.LIQDAVTGLTVN GQITGDK.R | 767 | 807 | 972.0258++ | V [b6] - 640.3665+[1] | 139259 |
| | | | | | G [b8] - 798.4356+[2] | 53886 |
| | | | | | G [y7] - 718.3730+[3] | 12518 |
| pigment epithelium-derived factor precursor | K.SSFVAPLEK.S | 768 | 1672 | 489.2687++ | A [y5] - 557.3293+[1] | 13436 |
| | | | | | V [y6] - 656.3978+[2] | 9350 |
| | | | | | F [y7] - 803.4662+[3] | 6672 |
| | | | | | P [y4] - 486.2922+[4] | 6753 |
| pigment epithelium-derived factor precursor | K.TVQAVLTVPK.L | 735 | 826 | 528.3266++ | Q [y8] - 855.5298+[1] | 26719 |
| | | | | | V [b2] - 201.1234+[2] | 21239 |
| | | | | | Q [y8] - 428.2686++[3] | 16900 |
| | | | | | A [y7] - 727.4713+[4] | 9518 |
| | | | | | L [y5] - 557.3657+[5] | 5108 |
| | | | | | Q [b3] - 329.1819+[6] | 5450 |
| | | | | | V [y6] - 656.4341+[7] | 4391 |
| pigment epithelium-derived factor precursor | R.ALYYDLISSPDIH GTYK.E | 352 | 1295 | 652.6632+++ | Y [y15] - 886.4305++[1] | 78073 |
| | | | | | Y [y14] - 804.8988++[2] | 26148 |
| pigment epithelium-derived factor precursor | R.DTDTGALLFIGK.I | 737 | 854 | 625.8350++ | G [y8] - 818.5135+[1] | 25553 |
| | | | | | T [b2] - 217.0819+[2] | 22716 |
| | | | | | T [b4] - 217.0819++[3] | 22716 |
| | | | | | L [y5] - 577.3708+[4] | 11600 |
| | | | | | I [y3] - 317.2183+[5] | 11089 |
| | | | | | A [b6] - 561.2151+[6] | 6956 |
| pigment epithelium-derived factor precursor | K.ELLDTVTAPQK.N | 769 | 1673 | 607.8350++ | T [y5] - 544.3089+[1] | 17139 |
| | | | | | D [y8] - 859.4520+[2] | 17440 |
| | | | | | L [y9] - 972.5360+[3] | 14344 |
| | | | | | A [y4] - 443.2613+[4] | 11474 |
| | | | | | T [y7] - 744.4250+[5] | 10808 |
| | | | | | V [y6] - 643.3774+[6] | 9064 |
| pregnancy-specific beta-1-glycoprotein 1 | K.FQLPGQK.L | 770 | 62 | 409.2320++ | L [y5] - 542.3297+[1] | 116611 |
| | | | | | P [y4] - 429.2456+[2] | 91769 |
| | | | | | Q [b2] - 276.1343+[3] | 93301 |
| pregnancy-specific beta-1-glycoprotein 1 | R.DLYHYITSYVVD GEIIIYGPAYSGR.E | 771 | 971 | 955.4762+++ | G [y7] - 707.3471+[1] | 5376 |
| | | | | | Y [y8] - 870.4104+[2] | 3610 |
| | | | | | P [y6] - 650.3257+[3] | 2770 |
| | | | | | I [y9] - 983.4945+[4] | 3361 |
| pregnancy-specific beta-1-glycoprotein 11 | K.LFIPQITPK.H | 772 | 1022 | 528.8262++ | P [y6] - 683.4087+[1] | 39754 |
| | | | | | F [b2] - 261.1598+[2] | 29966 |
| | | | | | I [y7] - 796.4927+[3] | 13162 |
| pregnancy-specific beta-1-glycoprotein 11 | NSATGEESSTSLTIR | 773 | 773 | 776.8761++ | E [b7] - 689.2737+[1] | 11009 |
| | | | | | T [y6] - 690.4145+[2] | 11284 |
| | | | | | L [y4] - 502.3348+[3] | 2265 |
| | | | | | S [y7] - 389.2269++[4] | 1200 |
| | | | | | T [y3] - 389.2507+[5] | 1200 |
| | | | | | I [y2] - 288.2030+[6] | 2248 |
| pregnancy-specific beta-1-glycoprotein 2 | K.FQQSGQNLFIP QITTK.H | 774 | 1674 | 617.3317+++ | F [y8] - 474.2817++[1] | 43682 |
| | | | | | G [y12] - 680.3852++[2] | 24166 |
| | | | | | S [b4] - 491.2249+[3] | 23548 |
| | | | | | Q [b3] - 404.1928+[4] | 17499 |
| | | | | | I [y4] - 462.2922+[5] | 17304 |
| | | | | | F [b9] - 525.7538++[6] | 17206 |
| | | | | | I [b10] - 582.2958++[7] | 16718 |
| | | | | | L [b8] - 452.2196++[8] | 16490 |

TABLE 11-continued

Candidate peptides and transitions for transferring to the MRM assay

| Protein | Peptide | Full peptide SEQ ID NO: | Core peptide SEQ ID NO: | m/z, charge | fragment ion, m/z, charge, rank | area |
|---|---|---|---|---|---|---|
| | | | | | P [y6] - 344.2054++[9] | 16198 |
| | | | | | G [b5] - 548.2463+[10] | 15320 |
| pregnancy-specific beta-1-glycoprotein 2 | IHPSYTNYR | 775 | 775 | 575.7856++ | N [b7] - 813.3890+[1] | 16879 |
| | | | | | Y [b5] - 598.2984+[2] | 18087 |
| | | | | | T [y4] - 553.2729+[3] | 2682 |
| pregnancy-specific beta-1-glycoprotein 2 | FQLSETNR | 776 | 776 | 497.7513++ | L [y6] - 719.3682+[1] | 358059 |
| | | | | | S [y5] - 606.2842+[2] | 182330 |
| | | | | | Q [b2] - 276.1343+[3] | 292482 |
| pregnancy-specific beta-1-glycoprotein 3 | VSAPSGTGHLPGLNPL | 777 | 777 | 506.2755+++ | T [b7] - 300.6530++[1] | 25346 |
| | | | | | H [y8] - 860.4989+[2] | 12159 |
| | | | | | H [y8] - 430.7531++[3] | 15522 |
| pregnancy-specific beta-1-glycoprotein 3 | EDAGSYTLHIVK | 778 | 778 | 666.8433++ | Y [b6] - 623.2307+[1] | 23965 |
| | | | | | Y [y7] - 873.5193+[2] | 21686 |
| | | | | | L [b8] - 837.3625+[3] | 4104 |
| | | | | | A [b3] - 316.1139+[4] | 1987 |
| pregnancy-specific beta-1-glycoprotein 4 | R.TLFIFGVTK.Y | 779 | 842 | 513.3051++ | F [y7] - 811.4713+[1] | 62145 |
| | | | | | L [b2] - 215.1390+[2] | 31687 |
| | | | | | F [y5] - 551.3188+[3] | 972 |
| pregnancy-specific beta-1-glycoprotein 4 | NYTYIWWLNGQSLPVSPR | 780 | 780 | 1097.5576++ | W [b6] - 841.3879+[1] | 25756 |
| | | | | | G [y9] - 940.5211+[2] | 25018 |
| | | | | | Y [b4] - 542.2245+[3] | 19778 |
| | | | | | Q [y8] - 883.4996+[4] | 6642 |
| | | | | | P [y2] - 272.1717+[5] | 5018 |
| pregnancy-specific beta-1-glycoprotein 5 | GVTGYFTFNLYLK | 781 | 781 | 508.2695+++ | L [y2] - 260.1969+[1] | 176797 |
| | | | | | T [y11] - 683.8557++[2] | 136231 |
| | | | | | F [b6] - 625.2980+[3] | 47523 |
| | | | | | L [y4] - 536.3443+[4] | 23513 |
| pregnancy-specific beta-1-glycoprotein 6 | SNPVTLNVLYGPDLPR | 782 | 782 | 585.6527+++ | Y [y7] - 817.4203+[1] | 14118 |
| | | | | | G [y6] - 654.3570+[2] | 10433 |
| | | | | | P [b3] - 299.1350+[3] | 87138* |
| | | | | | P [y5] - 299.1714++[4] | 77478* |
| | | | | | P [y5] - 597.3355+[5] | 68089* |
| pregnancy-specific beta-1-glycoprotein 7 | DVLLLVHNLPQNLTGHIWYK | 783 | 783 | 791.7741+++ | L [y8] - 1017.5516+[3] | 141169 |
| | | | | | G [y6] - 803.4199+[5] | 115905 |
| | | | | | W [y3] - 496.2554+[6] | 108565 |
| | | | | | P [y11] - 678.8566++[7] | 105493 |
| | | | | | V [b2] - 215.1026+[1] | 239492 |
| | | | | | L [b3] - 328.1867+[2] | 204413 |
| | | | | | N [b8] - 904.5251+[4] | 121880 |
| pregnancy-specific beta-1-glycoprotein 7 | YGPAYSGR | 784 | 784 | 435.7089++ | A [y5] - 553.2729+[1] | 25743* |
| | | | | | Y [y4] - 482.2358+[2] | 25580* |
| | | | | | P [y6] - 650.3257+[3] | 10831* |
| | | | | | S [y3] - 319.1724+[4] | 10559* |
| | | | | | G [b2] - 221.0921+[5] | 7837* |
| pregnancy-specific beta-1-glycoprotein 8 | LQLSETNR | 785 | 785 | 480.7591++ | S [b4] - 442.2660+[1] | 18766 |
| | | | | | L [b3] - 355.2340+[2] | 12050 |
| | | | | | Q [b2] - 242.1499+[3] | 1339 |
| | | | | | T [b6] - 672.3563+[4] | 2489 |
| pregnancy-specific beta-1-glycoprotein 9 | K.LFIPQITR.N | 786 | 996 | 494.3029++ | P [y5] - 614.3620+[1] | 53829 |
| | | | | | I [y6] - 727.4461+[2] | 13731 |
| | | | | | I [b3] - 374.2438+[3] | 4178 |
| | | | | | Q [y4] - 517.3093+[4] | 2984 |
| pregnancy-specific beta-1-glycoprotein 9 | K.LPIPYITINNLNPR.E | 787 | 1675 | 819.4723++ | P [b2] - 211.1441+[1] | 18814* |
| | | | | | P [b4] - 211.1441++[2] | 18814* |
| | | | | | T [b7] - 798.4760+[3] | 17287* |
| | | | | | T [y8] - 941.5163+[4] | 10205* |
| | | | | | Y [b5] - 584.3443+[5] | 10136* |
| | | | | | N [y6] - 727.3846+[6] | 9511* |

TABLE 11-continued

Candidate peptides and transitions for transferring to the MRM assay

| Protein | Peptide | Full peptide SEQ ID NO: | Core peptide SEQ ID NO: | m/z, charge | fragment ion, m/z, charge, rank | area |
|---|---|---|---|---|---|---|
| pregnancy-specific beta-1-glycoprotein 9 | R.SNPVILNVLYGP DLPR.I | 575 | 1509 | 589.6648+++ | P [y5] - 597.3355+[1] | 3994 |
| | | | | | Y [y7] - 817.4203+[2] | 3743 |
| | | | | | G [y6] - 654.3570+[3] | 3045 |
| pregnancy-specific beta-1-glycoprotein 9 | DVLLLVHNLPQNL PGYFWYK | 11 | 11 | 810.4387+++ | P [y7] - 960.4614+[1] | 120212 |
| | | | | | V [b2] - 215.1026+[2] | 65494 |
| | | | | | L [b3] - 328.1867+[3] | 54798 |
| pregnancy-specific beta-1-glycoprotein 9 | SENYTYIWWLNG QSLPVSPGVK | 788 | 788 | 846.7603+++ | W [y15] - 834.4488++[1] | 14788 |
| | | | | | P [y4] - 200.6314++[2] | 19000 |
| | | | | | Y [y17] - 972.5225++[3] | 4596 |
| | | | | | L [b10] - 678.8166++[4] | 2660 |
| | | | | | Y [b6] - 758.2992+[5] | 1705 |
| | | | | | P [y4] - 400.2554+[6] | 1847 |
| Pan-PSG | ILILPSVTR | 789 | 789 | 506.3317++ | P [y5] - 559.3198+[1] | 484395 |
| | | | | | L [b2] - 227.1754+[2] | 102774 |
| | | | | | L [b4] - 227.1754++[3] | 102774 |
| | | | | | I [y7] - 785.4880+[4] | 90153 |
| | | | | | I [b3] - 340.2595+[5] | 45515 |
| | | | | | L [y6] - 672.4039+[6] | 40368 |
| thyroxine-binding globulin precursor | K.AQWANPFDPS K.T | 790 | 1676 | 630.8040++ | A [b4] - 457.2194+[1] | 30802 |
| | | | | | S [y2] - 234.1448+[2] | 28255 |
| | | | | | D [y4] - 446.2245+[3] | 24933 |
| thyroxine-binding globulin precursor | K.AVLHIGEK.G | 586 | 817 | 289.5080+++ | I [y4] - 446.2609+[1] | 220841 |
| | | | | | H [y5] - 292.1636++[2] | 303815 |
| | | | | | H [y5] - 583.3198+[3] | 133795 |
| | | | | | V [b2] - 171.1128+[4] | 166139 |
| | | | | | L [y6] - 348.7056++[5] | 823533 |
| thyroxine-binding globulin precursor | K.FLNDVK.T | 791 | 1677 | 368.2054++ | N [y4] - 475.2511+[1] | 296859 |
| | | | | | V [y2] - 246.1812+[2] | 219597 |
| | | | | | L [b2] - 261.1598+[3] | 87504 |
| thyroxine-binding globulin precursor | K.FSISATYDLGATL LK.M | 587 | 1518 | 800.4351++ | Y [y9] - 993.5615+[1] | 34111 |
| | | | | | G [y6] - 602.3872+[2] | 17012 |
| | | | | | D [y8] - 830.4982+ | 45104 |
| | | | | | S [b2] - 235.1077+[4] | 15480 |
| thyroxine-binding globulin precursor | K.GWVDLFVPK.F | 790 | 1656 | 530.7949++ | W [b2] - 244.1081+[1] | 1261810 |
| | | | | | P [y2] - 244.1656+[2] | 1261810 |
| | | | | | V [b7] - 817.4243+[3] | 517675 |
| | | | | | V [y7] - 817.4818+[4] | 517675 |
| | | | | | D [y6] - 718.4134+[5] | 306994 |
| | | | | | F [b6] - 718.3559+[6] | 306994 |
| | | | | | V [y3] - 343.2340+[7] | 112565 |
| | | | | | V [b3] - 343.1765+[8] | 112565 |
| thyroxine-binding globulin precursor | K.NALALFVLPK.E | 792 | 1678 | 543.3395++ | A [y7] - 787.5076+[1] | 198085 |
| | | | | | L [b3] - 299.1714+[2] | 199857 |
| | | | | | P [y2] - 244.1656+[3] | 129799 |
| | | | | | L [y8] - 900.5917+[4] | 111572 |
| | | | | | L [y6] - 716.4705+[5] | 88773 |
| | | | | | F [y5] - 603.3865+[6] | 54020 |
| | | | | | L [y3] - 357.2496+[7] | 43353 |
| thyroxine-binding globulin precursor | R.SILFLGK.V | 400 | 881 | 389.2471++ | L [y5] - 577.3708+[1] | 1878736 |
| | | | | | I [b2] - 201.1234+[2] | 946031 |
| | | | | | G [y2] - 204.1343+[3] | 424248 |
| | | | | | L [y3] - 317.2183+[4] | 291162 |
| | | | | | F [y4] - 464.2867+[5] | 391171 |
| AFP | R.DFNQFSSGEK.N | 793 | 845 | 386.8402+++ | N [b3] - 189.0764++[1] | 42543 |
| | | | | | S [y4] - 210.6081++[2] | 21340 |
| | | | | | G [y3] - 333.1769+[3] | 53766 |
| | | | | | N [b3] - 377.1456+[4] | 58644 |
| | | | | | F [b2] - 263.1026+[5] | 5301 |

TABLE 11-continued

| Candidate peptides and transitions for transferring to the MRM assay | | | | | | |
|---|---|---|---|---|---|---|
| Protein | Peptide | Full peptide SEQ ID NO: | Core peptide SEQ ID NO: | m/z, charge | fragment ion, m/z, charge, rank | area |
| AFP | K.GYQELLEK.C | 794 | 956 | 490.2584++ | E [y5] - 631.3661+[1] | 110518 |
| | | | | | L [y4] - 502.3235+[2] | 74844 |
| | | | | | E [y2] - 276.1554+[3] | 42924 |
| | | | | | E [b4] - 478.1932+[4] | 20953 |
| AFP | K.GEEELQK.Y | 795 | 1679 | 416.7060++ | E [b2] - 187.0713+[1] | 37843 |
| | | | | | E [y4] - 517.2980+[2] | 56988 |
| AFP | K.FIYEIAR.R | 796 | 1680 | 456.2529++ | I [y3] - 359.2401+[1] | 34880 |
| | | | | | I [b2] - 261.1598+[2] | 7931 |
| AFP | R.HPFLYAPTILLW AAR.Y | 797 | 1681 | 590.3348+++ | I [y7] - 421.7660++[1] | 11471 |
| | | | | | L [y6] - 365.2239++[2] | 5001 |
| | | | | | A [b6] - 365.1896++[3] | 5001 |
| | | | | | L [y6] - 729.4406+[4] | 3218 |
| | | | | | F [b3] - 382.1874+[5] | 6536 |
| | | | | | A [b6] - 729.3719+[6] | 3218 |
| AFP | R.TFQAITVTK.L | 798 | 1682 | 504.7898++ | T [b6] - 662.3508+[1] | 11241 |
| | | | | | T [y4] - 448.2766+[2] | 7541 |
| | | | | | A [b4] - 448.2191+[3] | 7541 |
| AFP | K.LTTLER.G | 799 | 1683 | 366.7162++ | T [y4] - 518.2933+[1] | 7836 |
| | | | | | L [b4] - 215.1390++[2] | 4205 |
| | | | | | T [b2] - 215.1390+[3] | 4205 |
| AFP | R.HPQLAVSVILR.V | 800 | 1684 | | L[y2] - 288.2030+[1] | 3781 |
| | | | | | I [y3] - 401.2871+[2] | 2924 |
| | | | | | L [b4] - 476.2616+[3] | 2647 |
| AFP | K.LGEYYLQNAFLV AYTK.K | 801 | 1685 | 631.6646+++ | G [b2] - 171.1128+[1] | 10790 |
| | | | | | Y [y3] - 411.2238+[2] | 2303 |
| | | | | | F [b10] - 600.2902++[3] | 1780 |
| | | | | | Y [b4] - 463.2187+[4] | 2214 |
| | | | | | F [y7] - 421.2445++[6] | 3072 |
| PGH1 | R.ILPSVPK.D | 802 | 867 | 377.2471++ | P [y5] - 527.3188+[1] | 5340492 |
| | | | | | S [y4] - 430.2660+[5] | 419777 |
| | | | | | P [y2] - 244.1656+[2] | 4198508 |
| | | | | | P [y5] - 264.1630++[3] | 2771328 |
| | | | | | L [b2] - 227.1754+[4] | 2331263 |
| PGH1 | K.AEHPTWGDEQL FQTTR.L | 803 | 926 | 639.3026+++ | E [b9] - 512.2120++[1] | 64350 |
| | | | | | P [b4] - 218.1030++[2] | 38282 |
| | | | | | L [b11] - 632.7833++[3] | 129128 |
| | | | | | G [y10] - 597.7911++[4] | 19406 |
| | | | | | G [b7] - 779.3471+[5] | 51467 |
| | | | | | T [y3] - 189.1108++[6] | 10590 |
| | | | | | D [y9] - 569.2804++[7] | 12460 |
| | | | | | L [y6] - 765.4254+[8] | 6704 |
| | | | | | D [b8] - 447.6907++[9] | 4893 |
| | | | | | P [b4] - 435.1987+[10] | 8858 |
| | | | | | Q [y7] - 893.4839+[11] | 6101 |
| | | | | | T [b5] - 268.6268++[12] | 5456 |
| | | | | | T [b5] - 536.2463+[13] | 5549 |
| PGH1 | R.LILIGETIK.I | 804 | 1686 | 500.3261++ | G [y5] - 547.3086+[1] | 7649 |
| | | | | | T [y3] - 361.2445+[2] | 6680 |
| | | | | | E [y4] - 490.2871+[3] | 5234 |
| | | | | | L [y7] - 773.4767+[4] | 3342 |
| PGH1 | R.LQPFNEYR.K | 805 | 1687 | 533.7694++ | N [b5] - 600.3140+[1] | 25963 |
| | | | | | F [b4] - 486.2711+[2] | 6915 |
| | | | | | E [y3] - 467.2249+[3] | 15079 |

*QTRAP5500 data, all other peak areas are from Agilent 6490

Next, the top 2-10 transitions per peptide and up to 7 peptides per protein were selected for collision energy (CE) optimization on the Agilent 6490. Using Skyline or Mass-Hunter Qual software, the optimized CE value for each transition was determined based on the peak area or signal to noise. The two transitions with the largest peak areas per peptide and at least two peptides per protein were chosen for the final MRM method. Substitutions of transitions with lower peak areas were made when a transition with a larger peak area had a high background level or had a low m/z value that has more potential for interference.

Lastly, the retention times of selected peptides were mapped using the same column and gradient as our established sMRM assay. The newly discovered analytes were subsequently added to the sMRM method and used in a further hypothesis-dependent discovery study described in Example 5 below.

The above method was typical for most proteins. However, in some cases, the differentially expressed peptide identified in the shotgun method did not uniquely identify a protein, for example, in protein families with high sequence identity. In these cases, a MRM method was developed for each family member. Also, let it be noted that, for any given protein, peptides in addition to those found to be significant and fragment ions not observed on the Orbitrap may have been included in MRM optimization and added to the final sMRM method if those yielded the best signal intensities.

Example 5. Study IV to Identify and Confirm Preterm Birth Biomarkers

A further hypothesis-dependent discovery study was performed with the scheduled MRM assay used in Examples 3 but now augmented with newly discovered analytes from the Example 4. Less robust transitions (from the original 1708 described in Example 1) were removed to improve analytical performance and make room for the newly discovered analytes. Samples included approximately 30 cases and 60 matched controls from each of three gestational periods (early, 17-22 weeks, middle, 23-25 weeks and late, 26-28 weeks). Log transformed peak areas for each transition were corrected for run order and batch effects by regression. The ability of each analyte to separate cases and controls was determined by calculating univariate AUC values from ROC curves. Ranked univariate AUC values (0.6 or greater) are reported for individual gestational age window sample sets (Tables 12, 13, 15) and a combination of the middle and late window (Table 14). Multivariate classifiers were built using different subsets of analytes (described below) by Lasso and Random Forest methods. Lasso significant transitions correspond to those with non-zero coefficients and Random Forest analye ranking was determined by the Gini importance values (mean decrease in model accuracy if that variable is removed). We report all analytes with non-zero Lasso coefficients (Tables 16-32) and the top 30 analytes from each Random Forest analysis (Tables 33-49). Models were built considering the top univariate 32 or 100 analytes, the single best univariate analyte for the top 50 proteins or all analytes. Lastly 1000 rounds of bootstrap resampling were performed and the nonzero Lasso coefficients or Random Forest Gini importance values were summed for each analyte amongst panels with AUCs of 0.85 or greater.

TABLE 12

Early Window Individual Stats

| Transition | Peptide disclosed in adjacent column | Protein | AUC |
|---|---|---|---|
| ELIEELVNITQNQK_557.6_517.3 | (SEQ ID NO: 806) | IL13_HUMAN | 0.834 |
| ITLPDFTGDLR_624.3_288.2 | (SEQ ID NO: 3) | LBP_HUMAN | 0.822 |
| FLNWIK_410.7_560.3 | (SEQ ID NO: 4) | HABP2_HUMAN | 0.820 |
| ITLPDFTGDLR_624.3_920.5 | (SEQ ID NO: 3) | LBP_HUMAN | 0.808 |
| SFRPFVPR_335.9_635.3 | (SEQ ID NO: 18) | LBP_HUMAN | 0.800 |
| LIQDAVTGLTVNGQITGDK_972.0_798.4 | (SEQ ID NO: 807) | ITIH3_HUMAN | 0.800 |
| FSVVYAK_407.2_579.4 | (SEQ ID NO: 47) | FETUA_HUMAN | 0.796 |
| ITGFLKPGK_320.9_429.3 | (SEQ ID NO: 97) | LBP_HUMAN | 0.796 |
| AHYDLR_387.7_288.2 | (SEQ ID NO: 88) | FETUA_HUMAN | 0.796 |
| FSVVYAK_407.2_381.2 | (SEQ ID NO: 47) | FETUA_HUMAN | 0.795 |
| SFRPFVPR_335.9_272.2 | (SEQ ID NO: 18) | LBP_HUMAN | 0.795 |
| DVLLLVHNLPQNLPGYFWYK_810.4_967.5 | (SEQ ID NO: 11) | PSG9_HUMAN | 0.794 |
| ELIEELVNITQNQK_557.6_618.3 | (SEQ ID NO: 806) | IL13_HUMAN | 0.794 |
| QALEEFQK_496.8_680.3 | (SEQ ID NO: 808) | CO8B_HUMAN | 0.792 |
| DAGLSWGSAR_510.3_390.2 | (SEQ ID NO: 809) | NEUR4_HUMAN | 0.792 |
| AHYDLR_387.7_566.3 | (SEQ ID NO: 88) | FETUA_HUMAN | 0.791 |
| VFQFLEK_455.8_811.4 | (SEQ ID NO: 810) | CO5_HUMAN | 0.786 |
| ITGFLKPGK_320.9_301.2 | (SEQ ID NO: 97) | LBP_HUMAN | 0.783 |
| VFQFLEK_455.8_276.2 | (SEQ ID NO: 810) | CO5_HUMAN | 0.782 |

TABLE 12-continued

| | Early Window Individual Stats | | |
|---|---|---|---|
| Transition | Peptide<br>disclosed in<br>adjacent<br>column | Protein | AUC |
| SLLQPNK_400.2_599.4 | (SEQ ID NO: 98) | CO8A_HUMAN | 0.781 |
| VQTAHFK_277.5_431.2 | (SEQ ID NO: 811) | CO8A_HUMAN | 0.780 |
| SDLEVAHYK_531.3_617.3 | (SEQ ID NO: 812) | CO8B_HUMAN | 0.777 |
| SLLQPNK_400.2_358.2 | (SEQ ID NO: 98) | CO8A_HUMAN | 0.776 |
| TLLPVSKPEIR_418.3_288.2 | (SEQ ID NO: 25) | CO5_HUMAN | 0.776 |
| ALNHLPLEYNSALYSR_621.0_538.3 | (SEQ ID NO: 72) | CO6_HUMAN | 0.774 |
| DISEVVTPR_508.3_787.4 | (SEQ ID NO: 67) | CFAB_HUMAN | 0.774 |
| VSEADSSNADWVTK_754.9_533.3 | (SEQ ID NO: 813) | CFAB_HUMAN | 0.773 |
| LSSPAVITDK_515.8_743.4 | (SEQ ID NO: 26) | PLMN_HUMAN | 0.773 |
| VQEAHLTEDQIFYFPK_655.7_701.4 | (SEQ ID NO: 31) | CO8G_HUMAN | 0.772 |
| DVLLLVHNLPQNLPGYFWYK_810.4_594.3 | (SEQ ID NO: 11) | PSG9_HUMAN | 0.771 |
| ALVLELAK_428.8_672.4 | (SEQ ID NO: 9) | INHBE_HUMAN | 0.770 |
| FLNWIK_410.7_561.3 | (SEQ ID NO: 4) | HABP2_HUMAN | 0.770 |
| LSSPAVITDK_515.8_830.5 | (SEQ ID NO: 26) | PLMN_HUMAN | 0.769 |
| LPNNVLQEK_527.8_844.5 | (SEQ ID NO: 814) | AFAM_HUMAN | 0.769 |
| VSEADSSNADWVTK_754.9_347.2 | (SEQ ID NO: 813) | CFAB_HUMAN | 0.768 |
| HTLNQIDEVK_598.8_951.5 | (SEQ ID NO: 51) | FETUA_HUMAN | 0.767 |
| TTSDGGYSFK_531.7_860.4 | (SEQ ID NO: 815) | INHA_HUMAN | 0.761 |
| YENYTSSFFIR_713.8_756.4 | (SEQ ID NO: 816) | IL12B_HUMAN | 0.760 |
| HTLNQIDEVK_598.8_958.5 | (SEQ ID NO: 51) | FETUA_HUMAN | 0.760 |
| DISEVVTPR_508.3_472.3 | (SEQ ID NO: 67) | CFAB_HUMAN | 0.760 |
| LIQDAVTGLTVNGQITGDK_972.0_640.4 | (SEQ ID NO: 807) | ITIH3_HUMAN | 0.759 |
| EAQLPVIENK_570.8_699.4 | (SEQ ID NO: 22) | PLMN_HUMAN | 0.759 |
| SLPVSDSVLSGFEQR_810.9_836.4 | (SEQ ID NO: 59) | CO8G_HUMAN | 0.757 |
| AVLHIGEK_289.5_348.7 | (SEQ ID NO: 817) | THBG_HUMAN | 0.755 |
| GLQYAAQEGLLALQSELLR_1037.1_929.5 | (SEQ ID NO: 818) | LBP_HUMAN | 0.752 |
| FLQEQGHR_338.8_497.3 | (SEQ ID NO: 23) | CO8G_HUMAN | 0.750 |
| LPNNVLQEK_527.8_730.4 | (SEQ ID NO: 814) | AFAM_HUMAN | 0.750 |
| AVLHIGEK_289.5_292.2 | (SEQ ID NO: 817) | THBG_HUMAN | 0.749 |
| QLYGDTGVLGR_589.8_501.3 | (SEQ ID NO: 819) | CO8G_HUMAN | 0.748 |
| WWGGQPLWITATK__772.4_929.5 | (SEQ ID NO: 15) | ENPP2_HUMAN | 0.747 |
| NADYSYSVWK_616.8_769.4 | (SEQ ID NO: 60) | CO5_HUMAN | 0.746 |
| GLQYAAQEGLLALQSELLR_1037.1_858.5 | (SEQ ID NO: 818) | LBP_HUMAN | 0.746 |
| SLPVSDSVLSGFEQR_810.9_723.3 | (SEQ ID NO: 59) | CO8G_HUMAN | 0.745 |
| IEEIAAK_387.2_531.3 | (SEQ ID NO: 30) | CO5_HUMAN | 0.743 |
| TYLHTYESEI_628.3_908.4 | (SEQ ID NO: 100) | ENPP2_HUMAN | 0.742 |
| WWGGQPLWITATK__772.4_373.2 | (SEQ ID NO: 15) | ENPP2_HUMAN | 0.742 |

TABLE 12-continued

| | Early Window Individual Stats | | |
|---|---|---|---|
| Transition | Peptide disclosed in adjacent column | Protein | AUC |
| FQLSETNR_497.8_605.3 | (SEQ ID NO: 776) | PSG2_HUMAN | 0.741 |
| NIQSVNVK_451.3_674.4 | (SEQ ID NO: 821) | GROA_HUMAN | 0.741 |
| TGVAVNKPAEFTVDAK_549.6_258.1 | (SEQ ID NO: 822) | FLNA_HUMAN | 0.740 |
| LQGTLPVEAR_542.3_571.3 | (SEQ ID NO: 28) | CO5_HUMAN | 0.740 |
| SGFSFGFK_438.7_732.4 | (SEQ ID NO: 53) | CO8B_HUMAN | 0.740 |
| HELTDEELQSLFTNFANVVDK_817.1_906.5 | (SEQ ID NO: 823) | AFAM_HUMAN | 0.740 |
| VQTAHFK_277.5_502.3 | (SEQ ID NO: 811) | CO8A_HUMAN | 0.739 |
| YENYTSSFFIR_713.8_293.1 | (SEQ ID NO: 816) | IL12B_HUMAN | 0.739 |
| AFTECCVVASQLR_770.9_574.3 | (SEQ ID NO: 1) | CO5_HUMAN | 0.736 |
| EAQLPVIENK_570.8_329.2 | (SEQ ID NO: 22) | PLMN_HUMAN | 0.734 |
| QALEEFQK_496.8_551.3 | (SEQ ID NO: 808) | CO8B_HUMAN | 0.734 |
| DAQYAPGYDK_564.3_813.4 | (SEQ ID NO: 61) | CFAB_HUMAN | 0.734 |
| TEFLSNYLTNVDDITLVPGTLGR_846.8_600.3 | (SEQ ID NO: 824) | ENPP2_HUMAN | 0.734 |
| IAIDLFK_410.3_635.4 | (SEQ ID NO: 825) | HEP2_HUMAN | 0.733 |
| TASDFITK_441.7_781.4 | (SEQ ID NO: 37) | GELS_HUMAN | 0.731 |
| YEFLNGR_449.7_606.3 | (SEQ ID NO: 34) | PLMN_HUMAN | 0.731 |
| TVQAVLTVPK_528.3_428.3 | (SEQ ID NO: 826) | PEDF_HUMAN | 0.731 |
| LIENGYFHPVK_439.6_627.4 | (SEQ ID NO: 827) | F13B_HUMAN | 0.730 |
| DALSSVQESQVAQQAR_573.0_672.4 | (SEQ ID NO: 91) | APOC3_HUMAN | 0.730 |
| TVQAVLTVPK_528.3_855.5 | (SEQ ID NO: 826) | PEDF_HUMAN | 0.730 |
| ALQDQLVLVAAK_634.9_289.2 | (SEQ ID NO: 33) | ANGT_HUMAN | 0.727 |
| TYLHTYESEI_628.3_515.3 | (SEQ ID NO: 100) | ENPP2_HUMAN | 0.727 |
| SDLEVAHYK_531.3_746.4 | (SEQ ID NO: 812) | CO8B_HUMAN | 0.726 |
| FLPCENK_454.2_550.2 | (SEQ ID NO: 828) | IL10_HUMAN | 0.725 |
| HPWIVHWDQLPQYQLNR_744.0_1047.0 | (SEQ ID NO: 829) | KS6A3_HUMAN | 0.725 |
| AFTECCVVASQLR_770.9_673.4 | (SEQ ID NO: 1) | CO5_HUMAN | 0.725 |
| YGLVTYATYPK_638.3_843.4 | (SEQ ID NO: 63) | CFAB_HUMAN | 0.724 |
| TLEAQLTPR_514.8_685.4 | (SEQ ID NO: 68) | HEP2_HUMAN | 0.724 |
| DAQYAPGYDK_564.3_315.1 | (SEQ ID NO: 61) | CFAB_HUMAN | 0.724 |
| QGHNSVFLIK_381.6_260.2 | (SEQ ID NO: 830) | HEMO_HUMAN | 0.722 |
| HELTDEELQSLFTNFANVVDK_817.1_854.4 | (SEQ ID NO: 823) | AFAM_HUMAN | 0.722 |
| TLEAQLTPR_514.8_814.4 | (SEQ ID NO: 68) | HEP2_HUMAN | 0.721 |
| IEEIAAK_387.2_660.4 | (SEQ ID NO: 30) | CO5_HUMAN | 0.721 |
| HFQNLGK_422.2_527.2 | (SEQ ID NO: 831) | AFAM_HUMAN | 0.721 |
| IAPQLSTEELVSLGEK_857.5_333.2 | (SEQ ID NO: 832) | AFAM_HUMAN | 0.721 |
| DALSSVQESQVAQQAR_573.0_502.3 | (SEQ ID NO: 91) | APOC3_HUMAN | 0.720 |

TABLE 12-continued

| | Early Window Individual Stats | | |
|---|---|---|---|
| Transition | Peptide disclosed in adjacent column | Protein | AUC |
| ALNHLPLEYNSALYSR_621.0_696.4 | (SEQ ID NO: 72) | CO6_HUMAN | 0.719 |
| IAIDLFK_410.3_706.4 | (SEQ ID NO: 825) | HEP2_HUMAN | 0.719 |
| FLQEQGHR_338.8_369.2 | (SEQ ID NO: 23) | CO8G_HUMAN | 0.719 |
| ALQDQLVLVAAK_634.9_956.6 | (SEQ ID NO: 33) | ANGT_HUMAN | 0.718 |
| IEGNLIFDPNNYLPK_874.0_414.2 | (SEQ ID NO: 8) | APOB_HUMAN | 0.717 |
| YEFLNGR_449.7_293.1 | (SEQ ID NO: 34) | PLMN_HUMAN | 0.717 |
| TASDFITK_441.7_710.4 | (SEQ ID NO: 37) | GELS_HUMAN | 0.716 |
| DADPDTFFAK_563.8_825.4 | (SEQ ID NO: 833) | AFAM_HUMAN | 0.716 |
| TLLPVSKPEIR_418.3_514.3 | (SEQ ID NO: 25) | CO5_HUMAN | 0.716 |
| NADYSYSVWK_616.8_333.2 | (SEQ ID NO: 60) | CO5_HUMAN | 0.715 |
| YGLVTYATYPK_638.3_334.2 | (SEQ ID NO: 63) | CFAB_HUMAN | 0.715 |
| VNHVTLSQPK_374.9_459.3 | (SEQ ID NO: 834) | B2MG_HUMAN | 0.715 |
| HYGGLTGLNK_530.3_759.4 | (SEQ ID NO: 835) | PGAM1_HUMAN | 0.714 |
| DFHINLFQVLPWLK_885.5_400.2 | (SEQ ID NO: 94) | CFAB_HUMAN | 0.714 |
| NCSFSIIYPVVIK_770.4_555.4 | (SEQ ID NO: 836) | CRHBP_HUMAN | 0.714 |
| HPWIVHWDQLPQYQLNR_744.0_918.5 | (SEQ ID NO: 829) | KS6A3_HUMAN | 0.712 |
| AQPVQVAEGSEPDGFWEALGGK_758.0_574.3 | (SEQ ID NO: 837) | GELS_HUMAN | 0.711 |
| ALDLSLK__380.2_185.1 | (SEQ ID NO: 14) | ITIH3_HUMAN | 0.711 |
| ALDLSLK_380.2_575.3 | (SEQ ID NO: 14) | ITIH3_HUMAN | 0.710 |
| LDFHFSSDR_375.2_611.3 | (SEQ ID NO: 838) | INHBC_HUMAN | 0.709 |
| TLNAYDHR_330.5_312.2 | (SEQ ID NO: 839) | PAR3_HUMAN | 0.707 |
| EVFSKPISWEELLQ_852.9_260.2 | (SEQ ID NO: 840) | FA40A_HUMAN | 0.706 |
| IAPQLSTEELVSLGEK_857.5_533.3 | (SEQ ID NO: 832) | AFAM_HUMAN | 0.704 |
| LIENGYFHPVK_439.6_343.2 | (SEQ ID NO: 827) | F13B_HUMAN | 0.703 |
| NFPSPVDAAFR_610.8_775.4 | (SEQ ID NO: 841) | HEMO_HUMAN | 0.703 |
| QLYGDTGVLGR_589.8_345.2 | (SEQ ID NO: 819) | CO8G_HUMAN | 0.702 |
| LYYGDDEK_501.7_563.2 | (SEQ ID NO: 42) | CO8A_HUMAN | 0.702 |
| FQLSETNR_497.8_476.3 | (SEQ ID NO: 776) | PSG2_HUMAN | 0.701 |
| TGVAVNKPAEFTVDAK_549.6_977.5 | (SEQ ID NO: 822) | FLNA_HUMAN | 0.700 |
| IPGIFELGISSQSDR_809.9_679.3 | (SEQ ID NO: 103) | CO8B_HUMAN | 0.700 |
| TLFIFGVTK_513.3_215.1 | (SEQ ID NO: 842) | PSG4_HUMAN | 0.699 |
| YYGYTGAFR_549.3_450.3 | (SEQ ID NO: 843) | TRFL_HUMAN | 0.699 |
| QVFAVQR_424.2_473.3 | (SEQ ID NO: 844) | ELNE_HUMAN | 0.699 |
| AQPVQVAEGSEPDGFWEALGGK_758.0_623.4 | (SEQ ID NO: 837) | GELS_HUMAN | 0.699 |
| DFNQFSSGEK_386.8_189.1 | (SEQ ID NO: 845) | FETA_HUMAN | 0.699 |
| SVSLPSLDPASAK_636.4_473.3 | (SEQ ID NO: 846) | APOB_HUMAN | 0.699 |
| GNGLTWAEK_488.3_634.3 | (SEQ ID NO: 847) | C163B_HUMAN | 0.698 |

TABLE 12-continued

Early Window Individual Stats

| Transition | Peptide disclosed in adjacent column | Protein | AUC |
|---|---|---|---|
| LYYGDDEK_501.7_726.3 | (SEQ ID NO: 42) | CO8A_HUMAN | 0.698 |
| NFPSPVDAAFR_610.8_959.5 | (SEQ ID NO: 841) | HEMO_HUMAN | 0.698 |
| FAFNLYR_465.8_565.3 | (SEQ ID NO: 75) | HEP2_HUMAN | 0.697 |
| SGFSFGFK_438.7_585.3 | (SEQ ID NO: 53) | CO8B_HUMAN | 0.696 |
| DFHINLFQVLPWLK_885.5_543.3 | (SEQ ID NO: 94) | CFAB_HUMAN | 0.696 |
| LQGTLPVEAR_542.3_842.5 | (SEQ ID NO: 28) | CO5_HUMAN | 0.694 |
| GAVHVVVAETDYQSFAVLYLER_822.8_863.5 | (SEQ ID NO: 848) | CO8G_HUMAN | 0.694 |
| TSESTGSLPSPFLR_739.9_716.4 | (SEQ ID NO: 849) | PSMG1_HUMAN | 0.694 |
| YISPDQLADLYK_713.4_277.2 | (SEQ ID NO: 850) | ENOA_HUMAN | 0.694 |
| ESDTSYVSLK_564.8_347.2 | (SEQ ID NO: 851) | CRP_HUMAN | 0.693 |
| ILDDLSPR_464.8_587.3 | (SEQ ID NO: 852) | ITIH4_HUMAN | 0.693 |
| VQEAHLTEDQIFYFPK_655.7_391.2 | (SEQ ID NO: 31) | CO8G_HUMAN | 0.692 |
| SGVDLADSNQK_567.3_662.3 | (SEQ ID NO: 853) | VGFR3_HUMAN | 0.692 |
| DTDTGALLFIGK_625.8_217.1 | (SEQ ID NO: 854) | PEDF_HUMAN | 0.692 |
| HFQNLGK_422.2_285.1 | (SEQ ID NO: 831) | AFAM_HUMAN | 0.691 |
| NNQLVAGYLQGPNVNLEEK_700.7_999.5 | (SEQ ID NO: 991) | IL1RA_HUMAN | 0.691 |
| IPGIFELGISSQSDR_809.9_849.4 | (SEQ ID NO: 103) | CO8B_HUMAN | 0.691 |
| ESDTSYVSLK_564.8_696.4 | (SEQ ID NO: 851) | CRP_HUMAN | 0.690 |
| GAVHVVVAETDYQSFAVLYLER_822.8_580.3 | (SEQ ID NO: 848) | CO8G_HUMAN | 0.690 |
| DADPDTFFAK_563.8_302.1 | (SEQ ID NO: 833) | AFAM_HUMAN | 0.690 |
| LDFHFSSDR_375.2_464.2 | (SEQ ID NO: 838) | INHBC_HUMAN | 0.689 |
| TLFIFGVTK_513.3_811.5 | (SEQ ID NO: 842) | PSG4_HUMAN | 0.688 |
| DFNQFSSGEK_386.8_333.2 | (SEQ ID NO: 845) | FETA_HUMAN | 0.687 |
| IQTHSTTYR_369.5_627.3 | (SEQ ID NO: 104) | F13B_HUMAN | 0.686 |
| HYFIAAVER_553.3_658.4 | (SEQ ID NO: 855) | FA8_HUMAN | 0.686 |
| VNHVTLSQPK_374.9_244.2 | (SEQ ID NO: 834) | B2MG_HUMAN | 0.686 |
| DLHLSDVFLK_396.2_366.2 | (SEQ ID NO: 856) | CO6_HUMAN | 0.685 |
| DPTFIPAPIQAK_433.2_556.3 | (SEQ ID NO: 857) | ANGT_HUMAN | 0.684 |
| AGITIPR_364.2_272.2 | (SEQ ID NO: 858) | IL17_HUMAN | 0.684 |
| IAQYYYTFK_598.8_884.4 | (SEQ ID NO: 859) | F13B_HUMAN | 0.684 |
| SGVDLADSNQK_567.3_591.3 | (SEQ ID NO: 853) | VGFR3_HUMAN | 0.683 |
| VEPLYELVTATDFAYSSTVR_754.4_549.3 | (SEQ ID NO: 56) | CO8B_HUMAN | 0.682 |
| AGITIPR_364.2_486.3 | (SEQ ID NO: 858) | IL17_HUMAN | 0.682 |
| YEVQGEVFTKPQLWP_911.0_293.1 | (SEQ ID NO: 27) | CRP_HUMAN | 0.681 |
| APLTKPLK_289.9_357.2 | (SEQ ID NO: 85) | CRP_HUMAN | 0.681 |
| YNSQLLSFVR_613.8_508.3 | (SEQ ID NO: 860) | TFR1_HUMAN | 0.681 |

TABLE 12-continued

| | Early Window Individual Stats | | |
|---|---|---|---|
| Transition | Peptide disclosed in adjacent column | Protein | AUC |
| ANDQYLTAAALHNLDEAVK_686.4_301.1 | (SEQ ID NO: 861) | IL1A_HUMAN | 0.681 |
| IQTHSTTYR_369.5_540.3 | (SEQ ID NO: 104) | F13B_HUMAN | 0.681 |
| IHPSYTNYR_575.8_598.3 | (SEQ ID NO: 775) | PSG2_HUMAN | 0.681 |
| TEFLSNYLTNVDDITLVPGTLGR_846.8_699.4 | (SEQ ID NO: 824) | ENPP2_HUMAN | 0.681 |
| DPTFIPAPIQAK_433.2_461.2 | (SEQ ID NO: 857) | ANGT_HUMAN | 0.679 |
| FQSVFTVTR_542.8_623.4 | (SEQ ID NO: 862) | C1QC_HUMAN | 0.679 |
| LQVNTPLVGASLLR_741.0_925.6 | (SEQ ID NO: 863) | BPIA1_HUMAN | 0.679 |
| DEIPHNDIALLK_459.9_510.8 | (SEQ ID NO: 864) | HABP2_HUMAN | 0.678 |
| HATLSLSIPR_365.6_272.2 | (SEQ ID NO: 865) | VGFR3_HUMAN | 0.678 |
| EDTPNSVWEPAK_686.8_315.2 | (SEQ ID NO: 41) | C1S_HUMAN | 0.678 |
| TGISPLALIK_506.8_741.5 | (SEQ ID NO: 866) | APOB_HUMAN | 0.678 |
| ILPSVPK_377.2_244.2 | (SEQ ID NO: 867) | PGH1_HUMAN | 0.676 |
| HATLSLSIPR_365.6_472.3 | (SEQ ID NO: 865) | VGFR3_HUMAN | 0.676 |
| QGHNSVFLIK_381.6_520.4 | (SEQ ID NO: 830) | HEMO_HUMAN | 0.676 |
| LPATEKPVLLSK_432.6_460.3 | (SEQ ID NO: 868) | HYOU1_HUMAN | 0.675 |
| APLTKPLK_289.9_398.8 | (SEQ ID NO: 85) | CRP_HUMAN | 0.674 |
| GVTGYFTFNLYLK_508.3_683.9 | (SEQ ID NO: 781) | PSG5_HUMAN | 0.673 |
| TFLTVYWTPER_706.9_401.2 | (SEQ ID NO: 869) | ICAM1_HUMAN | 0.673 |
| GDTYPAELYITGSILR_885.0_274.1 | (SEQ ID NO: 870) | F13B_HUMAN | 0.672 |
| EDTPNSVWEPAK_686.8_630.3 | (SEQ ID NO: 41) | C1S_HUMAN | 0.672 |
| SLDFTELDVAAEK_719.4_316.2 | (SEQ ID NO: 871) | ANGT_HUMAN | 0.672 |
| VELAPLPSWQPVGK_760.9_342.2 | (SEQ ID NO: 872) | ICAM1_HUMAN | 0.671 |
| GPGEDFR_389.2_322.2 | (SEQ ID NO: 873) | PTGDS_HUMAN | 0.670 |
| TDAPDLPEENQAR_728.3_843.4 | (SEQ ID NO: 17) | CO5_HUMAN | 0.670 |
| GVTGYFTFNLYLK_508.3_260.2 | (SEQ ID NO: 781) | PSG5_HUMAN | 0.669 |
| FAFNLYR_465.8_712.4 | (SEQ ID NO: 75) | HEP2_HUMAN | 0.669 |
| ITENDIQIALDDAK_779.9_873.5 | (SEQ ID NO: 55) | APOB_HUMAN | 0.669 |
| ILNIFGVIK_508.8_790.5 | (SEQ ID NO: 874) | TFR1_HUMAN | 0.669 |
| ISQGEADINIAFYQR_575.6_684.4 | (SEQ ID NO: 875) | MMP8_HUMAN | 0.668 |
| GDTYPAELYITGSILR_885.0_1332.8 | (SEQ ID NO: 870) | F13B_HUMAN | 0.668 |
| ELLESYIDGR_597.8_710.4 | (SEQ ID NO: 2) | THRB_HUMAN | 0.668 |
| FTITAGSK_412.7_576.3 | (SEQ ID NO: 876) | FABPL_HUMAN | 0.667 |
| ILDGGNK_358.7_490.2 | (SEQ ID NO: 877) | CXCL5_HUMAN | 0.667 |
| GWVTDGFSSLK_598.8_854.4 | (SEQ ID NO: 54) | APOC3_HUMAN | 0.667 |
| FSLVSGWGQLLDR_493.3_403.2 | (SEQ ID NO: 878) | FA7_HUMAN | 0.665 |
| IHPSYTNYR_575.8_813.4 | (SEQ ID NO: 775) | PSG2_HUMAN | 0.665 |
| ELLESYIDGR_597.8_839.4 | (SEQ ID NO: 2) | THRB_HUMAN | 0.665 |

TABLE 12-continued

| Transition | Peptide disclosed in adjacent column | Protein | AUC |
|---|---|---|---|
| Early Window Individual Stats | | | |
| SDGAKPGPR_442.7_213.6 | (SEQ ID NO: 879) | COLI_HUMAN | 0.664 |
| IAQYYYTFK_598.8_395.2 | (SEQ ID NO: 859) | F13B_HUMAN | 0.664 |
| SILFLGK_389.2_201.1 | (SEQ ID NO: 881) | THBG_HUMAN | 0.664 |
| IEVNESGTVASSSTAVIVSAR_693.0_545.3 | (SEQ ID NO: 882) | PAI1_HUMAN | 0.664 |
| VSAPSGTGHLPGLNPL_506.3_300.7 | (SEQ ID NO: 777) | PSG3_HUMAN | 0.664 |
| LLAPSDSPEWLSFDVTGVVR_730.1_430.3 | (SEQ ID NO: 883) | TGFB1_HUMAN | 0.664 |
| YYGYTGAFR_549.3_771.4 | (SEQ ID NO: 843) | TRFL_HUMAN | 0.663 |
| TDAPDLPEENQAR_728.3_613.3 | (SEQ ID NO: 17) | CO5_HUMAN | 0.663 |
| IEVIITLK_464.8_815.5 | (SEQ ID NO: 884) | CXL11_HUMAN | 0.662 |
| ILPSVPK_377.2_227.2 | (SEQ ID NO: 867) | PGH1_HUMAN | 0.662 |
| FGFGGSTDSGPIR_649.3_745.4 | (SEQ ID NO: 5) | ADA12_HUMAN | 0.661 |
| DYWSTVK_449.7_347.2 | (SEQ ID NO: 885) | APOC3_HUMAN | 0.661 |
| IEGNLIFDPNNYLPK_874.0_845.5 | (SEQ ID NO: 8) | APOB_HUMAN | 0.661 |
| WILTAAHTLYPK_471.9_407.2 | (SEQ ID NO: 886) | C1R_HUMAN | 0.661 |
| WNFAYWAAHQPWSR_607.3_545.3 | (SEQ ID NO: 1050) | PRG2_HUMAN | 0.661 |
| SILFLGK_389.2_577.4 | (SEQ ID NO: 881) | THBG_HUMAN | 0.661 |
| FSLVSGWGQLLDR_493.3_516.3 | (SEQ ID NO: 878) | FA7_HUMAN | 0.661 |
| DTDTGALLFIGK_625.8_818.5 | (SEQ ID NO: 854) | PEDF_HUMAN | 0.661 |
| SEYGAALAWEK_612.8_845.5 | (SEQ ID NO: 1051) | CO6_HUMAN | 0.660 |
| LWAYLTIQELLAK_781.5_371.2 | (SEQ ID NO: 1052) | ITIH1_HUMAN | 0.660 |
| LLEVPEGR_456.8_356.2 | (SEQ ID NO: 1053) | C1S_HUMAN | 0.659 |
| ITENDIQIALDDAK_779.9_632.3 | (SEQ ID NO: 55) | APOB_HUMAN | 0.659 |
| LTTVDIVTLR_565.8_716.4 | (SEQ ID NO: 1054) | IL2RB_HUMAN | 0.658 |
| IEVIITLK_464.8_587.4 | (SEQ ID NO: 884) | CXL11_HUMAN | 0.658 |
| QLGLPGPPDVPDHAAYHPF_676.7_299.2 | (SEQ ID NO: 105) | ITIH4_HUMAN | 0.658 |
| TLAFVR_353.7_492.3 | (SEQ ID NO: 1055) | FA7_HUMAN | 0.656 |
| NSDQEIDFK_548.3_294.2 | (SEQ ID NO: 1056) | S10A5_HUMAN | 0.656 |
| YHFEALADTGISSEFYDNANDLLSK_940.8_874.5 | (SEQ ID NO: 1057) | CO8A_HUMAN | 0.656 |
| SEPRPGVLLR_375.2_454.3 | (SEQ ID NO: 12) | FA7_HUMAN | 0.655 |
| FLPCENK_454.2_390.2 | (SEQ ID NO: 828) | IL10_HUMAN | 0.654 |
| NCSFSIIYPVVIK_770.4_831.5 | (SEQ ID NO: 836) | CRHBP_HUMAN | 0.654 |
| SLDFTELDVAAEK_719.4_874.5 | (SEQ ID NO: 871) | ANGT_HUMAN | 0.654 |
| ILLLGTAVESAWGDEQSAFR_721.7_909.4 | (SEQ ID NO: 1058) | CXA1_HUMAN | 0.653 |
| SVSLPSLDPASAK_636.4_885.5 | (SEQ ID NO: 846) | APOB_HUMAN | 0.653 |
| TGISPLALIK_506.8_654.5 | (SEQ ID NO: 866) | APOB_HUMAN | 0.653 |
| YNQLLR_403.7_288.2 | (SEQ ID NO: 1059) | ENOA_HUMAN | 0.653 |

TABLE 12-continued

| Transition | Peptide disclosed in adjacent column | Protein | AUC |
|---|---|---|---|
| YEVQGEVFTKPQLWP_911.0_392.2 | (SEQ ID NO: 27) | CRP_HUMAN | 0.652 |
| VPGLYYFTYHASSR_554.3_720.3 | (SEQ ID NO: 1060) | C1QB_HUMAN | 0.650 |
| SLQNASAIESILK_687.4_589.4 | (SEQ ID NO: 1069) | IL3_HUMAN | 0.650 |
| WILTAAHTLYPK_471.9_621.4 | (SEQ ID NO: 886) | C1R_HUMAN | 0.650 |
| GWVTDGFSSLK_598.8_953.5 | (SEQ ID NO: 54) | APOC3_HUMAN | 0.650 |
| YGIEEHGK_311.5_599.3 | (SEQ ID NO: 1061) | CXA1_HUMAN | 0.649 |
| QDLGWK_373.7_503.3 | (SEQ ID NO: 880) | TGFB3_HUMAN | 0.649 |
| DYWSTVK_449.7_620.3 | (SEQ ID NO: 885) | APOC3_HUMAN | 0.648 |
| ALVLELAK_428.8_331.2 | (SEQ ID NO: 9) | INHBE_HUMAN | 0.647 |
| QLGLPGPPDVPDHAAYHPF_676.7_263.1 | (SEQ ID NO: 105) | ITIH4_HUMAN | 0.646 |
| SEYGAALAWEK_612.8_788.4 | (SEQ ID NO: 1051) | CO6_HUMAN | 0.645 |
| TFLTVYWTPER_706.9_502.3 | (SEQ ID NO: 869) | ICAM1_HUMAN | 0.644 |
| FQSVFTVTR_542.8_722.4 | (SEQ ID NO: 862) | C1QC_HUMAN | 0.643 |
| DPNGLPPEAQK_583.3_669.4 | (SEQ ID NO: 1063) | RET4_HUMAN | 0.642 |
| ETLLQDFR_511.3_322.2 | (SEQ ID NO: 1064) | AMBP_HUMAN | 0.642 |
| IIEVEEEQEDPYLNDR_996.0_777.4 | (SEQ ID NO: 1065) | FBLN1_HUMAN | 0.641 |
| ELCLDPK_437.7_359.2 | (SEQ ID NO: 1066) | IL8_HUMAN | 0.641 |
| TPSAAYLWVGTGASEAEK_919.5_849.4 | (SEQ ID NO: 35) | GELS_HUMAN | 0.641 |
| NQSPVLEPVGR_598.3_866.5 | (SEQ ID NO: 1067) | KS6A3_HUMAN | 0.641 |
| FNAVLTNPQGDYDTSTGK_964.5_333.2 | (SEQ ID NO: 70) | C1QC_HUMAN | 0.641 |
| LLEVPEGR_456.8_686.4 | (SEQ ID NO: 1053) | C1S_HUMAN | 0.641 |
| FFQYDTWK_567.8_840.4 | (SEQ ID NO: 1068) | IGF2_HUMAN | 0.640 |
| SPEAEDPLGVER_649.8_670.4 | (SEQ ID NO: 887) | Z512B_HUMAN | 0.639 |
| SEPRPGVLLR_375.2_654.4 | (SEQ ID NO: 12) | FA7_HUMAN | 0.639 |
| SGAQATWTELPWPHEK_613.3_793.4 | (SEQ ID NO: 888) | HEMO_HUMAN | 0.638 |
| YSHYNER_323.5_581.3 | (SEQ ID NO: 889) | HABP2_HUMAN | 0.638 |
| YHFEALADTGISSEFYDNANDLLSK_940.8_301.1 | (SEQ ID NO: 1057) | CO8A_HUMAN | 0.637 |
| DLHLSDVFLK_396.2_260.2 | (SEQ ID NO: 856) | CO6_HUMAN | 0.637 |
| YSHYNER_323.5_418.2 | (SEQ ID NO: 889) | HABP2_HUMAN | 0.637 |
| YYLQGAK_421.7_327.1 | (SEQ ID NO: 48) | ITIH4_HUMAN | 0.636 |
| EVPLSALTNILSAQLISHWK_740.8_996.6 | (SEQ ID NO: 890) | PAI1_HUMAN | 0.636 |
| VPGLYYFTYHASSR_554.3_420.2 | (SEQ ID NO: 1060) | C1QB_HUMAN | 0.636 |
| AALAAFNAQNNGSNFQLEEISR_789.1_746.4 | (SEQ ID NO: 891) | FETUA_HUMAN | 0.636 |
| ETLLQDFR_511.3_565.3 | (SEQ ID NO: 1064) | AMBP_HUMAN | 0.635 |
| IVLSLDVPIGLLQILLEQAR_735.1_503.3 | (SEQ ID NO: 892) | UCN2_HUMAN | 0.635 |
| ENPAVIDFELAPIVDLVR_670.7_811.5 | (SEQ ID NO: 893) | CO6_HUMAN | 0.635 |
| LQLSETNR_480.8_355.2 | (SEQ ID NO: 785) | PSG8_HUMAN | 0.635 |

TABLE 12-continued

| Early Window Individual Stats | | | |
|---|---|---|---|
| Transition | Peptide disclosed in adjacent column | Protein | AUC |
| DPDQTDGLGLSYLSSHIANVER_796.4_456.2 | (SEQ ID NO: 57) | GELS_HUMAN | 0.635 |
| NVNQSLLELHK_432.2_656.3 | (SEQ ID NO: 894) | FRIH_HUMAN | 0.634 |
| EIGELYLPK_531.3_633.4 | (SEQ ID NO: 895) | AACT_HUMAN | 0.634 |
| SPEQQETVLDGNLIIR_906.5_699.3 | (SEQ ID NO: 71) | ITIH4_HUMAN | 0.634 |
| NKPGVYTDVAYYLAWIR_677.0_545.3 | (SEQ ID NO: 896) | FA12_HUMAN | 0.632 |
| QNYHQDSEAAINR_515.9_544.3 | (SEQ ID NO: 897) | FRIH_HUMAN | 0.632 |
| EKPAGGIPVLGSLVNTVLK_631.4_930.6 | (SEQ ID NO: 96) | BPIB1_HUMAN | 0.632 |
| VTFEYR_407.7_614.3 | (SEQ ID NO: 898) | CRHBP_HUMAN | 0.630 |
| DLPHITVDR_533.3_490.3 | (SEQ ID NO: 899) | MMP7_HUMAN | 0.630 |
| VEHSDLSFSK_383.5_234.1 | (SEQ ID NO: 7) | B2MG_HUMAN | 0.630 |
| ENPAVIDFELAPIVDLVR_670.7_601.4 | (SEQ ID NO: 893) | CO6_HUMAN | 0.630 |
| YGFYTHVFR_397.2_659.4 | (SEQ ID NO: 50) | THRB_HUMAN | 0.629 |
| ILDDLSPR_464.8_702.3 | (SEQ ID NO: 852) | ITIH4_HUMAN | 0.629 |
| DPNGLPPEAQK_583.3_497.2 | (SEQ ID NO: 1063) | RET4_HUMAN | 0.629 |
| GSLVQASEANLQAAQDFVR_668.7_806.4 | (SEQ ID NO: 900) | ITIH1_HUMAN | 0.629 |
| FLYHK_354.2_447.2 | (SEQ ID NO: 901) | AMBP_HUMAN | 0.627 |
| FNAVLTNPQGDYDTSTGK_964.5_262.1 | (SEQ ID NO: 70) | C1QC_HUMAN | 0.627 |
| LQDAGVYR_461.2_680.3 | (SEQ ID NO: 902) | PD1L1_HUMAN | 0.627 |
| INPASLDK_429.2_630.4 | (SEQ ID NO: 903) | C163A_HUMAN | 0.626 |
| LEEHYELR_363.5_580.3 | (SEQ ID NO: 904) | PAI2_HUMAN | 0.625 |
| VEHSDLSFSK_383.5_468.2 | (SEQ ID NO: 7) | B2MG_HUMAN | 0.624 |
| TSDQIHFFFAK_447.6_659.4 | (SEQ ID NO: 905) | ANT3_HUMAN | 0.624 |
| ATLSAAPSNPR_542.8_570.3 | (SEQ ID NO: 906) | CXCL2_HUMAN | 0.624 |
| YGFYTHVFR_397.2_421.3 | (SEQ ID NO: 50) | THRB_HUMAN | 0.624 |
| EANQSTLENFLER_775.9_678.4 | (SEQ ID NO: 907) | IL4_HUMAN | 0.623 |
| GQQPADVTGTALPR_705.9_314.2 | (SEQ ID NO: 908) | CSF1_HUMAN | 0.623 |
| VELAPLPSWQPVGK_760.9_400.3 | (SEQ ID NO: 872) | ICAM1_HUMAN | 0.622 |
| GEVTYTTSQVSK_650.3_750.4 | (SEQ ID NO: 909) | EGLN_HUMAN | 0.622 |
| SLQAFVAVAAR_566.8_487.3 | (SEQ ID NO: 910) | IL23A_HUMAN | 0.622 |
| HYGGLTGLNK_530.3_301.1 | (SEQ ID NO: 835) | PGAM1_HUMAN | 0.622 |
| GPEDQDISISFAWDK_854.4_753.4 | (SEQ ID NO: 911) | DEF4_HUMAN | 0.622 |
| YVVISQGLDKPR_458.9_400.3 | (SEQ ID NO: 912) | LRP1_HUMAN | 0.621 |
| LWAYLTIQELLAK_781.5_300.2 | (SEQ ID NO: 1052) | ITIH1_HUMAN | 0.621 |
| SGAQATWTELPWPHEK_613.3_510.3 | (SEQ ID NO: 888) | HEMO_HUMAN | 0.621 |
| GTAEWLSFDVTDTVR_848.9_952.5 | (SEQ ID NO: 913) | TGFB3_HUMAN | 0.621 |
| FFQYDTWK_567.8_712.3 | (SEQ ID NO: 1068) | IGF2_HUMAN | 0.621 |

TABLE 12-continued

| | Peptide disclosed in adjacent | | |
|---|---|---|---|
| Transition | column | Protein | AUC |
| AHQLAIDTYQEFEETYIPK_766.0_634.4 | (SEQ ID NO: 914) | CSH_HUMAN | 0.620 |
| LPATEKPVLLSK_432.6_347.2 | (SEQ ID NO: 868) | HYOU1_HUMAN | 0.620 |
| NIQSVNVK_451.3_546.3 | (SEQ ID NO: 821) | GROA_HUMAN | 0.620 |
| TAVTANLDIR_537.3_288.2 | (SEQ ID NO: 915) | CHL1_HUMAN | 0.619 |
| WSAGLTSSQVDLYIPK_883.0_515.3 | (SEQ ID NO: 916) | CBG_HUMAN | 0.616 |
| QINSYVK_426.2_496.3 | (SEQ ID NO: 917) | CBG_HUMAN | 0.616 |
| GFQALGDAADIR_617.3_288.2 | (SEQ ID NO: 918) | TIMP1_HUMAN | 0.615 |
| WNFAYWAAHQPWSR_607.3_673.3 | (SEQ ID NO: 1050) | PRG2_HUMAN | 0.615 |
| NEIWYR_440.7_357.2 | (SEQ ID NO: 919) | FA12_HUMAN | 0.615 |
| VLEPTLK_400.3_587.3 | (SEQ ID NO: 920) | VTDB_HUMAN | 0.614 |
| YYLQGAK_421.7_516.3 | (SEQ ID NO: 48) | ITIH4_HUMAN | 0.614 |
| ALNSIIDVYHK_424.9_774.4 | (SEQ ID NO: 921) | S10A8_HUMAN | 0.614 |
| ETPEGAEAKPWYEPIYLGGVFQLEK_951.1_877.5 | (SEQ ID NO: 922) | TNFA_HUMAN | 0.614 |
| LNIGYIEDLK_589.3_837.4 | (SEQ ID NO: 923) | PAI2_HUMAN | 0.614 |
| NVNQSLLELHK_432.2_543.3 | (SEQ ID NO: 894) | FRIH_HUMAN | 0.613 |
| ILLLGTAVESAWGDEQSAFR_721.7_910.6 | (SEQ ID NO: 1058) | CXA1_HUMAN | 0.613 |
| AALAAFNAQNNGSNFQLEEISR_789.1_633.3 | (SEQ ID NO: 891) | FETUA_HUMAN | 0.613 |
| VLEPTLK_400.3_458.3 | (SEQ ID NO: 920) | VTDB_HUMAN | 0.613 |
| VGEYSLYIGR_578.8_708.4 | (SEQ ID NO: 58) | SAMP_HUMAN | 0.613 |
| DIPHWLNPTR_416.9_373.2 | (SEQ ID NO: 924) | PAPP1_HUMAN | 0.612 |
| NEIVFPAGILQAPFYTR_968.5_357.2 | (SEQ ID NO: 925) | ECE1_HUMAN | 0.612 |
| AEHPTWGDEQLFQTTR_639.3_765.4 | (SEQ ID NO: 926) | PGH1_HUMAN | 0.612 |
| VEPLYELVTATDFAYSSTVR_754.4_712.4 | (SEQ ID NO: 56) | CO8B_HUMAN | 0.611 |
| DEIPHNDIALLK_459.9_260.2 | (SEQ ID NO: 864) | HABP2_HUMAN | 0.611 |
| QINSYVK_426.2_610.3 | (SEQ ID NO: 917) | CBG_HUMAN | 0.610 |
| SWNEPLYHLVTEVR_581.6_614.3 | (SEQ ID NO: 927) | PRL_HUMAN | 0.610 |
| YGIEEHGK_311.5_341.2 | (SEQ ID NO: 1061) | CXA1_HUMAN | 0.610 |
| FGFGGSTDSGPIR_649.3_946.5 | (SEQ ID NO: 5) | ADA12_HUMAN | 0.610 |
| ANDQYLTAAALHNLDEAVK_686.4_317.2 | (SEQ ID NO: 861) | IL1A_HUMAN | 0.610 |
| VRPQQLVK_484.3_609.4 | (SEQ ID NO: 29) | ITIH4_HUMAN | 0.609 |
| IPKPEASFSPR_410.2_506.3 | (SEQ ID NO: 928) | ITIH4_HUMAN | 0.609 |
| SPEQQETVLDGNLIIR_906.5_685.4 | (SEQ ID NO: 71) | ITIH4_HUMAN | 0.609 |
| DDLYVSDAFHK_655.3_704.3 | (SEQ ID NO: 929) | ANT3_HUMAN | 0.609 |
| ELPEHTVK_476.8_347.2 | (SEQ ID NO: 87) | VTDB_HUMAN | 0.609 |
| FLYHK_354.2_284.2 | (SEQ ID NO: 901) | AMBP_HUMAN | 0.608 |
| QRPPDLDTSSNAVDLLFFTDESGDSR_961.5_262.2 | (SEQ ID NO: 930) | C1R_HUMAN | 0.608 |
| DPDQTDGLGLSYLSSHIANVER_796.4_328.1 | (SEQ ID NO: 57) | GELS_HUMAN | 0.608 |

TABLE 12-continued

| Transition | Peptide disclosed in adjacent column | Protein | AUC |
|---|---|---|---|
| NEIWYR_440.7_637.4 | (SEQ ID NO: 919) | FA12_HUMAN | 0.607 |
| LQLSETNR_480.8_672.4 | (SEQ ID NO: 785) | PSG8_HUMAN | 0.606 |
| GQVPENEANVVITTLK_571.3_462.3 | (SEQ ID NO: 931) | CADH1_HUMAN | 0.606 |
| FTGSQPFGQGVEHATANK_626.0_521.2 | (SEQ ID NO: 932) | TSP1_HUMAN | 0.605 |
| LEPLYSASGPGLRPLVIK_637.4_260.2 | (SEQ ID NO: 933) | CAA60698 | 0.605 |
| QRPPDLDTSSNAVDLLFFTDESGDSR_961.5_866.3 | (SEQ ID NO: 930) | C1R_HUMAN | 0.604 |
| LTTVDIVTLR_565.8_815.5 | (SEQ ID NO: 1054) | IL2RB_HUMAN | 0.604 |
| TSDQIHFFFAK_447.6_512.3 | (SEQ ID NO: 905) | ANT3_HUMAN | 0.604 |
| IQHPFTVEEFVLPK_562.0_861.5 | (SEQ ID NO: 934) | PZP_HUMAN | 0.603 |
| NKPGVYTDVAYYLAWIR_677.0_821.5 | (SEQ ID NO: 896) | FA12_HUMAN | 0.603 |
| TEQAAVAR_423.2_615.4 | (SEQ ID NO: 935) | FA12_HUMAN | 0.603 |
| EIGELYLPK_531.3_819.5 | (SEQ ID NO: 895) | AACT_HUMAN | 0.602 |
| LFYADHPFIFLVR_546.6_647.4 | (SEQ ID NO: 936) | SERPH_HUMAN | 0.602 |
| AEHPTWGDEQLFQTTR_639.3_569.3 | (SEQ ID NO: 926) | PGH1_HUMAN | 0.601 |
| TSYQVYSK_488.2_787.4 | (SEQ ID NO: 937) | C163A_HUMAN | 0.601 |
| YTTEIIK_434.2_704.4 | (SEQ ID NO: 40) | C1R_HUMAN | 0.601 |
| NVIQISNDLENLR_509.9_402.3 | (SEQ ID NO: 938) | LEP_HUMAN | 0.600 |
| AFLEVNEEGSEAAASTAVVIAGR_764.4_685.4 | (SEQ ID NO: 939) | ANT3_HUMAN | 0.600 |

TABLE 13

Middle Window Individual Stats

| Transition | Peptide disclosed in adjacent column | Protein | AUC |
|---|---|---|---|
| SEYGAALAWEK_612.8_788.4 | (SEQ ID NO: 1051) | CO6_HUMAN | 0.738 |
| VFQFLEK_455.8_811.4 | (SEQ ID NO: 810) | CO5_HUMAN | 0.709 |
| ALNHLPLEYNSALYSR_621.0_696.4 | (SEQ ID NO: 72) | CO6_HUMAN | 0.705 |
| SLDFTELDVAAEK_719.4_316.2 | (SEQ ID NO: 871) | ANGT_HUMAN | 0.692 |
| VEHSDLSFSK_383.5_234.1 | (SEQ ID NO: 7) | B2MG_HUMAN | 0.686 |
| LLAPSDSPEWLSFDVTGVVR_730.1_430.3 | (SEQ ID NO: 883) | TGFB1_HUMAN | 0.683 |
| ALNHLPLEYNSALYSR_621.0_538.3 | (SEQ ID NO: 72) | CO6_HUMAN | 0.683 |
| VLEPTLK_400.3_458.3 | (SEQ ID NO: 920) | VTDB_HUMAN | 0.681 |
| LHEAFSPVSYQHDLALLR_699.4_251.2 | (SEQ ID NO: 940) | FA12_HUMAN | 0.681 |
| SEYGAALAWEK_612.8_845.5 | (SEQ ID NO: 1051) | CO6_HUMAN | 0.679 |
| YGIEEHGK_311.5_599.3 | (SEQ ID NO: 1061) | CXA1_HUMAN | 0.677 |
| ALQDQLVLVAAK_634.9_289.2 | (SEQ ID NO: 33) | ANGT_HUMAN | 0.675 |

TABLE 13-continued

| | Middle Window Individual Stats | | |
|---|---|---|---|
| Transition | Peptide disclosed in adjacent column | Protein | AUC |
| VLEPTLK_400.3_587.3 | (SEQ ID NO: 920) | VTDB_HUMAN | 0.667 |
| VNHVTLSQPK_374.9_244.2 | (SEQ ID NO: 834) | B2MG_HUMAN | 0.665 |
| IEEIAAK_387.2_660.4 | (SEQ ID NO: 30) | CO5_HUMAN | 0.664 |
| DALSSVQESQVAQQAR_573.0_502.3 | (SEQ ID NO: 91) | APOC3_HUMAN | 0.664 |
| TLLPVSKPEIR_418.3_514.3 | (SEQ ID NO: 25) | CO5_HUMAN | 0.662 |
| ALQDQLVLVAAK_634.9_956.6 | (SEQ ID NO: 33) | ANGT_HUMAN | 0.661 |
| TLAFVR_353.7_492.3 | (SEQ ID NO: 1055) | FA7_HUMAN | 0.661 |
| SEPRPGVLLR_375.2_654.4 | (SEQ ID NO: 12) | FA7_HUMAN | 0.658 |
| VEHSDLSFSK_383.5_468.2 | (SEQ ID NO: 7) | B2MG_HUMAN | 0.653 |
| DPTFIPAPIQAK_433.2_461.2 | (SEQ ID NO: 857) | ANGT_HUMAN | 0.653 |
| QGHNSVFLIK_381.6_260.2 | (SEQ ID NO: 830) | HEMO_HUMAN | 0.650 |
| SLDFTELDVAAEK_719.4_874.5 | (SEQ ID NO: 871) | ANGT_HUMAN | 0.650 |
| ELPQSIVYK_538.8_417.7 | (SEQ ID NO: 820) | FBLN3_HUMAN | 0.649 |
| TYLHTYESEI_628.3_515.3 | (SEQ ID NO: 100) | ENPP2_HUMAN | 0.647 |
| SLQAFVAVAAR_566.8_804.5 | (SEQ ID NO: 910) | IL23A_HUMAN | 0.646 |
| AQPVQVAEGSEPDGFWEALGGK_758.0_574.3 | (SEQ ID NO: 837) | GELS_HUMAN | 0.644 |
| QGHNSVFLIK_381.6_520.4 | (SEQ ID NO: 830) | HEMO_HUMAN | 0.644 |
| VNHVTLSQPK_374.9_459.3 | (SEQ ID NO: 834) | B2MG_HUMAN | 0.643 |
| DLHLSDVFLK_396.2_260.2 | (SEQ ID NO: 856) | CO6_HUMAN | 0.643 |
| TEQAAVAR_423.2_615.4 | (SEQ ID NO: 935) | FA12_HUMAN | 0.643 |
| GPITSAAELNDPQSILLR_632.4_826.5 | (SEQ ID NO: 941) | EGLN_HUMAN | 0.643 |
| HFQNLGK_422.2_527.2 | (SEQ ID NO: 831) | AFAM_HUMAN | 0.642 |
| TEQAAVAR_423.2_487.3 | (SEQ ID NO: 935) | FA12_HUMAN | 0.642 |
| AVDIPGLEAATPYR_736.9_399.2 | (SEQ ID NO: 942) | TENA_HUMAN | 0.642 |
| TLFIFGVTK_513.3_811.5 | (SEQ ID NO: 842) | PSG4_HUMAN | 0.642 |
| DLHLSDVFLK_396.2_366.2 | (SEQ ID NO: 856) | CO6_HUMAN | 0.641 |
| AFTECCVVASQLR_770.9_574.3 | (SEQ ID NO: 1) | CO5_HUMAN | 0.640 |
| EVFSKPISWEELLQ_852.9_376.2 | (SEQ ID NO: 840) | FA40A_HUMAN | 0.639 |
| DPTFIPAPIQAK_433.2_556.3 | (SEQ ID NO: 857) | ANGT_HUMAN | 0.639 |
| FSLVSGWGQLLDR_493.3_403.2 | (SEQ ID NO: 878) | FA7_HUMAN | 0.638 |
| HYINLITR_515.3_301.1 | (SEQ ID NO: 102) | NPY_HUMAN | 0.637 |
| HFQNLGK_422.2_285.1 | (SEQ ID NO: 831) | AFAM_HUMAN | 0.637 |
| VPLALFALNR_557.3_620.4 | (SEQ ID NO: 943) | PEPD_HUMAN | 0.636 |
| IHPSYTNYR_575.8_813.4 | (SEQ ID NO: 775) | PSG2_HUMAN | 0.635 |
| IEEIAAK_387.2_531.3 | (SEQ ID NO: 30) | CO5_HUMAN | 0.635 |
| GEVTYTTSQVSK_650.3_750.4 | (SEQ ID NO: 909) | EGLN_HUMAN | 0.634 |
| DFNQFSSGEK_386.8_333.2 | (SEQ ID NO: 845) | FETA_HUMAN | 0.634 |

TABLE 13-continued

| | | | |
|---|---|---|---|
| Middle Window Individual Stats | | | |
| Transition | Peptide disclosed in adjacent column | Protein | AUC |
| VVGGLVALR_442.3_784.5 | (SEQ ID NO: 944) | FA12_HUMAN | 0.634 |
| SDGAKPGPR_442.7_459.2 | (SEQ ID NO: 879) | COLI_HUMAN | 0.634 |
| DVLLLVHNLPQNLTGHIWYK_791.8_310.2 | (SEQ ID NO: 783) | PSG7_HUMAN | 0.634 |
| TLLPVSKPEIR_418.3_288.2 | (SEQ ID NO: 25) | CO5_HUMAN | 0.633 |
| NKPGVYTDVAYYLAWIR_677.0_821.5 | (SEQ ID NO: 896) | FA12_HUMAN | 0.630 |
| QVFAVQR_424.2_473.3 | (SEQ ID NO: 844) | ELNE_HUMAN | 0.630 |
| NHYTESISVAK_624.8_415.2 | (SEQ ID NO: 945) | NEUR1_HUMAN | 0.630 |
| IAPQLSTEELVSLGEK_857.5_333.2 | (SEQ ID NO: 832) | AFAM_HUMAN | 0.629 |
| IHPSYTNYR_575.8_598.3 | (SEQ ID NO: 775) | PSG2_HUMAN | 0.627 |
| EVFSKPISWEELLQ_852.9_260.2 | (SEQ ID NO: 840) | FA40A_HUMAN | 0.627 |
| SILFLGK_389.2_201.1 | (SEQ ID NO: 881) | THBG_HUMAN | 0.626 |
| IEVIITLK_464.8_587.4 | (SEQ ID NO: 884) | CXL11_HUMAN | 0.625 |
| VVGGLVALR_442.3_685.4 | (SEQ ID NO: 944) | FA12_HUMAN | 0.624 |
| VVLSSGSGPGLDLPLVLGLPLQLK_791.5_598.4 | (SEQ ID NO: 946) | SHBG_HUMAN | 0.624 |
| FGFGGSTDSGPIR_649.3_946.5 | (SEQ ID NO: 5) | ADA12_HUMAN | 0.623 |
| VVLSSGSGPGLDLPLVLGLPLQLK_791.5_768.5 | (SEQ ID NO: 946) | SHBG_HUMAN | 0.622 |
| YGIEEHGK_311.5_341.2 | (SEQ ID NO: 1061) | CXA1_HUMAN | 0.621 |
| LHEAFSPVSYQHDLALLR_699.4_380.2 | (SEQ ID NO: 940) | FA12_HUMAN | 0.621 |
| AHYDLR_387.7_566.3 | (SEQ ID NO: 88) | FETUA_HUMAN | 0.620 |
| FSVVYAK_407.2_381.2 | (SEQ ID NO: 47) | FETUA_HUMAN | 0.618 |
| ALALPPLGLAPLLNLWAKPQGR_770.5_256.2 | (SEQ ID NO: 947) | SHBG_HUMAN | 0.618 |
| YENYTSSFFIR_713.8_293.1 | (SEQ ID NO: 816) | IL12B_HUMAN | 0.617 |
| VELAPLPSWQPVGK_760.9_342.2 | (SEQ ID NO: 872) | ICAM1_HUMAN | 0.617 |
| SILFLGK_389.2_577.4 | (SEQ ID NO: 881) | THBG_HUMAN | 0.616 |
| ILPSVPK_377.2_227.2 | (SEQ ID NO: 867) | PGH1_HUMAN | 0.615 |
| IPSNPSHR_303.2_496.3 | (SEQ ID NO: 948) | FBLN3_HUMAN | 0.615 |
| HYFIAAVER_553.3_301.1 | (SEQ ID NO: 855) | FA8_HUMAN | 0.615 |
| FSVVYAK_407.2_579.4 | (SEQ ID NO: 47) | FETUA_HUMAN | 0.613 |
| VFQFLEK_455.8_276.2 | (SEQ ID NO: 810) | CO5_HUMAN | 0.613 |
| IAPQLSTEELVSLGEK_857.5_533.3 | (SEQ ID NO: 832) | AFAM_HUMAN | 0.613 |
| ILPSVPK_377.2_244.2 | (SEQ ID NO: 867) | PGH1_HUMAN | 0.613 |
| NKPGVYTDVAYYLAWIR_677.0_545.3 | (SEQ ID NO: 896) | FA12_HUMAN | 0.613 |
| WSAGLTSSQVDLYIPK_883.0_515.3 | (SEQ ID NO: 916) | CBG_HUMAN | 0.612 |
| TPSAAYLWVGTGASEAEK_919.5_849.4 | (SEQ ID NO: 35) | GELS_HUMAN | 0.612 |
| ALALPPLGLAPLLNLWAKPQGR_770.5_457.3 | (SEQ ID NO: 947) | SHBG_HUMAN | 0.612 |
| QLGLPGPPDVPDHAAYHPF_676.7_299.2 | (SEQ ID NO: 105) | ITIH4_HUMAN | 0.612 |

TABLE 13-continued

| | | | |
|---|---|---|---|
| | Middle Window Individual Stats | | |
| Transition | Peptide disclosed in adjacent column | Protein | AUC |
| ILDDLSPR_464.8_587.3 | (SEQ ID NO: 852) | ITIH4_HUMAN | 0.611 |
| VELAPLPSWQPVGK_760.9_400.3 | (SEQ ID NO: 872) | ICAM1_HUMAN | 0.611 |
| DADPDTFFAK_563.8_825.4 | (SEQ ID NO: 833) | AFAM_HUMAN | 0.611 |
| NHYTESISVAK_624.8_252.1 | (SEQ ID NO: 945) | NEUR1_HUMAN | 0.611 |
| SEPRPGVLLR_375.2_454.3 | (SEQ ID NO: 12) | FA7_HUMAN | 0.611 |
| LNIGYIEDLK_589.3_950.5 | (SEQ ID NO: 923) | PAI2_HUMAN | 0.611 |
| ANLINNIFELAGLGK_793.9_299.2 | (SEQ ID NO: 949) | LCAP_HUMAN | 0.609 |
| LTTVDIVTLR_565.8_716.4 | (SEQ ID NO: 1054) | IL2RB_HUMAN | 0.608 |
| TQILEWAAER_608.8_761.4 | (SEQ ID NO: 10) | EGLN_HUMAN | 0.608 |
| NEPEETPSIEK_636.8_573.3 | (SEQ ID NO: 950) | SOX5_HUMAN | 0.608 |
| AQPVQVAEGSEPDGFWEALGGK_758.0_623.4 | (SEQ ID NO: 837) | GELS_HUMAN | 0.607 |
| LQVNTPLVGASLLR_741.0_925.6 | (SEQ ID NO: 863) | BPIA1_HUMAN | 0.607 |
| VPSHAVVAR_312.5_345.2 | (SEQ ID NO: 951) | TRFL_HUMAN | 0.607 |
| SLQNASAIESILK_687.4_860.5 | (SEQ ID NO: 1069) | IL3_HUMAN | 0.607 |
| GVTGYFTFNLYLK_508.3_260.2 | (SEQ ID NO: 781) | PSG5_HUMAN | 0.605 |
| DFNQFSSGEK_386.8_189.1 | (SEQ ID NO: 845) | FETA_HUMAN | 0.605 |
| QLGLPGPPDVPDHAAYHPF_676.7_263.1 | (SEQ ID NO: 105) | ITIH4_HUMAN | 0.605 |
| TLEAQLTPR_514.8_814.4 | (SEQ ID NO: 68) | HEP2_HUMAN | 0.604 |
| AFTECCVVASQLR_770.9_673.4 | (SEQ ID NO: 1) | CO5_HUMAN | 0.604 |
| LTTVDIVTLR_565.8_815.5 | (SEQ ID NO: 1054) | IL2RB_HUMAN | 0.604 |
| TLNAYDHR_330.5_312.2 | (SEQ ID NO: 839) | PAR3_HUMAN | 0.603 |
| LWAYLTIQELLAK_781.5_300.2 | (SEQ ID NO: 1052) | ITIH1_HUMAN | 0.603 |
| GGLFADIASHPWQAAIFAK_667.4_375.2 | (SEQ ID NO: 952) | TPA_HUMAN | 0.603 |
| IPSNPSHR_303.2_610.3 | (SEQ ID NO: 948) | FBLN3_HUMAN | 0.603 |
| TDAPDLPEENQAR_728.3_843.4 | (SEQ ID NO: 17) | CO5_HUMAN | 0.603 |
| SPQAFYR_434.7_684.4 | (SEQ ID NO: 953) | REL3_HUMAN | 0.602 |
| SSNNPHSPIVEEFQVPYNK_729.4_261.2 | (SEQ ID NO: 954) | C1S_HUMAN | 0.601 |
| AHYDLR_387.7_288.2 | (SEQ ID NO: 88) | FETUA_HUMAN | 0.600 |
| DGSPDVTTADIGANTPDATK_973.5_844.4 | (SEQ ID NO: 44) | PGRP2_HUMAN | 0.600 |
| SPQAFYR_434.7_556.3 | (SEQ ID NO: 953) | REL3_HUMAN | 0.600 |

TABLE 14

| Transition | Peptide disclosed in adjacent column | Protein | AUC |
|---|---|---|---|
| ALNHLPLEYNSALYSR_621.0_696.4 | (SEQ ID NO: 72) | CO6_HUMAN | 0.656 |
| VPLALFALNR_557.3_620.4 | (SEQ ID NO: 943) | PEPD_HUMAN | 0.655 |
| ALNHLPLEYNSALYSR_621.0_538.3 | (SEQ ID NO: 72) | CO6_HUMAN | 0.652 |
| AVYEAVLR_460.8_587.4 | (SEQ ID NO: 78) | PEPD_HUMAN | 0.649 |
| SEPRPGVLLR_375.2_654.4 | (SEQ ID NO: 12) | FA7_HUMAN | 0.644 |
| VFQFLEK_455.8_811.4 | (SEQ ID NO: 810) | CO5_HUMAN | 0.643 |
| AQPVQVAEGSEPDGFWEALGGK_758.0_574.3 | (SEQ ID NO: 837) | GELS_HUMAN | 0.640 |
| TLAFVR_353.7_492.3 | (SEQ ID NO: 1055) | FA7_HUMAN | 0.639 |
| TEQAAVAR_423.2_615.4 | (SEQ ID NO: 935) | FA12_HUMAN | 0.637 |
| YGIEEHGK_311.5_599.3 | (SEQ ID NO: 1061) | CXA1_HUMAN | 0.637 |
| TEQAAVAR_423.2_487.3 | (SEQ ID NO: 935) | FA12_HUMAN | 0.633 |
| QINSYVK_426.2_496.3 | (SEQ ID NO: 917) | CBG_HUMAN | 0.633 |
| LIEIANHVDK_384.6_683.4 | (SEQ ID NO: 955) | ADA12_HUMAN | 0.633 |
| SEYGAALAWEK_612.8_845.5 | (SEQ ID NO: 1051) | CO6_HUMAN | 0.633 |
| ALQDQLVLVAAK_634.9_956.6 | (SEQ ID NO: 33) | ANGT_HUMAN | 0.628 |
| VLEPTLK_400.3_587.3 | (SEQ ID NO: 920) | VTDB_HUMAN | 0.628 |
| DFNQFSSGEK_386.8_333.2 | (SEQ ID NO: 845) | FETA_HUMAN | 0.628 |
| TYLHTYESEI_628.3_515.3 | (SEQ ID NO: 100) | ENPP2_HUMAN | 0.628 |
| LIEIANHVDK_384.6_498.3 | (SEQ ID NO: 955) | ADA12_HUMAN | 0.626 |
| QINSYVK_426.2_610.3 | (SEQ ID NO: 917) | CBG_HUMAN | 0.625 |
| SLDFTELDVAAEK_719.4_316.2 | (SEQ ID NO: 871) | ANGT_HUMAN | 0.625 |
| DPTFIPAPIQAK_433.2_461.2 | (SEQ ID NO: 857) | ANGT_HUMAN | 0.625 |
| AVYEAVLR_460.8_750.4 | (SEQ ID NO: 78) | PEPD_HUMAN | 0.623 |
| YENYTSSFFIR_713.8_756.4 | (SEQ ID NO: 816) | IL12B_HUMAN | 0.623 |
| SEYGAALAWEK_612.8_788.4 | (SEQ ID NO: 1051) | CO6_HUMAN | 0.623 |
| WSAGLTSSQVDLYIPK_883.0_515.3 | (SEQ ID NO: 916) | CBG_HUMAN | 0.622 |
| DALSSVQESQVAQQAR_573.0_502.3 | (SEQ ID NO: 91) | APOC3_HUMAN | 0.622 |
| ALQDQLVLVAAK_634.9_289.2 | (SEQ ID NO: 33) | ANGT_HUMAN | 0.621 |
| SLQAFVAVAAR_566.8_804.5 | (SEQ ID NO: 910) | IL23A_HUMAN | 0.621 |
| DPTFIPAPIQAK_433.2_556.3 | (SEQ ID NO: 857) | ANGT_HUMAN | 0.620 |
| FGFGGSTDSGPIR_649.3_946.5 | (SEQ ID NO: 5) | ADA12_HUMAN | 0.619 |
| VLEPTLK_400.3_458.3 | (SEQ ID NO: 920) | VTDB_HUMAN | 0.619 |
| SLDFTELDVAAEK_719.4_874.5 | (SEQ ID NO: 871) | ANGT_HUMAN | 0.618 |
| EVFSKPISWEELLQ_852.9_376.2 | (SEQ ID NO: 840) | FA40A_HUMAN | 0.618 |
| FGFGGSTDSGPIR_649.3_745.4 | (SEQ ID NO: 5) | ADA12_HUMAN | 0.618 |
| TPSAAYLWVGTGASEAEK_919.5_849.4 | (SEQ ID NO: 35) | GELS_HUMAN | 0.615 |
| LHEAFSPVSYQHDLALLR_699.4_251.2 | (SEQ ID NO: 940) | FA12_HUMAN | 0.615 |
| TLEAQLTPR_514.8_685.4 | (SEQ ID NO: 68) | HEP2_HUMAN | 0.613 |

TABLE 14-continued

Middle Late Individual Stats

| Transition | Peptide disclosed in adjacent column | Protein | AUC |
|---|---|---|---|
| ELPQSIVYK_538.8_417.7 | (SEQ ID NO: 820) | FBLN3_HUMAN | 0.612 |
| GYQELLEK_490.3_631.4 | (SEQ ID NO: 956) | FETA_HUMAN | 0.612 |
| VPLALFALNR_557.3_917.6 | (SEQ ID NO: 943) | PEPD_HUMAN | 0.611 |
| DLHLSDVFLK_396.2_260.2 | (SEQ ID NO: 856) | CO6_HUMAN | 0.611 |
| LTTVDIVTLR_565.8_815.5 | (SEQ ID NO: 1054) | IL2RB_HUMAN | 0.608 |
| WSAGLTSSQVDLYIPK_883.0_357.2 | (SEQ ID NO: 916) | CBG_HUMAN | 0.608 |
| ITQDAQLK_458.8_702.4 | (SEQ ID NO: 13) | CBG_HUMAN | 0.608 |
| NIQSVNVK_451.3_674.4 | (SEQ ID NO: 821) | GROA_HUMAN | 0.607 |
| ALEQDLPVNIK_620.4_570.4 | (SEQ ID NO: 93) | CNDP1_HUMAN | 0.607 |
| TLNAYDHR_330.5_312.2 | (SEQ ID NO: 839) | PAR3_HUMAN | 0.606 |
| LWAYLTIQELLAK_781.5_300.2 | (SEQ ID NO: 1052) | ITIH1_HUMAN | 0.606 |
| VVGGLVALR_442.3_784.5 | (SEQ ID NO: 944) | FA12_HUMAN | 0.605 |
| AQPVQVAEGSEPDGFWEALGGK_758.0_623.4 | (SEQ ID NO: 837) | GELS_HUMAN | 0.603 |
| SVVLIPLGAVDDGEHSQNEK_703.0_798.4 | (SEQ ID NO: 957) | CNDP1_HUMAN | 0.603 |
| SETEIHQGFQHLHQLFAK_717.4_318.1 | (SEQ ID NO: 958) | CBG_HUMAN | 0.603 |
| LLAPSDSPEWLSFDVTGVVR_730.1_430.3 | (SEQ ID NO: 883) | TGFB1_HUMAN | 0.603 |
| IEVIITLK_464.8_587.4 | (SEQ ID NO: 884) | CXL11_HUMAN | 0.602 |
| ITQDAQLK_458.8_803.4 | (SEQ ID NO: 13) | CBG_HUMAN | 0.602 |
| AEIEYLEK_497.8_552.3 | (SEQ ID NO: 959) | LYAM1_HUMAN | 0.601 |
| AVDIPGLEAATPYR_736.9_399.2 | (SEQ ID NO: 942) | TENA_HUMAN | 0.601 |
| LTTVDIVTLR_565.8_716.4 | (SEQ ID NO: 1054) | IL2RB_HUMAN | 0.600 |
| WWGGQPLWITATK__772.4_929.5 | (SEQ ID NO: 15) | ENPP2_HUMAN | 0.600 |

TABLE 15

Late Window Individual Stats

| Transition | Peptide disclosed in adjacent column | Protein | AUC |
|---|---|---|---|
| AVYEAVLR_460.8_587.4 | (SEQ ID NO: 78) | PEPD_HUMAN | 0.724 |
| AEIEYLEK_497.8_552.3 | (SEQ ID NO: 959) | LYAM1_HUMAN | 0.703 |
| QINSYVK_426.2_496.3 | (SEQ ID NO: 917) | CBG_HUMAN | 0.695 |
| AVYEAVLR_460.8_750.4 | (SEQ ID NO: 78) | PEPD_HUMAN | 0.693 |
| AALAAFNAQNNGSNFQLEEISR_789.1_746.4 | (SEQ ID NO: 891) | FETUA_HUMAN | 0.684 |
| QINSYVK_426.2_610.3 | (SEQ ID NO: 917) | CBG_HUMAN | 0.681 |
| VPLALFALNR_557.3_620.4 | (SEQ ID NO: 943) | PEPD_HUMAN | 0.678 |
| VGVISFAQK_474.8_580.3 | (SEQ ID NO: 960) | TFR2_HUMAN | 0.674 |
| TGVAVNKPAEFTVDAK_549.6_258.1 | (SEQ ID NO: 822) | FLNA_HUMAN | 0.670 |
| LIEIANHVDK_384.6_683.4 | (SEQ ID NO: 955) | ADA12_HUMAN | 0.670 |

TABLE 15-continued

| Late Window Individual Stats | | | |
| --- | --- | --- | --- |
| Transition | Peptide disclosed in adjacent column | Protein | AUC |
| LIEIANHVDK_384.6_498.3 | (SEQ ID NO: 955) | ADA12_HUMAN | 0.660 |
| SGVDLADSNQK_567.3_662.3 | (SEQ ID NO: 853) | VGFR3_HUMAN | 0.660 |
| TSYQVYSK_488.2_787.4 | (SEQ ID NO: 937) | C163A_HUMAN | 0.657 |
| ITQDAQLK_458.8_702.4 | (SEQ ID NO: 13) | CBG_HUMAN | 0.652 |
| YYGYTGAFR_549.3_450.3 | (SEQ ID NO: 843) | TRFL_HUMAN | 0.650 |
| ALEQDLPVNIK_620.4_798.5 | (SEQ ID NO: 93) | CNDP1_HUMAN | 0.650 |
| VFQYIDLHQDEFVQTLK_708.4_375.2 | (SEQ ID NO: 961) | CNDP1_HUMAN | 0.650 |
| SGVDLADSNQK_567.3_591.3 | (SEQ ID NO: 853) | VGFR3_HUMAN | 0.648 |
| YENYTSSFFIR_713.8_756.4 | (SEQ ID NO: 816) | IL12B_HUMAN | 0.647 |
| VLSSIEQK_452.3_691.4 | (SEQ ID NO: 962) | 1433S_HUMAN | 0.647 |
| YSHYNER_323.5_418.2 | (SEQ ID NO: 889) | HABP2_HUMAN | 0.646 |
| ILDGGNK_358.7_603.3 | (SEQ ID NO: 877) | CXCL5_HUMAN | 0.645 |
| GTYLYNDCPGPGQDTDCR_697.0_666.3 | (SEQ ID NO: 990) | TNR1A_HUMAN | 0.645 |
| AEIEYLEK_497.8_389.2 | (SEQ ID NO: 959) | LYAM1_HUMAN | 0.645 |
| TLPFSR_360.7_506.3 | (SEQ ID NO: 963) | LYAM1_HUMAN | 0.645 |
| DEIPHNDIALLK_459.9_510.8 | (SEQ ID NO: 864) | HABP2_HUMAN | 0.644 |
| ALEQDLPVNIK_620.4_570.4 | (SEQ ID NO: 93) | CNDP1_HUMAN | 0.644 |
| SPEAEDPLGVER_649.8_314.1 | (SEQ ID NO: 887) | Z512B_HUMAN | 0.644 |
| FGFGGSTDSGPIR_649.3_745.4 | (SEQ ID NO: 5) | ADA12_HUMAN | 0.642 |
| TASDFITK_441.7_781.4 | (SEQ ID NO: 37) | GELS_HUMAN | 0.641 |
| SETEIHQGFQHLHQLFAK_717.4_447.2 | (SEQ ID NO: 958) | CBG_HUMAN | 0.640 |
| SPQAFYR_434.7_556.3 | (SEQ ID NO: 953) | REL3_HUMAN | 0.639 |
| TAVTANLDIR_537.3_288.2 | (SEQ ID NO: 915) | CHL1_HUMAN | 0.636 |
| VPLALFALNR_557.3_917.6 | (SEQ ID NO: 943) | PEPD_HUMAN | 0.636 |
| YISPDQLADLYK_713.4_277.2 | (SEQ ID NO: 850) | ENOA_HUMAN | 0.633 |
| SETEIHQGFQHLHQLFAK_717.4_318.1 | (SEQ ID NO: 958) | CBG_HUMAN | 0.633 |
| SEPRPGVLLR_375.2_654.4 | (SEQ ID NO: 12) | FA7_HUMAN | 0.633 |
| GYQELLEK_490.3_631.4 | (SEQ ID NO: 956) | FETA_HUMAN | 0.633 |
| AYSDLSR_406.2_375.2 | (SEQ ID NO: 90) | SAMP_HUMAN | 0.633 |
| SVVLIPLGAVDDGEHSQNEK_703.0_798.4 | (SEQ ID NO: 957) | CNDP1_HUMAN | 0.632 |
| TLEAQLTPR_514.8_685.4 | (SEQ ID NO: 68) | HEP2_HUMAN | 0.631 |
| WSAGLTSSQVDLYIPK_883.0_515.3 | (SEQ ID NO: 916) | CBG_HUMAN | 0.631 |
| TEQAAVAR_423.2_615.4 | (SEQ ID NO: 935) | FA12_HUMAN | 0.628 |
| AQPVQVAEGSEPDGFWEALGGK_758.0_574.3 | (SEQ ID NO: 837) | GELS_HUMAN | 0.626 |
| AGITIPR_364.2_486.3 | (SEQ ID NO: 858) | IL17_HUMAN | 0.626 |
| AEVIWTSSDHQVLSGK_586.3_300.2 | (SEQ ID NO: 964) | PD1L1_HUMAN | 0.625 |
| TEQAAVAR_423.2_487.3 | (SEQ ID NO: 935) | FA12_HUMAN | 0.625 |
| NHYTESISVAK_624.8_415.2 | (SEQ ID NO: 945) | NEUR1_HUMAN | 0.625 |

TABLE 15-continued

| Transition | Peptide disclosed in adjacent column | Protein | AUC |
|---|---|---|---|
| Late Window Individual Stats | | | |
| WSAGLTSSQVDLYIPK_883.0_357.2 | (SEQ ID NO: 916) | CBG_HUMAN | 0.623 |
| YSHYNER_323.5_581.3 | (SEQ ID NO: 889) | HABP2_HUMAN | 0.623 |
| DFNQFSSGEK_386.8_333.2 | (SEQ ID NO: 845) | FETA_HUMAN | 0.621 |
| NIQSVNVK_451.3_674.4 | (SEQ ID NO: 821) | GROA_HUMAN | 0.620 |
| SVVLIPLGAVDDGEHSQNEK_703.0_286.2 | (SEQ ID NO: 957) | CNDP1_HUMAN | 0.620 |
| TLAFVR_353.7_492.3 | (SEQ ID NO: 1055) | FA7_HUMAN | 0.619 |
| AVDIPGLEAATPYR_736.9_286.1 | (SEQ ID NO: 942) | TENA_HUMAN | 0.619 |
| TEFLSNYLTNVDDITLVPGTLGR_846.8_600.3 | (SEQ ID NO: 824) | ENPP2_HUMAN | 0.618 |
| YWGVASFLQK_599.8_849.5 | (SEQ ID NO: 965) | RET4_HUMAN | 0.618 |
| TPSAAYLWVGTGASEAEK_919.5_428.2 | (SEQ ID NO: 35) | GELS_HUMAN | 0.618 |
| DPNGLPPEAQK_583.3_669.4 | (SEQ ID NO: 1063) | RET4_HUMAN | 0.617 |
| TYLHTYESEI_628.3_908.4 | (SEQ ID NO: 100) | ENPP2_HUMAN | 0.616 |
| SPQAFYR_434.7_684.4 | (SEQ ID NO: 953) | REL3_HUMAN | 0.616 |
| TPSAAYLWVGTGASEAEK_919.5_849.4 | (SEQ ID NO: 35) | GELS_HUMAN | 0.615 |
| ALNHLPLEYNSALYSR_621.0_538.3 | (SEQ ID NO: 72) | CO6_HUMAN | 0.615 |
| IEVNESGTVASSSTAVIVSAR_693.0_545.3 | (SEQ ID NO: 882) | PAI1_HUMAN | 0.615 |
| LTTVDIVTLR_565.8_815.5 | (SEQ ID NO: 1054) | IL2RB_HUMAN | 0.615 |
| LWAYLTIQELLAK_781.5_371.2 | (SEQ ID NO: 1052) | ITIH1_HUMAN | 0.613 |
| SYTITGLQPGTDYK_772.4_352.2 | (SEQ ID NO: 966) | FINC_HUMAN | 0.612 |
| GAVHVVVAETDYQSFAVLYLER_822.8_863.5 | (SEQ ID NO: 848) | CO8G_HUMAN | 0.612 |
| FQLPGQK_409.2_276.1 | (SEQ ID NO: 62) | PSG1_HUMAN | 0.612 |
| ILDGGNK_358.7_490.2 | (SEQ ID NO: 877) | CXCL5_HUMAN | 0.611 |
| DYWSTVK_449.7_620.3 | (SEQ ID NO: 885) | APOC3_HUMAN | 0.611 |
| AGLLRPDYALLGHR_518.0_595.4 | (SEQ ID NO: 95) | PGRP2_HUMAN | 0.611 |
| ALNFGGIGVVVGHELTHAFDDQGR_837.1_360.2 | (SEQ ID NO: 967) | ECE1_HUMAN | 0.611 |
| GYQELLEK_490.3_502.3 | (SEQ ID NO: 956) | FETA_HUMAN | 0.611 |
| HATLSLSIPR_365.6_472.3 | (SEQ ID NO: 865) | VGFR3_HUMAN | 0.610 |
| SVPVTKPVPVTKPITVTK_631.1_658.4 | (SEQ ID NO: 968) | Z512B_HUMAN | 0.610 |
| FQLPGQK_409.2_429.2 | (SEQ ID NO: 62) | PSG1_HUMAN | 0.610 |
| IYLQPGR_423.7_329.2 | (SEQ ID NO: 969) | ITIH2_HUMAN | 0.610 |
| TLNAYDHR_330.5_312.2 | (SEQ ID NO: 839) | PAR3_HUMAN | 0.609 |
| DPNGLPPEAQK_583.3_497.2 | (SEQ ID NO: 1063) | RET4_HUMAN | 0.609 |
| FGFGGSTDSGPIR_649.3_946.5 | (SEQ ID NO: 5) | ADA12_HUMAN | 0.609 |
| TYLHTYESEI_628.3_515.3 | (SEQ ID NO: 100) | ENPP2_HUMAN | 0.608 |
| GAVHVVVAETDYQSFAVLYLER_822.8_580.3 | (SEQ ID NO: 848) | CO8G_HUMAN | 0.608 |
| VPSHAVVAR_312.5_515.3 | (SEQ ID NO: 951) | TRFL_HUMAN | 0.608 |
| YWGVASFLQK_599.8_350.2 | (SEQ ID NO: 965) | RET4_HUMAN | 0.608 |

TABLE 15-continued

| | Peptide disclosed in | | |
|---|---|---|---|
| Transition | adjacent column | Protein | AUC |

Late Window Individual Stats

| Transition | Peptide disclosed in adjacent column | Protein | AUC |
|---|---|---|---|
| EWVAIESDSVQPVPR_856.4_468.3 | (SEQ ID NO: 970) | CNDP1_HUMAN | 0.607 |
| LQDAGVYR_461.2_680.3 | (SEQ ID NO: 902) | PD1L1_HUMAN | 0.607 |
| DLYHYITSYVVDGEIIIYGPAYSGR_955.5_650.3 | (SEQ ID NO: 971) | PSG1_HUMAN | 0.607 |
| LWAYLTIQELLAK_781.5_300.2 | (SEQ ID NO: 1052) | ITIH1_HUMAN | 0.606 |
| ITENDIQIALDDAK_779.9_632.3 | (SEQ ID NO: 55) | APOB_HUMAN | 0.606 |
| SYTITGLQPGTDYK_772.4_680.3 | (SEQ ID NO: 966) | FINC_HUMAN | 0.606 |
| FFQYDTWK_567.8_712.3 | (SEQ ID NO: 1068) | IGF2_HUMAN | 0.605 |
| IYLQPGR_423.7_570.3 | (SEQ ID NO: 969) | ITIH2_HUMAN | 0.605 |
| YNQLLR_403.7_529.4 | (SEQ ID NO: 1059) | ENOA_HUMAN | 0.605 |
| WWGGQPLWITATK__772.4_929.5 | (SEQ ID NO: 15) | ENPP2_HUMAN | 0.605 |
| WWGGQPLWITATK_772.4_373.2 | (SEQ ID NO: 15) | ENPP2_HUMAN | 0.605 |
| TASDFITK_441.7_710.4 | (SEQ ID NO: 37) | GELS_HUMAN | 0.605 |
| EWVAIESDSVQPVPR_856.4_486.2 | (SEQ ID NO: 970) | CNDP1_HUMAN | 0.605 |
| YEFLNGR_449.7_606.3 | (SEQ ID NO: 34) | PLMN_HUMAN | 0.604 |
| SNPVTLNVLYGPDLPR_585.7_654.4 | (SEQ ID NO: 782) | PSG6_HUMAN | 0.604 |
| ITQDAQLK_458.8_803.4 | (SEQ ID NO: 13) | CBG_HUMAN | 0.603 |
| LTTVDIVTLR_565.8_716.4 | (SEQ ID NO: 1054) | IL2RB_HUMAN | 0.602 |
| FNAVLTNPQGDYDTSTGK_964.5_2621 | (SEQ ID NO: 70) | C1QC_HUMAN | 0.602 |
| ITGFLKPGK_320.9_301.2 | (SEQ ID NO: 97) | LBP_HUMAN | 0.601 |
| DYWSTVK_449.7_347.2 | (SEQ ID NO: 885) | APOC3_HUMAN | 0.601 |
| DPTFIPAPIQAK_433.2_556.3 | (SEQ ID NO: 857) | ANGT_HUMAN | 0.601 |
| GWVTDGFSSLK_598.8_953.5 | (SEQ ID NO: 54) | APOC3_HUMAN | 0.601 |
| YYGYTGAFR_549.3_771.4 | (SEQ ID NO: 843) | TRFL_HUMAN | 0.601 |
| ELPEHTVK_476.8_347.2 | (SEQ ID NO: 87) | VTDB_HUMAN | 0.601 |
| FTFTLHLETPKPSISSSNLNPR_829.4_874.4 | (SEQ ID NO: 82) | PSG1_HUMAN | 0.601 |
| DLYHYITSYVVDGEIIIYGPAYSGR_955.5_707.3 | (SEQ ID NO: 971) | PSG1_HUMAN | 0.601 |
| SPQAFYR_434.7_684.4 | (SEQ ID NO: 953) | REL3_HUMAN | 0.616 |
| TPSAAYLWVGTGASEAEK_919.5_849.4 | (SEQ ID NO: 35) | GELS_HUMAN | 0.615 |
| ALNHLPLEYNSALYSR_621.0_538.3 | (SEQ ID NO: 72) | CO6_HUMAN | 0.615 |
| IEVNESGTVASSSTAVIVSAR_693.0_545.3 | (SEQ ID NO: 882) | PAI1_HUMAN | 0.615 |
| LTTVDIVTLR_565.8_815.5 | (SEQ ID NO: 1054) | IL2RB_HUMAN | 0.615 |
| LWAYLTIQELLAK_781.5_371.2 | (SEQ ID NO: 1052) | ITIH1_HUMAN | 0.613 |
| SYTITGLQPGTDYK_772.4_352.2 | (SEQ ID NO: 966) | FINC_HUMAN | 0.612 |
| GAVHVVVAETDYQSFAVLYLER_822.8_863.5 | (SEQ ID NO: 848) | CO8G_HUMAN | 0.612 |
| FQLPGQK_409.2_276.1 | (SEQ ID NO: 62) | PSG1_HUMAN | 0.612 |
| DLYHYITSYVVDGEIIIYGPAYSGR_955.5_707.3 | (SEQ ID NO: 971) | PSG1_HUMAN | 0.601 |

TABLE 16

| Variable | Peptide disclosed in adjacent column | Protein | Coefficient |
|---|---|---|---|
| | Lasso Early 32 | | |
| LIQDAVTGLTVNGQITGDK_972.0_798.4 | (SEQ ID NO: 807) | ITIH3_HUMAN | 9.53 |
| VQTAHFK_277.5_431.2 | (SEQ ID NO: 811) | CO8A_HUMAN | 9.09 |
| FLNWIK_410.7_560.3 | (SEQ ID NO: 4) | HABP2_HUMAN | 6.15 |
| ITGFLKPGK_320.9_429.3 | (SEQ ID NO: 97) | LBP_HUMAN | 5.29 |
| ELIEELVNITQNQK_557.6_517.3 | (SEQ ID NO: 806) | IL13_HUMAN | 3.83 |
| ALNHLPLEYNSALYSR_621.0_538.3 | (SEQ ID NO: 72) | CO6_HUMAN | 3.41 |
| DISEVVTPR_508.3_787.4 | (SEQ ID NO: 67) | CFAB_HUMAN | 0.44 |
| AHYDLR_387.7_288.2 | (SEQ ID NO: 88) | FETUA_HUMAN | 0.1 |

TABLE 17

| Variable | Peptide disclosed in adjacent column | Protein | Coefficient |
|---|---|---|---|
| | Lasso Early 100 | | |
| LIQDAVTGLTVNGQITGDK_972.0_798.4 | (SEQ ID NO: 807) | ITIH3_HUMAN | 6.56 |
| ALNHLPLEYNSALYSR_621.0_538.3 | (SEQ ID NO: 72) | CO6_HUMAN | 6.51 |
| VQTAHFK_277.5_431.2 | (SEQ ID NO: 811) | CO8A_HUMAN | 4.51 |
| NIQSVNVK_451.3_674.4 | (SEQ ID NO: 821) | GROA_HUMAN | 3.12 |
| TYLHTYESEI_628.3_908.4 | (SEQ ID NO: 100) | ENPP2_HUMAN | 2.68 |
| LIENGYFHPVK_439.6_627.4 | (SEQ ID NO: 827) | F13B_HUMAN | 2.56 |
| AVLHIGEK_289.5_292.2 | (SEQ ID NO: 817) | THBG_HUMAN | 2.11 |
| FLNWIK_410.7_560.3 | (SEQ ID NO: 4) | HABP2_HUMAN | 1.85 |
| ITGFLKPGK_320.9_429.3 | (SEQ ID NO: 97) | LBP_HUMAN | 1.36 |
| DALSSVQESQVAQQAR_573.0_672.4 | (SEQ ID NO: 91) | APOC3_HUMAN | 1.3 |
| DALSSVQESQVAQQAR_573.0_502.3 | (SEQ ID NO: 91) | APOC3_HUMAN | 0.83 |
| FLPCENK_454.2_550.2 | (SEQ ID NO: 828) | IL10_HUMAN | 0.39 |

TABLE 17-continued

| | Lasso Early 100 | | |
|---|---|---|---|
| Variable | Peptide disclosed in adjacent column | Protein | Coefficient |
| ELIEELVNITQNQK_557.6_517.3 | (SEQ ID NO: 806) | IL13_HUMAN | 0.3 |
| TEFLSNYLTNVDDITLVPGTLGR_846.8_600.3 | (SEQ ID NO: 824) | ENPP2_HUMAN | 0.29 |
| VSEADSSNADWVTK_754.9_347.2 | (SEQ ID NO: 813) | CFAB_HUMAN | 0.27 |
| ITLPDFTGDLR_624.3_288.2 | (SEQ ID NO: 3) | LBP_HUMAN | 0.13 |
| TGVAVNKPAEFTVDAK_549.6_258.1 | (SEQ ID NO: 822) | FLNA_HUMAN | 0.04 |
| TASDFITK_441.7_781.4 | (SEQ ID NO: 37) | GELS_HUMAN | -5.91 |
| LIQDAVTGLTVNGQITGDK_972.0_798.4 | (SEQ ID NO: 807) | ITIH3_HUMAN | 6.56 |

TABLE 18

| | Lasso Protein Early Window | | |
|---|---|---|---|
| Variable | Peptide disclosed in adjacent column | Protein | Coefficient |
| ALNHLPLEYNSALYSR_621.0_538.3 | (SEQ ID NO: 72) | CO6_HUMAN | 7.17 |
| LIQDAVTGLTVNGQITGDK_972.0_798.4 | (SEQ ID NO: 807) | ITIH3_HUMAN | 6.06 |
| LIENGYFHPVK_439.6_627.4 | (SEQ ID NO: 827) | F13B_HUMAN | 3.23 |
| WWGGQPLWITATK_772.4_929.5 | (SEQ ID NO: 15) | ENPP2_HUMAN | 2.8 |
| QALEEFQK_496.8_680.3 | (SEQ ID NO: 808) | CO8B_HUMAN | 2.73 |
| NIQSVNVK_451.3_674.4 | (SEQ ID NO: 821) | GROA_HUMAN | 2.53 |
| DALSSVQESQVAQQAR_573.0_672.4 | (SEQ ID NO: 91) | APOC3_HUMAN | 2.51 |
| AVLHIGEK_289.5_348.7 | (SEQ ID NO: 817) | THBG_HUMAN | 2.33 |
| FLNWIK_410.7_560.3 | (SEQ ID NO: 4) | HABP2_HUMAN | 1.05 |
| FLPCENK_454.2_550.2 | (SEQ ID NO: 828) | IL10_HUMAN | 0.74 |
| ITLPDFTGDLR_624.3_288.2 | (SEQ ID NO: 3) | LBP_HUMAN | 0.7 |
| DISEVVTPR_508.3_787.4 | (SEQ ID NO: 67) | CFAB_HUMAN | 0.45 |
| EVFSKPISWEELLQ_852.9_260.2 | (SEQ ID NO: 840) | FA40A_HUMAN | 0.17 |

TABLE 18-continued

| | Lasso Protein Early Window | | |
| --- | --- | --- | --- |
| Variable | Peptide disclosed in adjacent column | Protein | Coefficient |
| YYGYTGAFR_549.3_450.3 | (SEQ ID NO: 843) | TRFL_HUMAN | 0.06 |
| TASDFITK_441.7_781.4 | (SEQ ID NO: 37 | GELS_HUMAN | -7.65 |

TABLE 19

| | Lasso All Early Window | | |
| --- | --- | --- | --- |
| Variable | Peptide disclosed in adjacent column | Protein | Coefficient |
| FLNWIK_410.7_560.3 | (SEQ ID NO: 4) | HABP2_HUMAN | 3.74 |
| AHYDLR_387.7_288.2 | (SEQ ID NO: 88) | FETUA_HUMAN | 0.07 |
| ALNHLPLEYNSALYSR_621.0_538.3 | (SEQ ID NO: 72) | CO6_HUMAN | 6.07 |
| LIQDAVTGLTVNGQITGDK_972.0_798.4 | (SEQ ID NO: 807) | ITIH3_HUMAN | 8.85 |
| TYLHTYESEI_628.3_908.4 | (SEQ ID NO: 100) | ENPP2_HUMAN | 2.97 |
| VQTAHFK_277.5_431.2 | (SEQ ID NO: 811) | CO8A_HUMAN | 3.36 |
| ELIEELVNITQNQK_557.6_618.3 | (SEQ ID NO: 806) | IL13_HUMAN | 11.24 |
| VSEADSSNADWVTK_754.9_347.2 | (SEQ ID NO: 813) | CFAB_HUMAN | 0.63 |
| AVLHIGEK_289.5_292.2 | (SEQ ID NO: 817) | THBG_HUMAN | 0.51 |
| TGVAVNKPAEFTVDAK_549.6_977.5 | (SEQ ID NO: 822) | FLNA_HUMAN | 0.17 |
| LIENGYFHPVK_439.6_343.2 | (SEQ ID NO: 827) | F13B_HUMAN | 1.7 |
| AQPVQVAEGSEPDGFWEALGGK_758.0_574.3 | (SEQ ID NO: 837) | GELS_HUMAN | -0.93 |
| YYGYTGAFR_549.3_450.3 | (SEQ ID NO: 843) | TRFL_HUMAN | 1.4 |
| TASDFITK_441.7_781.4 | (SEQ ID NO: 37) | GELS_HUMAN | -0.07 |
| NIQSVNVK_451.3_674.4 | (SEQ ID NO: 821) | GROA_HUMAN | 2.12 |
| DALSSVQESQVAQQAR_573.0_672.4 | (SEQ ID NO: 91) | APOC3_HUMAN | 1.15 |
| DALSSVQESQVAQQAR_573.0_502.3 | (SEQ ID NO: 91) | APOC3_HUMAN | 0.09 |
| FGFGGSTDSGPIR_649.3_745.4 | (SEQ ID NO: 5) | ADA12_HUMAN | 2.45 |

TABLE 19-continued

| | Lasso All Early Window | | |
| --- | --- | --- | --- |
| Variable | Peptide disclosed in adjacent column | Protein | Coefficient |
| ALDLSLK_380.2_575.3 | (SEQ ID NO: 14) | ITIH3_HUMAN | 2.51 |
| TLFIFGVTK_513.3_811.5 | (SEQ ID NO: 842) | PSG4_HUMAN | 4.12 |
| ISQGEADINIAFYQR_575.6_684.4 | (SEQ ID NO: 875) | MMP8_HUMAN | 1.29 |
| SGVDLADSNQK_567.3_591.3 | (SEQ ID NO: 853) | VGFR3_HUMAN | 0.55 |
| GPGEDFR_389.2_322.2 | (SEQ ID NO: 873) | PTGDS_HUMAN | 0.07 |
| DPNGLPPEAQK_583.3_669.4 | (SEQ ID NO: 1063) | RET4_HUMAN | 1.36 |
| WNFAYWAAHQPWSR_607.3_545.3 | (SEQ ID NO: 1050) | PRG2_HUMAN | -1.27 |
| ELCLDPK_437.7_359.2 | (SEQ ID NO: 1066) | IL8_HUMAN | 0.3 |
| FFQYDTWK_567.8_840.4 | (SEQ ID NO: 1068) | IGF2_HUMAN | 1.83 |
| IIEVEEEQEDPYLNDR_996.0_777.4 | (SEQ ID NO: 1065) | FBLN1_HUMAN | 1.14 |
| ECEELEEK_533.2_405.2 | (SEQ ID NO: 972) | IL15_HUMAN | 1.78 |
| LEEHYELR_363.5_580.3 | (SEQ ID NO: 904) | PAI2_HUMAN | 0.15 |
| LNIGYIEDLK_589.3_837.4 | (SEQ ID NO: 923) | PAI2_HUMAN | 0.32 |
| TAVTANLDIR_537.3_288.2 | (SEQ ID NO: 915) | CHL1_HUMAN | -0.98 |
| SWNEPLYHLVTEVR_581.6_716.4 | (SEQ ID NO: 927) | PRL_HUMAN | 1.88 |
| ILNIFGVIK_508.8_790.5 | (SEQ ID NO: 874) | TFR1_HUMAN | 0.05 |
| TPSAAYLWVGTGASEAEK_919.5_849.4 | (SEQ ID NO: 35) | GELS_HUMAN | -2.69 |
| VGVISFAQK_474.8_693.4 | (SEQ ID NO: 960) | TFR2_HUMAN | -5.68 |
| LNIGYIEDLK_589.3_950.5 | (SEQ ID NO: 923) | PAI2_HUMAN | -1.43 |
| GQVPENEANVVITTLK_571.3_462.3 | (SEQ ID NO: 931) | CADH1_HUMAN | -0.55 |
| STPSLTTK_417.7_549.3 | (SEQ ID NO: 973) | IL6RA_HUMAN | -0.59 |
| ALLLGWVPTR_563.3_373.2 | (SEQ ID NO: 974) | PAR4_HUMAN | -0.97 |

TABLE 20

| | Lasso SummedCoef Early Window | | |
|---|---|---|---|
| Variable | Peptide disclosed in adjacent column | Protein | Coefficient |
| LIQDAVTGLTVNGQITGDK_972.0_798.4 | (SEQ ID NO: 807) | ITIH3_HUMAN | 1173.723955 |
| ALNHLPLEYNSALYSR_621.0_538.3 | (SEQ ID NO: 72) | CO6_HUMAN | 811.0150364 |
| ELIEELVNITQNQK_557.6_618.3 | (SEQ ID NO: 806) | IL13_HUMAN | 621.9659363 |
| VQTAHFK_277.5_431.2 | (SEQ ID NO: 811) | CO8A_HUMAN | 454.178544 |
| NIQSVNVK_451.3_674.4 | (SEQ ID NO: 821) | GROA_HUMAN | 355.9550674 |
| TLFIFGVTK_513.3_811.5 | (SEQ ID NO: 842) | PSG4_HUMAN | 331.8629189 |
| GPGEDFR_389.2_322.2 | (SEQ ID NO: 873) | PTGDS_HUMAN | 305.9079494 |
| FLPCENK_454.2_550.2 | (SEQ ID NO: 828) | IL10_HUMAN | 296.9473975 |
| FLNWIK_410.7_560.3 | (SEQ ID NO: 4) | HABP2_HUMAN | 282.9841332 |
| LIENGYFHPVK_439.6_627.4 | (SEQ ID NO: 827) | F13B_HUMAN | 237.5320227 |
| ECEELEEK_533.2_405.2 | (SEQ ID NO: 972) | IL15_HUMAN | 200.38281 |
| FGFGGSTDSGPIR_649.3_745.4 | (SEQ ID NO: 5) | ADA12_HUMAN | 194.6252869 |
| QALEEFQK_496.8_680.3 | (SEQ ID NO: 808) | CO8B_HUMAN | 179.2518843 |
| IIEVEEEQEDPYLNDR_996.0_777.4 | (SEQ ID NO: 1065) | FBLN1_HUMAN | 177.7534111 |
| TYLHTYESEI_628.3_908.4 | (SEQ ID NO: 100) | ENPP2_HUMAN | 164.9735228 |
| ELIEELVNITQNQK_557.6_517.3 | (SEQ ID NO: 806) | IL13_HUMAN | 162.2414693 |
| LEEHYELR_363.5_580.3 | (SEQ ID NO: 904) | PAI2_HUMAN | 152.9262386 |
| ISQGEADINIAFYQR_575.6_684.4 | (SEQ ID NO: 875) | MMP8_HUMAN | 144.2445011 |
| HPWIVHWDQLPQYQLNR_744.0_918.5 | (SEQ ID NO: 829) | KS6A3_HUMAN | 140.2287926 |
| AHYDLR_387.7_288.2 | (SEQ ID NO: 88) | FETUA_HUMAN | 137.9737525 |
| GFQALGDAADIR_617.3_288.2 | (SEQ ID NO: 918) | TIMP1_HUMAN | 130.4945567 |
| SWNEPLYHLVTEVR_581.6_716.4 | (SEQ ID NO: 927) | PRL_HUMAN | 127.442646 |
| SGVDLADSNQK_567.3_591.3 | (SEQ ID NO: 853) | VGFR3_HUMAN | 120.5149446 |
| YENYTSSFFIR_713.8_293.1 | (SEQ ID NO: 816) | IL12B_HUMAN | 117.0947487 |

TABLE 20-continued

| Lasso SummedCoef Early Window | | | |
| --- | --- | --- | --- |
| Variable | Peptide disclosed in adjacent column | Protein | Coefficient |
| FFQYDTWK_567.8_840.4 | (SEQ ID NO: 1068) | IGF2_HUMAN | 109.8569617 |
| HYFIAAVER_553.3_658.4 | (SEQ ID NO: 855) | FA8_HUMAN | 106.9426543 |
| ITGFLKPGK_320.9_429.3 | (SEQ ID NO: 97) | LBP_HUMAN | 103.8056505 |
| DALSSVQESQVAQQAR_573.0_502.3 | (SEQ ID NO: 91) | APOC3_HUMAN | 98.50490812 |
| SGVDLADSNQK_567.3_662.3 | (SEQ ID NO: 853) | VGFR3_HUMAN | 97.19989285 |
| ALDLSLK__380.2_575.3 | (SEQ ID NO: 14) | ITIH3_HUMAN | 94.84900337 |
| TGVAVNKPAEFTVDAK_549.6_258.1 | (SEQ ID NO: 822) | FLNA_HUMAN | 92.52335783 |
| HPWIVHWDQLPQYQLNR_744.0_1047.0 | (SEQ ID NO: 829) | KS6A3_HUMAN | 91.77547608 |
| LIQDAVTGLTVNGQITGDK_972.0_640.4 | (SEQ ID NO: 807) | ITIH3_HUMAN | 83.6483639 |
| LNIGYIEDLK_589.3_837.4 | (SEQ ID NO: 923) | PAI2_HUMAN | 83.50221521 |
| IALGGLLFPASNLR_481.3_657.4 | (SEQ ID NO: 975) | SHBG_HUMAN | 79.33146741 |
| LPATEKPVLLSK_432.6_460.3 | (SEQ ID NO: 868) | HYOU1_HUMAN | 78.89429168 |
| FQLSETNR_497.8_605.3 | (SEQ ID NO: 776) | PSG2_HUMAN | 78.13445824 |
| NEIVFPAGILQAPFYTR_968.5_357.2 | (SEQ ID NO: 925) | ECE1_HUMAN | 75.12145257 |
| ALDLSLK_380.2_185.1 | (SEQ ID NO: 14) | ITIH3_HUMAN | 63.05454715 |
| DLHLSDVFLK_396.2_366.2 | (SEQ ID NO: 856) | CO6_HUMAN | 58.26831142 |
| TQILEWAAER_608.8_761.4 | (SEQ ID NO: 10) | EGLN_HUMAN | 57.29461621 |
| FSVVYAK_407.2_381.2 | (SEQ ID NO: 47) | FETUA_HUMAN | 54.78436389 |
| VSEADSSNADWVTK_754.9_347.2 | (SEQ ID NO: 813) | CFAB_HUMAN | 54.40003244 |
| DPNGLPPEAQK_583.3_669.4 | (SEQ ID NO: 1063) | RET4_HUMAN | 53.89169348 |
| VQEAHLTEDQIFYFPK_655.7_701.4 | (SEQ ID NO: 31) | CO8G_HUMAN | 53.33747599 |
| LSSPAVITDK_515.8_830.5 | (SEQ ID NO: 26) | PLMN_HUMAN | 53.22513181 |
| ITLPDFTGDLR_624.3_288.2 | (SEQ ID NO: 3) | LBP_HUMAN | 51.5477235 |
| AVLHIGEK_289.5_292.2 | (SEQ ID NO: 817) | THBG_HUMAN | 49.73092632 |

TABLE 20-continued

| Lasso SummedCoef Early Window | | | |
| --- | --- | --- | --- |
| Variable | Peptide disclosed in adjacent column | Protein | Coefficient |
| GEVTYTTSQVSK_650.3_750.4 | (SEQ ID NO: 909) | EGLN_HUMAN | 45.14743629 |
| GYVIIKPLVWV_643.9_854.6 | (SEQ ID NO: 976) | SAMP_HUMAN | 44.05164273 |
| TGVAVNKPAEFTVDAK_549.6_977.5 | (SEQ ID NO: 822) | FLNA_HUMAN | 42.99898046 |
| YYGYTGAFR_549.3_450.3 | (SEQ ID NO: 843) | TRFL_HUMAN | 42.90897411 |
| ILDGGNK_358.7_490.2 | (SEQ ID NO: 877) | CXCL5_HUMAN | 42.60771281 |
| FLPCENK_454.2_390.2 | (SEQ ID NO: 828) | IL10_HUMAN | 42.56799651 |
| GFQALGDAADIR_617.3_717.4 | (SEQ ID NO: 918) | TIMP1_HUMAN | 38.68456017 |
| SDGAKPGPR_442.7_213.6 | (SEQ ID NO: 879) | COLI_HUMAN | 38.47800265 |
| NTGVISVVTTGLDR_716.4_662.4 | (SEQ ID NO: 977) | CADH1_HUMAN | 32.62953675 |
| SERPPIFEIR_415.2_288.2 | (SEQ ID NO: 978) | LRP1_HUMAN | 31.48248968 |
| DFHINLFQVLPWLK_885.5_400.2 | (SEQ ID NO: 94) | CFAB_HUMAN | 31.27286268 |
| DALSSVQESQVAQQAR_573.0_672.4 | (SEQ ID NO: 91) | APOC3_HUMAN | 31.26972354 |
| ELCLDPK_437.7_359.2 | (SEQ ID NO: 1066) | IL8_HUMAN | 29.91108737 |
| ILNIFGVIK_508.8_790.5 | (SEQ ID NO: 874) | TFR1_HUMAN | 29.88784921 |
| TEFLSNYLTNVDDITLVPGTLGR_846.8_600.3 | (SEQ ID NO: 824) | ENPP2_HUMAN | 29.42327998 |
| GAVHVVVAETDYQSFAVLYLER_822.8_863.5 | (SEQ ID NO: 848) | CO8G_HUMAN | 26.70286929 |
| AVLHIGEK_289.5_348.7 | (SEQ ID NO: 817) | THBG_HUMAN | 25.78703299 |
| TFLTVYWTPER_706.9_401.2 | (SEQ ID NO: 869) | ICAM1_HUMAN | 24.73090242 |
| AGITIPR_364.2_486.3 | (SEQ ID NO: 858) | IL17_HUMAN | 23.84580477 |
| GAVHVVVAETDYQSFAVLYLER_822.8_580.3 | (SEQ ID NO: 848) | CO8G_HUMAN | 23.81167843 |
| SLQAFVAVAAR_566.8_487.3 | (SEQ ID NO: 910) | IL23A_HUMAN | 23.61468839 |
| SWNEPLYHLVTEVR_581.6_614.3 | (SEQ ID NO: 927) | PRL_HUMAN | 23.2538221 |
| TYLHTYESEI_628.3_515.3 | (SEQ ID NO: 100) | ENPP2_HUMAN | 22.70115313 |
| TAHISGLPPSTDFIVYLSGLAPSIR_871.5_800.5 | (SEQ ID NO: 979) | TENA_HUMAN | 22.42695892 |

TABLE 20-continued

| | Lasso SummedCoef Early Window | | |
|---|---|---|---|
| Variable | Peptide disclosed in adjacent column | Protein | Coefficient |
| QNYHQDSEAAINR_515.9_544.3 | (SEQ ID NO: 897) | FRIH_HUMAN | 21.96827269 |
| AHQLAIDTYQEFEETYIPK_766.0_634.4 | (SEQ ID NO: 914) | CSH_HUMAN | 21.75765717 |
| GDTYPAELYITGSILR_885.0_274.1 | (SEQ ID NO: 870) | F13B_HUMAN | 20.89751398 |
| AHYDLR_387.7_566.3 | (SEQ ID NO: 88) | FETUA_HUMAN | 20.67629529 |
| IALGGLLFPASNLR_481.3_412.3 | (SEQ ID NO: 975) | SHBG_HUMAN | 19.28973033 |
| ATNATLDPR_479.8_272.2 | (SEQ ID NO: 980) | PAR1_HUMAN | 18.77604574 |
| FSVVYAK_407.2_579.4 | (SEQ ID NO: 47) | FETUA_HUMAN | 17.81136564 |
| HTLNQIDEVK_598.8_951.5 | (SEQ ID NO: 51) | FETUA_HUMAN | 17.29763288 |
| DIPHWLNPTR_416.9_373.2 | (SEQ ID NO: 924) | PAPP1_HUMAN | 17.00562521 |
| LYYGDDEK_501.7_563.2 | (SEQ ID NO: 42) | CO8A_HUMAN | 16.78897272 |
| AALAAFNAQNNGSNFQLEEISR_789.1_633.3 | (SEQ ID NO: 891) | FETUA_HUMAN | 16.41986569 |
| IQTHSTTYR_369.5_627.3 | (SEQ ID NO: 104) | F13B_HUMAN | 15.78335174 |
| GPITSAAELNDPQSILLR_632.4_826.5 | (SEQ ID NO: 941) | EGLN_HUMAN | 15.3936876 |
| QTLSWTVTPK_580.8_818.4 | (SEQ ID NO: 981) | PZP_HUMAN | 14.92509259 |
| AVGYLITGYQR_620.8_737.4 | (SEQ ID NO: 69) | PZP_HUMAN | 13.9795325 |
| DIIKPDPPK_511.8_342.2 | (SEQ ID NO: 982) | IL12B_HUMAN | 13.76508282 |
| YNQLLR_403.7_288.2 | (SEQ ID NO: 1059) | ENOA_HUMAN | 12.61733711 |
| GNGLTWAEK_488.3_634.3 | (SEQ ID NO: 847) | C163B_HUMAN | 12.5891421 |
| QVFAVQR_424.2_473.3 | (SEQ ID NO: 844) | ELNE_HUMAN | 12.57709327 |
| FLQEQGHR_338.8_497.3 | (SEQ ID NO: 23) | CO8G_HUMAN | 12.51843475 |
| HVVQLR_376.2_515.3 | (SEQ ID NO: 983) | IL6RA_HUMAN | 11.83747559 |
| DVLLLVHNLPQNLTGHIWYK_791.8_883.0 | (SEQ ID NO: 783) | PSG7_HUMAN | 11.69074708 |
| TFLTVYWTPER_706.9_502.3 | (SEQ ID NO: 869) | ICAM1_HUMAN | 11.63709776 |
| VELAPLPSWQPVGK_760.9_400.3 | (SEQ ID NO: 872) | ICAM1_HUMAN | 10.79897269 |

TABLE 20-continued

| | Peptide disclosed in adjacent | | |
| Variable | column | Protein | Coefficient |
| --- | --- | --- | --- |

Lasso SummedCoef Early Window

| Variable | Peptide disclosed in adjacent column | Protein | Coefficient |
| --- | --- | --- | --- |
| TLFIFGVTK_513.3_215.1 | (SEQ ID NO: 842) | PSG4_HUMAN | 10.2831751 |
| AYSDLSR_406.2_375.2 | (SEQ ID NO: 90) | SAMP_HUMAN | 10.00461148 |
| HATLSLSIPR_365.6_472.3 | (SEQ ID NO: 865) | VGFR3_HUMAN | 9.967933028 |
| LQGTLPVEAR_542.3_571.3 | (SEQ ID NO: 28) | CO5_HUMAN | 9.963760572 |
| NTVISVNPSTK_580.3_732.4 | (SEQ ID NO: 984) | VCAM1_HUMAN | 9.124228658 |
| EVFSKPISWEELLQ_852.9_260.2 | (SEQ ID NO: 840) | FA40A_HUMAN | 8.527980294 |
| SLQNASAIESILK_687.4_860.5 | (SEQ ID NO: 1069) | IL3_HUMAN | 8.429061621 |
| IQHPFTVEEFVLPK_562.0_861.5 | (SEQ ID NO: 934) | PZP_HUMAN | 7.996504258 |
| GVTGYFTFNLYLK_508.3_683.9 | (SEQ ID NO: 781) | PSG5_HUMAN | 7.94396229 |
| VFQYIDLHQDEFVQTLK_708.4_361.2 | (SEQ ID NO: 961) | CNDP1_HUMAN | 7.860590049 |
| ILDDLSPR_464.8_587.3 | (SEQ ID NO: 852) | ITIH4_HUMAN | 7.593889262 |
| LIENGYFHPVK_439.6_343.2 | (SEQ ID NO: 827) | F13B_HUMAN | 7.05838337 |
| VFQFLEK_455.8_811.4 | (SEQ ID NO: 810) | CO5_HUMAN | 6.976884759 |
| AFTECCVVASQLR_770.9_574.3 | (SEQ ID NO: 1) | CO5_HUMAN | 6.847474286 |
| WWGGQPLWITATK__772.4_929.5 | (SEQ ID NO: 15) | ENPP2_HUMAN | 6.744837357 |
| IQTHSTTYR_369.5_540.3 | (SEQ ID NO: 104) | F13B_HUMAN | 6.71464509 |
| IAQYYYTFK_598.8_395.2 | (SEQ ID NO: 859) | F13B_HUMAN | 6.540497911 |
| YGFYTHVFR_397.2_421.3 | (SEQ ID NO: 50) | THRB_HUMAN | 6.326347548 |
| YHFEALADTGISSEFYDNANDLLSK_940.8_874.5 | (SEQ ID NO: 1057) | CO8A_HUMAN | 6.261787525 |
| ANDQYLTAAALHNLDEAVK_686.4_301.1 | (SEQ ID NO: 861) | IL1A_HUMAN | 6.217191651 |
| FSLVSGWGQLLDR_493.3_403.2 | (SEQ ID NO: 878) | FA7_HUMAN | 6.1038295 |
| GWVTDGFSSLK_598.8_854.4 | (SEQ ID NO: 54) | APOC3_HUMAN | 6.053494609 |
| TLEAQLTPR_514.8_814.4 | (SEQ ID NO: 68) | HEP2_HUMAN | 5.855967278 |
| VSAPSGTGHLPGLNPL_506.3_300.7 | (SEQ ID NO: 777) | PSG3_HUMAN | 5.625944609 |

TABLE 20-continued

| | Lasso SummedCoef Early Window | | |
|---|---|---|---|
| Variable | Peptide disclosed in adjacent column | Protein | Coefficient |
| EAQLPVIENK_570.8_699.4 | (SEQ ID NO: 22) | PLMN_HUMAN | 5.407703773 |
| SPEAEDPLGVER_649.8_670.4 | (SEQ ID NO: 887) | Z512B_HUMAN | 5.341420139 |
| IAIDLFK_410.3_635.4 | (SEQ ID NO: 825) | HEP2_HUMAN | 4.698739039 |
| YEFLNGR_449.7_293.1 | (SEQ ID NO: 34) | PLMN_HUMAN | 4.658286706 |
| VQTAHFK_277.5_502.3 | (SEQ ID NO: 811) | CO8A_HUMAN | 4.628247194 |
| IEVIITLK_464.8_815.5 | (SEQ ID NO: 884) | CXL11_HUMAN | 4.57198762 |
| ILTPEVR_414.3_601.3 | (SEQ ID NO: 985) | GDF15_HUMAN | 4.452884608 |
| LEEHYELR_363.5_288.2 | (SEQ ID NO: 904) | PAI2_HUMAN | 4.411983862 |
| HATLSLSIPR_365.6_272.2 | (SEQ ID NO: 865) | VGFR3_HUMAN | 4.334242077 |
| NSDQEIDFK_548.3_294.2 | (SEQ ID NO: 1056) | S10A5_HUMAN | 4.25302369 |
| LPNNVLQEK_527.8_844.5 | (SEQ ID NO: 814) | AFAM_HUMAN | 4.183602548 |
| ELANTIK_394.7_475.3 | (SEQ ID NO: 986) | S10AC_HUMAN | 4.13558153 |
| LSIPQITTK_500.8_687.4 | (SEQ ID NO: 987) | PSG5_HUMAN | 3.966238797 |
| TLNAYDHR_330.5_312.2 | (SEQ ID NO: 839) | PAR3_HUMAN | 3.961140111 |
| WWGGQPLWITATK__772.4_373.2 | (SEQ ID NO: 15) | ENPP2_HUMAN | 3.941476057 |
| ELLESYIDGR_597.8_710.4 | (SEQ ID NO: 2) | THRB_HUMAN | 3.832723338 |
| ATLSAAPSNPR_542.8_570.3 | (SEQ ID NO: 906) | CXCL2_HUMAN | 3.82834767 |
| VVLSSGSGPGLDLPLVLGLPLQLK_791.5_598.4 | (SEQ ID NO: 946) | SHBG_HUMAN | 3.80737887 |
| NADYSYSVWK_616.8_333.2 | (SEQ ID NO: 60) | CO5_HUMAN | 3.56404167 |
| ILILPSVTR_506.3_559.3 | (SEQ ID NO: 789) | PSGx_HUMAN | 3.526998593 |
| ALEQDLPVNIK_620.4_798.5 | (SEQ ID NO: 93) | CNDP1_HUMAN | 3.410412424 |
| QVCADPSEEWVQK_788.4_275.2 | (SEQ ID NO: 1062) | CCL3_HUMAN | 3.30795151 |
| SVQNDSQAIAEVLNQLK_619.7_914.5 | (SEQ ID NO: 988) | DESP_HUMAN | 3.259270741 |
| QVFAVQR_424.2_620.4 | (SEQ ID NO: 844) | ELNE_HUMAN | 3.211482663 |

TABLE 20-continued

| Lasso SummedCoef Early Window | | | |
| --- | --- | --- | --- |
| Variable | Peptide disclosed in adjacent column | Protein | Coefficient |
| ALPGEQQPLHALTR_511.0_807.5 | (SEQ ID NO: 989) | IBP1_HUMAN | 3.211207158 |
| LEPLYSASGPGLRPLVIK_637.4_260.2 | (SEQ ID NO: 933) | CAA60698 | 3.203088951 |
| GTYLYNDCPGPGQDTDCR_697.0_666.3 | (SEQ ID NO: 990) | TNR1A_HUMAN | 3.139418139 |
| DAGLSWGSAR_510.2_576.3 | (SEQ ID NO: 809) | NEUR4_HUMAN | 3.005197927 |
| YGFYTHVFR_397.2_659.4 | (SEQ ID NO: 50) | THRB_HUMAN | 2.985663918 |
| NNQLVAGYLQGPNVNLEEK_700.7_357.2 | (SEQ ID NO: 991) | IL1RA_HUMAN | 2.866983196 |
| EKPAGGIPVLGSLVNTVLK_631.4_930.6 | (SEQ ID NO: 96) | BPIB1_HUMAN | 2.798965142 |
| FGSDDEGR_441.7_735.3 | (SEQ ID NO: 992) | PTHR_HUMAN | 2.743283546 |
| IEVNESGTVASSSTAVIVSAR_693.0_545.3 | (SEQ ID NO: 882) | PAI1_HUMAN | 2.699725572 |
| FATTFYQHLADSK_510.3_533.3 | (SEQ ID NO: 993) | ANT3_HUMAN | 2.615073729 |
| DYWSTVK_449.7_347.2 | (SEQ ID NO: 885) | APOC3_HUMAN | 2.525459346 |
| QLGLPGPPDVPDHAAYHPF_676.7_263.1 | (SEQ ID NO: 105) | ITIH4_HUMAN | 2.525383799 |
| LSSPAVITDK_515.8_743.4 | (SEQ ID NO: 26) | PLMN_HUMAN | 2.522306831 |
| TEFLSNYLTNVDDITLVPGTLGR_846.8_699.4 | (SEQ ID NO: 824) | ENPP2_HUMAN | 2.473366805 |
| SILFLGK_389.2_201.1 | (SEQ ID NO: 881) | THBG_HUMAN | 2.472413913 |
| VTFEYR_407.7_614.3 | (SEQ ID NO: 898) | CRHBP_HUMAN | 2.425338167 |
| SVVLIPLGAVDDGEHSQNEK_703.0_798.4 | (SEQ ID NO: 957) | CNDP1_HUMAN | 2.421340244 |
| HTLNQIDEVK_598.8_958.5 | (SEQ ID NO: 51) | FETUA_HUMAN | 2.419851187 |
| ALNSIIDVYHK_424.9_661.3 | (SEQ ID NO: 921) | S10A8_HUMAN | 2.367904596 |
| ETLALLSTHR_570.8_500.3 | (SEQ ID NO: 994) | IL5_HUMAN | 2.230076769 |
| GLQYAAQEGLLALQSELLR_1037.1_858.5 | (SEQ ID NO: 818) | LBP_HUMAN | 2.205949216 |
| TYNVDK_370.2_262.1 | (SEQ ID NO: 995) | PPB1_HUMAN | 2.11849772 |
| FTITAGSK_412.7_576.3 | (SEQ ID NO: 876) | FABPL_HUMAN | 2.098589805 |
| GIVEECCFR_585.3_900.3 | (SEQ ID NO: 74) | IGF2_HUMAN | 2.059942995 |

TABLE 20-continued

| | Lasso SummedCoef Early Window | | |
|---|---|---|---|
| Variable | Peptide disclosed in adjacent column | Protein | Coefficient |
| YGIEEHGK_311.5_599.3 | (SEQ ID NO: 1061) | CXA1_HUMAN | 2.033828589 |
| ALVLELAK_428.8_331.2 | (SEQ ID NO: 9) | INHBE_HUMAN | 1.993820617 |
| ITLPDFTGDLR_624.3_920.5 | (SEQ ID NO: 3) | LBP_HUMAN | 1.968753183 |
| HELTDEELQSLFTNFANVVDK_817.1_906.5 | (SEQ ID NO: 823) | AFAM_HUMAN | 1.916438806 |
| EANQSTLENFLER_775.9_678.4 | (SEQ ID NO: 907) | IL4_HUMAN | 1.902033355 |
| DADPDTFFAK_563.8_825.4 | (SEQ ID NO: 833) | AFAM_HUMAN | 1.882254674 |
| LFIPQITR_494.3_727.4 | (SEQ ID NO: 996) | PSG9_HUMAN | 1.860649392 |
| DPNGLPPEAQK_583.3_497.2 | (SEQ ID NO: 1063) | RET4_HUMAN | 1.847702127 |
| VEPLYELVTATDFAYSSTVR_754.4_549.3 | (SEQ ID NO: 56) | CO8B_HUMAN | 1.842159131 |
| FQLSETNR_497.8_476.3 | (SEQ ID NO: 776) | PSG2_HUMAN | 1.834693717 |
| FSLVSGWGQLLDR_493.3_516.3 | (SEQ ID NO: 878) | FA7_HUMAN | 1.790582748 |
| NKPGVYTDVAYYLAWIR_677.0_545.3 | (SEQ ID NO: 896) | FA12_HUMAN | 1.777303353 |
| FTGSQPFGQGVEHATANK_626.0_521.2 | (SEQ ID NO: 932) | TSP1_HUMAN | 1.736517431 |
| DDLYVSDAFHK_655.3_704.3 | (SEQ ID NO: 929) | ANT3_HUMAN | 1.717534082 |
| AFLEVNEEGSEAAASTAVVIAGR_764.4_685.4 | (SEQ ID NO: 939) | ANT3_HUMAN | 1.679420475 |
| LPNNVLQEK_527.8_730.4 | (SEQ ID NO: 814) | AFAM_HUMAN | 1.66321148 |
| IVLSLDVPIGLLQILLEQAR_735.1_503.3 | (SEQ ID NO: 892) | UCN2_HUMAN | 1.644983604 |
| DPTFIPAPIQAK_433.2_556.3 | (SEQ ID NO: 857) | ANGT_HUMAN | 1.625411496 |
| SDLEVAHYK_531.3_617.3 | (SEQ ID NO: 812) | CO8B_HUMAN | 1.543640117 |
| QLYGDTGVLGR_589.8_501.3 | (SEQ ID NO: 819) | CO8G_HUMAN | 1.505242962 |
| VNHVTLSQPK_374.9_459.3 | (SEQ ID NO: 834) | B2MG_HUMAN | 1.48233058 |
| TLLPVSKPEIR_418.3_288.2 | (SEQ ID NO: 25) | CO5_HUMAN | 1.439531341 |
| SEYGAALAWEK_612.8_845.5 | (SEQ ID NO: 1051) | CO6_HUMAN | 1.424401638 |
| YGIEEHGK_311.5_341.2 | (SEQ ID NO: 1061) | CXA1_HUMAN | 1.379872204 |

TABLE 20-continued

| Lasso SummedCoef Early Window | | | |
|---|---|---|---|
| Variable | Peptide disclosed in adjacent column | Protein | Coefficient |
| DAGLSWGSAR_510.3_390.2 | (SEQ ID NO: 809) | NEUR4_HUMAN | 1.334272677 |
| AEHPTWGDEQLFQTTR_639.3_569.3 | (SEQ ID NO: 926) | PGH1_HUMAN | 1.30549273 |
| FQSVFTVTR_542.8_623.4 | (SEQ ID NO: 862) | C1QC_HUMAN | 1.302847429 |
| VPGLYYFTYHASSR_554.3_420.2 | (SEQ ID NO: 1060) | C1QB_HUMAN | 1.245565877 |
| AYSDLSR_406.2_577.3 | (SEQ ID NO: 90) | SAMP_HUMAN | 1.220777002 |
| ALEQDLPVNIK_620.4_570.4 | (SEQ ID NO: 93) | CNDP1_HUMAN | 1.216612522 |
| NAVVQGLEQPHGLVVHPLR_688.4_890.6 | (SEQ ID NO: 997) | LRP1_HUMAN | 1.212935735 |
| TSDQIHFFFAK_447.6_659.4 | (SEQ ID NO: 905) | ANT3_HUMAN | 1.176238265 |
| GTYLYNDCPGPGQDTDCR_697.0_335.2 | (SEQ ID NO: 990) | TNR1A_HUMAN | 1.1455649 |
| TSYQVYSK_488.2_787.4 | (SEQ ID NO: 937) | C163A_HUMAN | 1.048896429 |
| ALNSIIDVYHK_424.9_774.4 | (SEQ ID NO: 921) | S10A8_HUMAN | 1.028522516 |
| VELAPLPSWQPVGK_760.9_342.2 | (SEQ ID NO: 872) | ICAM1_HUMAN | 0.995831393 |
| LSETNR_360.2_330.2 | (SEQ ID NO: 16) | PSG1_HUMAN | 0.976094717 |
| HFQNLGK_422.2_527.2 | (SEQ ID NO: 831) | AFAM_HUMAN | 0.956286531 |
| ELPQSIVYK_538.8_417.7 | (SEQ ID NO: 820) | FBLN3_HUMAN | 0.947931674 |
| LPATEKPVLLSK_432.6_347.2 | (SEQ ID NO: 868) | HYOU1_HUMAN | 0.932537153 |
| SPEAEDPLGVER_649.8_314.1 | (SEQ ID NO: 887) | Z512B_HUMAN | 0.905955419 |
| DEIPHNDIALLK_459.9_510.8 | (SEQ ID NO: 864) | HABP2_HUMAN | 0.9032484 |
| FFQYDTWK_567.8_712.3 | (SEQ ID NO: 1068) | IGF2_HUMAN | 0.884340285 |
| LIEIANHVDK_384.6_498.3 | (SEQ ID NO: 955) | ADA12_HUMAN | 0.881493383 |
| AGFAGDDAPR_488.7_701.3 | (SEQ ID NO: 998) | ACTB_HUMAN | 0.814836556 |
| YEFLNGR_449.7_606.3 | (SEQ ID NO: 34) | PLMN_HUMAN | 0.767373087 |
| VIAVNEVGR_478.8_284.2 | (SEQ ID NO: 999) | CHL1_HUMAN | 0.721519592 |
| SLSQQIENIR_594.3_531.3 | (SEQ ID NO: 1000) | CO1A1_HUMAN | 0.712051082 |

TABLE 20-continued

| | Lasso SummedCoef Early Window | | |
|---|---|---|---|
| Variable | Peptide disclosed in adjacent column | Protein | Coefficient |
| EWVAIESDSVQPVPR_856.4_486.2 | (SEQ ID NO: 970) | CNDP1_HUMAN | 0.647712421 |
| YGLVTYATYPK_638.3_843.4 | (SEQ ID NO: 63) | CFAB_HUMAN | 0.618499569 |
| SVVLIPLGAVDDGEHSQNEK_703.0_286.2 | (SEQ ID NO: 957) | CNDP1_HUMAN | 0.606626346 |
| NSDQEIDFK_548.3_409.2 | (SEQ ID NO: 1056) | S10A5_HUMAN | 0.601928175 |
| NVNQSLLELHK_432.2_543.3 | (SEQ ID NO: 894) | FRIH_HUMAN | 0.572008792 |
| IAQYYYTFK_598.8_884.4 | (SEQ ID NO: 859) | F13B_HUMAN | 0.495062844 |
| GPITSAAELNDPQSILLR_632.4_601.4 | (SEQ ID NO: 941) | EGLN_HUMAN | 0.47565795 |
| YTTEIIK_434.2_704.4 | (SEQ ID NO: 40) | C1R_HUMAN | 0.433318952 |
| GYVIIKPLVWV_643.9_304.2 | (SEQ ID NO: 976) | SAMP_HUMAN | 0.427905264 |
| LDFHFSSDR_375.2_464.2 | (SEQ ID NO: 838) | INHBC_HUMAN | 0.411898116 |
| IPSNPSHR_303.2_496.3 | (SEQ ID NO: 948) | FBLN3_HUMAN | 0.390037291 |
| APLTKPLK_289.9_357.2 | (SEQ ID NO: 85) | CRP_HUMAN | 0.38859469 |
| EVFSKPISWEELLQ_852.9_376.2 | (SEQ ID NO: 840) | FA40A_HUMAN | 0.371359974 |
| YENYTSSFFIR_713.8_756.4 | (SEQ ID NO: 816) | IL12B_HUMAN | 0.346336267 |
| SPQAFYR_434.7_556.3 | (SEQ ID NO: 953) | REL3_HUMAN | 0.345901234 |
| SVDEALR_395.2_488.3 | (SEQ ID NO: 1001) | PRDX2_HUMAN | 0.307518869 |
| FVFGTTPEDILR_697.9_742.4 | (SEQ ID NO: 1002) | TSP1_HUMAN | 0.302313589 |
| FTFTLHLETPKPSISSSNLNPR_829.4_787.4 | (SEQ ID NO: 82) | PSG1_HUMAN | 0.269826678 |
| VGEYSLYIGR_578.8_708.4 | (SEQ ID NO: 58) | SAMP_HUMAN | 0.226573173 |
| ILPSVPK_377.2_244.2 | (SEQ ID NO: 867) | PGH1_HUMAN | 0.225429414 |
| LFIPQITR_494.3_614.4 | (SEQ ID NO: 996) | PSG9_HUMAN | 0.18285533 |
| TGYYFDGISR_589.8_857.4 | (SEQ ID NO: 1003) | FBLN1_HUMAN | 0.182474114 |
| HYGGLTGLNK_530.3_759.4 | (SEQ ID NO: 835) | PGAM1_HUMAN | 0.152397007 |
| NQSPVLEPVGR_598.3_866.5 | (SEQ ID NO: 1067) | KS6A3_HUMAN | 0.128963949 |

TABLE 20-continued

Lasso SummedCoef Early Window

| Variable | Peptide disclosed in adjacent column | Protein | Coefficient |
|---|---|---|---|
| IGKPAPDFK_324.9_294.2 | (SEQ ID NO: 1004) | PRDX2_HUMAN | 0.113383235 |
| TSESTGSLPSPFLR_739.9_716.4 | (SEQ ID NO: 849) | PSMG1_HUMAN | 0.108159874 |
| ESDTSYVSLK_564.8_347.2 | (SEQ ID NO: 851) | CRP_HUMAN | 0.08569303 |
| ETPEGAEAKPWYEPIYLGGVFQLEK_951.1_877.5 | (SEQ ID NO: 922) | TNFA_HUMAN | 0.039781728 |
| TSDQIHFFFAK_447.6_512.3 | (SEQ ID NO: 905) | ANT3_HUMAN | 0.008064465 |

TABLE 21

Lasso32 Middle Window

| Variable | Peptide disclosed in adjacent column | UniProt_ID | Coefficient |
|---|---|---|---|
| SEYGAALAWEK_612.8_788.4 | (SEQ ID NO: 1051) | CO6_HUMAN | 6.99 |
| VFQFLEK_455.8_811.4 | (SEQ ID NO: 810) | CO5_HUMAN | 6.43 |
| VLEPTLK_400.3_458.3 | (SEQ ID NO: 920) | VTDB_HUMAN | 3.99 |
| SLDFTELDVAAEK_719.4_316.2 | (SEQ ID NO: 871) | ANGT_HUMAN | 3.33 |
| TLAFVR_353.7_492.3 | (SEQ ID NO: 1055) | FA7_HUMAN | 2.44 |
| YGIEEHGK_311.5_599.3 | (SEQ ID NO: 1061) | CXA1_HUMAN | 2.27 |
| LHEAFSPVSYQHDLALLR_699.4_251.2 | (SEQ ID NO: 940) | FA12_HUMAN | 2.14 |
| QGHNSVFLIK_381.6_520.4 | (SEQ ID NO: 830) | HEMO_HUMAN | 0.25 |
| LLAPSDSPEWLSFDVTGVVR_730.1_430.3 | (SEQ ID NO: 883) | TGFB1_HUMAN | -2.81 |
| ELPQSIVYK_538.8_417.7 | (SEQ ID NO: 820) | FBLN3_HUMAN | -3.46 |
| VNHVTLSQPK_374.9_244.2 | (SEQ ID NO: 834) | B2MG_HUMAN | -6.61 |

TABLE 22

| | Lasso 100 Middle Window | | |
| --- | --- | --- | --- |
| Variable | Peptide disclosed in adjacent column | UniProt_ID | Coefficient |
| VFQFLEK_455.8_811.4 | (SEQ ID NO: 810) | CO5_HUMAN | 6.89 |
| SEYGAALAWEK_612.8_788.4 | (SEQ ID NO: 1051) | CO6_HUMAN | 4.67 |
| GEVTYTTSQVSK_650.3_750.4 | (SEQ ID NO: 909) | EGLN_HUMAN | 3.4 |
| QVFAVQR_424.2_473.3 | (SEQ ID NO: 844) | ELNE_HUMAN | 1.94 |
| VELAPLPSWQPVGK_760.9_342.2 | (SEQ ID NO: 872) | ICAM1_HUMAN | 1.91 |
| LHEAFSPVSYQHDLALLR_699.4_251.2 | (SEQ ID NO: 940) | FA12_HUMAN | 1.8 |
| SLDFTELDVAAEK_719.4_316.2 | (SEQ ID NO: 871) | ANGT_HUMAN | 1.67 |
| YGIEEHGK_311.5_599.3 | (SEQ ID NO: 1061) | CXA1_HUMAN | 1.53 |
| YGIEEHGK_311.5_341.2 | (SEQ ID NO: 1061) | CXA1_HUMAN | 1.51 |
| HYINLITR_515.3_301.1 | (SEQ ID NO: 102) | NPY_HUMAN | 1.47 |
| TLAFVR_353.7_492.3 | (SEQ ID NO: 1055) | FA7_HUMAN | 1.46 |
| GVTGYFTFNLYLK_508.3_260.2 | (SEQ ID NO: 781) | PSG5_HUMAN | 1.28 |
| FSLVSGWGQLLDR_493.3_403.2 | (SEQ ID NO: 878) | FA7_HUMAN | 0.84 |
| DALSSVQESQVAQQAR_573.0_502.3 | (SEQ ID NO: 91) | APOC3_HUMAN | 0.41 |
| VELAPLPSWQPVGK_760.9_400.3 | (SEQ ID NO: 872) | ICAM1_HUMAN | 0.3 |
| AVDIPGLEAATPYR_736.9_399.2 | (SEQ ID NO: 942) | TENA_HUMAN | -0.95 |
| ELPQSIVYK_538.8_417.7 | (SEQ ID NO: 820) | FBLN3_HUMAN | -1.54 |
| DVLLLVHNLPQNLTGHIWYK_791.8_310.2 | (SEQ ID NO: 783) | PSG7_HUMAN | -1.54 |
| VPLALFALNR_557.3_620.4 | (SEQ ID NO: 943) | PEPD_HUMAN | -1.91 |
| LLAPSDSPEWLSFDVTGVVR_730.1_430.3 | (SEQ ID NO: 883) | TGFB1_HUMAN | -2.3 |
| VNHVTLSQPK_374.9_244.2 | (SEQ ID NO: 834) | B2MG_HUMAN | -3.6 |
| EVFSKPISWEELLQ_852.9_376.2 | (SEQ ID NO: 840) | FA40A_HUMAN | -3.96 |

TABLE 23

| Lasso Protein Middle Window | | | |
|---|---|---|---|
| Variable | Peptide disclosed in adjacent column | UniProt_ID | Coefficient |
| SEYGAALAWEK_612.8_788.4 | (SEQ ID NO: 1051) | CO6_HUMAN | 5.84 |
| VFQFLEK_455.8_811.4 | (SEQ ID NO: 810) | CO5_HUMAN | 5.58 |
| SLDFTELDVAAEK_719.4_316.2 | (SEQ ID NO: 871) | ANGT_HUMAN | 2.11 |
| TLAFVR_353.7_492.3 | (SEQ ID NO: 1055) | FA7_HUMAN | 1.83 |
| LHEAFSPVSYQHDLALLR_699.4_251.2 | (SEQ ID NO: 940) | FA12_HUMAN | 1.62 |
| HYINLITR_515.3_301.1 | (SEQ ID NO: 102) | NPY_HUMAN | 1.39 |
| VLEPTLK_400.3_458.3 | (SEQ ID NO: 920) | VTDB_HUMAN | 1.37 |
| YGIEEHGK_311.5_599.3 | (SEQ ID NO: 1061) | CXA1_HUMAN | 1.17 |
| VELAPLPSWQPVGK_760.9_342.2 | (SEQ ID NO: 872) | ICAM1_HUMAN | 1.13 |
| QVFAVQR_424.2_473.3 | (SEQ ID NO: 844) | ELNE_HUMAN | 0.79 |
| ANLINNIFELAGLGK_793.9_299.2 | (SEQ ID NO: 949) | LCAP_HUMAN | 0.23 |
| DVLLLVHNLPQNLTGHIWYK_791.8_310.2 | (SEQ ID NO: 783) | PSG7_HUMAN | -0.61 |
| VEHSDLSFSK_383.5_234.1 | (SEQ ID NO: 7) | B2MG_HUMAN | -0.69 |
| AVDIPGLEAATPYR_736.9_399.2 | (SEQ ID NO: 942) | TENA_HUMAN | -0.85 |
| VPLALFALNR_557.3_620.4 | (SEQ ID NO: 943) | PEPD_HUMAN | -1.45 |
| ELPQSIVYK_538.8_417.7 | (SEQ ID NO: 820) | FBLN3_HUMAN | -1.9 |
| LLAPSDSPEWLSFDVTGVVR_730.1_430.3 | (SEQ ID NO: 883) | TGFB1_HUMAN | -2.07 |
| EVFSKPISWEELLQ_852.9_376.2 | (SEQ ID NO: 840) | FA40A_HUMAN | -2.32 |

TABLE 24

| Lasso All Middle Window | | | |
|---|---|---|---|
| Variable | Peptide disclosed in adjacent column | UniProt_ID | Coefficient |
| SEYGAALAWEK_612.8_788.4 | (SEQ ID NO: 1051) | CO6_HUMAN | 2.48 |
| VFQFLEK_455.8_811.4 | (SEQ ID NO: 810) | CO5_HUMAN | 2.41 |

TABLE 24-continued

| | Peptide disclosed in adjacent | | |
|---|---|---|---|
| Variable | column | UniProt_ID | Coefficient |

Lasso All Middle Window

| Variable | Peptide disclosed in adjacent column | UniProt_ID | Coefficient |
|---|---|---|---|
| SLDFTELDVAAEK_719.4_316.2 | (SEQ ID NO: 871) | ANGT_HUMAN | 1.07 |
| YGIEEHGK_311.5_599.3 | (SEQ ID NO: 1061) | CXA1_HUMAN | 0.64 |
| VLEPTLK_400.3_458.3 | (SEQ ID NO: 920) | VTDB_HUMAN | 0.58 |
| LHEAFSPVSYQHDLALLR_699.4_251.2 | (SEQ ID NO: 940) | FA12_HUMAN | 0.21 |
| LLAPSDSPEWLSFDVTGVVR_730.1_430.3 | (SEQ ID NO: 883) | TGFB1_HUMAN | -0.62 |
| VNHVTLSQPK_374.9_244.2 | (SEQ ID NO: 834) | B2MG_HUMAN | -1.28 |

TABLE 25

Lasso32 Middle-Late Window

| Variable | Peptide disclosed in adjacent column | UniProt_ID | Coefficient |
|---|---|---|---|
| SEYGAALAWEK_612.8_845.5 | (SEQ ID NO: 1051) | CO6_HUMAN | 4.35 |
| TLAFVR_353.7_492.3 | (SEQ ID NO: 1055) | FA7_HUMAN | 2.42 |
| YGIEEHGK_311.5_599.3 | (SEQ ID NO: 1061) | CXA1_HUMAN | 1.46 |
| DFNQFSSGEK_386.8_333.2 | (SEQ ID NO: 845) | FETA_HUMAN | 1.37 |
| VFQFLEK_455.8_811.4 | (SEQ ID NO: 810) | CO5_HUMAN | 0.89 |
| LIEIANHVDK_384.6_683.4 | (SEQ ID NO: 955) | ADA12_HUMAN | 0.85 |
| QINSYVK_426.2_496.3 | (SEQ ID NO: 917) | CBG_HUMAN | 0.56 |
| TYLHTYESEI_628.3_515.3 | (SEQ ID NO: 100) | ENPP2_HUMAN | 0.53 |
| SLQAFVAVAAR_566.8_804.5 | (SEQ ID NO: 910) | IL23A_HUMAN | 0.39 |
| TEQAAVAR_423.2_615.4 | (SEQ ID NO: 935) | FA12_HUMAN | 0.26 |
| VLEPTLK_400.3_587.3 | (SEQ ID NO: 920) | VTDB_HUMAN | 0.24 |
| AQPVQVAEGSEPDGFWEALGGK_758.0_574.3 | (SEQ ID NO: 837) | GELS_HUMAN | -2.08 |
| VPLALFALNR_557.3_620.4 | (SEQ ID NO: 943) | PEPD_HUMAN | -2.09 |
| AVYEAVLR_460.8_587.4 | (SEQ ID NO: 78) | PEPD_HUMAN | -3.37 |

TABLE 26

| | Peptide disclosed in adjacent | | |
|---|---|---|---|
| Variable | column | UniProt_ID | Coefficient |
| VFQFLEK_455.8_811.4 | (SEQ ID NO: 810) | CO5_HUMAN | 3.82 |
| SEYGAALAWEK_612.8_845.5 | (SEQ ID NO: 1051) | CO6_HUMAN | 2.94 |
| YGIEEHGK_311.5_599.3 | (SEQ ID NO: 1061) | CXA1_HUMAN | 2.39 |
| DPTFIPAPIQAK_433.2_556.3 | (SEQ ID NO: 857) | ANGT_HUMAN | 2.05 |
| TLAFVR_353.7_492.3 | (SEQ ID NO: 1055) | FA7_HUMAN | 1.9 |
| NQSPVLEPVGR_598.3_866.5 | (SEQ ID NO: 1067) | KS6A3_HUMAN | 1.87 |
| ALNHLPLEYNSALYSR_621.0_538.3 | (SEQ ID NO: 72) | CO6_HUMAN | 1.4 |
| TQILEWAAER_608.8_761.4 | (SEQ ID NO: 10) | EGLN_HUMAN | 1.29 |
| VVGGLVALR_442.3_784.5 | (SEQ ID NO: 944) | FA12_HUMAN | 1.24 |
| QINSYVK_426.2_496.3 | (SEQ ID NO: 917) | CBG_HUMAN | 1.14 |
| YGIEEHGK_311.5_341.2 | (SEQ ID NO: 1061) | CXA1_HUMAN | 0.84 |
| ALEQDLPVNIK_620.4_570.4 | (SEQ ID NO: 93) | CNDP1_HUMAN | 0.74 |
| GTYLYNDCPGPGQDTDCR_697.0_666.3 | (SEQ ID NO: 990) | TNR1A_HUMAN | 0.51 |
| SLQNASAIESILK_687.4_860.5 | (SEQ ID NO: 1069) | IL3_HUMAN | 0.44 |
| DLHLSDVFLK_396.2_260.2 | (SEQ ID NO: 856) | CO6_HUMAN | 0.38 |
| LIEIANHVDK_384.6_683.4 | (SEQ ID NO: 955) | ADA12_HUMAN | 0.37 |
| NIQSVNVK_451.3_674.4 | (SEQ ID NO: 821) | GROA_HUMAN | 0.3 |
| FFQYDTWK_567.8_712.3 | (SEQ ID NO: 1068) | IGF2_HUMAN | 0.19 |
| ANLINNIFELAGLGK_793.9_299.2 | (SEQ ID NO: 949) | LCAP_HUMAN | 0.19 |
| TYLHTYESEI_628.3_515.3 | (SEQ ID NO: 100) | ENPP2_HUMAN | 0.15 |
| AALAAFNAQNNGSNFQLEEISR_789.1_746.4 | (SEQ ID NO: 891) | FETUA_HUMAN | -0.09 |
| AQPVQVAEGSEPDGFWEALGGK_758.0_574.3 | (SEQ ID NO: 837) | GELS_HUMAN | -0.52 |
| TSYQVYSK_488.2_787.4 | (SEQ ID NO: 937) | C163A_HUMAN | -0.62 |
| AVDIPGLEAATPYR_736.9_399.2 | (SEQ ID NO: 942) | TENA_HUMAN | -1.29 |

TABLE 26-continued

| | Lasso100 Middle-Late Window | | |
|---|---|---|---|
| Variable | Peptide disclosed in adjacent column | UniProt_ID | Coefficient |
| TAHISGLPPSTDFIVYLSGLAPSIR_871.5_472.3 | (SEQ ID NO: 979) | TENA_HUMAN | -1.53 |
| AEIEYLEK_497.8_552.3 | (SEQ ID NO: 959) | LYAM1_HUMAN | -1.73 |
| LLAPSDSPEWLSFDVTGVVR_730.1_430.3 | (SEQ ID NO: 883) | TGFB1_HUMAN | -1.95 |
| VPLALFALNR_557.3_620.4 | (SEQ ID NO: 943) | PEPD_HUMAN | -2.9 |
| AVYEAVLR_460.8_587.4 | (SEQ ID NO: 78) | PEPD_HUMAN | -3.04 |
| ELPQSIVYK_538.8_417.7 | (SEQ ID NO: 820) | FBLN3_HUMAN | -3.49 |
| EVFSKPISWEELLQ_852.9_376.2 | (SEQ ID NO: 840) | FA40A_HUMAN | -3.71 |

TABLE 27

| | Lasso Protein Middle-LateWindow | | |
|---|---|---|---|
| Variable | Peptide disclosed in adjacent column | UniProt_ID | Coefficient |
| VFQFLEK_455.8_811.4 | (SEQ ID NO: 810) | CO5_HUMAN | 4.25 |
| ALNHLPLEYNSALYSR_621.0_696.4 | (SEQ ID NO: 72) | CO6_HUMAN | 3.06 |
| YGIEEHGK_311.5_599.3 | (SEQ ID NO: 1061) | CXA1_HUMAN | 2.36 |
| SEPRPGVLLR_375.2_654.4 | (SEQ ID NO: 12) | FA7_HUMAN | 2.11 |
| TQILEWAAER_608.8_761.4 | (SEQ ID NO: 10) | EGLN_HUMAN | 1.81 |
| NQSPVLEPVGR_598.3_866.5 | (SEQ ID NO: 1067) | KS6A3_HUMAN | 1.79 |
| TEQAAVAR_423.2_615.4 | (SEQ ID NO: 935) | FA12_HUMAN | 1.72 |
| QINSYVK_426.2_496.3 | (SEQ ID NO: 917) | CBG_HUMAN | 0.98 |
| ALEQDLPVNIK_620.4_570.4 | (SEQ ID NO: 93) | CNDP1_HUMAN | 0.98 |
| NCSFSIIYPVVIK_770.4_555.4 | (SEQ ID NO: 836) | CRHBP_HUMAN | 0.76 |
| LIEIANHVDK_384.6_683.4 | (SEQ ID NO: 955) | ADA12_HUMAN | 0.63 |
| SLQNASAIESILK_687.4_860.5 | (SEQ ID NO: 1069) | IL3_HUMAN | 0.59 |
| ANLINNIFELAGLGK_793.9_299.2 | (SEQ ID NO: 949) | LCAP_HUMAN | 0.55 |

TABLE 27-continued

| | Lasso Protein Middle-LateWindow | | |
| --- | --- | --- | --- |
| Variable | Peptide disclosed in adjacent column | UniProt_ID | Coefficient |
| GTYLYNDCPGPGQDTDCR_697.0_666.3 | (SEQ ID NO: 990) | TNR1A_HUMAN | 0.55 |
| TYLHTYESEI_628.3_515.3 | (SEQ ID NO: 100) | ENPP2_HUMAN | 0.46 |
| NIQSVNVK_451.3_674.4 | (SEQ ID NO: 821) | GROA_HUMAN | 0.22 |
| LTTVDIVTLR_565.8_815.5 | (SEQ ID NO: 1054) | IL2RB_HUMAN | 0.11 |
| FFQYDTWK_567.8_712.3 | (SEQ ID NO: 1068) | IGF2_HUMAN | 0.01 |
| TSYQVYSK_488.2_787.4 | (SEQ ID NO: 937) | C163A_HUMAN | -0.76 |
| AQPVQVAEGSEPDGFWEALGGK_758.0_574.3 | (SEQ ID NO: 837) | GELS_HUMAN | -1.31 |
| AEIEYLEK_497.8_552.3 | (SEQ ID NO: 959) | LYAM1_HUMAN | -1.59 |
| LLAPSDSPEWLSFDVTGVVR_730.1_430.3 | (SEQ ID NO: 883) | TGFB1_HUMAN | -1.73 |
| AVDIPGLEAATPYR_736.9_399.2 | (SEQ ID NO: 942) | TENA_HUMAN | -2.02 |
| EVFSKPISWEELLQ_852.9_376.2 | (SEQ ID NO: 840) | FA40A_HUMAN | -3 |
| TGVAVNKPAEFTVDAK_549.6_258.1 | (SEQ ID NO: 822) | FLNA_HUMAN | -3.15 |
| ELPQSIVYK_538.8_417.7 | (SEQ ID NO: 820) | FBLN3_HUMAN | -3.49 |
| VNHVTLSQPK_374.9_244.2 | (SEQ ID NO: 834) | B2MG_HUMAN | -3.82 |
| VPLALFALNR_557.3_620.4 | (SEQ ID NO: 943) | PEPD_HUMAN | -4.94 |

45

TABLE 28

| | Lasso All Middle-LateWindow | | |
| --- | --- | --- | --- |
| Variable | Peptide disclosed in adjacent column | UniProt_ID | Coefficient |
| ALNHLPLEYNSALYSR_621.0_538.3 | (SEQ ID NO: 72) | CO6_HUMAN | 2.38 |
| TLAFVR_353.7_492.3 | (SEQ ID NO: 1055) | FA7_HUMAN | 0.96 |
| YGIEEHGK_311.5_599.3 | (SEQ ID NO: 1061) | CXA1_HUMAN | 0.34 |
| DPTFIPAPIQAK_433.2_461.2 | (SEQ ID NO: 857) | ANGT_HUMAN | 0.33 |
| DFNQFSSGEK_386.8_333.2 | (SEQ ID NO: 845) | FETA_HUMAN | 0.13 |
| QINSYVK_426.2_496.3 | (SEQ ID NO: 917) | CBG_HUMAN | 0.03 |
| TYLHTYESEI_628.3_515.3 | (SEQ ID NO: 100) | ENPP2_HUMAN | 0 |
| AQPVQVAEGSEPDGFWEALGGK_758.0_574.3 | (SEQ ID NO: 837) | GELS_HUMAN | -0.02 |

TABLE 28-continued

| Lasso All Middle-LateWindow | | | |
|---|---|---|---|
| Variable | Peptide disclosed in adjacent column | UniProt_ID | Coefficient |
| AEIEYLEK_497.8_552.3 | (SEQ ID NO: 959) | LYAM1_HUMAN | -0.05 |
| VNHVTLSQPK_374.9_244.2 | (SEQ ID NO: 834) | B2MG_HUMAN | -0.12 |
| LLAPSDSPEWLSFDVTGVVR_730.1_430.3 | (SEQ ID NO: 883) | TGFB1_HUMAN | -0.17 |
| EVFSKPISWEELLQ_852.9_376.2 | (SEQ ID NO: 840) | FA40A_HUMAN | -0.31 |
| AVDIPGLEAATPYR_736.9_399.2 | (SEQ ID NO: 942) | TENA_HUMAN | -0.35 |
| VPLALFALNR_557.3_620.4 | (SEQ ID NO: 943) | PEPD_HUMAN | -0.43 |
| AVYEAVLR_460.8_587.4 | (SEQ ID NO: 78) | PEPD_HUMAN | -2.33 |

TABLE 29

| Lasso 32 LateWindow | | | |
|---|---|---|---|
| Variable | Peptide disclosed in adjacent column | UniProt_ID | Coefficient |
| QINSYVK_426.2_610.3 | (SEQ ID NO: 917) | CBG_HUMAN | 3.24 |
| ILDGGNK_358.7_603.3 | (SEQ ID NO: 877) | CXCL5_HUMAN | 2.65 |
| VFQYIDLHQDEFVQTLK_708.4_375.2 | (SEQ ID NO: 961) | CNDP1_HUMAN | 2.55 |
| SGVDLADSNQK_567.3_662.3 | (SEQ ID NO: 853) | VGFR3_HUMAN | 2.12 |
| YSHYNER_323.5_418.2 | (SEQ ID NO: 889) | HABP2_HUMAN | 1.63 |
| DEIPHNDIALLK_459.9_510.8 | (SEQ ID NO: 864) | HABP2_HUMAN | 1.22 |
| SGVDLADSNQK_567.3_591.3 | (SEQ ID NO: 853) | VGFR3_HUMAN | 0.96 |
| FGFGGSTDSGPIR_649.3_745.4 | (SEQ ID NO: 5) | ADA12_HUMAN | 0.86 |
| GTYLYNDCPGPGQDTDCR_697.0_666.3 | (SEQ ID NO: 990) | TNR1A_HUMAN | 0.45 |
| TSYQVYSK_488.2_787.4 | (SEQ ID NO: 937) | C163A_HUMAN | -1.73 |
| TGVAVNKPAEFTVDAK_549.6_258.1 | (SEQ ID NO: 822) | FLNA_HUMAN | -2.56 |
| SPEAEDPLGVER_649.8_314.1 | (SEQ ID NO: 887) | Z512B_HUMAN | -3.04 |
| VPLALFALNR_557.3_620.4 | (SEQ ID NO: 943) | PEPD_HUMAN | -3.33 |
| YYGYTGAFR_549.3_450.3 | (SEQ ID NO: 843) | TRFL_HUMAN | -4.24 |
| AVYEAVLR_460.8_587.4 | (SEQ ID NO: 78) | PEPD_HUMAN | -5.83 |
| AEIEYLEK_497.8_552.3 | (SEQ ID NO: 959) | LYAM1_HUMAN | -6.52 |
| AALAAFNAQNNGSNFQLEEISR_789.1_746.4 | (SEQ ID NO: 891) | FETUA_HUMAN | -6.55 |

TABLE 30

| Variable | Peptide disclosed in adjacent column | | UniProt_ID | Coefficient |
|---|---|---|---|---|
| SGVDLADSNQK_567.3_662.3 | (SEQ ID NO: 853) | | VGFR3_HUMAN | 4.13 |
| ILDGGNK_358.7_603.3 | (SEQ ID NO: 877) | | CXCL5_HUMAN | 3.57 |
| QINSYVK_426.2_610.3 | (SEQ ID NO: 917) | | CBG_HUMAN | 3.41 |
| DEIPHNDIALLK_459.9_510.8 | (SEQ ID NO: 864) | | HABP2_HUMAN | 1.64 |
| VFQYIDLHQDEFVQTLK_708.4_375.2 | (SEQ ID NO: 961) | | CNDP1_HUMAN | 1.57 |
| FGFGGSTDSGPIR_649.3_745.4 | (SEQ ID NO: 5) | | ADA12_HUMAN | 1.45 |
| LTTVDIVTLR_565.8_815.5 | (SEQ ID NO: 1054) | | IL2RB_HUMAN | 0.71 |
| YSHYNER_323.5_418.2 | (SEQ ID NO: 889) | | HABP2_HUMAN | 0.68 |
| FFQYDTWK_567.8_712.3 | (SEQ ID NO: 882) | | IGF2_HUMAN | 0.42 |
| IEVNESGTVASSSTAVIVSAR_693.0_545.3 | (SEQ ID NO: 1068) | | PAI1_HUMAN | 0.36 |
| GTYLYNDCPGPGQDTDCR_697.0_666.3 | (SEQ ID NO: 990) | | TNR1A_HUMAN | 0.21 |
| LIEIANHVDK_384.6_683.4 | (SEQ ID NO: 955) | | ADA12_HUMAN | 0.1 |
| VGVISFAQK_474.8_580.3 | (SEQ ID NO: 960) | | TFR2_HUMAN | 0.08 |
| TSYQVYSK_488.2_787.4 | (SEQ ID NO: 937) | | C163A_HUMAN | −0.36 |
| ALNFGGIGVVVGHELTHAFDDQGR_837.1_360.2 | (SEQ ID NO: 967) | | ECE1_HUMAN | −0.65 |
| AYSDLSR_406.2_375.2 | (SEQ ID NO: 90) | | SAMP_HUMAN | −1.23 |
| TGVAVNKPAEFTVDAK_549.6_258.1 | (SEQ ID NO: 822) | | FLNA_HUMAN | −1.63 |
| SPEAEDPLGVER_649.8_314.1 | (SEQ ID NO: 887) | | Z512B_HUMAN | −2.29 |
| YYGYTGAFR_549.3_450.3 | (SEQ ID NO: 843) | | TRFL_HUMAN | −2.58 |
| VPLALFALNR_557.3_620.4 | (SEQ ID NO: 943) | | PEPD_HUMAN | −2.73 |
| YISPDQLADLYK_713.4_277.2 | (SEQ ID NO: 850) | | ENOA_HUMAN | −2.87 |
| AVDIPGLEAATPYR_736.9_286.1 | (SEQ ID NO: 942) | | TENA_HUMAN | −3.9 |
| AEIEYLEK_497.8_552.3 | (SEQ ID NO: 959) | | LYAM1_HUMAN | −5.29 |
| AVYEAVLR_460.8_587.4 | (SEQ ID NO: 78) | | PEPD_HUMAN | −5.51 |
| AALAAFNAQNNGSNFQLEEISR_789.1_746.4 | (SEQ ID NO: 891) | | FETUA_HUMAN | −6.49 |

TABLE 31

| Variable | Peptide disclosed in adjacent column | | UniProt_ID | Coefficient |
|---|---|---|---|---|
| SGVDLADSNQK_567.3_662.3 | (SEQ ID NO: 853) | | VGFR3_HUMAN | 3.33 |
| ILDGGNK_358.7_603.3 | (SEQ ID NO: 877) | | CXCL5_HUMAN | 3.25 |
| QINSYVK_426.2_496.3 | (SEQ ID NO: 917) | | CBG_HUMAN | 2.41 |
| YSHYNER_323.5_418.2 | (SEQ ID NO: 889) | | HABP2_HUMAN | 1.82 |
| ALEQDLPVNIK_620.4_798.5 | (SEQ ID NO: 93) | | CNDP1_HUMAN | 1.32 |

TABLE 31-continued

| | Lasso Protein Late Window | | |
|---|---|---|---|
| Variable | Peptide disclosed in adjacent column | UniProt_ID | Coefficient |
| LIEIANHVDK_384.6_683.4 | (SEQ ID NO: 955) | ADA12_HUMAN | 1.27 |
| GTYLYNDCPGPGQDTDCR_697.0_666.3 | (SEQ ID NO: 990) | TNR1A_HUMAN | 0.26 |
| IEVNESGTVASSSTAVIVSAR_693.0_545.3 | (SEQ ID NO: 882) | PAI1_HUMAN | 0.18 |
| LTTVDIVTLR_565.8_815.5 | (SEQ ID NO: 1054) | IL2RB_HUMAN | 0.18 |
| TSYQVYSK_488.2_787.4 | (SEQ ID NO: 937) | C163A_HUMAN | −0.11 |
| TGVAVNKPAEFTVDAK_549.6_258.1 | (SEQ ID NO: 822) | FLNA_HUMAN | −0.89 |
| AYSDLSR_406.2_375.2 | (SEQ ID NO: 90) | SAMP_HUMAN | −1.47 |
| SPEAEDPLGVER_649.8_314.1 | (SEQ ID NO: 887) | Z512B_HUMAN | −1.79 |
| YYGYTGAFR_549.3_450.3 | (SEQ ID NO: 843) | TRFL_HUMAN | −2.22 |
| YISPDQLADLYK_713.4_277.2 | (SEQ ID NO: 850) | ENOA_HUMAN | −2.41 |
| AVDIPGLEAATPYR_736.9_286.1 | (SEQ ID NO: 942) | TENA_HUMAN | −2.94 |
| AEIEYLEK_497.8_552.3 | (SEQ ID NO: 959) | LYAM1_HUMAN | −5.18 |
| AALAAFNAQNNGSNFQLEEISR_789.1_746.4 | (SEQ ID NO: 891) | FETUA_HUMAN | −5.71 |
| AVYEAVLR_460.8_587.4 | (SEQ ID NO: 78) | PEPD_HUMAN | −7.33 |

TABLE 32

| | Lasso All Late Window | | |
|---|---|---|---|
| Variable | Peptide disclosed in adjacent column | UniProt_ID | Coefficient |
| QINSYVK_426.2_496.3 | (SEQ ID NO: 917) | CBG_HUMAN | 0.5 |
| DEIPHNDIALLK_459.9_510.8 | (SEQ ID NO: 964) | HABP2_HUMAN | 0.15 |
| ALEQDLPVNIK_620.4_570.4 | (SEQ ID NO: 93) | CNDP1_HUMAN | 0.11 |
| ILDGGNK_358.7_603.3 | (SEQ ID NO: 877) | CXCL5_HUMAN | 0.08 |
| LIEIANHVDK_384.6_683.4 | (SEQ ID NO: 955) | ADA12_HUMAN | 0.06 |
| YYGYTGAFR_549.3_450.3 | (SEQ ID NO: 843) | TRFL_HUMAN | −0.39 |
| AALAAFNAQNNGSNFQLEEISR_789.1_746.4 | (SEQ ID NO: 891) | FETUA_HUMAN | −1.57 |
| AEIEYLEK_497.8_552.3 | (SEQ ID NO: 959) | LYAM1_HUMAN | −2.46 |
| AVYEAVLR_460.8_587.4 | (SEQ ID NO: 78) | PEPD_HUMAN | −2.92 |

TABLE 33

| | Random Forest 32 Early Window | | |
|---|---|---|---|
| Variable | Peptide disclosed in adjacent column | UniProt_ID | Coefficient |
| ELIEELVNITQNQK_557.6_517.3 | (SEQ ID NO: 806) | IL13_HUMAN | 3.224369171 |
| AHYDLR_387.7_288.2 | (SEQ ID NO: 88) | FETUA_HUMAN | 1.869007658 |

TABLE 33-continued

| | Random Forest 32 Early Window | | |
|---|---|---|---|
| Variable | Peptide disclosed in adjacent column | UniProt_ID | Coefficient |
| FSVVYAK_407.2_381.2 | (SEQ ID NO: 47) | FETUA_HUMAN | 1.770198171 |
| ITLPDFTGDLR_624.3_288.2 | (SEQ ID NO: 3) | LBP_HUMAN | 1.710936472 |
| ITGFLKPGK_320.9_301.2 | (SEQ ID NO: 97) | LBP_HUMAN | 1.623922439 |
| ITGFLKPGK_320.9_429.3 | (SEQ ID NO: 97) | LBP_HUMAN | 1.408035272 |
| ELIEELVNITQNQK_557.6_618.3 | (SEQ ID NO: 806) | IL13_HUMAN | 1.345412168 |
| VFQFLEK_455.8_811.4 | (SEQ ID NO: 810) | CO5_HUMAN | 1.311332013 |
| VQTAHFK_277.5_431.2 | (SEQ ID NO: 811) | CO8A_HUMAN | 1.308902373 |
| FLNWIK_410.7_560.3 | (SEQ ID NO: 4) | HABP2_HUMAN | 1.308093745 |
| DAGLSWGSAR_510.3_390.2 | (SEQ ID NO: 809) | NEUR4_HUMAN | 1.297033607 |
| TLLPVSKPEIR_418.3_288.2 | (SEQ ID NO: 25) | CO5_HUMAN | 1.291280928 |
| LIQDAVTGLTVNGQITGDK_972.0_798.4 | (SEQ ID NO: 807) | ITIH3_HUMAN | 1.28622301 |
| QALEEFQK_496.8_680.3 | (SEQ ID NO: 808) | CO8B_HUMAN | 1.191731825 |
| FSVVYAK_407.2_579.4 | (SEQ ID NO: 47) | FETUA_HUMAN | 1.078909138 |
| ITLPDFTGDLR_624.3_920.5 | (SEQ ID NO: 3) | LBP_HUMAN | 1.072613747 |
| AHYDLR_387.7_566.3 | (SEQ ID NO: 88) | FETUA_HUMAN | 1.029562263 |
| ALNHLPLEYNSALYSR_621.0_538.3 | (SEQ ID NO: 72) | CO6_HUMAN | 1.00992071 |
| DVLLLVHNLPQNLPGYFWYK_810.4_967.5 | (SEQ ID NO: 11) | PSG9_HUMAN | 1.007095529 |
| SFRPFVPR_335.9_635.3 | (SEQ ID NO: 18) | LBP_HUMAN | 0.970312536 |
| SDLEVAHYK_531.3_617.3 | (SEQ ID NO: 812) | CO8B_HUMAN | 0.967904893 |
| VQEAHLTEDQIFYFPK_655.7_701.4 | (SEQ ID NO: 31) | CO8G_HUMAN | 0.960398254 |
| VFQFLEK_455.8_276.2 | (SEQ ID NO: 810) | CO5_HUMAN | 0.931652095 |
| SLLQPNK_400.2_599.4 | (SEQ ID NO: 98) | CO8A_HUMAN | 0.926470249 |
| SFRPFVPR_335.9_272.2 | (SEQ ID NO: 18) | LBP_HUMAN | 0.911599611 |
| FLNWIK_410.7_561.3 | (SEQ ID NO: 4) | HABP2_HUMAN | 0.852022868 |
| LSSPAVITDK_515.8_743.4 | (SEQ ID NO: 26) | PLMN_HUMAN | 0.825455824 |
| DVLLLVHNLPQNLPGYFWYK_810.4_594.3 | (SEQ ID NO: 11) | PSG9_HUMAN | 0.756797142 |
| ALVLELAK_428.8_672.4 | (SEQ ID NO: 9) | INHBE_HUMAN | 0.748802555 |
| DISEVVTPR_508.3_787.4 | (SEQ ID NO: 67) | CFAB_HUMAN | 0.733731518 |

TABLE 34

| | Random Forest 100 Early Window | | |
|---|---|---|---|
| Variable | Peptide disclosed in adjacent column | UniProt_ID | Coefficient |
| ELIEELVNITQNQK_557.6_517.3 | (SEQ ID NO: 806) | IL13_HUMAN | 1.709778508 |
| LPNNVLQEK_527.8_844.5 | (SEQ ID NO: 814) | AFAM_HUMAN | 0.961692716 |
| AHYDLR_387.7_288.2 | (SEQ ID NO: 88) | FETUA_HUMAN | 0.901586746 |

TABLE 34-continued

| Random Forest 100 Early Window | | | |
| --- | --- | --- | --- |
| Variable | Peptide disclosed in adjacent column | UniProt_ID | Coefficient |
| ITLPDFTGDLR_624.3_288.2 | (SEQ ID NO: 3) | LBP_HUMAN | 0.879119498 |
| IEGNLIFDPNNYLPK_874.0_414.2 | (SEQ ID NO: 8) | APOB_HUMAN | 0.842483095 |
| ITGFLKPGK_320.9_301.2 | (SEQ ID NO: 97) | LBP_HUMAN | 0.806905233 |
| FSVVYAK_407.2_381.2 | (SEQ ID NO: 47) | FETUA_HUMAN | 0.790429706 |
| ITGFLKPGK_320.9_429.3 | (SEQ ID NO: 97) | LBP_HUMAN | 0.710312386 |
| VFQFLEK_455.8_811.4 | (SEQ ID NO: 810) | CO5_HUMAN | 0.709531553 |
| LIQDAVTGLTVNGQITGDK_972.0_798.4 | (SEQ ID NO: 807) | ITIH3_HUMAN | 0.624325189 |
| DADPDTFFAK_563.8_825.4 | (SEQ ID NO: 833) | AFAM_HUMAN | 0.618684313 |
| FLNWIK_410.7_560.3 | (SEQ ID NO: 4) | HABP2_HUMAN | 0.617501242 |
| TASDFITK_441.7_781.4 | (SEQ ID NO: 37) | GELS_HUMAN | 0.609275999 |
| DAGLSWGSAR_510.3_390.2 | (SEQ ID NO: 809) | NEUR4_HUMAN | 0.588718595 |
| VQTAHFK_277.5_431.2 | (SEQ ID NO: 811) | CO8A_HUMAN | 0.58669845 |
| TLLPVSKPEIR_418.3_288.2 | (SEQ ID NO: 25) | CO5_HUMAN | 0.5670608 |
| ELIEELVNITQNQK_557.6_618.3 | (SEQ ID NO: 806) | IL13_HUMAN | 0.555624783 |
| TYLHTYESEI_628.3_908.4 | (SEQ ID NO: 100) | ENPP2_HUMAN | 0.537678415 |
| HFQNLGK_422.2_527.2 | (SEQ ID NO: 831) | AFAM_HUMAN | 0.535543137 |
| TASDFITK_441.7_710.4 | (SEQ ID NO: 37) | GELS_HUMAN | 0.532743323 |
| ITLPDFTGDLR_624.3_920.5 | (SEQ ID NO: 3) | LBP_HUMAN | 0.51667902 |
| QALEEFQK_496.8_680.3 | (SEQ ID NO: 808) | CO8B_HUMAN | 0.511314017 |
| AVLHIGEK_289.5_348.7 | (SEQ ID NO: 817) | THBG_HUMAN | 0.510284122 |
| FSVVYAK_407.2_579.4 | (SEQ ID NO: 47) | FETUA_HUMAN | 0.503907813 |
| LPNNVLQEK_527.8_730.4 | (SEQ ID NO: 814) | AFAM_HUMAN | 0.501281631 |
| AHYDLR_387.7_566.3 | (SEQ ID NO: 88) | FETUA_HUMAN | 0.474166711 |
| IAPQLSTEELVSLGEK_857.5_333.2 | (SEQ ID NO: 832) | AFAM_HUMAN | 0.459595701 |
| WWGGQPLWITATK_772.4_929.5 | (SEQ ID NO: 15) | ENPP2_HUMAN | 0.44680777 |
| TYLHTYESEI_628.3_515.3 | (SEQ ID NO: 100) | ENPP2_HUMAN | 0.434157773 |
| DALSSVQESQVAQQAR_573.0_502.3 | (SEQ ID NO: 91) | APOC3_HUMAN | 0.432484862 |

TABLE 35

| Random Forest Protein Early Window | | | |
| --- | --- | --- | --- |
| Variable | Peptide disclosed in adjacent column | UniProt_ID | Coefficient |
| ELIEELVNITQNQK_557.6_517.3 | (SEQ ID NO: 806) | IL13_HUMAN | 2.881452809 |
| LPNNVLQEK_527.8_844.5 | (SEQ ID NO: 814) | AFAM_HUMAN | 1.833987752 |
| ITLPDFTGDLR_624.3_288.2 | (SEQ ID NO: 3) | LBP_HUMAN | 1.608843881 |

TABLE 35-continued

| | Random Forest Protein Early Window | | |
|---|---|---|---|
| Variable | Peptide disclosed in adjacent column | UniProt_ID | Coefficient |
| IEGNLIFDPNNYLPK_874.0_414.2 | (SEQ ID NO: 8) | APOB_HUMAN | 1.594658208 |
| VFQFLEK_455.8_811.4 | (SEQ ID NO: 810) | CO5_HUMAN | 1.290134412 |
| LIQDAVTGLTVNGQITGDK_972.0_798.4 | (SEQ ID NO: 807) | ITIH3_HUMAN | 1.167981736 |
| TASDFITK_441.7_781.4 | (SEQ ID NO: 37) | GELS_HUMAN | 1.152847453 |
| DAGLSWGSAR_510.3_390.2 | (SEQ ID NO: 809) | NEUR4_HUMAN | 1.146752656 |
| FSVVYAK_407.2_579.4 | (SEQ ID NO: 47) | FETUA_HUMAN | 1.060168583 |
| AVLHIGEK_289.5_348.7 | (SEQ ID NO: 817) | THBG_HUMAN | 1.033625773 |
| FLNWIK_410.7_560.3 | (SEQ ID NO: 4) | HABP2_HUMAN | 1.022356789 |
| QALEEFQK_496.8_680.3 | (SEQ ID NO: 808) | CO8B_HUMAN | 0.990074129 |
| DVLLLVHNLPQNLPGYFWYK_810.4_967.5 | (SEQ ID NO: 11) | PSG9_HUMAN | 0.929633865 |
| WWGGQPLWITATK_772.4_929.5 | (SEQ ID NO: 15) | ENPP2_HUMAN | 0.905895642 |
| VQEAHLTEDQIFYFPK_655.7_701.4 | (SEQ ID NO: 31) | CO8G_HUMAN | 0.883887371 |
| NNQLVAGYLQGPNVNLEEK_700.7_999.5 | (SEQ ID NO: 991) | IL1RA_HUMAN | 0.806472085 |
| SLLQPNK_400.2_599.4 | (SEQ ID NO: 98) | CO8A_HUMAN | 0.783623222 |
| DALSSVQESQVAQQAR_573.0_672.4 | (SEQ ID NO: 91) | APOC3_HUMAN | 0.774365756 |
| NIQSVNVK_451.3_674.4 | (SEQ ID NO: 821) | GROA_HUMAN | 0.767963386 |
| HPWIVHWDQLPQYQLNR_744.0_1047.0 | (SEQ ID NO: 829) | KS6A3_HUMAN | 0.759960139 |
| TTSDGGYSFK_531.7_860.4 | (SEQ ID NO: 815) | INHA_HUMAN | 0.732813448 |
| ALNHLPLEYNSALYSR_621.0_538.3 | (SEQ ID NO: 72) | CO6_HUMAN | 0.718779092 |
| LSSPAVITDK_515.8_743.4 | (SEQ ID NO: 26) | PLMN_HUMAN | 0.699547739 |
| TGVAVNKPAEFTVDAK_549.6_258.1 | (SEQ ID NO: 822) | FLNA_HUMAN | 0.693159192 |
| TLNAYDHR_330.5_312.2 | (SEQ ID NO: 839) | PAR3_HUMAN | 0.647300964 |
| DISEVVTPR_508.3_787.4 | (SEQ ID NO: 97) | CFAB_HUMAN | 0.609165621 |
| LIENGYFHPVK_439.6_627.4 | (SEQ ID NO: 827) | F13B_HUMAN | 0.60043345 |
| SGVDLADSNQK_567.3_662.3 | (SEQ ID NO: 853) | VGFR3_HUMAN | 0.596079858 |
| ALQDQLVLVAAK_634.9_289.2 | (SEQ ID NO: 33) | ANGT_HUMAN | 0.579034994 |
| ALVLELAK_428.8_672.4 | (SEQ ID NO: 9) | INHBE_HUMAN | 0.573458483 |

TABLE 36

| | Random Forest All Early Window | | |
|---|---|---|---|
| Variable | Peptide disclosed in adjacent column | UniProt_ID | Coefficient |
| ELIEELVNITQNQK_557.6_517.3 | (SEQ ID NO: 806) | IL13_HUMAN | 0.730972421 |
| ITLPDFTGDLR_624.3_288.2 | (SEQ ID NO: 3) | LBP_HUMAN | 0.409808774 |
| AHYDLR_387.7_288.2 | (SEQ ID NO: 88) | FETUA_HUMAN | 0.409298983 |
| FSVVYAK_407.2_381.2 | (SEQ ID NO: 47) | FETUA_HUMAN | 0.367730833 |

TABLE 36-continued

| | Peptide disclosed in adjacent | | |
|---|---|---|---|
| Variable | column | UniProt_ID | Coefficient |
| ITGFLKPGK_320.9_301.2 | (SEQ ID NO: 97) | LBP_HUMAN | 0.350485117 |
| VFQFLEK_455.8_811.4 | (SEQ ID NO: 810) | CO5_HUMAN | 0.339289475 |
| ELIEELVNITQNQK_557.6_618.3 | (SEQ ID NO: 806) | IL13_HUMAN | 0.334303166 |
| LPNNVLQEK_527.8_844.5 | (SEQ ID NO: 814) | AFAM_HUMAN | 0.329800706 |
| IEGNLIFDPNNYLPK_874.0_414.2 | (SEQ ID NO: 8) | APOB_HUMAN | 0.325596677 |
| ITGFLKPGK_320.9_429.3 | (SEQ ID NO: 97) | LBP_HUMAN | 0.31473104 |
| FLNWIK_410.7_560.3 | (SEQ ID NO: 4) | HABP2_HUMAN | 0.299810081 |
| LIQDAVTGLTVNGQITGDK_972.0_798.4 | (SEQ ID NO: 807) | ITIH3_HUMAN | 0.295613448 |
| ITLPDFTGDLR_624.3_920.5 | (SEQ ID NO: 3) | LBP_HUMAN | 0.292212699 |
| DAGLSWGSAR_510.3_390.2 | (SEQ ID NO: 809) | NEUR4_HUMAN | 0.285812225 |
| TLLPVSKPEIR_418.3_288.2 | (SEQ ID NO: 25) | CO5_HUMAN | 0.280857718 |
| FSVVYAK_407.2_579.4 | (SEQ ID NO: 47) | FETUA_HUMAN | 0.278531322 |
| DADPDTFFAK_563.8_825.4 | (SEQ ID NO: 833) | AFAM_HUMAN | 0.258938798 |
| AHYDLR_387.7_566.3 | (SEQ ID NO: 88) | FETUA_HUMAN | 0.256160046 |
| QALEEFQK_496.8_680.3 | (SEQ ID NO: 808) | CO8B_HUMAN | 0.245543641 |
| HTLNQIDEVK_598.8_951.5 | (SEQ ID NO: 51) | FETUA_HUMAN | 0.239528081 |
| TASDFITK_441.7_781.4 | (SEQ ID NO: 37) | GELS_HUMAN | 0.227485958 |
| VFQFLEK_455.8_276.2 | (SEQ ID NO: 810) | CO5_HUMAN | 0.226172392 |
| DVLLLVHNLPQNLPGYFWYK_810.4_967.5 | (SEQ ID NO: 11) | PSG9_HUMAN | 0.218613384 |
| VQTAHFK_277.5_431.2 | (SEQ ID NO: 811) | CO8A_HUMAN | 0.217171548 |
| SFRPFVPR_335.9_635.3 | (SEQ ID NO: 18) | LBP_HUMAN | 0.214798112 |
| HFQNLGK_422.2_527.2 | (SEQ ID NO: 831) | AFAM_HUMAN | 0.211756476 |
| SVSLPSLDPASAK_636.4_473.3 | (SEQ ID NO: 846) | APOB_HUMAN | 0.211319422 |
| FGFGGSTDSGPIR_649.3_745.4 | (SEQ ID NO: 5) | ADA12_HUMAN | 0.206574494 |
| HFQNLGK_422.2_285.1 | (SEQ ID NO: 831) | AFAM_HUMAN | 0.204024196 |
| AVLHIGEK_289.5_348.7 | (SEQ ID NO: 817) | THBG_HUMAN | 0.201102917 |

TABLE 37

Random Forest SummedGini Early Window

| | Peptide disclosed in adjacent | | |
|---|---|---|---|
| Transition | column | Protein | SumBestGini |
| ELIEELVNITQNQK_557.6_517.3 | (SEQ ID NO: 806) | IL13_HUMAN | 242.5373659 |
| VFQFLEK_455.8_811.4 | (SEQ ID NO: 810) | CO5_HUMAN | 115.1113943 |
| FLNWIK_410.7_560.3 | (SEQ ID NO: 4) | HABP2_HUMAN | 107.4572447 |
| ITLPDFTGDLR_624.3_288.2 | (SEQ ID NO: 3) | LBP_HUMAN | 104.0742727 |

TABLE 37-continued

| Random Forest SummedGini Early Window | | | |
|---|---|---|---|
| Transition | Peptide disclosed in adjacent column | Protein | SumBestGini |
| LIQDAVTGLTVNGQITGDK_972.0_798.4 | (SEQ ID NO: 807) | ITIH3_HUMAN | 103.3238077 |
| DAGLSWGSAR_510.3_390.2 | (SEQ ID NO: 809) | NEUR4_HUMAN | 70.4151533 |
| AHYDLR_387.7_288.2 | (SEQ ID NO: 88) | FETUA_HUMAN | 140.2670822 |
| FSVVYAK_407.2_381.2 | (SEQ ID NO: 47) | FETUA_HUMAN | 121.3664352 |
| LPNNVLQEK_527.8_844.5 | (SEQ ID NO: 814) | AFAM_HUMAN | 115.5211679 |
| ITGFLKPGK_320.9_429.3 | (SEQ ID NO: 97) | LBP_HUMAN | 114.9512704 |
| ITGFLKPGK_320.9_301.2 | (SEQ ID NO: 97) | LBP_HUMAN | 112.916627 |
| IEGNLIFDPNNYLPK_874.0_414.2 | (SEQ ID NO: 8) | APOB_HUMAN | 52.21169288 |
| VQTAHFK_277.5_431.2 | (SEQ ID NO: 811) | CO8A_HUMAN | 144.5237215 |
| TLLPVSKPEIR_418.3_288.2 | (SEQ ID NO: 25) | CO5_HUMAN | 96.16982897 |
| QALEEFQK_496.8_680.3 | (SEQ ID NO: 808) | CO8B_HUMAN | 85.35050759 |
| FSVVYAK_407.2_579.4 | (SEQ ID NO: 47) | FETUA_HUMAN | 73.23969945 |
| ELIEELVNITQNQK_557.6_618.3 | (SEQ ID NO: 806) | IL13_HUMAN | 61.61450671 |
| TASDFITK_441.7_781.4 | (SEQ ID NO: 37) | GELS_HUMAN | 61.32155633 |
| DVLLLVHNLPQNLPGYFWYK_810.4_967.5 | (SEQ ID NO: 11) | PSG9_HUMAN | 99.68404123 |
| AVLHIGEK_289.5_348.7 | (SEQ ID NO: 817) | THBG_HUMAN | 69.96748485 |
| ITLPDFTGDLR_624.3_920.5 | (SEQ ID NO: 3) | LBP_HUMAN | 56.66810872 |
| WWGGQPLWITATK_772.4_929.5 | (SEQ ID NO: 15) | ENPP2_HUMAN | 56.54173176 |
| VQEAHLTEDQIFYFPK_655.7_701.4 | (SEQ ID NO: 31) | CO8G_HUMAN | 47.92505575 |
| DADPDTFFAK_563.8_825.4 | (SEQ ID NO: 833) | AFAM_HUMAN | 40.34147696 |
| DALSSVQESQVAQQAR_573.0_502.3 | (SEQ ID NO: 91) | APOC3_HUMAN | 145.0311483 |
| FGFGGSTDSGPIR_649.3_745.4 | (SEQ ID NO: 5) | ADA12_HUMAN | 109.4072996 |
| FLPCENK_454.2_550.2 | (SEQ ID NO: 828) | IL10_HUMAN | 105.7756691 |
| VQTAHFK_277.5_502.3 | (SEQ ID NO: 811) | CO8A_HUMAN | 101.5877845 |
| VFQFLEK_455.8_276.2 | (SEQ ID NO: 810) | CO5_HUMAN | 95.71159157 |
| TYLHTYESEI_628.3_908.4 | (SEQ ID NO: 100) | ENPP2_HUMAN | 94.92157517 |
| ALNHLPLEYNSALYSR_621.0_538.3 | (SEQ ID NO: 72) | CO6_HUMAN | 90.67568777 |
| NKPGVYTDVAYYLAWIR_677.0_545.3 | (SEQ ID NO: 896) | FA12_HUMAN | 90.35890105 |
| LEEHYELR_363.5_580.3 | (SEQ ID NO: 904) | PAI2_HUMAN | 88.44833508 |
| HPWIVHWDQLPQYQLNR_744.0_1047.0 | (SEQ ID NO: 829) | KS6A3_HUMAN | 88.37680942 |
| HTLNQIDEVK_598.8_951.5 | (SEQ ID NO: 51) | FETUA_HUMAN | 87.63064143 |
| LPNNVLQEK_527.8_730.4 | (SEQ ID NO: 814) | AFAM_HUMAN | 86.64484642 |
| ALDLSLK_380.2_575.3 | (SEQ ID NO: 14) | ITIH3_HUMAN | 83.51201287 |
| YGIEEHGK_311.5_599.3 | (SEQ ID NO: 1061) | CXA1_HUMAN | 82.47620831 |
| LSSPAVITDK_515.8_830.5 | (SEQ ID NO: 26) | PLMN_HUMAN | 81.5433587 |
| LEEHYELR_363.5_288.2 | (SEQ ID NO: 904) | PAI2_HUMAN | 79.01571985 |
| NVIQISNDLENLR_509.9_402.3 | (SEQ ID NO: 938) | LEP_HUMAN | 78.86670236 |

TABLE 37-continued

| Random Forest SummedGini Early Window | | | |
|---|---|---|---|
| Transition | Peptide disclosed in adjacent column | Protein | SumBestGini |
| SGFSFGFK_438.7_732.4 | (SEQ ID NO: 53) | CO8B_HUMAN | 78.71961929 |
| SDLEVAHYK_531.3_617.3 | (SEQ ID NO: 812) | CO8B_HUMAN | 78.24005567 |
| NADYSYSVWK_616.8_333.2 | (SEQ ID NO: 60) | CO5_HUMAN | 76.07974354 |
| AHYDLR_387.7_566.3 | (SEQ ID NO: 88) | FETUA_HUMAN | 74.68253347 |
| GAVHVVVAETDYQSFAVLYLER_822.8_580.3 | (SEQ ID NO: 848) | CO8G_HUMAN | 73.75860248 |
| LIENGYFHPVK_439.6_627.4 | (SEQ ID NO: 827) | F13B_HUMAN | 73.74965194 |
| ALDLSLK_380.2_185.1 | (SEQ ID NO: 14) | ITIH3_HUMAN | 72.760739 |
| WWGGQPLWITATK_772.4_373.2 | (SEQ ID NO: 15) | ENPP2_HUMAN | 72.51936706 |
| FGFGGSTDSGPIR_649.3_946.5 | (SEQ ID NO: 5) | ADA12_HUMAN | 72.49183198 |
| GLQYAAQEGLLALQSELLR_1037.1_929.5 | (SEQ ID NO: 818) | LBP_HUMAN | 67.17588648 |
| HFQNLGK_422.2_527.2 | (SEQ ID NO: 831) | AFAM_HUMAN | 66.11702719 |
| YSHYNER_323.5_581.3 | (SEQ ID NO: 889) | HABP2_HUMAN | 65.56238612 |
| ISQGEADINIAFYQR_575.6_684.4 | (SEQ ID NO: 875) | MMP8_HUMAN | 65.50301246 |
| TGVAVNKPAEFTVDAK_549.6_258.1 | (SEQ ID NO: 822) | FLNA_HUMAN | 64.85259525 |
| NIQSVNVK_451.3_674.4 | (SEQ ID NO: 821) | GROA_HUMAN | 64.53010225 |
| DALSSVQESQVAQQAR_573.0_672.4 | (SEQ ID NO: 91) | APOC3_HUMAN | 64.12149927 |
| SLLQPNK_400.2_599.4 | (SEQ ID NO: 98) | CO8A_HUMAN | 62.68167847 |
| SFRPFVPR_335.9_635.3 | (SEQ ID NO: 18) | LBP_HUMAN | 61.90157662 |
| NNQLVAGYLQGPNVNLEEK_700.7_999.5 | (SEQ ID NO: 991) | IL1RA_HUMAN | 61.54435815 |
| LYYGDDEK_501.7_563.2 | (SEQ ID NO: 42) | CO8A_HUMAN | 60.16700473 |
| SWNEPLYHLVTEVR_581.6_716.4 | (SEQ ID NO: 927) | PRL_HUMAN | 59.78209065 |
| SGVDLADSNQK_567.3_662.3 | (SEQ ID NO: 853) | VGFR3_HUMAN | 58.93982896 |
| GTYLYNDCPGPGQDTDCR_697.0_335.2 | (SEQ ID NO: 990) | TNR1A_HUMAN | 58.72963941 |
| HATLSLSIPR_365.6_472.3 | (SEQ ID NO: 865) | VGFR3_HUMAN | 57.98669834 |
| FIVGFTR_420.2_261.2 | (SEQ ID NO: 1005) | CCL20_HUMAN | 57.23165578 |
| QNYHQDSEAAINR_515.9_544.3 | (SEQ ID NO: 897) | FRIH_HUMAN | 57.21116697 |
| DVLLLVHNLPQNLPGYFWYK_810.4_594.3 | (SEQ ID NO: 11) | PSG9_HUMAN | 56.84150484 |
| FLNWIK_410.7_561.3 | (SEQ ID NO: 4) | HABP2_HUMAN | 56.37258274 |
| SLQAFVAVAAR_566.8_487.3 | (SEQ ID NO: 910) | IL23A_HUMAN | 56.09012981 |
| HFQNLGK_422.2_285.1 | (SEQ ID NO: 831) | AFAM_HUMAN | 56.04480022 |
| GPGEDFR_389.2_322.2 | (SEQ ID NO: 873) | PTGDS_HUMAN | 55.7583763 |
| NKPGVYTDVAYYLAWIR_677.0_821.5 | (SEQ ID NO: 896) | FA12_HUMAN | 55.53857645 |
| LIQDAVTGLTVNGQITGDK_972.0_640.4 | (SEQ ID NO: 807) | ITIH3_HUMAN | 55.52577583 |
| YYGYTGAFR_549.3_450.3 | (SEQ ID NO: 843) | TRFL_HUMAN | 54.27147366 |
| TLNAYDHR_330.5_312.2 | (SEQ ID NO: 839) | PAR3_HUMAN | 54.19190934 |
| IQTHSTTYR_369.5_627.3 | (SEQ ID NO: 104) | F13B_HUMAN | 54.18950583 |

TABLE 37-continued

| Transition | Peptide disclosed in adjacent column | Protein | SumBestGini |
|---|---|---|---|
| Random Forest SummedGini Early Window | | | |
| TASDFITK_441.7_710.4 | (SEQ ID NO: 37) | GELS_HUMAN | 54.1056456 |
| ALNHLPLEYNSALYSR_621.0_696.4 | (SEQ ID NO: 72) | CO6_HUMAN | 53.8997252 |
| DADPDTFFAK_563.8_302.1 | (SEQ ID NO: 833) | AFAM_HUMAN | 53.85914848 |
| SVSLPSLDPASAK_636.4_473.3 | (SEQ ID NO: 846) | APOB_HUMAN | 53.41996191 |
| TTSDGGYSFK_531.7_860.4 | (SEQ ID NO: 815) | INHA_HUMAN | 52.24655536 |
| AFTECCVVASQLR_770.9_574.3 | (SEQ ID NO: 1) | CO5_HUMAN | 51.67853429 |
| ELPQSIVYK_538.8_409.2 | (SEQ ID NO: 820) | FBLN3_HUMAN | 51.35853002 |
| TYLHTYESEI_628.3_515.3 | (SEQ ID NO: 100) | ENPP2_HUMAN | 51.23842124 |
| FQLSETNR_497.8_605.3 | (SEQ ID NO: 776) | PSG2_HUMAN | 51.01576848 |
| GSLVQASEANLQAAQDFVR_668.7_806.4 | (SEQ ID NO: 900) | ITIH1_HUMAN | 50.81923338 |
| FSLVSGWGQLLDR_493.3_403.2 | (SEQ ID NO: 878) | FA7_HUMAN | 50.54425114 |
| ECEELEEK_533.2_405.2 | (SEQ ID NO: 972) | IL15_HUMAN | 50.41977421 |
| NADYSYSVWK_616.8_769.4 | (SEQ ID NO: 60) | CO5_HUMAN | 50.36434595 |
| SLLQPNK_400.2_358.2 | (SEQ ID NO: 98) | CO8A_HUMAN | 49.75593162 |
| LIEIANHVDK_384.6_683.4 | (SEQ ID NO: 955) | ADA12_HUMAN | 49.43389721 |
| DISEVVTPR_508.3_787.4 | (SEQ ID NO: 67) | CFAB_HUMAN | 49.00234897 |
| AEVIWTSSDHQVLSGK_586.3_300.2 | (SEQ ID NO: 964) | PD1L1_HUMAN | 48.79028835 |
| SGVDLADSNQK_567.3_591.3 | (SEQ ID NO: 853) | VGFR3_HUMAN | 48.70665587 |
| SILFLGK_389.2_201.1 | (SEQ ID NO: 881) | THBG_HUMAN | 48.5997957 |
| AVLHIGEK_289.5_292.2 | (SEQ ID NO: 817) | THBG_HUMAN | 48.4605866 |
| QLYGDTGVLGR_589.8_501.3 | (SEQ ID NO: 819) | CO8G_HUMAN | 48.11414904 |
| FSLVSGWGQLLDR_493.3_516.3 | (SEQ ID NO: 878) | FA7_HUMAN | 47.59635333 |
| DSPVLIDFFEDTER_841.9_399.2 | (SEQ ID NO: 1006) | HRG_HUMAN | 46.83840473 |
| INPASLDK_429.2_630.4 | (SEQ ID NO: 903) | C163A_HUMAN | 46.78947931 |
| GAVHVVVAETDYQSFAVLYLER_822.8_863.5 | (SEQ ID NO: 848) | CO8G_HUMAN | 46.66185339 |
| FLQEQGHR_338.8_497.3 | (SEQ ID NO: 23) | CO8G_HUMAN | 46.64415952 |
| LNIGYIEDLK_589.3_837.4 | (SEQ ID NO: 923) | PAI2_HUMAN | 46.5879123 |
| LSSPAVITDK_515.8_743.4 | (SEQ ID NO: 26) | PLMN_HUMAN | 46.2857838 |
| GLQYAAQEGLLALQSELLR_1037.1_858.5 | (SEQ ID NO: 818) | LBP_HUMAN | 45.7427767 |
| SDGAKPGPR_442.7_213.6 | (SEQ ID NO: 879) | COLI_HUMAN | 45.27828366 |
| GYQELLEK_490.3_502.3 | (SEQ ID NO: 956) | FETA_HUMAN | 43.52928868 |
| GGEGTGYFVDFSVR_745.9_869.5 | (SEQ ID NO: 73) | HRG_HUMAN | 43.24514327 |
| ADLFYDVEALDLESPK_913.0_447.2 | (SEQ ID NO: 1042) | HRG_HUMAN | 42.56268679 |
| ADLFYDVEALDLESPK_913.0_331.2 | (SEQ ID NO: 1042) | HRG_HUMAN | 42.48967422 |
| EAQLPVIENK_570.8_699.4 | (SEQ ID NO: 22) | PLMN_HUMAN | 42.21213429 |
| SILFLGK_389.2_577.4 | (SEQ ID NO: 881) | THBG_HUMAN | 42.03379581 |
| HTLNQIDEVK_598.8_958.5 | (SEQ ID NO: 51) | FETUA_HUMAN | 41.98377176 |

TABLE 37-continued

| Random Forest SummedGini Early Window | | | |
|---|---|---|---|
| Transition | Peptide<br>disclosed in<br>adjacent<br>column | Protein | SumBestGini |
| AQPVQVAEGSEPDGFWEALGGK_758.0_574.3 | (SEQ ID NO: 837) | GELS_HUMAN | 41.89547273 |
| FLPCENK_454.2_390.2 | (SEQ ID NO: 828) | IL10_HUMAN | 41.66612478 |
| LIEIANHVDK_384.6_498.3 | (SEQ ID NO: 955) | ADA12_HUMAN | 41.50878046 |
| DEIPHNDIALLK_459.9_510.8 | (SEQ ID NO: 964) | HABP2_HUMAN | 41.27830935 |
| SLQAFVAVAAR_566.8_804.5 | (SEQ ID NO: 910) | IL23A_HUMAN | 41.00430596 |
| YISPDQLADLYK_713.4_277.2 | (SEQ ID NO: 850) | ENOA_HUMAN | 40.90053801 |
| SLPVSDSVLSGFEQR_810.9_836.4 | (SEQ ID NO: 59) | CO8G_HUMAN | 40.62020941 |
| DGSPDVTTADIGANTPDATK_973.5_531.3 | (SEQ ID NO: 44) | PGRP2_HUMAN | 40.33913091 |
| NTGVISVVTTGLDR_716.4_662.4 | (SEQ ID NO: 977) | CADH1_HUMAN | 40.05291612 |
| ALVLELAK_428.8_672.4 | (SEQ ID NO: 9) | INHBE_HUMAN | 40.01646465 |
| YEFLNGR_449.7_293.1 | (SEQ ID NO: 34) | PLMN_HUMAN | 39.83344278 |
| WGAAPYR_410.7_577.3 | (SEQ ID NO: 1012) | PGRP2_HUMAN | 39.52766213 |
| TFLTVYWTPER_706.9_401.2 | (SEQ ID NO: 869) | ICAM1_HUMAN | 39.13662034 |
| SEYGAALAWEK_612.8_845.5 | (SEQ ID NO: 1051) | CO6_HUMAN | 38.77511119 |
| VGVISFAQK_474.8_693.4 | (SEQ ID NO: 960) | TFR2_HUMAN | 38.5823457 |
| IIEVEEQEDPYLNDR_996.0_777.4 | (SEQ ID NO: 1065) | FBLN1_HUMAN | 38.30913304 |
| TGYYFDGISR_589.8_694.4 | (SEQ ID NO: 1003) | FBLN1_HUMAN | 38.30617106 |
| LQGTLPVEAR_542.3_571.3 | (SEQ ID NO: 28) | CO5_HUMAN | 37.93064544 |
| DSPVLIDFFEDTER_841.9_512.3 | (SEQ ID NO: 1006) | HRG_HUMAN | 37.4447737 |
| AALAAFNAQNNGSNFQLEEISR_789.1_746.4 | (SEQ ID NO: 891) | FETUA_HUMAN | 37.02483715 |
| DGSPDVTTADIGANTPDATK_973.5_844.4 | (SEQ ID NO: 44) | PGRP2_HUMAN | 36.59864788 |
| ILILPSVTR_506.3_785.5 | (SEQ ID NO: 789) | PSGx_HUMAN | 36.43814815 |
| SVSLPSLDPASAK_636.4_885.5 | (SEQ ID NO: 846) | APOB_HUMAN | 36.27689491 |
| TLAFVR_353.7_492.3 | (SEQ ID NO: 1055) | FA7_HUMAN | 36.18771771 |
| VAPGVANPGTPLA_582.3_555.3 | (SEQ ID NO: 1007) | A6NIT4_HUMAN | 35.70677357 |
| HELTDEELQSLFTNFANVVDK_817.1_906.5 | (SEQ ID NO: 823) | AFAM_HUMAN | 35.14441609 |
| AGLLRPDYALLGHR_518.0_369.2 | (SEQ ID NO: 95) | PGRP2_HUMAN | 35.13047098 |
| GDTYPAELYITGSILR_885.0_1332.8 | (SEQ ID NO: 870) | F13B_HUMAN | 34.97832404 |
| LFIPQITR_494.3_727.4 | (SEQ ID NO: 996) | PSG9_HUMAN | 34.76811249 |
| GYQELLEK_490.3_631.4 | (SEQ ID NO: 956) | FETA_HUMAN | 34.76117605 |
| VSEADSSNADWVTK_754.9_533.3 | (SEQ ID NO: 813) | CFAB_HUMAN | 34.49787512 |
| LNIGYIEDLK_589.3_950.5 | (SEQ ID NO: 923) | PAI2_HUMAN | 34.48448691 |
| SFRPFVPR_335.9_272.2 | (SEQ ID NO: 18) | LBP_HUMAN | 34.27529415 |
| ILDGGNK_358.7_490.2 | (SEQ ID NO: 877) | CXCL5_HUMAN | 34.2331388 |
| EANQSTLENFLER_775.9_678.4 | (SEQ ID NO: 907) | IL4_HUMAN | 34.14295797 |
| DFNQFSSGEK_386.8_189.1 | (SEQ ID NO: 845) | FETA_HUMAN | 34.05459951 |

TABLE 37-continued

| Transition | Peptide disclosed in adjacent column | Protein | SumBestGini |
|---|---|---|---|
| | Random Forest SummedGini Early Window | | |
| IEEIAAK_387.2_660.4 | (SEQ ID NO: 30) | CO5_HUMAN | 33.93778148 |
| TEFLSNYLTNVDDITLVPGTLGR_846.8_600.3 | (SEQ ID NO: 824) | ENPP2_HUMAN | 33.87864446 |
| LPATEKPVLLSK_432.6_347.2 | (SEQ ID NO: 868) | HYOU1_HUMAN | 33.69005522 |
| FLQEQGHR_338.8_369.2 | (SEQ ID NO: 23) | CO8G_HUMAN | 33.61179024 |
| APLTKPLK_289.9_357.2 | (SEQ ID NO: 85) | CRP_HUMAN | 33.59900279 |
| YSHYNER_323.5_418.2 | (SEQ ID NO: 889) | HABP2_HUMAN | 33.50888447 |
| TSYQVYSK_488.2_787.4 | (SEQ ID NO: 937) | C163A_HUMAN | 33.11650018 |
| IALGGLLFPASNLR_481.3_657.4 | (SEQ ID NO: 975) | SHBG_HUMAN | 33.02974341 |
| TGISPLALIK_506.8_741.5 | (SEQ ID NO: 866) | APOB_HUMAN | 32.64471573 |
| LYYGDDEK_501.7_726.3 | (SEQ ID NO: 42) | CO8A_HUMAN | 32.60782458 |
| IVLSLDVPIGLLQILLEQAR_735.1_503.3 | (SEQ ID NO: 892) | UCN2_HUMAN | 32.37907686 |
| EAQLPVIENK_570.8_329.2 | (SEQ ID NO: 22) | PLMN_HUMAN | 32.34049256 |
| TGYYFDGISR_589.8_857.4 | (SEQ ID NO: 1003) | FBLN1_HUMAN | 32.14526507 |
| VGVISFAQK_474.8_580.3 | (SEQ ID NO: 960) | TFR2_HUMAN | 32.11753213 |
| FQSVFTVTR_542.8_623.4 | (SEQ ID NO: 862) | C1QC_HUMAN | 32.11360444 |
| TSDQIHFFFAK_447.6_659.4 | (SEQ ID NO: 905) | ANT3_HUMAN | 31.95867038 |
| IAPQLSTEELVSLGEK_857.5_333.2 | (SEQ ID NO: 832) | AFAM_HUMAN | 31.81531364 |
| EVFSKPISWEELLQ_852.9_260.2 | (SEQ ID NO: 840) | FA40A_HUMAN | 31.36698726 |
| DEIPHNDIALLK_459.9_260.2 | (SEQ ID NO: 864) | HABP2_HUMAN | 31.1839869 |
| NYFTSVAHPNLFIATK_608.3_319.2 | (SEQ ID NO: 1008) | IL1A_HUMAN | 31.09867061 |
| ITENDIQIALDDAK_779.9_632.3 | (SEQ ID NO: 55) | APOB_HUMAN | 30.77026845 |
| DTYVSSFPR_357.8_272.2 | (SEQ ID NO: 1009) | TCEA1_HUMAN | 30.67784731 |
| TDAPDLPEENQAR_728.3_843.4 | (SEQ ID NO: 17) | CO5_HUMAN | 30.66251941 |
| LFYADHPFIFLVR_546.6_647.4 | (SEQ ID NO: 936) | SERPH_HUMAN | 30.65831566 |
| TEQAAVAR_423.2_487.3 | (SEQ ID NO: 935) | FA12_HUMAN | 30.44356842 |
| AVGYLITGYQR_620.8_737.4 | (SEQ ID NO: 69) | PZP_HUMAN | 30.36425528 |
| HSHESQDLR_370.2_288.2 | (SEQ ID NO: 1010) | HRG_HUMAN | 30.34684703 |
| IALGGLLFPASNLR_481.3_412.3 | (SEQ ID NO: 975) | SHBG_HUMAN | 30.34101643 |
| IAQYYYTFK_598.8_884.4 | (SEQ ID NO: 859) | F13B_HUMAN | 30.23453833 |
| SLPVSDSVLSGFEQR_810.9_723.3 | (SEQ ID NO: 59) | CO8G_HUMAN | 30.11396489 |
| IIGGSDADIK_494.8_762.4 | (SEQ ID NO: 39) | C1S_HUMAN | 30.06572687 |
| QTLSWTVTPK_580.8_545.3 | (SEQ ID NO: 981) | PZP_HUMAN | 30.04139865 |
| HYFIAAVER_553.3_658.4 | (SEQ ID NO: 855) | FA8_HUMAN | 29.80239884 |
| QVCADPSEEWVQK_788.4_374.2 | (SEQ ID NO: 1062) | CCL3_HUMAN | 29.61435573 |
| DLHLSDVFLK_396.2_366.2 | (SEQ ID NO: 856) | CO6_HUMAN | 29.60077507 |
| NIQSVNVK_451.3_546.3 | (SEQ ID NO: 821) | GROA_HUMAN | 29.47619619 |
| QTLSWTVTPK_580.8_818.4 | (SEQ ID NO: 981) | PZP_HUMAN | 29.40047934 |

TABLE 37-continued

| | | | |
|---|---|---|---|
| Random Forest SummedGini Early Window | | | |
| Transition | Peptide disclosed in adjacent column | Protein | SumBestGini |
| HSHESQDLR_370.2_403.2 | (SEQ ID NO: 1010) | HRG_HUMAN | 29.32242262 |
| LLEVPEGR_456.8_356.2 | (SEQ ID NO: 1053) | C1S_HUMAN | 29.14169137 |
| LIENGYFHPVK_439.6_343.2 | (SEQ ID NO: 827) | F13B_HUMAN | 28.63056809 |
| EDTPNSVWEPAK_686.8_630.3 | (SEQ ID NO: 41) | C1S_HUMAN | 28.61352686 |
| AFTECCVVASQLR_770.9_673.4 | (SEQ ID NO: 1) | CO5_HUMAN | 28.57830281 |
| VNHVTLSQPK_374.9_459.3 | (SEQ ID NO: 834) | B2MG_HUMAN | 28.27203693 |
| VSFSSPLVAISGVALR_802.0_715.4 | (SEQ ID NO: 1011) | PAPP1_HUMAN | 28.13008712 |
| DPDQTDGLGLSYLSSHIANVER_796.4_456.2 | (SEQ ID NO: 57) | GELS_HUMAN | 28.06549895 |
| VVGGLVALR_442.3_784.5 | (SEQ ID NO: 944) | FA12_HUMAN | 28.00684006 |
| NEIVFPAGILQAPFYTR_968.5_357.2 | (SEQ ID NO: 925) | ECE1_HUMAN | 27.97758456 |
| QVCADPSEEWVQK_788.4_275.2 | (SEQ ID NO: 1062) | CCL3_HUMAN | 27.94276837 |
| LQDAGVYR_461.2_680.3 | (SEQ ID NO: 902) | PD1L1_HUMAN | 27.88063261 |
| IQTHSTTYR_369.5_540.3 | (SEQ ID NO: 104) | F13B_HUMAN | 27.68873826 |
| TPSAAYLWVGTGASEAEK_919.5_849.4 | (SEQ ID NO: 35) | GELS_HUMAN | 27.66889639 |
| ALALPPLGLAPLLNLWAKPQGR_770.5_256.2 | (SEQ ID NO: 947) | SHBG_HUMAN | 27.63105727 |
| ALQDQLVLVAAK_634.9_289.2 | (SEQ ID NO: 33) | ANGT_HUMAN | 27.63097319 |
| IEEIAAK_387.2_531.3 | (SEQ ID NO: 30) | CO5_HUMAN | 27.52427934 |
| TAVTANLDIR_537.3_288.2 | (SEQ ID NO: 915) | CHL1_HUMAN | 27.44246841 |
| VSEADSSNADWVTK_754.9_347.2 | (SEQ ID NO: 813) | CFAB_HUMAN | 27.43976782 |
| ITENDIQIALDDAK_779.9_873.5 | (SEQ ID NO: 55) | APOB_HUMAN | 27.39263522 |
| SSNNPHSPIVEEFQVPYNK_729.4_521.3 | (SEQ ID NO: 954) | C1S_HUMAN | 27.34493617 |
| HPWIVHWDQLPQYQLNR_744.0_918.5 | (SEQ ID NO: 829) | KS6A3_HUMAN | 27.19681613 |
| TPSAAYLWVGTGASEAEK_919.5_428.2 | (SEQ ID NO: 35) | GELS_HUMAN | 27.17319953 |
| AFLEVNEEGSEAAASTAVVIAGR_764.4_614.4 | (SEQ ID NO: 939) | ANT3_HUMAN | 27.10487351 |
| WGAAPYR_410.7_634.3 | (SEQ ID NO: 1012) | PGRP2_HUMAN | 27.09930054 |
| IEVNESGTVASSSTAVIVSAR_693.0_545.3 | (SEQ ID NO: 882) | PAI1_HUMAN | 27.02567296 |
| AEAQAQYSAAVAK_654.3_908.5 | (SEQ ID NO: 89) | ITIH4_HUMAN | 26.98305259 |
| VPLALFALNR_557.3_917.6 | (SEQ ID NO: 943) | PEPD_HUMAN | 26.96988826 |
| TLEAQLTPR_514.8_685.4 | (SEQ ID NO: 68) | HEP2_HUMAN | 26.94672621 |
| QALEEFQK_496.8_551.3 | (SEQ ID NO: 808) | CO8B_HUMAN | 26.67037155 |
| WNFAYWAAHQPWSR_607.3_545.3 | (SEQ ID NO: 1050) | PRG2_HUMAN | 26.62600679 |
| IYLQPGR_423.7_570.3 | (SEQ ID NO: 969) | ITIH2_HUMAN | 26.58752589 |
| FFQYDTWK_567.8_840.4 | (SEQ ID NO: 1068) | IGF2_HUMAN | 26.39942037 |
| NEIWYR_440.7_357.2 | (SEQ ID NO: 919) | FA12_HUMAN | 26.35177282 |
| GGEGTGYFVDFSVR_745.9_722.4 | (SEQ ID NO: 73) | HRG_HUMAN | 26.31688167 |
| VGEYSLYIGR_578.8_708.4 | (SEQ ID NO: 58) | SAMP_HUMAN | 26.17367498 |

TABLE 37-continued

| Random Forest SummedGini Early Window | | | |
|---|---|---|---|
| Transition | Peptide disclosed in adjacent column | Protein | SumBestGini |
| TAHISGLPPSTDFIVYLSGLAPSIR_871.5_800.5 | (SEQ ID NO: 979) | TENA_HUMAN | 26.13688183 |
| GVTGYFTFNLYLK_508.3_260.2 | (SEQ ID NO: 781) | PSG5_HUMAN | 26.06007032 |
| DYWSTVK_449.7_620.3 | (SEQ ID NO: 885) | APOC3_HUMAN | 26.03765187 |
| YENYTSSFFIR_713.8_756.4 | (SEQ ID NO: 816) | IL12B_HUMAN | 25.9096605 |
| YGLVTYATYPK_638.3_334.2 | (SEQ ID NO: 63) | CFAB_HUMAN | 25.84440452 |
| LFIPQITR_494.3_614.4 | (SEQ ID NO: 996) | PSG9_HUMAN | 25.78081129 |
| YEFLNGR_449.7_606.3 | (SEQ ID NO: 34) | PLMN_HUMAN | 25.17159874 |
| SEPRPGVLLR_375.2_454.3 | (SEQ ID NO: 12) | FA7_HUMAN | 25.16444381 |
| NSDQEIDFK_548.3_294.2 | (SEQ ID NO: 1056) | S10A5_HUMAN | 25.12266401 |
| YEVQGEVFTKPQLWP_911.0_293.1 | (SEQ ID NO: 27) | CRP_HUMAN | 24.77595195 |
| GVTGYFTFNLYLK_508.3_683.9 | (SEQ ID NO: 781) | PSG5_HUMAN | 24.75289081 |
| ISLLLIESWLEPVR_834.5_371.2 | (SEQ ID NO: 32) | CSH_HUMAN | 24.72379326 |
| ALLLGWVPTR_563.3_373.2 | (SEQ ID NO: 974) | PAR4_HUMAN | 24.68096599 |
| VNHVTLSQPK_374.9_244.2 | (SEQ ID NO: 834) | B2MG_HUMAN | 24.53420489 |
| SGAQATWTELPWPHEK_613.3_793.4 | (SEQ ID NO: 888) | HEMO_HUMAN | 24.25610995 |
| AQPVQVAEGSEPDGFWEALGGK_758.0_623.4 | (SEQ ID NO: 837) | GELS_HUMAN | 24.18769142 |
| DLPHITVDR_533.3_490.3 | (SEQ ID NO: 899) | MMP7_HUMAN | 24.02606052 |
| SEYGAALAWEK_612.8_788.4 | (SEQ ID NO: 1051) | CO6_HUMAN | 24.00163743 |
| AVGYLITGYQR_620.8_523.3 | (SEQ ID NO: 69) | PZP_HUMAN | 23.93958524 |
| GFQALGDAADIR_617.3_717.4 | (SEQ ID NO: 918) | TIMP1_HUMAN | 23.69249513 |
| YEVQGEVFTKPQLWP_911.0_392.2 | (SEQ ID NO: 27) | CRP_HUMAN | 23.67764212 |
| SDGAKPGPR_442.7_459.2 | (SEQ ID NO: 879) | COLI_HUMAN | 23.63551614 |
| GFQALGDAADIR_617.3_288.2 | (SEQ ID NO: 918) | TIMP1_HUMAN | 23.55832742 |
| IAPQLSTEELVSLGEK_857.5_533.3 | (SEQ ID NO: 832) | AFAM_HUMAN | 23.38139357 |
| DTDTGALLFIGK_625.8_217.1 | (SEQ ID NO: 854) | PEDF_HUMAN | 23.33375418 |
| LHEAFSPVSYQHDLALLR_699.4_380.2 | (SEQ ID NO: 940) | FA12_HUMAN | 23.27455931 |
| IYLQPGR_423.7_329.2 | (SEQ ID NO: 969) | ITIH2_HUMAN | 23.19122626 |

TABLE 38

| Random Forest 32 Middle Window | | | |
|---|---|---|---|
| Variable | Peptide disclosed in adjacent column | UniProt_ID | MeanDecreaseGini |
| SEYGAALAWEK_612.8_788.4 | (SEQ ID NO: 1051) | CO6_HUMAN | 2.27812193 |
| LLAPSDSPEWLSFDVTGVVR_730.1_430.3 | (SEQ ID NO: 883) | TGFB1_HUMAN | 2.080133179 |
| ALNHLPLEYNSALYSR_621.0_696.4 | (SEQ ID NO: 72) | CO6_HUMAN | 1.952233942 |

TABLE 38-continued

| Variable | Peptide disclosed in adjacent column | | UniProt_ID | MeanDecreaseGini |
|---|---|---|---|---|
| ELPQSIVYK_538.8_417.7 | (SEQ ID NO: 820) | FBLN3_HUMAN | | 1.518833357 |
| VEHSDLSFSK_383.5_234.1 | (SEQ ID NO: 7) | B2MG_HUMAN | | 1.482593086 |
| VFQFLEK_455.8_811.4 | (SEQ ID NO: 810) | CO5_HUMAN | | 1.448810425 |
| VNHVTLSQPK_374.9_244.2 | (SEQ ID NO: 834) | B2MG_HUMAN | | 1.389922815 |
| YGIEEHGK_311.5_599.3 | (SEQ ID NO: 1061) | CXA1_HUMAN | | 1.386794676 |
| TLAFVR_353.7_492.3 | (SEQ ID NO: 1055) | FA7_HUMAN | | 1.371530925 |
| VLEPTLK_400.3_587.3 | (SEQ ID NO: 920) | VTDB_HUMAN | | 1.368583173 |
| VLEPTLK_400.3_458.3 | (SEQ ID NO: 920) | VTDB_HUMAN | | 1.336029064 |
| DALSSVQESQVAQQAR_573.0_502.3 | (SEQ ID NO: 91) | APOC3_HUMAN | | 1.307024357 |
| AQPVQVAEGSEPDGFWEALGGK_758.0_574.3 | (SEQ ID NO: 837) | GELS_HUMAN | | 1.282930911 |
| LHEAFSPVSYQHDLALLR_699.4_251.2 | (SEQ ID NO: 940) | FA12_HUMAN | | 1.25362163 |
| SEPRPGVLLR_375.2_654.4 | (SEQ ID NO: 12) | FA7_HUMAN | | 1.205539225 |
| VEHSDLSFSK_383.5_468.2 | (SEQ ID NO: 7) | B2MG_HUMAN | | 1.201047302 |
| SLDFTELDVAAEK_719.4_316.2 | (SEQ ID NO: 871) | ANGT_HUMAN | | 1.189617326 |
| SEYGAALAWEK_612.8_845.5 | (SEQ ID NO: 1051) | CO6_HUMAN | | 1.120706696 |
| TYLHTYESEI_628.3_515.3 | (SEQ ID NO: 100) | ENPP2_HUMAN | | 1.107036657 |
| VNHVTLSQPK_374.9_459.3 | (SEQ ID NO: 834) | B2MG_HUMAN | | 1.083264902 |
| IEEIAAK_387.2_660.4 | (SEQ ID NO: 30) | CO5_HUMAN | | 1.043635292 |
| ALNHLPLEYNSALYSR_621.0_538.3 | (SEQ ID NO: 72) | CO6_HUMAN | | 0.962643698 |
| TLLPVSKPEIR_418.3_514.3 | (SEQ ID NO: 25) | CO5_HUMAN | | 0.933440467 |
| TEQAAVAR_423.2_615.4 | (SEQ ID NO: 935) | FA12_HUMAN | | 0.878933553 |
| DLHLSDVFLK_396.2_260.2 | (SEQ ID NO: 856) | CO6_HUMAN | | 0.816855601 |
| ALQDQLVLVAAK_634.9_289.2 | (SEQ ID NO: 33) | ANGT_HUMAN | | 0.812620232 |
| SLQAFVAVAAR_566.8_804.5 | (SEQ ID NO: 910) | IL23A_HUMAN | | 0.792274782 |
| QGHNSVFLIK_381.6_260.2 | (SEQ ID NO: 830) | HEMO_HUMAN | | 0.770830031 |
| ALQDQLVLVAAK_634.9_956.6 | (SEQ ID NO: 33) | ANGT_HUMAN | | 0.767468246 |
| SLDFTELDVAAEK_719.4_874.5 | (SEQ ID NO: 871) | ANGT_HUMAN | | 0.745827911 |

TABLE 39

Random Forest 100 Middle Window

| Variable | Peptide disclosed in adjacent column | | UniProt_ID | MeanDecreaseGini |
|---|---|---|---|---|
| SEYGAALAWEK_612.8_788.4 | (SEQ ID NO: 1051) | CO6_HUMAN | | 1.241568411 |
| ALNHLPLEYNSALYSR_621.0_696.4 | (SEQ ID NO: 72) | CO6_HUMAN | | 0.903126414 |

TABLE 39-continued

Random Forest 100 Middle Window

| Variable | Peptide disclosed in adjacent column | | UniProt_ID | MeanDecreaseGini |
|---|---|---|---|---|
| LLAPSDSPEWLSFDVTGVVR_730.1_430.3 | (SEQ ID NO: 883) | | TGFB1_HUMAN | 0.846216563 |
| ANLINNIFELAGLGK_793.9_299.2 | (SEQ ID NO: 949) | | LCAP_HUMAN | 0.748261193 |
| VFQFLEK_455.8_811.4 | (SEQ ID NO: 810) | | CO5_HUMAN | 0.717545171 |
| VEHSDLSFSK_383.5_234.1 | (SEQ ID NO: 7) | | B2MG_HUMAN | 0.683219617 |
| ELPQSIVYK_538.8_417.7 | (SEQ ID NO: 820) | | FBLN3_HUMAN | 0.671091545 |
| LNIGYIEDLK_589.3_950.5 | (SEQ ID NO: 923) | | PAI2_HUMAN | 0.652293621 |
| VLEPTLK_400.3_587.3 | (SEQ ID NO: 920) | | VTDB_HUMAN | 0.627095631 |
| VNHVTLSQPK_374.9_244.2 | (SEQ ID NO: 834) | | B2MG_HUMAN | 0.625773888 |
| VLEPTLK_400.3_458.3 | (SEQ ID NO: 920) | | VTDB_HUMAN | 0.613655529 |
| AQPVQVAEGSEPDGFWEALGGK_758.0_574.3 | (SEQ ID NO: 837) | | GELS_HUMAN | 0.576305627 |
| TLFIFGVTK_513.3_811.5 | (SEQ ID NO: 842) | | PSG4_HUMAN | 0.574056825 |
| YGIEEHGK_311.5_599.3 | (SEQ ID NO: 1061) | | CXA1_HUMAN | 0.570270447 |
| VPLALFALNR_557.3_620.4 | (SEQ ID NO: 943) | | PEPD_HUMAN | 0.556087614 |
| EVFSKPISWEELLQ_852.9_376.2 | (SEQ ID NO: 840) | | FA40A_HUMAN | 0.531461012 |
| VEHSDLSFSK_383.5_468.2 | (SEQ ID NO: 7) | | B2MG_HUMAN | 0.531214597 |
| TLAFVR_353.7_492.3 | (SEQ ID NO: 1055) | | FA7_HUMAN | 0.53070743 |
| DALSSVQESQVAQQAR_573.0_502.3 | (SEQ ID NO: 91) | | APOC3_HUMAN | 0.521633041 |
| SEYGAALAWEK_612.8_845.5 | (SEQ ID NO: 1051) | | CO6_HUMAN | 0.514509661 |
| SLDFTELDVAAEK_719.4_316.2 | (SEQ ID NO: 871) | | ANGT_HUMAN | 0.50489698 |
| SEPRPGVLLR_375.2_654.4 | (SEQ ID NO: 12) | | FA7_HUMAN | 0.4824926 |
| LHEAFSPVSYQHDLALLR_699.4_251.2 | (SEQ ID NO: 940) | | FA12_HUMAN | 0.48217238 |
| TYLHTYESEI_628.3_515.3 | (SEQ ID NO: 100) | | ENPP2_HUMAN | 0.472286273 |
| AVDIPGLEAATPYR_736.9_399.2 | (SEQ ID NO: 942) | | TENA_HUMAN | 0.470892051 |
| FSLVSGWGQLLDR_493.3_403.2 | (SEQ ID NO: 878) | | FA7_HUMAN | 0.465839813 |
| GEVTYTTSQVSK_650.3_750.4 | (SEQ ID NO: 909) | | EGLN_HUMAN | 0.458736205 |
| VNHVTLSQPK_374.9_459.3 | (SEQ ID NO: 834) | | B2MG_HUMAN | 0.454348892 |
| HFQNLGK_422.2_527.2 | (SEQ ID NO: 831) | | AFAM_HUMAN | 0.45127405 |
| YGIEEHGK_311.5_341.2 | (SEQ ID NO: 1061) | | CXA1_HUMAN | 0.430641646 |

TABLE 40

Random Forest Protein Middle Window

| Variable | Peptide disclosed in adjacent column | | UniProt_ID | MeanDecreaseGini |
|---|---|---|---|---|
| SEYGAALAWEK_612.8_788.4 | (SEQ ID NO: 1051) | | CO6_HUMAN | 2.09649626 |
| LLAPSDSPEWLSFDVTGVVR_730.1_430.3 | (SEQ ID NO: 883) | | TGFB1_HUMAN | 1.27664656 |

TABLE 40-continued

| | Random Forest Protein Middle Window | | |
|---|---|---|---|
| Variable | Peptide disclosed in adjacent column | UniProt_ID | MeanDecreaseGini |
| VFQFLEK_455.8_811.4 | (SEQ ID NO: 810) | CO5_HUMAN | 1.243884833 |
| ANLINNIFELAGLGK_793.9_299.2 | (SEQ ID NO: 949) | LCAP_HUMAN | 1.231814882 |
| VEHSDLSFSK_383.5_234.1 | (SEQ ID NO: 7) | B2MG_HUMAN | 1.188808078 |
| ELPQSIVYK_538.8_417.7 | (SEQ ID NO: 820) | FBLN3_HUMAN | 1.185075445 |
| LNIGYIEDLK_589.3_950.5 | (SEQ ID NO: 923) | PAI2_HUMAN | 1.122351536 |
| VLEPTLK_400.3_458.3 | (SEQ ID NO: 920) | VTDB_HUMAN | 1.062664798 |
| VPLALFALNR_557.3_620.4 | (SEQ ID NO: 943) | PEPD_HUMAN | 1.019466776 |
| TLAFVR_353.7_492.3 | (SEQ ID NO: 1055) | FA7_HUMAN | 0.98797064 |
| TLFIFGVTK_513.3_811.5 | (SEQ ID NO: 942) | PSG4_HUMAN | 0.980159531 |
| AQPVQVAEGSEPDGFWEALGGK_758.0_574.3 | (SEQ ID NO: 837) | GELS_HUMAN | 0.960286027 |
| DALSSVQESQVAQQAR_573.0_502.3 | (SEQ ID NO: 91) | APOC3_HUMAN | 0.947091926 |
| YGIEEHGK_311.5_599.3 | (SEQ ID NO: 1061) | CXA1_HUMAN | 0.946937719 |
| EVFSKPISWEELLQ_852.9_376.2 | (SEQ ID NO: 840) | FA40A_HUMAN | 0.916262164 |
| LHEAFSPVSYQHDLALLR_699.4_251.2 | (SEQ ID NO: 940) | FA12_HUMAN | 0.891310053 |
| SLDFTELDVAAEK_719.4_316.2 | (SEQ ID NO: 971) | ANGT_HUMAN | 0.884498494 |
| TYLHTYESEI_628.3_515.3 | (SEQ ID NO: 100) | ENPP2_HUMAN | 0.869043942 |
| HFQNLGK_422.2_527.2 | (SEQ ID NO: 831) | AFAM_HUMAN | 0.865435217 |
| AVDIPGLEAATPYR_736.9_399.2 | (SEQ ID NO: 942) | TENA_HUMAN | 0.844842109 |
| TLNAYDHR_330.5_312.2 | (SEQ ID NO: 839) | PAR3_HUMAN | 0.792615068 |
| DVLLLVHNLPQNLTGHIWYK_791.8_310.2 | (SEQ ID NO: 783) | PSG7_HUMAN | 0.763629346 |
| GPITSAAELNDPQSILLR_632.4_826.5 | (SEQ ID NO: 941) | EGLN_HUMAN | 0.762305265 |
| VVLSSGSGPGLDLPLVLGLPLQLK_791.5_598.4 | (SEQ ID NO: 946) | SHBG_HUMAN | 0.706312721 |
| SLQNASAIESILK_687.4_860.5 | (SEQ ID NO: 1069) | IL3_HUMAN | 0.645503581 |
| HYINLITR_515.3_301.1 | (SEQ ID NO: 102) | NPY_HUMAN | 0.62631682 |
| VELAPLPSWQPVGK_760.9_342.2 | (SEQ ID NO: 872) | ICAM1_HUMAN | 0.608991877 |
| LQVNTPLVGASLLR_741.0_925.6 | (SEQ ID NO: 863) | BPIA1_HUMAN | 0.607801279 |
| TLEAQLTPR_514.8_814.4 | (SEQ ID NO: 68) | HEP2_HUMAN | 0.597771074 |
| SDGAKPGPR_442.7_459.2 | (SEQ ID NO: 879) | COLI_HUMAN | 0.582773073 |

TABLE 41

| | Peptide disclosed in adjacent | | |
| Variable | column | UniProt_ID | MeanDecreaseGini |
|---|---|---|---|
| SEYGAALAWEK_612.8_788.4 | (SEQ ID NO: 1051) | CO6_HUMAN | 0.493373282 |
| ALNHLPLEYNSALYSR_621.0_696.4 | (SEQ ID NO: 72) | CO6_HUMAN | 0.382180772 |
| VFQFLEK_455.8_811.4 | (SEQ ID NO: 810) | CO5_HUMAN | 0.260292083 |
| LLAPSDSPEWLSFDVTGVVR_730.1_430.3 | (SEQ ID NO: 883) | TGFB1_HUMAN | 0.243156718 |
| NADYSYSVWK_616.8_769.4 | (SEQ ID NO: 60) | CO5_HUMAN | 0.242388196 |
| VLEPTLK_400.3_458.3 | (SEQ ID NO: 820) | VTDB_HUMAN | 0.238171849 |
| VEHSDLSFSK_383.5_234.1 | (SEQ ID NO: 7) | B2MG_HUMAN | 0.236873731 |
| ELPQSIVYK_538.8_417.7 | (SEQ ID NO: 820) | FBLN3_HUMAN | 0.224727161 |
| VLEPTLK_400.3_587.3 | (SEQ ID NO: 920) | VTDB_HUMAN | 0.222105614 |
| TLFIFGVTK_513.3_811.5 | (SEQ ID NO: 842) | PSG4_HUMAN | 0.210807574 |
| ANLINNIFELAGLGK_793.9_299.2 | (SEQ ID NO: 949) | LCAP_HUMAN | 0.208714978 |
| LNIGYIEDLK_589.3_950.5 | (SEQ ID NO: 923) | PAI2_HUMAN | 0.208027555 |
| SEYGAALAWEK_612.8_845.5 | (SEQ ID NO: 1051) | CO6_HUMAN | 0.197362212 |
| VNHVTLSQPK_374.9_244.2 | (SEQ ID NO: 834) | B2MG_HUMAN | 0.195728091 |
| YGIEEHGK_311.5_599.3 | (SEQ ID NO: 1061) | CXA1_HUMAN | 0.189969499 |
| HFQNLGK_422.2_527.2 | (SEQ ID NO: 831) | AFAM_HUMAN | 0.189572857 |
| AGITIPR_364.2_486.3 | (SEQ ID NO: 858) | IL17_HUMAN | 0.188351054 |
| AQPVQVAEGSEPDGFWEALGGK_758.0_574.3 | (SEQ ID NO: 837) | GELS_HUMAN | 0.185069517 |
| SLDFTELDVAAEK_719.4_316.2 | (SEQ ID NO: 871) | ANGT_HUMAN | 0.173688295 |
| TLAFVR_353.7_492.3 | (SEQ ID NO: 1055) | FA7_HUMAN | 0.170636045 |
| SEPRPGVLLR_375.2_654.4 | (SEQ ID NO: 12) | FA7_HUMAN | 0.170608352 |
| TLLIANETLR_572.3_703.4 | (SEQ ID NO: 65) | IL5_HUMAN | 0.16745571 |
| ALNHLPLEYNSALYSR_621.0_538.3 | (SEQ ID NO: 72) | CO6_HUMAN | 0.161514946 |
| LHEAFSPVSYQHDLALLR_699.4_251.2 | (SEQ ID NO: 940) | FA12_HUMAN | 0.15852146 |
| DGSPDVTTADIGANTPDATK_973.5_844.4 | (SEQ ID NO: 44) | PGRP2_HUMAN | 0.154028378 |
| VPLALFALNR_557.3_620.4 | (SEQ ID NO: 943) | PEPD_HUMAN | 0.153725879 |
| AVDIPGLEAATPYR_736.9_399.2 | (SEQ ID NO: 942) | TENA_HUMAN | 0.150920884 |
| YGIEEHGK_311.5_341.2 | (SEQ ID NO: 1061) | CXA1_HUMAN | 0.150319671 |
| FSLVSGWGQLLDR_493.3_403.2 | (SEQ ID NO: 878) | FA7_HUMAN | 0.144781622 |
| IEEIAAK_387.2_660.4 | (SEQ ID NO: 30) | CO5_HUMAN | 0.141983196 |

TABLE 42

| | Random Forest 32 Middle-Late Window | | |
|---|---|---|---|
| Variable | Peptide disclosed in adjacent column | UniProt_ID | MeanDecreaseGini |
| VPLALFALNR_557.3_620.4 | (SEQ ID NO: 943) | PEPD_HUMAN | 4.566619475 |
| VFQFLEK_455.8_811.4 | (SEQ ID NO: 810) | CO5_HUMAN | 3.062474666 |
| AQPVQVAEGSEPDGFWEALGGK_758.0_574.3 | (SEQ ID NO: 837) | GELS_HUMAN | 3.033740627 |
| LIEIANHVDK_384.6_498.3 | (SEQ ID NO: 955) | ADA12_HUMAN | 2.825082394 |
| DALSSVQESQVAQQAR_573.0_502.3 | (SEQ ID NO: 91) | APOC3_HUMAN | 2.787777983 |
| TLAFVR_353.7_492.3 | (SEQ ID NO: 1055) | FA7_HUMAN | 2.730532075 |
| ALNHLPLEYNSALYSR_621.0_696.4 | (SEQ ID NO: 72) | CO6_HUMAN | 2.671290375 |
| AVYEAVLR_460.8_587.4 | (SEQ ID NO: 78) | PEPD_HUMAN | 2.621357053 |
| SEPRPGVLLR_375.2_654.4 | (SEQ ID NO: 12) | FA7_HUMAN | 2.57568964 |
| TYLHTYESEI_628.3_515.3 | (SEQ ID NO: 100) | ENPP2_HUMAN | 2.516708906 |
| ALNHLPLEYNSALYSR_621.0_538.3 | (SEQ ID NO: 72) | CO6_HUMAN | 2.497348374 |
| LIEIANHVDK_384.6_683.4 | (SEQ ID NO: 955) | ADA12_HUMAN | 2.457401462 |
| YGIEEHGK_311.5_599.3 | (SEQ ID NO: 1061) | CXA1_HUMAN | 2.396824268 |
| VLEPTLK_400.3_587.3 | (SEQ ID NO: 920) | VTDB_HUMAN | 2.388105564 |
| SEYGAALAWEK_612.8_788.4 | (SEQ ID NO: 1051) | CO6_HUMAN | 2.340473883 |
| WSAGLTSSQVDLYIPK_883.0_515.3 | (SEQ ID NO: 916) | CBG_HUMAN | 2.332007976 |
| FGFGGSTDSGPIR_649.3_946.5 | (SEQ ID NO: 5) | ADA12_HUMAN | 2.325669514 |
| SEYGAALAWEK_612.8_845.5 | (SEQ ID NO: 1051) | CO6_HUMAN | 2.31761671 |
| QINSYVK_426.2_496.3 | (SEQ ID NO: 917) | CBG_HUMAN | 2.245221163 |
| QINSYVK_426.2_610.3 | (SEQ ID NO: 917) | CBG_HUMAN | 2.212307699 |
| TEQAAVAR_423.2_615.4 | (SEQ ID NO: 935) | FA12_HUMAN | 2.105860336 |
| AVYEAVLR_460.8_750.4 | (SEQ ID NO: 78) | PEPD_HUMAN | 2.098321893 |
| TEQAAVAR_423.2_487.3 | (SEQ ID NO: 935) | FA12_HUMAN | 2.062684763 |
| DFNQFSSGEK_386.8_333.2 | (SEQ ID NO: 845) | FETA_HUMAN | 2.05160689 |
| SLQAFVAVAAR_566.8_804.5 | (SEQ ID NO: 910) | IL23A_HUMAN | 1.989521006 |
| SLDFTELDVAAEK_719.4_316.2 | (SEQ ID NO: 871) | ANGT_HUMAN | 1.820628782 |
| DPTFIPAPIQAK_433.2_556.3 | (SEQ ID NO: 857) | ANGT_HUMAN | 1.763514326 |
| DPTFIPAPIQAK_433.2_461.2 | (SEQ ID NO: 857) | ANGT_HUMAN | 1.760870392 |
| VLEPTLK_400.3_458.3 | (SEQ ID NO: 920) | VTDB_HUMAN | 1.723389354 |
| YENYTSSFFIR_713.8_756.4 | (SEQ ID NO: 816) | IL12B_HUMAN | 1.63355187 |

TABLE 43

| | Random Forest 100 Middle-Late Window | | |
|---|---|---|---|
| Variable | Peptide disclosed in adjacent column | UniProt_ID | MeanDecreaseGini |
| VPLALFALNR_557.3_620.4 | (SEQ ID NO: 943) | PEPD_HUMAN | 1.995805024 |
| VFQFLEK_455.8_811.4 | (SEQ ID NO: 810) | CO5_HUMAN | 1.235926416 |
| DALSSVQESQVAQQAR_573.0_502.3 | (SEQ ID NO: 91) | APOC3_HUMAN | 1.187464899 |
| EVFSKPISWEELLQ_852.9_376.2 | (SEQ ID NO: 840) | FA40A_HUMAN | 1.166642578 |
| AQPVQVAEGSEPDGFWEALGGK_758.0_574.3 | (SEQ ID NO: 837) | GELS_HUMAN | 1.146077071 |
| TLAFVR_353.7_492.3 | (SEQ ID NO: 1055) | FA7_HUMAN | 1.143038275 |
| ANLINNIFELAGLGK_793.9_299.2 | (SEQ ID NO: 949) | LCAP_HUMAN | 1.130656591 |
| ALNHLPLEYNSALYSR_621.0_538.3 | (SEQ ID NO: 72) | CO6_HUMAN | 1.098305298 |
| ELPQSIVYK_538.8_417.7 | (SEQ ID NO: 820) | FBLN3_HUMAN | 1.096715712 |
| LLAPSDSPEWLSFDVTGVVR_730.1_430.3 | (SEQ ID NO: 883) | TGFB1_HUMAN | 1.086171713 |
| YGIEEHGK_311.5_341.2 | (SEQ ID NO: 1061) | CXA1_HUMAN | 1.071880823 |
| ALNHLPLEYNSALYSR_621.0_696.4 | (SEQ ID NO: 72) | CO6_HUMAN | 1.062278869 |
| TQILEWAAER_608.8_761.4 | (SEQ ID NO: 10) | EGLN_HUMAN | 1.059019017 |
| AVYEAVLR_460.8_587.4 | (SEQ ID NO: 78) | PEPD_HUMAN | 1.057920661 |
| AEIEYLEK_497.8_552.3 | (SEQ ID NO: 959) | LYAM1_HUMAN | 1.038388955 |
| SEPRPGVLLR_375.2_654.4 | (SEQ ID NO: 12) | FA7_HUMAN | 1.028275728 |
| AVDIPGLEAATPYR_736.9_399.2 | (SEQ ID NO: 942) | TENA_HUMAN | 1.026032369 |
| LIEIANHVDK_384.6_498.3 | (SEQ ID NO: 955) | ADA12_HUMAN | 1.015065282 |
| YGIEEHGK_311.5_599.3 | (SEQ ID NO: 1061) | CXA1_HUMAN | 0.98667651 |
| VLEPTLK_400.3_587.3 | (SEQ ID NO: 920) | VTDB_HUMAN | 0.970330675 |
| DVLLLVHNLPQNLTGHIWYK_791.8_883.0 | (SEQ ID NO: 783) | PSG7_HUMAN | 0.934747674 |
| TAHISGLPPSTDFIVYLSGLAPSIR_871.5_472.3 | (SEQ ID NO: 979) | TENA_HUMAN | 0.889111923 |
| TLNAYDHR_330.5_312.2 | (SEQ ID NO: 839) | PAR3_HUMAN | 0.887605636 |
| FGFGGSTDSGPIR_649.3_946.5 | (SEQ ID NO: 5) | ADA12_HUMAN | 0.884305889 |
| LIEIANHVDK_384.6_683.4 | (SEQ ID NO: 955) | ADA12_HUMAN | 0.880889836 |
| SEYGAALAWEK_612.8_788.4 | (SEQ ID NO: 1051) | CO6_HUMAN | 0.863585472 |
| TYLHTYESEI_628.3_515.3 | (SEQ ID NO: 100) | ENPP2_HUMAN | 0.849232356 |
| FGFGGSTDSGPIR_649.3_745.4 | (SEQ ID NO: 5) | ADA12_HUMAN | 0.843334824 |
| SEYGAALAWEK_612.8_845.5 | (SEQ ID NO: 1051) | CO6_HUMAN | 0.842319271 |
| TPSAAYLWVGTGASEAEK_919.5_849.4 | (SEQ ID NO: 35) | GELS_HUMAN | 0.828959173 |

TABLE 44

| | Random Forest Protein Middle-Late Window | | |
|---|---|---|---|
| Variable | Peptide disclosed in adjacent column | UniProt_ID | MeanDecreaseGini |
| VPLALFALNR_557.3_620.4 | (SEQ ID NO: 943) | PEPD_HUMAN | 3.202123047 |
| ANLINNIFELAGLGK_793.9_299.2 | (SEQ ID NO: 949) | LCAP_HUMAN | 2.100447309 |
| VFQFLEK_455.8_811.4 | (SEQ ID NO: 810) | CO5_HUMAN | 2.096157529 |
| AQPVQVAEGSEPDGFWEALGGK_758.0_574.3 | (SEQ ID NO: 837) | GELS_HUMAN | 2.052960939 |
| ALNHLPLEYNSALYSR_621.0_696.4 | (SEQ ID NO: 72) | CO6_HUMAN | 2.046139797 |
| TQILEWAAER_608.8_761.4 | (SEQ ID NO: 10) | EGLN_HUMAN | 1.99287941 |
| ELPQSIVYK_538.8_417.7 | (SEQ ID NO: 820) | FBLN3_HUMAN | 1.920894959 |
| TGVAVNKPAEFTVDAK_549.6_258.1 | (SEQ ID NO: 822) | FLNA_HUMAN | 1.917665697 |
| SEPRPGVLLR_375.2_654.4 | (SEQ ID NO: 12) | FA7_HUMAN | 1.883557705 |
| DALSSVQESQVAQQAR_573.0_502.3 | (SEQ ID NO: 91) | APOC3_HUMAN | 1.870232155 |
| EVFSKPISWEELLQ_852.9_376.2 | (SEQ ID NO: 840) | FA40A_HUMAN | 1.869000136 |
| LIEIANHVDK_384.6_683.4 | (SEQ ID NO: 955) | ADA12_HUMAN | 1.825457092 |
| VLEPTLK_400.3_587.3 | (SEQ ID NO: 920) | VTDB_HUMAN | 1.695327774 |
| TEQAAVAR_423.2_615.4 | (SEQ ID NO: 935) | FA12_HUMAN | 1.685013152 |
| LLAPSDSPEWLSFDVTGVVR_730.1_430.3 | (SEQ ID NO: 883) | TGFB1_HUMAN | 1.684068039 |
| TLNAYDHR_330.5_312.2 | (SEQ ID NO: 839) | PAR3_HUMAN | 1.673758239 |
| AVDIPGLEAATPYR_736.9_399.2 | (SEQ ID NO: 842) | TENA_HUMAN | 1.648896853 |
| DVLLLVHNLPQNLTGHIWYK_791.8_883.0 | (SEQ ID NO: 783) | PSG7_HUMAN | 1.648146088 |
| AEIEYLEK_497.8_552.3 | (SEQ ID NO: 959) | LYAM1_HUMAN | 1.645833005 |
| TYLHTYESEI_628.3_515.3 | (SEQ ID NO: 100) | ENPP2_HUMAN | 1.639121965 |
| AGLLRPDYALLGHR_518.0_595.4 | (SEQ ID NO: 95) | PGRP2_HUMAN | 1.610227875 |
| YGIEEHGK_311.5_599.3 | (SEQ ID NO: 1061) | CXA1_HUMAN | 1.606978339 |
| QINSYVK_426.2_496.3 | (SEQ ID NO: 917) | CBG_HUMAN | 1.554905578 |
| LTTVDIVTLR_565.8_815.5 | (SEQ ID NO: 1054) | IL2RB_HUMAN | 1.484081016 |
| AALAAFNAQNNGSNFQLEEISR_789.1_746.4 | (SEQ ID NO: 891) | FETUA_HUMAN | 1.43173022 |
| AEVIWTSSDHQVLSGK_586.3_300.2 | (SEQ ID NO: 964) | PD1L1_HUMAN | 1.394857397 |
| ALEQDLPVNIK_620.4_570.4 | (SEQ ID NO: 93) | CNDP1_HUMAN | 1.393464547 |
| DFNQFSSGEK_386.8_333.2 | (SEQ ID NO: 845) | FETA_HUMAN | 1.374296237 |
| TSYQVYSK_488.2_787.4 | (SEQ ID NO: 937) | C163A_HUMAN | 1.36141387 |
| TLEAQLTPR_514.8_685.4 | (SEQ ID NO: 68) | HEP2_HUMAN | 1.311118611 |

TABLE 45

| | Random Forest All Middle-Late Window | | |
|---|---|---|---|
| Variable | Peptide disclosed in adjacent column | UniProt_ID | MeanDecreaseGini |
| VPLALFALNR_557.3_620.4 | (SEQ ID NO: 943) | PEPD_HUMAN | 0.685165163 |
| VFQFLEK_455.8_811.4 | (SEQ ID NO: 810) | CO5_HUMAN | 0.426827804 |
| ALNHLPLEYNSALYSR_621.0_538.3 | (SEQ ID NO: 72) | CO6_HUMAN | 0.409942379 |
| YGIEEHGK_311.5_341.2 | (SEQ ID NO: 1061) | CXA1_HUMAN | 0.406589512 |
| ALNHLPLEYNSALYSR_621.0_696.4 | (SEQ ID NO: 72) | CO6_HUMAN | 0.402152062 |
| AQPVQVAEGSEPDGFWEALGGK_758.0_574.3 | (SEQ ID NO: 837) | GELS_HUMAN | 0.374861014 |
| ANLINNIFELAGLGK_793.9_299.2 | (SEQ ID NO: 949) | LCAP_HUMAN | 0.367089422 |
| TQILEWAAER_608.8_761.4 | (SEQ ID NO: 10) | EGLN_HUMAN | 0.353757524 |
| AVYEAVLR_460.8_587.4 | (SEQ ID NO: 78) | PEPD_HUMAN | 0.350518668 |
| TLAFVR_353.7_492.3 | (SEQ ID NO: 1055) | FA7_HUMAN | 0.344669505 |
| SEPRPGVLLR_375.2_654.4 | (SEQ ID NO: 12) | FA7_HUMAN | 0.338752336 |
| LIEIANHVDK_384.6_683.4 | (SEQ ID NO: 955) | ADA12_HUMAN | 0.321850027 |
| ELPQSIVYK_538.8_417.7 | (SEQ ID NO: 820) | FBLN3_HUMAN | 0.301819017 |
| EVFSKPISWEELLQ_852.9_376.2 | (SEQ ID NO: 840) | FA40A_HUMAN | 0.299561811 |
| LIEIANHVDK_384.6_498.3 | (SEQ ID NO: 955) | ADA12_HUMAN | 0.298253589 |
| VLEPTLK_400.3_587.3 | (SEQ ID NO: 920) | VTDB_HUMAN | 0.296206088 |
| YGIEEHGK_311.5_599.3 | (SEQ ID NO: 1061) | CXA1_HUMAN | 0.295621408 |
| DVLLLVHNLPQNLTGHIWYK_791.8_883.0 | (SEQ ID NO: 783) | PSG7_HUMAN | 0.292937475 |
| TYLHTYESEI_628.3_515.3 | (SEQ ID NO: 100) | ENPP2_HUMAN | 0.275902848 |
| DALSSVQESQVAQQAR_573.0_502.3 | (SEQ ID NO: 91) | APOC3_HUMAN | 0.275664578 |
| FGFGGSTDSGPIR_649.3_745.4 | (SEQ ID NO: 5) | ADA12_HUMAN | 0.27120436 |
| AVDIPGLEAATPYR_736.9_399.2 | (SEQ ID NO: 942) | TENA_HUMAN | 0.266568271 |
| TGVAVNKPAEFTVDAK_549.6_258.1 | (SEQ ID NO: 922) | FLNA_HUMAN | 0.262537889 |
| TLNAYDHR_330.5_312.2 | (SEQ ID NO: 938) | PAR3_HUMAN | 0.259901193 |
| IYLQPGR_423.7_329.2 | (SEQ ID NO: 969) | ITIH2_HUMAN | 0.259086112 |
| AEVIWTSSDHQVLSGK_586.3_300.2 | (SEQ ID NO: 964) | PD1L1_HUMAN | 0.25722354 |
| VPSHAVVAR_312.5_515.3 | (SEQ ID NO: 951) | TRFL_HUMAN | 0.256151812 |
| SEYGAALAWEK_612.8_845.5 | (SEQ ID NO: 1051) | CO6_HUMAN | 0.251704855 |
| FGFGGSTDSGPIR_649.3_946.5 | (SEQ ID NO: 5) | ADA12_HUMAN | 0.249400642 |
| SEYGAALAWEK_612.8_788.4 | (SEQ ID NO: 1051) | CO6_HUMAN | 0.245930393 |

TABLE 46

| | Peptide disclosed in adjacent | | |
|---|---|---|---|
| Variable | column | UniProt_ID | MeanDecreaseGini |
| AVYEAVLR_460.8_587.4 | (SEQ ID NO: 78) | PEPD_HUMAN | 1.889521223 |
| AEIEYLEK_497.8_552.3 | (SEQ ID NO: 959) | LYAM1_HUMAN | 1.75233545 |
| AALAAFNAQNNGSNFQLEEISR_789.1_746.4 | (SEQ ID NO: 891) | FETUA_HUMAN | 1.676813493 |
| TGVAVNKPAEFTVDAK_549.6_258.1 | (SEQ ID NO: 822) | FLNA_HUMAN | 1.600684153 |
| AVYEAVLR_460.8_750.4 | (SEQ ID NO: 78) | PEPD_HUMAN | 1.462889662 |
| LIEIANHVDK_384.6_683.4 | (SEQ ID NO: 955) | ADA12_HUMAN | 1.364115361 |
| VPLALFALNR_557.3_620.4 | (SEQ ID NO: 943) | PEPD_HUMAN | 1.324317148 |
| QINSYVK_426.2_610.3 | (SEQ ID NO: 917) | CBG_HUMAN | 1.305932064 |
| ITQDAQLK_458.8_702.4 | (SEQ ID NO: 13) | CBG_HUMAN | 1.263533228 |
| FGFGGSTDSGPIR_649.3_745.4 | (SEQ ID NO: 5) | ADA12_HUMAN | 1.245153376 |
| LIEIANHVDK_384.6_498.3 | (SEQ ID NO: 955) | ADA12_HUMAN | 1.236529173 |
| QINSYVK_426.2_496.3 | (SEQ ID NO: 917) | CBG_HUMAN | 1.221866266 |
| YSHYNER_323.5_418.2 | (SEQ ID NO: 889) | HABP2_HUMAN | 1.169575572 |
| YYGYTGAFR_549.3_450.3 | (SEQ ID NO: 843) | TRFL_HUMAN | 1.126684146 |
| VGVISFAQK_474.8_580.3 | (SEQ ID NO: 960) | TFR2_HUMAN | 1.075283855 |
| VFQYIDLHQDEFVQTLK_708.4_375.2 | (SEQ ID NO: 961) | CNDP1_HUMAN | 1.07279097 |
| SPEAEDPLGVER_649.8_314.1 | (SEQ ID NO: 887) | Z512B_HUMAN | 1.05759256 |
| DEIPHNDIALLK_459.9_510.8 | (SEQ ID NO: 964) | HABP2_HUMAN | 1.028933332 |
| ALEQDLPVNIK_620.4_798.5 | (SEQ ID NO: 93) | CNDP1_HUMAN | 1.014443799 |
| ALEQDLPVNIK_620.4_570.4 | (SEQ ID NO: 93) | CNDP1_HUMAN | 1.010573267 |
| ILDGGNK_358.7_603.3 | (SEQ ID NO: 877) | CXCL5_HUMAN | 0.992175141 |
| TSYQVYSK_488.2_787.4 | (SEQ ID NO: 937) | C163A_HUMAN | 0.95649585 |
| YENYTSSFFIR_713.8_756.4 | (SEQ ID NO: 816) | IL12B_HUMAN | 0.955085198 |
| SETEIHQGFQHLHQLFAK_717.4_447.2 | (SEQ ID NO: 958) | CBG_HUMAN | 0.944726739 |
| TLPFSR_360.7_506.3 | (SEQ ID NO: 963) | LYAM1_HUMAN | 0.944426109 |
| VLSSIEQK_452.3_691.4 | (SEQ ID NO: 962) | 1433S_HUMAN | 0.933902495 |
| AEIEYLEK_497.8_389.2 | (SEQ ID NO: 959) | LYAM1_HUMAN | 0.891235263 |
| GTYLYNDCPGPGQDTDCR_697.0_666.3 | (SEQ ID NO: 990) | TNR1A_HUMAN | 0.87187037 |
| SGVDLADSNQK_567.3_662.3 | (SEQ ID NO: 853) | VGFR3_HUMAN | 0.869821307 |
| SGVDLADSNQK_567.3_591.3 | (SEQ ID NO: 853) | VGFR3_HUMAN | 0.839946466 |

TABLE 47

| Random Forest 100 Late Window | | | |
| --- | --- | --- | --- |
| Variable | Peptide disclosed in adjacent column | UniProt_ID | MeanDecreaseGini |
| AVYEAVLR_460.8_587.4 | (SEQ ID NO: 78) | PEPD_HUMAN | 0.971695767 |
| AEIEYLEK_497.8_552.3 | (SEQ ID NO: 959) | LYAM1_HUMAN | 0.920098693 |
| TGVAVNKPAEFTVDAK_549.6_258.1 | (SEQ ID NO: 822) | FLNA_HUMAN | 0.786924487 |
| AVYEAVLR_460.8_750.4 | (SEQ ID NO: 78) | PEPD_HUMAN | 0.772867983 |
| AALAAFNAQNNGSNFQLEEISR_789.1_746.4 | (SEQ ID NO: 891) | FETUA_HUMAN | 0.744138513 |
| AYSDLSR_406.2_375.2 | (SEQ ID NO: 90) | SAMP_HUMAN | 0.736078079 |
| VPLALFALNR_557.3_620.4 | (SEQ ID NO: 943) | PEPD_HUMAN | 0.681784822 |
| QINSYVK_426.2_610.3 | (SEQ ID NO: 917) | CBG_HUMAN | 0.585819307 |
| LIEIANHVDK_384.6_498.3 | (SEQ ID NO: 955) | ADA12_HUMAN | 0.577161158 |
| FGFGGSTDSGPIR_649.3_745.4 | (SEQ ID NO: 5) | ADA12_HUMAN | 0.573055613 |
| WSAGLTSSQVDLYIPK_883.0_515.3 | (SEQ ID NO: 916) | CBG_HUMAN | 0.569156128 |
| ITQDAQLK_458.8_702.4 | (SEQ ID NO: 13) | CBG_HUMAN | 0.551017844 |
| LIEIANHVDK_384.6_683.4 | (SEQ ID NO: 955) | ADA12_HUMAN | 0.539330047 |
| YYGYTGAFR_549.3_450.3 | (SEQ ID NO: 843) | TRFL_HUMAN | 0.527652175 |
| VFQYIDLHQDEFVQTLK_708.4_375.2 | (SEQ ID NO: 961) | CNDP1_HUMAN | 0.484155289 |
| FQLPGQK_409.2_429.2 | (SEQ ID NO: 62) | PSG1_HUMAN | 0.480394031 |
| AVDIPGLEAATPYR_736.9_286.1 | (SEQ ID NO: 942) | TENA_HUMAN | 0.475252565 |
| QINSYVK_426.2_496.3 | (SEQ ID NO: 917) | CBG_HUMAN | 0.4728541 |
| YISPDQLADLYK_713.4_277.2 | (SEQ ID NO: 850) | ENOA_HUMAN | 0.470079977 |
| TLPFSR_360.7_506.3 | (SEQ ID NO: 963) | LYAM1_HUMAN | 0.46881451 |
| SPEAEDPLGVER_649.8_314.1 | (SEQ ID NO: 887) | Z512B_HUMAN | 0.4658941 |
| ALEQDLPVNIK_620.4_798.5 | (SEQ ID NO: 93) | CNDP1_HUMAN | 0.463604174 |
| YSHYNER_323.5_418.2 | (SEQ ID NO: 889) | HABP2_HUMAN | 0.453076307 |
| VGVISFAQK_474.8_580.3 | (SEQ ID NO: 960) | TFR2_HUMAN | 0.437768219 |
| LQDAGVYR_461.2_680.3 | (SEQ ID NO: 902) | PD1L1_HUMAN | 0.428524689 |
| AEIEYLEK_497.8_389.2 | (SEQ ID NO: 959) | LYAM1_HUMAN | 0.42041448 |
| TSYQVYSK_488.2_787.4 | (SEQ ID NO: 937) | C163A_HUMAN | 0.419411932 |
| SVVLIPLGAVDDGEHSQNEK_703.0_798.4 | (SEQ ID NO: 957) | CNDP1_HUMAN | 0.415325735 |
| ALEQDLPVNIK_620.4_570.4 | (SEQ ID NO: 93) | CNDP1_HUMAN | 0.407951733 |
| ILDGGNK_358.7_603.3 | (SEQ ID NO: 877) | CXCL5_HUMAN | 0.401059572 |

TABLE 48

| | Random Forest Protein Late Window | | |
|---|---|---|---|
| Variable | Peptide disclosed in adjacent column | UniProt_ID | MeanDecreaseGini |
| AVYEAVLR_460.8_587.4 | (SEQ ID NO: 78) | PEPD_HUMAN | 1.836010146 |
| AEIEYLEK_497.8_552.3 | (SEQ ID NO: 959) | LYAM1_HUMAN | 1.739802548 |
| AALAAFNAQNNGSNFQLEEISR_789.1_746.4 | (SEQ ID NO: 891) | FETUA_HUMAN | 1.455337749 |
| TGVAVNKPAEFTVDAK_549.6_258.1 | (SEQ ID NO: 822) | FLNA_HUMAN | 1.395043941 |
| AYSDLSR_406.2_375.2 | (SEQ ID NO: 90) | SAMP_HUMAN | 1.177349958 |
| LIEIANHVDK_384.6_683.4 | (SEQ ID NO: 955) | ADA12_HUMAN | 1.14243936 |
| QINSYVK_426.2_496.3 | (SEQ ID NO: 917) | CBG_HUMAN | 1.05284482 |
| ALEQDLPVNIK_620.4_798.5 | (SEQ ID NO: 93) | CNDP1_HUMAN | 0.971678206 |
| YISPDQLADLYK_713.4_277.2 | (SEQ ID NO: 950) | ENOA_HUMAN | 0.902293734 |
| AVDIPGLEAATPYR_736.9_286.1 | (SEQ ID NO: 942) | TENA_HUMAN | 0.893163413 |
| SPEAEDPLGVER_649.8_314.1 | (SEQ ID NO: 887) | Z512B_HUMAN | 0.856551531 |
| ILDGGNK_358.7_603.3 | (SEQ ID NO: 877) | CXCL5_HUMAN | 0.841485153 |
| VGVISFAQK_474.8_580.3 | (SEQ ID NO: 960) | TFR2_HUMAN | 0.835256078 |
| YYGYTGAFR_549.3_450.3 | (SEQ ID NO: 943) | TRFL_HUMAN | 0.831195917 |
| YSHYNER_323.5_418.2 | (SEQ ID NO: 889) | HABP2_HUMAN | 0.814479968 |
| FQLPGQK_409.2_276.1 | (SEQ ID NO: 62) | PSG1_HUMAN | 0.77635168 |
| YENYTSSFFIR_713.8_756.4 | (SEQ ID NO: 916) | IL12B_HUMAN | 0.761241391 |
| TEQAAVAR_423.2_615.4 | (SEQ ID NO: 935) | FA12_HUMAN | 0.73195592 |
| SGVDLADSNQK_567.3_662.3 | (SEQ ID NO: 853) | VGFR3_HUMAN | 0.72504131 |
| VLSSIEQK_452.3_691.4 | (SEQ ID NO: 962) | 1433S_HUMAN | 0.713380314 |
| GTYLYNDCPGPGQDTDCR_697.0_666.3 | (SEQ ID NO: 990) | TNR1A_HUMAN | 0.704248586 |
| TSYQVYSK_488.2_787.4 | (SEQ ID NO: 937) | C163A_HUMAN | 0.69026345 |
| TLEAQLTPR_514.8_685.4 | (SEQ ID NO: 68) | HEP2_HUMAN | 0.654641588 |
| AEVIWTSSDHQVLSGK_586.3_300.2 | (SEQ ID NO: 964) | PD1L1_HUMAN | 0.634751081 |
| TAVTANLDIR_537.3_288.2 | (SEQ ID NO: 915) | CHL1_HUMAN | 0.619871203 |
| ITENDIQIALDDAK_779.9_632.3 | (SEQ ID NO: 55) | APOB_HUMAN | 0.606313398 |
| TASDFITK_441.7_781.4 | (SEQ ID NO: 37) | GELS_HUMAN | 0.593535076 |
| SPQAFYR_434.7_556.3 | (SEQ ID NO: 953) | REL3_HUMAN | 0.592004045 |
| NHYTESISVAK_624.8_415.2 | (SEQ ID NO: 645) | NEUR1_HUMAN | 0.588383911 |
| LTTVDIVTLR_565.8_815.5 | (SEQ ID NO: 1054) | IL2RB_HUMAN | 0.587343951 |

TABLE 49

| | Peptide disclosed in adjacent | | |
|---|---|---|---|
| Variable | column | UniProt_ID | MeanDecreaseGini |
| AVYEAVLR_460.8_587.4 | (SEQ ID NO: 78) | PEPD_HUMAN | 0.437300283 |
| AEIEYLEK_497.8_552.3 | (SEQ ID NO: 959) | LYAM1_HUMAN | 0.371624293 |
| AALAAFNAQNNGSNFQLEEISR_789.1_746.4 | (SEQ ID NO: 891) | FETUA_HUMAN | 0.304039734 |
| TGVAVNKPAEFTVDAK_549.6_258.1 | (SEQ ID NO: 822) | FLNA_HUMAN | 0.280588526 |
| AVYEAVLR_460.8_750.4 | (SEQ ID NO: 78) | PEPD_HUMAN | 0.266788699 |
| AYSDLSR_406.2_375.2 | (SEQ ID NO: 90) | SAMP_HUMAN | 0.247412666 |
| VPLALFALNR_557.3_620.4 | (SEQ ID NO: 943) | PEPD_HUMAN | 0.229955358 |
| LIEIANHVDK_384.6_683.4 | (SEQ ID NO: 955) | ADA12_HUMAN | 0.218186524 |
| ITQDAQLK_458.8_702.4 | (SEQ ID NO: 13) | CBG_HUMAN | 0.217646659 |
| WSAGLTSSQVDLYIPK_883.0_515.3 | (SEQ ID NO: 916) | CBG_HUMAN | 0.213840705 |
| FGFGGSTDSGPIR_649.3_745.4 | (SEQ ID NO: 5) | ADA12_HUMAN | 0.212794469 |
| LIEIANHVDK_384.6_498.3 | (SEQ ID NO: 955) | ADA12_HUMAN | 0.208620264 |
| QINSYVK_426.2_610.3 | (SEQ ID NO: 917) | CBG_HUMAN | 0.202054546 |
| QINSYVK_426.2_496.3 | (SEQ ID NO: 917) | CBG_HUMAN | 0.197235139 |
| FQLPGQK_409.2_429.2 | (SEQ ID NO: 62) | PSG1_HUMAN | 0.188311102 |
| VFQYIDLHQDEFVQTLK_708.4_375.2 | (SEQ ID NO: 961) | CNDP1_HUMAN | 0.180534913 |
| ALEQDLPVNIK_620.4_798.5 | (SEQ ID NO: 93) | CNDP1_HUMAN | 0.178464358 |
| YYGYTGAFR_549.3_450.3 | (SEQ ID NO: 843) | TRFL_HUMAN | 0.176050092 |
| ALFLDALGPPAVTR_720.9_640.4 | (SEQ ID NO: 1013) | INHA_HUMAN | 0.171492975 |
| FQLPGQK_409.2_276.1 | (SEQ ID NO: 62) | PSG1_HUMAN | 0.167576198 |
| SETEIHQGFQHLHQLFAK_717.4_447.2 | (SEQ ID NO: 958) | CBG_HUMAN | 0.162231844 |
| ALEQDLPVNIK_620.4_570.4 | (SEQ ID NO: 93) | CNDP1_HUMAN | 0.162165399 |
| VPSHAVVAR_312.5_515.3 | (SEQ ID NO: 951) | TRFL_HUMAN | 0.156742065 |
| AVDIPGLEAATPYR_736.9_286.1 | (SEQ ID NO: 942) | TENA_HUMAN | 0.153681405 |
| FTFTLHLETPKPSISSSNLNPR_829.4_874.4 | (SEQ ID NO: 82) | PSG1_HUMAN | 0.152042057 |
| VGVISFAQK_474.8_580.3 | (SEQ ID NO: 960) | TFR2_HUMAN | 0.149034355 |
| TLPFSR_360.7_506.3 | (SEQ ID NO: 963) | LYAM1_HUMAN | 0.143223501 |
| SLDFTELDVAAEK_719.4_874.5 | (SEQ ID NO: 871) | ANGT_HUMAN | 0.141216186 |
| SPEAEDPLGVER_649.8_314.1 | (SEQ ID NO: 887) | Z512B_HUMAN | 0.139843479 |
| YGIEEHGK_311.5_341.2 | (SEQ ID NO: 1061) | CXA1_HUMAN | 0.135236953 |

TABLE 50

| Selected Transitions for Early Window | | |
|---|---|---|
| Transition | Peptide disclosed in adjacent column | Parent Protein |
| LIQDAVTGLTVNGQITGDK_972.0_798.4 | (SEQ ID NO: 807) | ITIH3_HUMAN |
| VQTAHFK_277.5_431.2 | (SEQ ID NO: 811) | CO8A_HUMAN |
| FLNWIK_410.7_560.3 | (SEQ ID NO: 4) | HABP2_HUMAN |
| ITGFLKPGK_320.9_429.3 | (SEQ ID NO: 97) | LBP_HUMAN |
| ALNHLPLEYNSALYSR_621.0_538.3 | (SEQ ID NO: 72) | CO6_HUMAN |
| TYLHTYESEI_628.3_908.4 | (SEQ ID NO: 100) | ENPP2_HUMAN |
| LIENGYFHPVK_439.6_627.4 | (SEQ ID NO: 827) | F13B_HUMAN |
| AVLHIGEK_289.5_292.2 | (SEQ ID NO: 817) | THBG_HUMAN |
| QALEEFQK_496.8_680.3 | (SEQ ID NO: 808) | CO8B_HUMAN |
| TEFLSNYLTNVDDITLVPGTLGR_846.8_600.3 | (SEQ ID NO: 824) | ENPP2_HUMAN |
| TASDFITK_441.7_781.4 | (SEQ ID NO: 37) | GELS_HUMAN |
| LPNNVLQEK_527.8_844.5 | (SEQ ID NO: 814) | AFAM_HUMAN |
| AHYDLR_387.7_288.2 | (SEQ ID NO: 88) | FETUA_HUMAN |
| ITLPDFTGDLR_624.3_288.2 | (SEQ ID NO: 3) | LBP_HUMAN |
| IEGNLIFDPNNYLPK_874.0_414.2 | (SEQ ID NO: 8) | APOB_HUMAN |
| ITGFLKPGK_320.9_301.2 | (SEQ ID NO: 97) | LBP_HUMAN |
| FSVVYAK_407.2_381.2 | (SEQ ID NO: 47) | FETUA_HUMAN |
| ITGFLKPGK_320.9_429.3 | (SEQ ID NO: 97) | LBP_HUMAN |
| VFQFLEK_455.8_811.4 | (SEQ ID NO: 810) | CO5_HUMAN |
| LIQDAVTGLTVNGQITGDK_972.0_798.4 | (SEQ ID NO: 807) | ITIH3_HUMAN |
| DADPDTFFAK_563.8_825.4 | (SEQ ID NO: 833) | AFAM_HUMAN |

TABLE 51

| Selected Proteins for Early Window | |
|---|---|
| Protein | |
| complement component C6 precursor | CO6_HUMAN |
| inter-alpha-trypsin inhibitor heavy chain H3 preproprotein | ITIH3_HUMAN |
| Coagulation factor XIII B chain | F13B_HUMAN |
| Ectonucleotide pyrophosphatase/phosphodiesterase family member 2 | ENPP2_HUMAN |
| Complement component C8 beta chain | CO8B_HUMAN |
| thyroxine-binding globulin precursor | THBG_HUMAN |
| Hyaluronan-binding protein 2 | HABP2_HUMAN |
| lipopolysaccharide-binding protein | LBP_HUMAN |
| Complement factor B | CFAB_HUMAN |

TABLE 51-continued

| Selected Proteins for Early Window | |
|---|---|
| Protein | |
| Gelsolin | GELS_HUMAN |
| afamin precursor | AFAM_HUMAN |
| apolipoprotein B-100 precursor | APOB_HUMAN |
| complement component C5 | CO5_HUMAN |
| Alpha-2-HS-glycoprotein | FETUA_HUMAN |
| complement component C8 gamma chain | CO8G_HUMAN |

TABLE 52

Selected Transitions for Middle-Late Window

| Transition | Peptide disclosed in adjacent column | | Patent Protein |
|---|---|---|---|
| VPLALFALNR_557.3_620.4 | (SEQ ID NO: | 942) | PEPD_HUMAN |
| VFQFLEK_455.8_811.4 | (SEQ ID NO: | 810) | CO5_HUMAN |
| AQPVQVAEGSEPDGFWEALGGK_758.0_574.3 | (SEQ ID NO: | 937) | GELS_HUMAN |
| LIEIANHVDK_384.6_498.3 | (SEQ ID NO: | 955) | ADA12_HUMAN |
| TLAFVR_353.7_492.3 | (SEQ ID NO: | 1055) | FA7_HUMAN |
| ALNHLPLEYNSALYSR_621.0_696.4 | (SEQ ID NO: | 72) | CO6_HUMAN |
| AVYEAVLR_460.8_587.4 | (SEQ ID NO: | 78) | PEPD_HUMAN |
| SEPRPGVLLR_375.2_654.4 | (SEQ ID NO: | 12) | FA7_HUMAN |
| TYLHTYESEI_628.3_515.3 | (SEQ ID NO: | 100) | ENPP2_HUMAN |
| ALNHLPLEYNSALYSR_621.0_538.3 | (SEQ ID NO: | 72) | CO6_HUMAN |

TABLE 53

Selected Proteins for Middle-Late Window

| Protein | |
|---|---|
| Xaa-Pro dipeptidase | PEPD_HUMAN |
| Leucyl-cystinyl aminopeptidase | LCAP_HUMAN |
| complement component C5 | CO5_HUMAN |
| Gelsolin | GELS_HUMAN |
| complement component C6 precursor | CO6_HUMAN |
| Endoglin precursor | EGLN_HUMAN |
| EGF-containing fibulin-like extracellular matrix protein 1 | FBLN3_HUMAN |
| coagulation factor VII isoform a | FA7_HUMAN |
| Disintegrin and metalloproteinase domain-containing protein 12 | ADA12_HUMAN |
| vitamin D-binding protein isoform 1 precursor | VTDB_HUMAN |
| coagulation factor XII precursor | FA12_HUMAN |
| Corticosteroid-binding globulin | CBG_HUMAN |

Example 6. Study V to Further Refine Preterm Birth Biomarkers

A additional hypothesis-dependent discovery study was performed with a further refined scheduled MRM assay. Less robust transitions were again removed to improve analytical performance and make room for the inclusion of stable-isotope labeled standards (SIS) corresponding to 79 analytes of interest identified in previous studies. SIS peptides have identical amino acid sequence, chromatographic and MS fragmentation behaviour as their endogenous peptide counterparts, but differ in mass. Therefore they can be used to reduce LC-MS analytical variability and confirm analyte identity. Samples included approximately 60 spontaneous PTB cases (delivery at less than 37 weeks, 0 days), and 180 term controls (delivery at greater than or equal to 37 weeks, 0 days). Each case was designated a "matched" control to within one day of blood draw and two "random" controls matched to the same 3 week blood draw window (17-19, 20-22 or 23-25 weeks gestation). For the purposes of analysis these three blood draw windows were combined. Samples were processed essentially as described previously, except that in this study, tryptic digests were reconstituted in a solution containing SIS standards. Raw analyte peak areas were Box-Cox transformed, corrected for run order and batch effects by regression and used for univariate and multivariate statistical analyses. Univariate analysis included determination of p-values for adjusted peak areas for all analytes from t-tests considering cases vs controls defined as either deliveries at >37 weeks (Table 54) or deliveries at >40 weeks (Table 55). Univariate analysis also included the determination of p-values for a linear model that evaluates the dependence of each analyte's adjusted peak area on the time to birth (gestational age at birth minus the gestational age at blood draw) (Table 56) and the gestational age at birth (Table 57). Additionally raw peak area ratios were calculated for endogenous analytes and their corresponding SIS counterparts, Box-Cox transformed and then used for univariate and multivariate statistical analyses. The above univariate analysis was repeated for analyte/SIS peak area ratio values, summarized in Tables 58-61, respectively.

Multivariate random forest regression models were built using analyte values and clinical variables (e.g. Maternal age, (MAGE), Body mass index, (BMI)) to predict Gestational Age at Birth (GAB). The accuracy of the random forest was evaluated with respect to correlation of the predicted and actual GAB, and with respect to the mean absolute deviation (MAD) of the predicted from actual GAB. The accuracy was further evaluated by determining the area under the receiver operating characteristic curve (AUC) when using the predicted GAB as a quantitative variable to classify subjects as full term or pre-term. Random Forest Importance Values were fit to an Empirical Cumulative Disribution Function and probabilities (P) were calculated. We report the analytes by importance ranking (P>0.7) in the random forest models, using adjusted analyte peak area values (Table 62) and analyte/SIS peak area ratio values (Table 63).

The probability of pre-term birth, p (PTB), may be estimated using the predicted gestational age at birth (GAB) as follows. The estimate will be based on women enrolled in the Sera PAPR clinical trial, which provided the subjects used to develop the PTB prediction methods.

Among women with a predicted GAB of j days plus or minus k days, p (PTB) was estimated as the proportion of women in the PAPR clinical trial with a predicted GAB of j days plus or minus k days who actually deliver before 37 weeks gestational age.

Figure 2:
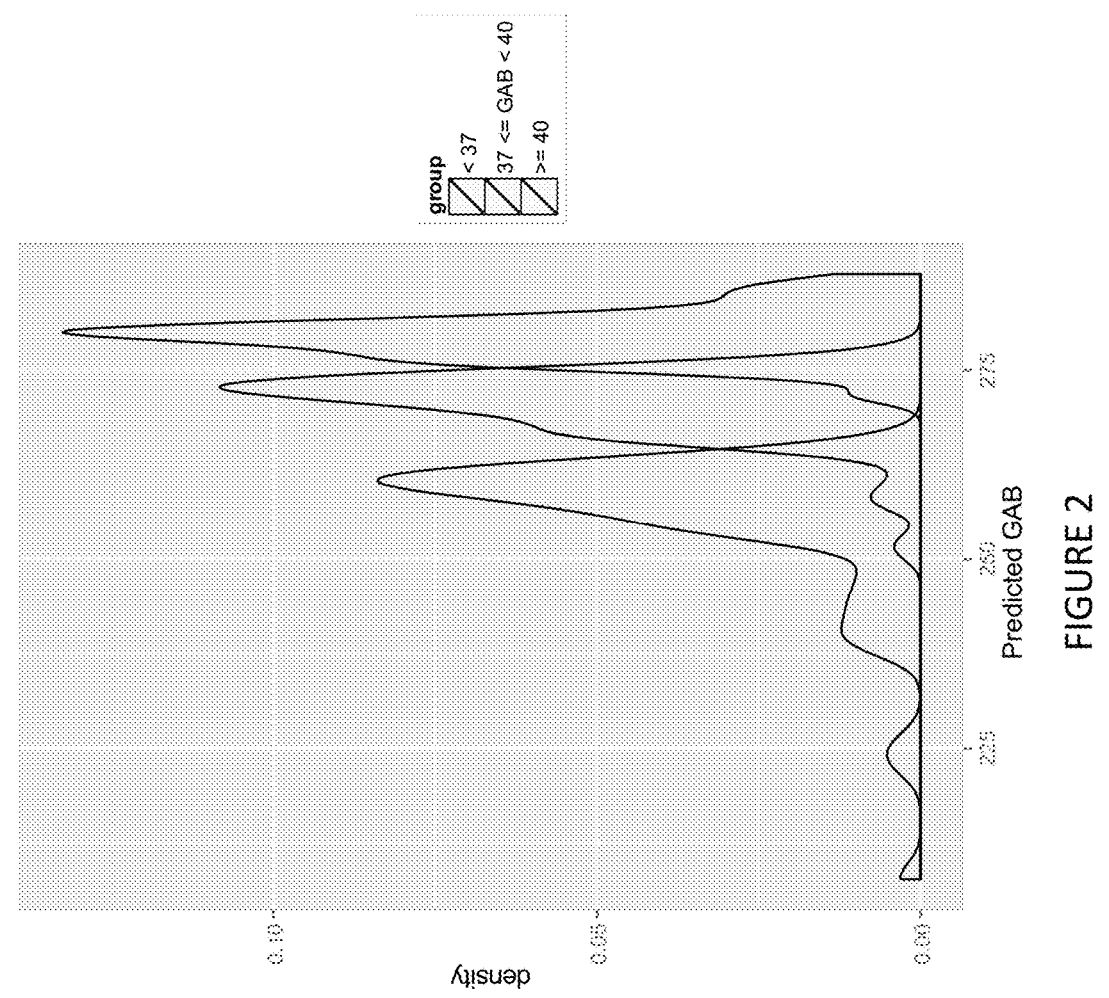
FIG. 2. Distribution of predicted gestational age from random forest regression model versus actual gestational age at birth (GAB), where actual GAB is given in categories of (i) less than 37 weeks, (ii) 37 to 39 weeks, and (iii) 40 weeks or greater (peaks left to right, respectively).

More generally, for women with a predicted GAB of j days plus or minus k days, the probability that the actual gestational age at birth will be less than a specified gestational age, p (actual GAB<specified GAB), was estimated as the proportion of women in the PAPR clinical trial with a predicted GAB of j days plus or minus k days who actually deliver before the specified gestational age. FIG. 1 depicts a scatterplot of actual gestational age at birth versus predicted gestational age from random forest regression model. FIG. 2 shows the distribution of predicted gestational age from random forest regression model versus actual gestational age at birth (GAB), where actual GAB was given in categories of (i) less than 37 weeks, (ii) 37 to 39 weeks, and (iii) 40 weeks or greater.

TABLE 54

| Univariate p-values for Adjusted Peak Areas (<37 vs >37 weeks) | | | |
|---|---|---|---|
| Transition | Peptide disclosed in adjacent column | Protein | pvalue |
| SPELQAEAK_486.8_659.4 | (SEQ ID NO: 99) | APOA2_HUMAN | 0.00246566 |
| ALALPPLGLAPLLNLWAKPQGR_770.5_457.3 | (SEQ ID NO: 947) | SHBG_HUMAN | 0.002623332 |
| ALALPPLGLAPLLNLWAKPQGR_770.5_256.2 | (SEQ ID NO: 947) | SHBG_HUMAN | 0.002822593 |
| SPELQAEAK_486.8_788.4 | (SEQ ID NO: 99) | APOA2_HUMAN | 0.003183869 |
| VVLSSGSGPGLDLPLVLGLPLQLK_791.5_768.5 | (SEQ ID NO: 946) | SHBG_HUMAN | 0.004936049 |
| VVLSSGSGPGLDLPLVLGLPLQLK_791.5_598.4 | (SEQ ID NO: 946) | SHBG_HUMAN | 0.005598977 |
| DYWSTVK_449.7_347.2 | (SEQ ID NO: 885) | APOC3_HUMAN | 0.005680405 |
| DYWSTVK_449.7_620.3 | (SEQ ID NO: 885) | APOC3_HUMAN | 0.006288693 |
| WGAAPYR_410.7_634.3 | (SEQ ID NO: 1012) | PGRP2_HUMAN | 0.006505238 |
| DALSSVQESQVAQQAR_573.0_502.3 | (SEQ ID NO: 91) | APOC3_HUMAN | 0.007626246 |
| DALSSVQESQVAQQAR_573.0_672.4 | (SEQ ID NO: 91) | APOC3_HUMAN | 0.008149335 |
| LSIPQITTK_500.8_687.4 | (SEQ ID NO: 987) | PSG5_HUMAN | 0.009943955 |
| GWVTDGFSSLK_598.8_854.4 | (SEQ ID NO: 54) | APOC3_HUMAN | 0.010175055 |
| IALGGLLFPASNLR_481.3_657.4 | (SEQ ID NO: 975) | SHBG_HUMAN | 0.010784167 |
| AKPALEDLR_506.8_813.5 | (SEQ ID NO: 1014) | APOA1_HUMAN | 0.011331968 |
| WGAAPYR_410.7_577.3 | (SEQ ID NO: 1012) | PGRP2_HUMAN | 0.011761088 |
| VPLALFALNR_557.3_620.4 | (SEQ ID NO: 943) | PEPD_HUMAN | 0.014050395 |
| FSLVSGWGQLLDR_493.3_447.3 | (SEQ ID NO: 878) | FA7_HUMAN | 0.014271151 |
| LSIPQITTK_500.8_800.5 | (SEQ ID NO: 987) | PSG5_HUMAN | 0.014339942 |
| TLAFVR_353.7_274.2 | (SEQ ID NO: 1055) | FA7_HUMAN | 0.014459876 |
| DVLLLVHNLPQNLPGYFWYK_810.4_960.5 | (SEQ ID NO: 11) | PSG9_HUMAN | 0.016720007 |
| FSVVYAK_407.2_381.2 | (SEQ ID NO: 47) | FETUA_HUMAN | 0.016792786 |
| DVLLLVHNLPQNLPGYFWYK_810.4_215.1 | (SEQ ID NO: 11) | PSG9_HUMAN | 0.017335929 |
| SEPRPGVLLR_375.2_654.4 | (SEQ ID NO: 12) | FA7_HUMAN | 0.018147773 |
| ALNHLPLEYNSALYSR_621.0_538.3 | (SEQ ID NO: 72) | CO6_HUMAN | 0.019056484 |
| WNFAYWAAHQPWSR_607.3_545.3 | (SEQ ID NO: 1050) | PRG2_HUMAN | 0.019190043 |
| ALNHLPLEYNSALYSR_621.0_696.4 | (SEQ ID NO: 72) | CO6_HUMAN | 0.020218682 |
| AQPVQVAEGSEPDGFWEALGGK_758.0_623.4 | (SEQ ID NO: 837) | GELS_HUMAN | 0.020226218 |
| GWVTDGFSSLK_598.8_953.5 | (SEQ ID NO: 54) | APOC3_HUMAN | 0.023192703 |
| IALGGLLFPASNLR_481.3_412.3 | (SEQ ID NO: 975) | SHBG_HUMAN | 0.023916911 |

TABLE 54-continued

| Univariate p-values for Adjusted Peak Areas (<37 vs >37 weeks) | | | |
|---|---|---|---|
| Transition | Peptide disclosed in adjacent column | Protein | pvalue |
| WNFAYWAAHQPWSR_607.3_673.3 | (SEQ ID NO: 1050) | PRG2_HUMAN | 0.026026975 |
| FGFGGSTDSGPIR_649.3_745.4 | (SEQ ID NO: 5) | ADA12_HUMAN | 0.027731407 |
| SEYGAALAWEK_612.8_788.4 | (SEQ ID NO: 1051) | CO6_HUMAN | 0.031865281 |
| DADPDTFFAK_563.8_302.1 | (SEQ ID NO: 833) | AFAM_HUMAN | 0.0335897 |
| LFIPQITR_494.3_614.4 | (SEQ ID NO: 996) | PSG9_HUMAN | 0.034140767 |
| DVLLLVHNLPQNLPGYFWYK_810.4_328.2 | (SEQ ID NO: 11) | PSG9_HUMAN | 0.034653304 |
| TLAFVR_353.7_492.3 | (SEQ ID NO: 1055) | FA7_HUMAN | 0.036441189 |
| AVLHIGEK_289.5_292.2 | (SEQ ID NO: 817) | THBG_HUMAN | 0.038539433 |
| IHPSYTNYR_384.2_452.2 | (SEQ ID NO: 775) | PSG2_HUMAN | 0.039733019 |
| AGLLRPDYALLGHR_518.0_369.2 | (SEQ ID NO: 95) | PGRP2_HUMAN | 0.040916226 |
| ILILPSVTR_506.3_559.3 | (SEQ ID NO: 789) | PSGx_HUMAN | 0.042460036 |
| YYLQGAK_421.7_516.3 | (SEQ ID NO: 48) | ITIH4_HUMAN | 0.044511962 |
| TPSAAYLWVGTGASEAEK_919.5_849.4 | (SEQ ID NO: 35) | GELS_HUMAN | 0.046362381 |
| AGLLRPDYALLGHR_518.0_595.4 | (SEQ ID NO: 95) | PGRP2_HUMAN | 0.046572355 |
| TYLHTYESEI_628.3_908.4 | (SEQ ID NO: 100) | ENPP2_HUMAN | 0.04754503 |
| FSLVSGWGQLLDR_493.3_403.2 | (SEQ ID NO: 878) | FA7_HUMAN | 0.048642964 |
| VNFTEIQK_489.8_765.4 | (SEQ ID NO: 1015) | FETA_HUMAN | 0.04871392 |
| LFIPQITR_494.3_727.4 | (SEQ ID NO: 996) | PSG9_HUMAN | 0.049288923 |
| DISEVVTPR_508.3_787.4 | (SEQ ID NO: 67) | CFAB_HUMAN | 0.049458374 |
| SEPRPGVLLR_375.2_454.3 | (SEQ ID NO: 12) | FA7_HUMAN | 0.049567047 |

TABLE 55

| Univariate p-values for Adjusted Peak Areas (<37 vs >40 weeks) | | | |
|---|---|---|---|
| Transition | Peptide disclosed in adjacent column | Protein | pvalue |
| SPELQAEAK_486.8_659.4 | (SEQ ID NO: 99) | APOA2_HUMAN | 0.001457796 |
| DYWSTVK_449.7_347.2 | (SEQ ID NO: 885) | APOC3_HUMAN | 0.001619622 |
| DYWSTVK_449.7_620.3 | (SEQ ID NO: 885) | APOC3_HUMAN | 0.002068704 |
| DALSSVQESQVAQQAR_573.0_502.3 | (SEQ ID NO: 91) | APOC3_HUMAN | 0.00250563 |
| GWVTDGFSSLK_598.8_854.4 | (SEQ ID NO: 54) | APOC3_HUMAN | 0.002543943 |
| SPELQAEAK_486.8_788.4 | (SEQ ID NO: 99) | APOA2_HUMAN | 0.003108814 |
| SEPRPGVLLR_375.2_654.4 | (SEQ ID NO: 12) | FA7_HUMAN | 0.004035832 |
| DALSSVQESQVAQQAR_573.0_672.4 | (SEQ ID NO: 91) | APOC3_HUMAN | 0.00434652 |
| SEYGAALAWEK_612.8_788.4 | (SEQ ID NO: 1051) | CO6_HUMAN | 0.005306924 |

TABLE 55-continued

Univariate p-values for Adjusted Peak Areas
(<37 vs >40 weeks)

| Transition | Peptide disclosed in adjacent column | Protein | pvalue |
|---|---|---|---|
| GWVTDGFSSLK_598.8_953.5 | (SEQ ID NO: 54) | APOC3_HUMAN | 0.005685534 |
| ALNHLPLEYNSALYSR_621.0_696.4 | (SEQ ID NO: 72) | CO6_HUMAN | 0.005770384 |
| TYLHTYESEI_628.3_515.3 | (SEQ ID NO: 100) | ENPP2_HUMAN | 0.005798991 |
| ENPAVIDFELAPIVDLVR_670.7_601.4 | (SEQ ID NO: 893) | CO6_HUMAN | 0.006248095 |
| ALNHLPLEYNSALYSR_621.0_538.3 | (SEQ ID NO: 72) | CO6_HUMAN | 0.006735817 |
| TYLHTYESEI_628.3_908.4 | (SEQ ID NO: 100) | ENPP2_HUMAN | 0.007351774 |
| AGLLRPDYALLGHR_518.0_369.2 | (SEQ ID NO: 95) | PGRP2_HUMAN | 0.009541521 |
| AKPALEDLR_506.8_813.5 | (SEQ ID NO: 1014) | APOA1_HUMAN | 0.009780371 |
| SEYGAALAWEK_612.8_845.5 | (SEQ ID NO: 1051) | CO6_HUMAN | 0.010085363 |
| FSLVSGWGQLLDR_493.3_447.3 | (SEQ ID NO: 878) | FA7_HUMAN | 0.010401836 |
| WGAAPYR_410.7_634.3 | (SEQ ID NO: 1012) | PGRP2_HUMAN | 0.011233623 |
| ENPAVIDFELAPIVDLVR_670.7_811.5 | (SEQ ID NO: 893) | CO6_HUMAN | 0.012029564 |
| DVLLLVHNLPQNLPGYFWYK_810.4_215.1 | (SEQ ID NO: 11) | PSG9_HUMAN | 0.014808277 |
| LFIPQITR_494.3_614.4 | (SEQ ID NO: 996) | PSG9_HUMAN | 0.015879755 |
| WGAAPYR_410.7_577.3 | (SEQ ID NO: 1012) | PGRP2_HUMAN | 0.016562435 |
| AGLLRPDYALLGHR_518.0_595.4 | (SEQ ID NO: 95) | PGRP2_HUMAN | 0.016793521 |
| TLAFVR_353.7_492.3 | (SEQ ID NO: 1055) | FA7_HUMAN | 0.016919708 |
| FSLVSGWGQLLDR_493.3_403.2 | (SEQ ID NO: 878) | FA7_HUMAN | 0.016937583 |
| WWGGQPLWITATK_772.4_373.2 | (SEQ ID NO: 15) | ENPP2_HUMAN | 0.019050115 |
| GYVIIKPLVWV_643.9_304.2 | (SEQ ID NO: 976) | SAMP_HUMAN | 0.019675317 |
| DVLLLVHNLPQNLPGYFWYK_810.4_960.5 | (SEQ ID NO: 11) | PSG9_HUMAN | 0.020387647 |
| FGFGGSTDSGPIR_649.3_745.4 | (SEQ ID NO: 5) | ADA12_HUMAN | 0.020458335 |
| DVLLLVHNLPQNLPGYFWYK_810.4_328.2 | (SEQ ID NO: 11) | PSG9_HUMAN | 0.021488084 |
| WWGGQPLWITATK_772.4_929.5 | (SEQ ID NO: 15) | ENPP2_HUMAN | 0.021709354 |
| LDFHFSSDR_375.2_448.2 | (SEQ ID NO: 838) | INHBC_HUMAN | 0.022403383 |
| LFIPQITR_494.3_727.4 | (SEQ ID NO: 996) | PSG9_HUMAN | 0.025561103 |
| TEFLSNYLTNVDDITLVPGTLGR_846.8_600.3 | (SEQ ID NO: 824) | ENPP2_HUMAN | 0.029344366 |
| LSIPQITTK_500.8_800.5 | (SEQ ID NO: 987) | PSG5_HUMAN | 0.031361776 |
| ALVLELAK_428.8_672.4 | (SEQ ID NO: 9) | INHBE_HUMAN | 0.031690737 |
| SEPRPGVLLR_375.2_454.3 | (SEQ ID NO: 12) | FA7_HUMAN | 0.033067953 |
| LSIPQITTK_500.8_687.4 | (SEQ ID NO: 987) | PSG5_HUMAN | 0.033972449 |
| LDFHFSSDR_375.2_611.3 | (SEQ ID NO: 838) | INHBC_HUMAN | 0.034500249 |
| LDFHFSSDR_375.2_464.2 | (SEQ ID NO: 838) | INHBC_HUMAN | 0.035166664 |
| GAVHVVVAETDYQSFAVLYLER_822.8_580.3 | (SEQ ID NO: 848) | CO8G_HUMAN | 0.037334975 |
| HELTDEELQSLFTNFANVVDK_817.1_854.4 | (SEQ ID NO: 823) | AFAM_HUMAN | 0.039258528 |
| AYSDLSR_406.2_375.2 | (SEQ ID NO: 90) | SAMP_HUMAN | 0.04036485 |

TABLE 55-continued

| | Univariate p-values for Adjusted Peak Areas (<37 vs >40 weeks) | | | |
|---|---|---|---|
| Transition | Peptide disclosed in adjacent column | Protein | pvalue |
| YYLQGAK_421.7_516.3 | (SEQ ID NO: 48) | ITIH4_HUMAN | 0.042204165 |
| ILPSVPK_377.2_264.2 | (SEQ ID NO: 867) | PGH1_HUMAN | 0.042397885 |
| ELLESYIDGR_597.8_710.4 | (SEQ ID NO: 2) | THRB_HUMAN | 0.043053589 |
| ALALPPLGLAPLLNLWAKPQGR_770.5_256.2 | (SEQ ID NO: 947) | SHBG_HUMAN | 0.045692283 |
| VGEYSLYIGR_578.8_871.5 | (SEQ ID NO: 58) | SAMP_HUMAN | 0.04765767 |
| ANDQYLTAAALHNLDEAVK_686.4_317.2 | (SEQ ID NO: 861) | IL1A_HUMAN | 0.048928376 |
| YYGYTGAFR_549.3_551.3 | (SEQ ID NO: 843) | TRFL_HUMAN | 0.049568351 |

TABLE 56

| Univariate p-values for Adjusted Peak Areas in Time to Birth Linear Model | |
|---|---|
| Protein | pvalue |
| ADA12_HUMAN | 0.003412707 |
| ENPP2_HUMAN | 0.003767393 |
| ADA12_HUMAN | 0.004194234 |
| ENPP2_HUMAN | 0.004298493 |
| ADA12_HUMAN | 0.004627197 |
| ADA12_HUMAN | 0.004918852 |
| ENPP2_HUMAN | 0.005792374 |
| CO6_HUMAN | 0.005858282 |
| ENPP2_HUMAN | 0.007123606 |
| CO6_HUMAN | 0.007162317 |
| ENPP2_HUMAN | 0.008228726 |
| ENPP2_HUMAN | 0.009168492 |
| PSG9_HUMAN | 0.011531192 |
| PSG9_HUMAN | 0.019389627 |
| PSG9_HUMAN | 0.023680865 |
| INHBE_HUMAN | 0.02581564 |

TABLE 56-continued

| Univariate p-values for Adjusted Peak Areas in Time to Birth Linear Model | |
|---|---|
| Protein | pvalue |
| B2MG_HUMAN | 0.026544689 |
| LBP_HUMAN | 0.031068274 |
| PSG9_HUMAN | 0.031091843 |
| APOA2_HUMAN | 0.033130498 |
| INHBC_HUMAN | 0.03395215 |
| CBG_HUMAN | 0.034710348 |
| PSGx_HUMAN | 0.035719227 |
| CBG_HUMAN | 0.036331871 |
| CSH_HUMAN | 0.039896611 |
| CSH_HUMAN | 0.04244001 |
| SAMP_HUMAN | 0.047112128 |
| LBP_HUMAN | 0.048141371 |
| LBP_HUMAN | 0.048433174 |
| CO6_HUMAN | 0.04850949 |
| PSGx_HUMAN | 0.049640167 |

TABLE 57

| | Univariate p-values for Adjusted Peak Areas in Gestation Age at Birth Linear Model | | | |
|---|---|---|---|
| Transition | Peptide disclosed in adjacent column | Protein | pvalue |
| ENPAVIDFELAPIVDLVR_670.7_811.5 | (SEQ ID NO: 893) | CO6_HUMAN | 0.000117239 |
| ENPAVIDFELAPIVDLVR_670.7_601.4 | (SEQ ID NO: 893) | CO6_HUMAN | 0.000130113 |
| TYLHTYESEI_628.3_908.4 | (SEQ ID NO: 100) | ENPP2_HUMAN | 0.000160472 |
| TYLHTYESEI_628.3_515.3 | (SEQ ID NO: 100) | ENPP2_HUMAN | 0.000175167 |
| TEFLSNYLTNVDDITLVPGTLGR_846.8_600.3 | (SEQ ID NO: 824) | ENPP2_HUMAN | 0.000219886 |
| TEFLSNYLTNVDDITLVPGTLGR_846.8_699.4 | (SEQ ID NO: 824) | ENPP2_HUMAN | 0.000328416 |
| WWGGQPLWITATK_772.4_373.2 | (SEQ ID NO: 15) | ENPP2_HUMAN | 0.000354644 |
| WWGGQPLWITATK_772.4_929.5 | (SEQ ID NO: 15) | ENPP2_HUMAN | 0.000390821 |
| SEYGAALAWEK_612.8_788.4 | (SEQ ID NO: 1051) | CO6_HUMAN | 0.000511882 |
| LDFHFSSDR_375.2_448.2 | (SEQ ID NO: 838) | INHBC_HUMAN | 0.000600637 |

TABLE 57-continued

Univariate p-values for Adjusted Peak Areas in
Gestation Age at Birth Linear Model

| Transition | Peptide disclosed in adjacent column | Protein | pvalue |
|---|---|---|---|
| ALVLELAK_428.8_672.4 | (SEQ ID NO: 9) | INHBE_HUMAN | 0.000732445 |
| GLQYAAQEGLLALQSELLR_1037.1_929.5 | (SEQ ID NO: 818) | LBP_HUMAN | 0.000743924 |
| DVLLLVHNLPQNLPGYFWYK_810.4_960.5 | (SEQ ID NO: 11) | PSG9_HUMAN | 0.000759173 |
| FGFGGSTDSGPIR_649.3_745.4 | (SEQ ID NO: 5) | ADA12_HUMAN | 0.001224347 |
| DVLLLVHNLPQNLPGYFWYK_810.4_328.2 | (SEQ ID NO: 11) | PSG9_HUMAN | 0.001241329 |
| GYVIIKPLVWV_643.9_304.2 | (SEQ ID NO: 976) | SAMP_HUMAN | 0.001853785 |
| SPELQAEAK_486.8_659.4 | (SEQ ID NO: 99) | APOA2_HUMAN | 0.001856303 |
| GLQYAAQEGLLALQSELLR_1037.1_858.5 | (SEQ ID NO: 818) | LBP_HUMAN | 0.001978165 |
| LDFHFSSDR_375.2_611.3 | (SEQ ID NO: 838) | INHBC_HUMAN | 0.002098948 |
| LIEIANHVDK_384.6_683.4 | (SEQ ID NO: 855) | ADA12_HUMAN | 0.002212096 |
| SFRPFVPR_335.9_272.2 | (SEQ ID NO: 18) | LBP_HUMAN | 0.002545286 |
| SFRPFVPR_335.9_635.3 | (SEQ ID NO: 18) | LBP_HUMAN | 0.002620268 |
| WSAGLTSSQVDLYIPK_883.0_515.3 | (SEQ ID NO: 916) | CBG_HUMAN | 0.002787272 |
| DLHLSDVFLK_396.2_260.2 | (SEQ ID NO: 856) | CO6_HUMAN | 0.002954612 |
| LIEIANHVDK_384.6_498.3 | (SEQ ID NO: 955) | ADA12_HUMAN | 0.002955081 |
| DVLLLVHNLPQNLPGYFWYK_810.4_215.1 | (SEQ ID NO: 11) | PSG9_HUMAN | 0.003541011 |
| LFIPQITR_494.3_614.4 | (SEQ ID NO: 996) | PSG9_HUMAN | 0.003750666 |
| FGFGGSTDSGPIR_649.3_946.5 | (SEQ ID NO: 5) | ADA12_HUMAN | 0.003773696 |
| YYLQGAK_421.7_516.3 | (SEQ ID NO: 48) | ITIH4_HUMAN | 0.004064026 |
| SEYGAALAWEK_612.8_845.5 | (SEQ ID NO: 1051) | CO6_HUMAN | 0.004208136 |
| AITPPHPASQANIIFDITEGNLR_825.8_459.3 | (SEQ ID NO: 76) | FBLN1_HUMAN | 0.004709104 |
| LDFHFSSDR_375.2_464.2 | (SEQ ID NO: 838) | INHBC_HUMAN | 0.005355741 |
| HELTDEELQSLFTNFANVVDK_817.1_854.4 | (SEQ ID NO: 823) | AFAM_HUMAN | 0.005370567 |
| ALNHLPLEYNSALYSR_621.0_696.4 | (SEQ ID NO: 72) | CO6_HUMAN | 0.005705922 |
| ITQDAQLK_458.8_702.4 | (SEQ ID NO: 13) | CBG_HUMAN | 0.006762484 |
| ITLPDFTGDLR_624.3_920.5 | (SEQ ID NO: 3) | LBP_HUMAN | 0.006993268 |
| SILFLGK_389.2_577.4 | (SEQ ID NO: 881) | THBG_HUMAN | 0.007134146 |
| WSAGLTSSQVDLYIPK_883.0_357.2 | (SEQ ID NO: 916) | CBG_HUMAN | 0.007670388 |
| GVTSVSQIFHSPDLAIR_609.7_472.3 | (SEQ ID NO: 1016) | IC1_HUMAN | 0.007742729 |
| VGEYSLYIGR_578.8_871.5 | (SEQ ID NO: 58) | SAMP_HUMAN | 0.007778691 |
| ITLPDFTGDLR_624.3_288.2 | (SEQ ID NO: 3) | LBP_HUMAN | 0.008179918 |
| YYLQGAK_421.7_327.1 | (SEQ ID NO: 48) | ITIH4_HUMAN | 0.008404686 |
| ALNHLPLEYNSALYSR_621.0_538.3 | (SEQ ID NO: 72) | CO6_HUMAN | 0.008601162 |
| DYWSTVK_449.7_620.3 | (SEQ ID NO: 885) | APOC3_HUMAN | 0.008626786 |
| TVQAVLTVPK_528.3_855.5 | (SEQ ID NO: 826) | PEDF_HUMAN | 0.008907523 |
| ITGFLKPGK_320.9_301.2 | (SEQ ID NO: 97) | LBP_HUMAN | 0.009155417 |

TABLE 57-continued

Univariate p-values for Adjusted Peak Areas in
Gestation Age at Birth Linear Model

| Transition | Peptide disclosed in adjacent column | Protein | pvalue |
|---|---|---|---|
| LFIPQITR_494.3_727.4 | (SEQ ID NO: 996) | PSG9_HUMAN | 0.009571006 |
| SPELQAEAK_486.8_788.4 | (SEQ ID NO: 99) | APOA2_HUMAN | 0.009776508 |
| DYWSTVK_449.7_347.2 | (SEQ ID NO: 885) | APOC3_HUMAN | 0.00998356 |
| ITGFLKPGK_320.9_429.3 | (SEQ ID NO: 97) | LBP_HUMAN | 0.010050264 |
| FLNWIK_410.7_560.3 | (SEQ ID NO: 4) | HABP2_HUMAN | 0.010372454 |
| DLHLSDVFLK_396.2_366.2 | (SEQ ID NO: 856) | CO6_HUMAN | 0.010806378 |
| GVTSVSQIFHSPDLAIR_609.7_908.5 | (SEQ ID NO: 1016) | IC1_HUMAN | 0.011035991 |
| VEHSDLSFSK_383.5_468.2 | (SEQ ID NO: 7) | B2MG_HUMAN | 0.011113172 |
| LLDSLPSDTR_558.8_276.2 | (SEQ ID NO: 1017) | IC1_HUMAN | 0.011589013 |
| LLDSLPSDTR_558.8_890.4 | (SEQ ID NO: 1017) | IC1_HUMAN | 0.011629438 |
| QALEEFQK_496.8_551.3 | (SEQ ID NO: 808) | CO8B_HUMAN | 0.011693839 |
| LLDSLPSDTR_558.8_575.3 | (SEQ ID NO: 1017) | IC1_HUMAN | 0.012159314 |
| IIGGSDADIK_494.8_762.4 | (SEQ ID NO: 39) | C1S_HUMAN | 0.013080243 |
| AFIQLWAFDAVK_704.9_650.4 | (SEQ ID NO: 52) | AMBP_HUMAN | 0.013462234 |
| GFQALGDAADIR_617.3_717.4 | (SEQ ID NO: 918) | TIMP1_HUMAN | 0.014370997 |
| LPNNVLQEK_527.8_730.4 | (SEQ ID NO: 814) | AFAM_HUMAN | 0.014424891 |
| DTDTGALLFIGK_625.8_217.1 | (SEQ ID NO: 854) | PEDF_HUMAN | 0.014967952 |
| VQTAHFK_277.5_502.3 | (SEQ ID NO: 811) | CO8A_HUMAN | 0.01524844 |
| ILILPSVTR_506.3_559.3 | (SEQ ID NO: 789) | PSGx_HUMAN | 0.015263132 |
| SILFLGK_389.2_201.1 | (SEQ ID NO: 881) | THBG_HUMAN | 0.015265233 |
| TVQAVLTVPK_528.3_428.3 | (SEQ ID NO: 826) | PEDF_HUMAN | 0.015344052 |
| VEPLYELVTATDFAYSSTVR_754.4_712.4 | (SEQ ID NO: 56) | CO8B_HUMAN | 0.015451068 |
| FSLVSGWGQLLDR_493.3_447.3 | (SEQ ID NO: 878) | FA7_HUMAN | 0.015510454 |
| GWVTDGFSSLK_598.8_854.4 | (SEQ ID NO: 54) | APOC3_HUMAN | 0.01610797 |
| LSETNR_360.2_519.3 | (SEQ ID NO: 16) | PSG1_HUMAN | 0.016433362 |
| TQILEWAAER_608.8_632.3 | (SEQ ID NO: 10) | EGLN_HUMAN | 0.01644844 |
| SETEIHQGFQHLHQLFAK_717.4_318.1 | (SEQ ID NO: 958) | CBG_HUMAN | 0.016720367 |
| TNLESILSYPK_632.8_936.5 | (SEQ ID NO: 80) | IC1_HUMAN | 0.017314185 |
| TNLESILSYPK_632.8_807.5 | (SEQ ID NO: 80) | IC1_HUMAN | 0.017593786 |
| AYSDLSR_406.2_375.2 | (SEQ ID NO: 90) | SAMP_HUMAN | 0.018531348 |
| YEVQGEVFTKPQLWP_911.0_392.2 | (SEQ ID NO: 27) | CRP_HUMAN | 0.019111323 |
| AYSDLSR_406.2_577.3 | (SEQ ID NO: 90) | SAMP_HUMAN | 0.019271266 |
| QALEEFQK_496.8_680.3 | (SEQ ID NO: 808) | CO8B_HUMAN | 0.019429489 |
| APLTKPLK_289.9_398.8 | (SEQ ID NO: 85) | CRP_HUMAN | 0.020110081 |
| FQPTLLTLPR_593.4_276.1 | (SEQ ID NO: 1018) | IC1_HUMAN | 0.020114306 |
| ITQDAQLK_458.8_803.4 | (SEQ ID NO: 13) | CBG_HUMAN | 0.020401782 |

TABLE 57-continued

Univariate p-values for Adjusted Peak Areas in
Gestation Age at Birth Linear Model

| Transition | Peptide<br>disclosed in<br>adjacent<br>column | Protein | pvalue |
|---|---|---|---|
| AVLHIGEK_289.5_292.2 | (SEQ ID NO: 817) | THBG_HUMAN | 0.02056597 |
| ANDQYLTAAALHNLDEAVK_686.4_317.2 | (SEQ ID NO: 861) | IL1A_HUMAN | 0.020770124 |
| VGEYSLYIGR_578.8_708.4 | (SEQ ID NO: 58) | SAMP_HUMAN | 0.021126414 |
| TLYSSSPR_455.7_533.3 | (SEQ ID NO: 1019) | IC1_HUMAN | 0.021306106 |
| VEHSDLSFSK_383.5_234.1 | (SEQ ID NO: 7) | B2MG_HUMAN | 0.021640643 |
| HELTDEELQSLFTNFANVVDK_817.1_906.5 | (SEQ ID NO: 823) | AFAM_HUMAN | 0.021921609 |
| TLYSSSPR_455.7_696.3 | (SEQ ID NO: 1019) | IC1_HUMAN | 0.022196181 |
| GYVIIKPLVWV_643.9_854.6 | (SEQ ID NO: 976) | SAMP_HUMAN | 0.023126336 |
| DEIPHNDIALLK_459.9_260.2 | (SEQ ID NO: 864) | HABP2_HUMAN | 0.023232158 |
| ILILPSVTR_506.3_785.5 | (SEQ ID NO: 789) | PSGx_HUMAN | 0.023519909 |
| WNFAYWAAHQPWSR_607.3_545.3 | (SEQ ID NO: 1050) | PRG2_HUMAN | 0.023697087 |
| FQPTLLTLPR_593.4_712.5 | (SEQ ID NO: 1018) | IC1_HUMAN | 0.023751959 |
| AQPVQVAEGSEPDGFWEALGGK_758.0_623.4 | (SEQ ID NO: 837) | GELS_HUMAN | 0.024262721 |
| DEIPHNDIALLK_459.9_510.8 | (SEQ ID NO: 864) | HABP2_HUMAN | 0.024414348 |
| GDSGGAFAVQDPNDK_739.3_716.3 | (SEQ ID NO: 1020) | C1S_HUMAN | 0.025075028 |
| FLNWIK_410.7_561.3 | (SEQ ID NO: 4) | HABP2_HUMAN | 0.025649617 |
| APLTKPLK_289.9_357.2 | (SEQ ID NO: 85) | CRP_HUMAN | 0.025961162 |
| ALDLSLK_380.2_185.1 | (SEQ ID NO: 14) | ITIH3_HUMAN | 0.026233504 |
| GWVTDGFSSLK_598.8_953.5 | (SEQ ID NO: 54) | APOC3_HUMAN | 0.026291884 |
| SETEIHQGFQHLHQLFAK_717.4_447.2 | (SEQ ID NO: 958) | CBG_HUMAN | 0.026457136 |
| GDSGGAFAVQDPNDK_739.3_473.2 | (SEQ ID NO: 1020) | C1S_HUMAN | 0.02727457 |
| YEVQGEVFTKPQLWP_911.0_293.1 | (SEQ ID NO: 27) | CRP_HUMAN | 0.028244448 |
| HVVQLR_376.2_614.4 | (SEQ ID NO: 983) | IL6RA_HUMAN | 0.028428028 |
| DTDTGALLFIGK_625.8_818.5 | (SEQ ID NO: 854) | PEDF_HUMAN | 0.028773557 |
| EVPLSALTNILSAQLISHWK_740.8_996.6 | (SEQ ID NO: 890) | PAI1_HUMAN | 0.029150774 |
| AFTECCVVASQLR_770.9_574.3 | (SEQ ID NO: 1) | CO5_HUMAN | 0.029993325 |
| TLAFVR_353.7_492.3 | (SEQ ID NO: 1055) | FA7_HUMAN | 0.030064307 |
| LWAYLTIQELLAK_781.5_300.2 | (SEQ ID NO: 1052) | ITIH1_HUMAN | 0.030368674 |
| DEIPHNDIALLK_459.9_245.1 | (SEQ ID NO: 864) | HABP2_HUMAN | 0.031972082 |
| AGLLRPDYALLGHR_518.0_369.2 | (SEQ ID NO: 95) | PGRP2_HUMAN | 0.032057409 |
| AVYEAVLR_460.8_587.4 | (SEQ ID NO: 78) | PEPD_HUMAN | 0.032527521 |
| LPNNVLQEK_527.8_844.5 | (SEQ ID NO: 814) | AFAM_HUMAN | 0.033807082 |
| GAVHVVVAETDYQSFAVLYLER_822.8_580.3 | (SEQ ID NO: 848) | CO8G_HUMAN | 0.034370139 |
| WNFAYWAAHQPWSR_607.3_673.3 | (SEQ ID NO: 1050) | PRG2_HUMAN | 0.0349737 |
| EAQLPVIENK_570.8_329.2 | (SEQ ID NO: 22) | PLMN_HUMAN | 0.035304322 |
| VQEAHLTEDQIFYFPK_655.7_701.4 | (SEQ ID NO: 31) | CO8G_HUMAN | 0.035704382 |

TABLE 57-continued

Univariate p-values for Adjusted Peak Areas in
Gestation Age at Birth Linear Model

| Transition | Peptide disclosed in adjacent column | Protein | pvalue |
|---|---|---|---|
| AFIQLWAFDAVK_704.9_836.4 | (SEQ ID NO: 52) | AMBP_HUMAN | 0.035914532 |
| SGFSFGFK_438.7_585.3 | (SEQ ID NO: 53) | CO8B_HUMAN | 0.037168221 |
| SGFSFGFK_438.7_732.4 | (SEQ ID NO: 53) | CO8B_HUMAN | 0.040182596 |
| DADPDTFFAK_563.8_302.1 | (SEQ ID NO: 833) | AFAM_HUMAN | 0.041439744 |
| EAQLPVIENK_570.8_699.4 | (SEQ ID NO: 22) | PLMN_HUMAN | 0.041447675 |
| IIGGSDADIK_494.8_260.2 | (SEQ ID NO: 39) | C1S_HUMAN | 0.041683256 |
| AVLTIDEK_444.8_718.4 | (SEQ ID NO: 46) | A1AT_HUMAN | 0.043221658 |
| SEPRPGVLLR_375.2_654.4 | (SEQ ID NO: 12) | FA7_HUMAN | 0.044079127 |
| YHFEALADTGISSEFYDNANDLLSK_940.8_874.5 | (SEQ ID NO: 1057) | CO8A_HUMAN | 0.045313634 |
| HFQNLGK_422.2_527.2 | (SEQ ID NO: 831) | AFAM_HUMAN | 0.047118971 |
| LEQGENVFLQATDK_796.4_822.4 | (SEQ ID NO: 19) | C1QB_HUMAN | 0.047818928 |
| NTVISVNPSTK_580.3_732.4 | (SEQ ID NO: 984) | VCAM1_HUMAN | 0.048102262 |
| YYGYTGAFR_549.3_551.3 | (SEQ ID NO: 843) | TRFL_HUMAN | 0.048331316 |
| ISLLLIESWLEPVR_834.5_500.3 | (SEQ ID NO: 32) | CSH_HUMAN | 0.049561581 |
| LQVLGK_329.2_416.3 | (SEQ ID NO: 1021) | A2GL_HUMAN | 0.049738493 |

TABLE 58

Univariate p-values for Peak Area Ratios (<37 vs >37 weeks)

| UniProt_ID | Transition | Peptide disclosed in adjacent column | pvalue |
|---|---|---|---|
| SHBG_HUMAN | IALGGLLFPASNLR_481.3_657.4 | (SEQ ID NO: 975) | 0.006134652 |
| SHBG_HUMAN | IALGGLLFPASNLR_481.3_412.3 | (SEQ ID NO: 975) | 0.019049498 |
| APOC3_HUMAN | DALSSVQESQVAQQAR_573.0_672.4 | (SEQ ID NO: 91) | 0.020688543 |
| THBG_HUMAN | AVLHIGEK_289.5_292.2 | (SEQ ID NO: 817) | 0.0291698 |
| PSG9_HUMAN | DVLLLVHNLPQNLPGYFWYK_810.4_960.5 | (SEQ ID NO: 11) | 0.033518454 |
| APOC3_HUMAN | DALSSVQESQVAQQAR_573.0_502.3 | (SEQ ID NO: 91) | 0.043103265 |
| PSG9_HUMAN | LFIPQITR_494.3_614.4 | (SEQ ID NO: 996) | 0.04655948 |

TABLE 59

| | | Univariate p-values for Peak Area Ratios (<37 vs >40 weeks) | | |
|---|---|---|---|---|
| UniProt_ID | Transition | Peptide disclosed in adjacent column | | pvalue |
| APOC3_HUMAN | DALSSVQESQVAQQAR_573.0_672.4 | (SEQ ID NO: 91) | | 0.011174438 |
| APOC3_HUMAN | DALSSVQESQVAQQAR_573.0_502.3 | (SEQ ID NO: 91) | | 0.015231617 |
| PSG9_HUMAN | LFIPQITR_494.3_614.4 | (SEQ ID NO: 996) | | 0.018308413 |
| PSG9_HUMAN | LFIPQITR_494.3_727.4 | (SEQ ID NO: 996) | | 0.027616871 |
| PSG9_HUMAN | DVLLLVHNLPQNLPGYFWYK_810.4_960.5 | (SEQ ID NO: 11) | | 0.028117582 |
| THBG_HUMAN | AVLHIGEK_289.5_292.2 | (SEQ ID NO: 917) | | 0.038899107 |
| CO6_HUMAN | ALNHLPLEYNSALYSR_621.0_696.4 | (SEQ ID NO: 72) | | 0.040662269 |
| ENPP2_HUMAN | TYLHTYESEI_628.3_908.4 | (SEQ ID NO: 100) | | 0.044545826 |

TABLE 60

| | | Univariate p-values for Peak Area Ratios in Time to Birth Linear Model | | |
|---|---|---|---|---|
| UniProt_ID | Transition | Peptide disclosed in adjacent column | | pvalue |
| ADA12_HUMAN | FGFGGSTDSGPIR_649.3_946.5 | (SEQ ID NO: 5) | | 5.85E-27 |
| ADA12_HUMAN | FGFGGSTDSGPIR_649.3_745.4 | (SEQ ID NO: 5) | | 2.65E-24 |
| PSG4_HUMAN | TLFIFGVTK_513.3_215.1 | (SEQ ID NO: 842) | | 1.07E-20 |
| PSG4_HUMAN | TLFIFGVTK_513.3_811.5 | (SEQ ID NO: 842) | | 2.32E-20 |
| PSGx_HUMAN | ILILPSVTR_506.3_785.5 | (SEQ ID NO: 789) | | 8.25E-16 |
| PSGx_HUMAN | ILILPSVTR_506.3_559.3 | (SEQ ID NO: 789) | | 9.72E-16 |
| PSG1_HUMAN | FQLPGQK_409.2_429.2 | (SEQ ID NO: 62) | | 1.29E-12 |
| PSG11_HUMAN | LFIPQITPK_528.8_261.2 | (SEQ ID NO: 1022) | | 2.11E-12 |
| PSG1_HUMAN | FQLPGQK_409.2_276.1 | (SEQ ID NO: 62) | | 2.33E-12 |
| PSG11_HUMAN | LFIPQITPK_528.8_683.4 | (SEQ ID NO: 1022) | | 3.90E-12 |
| PSG6_HUMAN | SNPVTLNVLYGPDLPR_585.7_817.4 | (SEQ ID NO: 782) | | 5.71E-12 |
| PSG6_HUMAN | SNPVTLNVLYGPDLPR_585.7_654.4 | (SEQ ID NO: 782) | | 1.82E-11 |
| VGFR3_HUMAN | SGVDLADSNQK_567.3_662.3 | (SEQ ID NO: 853) | | 4.57E-11 |
| INHBE_HUMAN | ALVLELAK_428.8_331.2 | (SEQ ID NO: 9) | | 1.04E-08 |
| PSG2_HUMAN | IHPSYTNYR_384.2_452.2 | (SEQ ID NO: 775) | | 6.27E-08 |
| PSG9_HUMAN | LFIPQITR_494.3_727.4 | (SEQ ID NO: 996) | | 1.50E-07 |
| VGFR3_HUMAN | SGVDLADSNQK_567.3_591.3 | (SEQ ID NO: 853) | | 2.09E-07 |
| PSG9_HUMAN | LFIPQITR_494.3_614.4 | (SEQ ID NO: 996) | | 2.71E-07 |
| PSG9_HUMAN | DVLLLVHNLPQNLPGYFWYK_810.4_960.5 | (SEQ ID NO: 11) | | 3.10E-07 |
| PSG2_HUMAN | IHPSYTNYR_384.2_338.2 | (SEQ ID NO: 775) | | 2.55E-06 |
| ITIH3_HUMAN | LIQDAVTGLTVNGQITGDK_972.0_640.4 | (SEQ ID NO: 807) | | 2.76E-06 |

TABLE 60-continued

Univariate p-values for Peak Area Ratios in Time
to Birth Linear Model

| UniProt_ID | Transition | Peptide disclosed in adjacent column | pvalue |
|---|---|---|---|
| ENPP2_HUMAN | TYLHTYESEI_628.3_908.4 | (SEQ ID NO: 100) | 2.82E-06 |
| ENPP2_HUMAN | WWGGQPLWITATK_772.4_373.2 | (SEQ ID NO: 15) | 3.75E-06 |
| PSG9_HUMAN | DVLLLVHNLPQNLPGYFWYK_810.4_328.2 | (SEQ ID NO: 11) | 3.94E-06 |
| B2MG_HUMAN | VEHSDLSFSK_383.5_468.2 | (SEQ ID NO: 7) | 5.42E-06 |
| ENPP2_HUMAN | WWGGQPLWITATK_772.4_929.5 | (SEQ ID NO: 15) | 7.93E-06 |
| ANGT_HUMAN | ALQDQLVLVAAK_634.9_289.2 | (SEQ ID NO: 33) | 1.04E-05 |
| B2MG_HUMAN | VNHVTLSQPK_374.9_244.2 | (SEQ ID NO: 834) | 1.46E-05 |
| AFAM_HUMAN | LPNNVLQEK_527.8_730.4 | (SEQ ID NO: 814) | 1.50E-05 |
| AFAM_HUMAN | LPNNVLQEK_527.8_844.5 | (SEQ ID NO: 814) | 1.98E-05 |
| THBG_HUMAN | AVLHIGEK_289.5_292.2 | (SEQ ID NO: 817) | 2.15E-05 |
| ENPP2_HUMAN | TYLHTYESEI_628.3_515.3 | (SEQ ID NO: 100) | 2.17E-05 |
| IL12B_HUMAN | DIIKPDPPK_511.8_342.2 | (SEQ ID NO: 982) | 3.31E-05 |
| AFAM_HUMAN | DADPDTFFAK_563.8_302.1 | (SEQ ID NO: 833) | 6.16E-05 |
| THBG_HUMAN | AVLHIGEK_289.5_348.7 | (SEQ ID NO: 817) | 8.34E-05 |
| PSG9_HUMAN | DVLLLVHNLPQNLPGYFWYK_810.4_215.1 | (SEQ ID NO: 11) | 0.000104442 |
| B2MG_HUMAN | VEHSDLSFSK_383.5_234.1 | (SEQ ID NO: 7) | 0.000140786 |
| TRFL_HUMAN | YYGYTGAFR_549.3_450.3 | (SEQ ID NO: 843) | 0.000156543 |
| HEMO_HUMAN | QGHNSVFLIK_381.6_260.2 | (SEQ ID NO: 830) | 0.000164578 |
| A1BG_HUMAN | LLELTGPK_435.8_227.2 | (SEQ ID NO: 6) | 0.000171113 |
| CO6_HUMAN | ALNHLPLEYNSALYSR_621.0_696.4 | (SEQ ID NO: 72) | 0.000242116 |
| CO6_HUMAN | ALNHLPLEYNSALYSR_621.0_538.3 | (SEQ ID NO: 72) | 0.00024681 |
| ALS_HUMAN | IRPHTFTGLSGLR_485.6_432.3 | (SEQ ID NO: 1023) | 0.000314359 |
| ITIH2_HUMAN | LSNENHGIAQR_413.5_544.3 | (SEQ ID NO: 1024) | 0.0004877 |
| PEDF_HUMAN | TVQAVLTVPK_528.3_855.5 | (SEQ ID NO: 826) | 0.000508174 |
| AFAM_HUMAN | HFQNLGK_422.2_527.2 | (SEQ ID NO: 831) | 0.000522139 |
| FLNA_HUMAN | TGVAVNKPAEFTVDAK_549.6_258.1 | (SEQ ID NO: 822) | 0.000594403 |
| ANGT_HUMAN | ALQDQLVLVAAK_634.9_956.6 | (SEQ ID NO: 33) | 0.000640673 |
| AFAM_HUMAN | HFQNLGK_422.2_285.1 | (SEQ ID NO: 831) | 0.000718763 |
| HGFA_HUMAN | LHKPGVYTR_357.5_692.4 | (SEQ ID NO: 1025) | 0.000753293 |
| HGFA_HUMAN | LHKPGVYTR_357.5_479.3 | (SEQ ID NO: 1025) | 0.000909298 |
| HABP2_HUMAN | FLNWIK_410.7_561.3 | (SEQ ID NO: 4) | 0.001282014 |
| FETUA_HUMAN | HTLNQIDEVK_598.8_951.5 | (SEQ ID NO: 51) | 0.001389792 |
| AFAM_HUMAN | DADPDTFFAK_563.8_825.4 | (SEQ ID NO: 833) | 0.001498237 |
| B2MG_HUMAN | VNHVTLSQPK_374.9_459.3 | (SEQ ID NO: 834) | 0.001559862 |
| ALS_HUMAN | IRPHTFTGLSGLR_485.6_545.3 | (SEQ ID NO: 1023) | 0.001612361 |
| A1BG_HUMAN | LLELTGPK_435.8_644.4 | (SEQ ID NO: 6) | 0.002012656 |

TABLE 60-continued

Univariate p-values for Peak Area Ratios in Time
to Birth Linear Model

| UniProt_ID | Transition | Peptide disclosed in adjacent column | pvalue |
|---|---|---|---|
| F13B_HUMAN | LIENGYFHPVK_439.6_343.2 | (SEQ ID NO: 827) | 0.00275216 |
| ITIH2_HUMAN | LSNENHGIAQR_413.5_519.8 | (SEQ ID NO: 1024) | 0.00356561 |
| APOC3_HUMAN | DALSSVQESQVAQQAR_573.0_672.4 | (SEQ ID NO: 91) | 0.00392745 |
| F13B_HUMAN | LIENGYFHPVK_439.6_627.4 | (SEQ ID NO: 827) | 0.00434836 |
| PEDF_HUMAN | TVQAVLTVPK_528.3_428.3 | (SEQ ID NO: 826) | 0.00482765 |
| PLMN_HUMAN | YEFLNGR_449.7_293.1 | (SEQ ID NO: 34) | 0.007325436 |
| HEMO_HUMAN | QGHNSVFLIK_381.6_520.4 | (SEQ ID NO: 830) | 0.009508516 |
| FETUA_HUMAN | HTLNQIDEVK_598.8_958.5 | (SEQ ID NO: 51) | 0.010018936 |
| CO5_HUMAN | LQGTLPVEAR_542.3_842.5 | (SEQ ID NO: 28) | 0.011140661 |
| PLMN_HUMAN | YEFLNGR_449.7_606.3 | (SEQ ID NO: 34) | 0.01135322 |
| CO5_HUMAN | TLLPVSKPEIR_418.3_288.2 | (SEQ ID NO: 25) | 0.015045275 |
| HABP2_HUMAN | FLNWIK_410.7_560.3 | (SEQ ID NO: 4) | 0.01523134 |
| APOC3_HUMAN | DALSSVQESQVAQQAR_573.0_502.3 | (SEQ ID NO: 91) | 0.01584708 |
| CO5_HUMAN | LQGTLPVEAR_542.3_571.3 | (SEQ ID NO: 28) | 0.017298064 |
| CFAB_HUMAN | DISEVVTPR_508.3_472.3 | (SEQ ID NO: 67) | 0.021743221 |
| CERU_HUMAN | TTIEKPVWLGFLGPIIK_638.0_640.4 | (SEQ ID NO: 1026) | 0.02376225 |
| CO8G_HUMAN | SLPVSDSVLSGFEQR_810.9_723.3 | (SEQ ID NO: 59) | 0.041150397 |
| CO8G_HUMAN | FLQEQGHR_338.8_497.3 | (SEQ ID NO: 23) | 0.042038143 |
| CO5_HUMAN | VFQFLEK_455.8_811.4 | (SEQ ID NO: 810) | 0.043651929 |
| CO8B_HUMAN | QALEEFQK_496.8_680.3 | (SEQ ID NO: 808) | 0.04761631 |

TABLE 61

Univariate p-values for Peak Area Ratios in
Gestation Age at Birth Linear Model

| UniProt_ID | Transition | Peptide disclosed in adjacent column | pvalue |
|---|---|---|---|
| PSG9_HUMAN | DVLLLVHNLPQNLPGYFWYK_810.4_960.5 | (SEQ ID NO: 11) | 0.000431547 |
| B2MG_HUMAN | VEHSDLSFSK_383.5_468.2 | (SEQ ID NO: 7) | 0.000561148 |
| PSG9_HUMAN | DVLLLVHNLPQNLPGYFWYK_810.4_328.2 | (SEQ ID NO: 11) | 0.000957509 |
| ENPP2_HUMAN | TYLHTYESEI_628.3_908.4 | (SEQ ID NO: 100) | 0.001058809 |
| THBG_HUMAN | AVLHIGEK_289.5_292.2 | (SEQ ID NO: 817) | 0.001180484 |
| ENPP2_HUMAN | WWGGQPLWITATK_772.4_373.2 | (SEQ ID NO: 15) | 0.001524983 |
| PSG9_HUMAN | LFIPQITR_494.3_614.4 | (SEQ ID NO: 996) | 0.001542932 |
| ENPP2_HUMAN | WWGGQPLWITATK_772.4_929.5 | (SEQ ID NO: 15) | 0.002047607 |

TABLE 61-continued

Univariate p-values for Peak Area Ratios in
Gestation Age at Birth Linear Model

| UniProt_ID | Transition | Peptide disclosed in adjacent column | pvalue |
|---|---|---|---|
| ENPP2_HUMAN | TYLHTYESEI_628.3_515.3 | (SEQ ID NO: 100) | 0.003087492 |
| PSG9_HUMAN | LFIPQITR_494.3_727.4 | (SEQ ID NO: 996) | 0.00477154 |
| PSG9_HUMAN | DVLLLVHNLPQNLPGYFWYK_810.4_215.1 | (SEQ ID NO: 11) | 0.004824351 |
| THBG_HUMAN | AVLHIGEK_289.5_348.7 | (SEQ ID NO: 817) | 0.006668084 |
| AFAM_HUMAN | LPNNVLQEK_527.8_730.4 | (SEQ ID NO: 814) | 0.006877647 |
| ADA12_HUMAN | FGFGGSTDSGPIR_649.3_745.4 | (SEQ ID NO: 5) | 0.011738104 |
| PEDF_HUMAN | TVQAVLTVPK_528.3_855.5 | (SEQ ID NO: 826) | 0.013349511 |
| A1BG_HUMAN | LLELTGPK_435.8_227.2 | (SEQ ID NO: 6) | 0.015793885 |
| ITIH3_HUMAN | ALDLSLK_380.2_185.1 | (SEQ ID NO: 14) | 0.016080436 |
| ADA12_HUMAN | FGFGGSTDSGPIR_649.3_946.5 | (SEQ ID NO: 5) | 0.017037089 |
| B2MG_HUMAN | VEHSDLSFSK_383.5_234.1 | (SEQ ID NO: 7) | 0.017072093 |
| CO6_HUMAN | ALNHLPLEYNSALYSR_621.0_696.4 | (SEQ ID NO: 72) | 0.024592775 |
| TRFL_HUMAN | YYGYTGAFR_549.3_450.3 | (SEQ ID NO: 842) | 0.030890831 |
| AFAM_HUMAN | DADPDTFFAK_563.8_302.1 | (SEQ ID NO: 833) | 0.033791429 |
| CO6_HUMAN | ALNHLPLEYNSALYSR_621.0_538.3 | (SEQ ID NO: 72) | 0.034865341 |
| AFAM_HUMAN | LPNNVLQEK_527.8_844.5 | (SEQ ID NO: 814) | 0.039880594 |
| PEDF_HUMAN | TVQAVLTVPK_528.3_428.3 | (SEQ ID NO: 826) | 0.040854402 |
| PLMN_HUMAN | EAQLPVIENK_570.8_329.2 | (SEQ ID NO: 22) | 0.041023812 |
| LBP_HUMAN | ITLPDFTGDLR_624.3_920.5 | (SEQ ID NO: 3) | 0.042276813 |
| CO8G_HUMAN | VQEAHLTEDQIFYFPK_655.7_701.4 | (SEQ ID NO: 31) | 0.042353851 |
| PLMN_HUMAN | YEFLNGR_449.7_606.3 | (SEQ ID NO: 34) | 0.04416504 |
| B2MG_HUMAN | VNHVTLSQPK_374.9_459.3 | (SEQ ID NO: 834) | 0.045458409 |
| CFAB_HUMAN | DISEVVTPR_508.3_472.3 | (SEQ ID NO: 67) | 0.046493405 |
| INHBE_HUMAN | ALVLELAK_428.8_331.2 | (SEQ ID NO: 9) | 0.04789353 |

TABLE 62

Random Forest Importance Values Using Adjusted Peak Areas

| Transition | Peptide disclosed in adjacent column | Rank | Importance |
|---|---|---|---|
| INHBE_ALVLELAK_428.8_672.4 | (SEQ ID NO: 9) | 1 | 2964.951571 |
| EGLN_TQILEWAAER_608.8_761.4 | (SEQ ID NO: 10) | 2 | 1218.3406 |
| FA7_SEPRPGVLLR_375.2_654.4 | (SEQ ID NO: 12) | 3 | 998.92897 |
| CBG_ITQDAQLK_458.8_702.4 | (SEQ ID NO: 13) | 4 | 930.9931102 |
| ITIH3_ALDLSLK_380.2_185.1 | (SEQ ID NO: 14) | 5 | 869.6315408 |

TABLE 62-continued

| Random Forest Importance Values Using Adjusted Peak Areas | | | |
| --- | --- | --- | --- |
| Transition | Peptide disclosed in adjacent column | Rank | Importance |
| ENPP2_WWGGQPLWITATK_772.4_929.5 | (SEQ ID NO: 15) | 6 | 768.9182114 |
| CBG_ITQDAQLK_458.8_803.4 | (SEQ ID NO: 13) | 7 | 767.8940452 |
| PSG1_LSETNR_360.2_519.3 | (SEQ ID NO: 16) | 8 | 714.6160065 |
| CAA60698_LEPLYSASGPGLRPLVIK_637.4_834.5 | (SEQ ID NO: 933) | 9 | 713.4086612 |
| INHBC_LDFHFSSDR_375.2_611.3 | (SEQ ID NO: 838) | 11 | 681.2442909 |
| CBG_QINSYVK_426.2_610.3 | (SEQ ID NO: 917) | 12 | 674.3363415 |
| LBP_GLQYAAQEGLLALQSELLR_1037.1_858.5 | (SEQ ID NO: 818) | 13 | 603.197751 |
| A1BG_LLELTGPK_435.8_644.4 | (SEQ ID NO: 6) | 14 | 600.9902818 |
| CO6_DLHLSDVFLK_396.2_366.2 | (SEQ ID NO: 856) | 15 | 598.8214342 |
| VCAM1_TQIDSPLSGK_523.3_816.5 | (SEQ ID NO: 1027) | 16 | 597.4038769 |
| LRP1_NAVVQGLEQPHGLVVHPLR_688.4_285.2 | (SEQ ID NO: 997) | 17 | 532.0500081 |
| CBG_QINSYVK_426.2_496.3 | (SEQ ID NO: 917) | 18 | 516.5575201 |
| CO6_ENPAVIDFELAPIVDLVR_670.7_811.5 | (SEQ ID NO: 893) | 19 | 501.4669261 |
| ADA12_FGFGGSTDSGPIR_649.3_745.4 | (SEQ ID NO: 5) | 20 | 473.5510333 |
| CO6_DLHLSDVFLK_396.2_260.2 | (SEQ ID NO: 856) | 21 | 470.5473702 |
| ENPP2_TYLHTYESEI_628.3_908.4 | (SEQ ID NO: 100) | 22 | 444.7580726 |
| A1BG_LLELTGPK_435.8_227.2 | (SEQ ID NO: 6) | 23 | 444.696292 |
| FRIH_QNYHQDSEAAINR_515.9_544.3 | (SEQ ID NO: 897) | 24 | 439.2648872 |
| ENPP2_TEFLSNYLTNVDDITLVPGTLGR_846.8_600.3 | (SEQ ID NO: 824) | 25 | 389.3769604 |
| CBG_WSAGLTSSQVDLYIPK_883.0_515.3 | (SEQ ID NO: 916) | 26 | 374.0749768 |
| C1QC_FQSVFTVTR_542.8_623.4 | (SEQ ID NO: 862) | 27 | 370.6957977 |
| GELS_DPDQTDGLGLSYLSSHIANVER_796.4_456.2 | (SEQ ID NO: 57) | 28 | 353.1176588 |
| A1BG_ATWSGAVLAGR_544.8_643.4 | (SEQ ID NO: 1028) | 29 | 337.4580124 |
| APOA1_AKPALEDLR_506.8_813.5 | (SEQ ID NO: 1014) | 30 | 333.5742035 |
| ENPP2_TYLHTYESEI_628.3_515.3 | (SEQ ID NO: 100) | 31 | 322.6339162 |
| PEPD_AVYEAVLR_460.8_750.4 | (SEQ ID NO: 78) | 32 | 321.4377907 |
| TIMP1_GFQALGDAADIR_617.3_717.4 | (SEQ ID NO: 918) | 33 | 310.0997949 |
| ADA12_LIEIANHVDK_384.6_498.3 | (SEQ ID NO: 955) | 34 | 305.8803542 |
| PGRP2_WGAAPYR_410.7_577.3 | (SEQ ID NO: 1012) | 35 | 303.5539874 |
| PSG9_LFIPQITR_494.3_614.4 | (SEQ ID NO: 996) | 36 | 300.7877317 |
| HABP2_FLNWIK_410.7_560.3 | (SEQ ID NO: 4) | 37 | 298.3363186 |
| CBG_WSAGLTSSQVDLYIPK_883.0_357.2 | (SEQ ID NO: 916) | 38 | 297.2474385 |
| PSG2_IHPSYTNYR_384.2_452.2 | (SEQ ID NO: 775) | 39 | 292.6203405 |
| PSG5_LSIPQITTK_500.8_800.5 | (SEQ ID NO: 987) | 40 | 290.2023364 |
| HABP2_FLNWIK_410.7_561.3 | (SEQ ID NO: 4) | 41 | 289.5092933 |
| CO6_SEYGAALAWEK_612.8_788.4 | (SEQ ID NO: 1051) | 42 | 287.7634114 |

TABLE 62-continued

Random Forest Importance Values Using Adjusted Peak Areas

| Transition | Peptide disclosed in adjacent column | Rank | Importance |
|---|---|---|---|
| ADA12_LIEIANHVDK_384.6_683.4 | (SEQ ID NO: 955) | 43 | 286.5047372 |
| EGLN_TQILEWAAER_608.8_632.3 | (SEQ ID NO: 10) | 44 | 284.5138846 |
| CO6_ENPAVIDFELAPIVDLVR_670.7_601.4 | (SEQ ID NO: 893) | 45 | 273.5146272 |
| FA7_FSLVSGWGQLLDR_493.3_447.3 | (SEQ ID NO: 878) | 46 | 271.7850098 |
| ITIH3_ALDLSLK_380.2_575.3 | (SEQ ID NO: 14) | 47 | 269.9425709 |
| ADA12_FGFGGSTDSGPIR_649.3_946.5 | (SEQ ID NO: 5) | 48 | 264.5698225 |
| FETUA_AALAAFNAQNNGSNFQLEEISR_789.1_746.4 | (SEQ ID NO: 891) | 49 | 247.4728828 |
| FBLN1_AITPPHPASQANIIFDITEGNLR_825.8_459.3 | (SEQ ID NO: 76) | 50 | 246.572102 |
| TSP1_FVFGTTPEDILR_697.9_843.5 | (SEQ ID NO: 1002) | 51 | 245.0459575 |
| VCAM1_NTVISVNPSTK_580.3_732.4 | (SEQ ID NO: 984) | 52 | 240.576729 |
| ENPP2_TEFLSNYLTNVDDITLVPGTLGR_846.8_699.4 | (SEQ ID NO: 824) | 53 | 240.1949512 |
| FBLN3_ELPQSIVYK_538.8_409.2 | (SEQ ID NO: 820) | 55 | 233.6825304 |
| ACTB_VAPEEHPVLLTEAPLNPK_652.0_892.5 | (SEQ ID NO: 1029) | 56 | 226.9772749 |
| TSP1_FVFGTTPEDILR_697.9_742.4 | (SEQ ID NO: 1002) | 57 | 224.4627393 |
| PLMN_EAQLPVIENK_570.8_699.4 | (SEQ ID NO: 22) | 58 | 221.4663735 |
| C1S_IIGGSDADIK_494.8_260.2 | (SEQ ID NO: 39) | 59 | 218.069476 |
| IL1A_ANDQYLTAAALHNLDEAVK_686.4_317.2 | (SEQ ID NO: 861) | 60 | 216.5531949 |
| PGRP2_WGAAPYR_410.7_634.3 | (SEQ ID NO: 1012) | 61 | 211.0918302 |
| PSG5_LSIPQITTK_500.8_687.4 | (SEQ ID NO: 987) | 62 | 208.7871461 |
| PSG6_SNPVTLNVLYGPDLPR_585.7_654.4 | (SEQ ID NO: 782) | 63 | 207.9294937 |
| PRG2_WNFAYWAAHQPWSR_607.3_545.3 | (SEQ ID NO: 1050) | 64 | 202.9494031 |
| CXCL2_CQCLQTLQGIHLK_13p8RT_533.6_567.4 | (SEQ ID NO: 1030) | 65 | 202.9051326 |
| CXCL2_CQCLQTLQGIHLK_13p48RT_533.6_695.4 | (SEQ ID NO: 1030) | 66 | 202.6561548 |
| G6PE_LLDFEFSSGR_585.8_553.3 | (SEQ ID NO: 1031) | 67 | 201.004611 |
| GELS_TASDFITK_441.7_710.4 | (SEQ ID NO: 37) | 68 | 200.2704809 |
| B2MG_VEHSDLSFSK_383.5_468.2 | (SEQ ID NO: 7) | 69 | 199.880987 |
| CO8B_IPGIFELGISSQSDR_809.9_849.4 | (SEQ ID NO: 103) | 70 | 198.7563875 |
| PSG8_LQLSETNR_480.8_606.3 | (SEQ ID NO: 785) | 71 | 197.6739966 |
| LBP_GLQYAAQEGLLALQSELLR_1037.1_929.5 | (SEQ ID NO: 818) | 72 | 197.4094851 |
| AFAM_LPNNVLQEK_527.8_844.5 | (SEQ ID NO: 814) | 73 | 196.8123228 |
| MAGE | | 74 | 196.2410502 |
| PSG2_IHPSYTNYR_384.2_338.2 | (SEQ ID NO: 775) | 75 | 196.2410458 |
| PSG9_LFIPQITR_494.3_727.4 | (SEQ ID NO: 996) | 76 | 193.5329266 |
| TFR1_YNSQLLSFVR_613.8_734.5 | (SEQ ID NO: 860) | 77 | 193.2711994 |
| C1R_QRPPDLDTSSNAVDLLFFTDESGDSR_961.5_866.3 | (SEQ ID NO: 930) | 78 | 193.0625419 |
| PGH1_ILPSVPK_377.2_264.2 | (SEQ ID NO: 867) | 79 | 190.0504508 |

TABLE 62-continued

Random Forest Importance Values Using Adjusted Peak Areas

| Transition | Peptide disclosed in adjacent column | Rank | Importance |
|---|---|---|---|
| FA7_SEPRPGVLLR_375.2_454.3 | (SEQ ID NO: 12) | 80 | 188.2718422 |
| FA7_TLAFVR_353.7_274.2 | (SEQ ID NO: 1055) | 81 | 187.6895294 |
| PGRP2_DGSPDVTTADIGANTPDATK_973.5_844.4 | (SEQ ID NO: 44) | 82 | 185.6017519 |
| C1S_IIGGSDADIK_494.8_762.4 | (SEQ ID NO: 39) | 83 | 184.5985543 |
| PEPD_VPLALFALNR_557.3_620.4 | (SEQ ID NO: 943) | 84 | 184.3962957 |
| C1S_EDTPNSVWEPAK_686.8_630.3 | (SEQ ID NO: 41) | 85 | 179.2043504 |
| CHL1_TAVTANLDIR_537.3_802.4 | (SEQ ID NO: 915) | 86 | 174.9866792 |
| CHL1_VIAVNEVGR_478.8_744.4 | (SEQ ID NO: 999) | 88 | 172.2053147 |
| SDF1_ILNTPNCALQIVAR_791.9_341.2 | (SEQ ID NO: 1032) | 89 | 171.4604557 |
| PAI1_EVPLSALTNILSAQLISHWK_740.8_996.6 | (SEQ ID NO: 890) | 90 | 169.5635635 |
| AMBP_AFIQLWAFDAVK_704.9_650.4 | (SEQ ID NO: 52) | 91 | 169.2124477 |
| G6PE_LLDFEFSSGR_585.8_944.4 | (SEQ ID NO: 1031) | 92 | 168.2398598 |
| THBG_SILFLGK_389.2_577.4 | (SEQ ID NO: 881) | 93 | 166.3110206 |
| PRDX2_GLFIIDGK_431.8_545.3 | (SEQ ID NO: 1033) | 94 | 164.3125132 |
| ENPP2_WWGGQPLWITATK_772.4_373.2 | (SEQ ID NO: 15) | 95 | 163.4011689 |
| VGFR3_SGVDLADSNQK_567.3_662.3 | (SEQ ID NO: 853) | 96 | 162.8822352 |
| C1S_EDTPNSVWEPAK_686.8_315.2 | (SEQ ID NO: 41) | 97 | 161.6140915 |
| AFAM_DADPDTFFAK_563.8_302.1 | (SEQ ID NO: 833) | 98 | 159.5917449 |
| CBG_SETEIHQGFQHLHQLFAK_717.4_447.2 | (SEQ ID NO: 958) | 99 | 156.1357404 |
| C1S_LLEVPEGR_456.8_686.4 | (SEQ ID NO: 1053) | 100 | 155.1763293 |
| PTGDS_GPGEDFR_389.2_623.3 | (SEQ ID NO: 873) | 101 | 154.9205208 |
| ITIH2_IYLQPGR_423.7_329.2 | (SEQ ID NO: 969) | 102 | 154.6552717 |
| FA7_TLAFVR_353.7_492.3 | (SEQ ID NO: 1055) | 103 | 152.5009422 |
| FA7_FSLVSGWGQLLDR_493.3_403.2 | (SEQ ID NO: 878) | 104 | 151.9971204 |
| SAMP_VGEYSLYIGR_578.8_871.5 | (SEQ ID NO: 58) | 105 | 151.4738449 |
| APOH_EHSSLAFWK_552.8_267.1 | (SEQ ID NO: 1034) | 106 | 151.0052645 |
| PGRP2_AGLLRPDYALLGHR_518.0_595.4 | (SEQ ID NO: 95) | 107 | 150.4149907 |
| C1QC_FNAVLTNPQGDYDTSTGK_964.5_333.2 | (SEQ ID NO: 70) | 108 | 149.2592827 |
| PGRP2_AGLLRPDYALLGHR_518.0_369.2 | (SEQ ID NO: 95) | 109 | 147.3609354 |
| PGRP2_TFTLLDPK_467.8_686.4 | (SEQ ID NO: 1035) | 111 | 145.2145223 |
| CO5_TDAPDLPEENQAR_728.3_843.4 | (SEQ ID NO: 17) | 112 | 144.5213118 |
| THRB_ELLESYIDGR_597.8_839.4 | (SEQ ID NO: 2) | 113 | 143.924639 |
| GELS_DPDQTDGLGLSYLSSHIANVER_796.4_328.1 | (SEQ ID NO: 57) | 114 | 142.8936101 |
| TRFL_YYGYTGAFR_549.3_450.3 | (SEQ ID NO: 843) | 115 | 142.8651352 |
| HEMO_QGHNSVFLIK_381.6_260.2 | (SEQ ID NO: 830) | 116 | 142.703845 |
| C1S_GDSGGAFAVQDPNDK_739.3_716.3 | (SEQ ID NO: 1020) | 117 | 142.2799122 |

TABLE 62-continued

| Transition | Peptide disclosed in adjacent column | Rank | Importance |
|---|---|---|---|
| B1A4H9_AHQLAIDTYQEFR_531.3_450.3 | (SEQ ID NO: 1036) | 118 | 138.196407 |
| C1S_SSNNPHSPIVEEFQVPYNK_729.4_261.2 | (SEQ ID NO: 954) | 119 | 136.7868935 |
| HYOU1_LPATEKPVLLSK_432.6_347.2 | (SEQ ID NO: 868) | 120 | 136.1146437 |
| FETA_GYQELLEK_490.3_502.3 | (SEQ ID NO: 956) | 121 | 135.2890322 |
| LRP1_SERPPIFEIR_415.2_288.2 | (SEQ ID NO: 978) | 122 | 134.6569527 |
| CO6_SEYGAALAWEK_612.8_845.5 | (SEQ ID NO: 1051) | 124 | 132.8634704 |
| CERU_TTIEKPVWLGFLGPIIK_638.0_844.5 | (SEQ ID NO: 1026) | 125 | 132.1047746 |
| IBP1_AQETSGEEISK_589.8_850.4 | (SEQ ID NO: 1037) | 126 | 130.934446 |
| SHBG_VVLSSGSGPGLDLPLVLGLPLQLK_791.5_768.5 | (SEQ ID NO: 946) | 127 | 128.2052287 |
| CBG_SETEIHQGFQHLHQLFAK_717.4_318.1 | (SEQ ID NO: 958) | 128 | 127.9873837 |
| A1AT_LSITGTYDLK_555.8_696.4 | (SEQ ID NO: 1038) | 129 | 127.658818 |
| PGRP2_DGSPDVTTADIGANTPDATK_973.5_531.3 | (SEQ ID NO: 44) | 130 | 126.5775806 |
| C1QB_LEQGENVFLQATDK_796.4_675.4 | (SEQ ID NO: 19) | 131 | 126.1762726 |
| EGLN_GPITSAAELNDPQSILLR_632.4_826.5 | (SEQ ID NO: 941) | 132 | 125.7658253 |
| IL12B_YENYTSSFFIR_713.8_293.1 | (SEQ ID NO: 916) | 133 | 125.0476631 |
| B2MG_VEHSDLSFSK_383.5_234.1 | (SEQ ID NO: 7) | 134 | 124.9154706 |
| PGH1_AEHPTWGDEQLFQTTR_639.3_765.4 | (SEQ ID NO: 926) | 135 | 124.8913193 |
| INHBE_ALVLELAK_428.8_331.2 | (SEQ ID NO: 9) | 136 | 124.0109276 |
| HYOU1_LPATEKPVLLSK_432.6_460.3 | (SEQ ID NO: 868) | 137 | 123.1900369 |
| CXCL2_CQCLQTLQGIHLK_13p48RT_533.6_567.4 | (SEQ ID NO: 1030) | 138 | 122.8800873 |
| PZP_AVGYLITGYQR_620.8_523.3 | (SEQ ID NO: 69) | 139 | 122.4733204 |
| AFAM_IAPQLSTEELVSLGEK_857.5_333.2 | (SEQ ID NO: 832) | 140 | 122.4707849 |
| ICAM1_VELAPLPSWQPVGK_760.9_400.3 | (SEQ ID NO: 872) | 141 | 121.5494206 |
| CHL1_VIAVNEVGR_478.8_284.2 | (SEQ ID NO: 999) | 142 | 119.0877137 |
| APOB_ITENDIQIALDDAK_779.9_632.3 | (SEQ ID NO: 55) | 143 | 118.0222045 |
| SAMP_AYSDLSR_406.2_577.3 | (SEQ ID NO: 90) | 144 | 116.409429 |
| AMBP_AFIQLWAFDAVK_704.9_836.4 | (SEQ ID NO: 52) | 145 | 116.1900846 |
| EGLN_GPITSAAELNDPQSILLR_632.4_601.4 | (SEQ ID NO: 941) | 146 | 115.8438804 |
| LRP1_NAVVQGLEQPHGLVVHPLR_688.4_890.6 | (SEQ ID NO: 997) | 147 | 114.539707 |
| SHBG_VVLSSGSGPGLDLPLVLGLPLQLK_791.5_598.4 | (SEQ ID NO: 946) | 148 | 113.1931134 |
| IBP1_AQETSGEEISK_589.8_979.5 | (SEQ ID NO: 1037) | 149 | 112.9902709 |
| PSG6_SNPVTLNVLYGPDLPR_585.7_817.4 | (SEQ ID NO: 782) | 150 | 112.7910917 |
| APOC3_DYWSTVK_449.7_347.2 | (SEQ ID NO: 885) | 151 | 112.544736 |
| C1R_WILTAAHTLYPK_471.9_621.4 | (SEQ ID NO: 886) | 152 | 112.2199708 |
| ANGT_ADSQAQLLLSTVVGVFTAPGLHLK_822.5_983.6 | (SEQ ID NO: 86) | 153 | 111.9634671 |
| PSG9_DVLLLVHNLPQNLPGYFWYK_810.4_328.2 | (SEQ ID NO: 11) | 154 | 111.5743214 |

TABLE 62-continued

| Random Forest Importance Values Using Adjusted Peak Areas | | | |
|---|---|---|---|
| Transition | Peptide disclosed in adjacent column | Rank | Importance |
| A1AT_AVLTIDEK_444.8_605.3 | (SEQ ID NO: 46) | 155 | 111.216651 |
| PSGx_ILILPSVTR_506.3_785.5 | (SEQ ID NO: 789) | 156 | 110.8482935 |
| THRB_ELLESYIDGR_597.8_710.4 | (SEQ ID NO: 2) | 157 | 110.7496103 |
| SHBG_ALALPPLGLAPLLNLWAKPQGR_770.5_256.2 | (SEQ ID NO: 947) | 158 | 110.5091269 |
| PZP_QTLSWTVTPK_580.8_545.3 | (SEQ ID NO: 981) | 159 | 110.4675104 |
| SHBG_ALALPPLGLAPLLNLWAKPQGR_770.5_457.3 | (SEQ ID NO: 947) | 160 | 110.089808 |
| PSG4_TLFIFGVTK_513.3_811.5 | (SEQ ID NO: 842) | 161 | 109.9039967 |
| PLMN_YEFLNGR_449.7_293.1 | (SEQ ID NO: 34) | 162 | 109.6880397 |
| PEPD_AVYEAVLR_460.8_587.4 | (SEQ ID NO: 78) | 163 | 109.3697285 |
| PLMN_LSSPAVITDK_515.8_830.5 | (SEQ ID NO: 26) | 164 | 108.963353 |
| FINC_SYTITGLQPGTDYK_772.4_352.2 | (SEQ ID NO: 966) | 165 | 108.452612 |
| C1R_WILTAAHTLYPK_471.9_407.2 | (SEQ ID NO: 886) | 166 | 107.8348417 |
| CHL1_TAVTANLDIR_537.3_288.2 | (SEQ ID NO: 915) | 167 | 107.7278897 |
| TENA_AVDIPGLEAATPYR_736.9_286.1 | (SEQ ID NO: 942) | 168 | 107.6166195 |
| CRP_YEVQGEVFTKPQLWP_911.0_293.1 | (SEQ ID NO: 27) | 169 | 106.9739589 |
| APOB_SVSLPSLDPASAK_636.4_885.5 | (SEQ ID NO: 946) | 170 | 106.5901668 |
| PRDX2_SVDEALR_395.2_488.3 | (SEQ ID NO: 1001) | 171 | 106.2325046 |
| CO8A_YHFEALADTGISSEFYDNANDLLSK_940.8_301.1 | (SEQ ID NO: 1057) | 172 | 105.8963287 |
| C1QC_FQSVFTVTR_542.8_722.4 | (SEQ ID NO: 862) | 173 | 105.4338742 |
| PSGx_ILILPSVTR_506.3_559.3 | (SEQ ID NO: 789) | 174 | 105.1942655 |
| VCAM1_TQIDSPLSGK_523.3_703.4 | (SEQ ID NO: 1027) | 175 | 105.0091767 |
| VCAM1_NTVISVNPSTK_580.3_845.5 | (SEQ ID NO: 984) | 176 | 104.8754444 |
| CSH_ISLLLIESWLEPVR_834.5_500.3 | (SEQ ID NO: 32) | 177 | 104.6158295 |
| HGFA_EALVPLVADHK_397.9_439.8 | (SEQ ID NO: 1039) | 178 | 104.3383142 |
| CGB1_CRPINATLAVEK_457.9_660.4 | (SEQ ID NO: 1040) | 179 | 104.3378072 |
| APOB_IEGNLIFDPNNYLPK_874.0_414.2 | (SEQ ID NO: 8) | 180 | 103.9849346 |
| C1QB_LEQGENVFLQATDK_796.4_822.4 | (SEQ ID NO: 19) | 181 | 103.9153207 |
| APOH_EHSSLAFWK_552.8_838.4 | (SEQ ID NO: 1034) | 182 | 103.9052103 |
| CO5_LQGTLPVEAR_542.3_842.5 | (SEQ ID NO: 28) | 183 | 103.1061869 |
| SHBG_IALGGLLFPASNLR_481.3_412.3 | (SEQ ID NO: 975) | 184 | 102.2490294 |
| B2MG_VNHVTLSQPK_374.9_459.3 | (SEQ ID NO: 934) | 185 | 102.1204362 |
| APOA2_SPELQAEAK_486.8_659.4 | (SEQ ID NO: 99) | 186 | 101.9166647 |
| FLNA_TGVAVNKPAEFTVDAK_549.6_258.1 | (SEQ ID NO: 822) | 187 | 101.5207852 |
| PLMN_YEFLNGR_449.7_606.3 | (SEQ ID NO: 34) | 188 | 101.2531011 |

TABLE 63

| Variable | Peptide disclosed in adjacemt column | Rank | Importance |
|---|---|---|---|
| Random Forest Importance Values Using Peak Area Ratios | | | |
| HABP2_FLNWIK_410.7_561.3 | (SEQ ID NO: 4) | 1 | 3501.905733 |
| ADA12_FGFGGSTDSGPIR_649.3_946.5 | (SEQ ID NO: 5) | 2 | 3136.589992 |
| A1BG_LLELTGPK_435.8_227.2 | (SEQ ID NO: 6) | 3 | 2387.891934 |
| B2MG_VEHSDLSFSK_383.5_234.1 | (SEQ ID NO: 7) | 4 | 1431.31771 |
| ADA12_FGFGGSTDSGPIR_649.3_745.4 | (SEQ ID NO: 5) | 5 | 1400.917331 |
| B2MG_VEHSDLSFSK_383.5_468.2 | (SEQ ID NO: 7) | 6 | 1374.453629 |
| APOB_IEGNLIFDPNNYLPK_874.0_414.2 | (SEQ ID NO: 8) | 7 | 1357.812445 |
| PSG9_DVLLLVHNLPQNLPGYFWYK_810.4_960.5 | (SEQ ID NO: 11) | 8 | 1291.934596 |
| A1BG_LLELTGPK_435.8_644.4 | (SEQ ID NO: 6) | 9 | 1138.712941 |
| ITIH3_ALDLSLK_380.2_185.1 | (SEQ ID NO: 14) | 10 | 1137.127027 |
| ENPP2_TYLHTYESEI_628.3_908.4 | (SEQ ID NO: 100) | 11 | 1041.036693 |
| IL12B_YENYTSSFFIR_713.8_293.1 | (SEQ ID NO: 816) | 12 | 970.1662913 |
| ENPP2_WWGGQPLWITATK_772.4_373.2 | (SEQ ID NO: 15) | 13 | 953.0631062 |
| ENPP2_TYLHTYESEI_628.3_515.3 | (SEQ ID NO: 100) | 14 | 927.3512901 |
| PSG9_LFIPQITR_494.3_614.4 | (SEQ ID NO: 996) | 15 | 813.9965357 |
| MAGE | | 16 | 742.2425022 |
| ENPP2_WWGGQPLWITATK_772.4_929.5 | (SEQ ID NO: 15) | 17 | 731.5206413 |
| CERU_TTIEKPVWLGFLGPIIK_638.0_640.4 | (SEQ ID NO: 1026) | 18 | 724.7745695 |
| ITIH3_ALDLSLK_380.2_575.3 | (SEQ ID NO: 14) | 19 | 710.1982467 |
| PSG2_IHPSYTNYR_384.2_452.2 | (SEQ ID NO: 775) | 20 | 697.4750893 |
| ITIH1_LWAYLTIQELLAK_781.5_371.2 | (SEQ ID NO: 1052) | 21 | 644.7416886 |
| INHBE_ALVLELAK_428.8_331.2 | (SEQ ID NO: 9) | 22 | 643.008853 |
| HGFA_LHKPGVYTR_357.5_692.4 | (SEQ ID NO: 1025) | 23 | 630.8698445 |
| TRFL_YYGYTGAFR_549.3_450.3 | (SEQ ID NO: 843) | 24 | 609.5866675 |
| THBG_AVLHIGEK_289.5_348.7 | (SEQ ID NO: 817) | 25 | 573.9320948 |
| GELS_TASDFITK_441.7_710.4 | (SEQ ID NO: 37) | 26 | 564.3288862 |
| PSG9_LFIPQITR_494.3_727.4 | (SEQ ID NO: 996) | 27 | 564.1749327 |
| VGFR3_SGVDLADSNQK_567.3_662.3 | (SEQ ID NO: 853) | 28 | 563.8087791 |
| INHA_TTSDGGYSFK_531.7_860.4 | (SEQ ID NO: 815) | 29 | 554.210214 |
| PSG9_DVLLLVHNLPQNLPGYFWYK_810.4_328.2 | (SEQ ID NO: 11) | 30 | 545.1743627 |
| HYOU1_LPATEKPVLLSK_432.6_347.2 | (SEQ ID NO: 868) | 31 | 541.6208032 |
| CO8G_VQEAHLTEDQIFYFPK_655.7_701.4 | (SEQ ID NO: 31) | 32 | 541.3193428 |
| BMI | | 33 | 540.5028818 |
| HGFA_LHKPGVYTR_357.5_479.3 | (SEQ ID NO: 1025) | 34 | 536.6051948 |
| PSG2_IHPSYTNYR_384.2_338.2 | (SEQ ID NO: 775) | 35 | 536.5363489 |
| GELS_AQPVQVAEGSEPDGFWEAL-GGK_758.0_623.4 | (SEQ ID NO: 837) | 36 | 536.524931 |

TABLE 63-continued

| | Peptide disclosed in adjacemt column | Rank | Importance |
|---|---|---|---|
| Variable | | | |
| PSG6_SNPVTLNVLYGPDLPR_585.7_654.4 | (SEQ ID NO: 782) | 37 | 520.108646 |
| HABP2_FLNWIK_410.7_560.3 | (SEQ ID NO: 4) | 38 | 509.0707814 |
| PGH1_ILPSVPK_377.2_527.3 | (SEQ ID NO: 867) | 39 | 503.593718 |
| HYOU1_LPATEKPVLLSK_432.6_460.3 | (SEQ ID NO: 868) | 40 | 484.047422 |
| CO6_ALNHLPLEYNSALYSR_621.0_696.4 | (SEQ ID NO: 72) | 41 | 477.8773179 |
| INHBE_ALVLELAK_428.8_672.4 | (SEQ ID NO: 9) | 42 | 459.1998276 |
| PLMN_LSSPAVITDK_515.8_743.4 | (SEQ ID NO: 26) | 43 | 452.9466414 |
| PSG9_DVLLLVHNLPQNLPGYFWYK_810.4_215.1 | (SEQ ID NO: 11) | 44 | 431.8528248 |
| BGH3_LTLLAPLNSVFK_658.4_875.5 | (SEQ ID NO: 1041) | 45 | 424.2540315 |
| AFAM_LPNNVLQEK_527.8_730.4 | (SEQ ID NO: 814) | 46 | 421.4953221 |
| ITIH2_LSNENHGIAQR_413.5_519.8 | (SEQ ID NO: 1024) | 47 | 413.1231437 |
| GELS_TASDFITK_441.7_781.4 | (SEQ ID NO: 37) | 48 | 404.2679723 |
| FETUA_AHYDLR_387.7_566.3 | (SEQ ID NO: 88) | 49 | 400.4711207 |
| CERU_TTIEKPVWLGFLGPIIK_638.0_844.5 | (SEQ ID NO: 1026) | 50 | 396.2873451 |
| PSGx_ILILPSVTR_506.3_785.5 | (SEQ ID NO: 789) | 51 | 374.5672526 |
| APOB_SVSLPSLDPASAK_636.4_885.5 | (SEQ ID NO: 846) | 52 | 371.1416438 |
| FLNA_TGVAVNKPAEFTVDAK_549.6_258.1 | (SEQ ID NO: 822) | 53 | 370.4175588 |
| PLMN_YEFLNGR_449.7_606.3 | (SEQ ID NO: 34) | 54 | 367.2768078 |
| PSGx_ILILPSVTR_506.3_559.3 | (SEQ ID NO: 789) | 55 | 365.7704321 |

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of determining probability for preterm birth in a pregnant female, the method comprising detecting a level of disintegrin and metalloproteinase domain-containing protein 12 (ADA12) in a biological sample obtained from said pregnant female, analyzing said level to determine the probability for preterm birth in said pregnant female, calculating a risk score for ADA12 using gestational age matched controls as a reference, and administering to said pregnant female, where said risk score is different relative to that of the gestational age matched controls, a treatment regimen comprising a progesterone treatment, cervical cerclage, serial cervical length measurements, or an antenatal corticosteroid, wherein said detecting comprises: (i) subjecting said biological sample to mass spectrometry (MS) quantification; or (ii) binding an antibody specific for ADA binding an antibody to ADA12 or a fragment thereof comprising an amino acid sequence selected from FGFGGSTDSGPIR (SEQ ID NO: 5) and LIE-IANHVDK (SEQ ID NO: 955), wherein the antibody is specific for ADA12, in or from said biological sample, wherein the biological sample is selected from whole blood, plasma, and serum, and wherein the pregnant female is between 17 and 28 weeks of gestation at the time the biological sample is collected.

2. The method of claim 1, further comprising an initial step of providing a biomarker panel comprising ADA12, wherein said biomarker panel is utilized to detect the level of ADA12.

3. The method of claim 1, further comprising an initial step of providing the biological sample from the pregnant female.

4. A method of predicting gestational age at birth (GAB), the method comprising detecting a level of disintegrin and metalloproteinase domain-containing protein 12 (ADA12) in a biological sample obtained from a pregnant female, analyzing said level to predict GAB, calculating a risk score for ADA12 using gestational age matched controls as a reference, wherein the calculated risk score for ADA12 corresponds to a probability of GAB being (i) less than 37 weeks, (ii) 37 to 39 weeks, or (iii) 40 weeks or greater, and administering a prenatal intervention to the pregnant female when the GAB is predicted to be less than 37 weeks, wherein said detecting comprises: (i) subjecting said biological sample to mass spectrometry (MS) quantification; or (ii) binding an antibody to ADA12 or a fragment thereof comprising an amino acid sequence selected from FGFGGSTDSGPIR (SEQ ID NO: 5) and LIEIANHVDK (SEQ ID NO: 955), wherein the antibody is specific for ADA12, in or from said biological sample, wherein the biological sample is selected from whole blood, plasma, and serum, wherein the pregnant female is between 17 and 28 weeks of gestation at the time the biological sample is collected, and wherein the prenatal intervention comprises a progesterone treatment, cervical cerclage, serial cervical length measurements, or administration of an antenatal corticosteroid.

5. The method of claim 4, further comprising an initial step of providing the biological sample from the pregnant female.

6. The method of any one of claims 1 and 4, wherein the biological sample is a dry sample.

7. The method of any one of claims 1 and 4, wherein said binding of step (ii) utilizes an assay that is selected from the group consisting of enzyme immunoassay (EIA), enzyme-linked immunosorbent assay (ELISA), and radioimmunoassay (RIA).

8. The method of any one of claims 1 and 4, wherein said MS comprises affinity-capture MS (AC-MS), co-immunoprecipitation-mass spectrometry (co-IP MS), liquid chromatography-mass spectrometry (LC-MS), multiple reaction monitoring (MRM) or selected reaction monitoring (SRM).

*   *   *   *   *

SEQUENCE LISTING

<160> NUMBER OF SEQ ID NOS: 1687

<210> SEQ ID NO 1
<211> LENGTH: 13
<212> TYPE: PRT
<213> ORGANISM: Homo sapiens

<400> SEQUENCE: 1

Ala Phe Thr Glu Cys Cys Val Val Ala Ser Gln Leu Arg
1               5                   10

<210> SEQ ID NO 2
<211> LENGTH: 10
<212> TYPE: PRT

```
<213> ORGANISM: Homo sapiens

<400> SEQUENCE: 2

Glu Leu Leu Glu Ser Tyr Ile Asp Gly Arg
1               5                   10

<210> SEQ ID NO 3
<211> LENGTH: 11
<212> TYPE: PRT
<213> ORGANISM: Homo sapiens

<400> SEQUENCE: 3

Ile Thr Leu Pro Asp Phe Thr Gly Asp Leu Arg
1               5                   10

<210> SEQ ID NO 4
<211> LENGTH: 6
<212> TYPE: PRT
<213> ORGANISM: Homo sapiens

<400> SEQUENCE: 4

Phe Leu Asn Trp Ile Lys
1               5

<210> SEQ ID NO 5
<211> LENGTH: 13
<212> TYPE: PRT
<213> ORGANISM: Homo sapiens

<400> SEQUENCE: 5

Phe Gly Phe Gly Gly Ser Thr Asp Ser Gly Pro Ile Arg
1               5                   10

<210> SEQ ID NO 6
<211> LENGTH: 8
<212> TYPE: PRT
<213> ORGANISM: Homo sapiens

<400> SEQUENCE: 6

Leu Leu Glu Leu Thr Gly Pro Lys
1               5

<210> SEQ ID NO 7
<211> LENGTH: 10
<212> TYPE: PRT
<213> ORGANISM: Homo sapiens

<400> SEQUENCE: 7

Val Glu His Ser Asp Leu Ser Phe Ser Lys
1               5                   10

<210> SEQ ID NO 8
<211> LENGTH: 15
<212> TYPE: PRT
<213> ORGANISM: Homo sapiens

<400> SEQUENCE: 8

Ile Glu Gly Asn Leu Ile Phe Asp Pro Asn Asn Tyr Leu Pro Lys
1               5                   10                  15

<210> SEQ ID NO 9
<211> LENGTH: 8
<212> TYPE: PRT
<213> ORGANISM: Homo sapiens
```

```
<400> SEQUENCE: 9

Ala Leu Val Leu Glu Leu Ala Lys
1               5

<210> SEQ ID NO 10
<211> LENGTH: 10
<212> TYPE: PRT
<213> ORGANISM: Homo sapiens

<400> SEQUENCE: 10

Thr Gln Ile Leu Glu Trp Ala Ala Glu Arg
1               5                   10

<210> SEQ ID NO 11
<211> LENGTH: 20
<212> TYPE: PRT
<213> ORGANISM: Homo sapiens

<400> SEQUENCE: 11

Asp Val Leu Leu Leu Val His Asn Leu Pro Gln Asn Leu Pro Gly Tyr
1               5                   10                  15

Phe Trp Tyr Lys
            20

<210> SEQ ID NO 12
<211> LENGTH: 10
<212> TYPE: PRT
<213> ORGANISM: Homo sapiens

<400> SEQUENCE: 12

Ser Glu Pro Arg Pro Gly Val Leu Leu Arg
1               5                   10

<210> SEQ ID NO 13
<211> LENGTH: 8
<212> TYPE: PRT
<213> ORGANISM: Homo sapiens

<400> SEQUENCE: 13

Ile Thr Gln Asp Ala Gln Leu Lys
1               5

<210> SEQ ID NO 14
<211> LENGTH: 7
<212> TYPE: PRT
<213> ORGANISM: Homo sapiens

<400> SEQUENCE: 14

Ala Leu Asp Leu Ser Leu Lys
1               5

<210> SEQ ID NO 15
<211> LENGTH: 13
<212> TYPE: PRT
<213> ORGANISM: Homo sapiens

<400> SEQUENCE: 15

Trp Trp Gly Gly Gln Pro Leu Trp Ile Thr Ala Thr Lys
1               5                   10

<210> SEQ ID NO 16
<211> LENGTH: 6
<212> TYPE: PRT
<213> ORGANISM: Homo sapiens
```

<400> SEQUENCE: 16

Leu Ser Glu Thr Asn Arg
1               5

<210> SEQ ID NO 17
<211> LENGTH: 13
<212> TYPE: PRT
<213> ORGANISM: Homo sapiens

<400> SEQUENCE: 17

Thr Asp Ala Pro Asp Leu Pro Glu Glu Asn Gln Ala Arg
1               5                   10

<210> SEQ ID NO 18
<211> LENGTH: 8
<212> TYPE: PRT
<213> ORGANISM: Homo sapiens

<400> SEQUENCE: 18

Ser Phe Arg Pro Phe Val Pro Arg
1               5

<210> SEQ ID NO 19
<211> LENGTH: 14
<212> TYPE: PRT
<213> ORGANISM: Homo sapiens

<400> SEQUENCE: 19

Leu Glu Gln Gly Glu Asn Val Phe Leu Gln Ala Thr Asp Lys
1               5                   10

<210> SEQ ID NO 20
<211> LENGTH: 12
<212> TYPE: PRT
<213> ORGANISM: Homo sapiens

<400> SEQUENCE: 20

Glu Thr Ala Ala Ser Leu Leu Gln Ala Gly Tyr Lys
1               5                   10

<210> SEQ ID NO 21
<211> LENGTH: 8
<212> TYPE: PRT
<213> ORGANISM: Homo sapiens

<400> SEQUENCE: 21

Val Thr Gly Trp Gly Asn Leu Lys
1               5

<210> SEQ ID NO 22
<211> LENGTH: 10
<212> TYPE: PRT
<213> ORGANISM: Homo sapiens

<400> SEQUENCE: 22

Glu Ala Gln Leu Pro Val Ile Glu Asn Lys
1               5                   10

<210> SEQ ID NO 23
<211> LENGTH: 8
<212> TYPE: PRT
<213> ORGANISM: Homo sapiens

<400> SEQUENCE: 23

Phe Leu Gln Glu Gln Gly His Arg
1               5

<210> SEQ ID NO 24
<211> LENGTH: 8
<212> TYPE: PRT
<213> ORGANISM: Homo sapiens

<400> SEQUENCE: 24

Ile Arg Pro Phe Phe Pro Gln Gln
1               5

<210> SEQ ID NO 25
<211> LENGTH: 11
<212> TYPE: PRT
<213> ORGANISM: Homo sapiens

<400> SEQUENCE: 25

Thr Leu Leu Pro Val Ser Lys Pro Glu Ile Arg
1               5                   10

<210> SEQ ID NO 26
<211> LENGTH: 10
<212> TYPE: PRT
<213> ORGANISM: Homo sapiens

<400> SEQUENCE: 26

Leu Ser Ser Pro Ala Val Ile Thr Asp Lys
1               5                   10

<210> SEQ ID NO 27
<211> LENGTH: 15
<212> TYPE: PRT
<213> ORGANISM: Homo sapiens

<400> SEQUENCE: 27

Tyr Glu Val Gln Gly Glu Val Phe Thr Lys Pro Gln Leu Trp Pro
1               5                   10                  15

<210> SEQ ID NO 28
<211> LENGTH: 10
<212> TYPE: PRT
<213> ORGANISM: Homo sapiens

<400> SEQUENCE: 28

Leu Gln Gly Thr Leu Pro Val Glu Ala Arg
1               5                   10

<210> SEQ ID NO 29
<211> LENGTH: 8
<212> TYPE: PRT
<213> ORGANISM: Homo sapiens

<400> SEQUENCE: 29

Val Arg Pro Gln Gln Leu Val Lys
1               5

<210> SEQ ID NO 30
<211> LENGTH: 7
<212> TYPE: PRT
<213> ORGANISM: Homo sapiens

<400> SEQUENCE: 30

Ile Glu Glu Ile Ala Ala Lys

-continued

```
1               5

<210> SEQ ID NO 31
<211> LENGTH: 16
<212> TYPE: PRT
<213> ORGANISM: Homo sapiens

<400> SEQUENCE: 31

Val Gln Glu Ala His Leu Thr Glu Asp Gln Ile Phe Tyr Phe Pro Lys
1               5                   10                  15

<210> SEQ ID NO 32
<211> LENGTH: 14
<212> TYPE: PRT
<213> ORGANISM: Homo sapiens

<400> SEQUENCE: 32

Ile Ser Leu Leu Leu Ile Glu Ser Trp Leu Glu Pro Val Arg
1               5                   10

<210> SEQ ID NO 33
<211> LENGTH: 12
<212> TYPE: PRT
<213> ORGANISM: Homo sapiens

<400> SEQUENCE: 33

Ala Leu Gln Asp Gln Leu Val Leu Val Ala Ala Lys
1               5                   10

<210> SEQ ID NO 34
<211> LENGTH: 7
<212> TYPE: PRT
<213> ORGANISM: Homo sapiens

<400> SEQUENCE: 34

Tyr Glu Phe Leu Asn Gly Arg
1               5

<210> SEQ ID NO 35
<211> LENGTH: 18
<212> TYPE: PRT
<213> ORGANISM: Homo sapiens

<400> SEQUENCE: 35

Thr Pro Ser Ala Ala Tyr Leu Trp Val Gly Thr Gly Ala Ser Glu Ala
1               5                   10                  15

Glu Lys

<210> SEQ ID NO 36
<211> LENGTH: 13
<212> TYPE: PRT
<213> ORGANISM: Homo sapiens

<400> SEQUENCE: 36

Thr Ala Thr Ser Glu Tyr Gln Thr Phe Phe Asn Pro Arg
1               5                   10

<210> SEQ ID NO 37
<211> LENGTH: 8
<212> TYPE: PRT
<213> ORGANISM: Homo sapiens

<400> SEQUENCE: 37

Thr Ala Ser Asp Phe Ile Thr Lys
```

```
1               5

<210> SEQ ID NO 38
<211> LENGTH: 18
<212> TYPE: PRT
<213> ORGANISM: Homo sapiens

<400> SEQUENCE: 38

Ile Ile Thr Gly Leu Leu Glu Phe Glu Val Tyr Leu Glu Tyr Leu Gln
1               5                   10                  15

Asn Arg

<210> SEQ ID NO 39
<211> LENGTH: 10
<212> TYPE: PRT
<213> ORGANISM: Homo sapiens

<400> SEQUENCE: 39

Ile Ile Gly Gly Ser Asp Ala Asp Ile Lys
1               5                   10

<210> SEQ ID NO 40
<211> LENGTH: 7
<212> TYPE: PRT
<213> ORGANISM: Homo sapiens

<400> SEQUENCE: 40

Tyr Thr Thr Glu Ile Ile Lys
1               5

<210> SEQ ID NO 41
<211> LENGTH: 12
<212> TYPE: PRT
<213> ORGANISM: Homo sapiens

<400> SEQUENCE: 41

Glu Asp Thr Pro Asn Ser Val Trp Glu Pro Ala Lys
1               5                   10

<210> SEQ ID NO 42
<211> LENGTH: 8
<212> TYPE: PRT
<213> ORGANISM: Homo sapiens

<400> SEQUENCE: 42

Leu Tyr Tyr Gly Asp Asp Glu Lys
1               5

<210> SEQ ID NO 43
<211> LENGTH: 8
<212> TYPE: PRT
<213> ORGANISM: Homo sapiens

<400> SEQUENCE: 43

Gly Gly Glu Ile Glu Gly Phe Arg
1               5

<210> SEQ ID NO 44
<211> LENGTH: 20
<212> TYPE: PRT
<213> ORGANISM: Homo sapiens

<400> SEQUENCE: 44

Asp Gly Ser Pro Asp Val Thr Thr Ala Asp Ile Gly Ala Asn Thr Pro
```

-continued

```
1               5               10              15

Asp Ala Thr Lys
            20

<210> SEQ ID NO 45
<211> LENGTH: 6
<212> TYPE: PRT
<213> ORGANISM: Homo sapiens

<400> SEQUENCE: 45

Val Glu Ile Asp Thr Lys
1               5

<210> SEQ ID NO 46
<211> LENGTH: 8
<212> TYPE: PRT
<213> ORGANISM: Homo sapiens

<400> SEQUENCE: 46

Ala Val Leu Thr Ile Asp Glu Lys
1               5

<210> SEQ ID NO 47
<211> LENGTH: 7
<212> TYPE: PRT
<213> ORGANISM: Homo sapiens

<400> SEQUENCE: 47

Phe Ser Val Val Tyr Ala Lys
1               5

<210> SEQ ID NO 48
<211> LENGTH: 7
<212> TYPE: PRT
<213> ORGANISM: Homo sapiens

<400> SEQUENCE: 48

Tyr Tyr Leu Gln Gly Ala Lys
1               5

<210> SEQ ID NO 49
<211> LENGTH: 13
<212> TYPE: PRT
<213> ORGANISM: Homo sapiens

<400> SEQUENCE: 49

Glu Glu Asn Phe Tyr Val Asp Glu Thr Thr Val Val Lys
1               5                   10

<210> SEQ ID NO 50
<211> LENGTH: 9
<212> TYPE: PRT
<213> ORGANISM: Homo sapiens

<400> SEQUENCE: 50

Tyr Gly Phe Tyr Thr His Val Phe Arg
1               5

<210> SEQ ID NO 51
<211> LENGTH: 10
<212> TYPE: PRT
<213> ORGANISM: Homo sapiens

<400> SEQUENCE: 51
```

```
His Thr Leu Asn Gln Ile Asp Glu Val Lys
1               5                   10

<210> SEQ ID NO 52
<211> LENGTH: 12
<212> TYPE: PRT
<213> ORGANISM: Homo sapiens

<400> SEQUENCE: 52

Ala Phe Ile Gln Leu Trp Ala Phe Asp Ala Val Lys
1               5                   10

<210> SEQ ID NO 53
<211> LENGTH: 8
<212> TYPE: PRT
<213> ORGANISM: Homo sapiens

<400> SEQUENCE: 53

Ser Gly Phe Ser Phe Gly Phe Lys
1               5

<210> SEQ ID NO 54
<211> LENGTH: 11
<212> TYPE: PRT
<213> ORGANISM: Homo sapiens

<400> SEQUENCE: 54

Gly Trp Val Thr Asp Gly Phe Ser Ser Leu Lys
1               5                   10

<210> SEQ ID NO 55
<211> LENGTH: 14
<212> TYPE: PRT
<213> ORGANISM: Homo sapiens

<400> SEQUENCE: 55

Ile Thr Glu Asn Asp Ile Gln Ile Ala Leu Asp Asp Ala Lys
1               5                   10

<210> SEQ ID NO 56
<211> LENGTH: 20
<212> TYPE: PRT
<213> ORGANISM: Homo sapiens

<400> SEQUENCE: 56

Val Glu Pro Leu Tyr Glu Leu Val Thr Ala Thr Asp Phe Ala Tyr Ser
1               5                   10                  15

Ser Thr Val Arg
            20

<210> SEQ ID NO 57
<211> LENGTH: 22
<212> TYPE: PRT
<213> ORGANISM: Homo sapiens

<400> SEQUENCE: 57

Asp Pro Asp Gln Thr Asp Gly Leu Gly Leu Ser Tyr Leu Ser Ser His
1               5                   10                  15

Ile Ala Asn Val Glu Arg
            20

<210> SEQ ID NO 58
<211> LENGTH: 10
<212> TYPE: PRT
```

-continued

```
<213> ORGANISM: Homo sapiens

<400> SEQUENCE: 58

Val Gly Glu Tyr Ser Leu Tyr Ile Gly Arg
1               5                   10

<210> SEQ ID NO 59
<211> LENGTH: 15
<212> TYPE: PRT
<213> ORGANISM: Homo sapiens

<400> SEQUENCE: 59

Ser Leu Pro Val Ser Asp Ser Val Leu Ser Gly Phe Glu Gln Arg
1               5                   10                  15

<210> SEQ ID NO 60
<211> LENGTH: 10
<212> TYPE: PRT
<213> ORGANISM: Homo sapiens

<400> SEQUENCE: 60

Asn Ala Asp Tyr Ser Tyr Ser Val Trp Lys
1               5                   10

<210> SEQ ID NO 61
<211> LENGTH: 10
<212> TYPE: PRT
<213> ORGANISM: Homo sapiens

<400> SEQUENCE: 61

Asp Ala Gln Tyr Ala Pro Gly Tyr Asp Lys
1               5                   10

<210> SEQ ID NO 62
<211> LENGTH: 7
<212> TYPE: PRT
<213> ORGANISM: Homo sapiens

<400> SEQUENCE: 62

Phe Gln Leu Pro Gly Gln Lys
1               5

<210> SEQ ID NO 63
<211> LENGTH: 11
<212> TYPE: PRT
<213> ORGANISM: Homo sapiens

<400> SEQUENCE: 63

Tyr Gly Leu Val Thr Tyr Ala Thr Tyr Pro Lys
1               5                   10

<210> SEQ ID NO 64
<211> LENGTH: 18
<212> TYPE: PRT
<213> ORGANISM: Homo sapiens

<400> SEQUENCE: 64

Gly Ser Phe Ala Leu Ser Phe Pro Val Glu Ser Asp Val Ala Pro Ile
1               5                   10                  15

Ala Arg

<210> SEQ ID NO 65
<211> LENGTH: 10
<212> TYPE: PRT
```

-continued

<213> ORGANISM: Homo sapiens

<400> SEQUENCE: 65

```
Thr Leu Leu Ile Ala Asn Glu Thr Leu Arg
1               5                   10
```

<210> SEQ ID NO 66
<211> LENGTH: 22
<212> TYPE: PRT
<213> ORGANISM: Homo sapiens

<400> SEQUENCE: 66

```
Val Ile Leu Gly Ala His Gln Glu Val Asn Leu Glu Pro His Val Gln
1               5                   10                  15

Glu Ile Glu Val Ser Arg
            20
```

<210> SEQ ID NO 67
<211> LENGTH: 9
<212> TYPE: PRT
<213> ORGANISM: Homo sapiens

<400> SEQUENCE: 67

```
Asp Ile Ser Glu Val Val Thr Pro Arg
1               5
```

<210> SEQ ID NO 68
<211> LENGTH: 9
<212> TYPE: PRT
<213> ORGANISM: Homo sapiens

<400> SEQUENCE: 68

```
Thr Leu Glu Ala Gln Leu Thr Pro Arg
1               5
```

<210> SEQ ID NO 69
<211> LENGTH: 11
<212> TYPE: PRT
<213> ORGANISM: Homo sapiens

<400> SEQUENCE: 69

```
Ala Val Gly Tyr Leu Ile Thr Gly Tyr Gln Arg
1               5                   10
```

<210> SEQ ID NO 70
<211> LENGTH: 18
<212> TYPE: PRT
<213> ORGANISM: Homo sapiens

<400> SEQUENCE: 70

```
Phe Asn Ala Val Leu Thr Asn Pro Gln Gly Asp Tyr Asp Thr Ser Thr
1               5                   10                  15

Gly Lys
```

<210> SEQ ID NO 71
<211> LENGTH: 16
<212> TYPE: PRT
<213> ORGANISM: Homo sapiens

<400> SEQUENCE: 71

```
Ser Pro Glu Gln Gln Glu Thr Val Leu Asp Gly Asn Leu Ile Ile Arg
1               5                   10                  15
```

```
<210> SEQ ID NO 72
<211> LENGTH: 16
<212> TYPE: PRT
<213> ORGANISM: Homo sapiens

<400> SEQUENCE: 72

Ala Leu Asn His Leu Pro Leu Glu Tyr Asn Ser Ala Leu Tyr Ser Arg
1               5                   10                  15

<210> SEQ ID NO 73
<211> LENGTH: 14
<212> TYPE: PRT
<213> ORGANISM: Homo sapiens

<400> SEQUENCE: 73

Gly Gly Glu Gly Thr Gly Tyr Phe Val Asp Phe Ser Val Arg
1               5                   10

<210> SEQ ID NO 74
<211> LENGTH: 9
<212> TYPE: PRT
<213> ORGANISM: Homo sapiens

<400> SEQUENCE: 74

Gly Ile Val Glu Glu Cys Cys Phe Arg
1               5

<210> SEQ ID NO 75
<211> LENGTH: 7
<212> TYPE: PRT
<213> ORGANISM: Homo sapiens

<400> SEQUENCE: 75

Phe Ala Phe Asn Leu Tyr Arg
1               5

<210> SEQ ID NO 76
<211> LENGTH: 23
<212> TYPE: PRT
<213> ORGANISM: Homo sapiens

<400> SEQUENCE: 76

Ala Ile Thr Pro Pro His Pro Ala Ser Gln Ala Asn Ile Ile Phe Asp
1               5                   10                  15

Ile Thr Glu Gly Asn Leu Arg
            20

<210> SEQ ID NO 77
<211> LENGTH: 11
<212> TYPE: PRT
<213> ORGANISM: Homo sapiens

<400> SEQUENCE: 77

Glu Pro Gly Leu Cys Thr Trp Gln Ser Leu Arg
1               5                   10

<210> SEQ ID NO 78
<211> LENGTH: 8
<212> TYPE: PRT
<213> ORGANISM: Homo sapiens

<400> SEQUENCE: 78

Ala Val Tyr Glu Ala Val Leu Arg
1               5
```

<210> SEQ ID NO 79
<211> LENGTH: 6
<212> TYPE: PRT
<213> ORGANISM: Homo sapiens

<400> SEQUENCE: 79

Ala Trp Val Ala Trp Arg
1               5

<210> SEQ ID NO 80
<211> LENGTH: 11
<212> TYPE: PRT
<213> ORGANISM: Homo sapiens

<400> SEQUENCE: 80

Thr Asn Leu Glu Ser Ile Leu Ser Tyr Pro Lys
1               5                   10

<210> SEQ ID NO 81
<211> LENGTH: 11
<212> TYPE: PRT
<213> ORGANISM: Homo sapiens

<400> SEQUENCE: 81

His Leu Ser Leu Leu Thr Thr Leu Ser Asn Arg
1               5                   10

<210> SEQ ID NO 82
<211> LENGTH: 22
<212> TYPE: PRT
<213> ORGANISM: Homo sapiens

<400> SEQUENCE: 82

Phe Thr Phe Thr Leu His Leu Glu Thr Pro Lys Pro Ser Ile Ser Ser
1               5                   10                  15

Ser Asn Leu Asn Pro Arg
            20

<210> SEQ ID NO 83
<211> LENGTH: 16
<212> TYPE: PRT
<213> ORGANISM: Homo sapiens

<400> SEQUENCE: 83

Thr Glu Leu Arg Pro Gly Glu Thr Leu Asn Val Asn Phe Leu Leu Arg
1               5                   10                  15

<210> SEQ ID NO 84
<211> LENGTH: 9
<212> TYPE: PRT
<213> ORGANISM: Homo sapiens

<400> SEQUENCE: 84

Leu Pro Thr Ala Val Val Pro Leu Arg
1               5

<210> SEQ ID NO 85
<211> LENGTH: 8
<212> TYPE: PRT
<213> ORGANISM: Homo sapiens

<400> SEQUENCE: 85

Ala Pro Leu Thr Lys Pro Leu Lys
1               5

-continued

```
<210> SEQ ID NO 86
<211> LENGTH: 24
<212> TYPE: PRT
<213> ORGANISM: Homo sapiens

<400> SEQUENCE: 86

Ala Asp Ser Gln Ala Gln Leu Leu Leu Ser Thr Val Val Gly Val Phe
1               5                   10                  15

Thr Ala Pro Gly Leu His Leu Lys
            20

<210> SEQ ID NO 87
<211> LENGTH: 8
<212> TYPE: PRT
<213> ORGANISM: Homo sapiens

<400> SEQUENCE: 87

Glu Leu Pro Glu His Thr Val Lys
1               5

<210> SEQ ID NO 88
<211> LENGTH: 6
<212> TYPE: PRT
<213> ORGANISM: Homo sapiens

<400> SEQUENCE: 88

Ala His Tyr Asp Leu Arg
1               5

<210> SEQ ID NO 89
<211> LENGTH: 13
<212> TYPE: PRT
<213> ORGANISM: Homo sapiens

<400> SEQUENCE: 89

Ala Glu Ala Gln Ala Gln Tyr Ser Ala Ala Val Ala Lys
1               5                   10

<210> SEQ ID NO 90
<211> LENGTH: 7
<212> TYPE: PRT
<213> ORGANISM: Homo sapiens

<400> SEQUENCE: 90

Ala Tyr Ser Asp Leu Ser Arg
1               5

<210> SEQ ID NO 91
<211> LENGTH: 16
<212> TYPE: PRT
<213> ORGANISM: Homo sapiens

<400> SEQUENCE: 91

Asp Ala Leu Ser Ser Val Gln Glu Ser Gln Val Ala Gln Gln Ala Arg
1               5                   10                  15

<210> SEQ ID NO 92
<211> LENGTH: 10
<212> TYPE: PRT
<213> ORGANISM: Homo sapiens

<400> SEQUENCE: 92

Ala Asn Arg Pro Phe Leu Val Phe Ile Arg
```

-continued

```
1               5                    10

<210> SEQ ID NO 93
<211> LENGTH: 11
<212> TYPE: PRT
<213> ORGANISM: Homo sapiens

<400> SEQUENCE: 93

Ala Leu Glu Gln Asp Leu Pro Val Asn Ile Lys
1               5                    10

<210> SEQ ID NO 94
<211> LENGTH: 14
<212> TYPE: PRT
<213> ORGANISM: Homo sapiens

<400> SEQUENCE: 94

Asp Phe His Ile Asn Leu Phe Gln Val Leu Pro Trp Leu Lys
1               5                    10

<210> SEQ ID NO 95
<211> LENGTH: 14
<212> TYPE: PRT
<213> ORGANISM: Homo sapiens

<400> SEQUENCE: 95

Ala Gly Leu Leu Arg Pro Asp Tyr Ala Leu Leu Gly His Arg
1               5                    10

<210> SEQ ID NO 96
<211> LENGTH: 19
<212> TYPE: PRT
<213> ORGANISM: Homo sapiens

<400> SEQUENCE: 96

Glu Lys Pro Ala Gly Gly Ile Pro Val Leu Gly Ser Leu Val Asn Thr
1               5                    10                   15

Val Leu Lys

<210> SEQ ID NO 97
<211> LENGTH: 9
<212> TYPE: PRT
<213> ORGANISM: Homo sapiens

<400> SEQUENCE: 97

Ile Thr Gly Phe Leu Lys Pro Gly Lys
1               5

<210> SEQ ID NO 98
<211> LENGTH: 7
<212> TYPE: PRT
<213> ORGANISM: Homo sapiens

<400> SEQUENCE: 98

Ser Leu Leu Gln Pro Asn Lys
1               5

<210> SEQ ID NO 99
<211> LENGTH: 9
<212> TYPE: PRT
<213> ORGANISM: Homo sapiens

<400> SEQUENCE: 99

Ser Pro Glu Leu Gln Ala Glu Ala Lys
```

```
1               5

<210> SEQ ID NO 100
<211> LENGTH: 10
<212> TYPE: PRT
<213> ORGANISM: Homo sapiens

<400> SEQUENCE: 100

Thr Tyr Leu His Thr Tyr Glu Ser Glu Ile
1               5               10

<210> SEQ ID NO 101
<211> LENGTH: 12
<212> TYPE: PRT
<213> ORGANISM: Homo sapiens

<400> SEQUENCE: 101

Asp Ser Pro Ser Val Trp Ala Ala Val Pro Gly Lys
1               5               10

<210> SEQ ID NO 102
<211> LENGTH: 8
<212> TYPE: PRT
<213> ORGANISM: Homo sapiens

<400> SEQUENCE: 102

His Tyr Ile Asn Leu Ile Thr Arg
1               5

<210> SEQ ID NO 103
<211> LENGTH: 15
<212> TYPE: PRT
<213> ORGANISM: Homo sapiens

<400> SEQUENCE: 103

Ile Pro Gly Ile Phe Glu Leu Gly Ile Ser Ser Gln Ser Asp Arg
1               5               10              15

<210> SEQ ID NO 104
<211> LENGTH: 9
<212> TYPE: PRT
<213> ORGANISM: Homo sapiens

<400> SEQUENCE: 104

Ile Gln Thr His Ser Thr Thr Tyr Arg
1               5

<210> SEQ ID NO 105
<211> LENGTH: 19
<212> TYPE: PRT
<213> ORGANISM: Homo sapiens

<400> SEQUENCE: 105

Gln Leu Gly Leu Pro Gly Pro Pro Asp Val Pro Asp His Ala Ala Tyr
1               5               10              15

His Pro Phe

<210> SEQ ID NO 106
<211> LENGTH: 22
<212> TYPE: PRT
<213> ORGANISM: Homo sapiens

<400> SEQUENCE: 106

Phe Pro Leu Gly Ser Tyr Thr Ile Gln Asn Ile Val Ala Gly Ser Thr
```

-continued

```
1               5               10              15

Tyr Leu Phe Ser Thr Lys
                20

<210> SEQ ID NO 107
<211> LENGTH: 13
<212> TYPE: PRT
<213> ORGANISM: Homo sapiens

<400> SEQUENCE: 107

Lys Leu Val Ile Phe Asp Thr Met Leu Glu Ile Lys Lys
1               5               10

<210> SEQ ID NO 108
<211> LENGTH: 30
<212> TYPE: PRT
<213> ORGANISM: Homo sapiens

<400> SEQUENCE: 108

Lys Phe Ile Glu Asp Asn Ile Glu Tyr Ile Thr Ile Ile Ala Phe Ala
1               5               10              15

Gln Tyr Val Gln Glu Ala Thr Phe Glu Glu Met Glu Lys Leu
                20              25              30

<210> SEQ ID NO 109
<211> LENGTH: 18
<212> TYPE: PRT
<213> ORGANISM: Homo sapiens

<400> SEQUENCE: 109

Lys Ile Ala Pro Gln Leu Ser Thr Glu Glu Leu Val Ser Leu Gly Glu
1               5               10              15

Lys Met

<210> SEQ ID NO 110
<211> LENGTH: 25
<212> TYPE: PRT
<213> ORGANISM: Homo sapiens

<400> SEQUENCE: 110

Lys Leu Lys His Glu Leu Thr Asp Glu Glu Leu Gln Ser Leu Phe Thr
1               5               10              15

Asn Phe Ala Asn Val Val Asp Lys Cys
                20              25

<210> SEQ ID NO 111
<211> LENGTH: 11
<212> TYPE: PRT
<213> ORGANISM: Homo sapiens

<400> SEQUENCE: 111

Lys Leu Pro Asn Asn Val Leu Gln Glu Lys Ile
1               5               10

<210> SEQ ID NO 112
<211> LENGTH: 19
<212> TYPE: PRT
<213> ORGANISM: Homo sapiens

<400> SEQUENCE: 112

Lys Ser Asp Val Gly Phe Leu Pro Pro Phe Pro Thr Leu Asp Pro Glu
1               5               10              15
```

Glu Lys Cys

<210> SEQ ID NO 113
<211> LENGTH: 10
<212> TYPE: PRT
<213> ORGANISM: Homo sapiens

<400> SEQUENCE: 113

Lys Val Met Asn His Ile Cys Ser Lys Gln
1               5                   10

<210> SEQ ID NO 114
<211> LENGTH: 15
<212> TYPE: PRT
<213> ORGANISM: Homo sapiens

<400> SEQUENCE: 114

Arg Glu Ser Leu Leu Asn His Phe Leu Tyr Glu Val Ala Arg Arg
1               5                   10                  15

<210> SEQ ID NO 115
<211> LENGTH: 10
<212> TYPE: PRT
<213> ORGANISM: Homo sapiens

<400> SEQUENCE: 115

Arg Leu Cys Phe Phe Tyr Asn Lys Lys Ser
1               5                   10

<210> SEQ ID NO 116
<211> LENGTH: 21
<212> TYPE: PRT
<213> ORGANISM: Homo sapiens

<400> SEQUENCE: 116

Lys Ala Val Leu Asp Val Phe Glu Glu Gly Thr Glu Ala Ser Ala Ala
1               5                   10                  15

Thr Ala Val Lys Ile
            20

<210> SEQ ID NO 117
<211> LENGTH: 10
<212> TYPE: PRT
<213> ORGANISM: Homo sapiens

<400> SEQUENCE: 117

Lys Glu Gln Leu Ser Leu Leu Asp Arg Phe
1               5                   10

<210> SEQ ID NO 118
<211> LENGTH: 16
<212> TYPE: PRT
<213> ORGANISM: Homo sapiens

<400> SEQUENCE: 118

Lys Glu Gln Leu Ser Leu Leu Asp Arg Phe Thr Glu Asp Ala Lys Arg
1               5                   10                  15

<210> SEQ ID NO 119
<211> LENGTH: 17
<212> TYPE: PRT
<213> ORGANISM: Homo sapiens

<400> SEQUENCE: 119

-continued

```
Lys Glu Gln Leu Ser Leu Leu Asp Arg Phe Thr Glu Asp Ala Lys Arg
1               5                   10                  15

Leu

<210> SEQ ID NO 120
<211> LENGTH: 25
<212> TYPE: PRT
<213> ORGANISM: Homo sapiens

<400> SEQUENCE: 120

Lys Ile Thr Asp Leu Ile Lys Asp Leu Asp Ser Gln Thr Met Met Val
1               5                   10                  15

Leu Val Asn Tyr Ile Phe Phe Lys Ala
            20                  25

<210> SEQ ID NO 121
<211> LENGTH: 13
<212> TYPE: PRT
<213> ORGANISM: Homo sapiens

<400> SEQUENCE: 121

Lys Ile Thr Leu Leu Ser Ala Leu Val Glu Thr Arg Thr
1               5                   10

<210> SEQ ID NO 122
<211> LENGTH: 21
<212> TYPE: PRT
<213> ORGANISM: Homo sapiens

<400> SEQUENCE: 122

Lys Arg Leu Tyr Gly Ser Glu Ala Phe Ala Thr Asp Phe Gln Asp Ser
1               5                   10                  15

Ala Ala Ala Lys Lys
            20

<210> SEQ ID NO 123
<211> LENGTH: 11
<212> TYPE: PRT
<213> ORGANISM: Homo sapiens

<400> SEQUENCE: 123

Arg Glu Ile Gly Glu Leu Tyr Leu Pro Lys Phe
1               5                   10

<210> SEQ ID NO 124
<211> LENGTH: 16
<212> TYPE: PRT
<213> ORGANISM: Homo sapiens

<400> SEQUENCE: 124

Arg Cys Glu Gly Pro Ile Pro Asp Val Thr Phe Glu Leu Leu Arg Glu
1               5                   10                  15

<210> SEQ ID NO 125
<211> LENGTH: 7
<212> TYPE: PRT
<213> ORGANISM: Homo sapiens

<400> SEQUENCE: 125

Arg Phe Ala Leu Val Arg Glu
1               5

<210> SEQ ID NO 126
```

<211> LENGTH: 10
<212> TYPE: PRT
<213> ORGANISM: Homo sapiens

<400> SEQUENCE: 126

Lys Ser Pro Pro Gly Val Cys Ser Arg Asp
1               5                   10

<210> SEQ ID NO 127
<211> LENGTH: 21
<212> TYPE: PRT
<213> ORGANISM: Homo sapiens

<400> SEQUENCE: 127

Arg Asp Ser Phe His Leu Asp Glu Gln Phe Thr Val Pro Val Glu Met
1               5                   10                  15

Met Gln Ala Arg Thr
            20

<210> SEQ ID NO 128
<211> LENGTH: 9
<212> TYPE: PRT
<213> ORGANISM: Homo sapiens

<400> SEQUENCE: 128

Lys Cys Asn Leu Leu Ala Glu Lys Gln
1               5

<210> SEQ ID NO 129
<211> LENGTH: 16
<212> TYPE: PRT
<213> ORGANISM: Homo sapiens

<400> SEQUENCE: 129

Lys Glu His Ala Val Glu Gly Asp Cys Asp Phe Gln Leu Leu Lys Leu
1               5                   10                  15

<210> SEQ ID NO 130
<211> LENGTH: 44
<212> TYPE: PRT
<213> ORGANISM: Homo sapiens

<400> SEQUENCE: 130

Lys His Thr Leu Asn Gln Ile Asp Glu Val Lys Val Trp Pro Gln Gln
1               5                   10                  15

Pro Ser Gly Glu Leu Phe Glu Ile Glu Ile Asp Thr Leu Glu Thr Thr
            20                  25                  30

Cys His Val Leu Asp Pro Thr Pro Val Ala Arg Cys
        35                  40

<210> SEQ ID NO 131
<211> LENGTH: 15
<212> TYPE: PRT
<213> ORGANISM: Homo sapiens

<400> SEQUENCE: 131

Lys Met Val Ser Gly Phe Ile Pro Leu Lys Pro Thr Val Lys Met
1               5                   10                  15

<210> SEQ ID NO 132
<211> LENGTH: 19
<212> TYPE: PRT
<213> ORGANISM: Homo sapiens -continued

```
<400> SEQUENCE: 132

Arg Ala Phe Gln Pro Phe Phe Val Glu Leu Thr Met Pro Tyr Ser Val
1               5                   10                  15

Ile Arg Gly

<210> SEQ ID NO 133
<211> LENGTH: 15
<212> TYPE: PRT
<213> ORGANISM: Homo sapiens

<400> SEQUENCE: 133

Arg Asn Gln Gly Asn Thr Trp Leu Thr Ala Phe Val Leu Lys Thr
1               5                   10                  15

<210> SEQ ID NO 134
<211> LENGTH: 14
<212> TYPE: PRT
<213> ORGANISM: Homo sapiens

<400> SEQUENCE: 134

Lys Ile Asp Arg Phe Met Gln Ala Val Thr Gly Trp Lys Thr
1               5                   10

<210> SEQ ID NO 135
<211> LENGTH: 10
<212> TYPE: PRT
<213> ORGANISM: Homo sapiens

<400> SEQUENCE: 135

Lys Leu Asp Thr Glu Asp Lys Leu Arg Ala
1               5                   10

<210> SEQ ID NO 136
<211> LENGTH: 27
<212> TYPE: PRT
<213> ORGANISM: Homo sapiens

<400> SEQUENCE: 136

Lys Thr Gly Cys Ser Leu Met Gly Ala Ser Val Asp Ser Thr Leu Ala
1               5                   10                  15

Phe Asn Thr Tyr Val His Phe Gln Gly Lys Met
                20                  25

<210> SEQ ID NO 137
<211> LENGTH: 16
<212> TYPE: PRT
<213> ORGANISM: Homo sapiens

<400> SEQUENCE: 137

Arg Ala Ala Met Val Gly Met Leu Ala Asn Phe Leu Gly Phe Arg Ile
1               5                   10                  15

<210> SEQ ID NO 138
<211> LENGTH: 23
<212> TYPE: PRT
<213> ORGANISM: Homo sapiens

<400> SEQUENCE: 138

Lys Asn Asp Asn Asp Asn Ile Phe Leu Ser Pro Leu Ser Ile Ser Thr
1               5                   10                  15

Ala Phe Ala Met Thr Lys Leu
                20
```

```
<210> SEQ ID NO 139
<211> LENGTH: 24
<212> TYPE: PRT
<213> ORGANISM: Homo sapiens

<400> SEQUENCE: 139

Lys Ser Lys Leu Pro Gly Ile Val Ala Glu Gly Arg Asp Asp Leu Tyr
1               5                   10                  15

Val Ser Asp Ala Phe His Lys Ala
            20

<210> SEQ ID NO 140
<211> LENGTH: 14
<212> TYPE: PRT
<213> ORGANISM: Homo sapiens

<400> SEQUENCE: 140

Arg Glu Val Pro Leu Asn Thr Ile Ile Phe Met Gly Arg Val
1               5                   10

<210> SEQ ID NO 141
<211> LENGTH: 36
<212> TYPE: PRT
<213> ORGANISM: Homo sapiens

<400> SEQUENCE: 141

Arg Phe Ala Thr Thr Phe Tyr Gln His Leu Ala Asp Ser Lys Asn Asp
1               5                   10                  15

Asn Asp Asn Ile Phe Leu Ser Pro Leu Ser Ile Ser Thr Ala Phe Ala
            20                  25                  30

Met Thr Lys Leu
        35

<210> SEQ ID NO 142
<211> LENGTH: 27
<212> TYPE: PRT
<213> ORGANISM: Homo sapiens

<400> SEQUENCE: 142

Arg Ile Thr Asp Val Ile Pro Ser Glu Ala Ile Asn Glu Leu Thr Val
1               5                   10                  15

Leu Val Leu Val Asn Thr Ile Tyr Phe Lys Gly
            20                  25

<210> SEQ ID NO 143
<211> LENGTH: 9
<212> TYPE: PRT
<213> ORGANISM: Homo sapiens

<400> SEQUENCE: 143

Arg Arg Val Trp Glu Leu Ser Lys Ala
1               5

<210> SEQ ID NO 144
<211> LENGTH: 30
<212> TYPE: PRT
<213> ORGANISM: Homo sapiens

<400> SEQUENCE: 144

Arg Val Ala Glu Gly Thr Gln Val Leu Glu Leu Pro Phe Lys Gly Asp
1               5                   10                  15

Asp Ile Thr Met Val Leu Ile Leu Pro Lys Pro Glu Lys Ser
```

-continued

```
                20              25              30

<210> SEQ ID NO 145
<211> LENGTH: 23
<212> TYPE: PRT
<213> ORGANISM: Homo sapiens

<400> SEQUENCE: 145

Lys Ala Gly Thr Glu Leu Val Asn Phe Leu Ser Tyr Phe Val Glu Leu
1               5                   10                  15

Gly Thr Gln Pro Ala Thr Gln
            20

<210> SEQ ID NO 146
<211> LENGTH: 22
<212> TYPE: PRT
<213> ORGANISM: Homo sapiens

<400> SEQUENCE: 146

Lys Glu Pro Cys Val Glu Ser Leu Val Ser Gln Tyr Phe Gln Thr Val
1               5                   10                  15

Thr Asp Tyr Gly Lys Asp
            20

<210> SEQ ID NO 147
<211> LENGTH: 12
<212> TYPE: PRT
<213> ORGANISM: Homo sapiens

<400> SEQUENCE: 147

Lys Ala Leu Val Gln Gln Met Glu Gln Leu Arg Gln
1               5                   10

<210> SEQ ID NO 148
<211> LENGTH: 19
<212> TYPE: PRT
<213> ORGANISM: Homo sapiens

<400> SEQUENCE: 148

Lys Leu Gly Pro His Ala Gly Asp Val Glu Gly His Leu Ser Phe Leu
1               5                   10                  15

Glu Lys Asp

<210> SEQ ID NO 149
<211> LENGTH: 16
<212> TYPE: PRT
<213> ORGANISM: Homo sapiens

<400> SEQUENCE: 149

Lys Ser Glu Leu Thr Gln Gln Leu Asn Ala Leu Phe Gln Asp Lys Leu
1               5                   10                  15

<210> SEQ ID NO 150
<211> LENGTH: 20
<212> TYPE: PRT
<213> ORGANISM: Homo sapiens

<400> SEQUENCE: 150

Lys Ser Leu Ala Glu Leu Gly Gly His Leu Asp Gln Gln Val Glu Glu
1               5                   10                  15

Phe Arg Arg Arg
            20
```

<210> SEQ ID NO 151
<211> LENGTH: 14
<212> TYPE: PRT
<213> ORGANISM: Homo sapiens

<400> SEQUENCE: 151

Lys Val Lys Ile Asp Gln Thr Val Glu Glu Leu Arg Arg Ser
1               5                   10

<210> SEQ ID NO 152
<211> LENGTH: 11
<212> TYPE: PRT
<213> ORGANISM: Homo sapiens

<400> SEQUENCE: 152

Lys Val Asn Ser Phe Phe Ser Thr Phe Lys Glu
1               5                   10

<210> SEQ ID NO 153
<211> LENGTH: 18
<212> TYPE: PRT
<213> ORGANISM: Homo sapiens

<400> SEQUENCE: 153

Lys Ala Thr Phe Gln Thr Pro Asp Phe Ile Val Pro Leu Thr Asp Leu
1               5                   10                  15

Arg Ile

<210> SEQ ID NO 154
<211> LENGTH: 17
<212> TYPE: PRT
<213> ORGANISM: Homo sapiens

<400> SEQUENCE: 154

Lys Ala Val Ser Met Pro Ser Phe Ser Ile Leu Gly Ser Asp Val Arg
1               5                   10                  15

Val

<210> SEQ ID NO 155
<211> LENGTH: 13
<212> TYPE: PRT
<213> ORGANISM: Homo sapiens

<400> SEQUENCE: 155

Lys Glu Gln His Leu Phe Leu Pro Phe Ser Tyr Lys Asn
1               5                   10

<210> SEQ ID NO 156
<211> LENGTH: 13
<212> TYPE: PRT
<213> ORGANISM: Homo sapiens

<400> SEQUENCE: 156

Lys Lys Ile Ile Ser Asp Tyr His Gln Gln Phe Arg Tyr
1               5                   10

<210> SEQ ID NO 157
<211> LENGTH: 20
<212> TYPE: PRT
<213> ORGANISM: Homo sapiens

<400> SEQUENCE: 157

Lys Gln Val Phe Leu Tyr Pro Glu Lys Asp Glu Pro Thr Tyr Ile Leu

-continued

```
1               5               10              15

Asn Ile Lys Arg
            20

<210> SEQ ID NO 158
<211> LENGTH: 12
<212> TYPE: PRT
<213> ORGANISM: Homo sapiens

<400> SEQUENCE: 158

Lys Ser Pro Ala Phe Thr Asp Leu His Leu Arg Tyr
1               5               10

<210> SEQ ID NO 159
<211> LENGTH: 20
<212> TYPE: PRT
<213> ORGANISM: Homo sapiens

<400> SEQUENCE: 159

Lys Thr Ile Leu Gly Thr Met Pro Ala Phe Glu Val Ser Leu Gln Ala
1               5               10              15

Leu Gln Lys Ala
            20

<210> SEQ ID NO 160
<211> LENGTH: 14
<212> TYPE: PRT
<213> ORGANISM: Homo sapiens

<400> SEQUENCE: 160

Lys Val Leu Ala Asp Lys Phe Ile Ile Pro Gly Leu Lys Leu
1               5               10

<210> SEQ ID NO 161
<211> LENGTH: 32
<212> TYPE: PRT
<213> ORGANISM: Homo sapiens

<400> SEQUENCE: 161

Lys Tyr Ser Gln Pro Glu Asp Ser Leu Ile Pro Phe Phe Glu Ile Thr
1               5               10              15

Val Pro Glu Ser Gln Leu Thr Val Ser Gln Phe Thr Leu Pro Lys Ser
            20              25              30

<210> SEQ ID NO 162
<211> LENGTH: 13
<212> TYPE: PRT
<213> ORGANISM: Homo sapiens

<400> SEQUENCE: 162

Arg Asp Leu Lys Val Glu Asp Ile Pro Leu Ala Arg Ile
1               5               10

<210> SEQ ID NO 163
<211> LENGTH: 18
<212> TYPE: PRT
<213> ORGANISM: Homo sapiens

<400> SEQUENCE: 163

Arg Gly Ile Ile Ser Ala Leu Leu Val Pro Pro Glu Thr Glu Glu Ala
1               5               10              15

Lys Gln
```

-continued

```
<210> SEQ ID NO 164
<211> LENGTH: 21
<212> TYPE: PRT
<213> ORGANISM: Homo sapiens

<400> SEQUENCE: 164

Arg Ile Leu Gly Glu Glu Leu Gly Phe Ala Ser Leu His Asp Leu Gln
1               5                   10                  15

Leu Leu Gly Lys Leu
            20

<210> SEQ ID NO 165
<211> LENGTH: 26
<212> TYPE: PRT
<213> ORGANISM: Homo sapiens

<400> SEQUENCE: 165

Arg Leu Glu Leu Glu Leu Arg Pro Thr Gly Glu Ile Glu Gln Tyr Ser
1               5                   10                  15

Val Ser Ala Thr Tyr Glu Leu Gln Arg Glu
            20                  25

<210> SEQ ID NO 166
<211> LENGTH: 17
<212> TYPE: PRT
<213> ORGANISM: Homo sapiens

<400> SEQUENCE: 166

Arg Asn Ile Gln Glu Tyr Leu Ser Ile Leu Thr Asp Pro Asp Gly Lys
1               5                   10                  15

Gly

<210> SEQ ID NO 167
<211> LENGTH: 34
<212> TYPE: PRT
<213> ORGANISM: Homo sapiens

<400> SEQUENCE: 167

Arg Thr Phe Gln Ile Pro Gly Tyr Thr Val Pro Val Val Asn Val Glu
1               5                   10                  15

Val Ser Pro Phe Thr Ile Glu Met Ser Ala Phe Gly Tyr Val Phe Pro
            20                  25                  30

Lys Ala

<210> SEQ ID NO 168
<211> LENGTH: 22
<212> TYPE: PRT
<213> ORGANISM: Homo sapiens

<400> SEQUENCE: 168

Arg Thr Ile Asp Gln Met Leu Asn Ser Glu Leu Gln Trp Pro Val Pro
1               5                   10                  15

Asp Ile Tyr Leu Arg Asp
            20

<210> SEQ ID NO 169
<211> LENGTH: 13
<212> TYPE: PRT
<213> ORGANISM: Homo sapiens

<400> SEQUENCE: 169
```

-continued

```
Lys Met Arg Glu Trp Phe Ser Glu Thr Phe Gln Lys Val
1               5                   10

<210> SEQ ID NO 170
<211> LENGTH: 25
<212> TYPE: PRT
<213> ORGANISM: Homo sapiens

<400> SEQUENCE: 170

Lys Ser Thr Ala Ala Met Ser Thr Tyr Thr Gly Ile Phe Thr Asp Gln
1               5                   10                  15

Val Leu Ser Val Leu Lys Gly Glu Glu
            20                  25

<210> SEQ ID NO 171
<211> LENGTH: 13
<212> TYPE: PRT
<213> ORGANISM: Homo sapiens

<400> SEQUENCE: 171

Arg Gly Trp Val Thr Asp Gly Phe Ser Ser Leu Lys Asp
1               5                   10

<210> SEQ ID NO 172
<211> LENGTH: 17
<212> TYPE: PRT
<213> ORGANISM: Homo sapiens

<400> SEQUENCE: 172

Arg Ala Ala Thr Val Gly Ser Leu Ala Gly Gln Pro Leu Gln Glu Arg
1               5                   10                  15

Ala

<210> SEQ ID NO 173
<211> LENGTH: 16
<212> TYPE: PRT
<213> ORGANISM: Homo sapiens

<400> SEQUENCE: 173

Arg Leu Lys Ser Trp Phe Glu Pro Leu Val Glu Asp Met Gln Arg Gln
1               5                   10                  15

<210> SEQ ID NO 174
<211> LENGTH: 25
<212> TYPE: PRT
<213> ORGANISM: Homo sapiens

<400> SEQUENCE: 174

Arg Trp Val Gln Thr Leu Ser Glu Gln Val Gln Glu Glu Leu Leu Ser
1               5                   10                  15

Ser Gln Val Thr Gln Glu Leu Arg Ala
            20                  25

<210> SEQ ID NO 175
<211> LENGTH: 13
<212> TYPE: PRT
<213> ORGANISM: Homo sapiens

<400> SEQUENCE: 175

Lys Leu Cys Gly Gly Arg Trp Glu Leu Met Arg Ile
1               5                   10

<210> SEQ ID NO 176
```

<211> LENGTH: 8
<212> TYPE: PRT
<213> ORGANISM: Homo sapiens

<400> SEQUENCE: 176

Lys Leu Pro Gly Leu Leu Lys Arg
1               5

<210> SEQ ID NO 177
<211> LENGTH: 11
<212> TYPE: PRT
<213> ORGANISM: Homo sapiens

<400> SEQUENCE: 177

Lys Glu His Ser Ser Leu Ala Phe Trp Lys Thr
1               5                   10

<210> SEQ ID NO 178
<211> LENGTH: 19
<212> TYPE: PRT
<213> ORGANISM: Homo sapiens

<400> SEQUENCE: 178

Arg Thr Cys Pro Lys Pro Asp Asp Leu Pro Phe Ser Thr Val Val Pro
1               5                   10                  15

Leu Lys Thr

<210> SEQ ID NO 179
<211> LENGTH: 16
<212> TYPE: PRT
<213> ORGANISM: Homo sapiens

<400> SEQUENCE: 179

Arg Val Cys Pro Phe Ala Gly Ile Leu Glu Asn Gly Ala Val Arg Tyr
1               5                   10                  15

<210> SEQ ID NO 180
<211> LENGTH: 14
<212> TYPE: PRT
<213> ORGANISM: Homo sapiens

<400> SEQUENCE: 180

Lys Leu Phe Ala Ala Phe Phe Leu Glu Met Ala Gln Leu His
1               5                   10

<210> SEQ ID NO 181
<211> LENGTH: 12
<212> TYPE: PRT
<213> ORGANISM: Homo sapiens

<400> SEQUENCE: 181

Lys Ser His Leu Ile Ile Ala Gln Val Ala Lys Asn
1               5                   10

<210> SEQ ID NO 182
<211> LENGTH: 14
<212> TYPE: PRT
<213> ORGANISM: Homo sapiens

<400> SEQUENCE: 182

Lys Asn Ala Ile Trp Ile Asp Cys Gly Ile His Ala Arg Glu
1               5                   10

<210> SEQ ID NO 183

<211> LENGTH: 17
<212> TYPE: PRT
<213> ORGANISM: Homo sapiens

<400> SEQUENCE: 183

Arg Glu Ala Leu Ile Gln Phe Leu Glu Gln Val His Gln Gly Ile Lys
1               5                   10                  15

Gly

<210> SEQ ID NO 184
<211> LENGTH: 17
<212> TYPE: PRT
<213> ORGANISM: Homo sapiens

<400> SEQUENCE: 184

Arg Leu Leu Asn Ile Gln Thr Tyr Cys Ala Gly Pro Ala Tyr Leu Lys
1               5                   10                  15

Gly

<210> SEQ ID NO 185
<211> LENGTH: 20
<212> TYPE: PRT
<213> ORGANISM: Homo sapiens

<400> SEQUENCE: 185

Arg Leu Cys Glu Asn Ile Ala Gly His Leu Lys Asp Ala Gln Ile Phe
1               5                   10                  15

Ile Gln Lys Lys
            20

<210> SEQ ID NO 186
<211> LENGTH: 14
<212> TYPE: PRT
<213> ORGANISM: Homo sapiens

<400> SEQUENCE: 186

Lys Ala Glu Thr Gly Asp Lys Val Tyr Val His Leu Lys Asn
1               5                   10

<210> SEQ ID NO 187
<211> LENGTH: 16
<212> TYPE: PRT
<213> ORGANISM: Homo sapiens

<400> SEQUENCE: 187

Lys Ala Gly Leu Gln Ala Phe Phe Gln Val Gln Glu Cys Asn Lys Ser
1               5                   10                  15

<210> SEQ ID NO 188
<211> LENGTH: 16
<212> TYPE: PRT
<213> ORGANISM: Homo sapiens

<400> SEQUENCE: 188

Lys Asp Ile Ala Ser Gly Leu Ile Gly Pro Leu Ile Ile Cys Lys Lys
1               5                   10                  15

<210> SEQ ID NO 189
<211> LENGTH: 13
<212> TYPE: PRT
<213> ORGANISM: Homo sapiens

<400> SEQUENCE: 189

-continued

```
Lys Asp Ile Phe Thr Gly Leu Ile Gly Pro Met Lys Ile
1               5                   10

<210> SEQ ID NO 190
<211> LENGTH: 23
<212> TYPE: PRT
<213> ORGANISM: Homo sapiens

<400> SEQUENCE: 190

Lys Met Tyr Tyr Ser Ala Val Asp Pro Thr Lys Asp Ile Phe Thr Gly
1               5                   10                  15

Leu Ile Gly Pro Met Lys Ile
            20

<210> SEQ ID NO 191
<211> LENGTH: 14
<212> TYPE: PRT
<213> ORGANISM: Homo sapiens

<400> SEQUENCE: 191

Lys Pro Val Trp Leu Gly Phe Leu Gly Pro Ile Ile Lys Ala
1               5                   10

<210> SEQ ID NO 192
<211> LENGTH: 35
<212> TYPE: PRT
<213> ORGANISM: Homo sapiens

<400> SEQUENCE: 192

Arg Ala Asp Asp Lys Val Tyr Pro Gly Glu Gln Tyr Thr Tyr Met Leu
1               5                   10                  15

Leu Ala Thr Glu Glu Gln Ser Pro Gly Glu Gly Asp Gly Asn Cys Val
            20                  25                  30

Thr Arg Ile
        35

<210> SEQ ID NO 193
<211> LENGTH: 40
<212> TYPE: PRT
<213> ORGANISM: Homo sapiens

<400> SEQUENCE: 193

Arg Asp Thr Ala Asn Leu Phe Pro Gln Thr Ser Leu Thr Leu His Met
1               5                   10                  15

Trp Pro Asp Thr Glu Gly Thr Phe Asn Val Glu Cys Leu Thr Thr Asp
            20                  25                  30

His Tyr Thr Gly Gly Met Lys Gln
        35                  40

<210> SEQ ID NO 194
<211> LENGTH: 21
<212> TYPE: PRT
<213> ORGANISM: Homo sapiens

<400> SEQUENCE: 194

Arg Phe Asn Lys Asn Asn Glu Gly Thr Tyr Tyr Ser Pro Asn Tyr Asn
1               5                   10                  15

Pro Gln Ser Arg Ser
            20

<210> SEQ ID NO 195
<211> LENGTH: 37
```

<212> TYPE: PRT
<213> ORGANISM: Homo sapiens

<400> SEQUENCE: 195

Arg Ile Asp Thr Ile Asn Leu Phe Pro Ala Thr Leu Phe Asp Ala Tyr
1               5                   10                  15

Met Val Ala Gln Asn Pro Gly Glu Trp Met Leu Ser Cys Gln Asn Leu
            20                  25                  30

Asn His Leu Lys Ala
        35

<210> SEQ ID NO 196
<211> LENGTH: 25
<212> TYPE: PRT
<213> ORGANISM: Homo sapiens

<400> SEQUENCE: 196

Arg Lys Ala Glu Glu Glu His Leu Gly Ile Leu Gly Pro Gln Leu His
1               5                   10                  15

Ala Asp Val Gly Asp Lys Val Lys Ile
            20                  25

<210> SEQ ID NO 197
<211> LENGTH: 19
<212> TYPE: PRT
<213> ORGANISM: Homo sapiens

<400> SEQUENCE: 197

Arg Thr Thr Ile Glu Lys Pro Val Trp Leu Gly Phe Leu Gly Pro Ile
1               5                   10                  15

Ile Lys Ala

<210> SEQ ID NO 198
<211> LENGTH: 10
<212> TYPE: PRT
<213> ORGANISM: Homo sapiens

<400> SEQUENCE: 198

Arg Phe Trp Thr Ser Phe Phe Pro Lys Val
1               5                   10

<210> SEQ ID NO 199
<211> LENGTH: 19
<212> TYPE: PRT
<213> ORGANISM: Homo sapiens

<400> SEQUENCE: 199

Lys Leu Phe Asp Ser Asp Pro Ile Thr Val Thr Val Pro Val Glu Val
1               5                   10                  15

Ser Arg Lys

<210> SEQ ID NO 200
<211> LENGTH: 14
<212> TYPE: PRT
<213> ORGANISM: Homo sapiens

<400> SEQUENCE: 200

Arg Ala Ser Ser Ile Ile Asp Glu Leu Phe Gln Asp Arg Phe
1               5                   10

<210> SEQ ID NO 201
<211> LENGTH: 16

-continued

```
<212> TYPE: PRT
<213> ORGANISM: Homo sapiens

<400> SEQUENCE: 201

Lys Trp Ile Val Thr Ala Ala His Cys Val Glu Thr Gly Val Lys Ile
1               5                   10                  15

<210> SEQ ID NO 202
<211> LENGTH: 15
<212> TYPE: PRT
<213> ORGANISM: Homo sapiens

<400> SEQUENCE: 202

Arg Phe Ser Leu Val Ser Gly Trp Gly Gln Leu Leu Asp Arg Gly
1               5                   10                  15

<210> SEQ ID NO 203
<211> LENGTH: 13
<212> TYPE: PRT
<213> ORGANISM: Homo sapiens

<400> SEQUENCE: 203

Lys Glu Thr Tyr Asp Phe Asp Ile Ala Val Leu Arg Leu
1               5                   10

<210> SEQ ID NO 204
<211> LENGTH: 19
<212> TYPE: PRT
<213> ORGANISM: Homo sapiens

<400> SEQUENCE: 204

Lys Val Arg Gln Leu Glu Met Glu Ile Gly Gln Leu Asn Val His Tyr
1               5                   10                  15

Leu Arg Asn

<210> SEQ ID NO 205
<211> LENGTH: 9
<212> TYPE: PRT
<213> ORGANISM: Homo sapiens

<400> SEQUENCE: 205

Arg Pro Ala Phe Ser Ala Ile Arg Arg
1               5

<210> SEQ ID NO 206
<211> LENGTH: 24
<212> TYPE: PRT
<213> ORGANISM: Homo sapiens

<400> SEQUENCE: 206

Lys Val Val Thr Phe Cys Asp Tyr Ala Tyr Asn Thr Phe Gln Val Thr
1               5                   10                  15

Thr Gly Gly Met Val Leu Lys Leu
            20

<210> SEQ ID NO 207
<211> LENGTH: 11
<212> TYPE: PRT
<213> ORGANISM: Homo sapiens

<400> SEQUENCE: 207

Lys Phe Gln Ser Val Phe Thr Val Thr Arg Gln
1               5                   10
```

<210> SEQ ID NO 208
<211> LENGTH: 20
<212> TYPE: PRT
<213> ORGANISM: Homo sapiens

<400> SEQUENCE: 208

Lys Thr Leu Asp Glu Phe Thr Ile Ile Gln Asn Leu Gln Pro Gln Tyr
1               5                   10                  15

Gln Phe Arg Asp
            20

<210> SEQ ID NO 209
<211> LENGTH: 19
<212> TYPE: PRT
<213> ORGANISM: Homo sapiens

<400> SEQUENCE: 209

Arg Met Asp Val Phe Ser Gln Asn Met Phe Cys Ala Gly His Pro Ser
1               5                   10                  15

Leu Lys Gln

<210> SEQ ID NO 210
<211> LENGTH: 14
<212> TYPE: PRT
<213> ORGANISM: Homo sapiens

<400> SEQUENCE: 210

Arg Trp Ile Leu Thr Ala Ala His Thr Leu Tyr Pro Lys Glu
1               5                   10

<210> SEQ ID NO 211
<211> LENGTH: 23
<212> TYPE: PRT
<213> ORGANISM: Homo sapiens

<400> SEQUENCE: 211

Lys Phe Tyr Ala Ala Gly Leu Val Ser Trp Gly Pro Gln Cys Gly Thr
1               5                   10                  15

Tyr Gly Leu Tyr Thr Arg Val
            20

<210> SEQ ID NO 212
<211> LENGTH: 11
<212> TYPE: PRT
<213> ORGANISM: Homo sapiens

<400> SEQUENCE: 212

Lys Gly Phe Gln Val Val Val Thr Leu Arg Arg
1               5                   10

<210> SEQ ID NO 213
<211> LENGTH: 19
<212> TYPE: PRT
<213> ORGANISM: Homo sapiens

<400> SEQUENCE: 213

Arg Gly Ala Leu Ile Ser Asp Gln Trp Val Leu Thr Ala Ala His Cys
1               5                   10                  15

Phe Arg Asp

<210> SEQ ID NO 214
<211> LENGTH: 17

```
<212> TYPE: PRT
<213> ORGANISM: Homo sapiens

<400> SEQUENCE: 214

Arg Pro Ile Cys Leu Pro Cys Thr Met Glu Ala Asn Leu Ala Leu Arg
1               5                   10                  15

Arg

<210> SEQ ID NO 215
<211> LENGTH: 26
<212> TYPE: PRT
<213> ORGANISM: Homo sapiens

<400> SEQUENCE: 215

Arg Tyr Tyr Gly Gly Gly Tyr Gly Ser Thr Gln Ala Thr Phe Met Val
1               5                   10                  15

Phe Gln Ala Leu Ala Gln Tyr Gln Lys Asp
            20                  25

<210> SEQ ID NO 216
<211> LENGTH: 13
<212> TYPE: PRT
<213> ORGANISM: Homo sapiens

<400> SEQUENCE: 216

Lys Gly Leu Cys Val Ala Thr Pro Val Gln Leu Arg Val
1               5                   10

<210> SEQ ID NO 217
<211> LENGTH: 21
<212> TYPE: PRT
<213> ORGANISM: Homo sapiens

<400> SEQUENCE: 217

Lys Met Arg Pro Ser Thr Asp Thr Ile Thr Val Met Val Glu Asn Ser
1               5                   10                  15

His Gly Leu Arg Val
            20

<210> SEQ ID NO 218
<211> LENGTH: 23
<212> TYPE: PRT
<213> ORGANISM: Homo sapiens

<400> SEQUENCE: 218

Lys Val Gly Leu Ser Gly Met Ala Ile Ala Asp Val Thr Leu Leu Ser
1               5                   10                  15

Gly Phe His Ala Leu Arg Ala
            20

<210> SEQ ID NO 219
<211> LENGTH: 17
<212> TYPE: PRT
<213> ORGANISM: Homo sapiens

<400> SEQUENCE: 219

Lys Val Leu Ser Leu Ala Gln Glu Gln Val Gly Gly Ser Pro Glu Lys
1               5                   10                  15

Leu

<210> SEQ ID NO 220
<211> LENGTH: 15
```

```
<212> TYPE: PRT
<213> ORGANISM: Homo sapiens

<400> SEQUENCE: 220

Arg Glu Met Ser Gly Ser Pro Ala Ser Gly Ile Pro Val Lys Val
1               5                   10                  15

<210> SEQ ID NO 221
<211> LENGTH: 20
<212> TYPE: PRT
<213> ORGANISM: Homo sapiens

<400> SEQUENCE: 221

Arg Gly Cys Gly Glu Gln Thr Met Ile Tyr Leu Ala Pro Thr Leu Ala
1               5                   10                  15

Ala Ser Arg Tyr
            20

<210> SEQ ID NO 222
<211> LENGTH: 11
<212> TYPE: PRT
<213> ORGANISM: Homo sapiens

<400> SEQUENCE: 222

Arg Gly Leu Gln Asp Glu Asp Gly Tyr Arg Met
1               5                   10

<210> SEQ ID NO 223
<211> LENGTH: 13
<212> TYPE: PRT
<213> ORGANISM: Homo sapiens

<400> SEQUENCE: 223

Arg Gly Gln Ile Val Phe Met Asn Arg Glu Pro Lys Arg
1               5                   10

<210> SEQ ID NO 224
<211> LENGTH: 29
<212> TYPE: PRT
<213> ORGANISM: Homo sapiens

<400> SEQUENCE: 224

Arg Lys Lys Glu Val Tyr Met Pro Ser Ser Ile Phe Gln Asp Asp Phe
1               5                   10                  15

Val Ile Pro Asp Ile Ser Glu Pro Gly Thr Trp Lys Ile
            20                  25

<210> SEQ ID NO 225
<211> LENGTH: 8
<212> TYPE: PRT
<213> ORGANISM: Homo sapiens

<400> SEQUENCE: 225

Arg Leu Pro Met Ser Val Arg Arg
1               5

<210> SEQ ID NO 226
<211> LENGTH: 20
<212> TYPE: PRT
<213> ORGANISM: Homo sapiens

<400> SEQUENCE: 226

Arg Leu Thr Val Ala Ala Pro Pro Ser Gly Gly Pro Gly Phe Leu Ser
1               5                   10                  15
```

```
Ile Glu Arg Pro
          20

<210> SEQ ID NO 227
<211> LENGTH: 7
<212> TYPE: PRT
<213> ORGANISM: Homo sapiens

<400> SEQUENCE: 227

Arg Asn Phe Leu Val Arg Ala
1               5

<210> SEQ ID NO 228
<211> LENGTH: 34
<212> TYPE: PRT
<213> ORGANISM: Homo sapiens

<400> SEQUENCE: 228

Arg Asn Gly Glu Ser Val Lys Leu His Leu Glu Thr Asp Ser Leu Ala
1               5                   10                  15

Leu Val Ala Leu Gly Ala Leu Asp Thr Ala Leu Tyr Ala Ala Gly Ser
          20                  25                  30

Lys Ser

<210> SEQ ID NO 229
<211> LENGTH: 11
<212> TYPE: PRT
<213> ORGANISM: Homo sapiens

<400> SEQUENCE: 229

Arg Gln Gly Ser Phe Gln Gly Gly Phe Arg Ser
1               5                   10

<210> SEQ ID NO 230
<211> LENGTH: 25
<212> TYPE: PRT
<213> ORGANISM: Homo sapiens

<400> SEQUENCE: 230

Arg Thr Leu Glu Ile Pro Gly Asn Ser Asp Pro Asn Met Ile Pro Asp
1               5                   10                  15

Gly Asp Phe Asn Ser Tyr Val Arg Val
          20                  25

<210> SEQ ID NO 231
<211> LENGTH: 28
<212> TYPE: PRT
<213> ORGANISM: Homo sapiens

<400> SEQUENCE: 231

Arg Val Thr Ala Ser Asp Pro Leu Asp Thr Leu Gly Ser Glu Gly Ala
1               5                   10                  15

Leu Ser Pro Gly Gly Val Ala Ser Leu Leu Arg Leu
          20                  25

<210> SEQ ID NO 232
<211> LENGTH: 18
<212> TYPE: PRT
<213> ORGANISM: Homo sapiens

<400> SEQUENCE: 232

Arg Tyr Leu Asp Lys Thr Glu Gln Trp Ser Thr Leu Pro Pro Glu Thr
```

-continued

```
1               5               10              15

Lys Asp

<210> SEQ ID NO 233
<211> LENGTH: 32
<212> TYPE: PRT
<213> ORGANISM: Homo sapiens

<400> SEQUENCE: 233

Lys Ala Asp Asn Phe Leu Leu Glu Asn Thr Leu Pro Ala Gln Ser Thr
1               5               10              15

Phe Thr Leu Ala Ile Ser Ala Tyr Ala Leu Ser Leu Gly Asp Lys Thr
            20              25              30

<210> SEQ ID NO 234
<211> LENGTH: 18
<212> TYPE: PRT
<213> ORGANISM: Homo sapiens

<400> SEQUENCE: 234

Lys Ala Leu Val Glu Gly Val Asp Gln Leu Phe Thr Asp Tyr Gln Ile
1               5               10              15

Lys Asp

<210> SEQ ID NO 235
<211> LENGTH: 22
<212> TYPE: PRT
<213> ORGANISM: Homo sapiens

<400> SEQUENCE: 235

Lys Asp Gly His Val Ile Leu Gln Leu Asn Ser Ile Pro Ser Ser Asp
1               5               10              15

Phe Leu Cys Val Arg Phe
            20

<210> SEQ ID NO 236
<211> LENGTH: 16
<212> TYPE: PRT
<213> ORGANISM: Homo sapiens

<400> SEQUENCE: 236

Lys Asp Val Phe Leu Glu Met Asn Ile Pro Tyr Ser Val Val Arg Gly
1               5               10              15

<210> SEQ ID NO 237
<211> LENGTH: 15
<212> TYPE: PRT
<213> ORGANISM: Homo sapiens

<400> SEQUENCE: 237

Lys Glu Phe Pro Tyr Arg Ile Pro Leu Asp Leu Val Pro Lys Thr
1               5               10              15

<210> SEQ ID NO 238
<211> LENGTH: 14
<212> TYPE: PRT
<213> ORGANISM: Homo sapiens

<400> SEQUENCE: 238

Lys Phe Gln Asn Ser Ala Ile Leu Thr Ile Gln Pro Lys Gln
1               5               10
```

-continued

```
<210> SEQ ID NO 239
<211> LENGTH: 19
<212> TYPE: PRT
<213> ORGANISM: Homo sapiens

<400> SEQUENCE: 239

Lys Val Phe Lys Asp Val Phe Leu Glu Met Asn Ile Pro Tyr Ser Val
1               5                   10                  15

Val Arg Gly

<210> SEQ ID NO 240
<211> LENGTH: 9
<212> TYPE: PRT
<213> ORGANISM: Homo sapiens

<400> SEQUENCE: 240

Arg Val Phe Gln Phe Leu Glu Lys Ser
1               5

<210> SEQ ID NO 241
<211> LENGTH: 12
<212> TYPE: PRT
<213> ORGANISM: Homo sapiens

<400> SEQUENCE: 241

Lys Asp Leu His Leu Ser Asp Val Phe Leu Lys Ala
1               5                   10

<210> SEQ ID NO 242
<211> LENGTH: 21
<212> TYPE: PRT
<213> ORGANISM: Homo sapiens

<400> SEQUENCE: 242

Arg Thr Glu Cys Ile Lys Pro Val Val Gln Glu Val Leu Thr Ile Thr
1               5                   10                  15

Pro Phe Gln Arg Leu
            20

<210> SEQ ID NO 243
<211> LENGTH: 11
<212> TYPE: PRT
<213> ORGANISM: Homo sapiens

<400> SEQUENCE: 243

Lys Ser Ser Gly Trp His Phe Val Val Lys Phe
1               5                   10

<210> SEQ ID NO 244
<211> LENGTH: 10
<212> TYPE: PRT
<213> ORGANISM: Homo sapiens

<400> SEQUENCE: 244

Arg Ile Leu Pro Leu Thr Val Cys Lys Met
1               5                   10

<210> SEQ ID NO 245
<211> LENGTH: 15
<212> TYPE: PRT
<213> ORGANISM: Homo sapiens

<400> SEQUENCE: 245

Arg Ala Leu Asp Gln Tyr Leu Met Glu Phe Asn Ala Cys Arg Cys
```

-continued

```
1               5              10             15

<210> SEQ ID NO 246
<211> LENGTH: 19
<212> TYPE: PRT
<213> ORGANISM: Homo sapiens

<400> SEQUENCE: 246

Lys Tyr Gly Phe Cys Glu Ala Ala Asp Gln Phe His Val Leu Asp Glu
1               5              10             15

Val Arg Arg

<210> SEQ ID NO 247
<211> LENGTH: 15
<212> TYPE: PRT
<213> ORGANISM: Homo sapiens

<400> SEQUENCE: 247

Arg Ala Ile Glu Asp Tyr Ile Asn Glu Phe Ser Val Arg Lys Cys
1               5              10             15

<210> SEQ ID NO 248
<211> LENGTH: 31
<212> TYPE: PRT
<213> ORGANISM: Homo sapiens

<400> SEQUENCE: 248

Arg Thr Ala Gly Tyr Gly Ile Asn Ile Leu Gly Met Asp Pro Leu Ser
1               5              10             15

Thr Pro Phe Asp Asn Glu Phe Tyr Asn Gly Leu Cys Asn Arg Asp
            20             25             30

<210> SEQ ID NO 249
<211> LENGTH: 12
<212> TYPE: PRT
<213> ORGANISM: Homo sapiens

<400> SEQUENCE: 249

Lys Ala Leu Phe Val Ser Glu Glu Glu Lys Lys Leu
1               5              10

<210> SEQ ID NO 250
<211> LENGTH: 10
<212> TYPE: PRT
<213> ORGANISM: Homo sapiens

<400> SEQUENCE: 250

Lys Cys Leu Val Asn Leu Ile Glu Lys Val
1               5              10

<210> SEQ ID NO 251
<211> LENGTH: 18
<212> TYPE: PRT
<213> ORGANISM: Homo sapiens

<400> SEQUENCE: 251

Lys Glu Ala Gly Ile Pro Glu Phe Tyr Asp Tyr Asp Val Ala Leu Ile
1               5              10             15

Lys Leu

<210> SEQ ID NO 252
<211> LENGTH: 16
<212> TYPE: PRT
```

-continued

```
<213> ORGANISM: Homo sapiens

<400> SEQUENCE: 252

Lys Val Ser Glu Ala Asp Ser Ser Asn Ala Asp Trp Val Thr Lys Gln
1               5                   10                  15

<210> SEQ ID NO 253
<211> LENGTH: 20
<212> TYPE: PRT
<213> ORGANISM: Homo sapiens

<400> SEQUENCE: 253

Lys Tyr Gly Gln Thr Ile Arg Pro Ile Cys Leu Pro Cys Thr Glu Gly
1               5                   10                  15

Thr Thr Arg Ala
            20

<210> SEQ ID NO 254
<211> LENGTH: 20
<212> TYPE: PRT
<213> ORGANISM: Homo sapiens

<400> SEQUENCE: 254

Arg Asp Leu Glu Ile Glu Val Val Leu Phe His Pro Asn Tyr Asn Ile
1               5                   10                  15

Asn Gly Lys Lys
            20

<210> SEQ ID NO 255
<211> LENGTH: 19
<212> TYPE: PRT
<213> ORGANISM: Homo sapiens

<400> SEQUENCE: 255

Arg Phe Leu Cys Thr Gly Gly Val Ser Pro Tyr Ala Asp Pro Asn Thr
1               5                   10                  15

Cys Arg Gly

<210> SEQ ID NO 256
<211> LENGTH: 13
<212> TYPE: PRT
<213> ORGANISM: Homo sapiens

<400> SEQUENCE: 256

Lys Asp Gly Trp Ser Ala Gln Pro Thr Cys Ile Lys Ser
1               5                   10

<210> SEQ ID NO 257
<211> LENGTH: 14
<212> TYPE: PRT
<213> ORGANISM: Homo sapiens

<400> SEQUENCE: 257

Lys Glu Gly Trp Ile His Thr Val Cys Ile Asn Gly Arg Trp
1               5                   10

<210> SEQ ID NO 258
<211> LENGTH: 20
<212> TYPE: PRT
<213> ORGANISM: Homo sapiens

<400> SEQUENCE: 258

Lys Thr Asp Cys Leu Ser Leu Pro Ser Phe Glu Asn Ala Ile Pro Met
```

```
1               5               10              15

Gly Glu Lys Lys
            20

<210> SEQ ID NO 259
<211> LENGTH: 20
<212> TYPE: PRT
<213> ORGANISM: Homo sapiens

<400> SEQUENCE: 259

Arg Asp Thr Ser Cys Val Asn Pro Pro Thr Val Gln Asn Ala Tyr Ile
1               5               10              15

Val Ser Arg Gln
            20

<210> SEQ ID NO 260
<211> LENGTH: 13
<212> TYPE: PRT
<213> ORGANISM: Homo sapiens

<400> SEQUENCE: 260

Lys Cys Thr Ser Thr Gly Trp Ile Pro Ala Pro Arg Cys
1               5               10

<210> SEQ ID NO 261
<211> LENGTH: 10
<212> TYPE: PRT
<213> ORGANISM: Homo sapiens

<400> SEQUENCE: 261

Lys Ile Ile Tyr Lys Glu Asn Glu Arg Phe
1               5               10

<210> SEQ ID NO 262
<211> LENGTH: 21
<212> TYPE: PRT
<213> ORGANISM: Homo sapiens

<400> SEQUENCE: 262

Lys Ile Val Ser Ser Ala Met Glu Pro Asp Arg Glu Tyr His Phe Gly
1               5               10              15

Gln Ala Val Arg Phe
            20

<210> SEQ ID NO 263
<211> LENGTH: 14
<212> TYPE: PRT
<213> ORGANISM: Homo sapiens

<400> SEQUENCE: 263

Arg Cys Thr Leu Lys Pro Cys Asp Tyr Pro Asp Ile Lys His
1               5               10

<210> SEQ ID NO 264
<211> LENGTH: 13
<212> TYPE: PRT
<213> ORGANISM: Homo sapiens

<400> SEQUENCE: 264

Arg Lys Gly Glu Trp Val Ala Leu Asn Pro Leu Arg Lys
1               5               10

<210> SEQ ID NO 265
```

-continued

```
<211> LENGTH: 14
<212> TYPE: PRT
<213> ORGANISM: Homo sapiens

<400> SEQUENCE: 265

Arg Lys Gly Glu Trp Val Ala Leu Asn Pro Leu Arg Lys Cys
1               5                   10

<210> SEQ ID NO 266
<211> LENGTH: 12
<212> TYPE: PRT
<213> ORGANISM: Homo sapiens

<400> SEQUENCE: 266

Arg Arg Pro Tyr Phe Pro Val Ala Val Gly Lys Tyr
1               5                   10

<210> SEQ ID NO 267
<211> LENGTH: 13
<212> TYPE: PRT
<213> ORGANISM: Homo sapiens

<400> SEQUENCE: 267

Arg Glu Ile Met Glu Asn Tyr Asn Ile Ala Leu Arg Trp
1               5                   10

<210> SEQ ID NO 268
<211> LENGTH: 27
<212> TYPE: PRT
<213> ORGANISM: Homo sapiens

<400> SEQUENCE: 268

Lys Asp Ala Ser Gly Ile Thr Cys Gly Gly Ile Tyr Ile Gly Gly Cys
1               5                   10                  15

Trp Ile Leu Thr Ala Ala His Cys Leu Arg Ala
            20                  25

<210> SEQ ID NO 269
<211> LENGTH: 16
<212> TYPE: PRT
<213> ORGANISM: Homo sapiens

<400> SEQUENCE: 269

Lys Val Ala Asn Tyr Phe Asp Trp Ile Ser Tyr His Val Gly Arg Pro
1               5                   10                  15

<210> SEQ ID NO 270
<211> LENGTH: 24
<212> TYPE: PRT
<213> ORGANISM: Homo sapiens

<400> SEQUENCE: 270

Arg Ile Ile Phe His Glu Asn Tyr Asn Ala Gly Thr Tyr Gln Asn Asp
1               5                   10                  15

Ile Ala Leu Ile Glu Met Lys Lys
            20

<210> SEQ ID NO 271
<211> LENGTH: 18
<212> TYPE: PRT
<213> ORGANISM: Homo sapiens

<400> SEQUENCE: 271

Arg Tyr Gln Ile Trp Thr Thr Val Val Asp Trp Ile His Pro Asp Leu
```

-continued

```
1               5               10              15

Lys Arg

<210> SEQ ID NO 272
<211> LENGTH: 8
<212> TYPE: PRT
<213> ORGANISM: Homo sapiens

<400> SEQUENCE: 272

Lys Ile Ser Asn Leu Leu Lys Phe
1               5

<210> SEQ ID NO 273
<211> LENGTH: 18
<212> TYPE: PRT
<213> ORGANISM: Homo sapiens

<400> SEQUENCE: 273

Arg Trp Ser Ala Gly Leu Thr Ser Ser Gln Val Asp Leu Tyr Ile Pro
1               5               10              15

Lys Val

<210> SEQ ID NO 274
<211> LENGTH: 16
<212> TYPE: PRT
<213> ORGANISM: Homo sapiens

<400> SEQUENCE: 274

Lys Tyr Glu Val Gln Gly Glu Val Phe Thr Lys Pro Gln Leu Trp Pro
1               5               10              15

<210> SEQ ID NO 275
<211> LENGTH: 13
<212> TYPE: PRT
<213> ORGANISM: Homo sapiens

<400> SEQUENCE: 275

Arg His Val Leu Ala Ala Trp Ala Leu Gly Ala Lys Ala
1               5               10

<210> SEQ ID NO 276
<211> LENGTH: 16
<212> TYPE: PRT
<213> ORGANISM: Homo sapiens

<400> SEQUENCE: 276

Arg Ala Gly Leu Arg Tyr Val Cys Leu Ala Glu Pro Ala Glu Arg Arg
1               5               10              15

<210> SEQ ID NO 277
<211> LENGTH: 19
<212> TYPE: PRT
<213> ORGANISM: Homo sapiens

<400> SEQUENCE: 277

Arg Phe Thr Gln Leu Cys Val Lys Gly Gly Gly Gly Gly Gly Asn Gly
1               5               10              15

Ile Arg Asp

<210> SEQ ID NO 278
<211> LENGTH: 19
<212> TYPE: PRT
<213> ORGANISM: Homo sapiens
```

<400> SEQUENCE: 278

Arg Val Gln Leu Gly Pro Tyr Gln Pro Gly Arg Pro Ala Ala Cys Asp
1               5                   10                  15

Leu Arg Glu

<210> SEQ ID NO 279
<211> LENGTH: 24
<212> TYPE: PRT
<213> ORGANISM: Homo sapiens

<400> SEQUENCE: 279

Arg Gly Gly Leu Gly Ser Leu Phe Tyr Leu Thr Leu Asp Val Leu Glu
1               5                   10                  15

Thr Asp Cys His Val Leu Arg Lys
            20

<210> SEQ ID NO 280
<211> LENGTH: 23
<212> TYPE: PRT
<213> ORGANISM: Homo sapiens

<400> SEQUENCE: 280

Arg Glu Leu Leu Ser Gln Gly Ala Thr Leu Ser Gly Trp Tyr His Leu
1               5                   10                  15

Cys Leu Pro Glu Gly Arg Ala
            20

<210> SEQ ID NO 281
<211> LENGTH: 16
<212> TYPE: PRT
<213> ORGANISM: Homo sapiens

<400> SEQUENCE: 281

Lys Lys Thr Thr Asp Met Ile Leu Asn Glu Ile Lys Gln Gly Lys Phe
1               5                   10                  15

<210> SEQ ID NO 282
<211> LENGTH: 27
<212> TYPE: PRT
<213> ORGANISM: Homo sapiens

<400> SEQUENCE: 282

Lys Asn Trp Arg Asp Pro Asp Gln Thr Asp Gly Leu Gly Leu Ser Tyr
1               5                   10                  15

Leu Ser Ser His Ile Ala Asn Val Glu Arg Val
            20                  25

<210> SEQ ID NO 283
<211> LENGTH: 20
<212> TYPE: PRT
<213> ORGANISM: Homo sapiens

<400> SEQUENCE: 283

Lys Thr Pro Ser Ala Ala Tyr Leu Trp Val Gly Thr Gly Ala Ser Glu
1               5                   10                  15

Ala Glu Lys Thr
            20

<210> SEQ ID NO 284
<211> LENGTH: 29
<212> TYPE: PRT

-continued

<213> ORGANISM: Homo sapiens

<400> SEQUENCE: 284

Arg Val Glu Lys Phe Asp Leu Val Pro Val Pro Thr Asn Leu Tyr Gly
1               5                   10                  15

Asp Phe Phe Thr Gly Asp Ala Tyr Val Ile Leu Lys Thr
            20                  25

<210> SEQ ID NO 285
<211> LENGTH: 30
<212> TYPE: PRT
<213> ORGANISM: Homo sapiens

<400> SEQUENCE: 285

Arg Val Pro Phe Asp Ala Ala Thr Leu His Thr Ser Thr Ala Met Ala
1               5                   10                  15

Ala Gln His Gly Met Asp Asp Asp Gly Thr Gly Gln Lys Gln
            20                  25                  30

<210> SEQ ID NO 286
<211> LENGTH: 8
<212> TYPE: PRT
<213> ORGANISM: Homo sapiens

<400> SEQUENCE: 286

Lys Phe Tyr Thr Phe Leu Lys Asn
1               5

<210> SEQ ID NO 287
<211> LENGTH: 14
<212> TYPE: PRT
<213> ORGANISM: Homo sapiens

<400> SEQUENCE: 287

Lys Gly Asp Lys Val Trp Val Tyr Pro Pro Glu Lys Lys Glu
1               5                   10

<210> SEQ ID NO 288
<211> LENGTH: 23
<212> TYPE: PRT
<213> ORGANISM: Homo sapiens

<400> SEQUENCE: 288

Lys Leu Leu Gln Asp Glu Phe Pro Gly Ile Pro Ser Pro Leu Asp Ala
1               5                   10                  15

Ala Val Glu Cys His Arg Gly
            20

<210> SEQ ID NO 289
<211> LENGTH: 18
<212> TYPE: PRT
<213> ORGANISM: Homo sapiens

<400> SEQUENCE: 289

Lys Ser Gly Ala Gln Ala Thr Trp Thr Glu Leu Pro Trp Pro His Glu
1               5                   10                  15

Lys Val

<210> SEQ ID NO 290
<211> LENGTH: 27
<212> TYPE: PRT
<213> ORGANISM: Homo sapiens -continued

<400> SEQUENCE: 290

Lys Ser Gly Ala Gln Ala Thr Trp Thr Glu Leu Pro Trp Pro His Glu
1               5                   10                  15

Lys Val Asp Gly Ala Leu Cys Met Glu Lys Ser
            20                  25

<210> SEQ ID NO 291
<211> LENGTH: 11
<212> TYPE: PRT
<213> ORGANISM: Homo sapiens

<400> SEQUENCE: 291

Lys Val Asp Gly Ala Leu Cys Met Glu Lys Ser
1               5                   10

<210> SEQ ID NO 292
<211> LENGTH: 11
<212> TYPE: PRT
<213> ORGANISM: Homo sapiens

<400> SEQUENCE: 292

Arg Asp Tyr Phe Met Pro Cys Pro Gly Arg Gly
1               5                   10

<210> SEQ ID NO 293
<211> LENGTH: 14
<212> TYPE: PRT
<213> ORGANISM: Homo sapiens

<400> SEQUENCE: 293

Arg Glu Trp Phe Trp Asp Leu Ala Thr Gly Thr Met Lys Glu
1               5                   10

<210> SEQ ID NO 294
<211> LENGTH: 12
<212> TYPE: PRT
<213> ORGANISM: Homo sapiens

<400> SEQUENCE: 294

Arg Gln Gly His Asn Ser Val Phe Leu Ile Lys Gly
1               5                   10

<210> SEQ ID NO 295
<211> LENGTH: 32
<212> TYPE: PRT
<213> ORGANISM: Homo sapiens

<400> SEQUENCE: 295

Lys His Gln Gly Thr Ile Thr Val Asn Glu Glu Gly Thr Gln Ala Thr
1               5                   10                  15

Thr Val Thr Thr Val Gly Phe Met Pro Leu Ser Thr Gln Val Arg Phe
            20                  25                  30

<210> SEQ ID NO 296
<211> LENGTH: 13
<212> TYPE: PRT
<213> ORGANISM: Homo sapiens

<400> SEQUENCE: 296

Lys Tyr Glu Ile Thr Thr Ile His Asn Leu Phe Arg Lys
1               5                   10

<210> SEQ ID NO 297

```
<211> LENGTH: 9
<212> TYPE: PRT
<213> ORGANISM: Homo sapiens

<400> SEQUENCE: 297

Arg Leu Asn Ile Leu Asn Ala Lys Phe
1               5

<210> SEQ ID NO 298
<211> LENGTH: 9
<212> TYPE: PRT
<213> ORGANISM: Homo sapiens

<400> SEQUENCE: 298

Arg Asn Phe Gly Tyr Thr Leu Arg Ser
1               5

<210> SEQ ID NO 299
<211> LENGTH: 21
<212> TYPE: PRT
<213> ORGANISM: Homo sapiens

<400> SEQUENCE: 299

Arg Val Gln Leu Ser Pro Asp Leu Leu Ala Thr Leu Pro Glu Pro Ala
1               5                   10                  15

Ser Pro Gly Arg Gln
            20

<210> SEQ ID NO 300
<211> LENGTH: 11
<212> TYPE: PRT
<213> ORGANISM: Homo sapiens

<400> SEQUENCE: 300

Arg Asp Gly Tyr Leu Phe Gln Leu Leu Arg Ile
1               5                   10

<210> SEQ ID NO 301
<211> LENGTH: 8
<212> TYPE: PRT
<213> ORGANISM: Homo sapiens

<400> SEQUENCE: 301

Lys Phe Leu Asn Trp Ile Lys Ala
1               5

<210> SEQ ID NO 302
<211> LENGTH: 15
<212> TYPE: PRT
<213> ORGANISM: Homo sapiens

<400> SEQUENCE: 302

Lys Leu Lys Pro Val Asp Gly His Cys Ala Leu Glu Ser Lys Tyr
1               5                   10                  15

<210> SEQ ID NO 303
<211> LENGTH: 12
<212> TYPE: PRT
<213> ORGANISM: Homo sapiens

<400> SEQUENCE: 303

Lys Arg Pro Gly Val Tyr Thr Gln Val Thr Lys Phe
1               5                   10
```

<210> SEQ ID NO 304
<211> LENGTH: 23
<212> TYPE: PRT
<213> ORGANISM: Homo sapiens

<400> SEQUENCE: 304

Lys Ala Gly Ala Asp Thr His Gly Arg Leu Leu Gln Gly Asn Ile Cys
1               5                   10                  15

Asn Asp Ala Val Thr Lys Ala
            20

<210> SEQ ID NO 305
<211> LENGTH: 16
<212> TYPE: PRT
<213> ORGANISM: Homo sapiens

<400> SEQUENCE: 305

Lys Lys Ile Ile Glu Lys Met Ala Thr Phe Glu Ile Asp Glu Lys Arg
1               5                   10                  15

<210> SEQ ID NO 306
<211> LENGTH: 24
<212> TYPE: PRT
<213> ORGANISM: Homo sapiens

<400> SEQUENCE: 306

Arg Ser Phe Glu Gly Leu Gly Gln Leu Glu Val Leu Thr Leu Asp His
1               5                   10                  15

Asn Gln Leu Gln Glu Val Lys Ala
            20

<210> SEQ ID NO 307
<211> LENGTH: 11
<212> TYPE: PRT
<213> ORGANISM: Homo sapiens

<400> SEQUENCE: 307

Lys Glu Leu Ala Ala Gln Thr Ile Lys Lys Ser
1               5                   10

<210> SEQ ID NO 308
<211> LENGTH: 21
<212> TYPE: PRT
<213> ORGANISM: Homo sapiens

<400> SEQUENCE: 308

Lys Gly Ser Leu Val Gln Ala Ser Glu Ala Asn Leu Gln Ala Ala Gln
1               5                   10                  15

Asp Phe Val Arg Gly
            20

<210> SEQ ID NO 309
<211> LENGTH: 22
<212> TYPE: PRT
<213> ORGANISM: Homo sapiens

<400> SEQUENCE: 309

Lys Gln Leu Val His His Phe Glu Ile Asp Val Asp Ile Phe Glu Pro
1               5                   10                  15

Gln Gly Ile Ser Lys Leu
            20

<210> SEQ ID NO 310

```
<211> LENGTH: 15
<212> TYPE: PRT
<213> ORGANISM: Homo sapiens

<400> SEQUENCE: 310

Lys Gln Tyr Tyr Glu Gly Ser Glu Ile Val Val Ala Gly Arg Ile
1               5                   10                  15

<210> SEQ ID NO 311
<211> LENGTH: 33
<212> TYPE: PRT
<213> ORGANISM: Homo sapiens

<400> SEQUENCE: 311

Arg Glu Val Ala Phe Asp Leu Glu Ile Pro Lys Thr Ala Phe Ile Ser
1               5                   10                  15

Asp Phe Ala Val Thr Ala Asp Gly Asn Ala Phe Ile Gly Asp Ile Lys
            20                  25                  30

Asp

<210> SEQ ID NO 312
<211> LENGTH: 30
<212> TYPE: PRT
<213> ORGANISM: Homo sapiens

<400> SEQUENCE: 312

Arg Gly Met Ala Asp Gln Asp Gly Leu Lys Pro Thr Ile Asp Lys Pro
1               5                   10                  15

Ser Glu Asp Ser Pro Pro Leu Glu Met Leu Gly Pro Arg Arg
            20                  25                  30

<210> SEQ ID NO 313
<211> LENGTH: 41
<212> TYPE: PRT
<213> ORGANISM: Homo sapiens

<400> SEQUENCE: 313

Lys Phe Asp Pro Ala Lys Leu Asp Gln Ile Glu Ser Val Ile Thr Ala
1               5                   10                  15

Thr Ser Ala Asn Thr Gln Leu Val Leu Glu Thr Leu Ala Gln Met Asp
            20                  25                  30

Asp Leu Gln Asp Phe Leu Ser Lys Asp
        35                  40

<210> SEQ ID NO 314
<211> LENGTH: 14
<212> TYPE: PRT
<213> ORGANISM: Homo sapiens

<400> SEQUENCE: 314

Lys Lys Phe Tyr Asn Gln Val Ser Thr Pro Leu Leu Arg Asn
1               5                   10

<210> SEQ ID NO 315
<211> LENGTH: 18
<212> TYPE: PRT
<213> ORGANISM: Homo sapiens

<400> SEQUENCE: 315

Lys Asn Ile Leu Phe Val Ile Asp Val Ser Gly Ser Met Trp Gly Val
1               5                   10                  15

Lys Met
```

-continued

<210> SEQ ID NO 316
<211> LENGTH: 10
<212> TYPE: PRT
<213> ORGANISM: Homo sapiens

<400> SEQUENCE: 316

Arg Lys Leu Gly Ser Tyr Glu His Arg Ile
1               5                   10

<210> SEQ ID NO 317
<211> LENGTH: 13
<212> TYPE: PRT
<213> ORGANISM: Homo sapiens

<400> SEQUENCE: 317

Arg Leu Ser Asn Glu Asn His Gly Ile Ala Gln Arg Ile
1               5                   10

<210> SEQ ID NO 318
<211> LENGTH: 11
<212> TYPE: PRT
<213> ORGANISM: Homo sapiens

<400> SEQUENCE: 318

Arg Met Ala Thr Thr Met Ile Gln Ser Lys Val
1               5                   10

<210> SEQ ID NO 319
<211> LENGTH: 30
<212> TYPE: PRT
<213> ORGANISM: Homo sapiens

<400> SEQUENCE: 319

Arg Ser Ile Leu Gln Met Ser Leu Asp His His Ile Val Thr Pro Leu
1               5                   10                  15

Thr Ser Leu Val Ile Glu Asn Glu Ala Gly Asp Glu Arg Met
            20                  25                  30

<210> SEQ ID NO 320
<211> LENGTH: 12
<212> TYPE: PRT
<213> ORGANISM: Homo sapiens

<400> SEQUENCE: 320

Arg Thr Glu Val Asn Val Leu Pro Gly Ala Lys Val
1               5                   10

<210> SEQ ID NO 321
<211> LENGTH: 10
<212> TYPE: PRT
<213> ORGANISM: Homo sapiens

<400> SEQUENCE: 321

Lys Asn Val Val Phe Val Ile Asp Lys Ser
1               5                   10

<210> SEQ ID NO 322
<211> LENGTH: 15
<212> TYPE: PRT
<213> ORGANISM: Homo sapiens

<400> SEQUENCE: 322

Lys Trp Lys Glu Thr Leu Phe Ser Val Met Pro Gly Leu Lys Met

-continued

```
1              5              10             15
```

<210> SEQ ID NO 323
<211> LENGTH: 11
<212> TYPE: PRT
<213> ORGANISM: Homo sapiens

<400> SEQUENCE: 323

```
Lys Tyr Ile Phe His Asn Phe Met Glu Arg Leu
1              5              10
```

<210> SEQ ID NO 324
<211> LENGTH: 11
<212> TYPE: PRT
<213> ORGANISM: Homo sapiens

<400> SEQUENCE: 324

```
Arg Phe Ala His Thr Val Val Thr Ser Arg Val
1              5              10
```

<210> SEQ ID NO 325
<211> LENGTH: 12
<212> TYPE: PRT
<213> ORGANISM: Homo sapiens

<400> SEQUENCE: 325

```
Arg Phe Lys Pro Thr Leu Ser Gln Gln Gln Lys Ser
1              5              10
```

<210> SEQ ID NO 326
<211> LENGTH: 46
<212> TYPE: PRT
<213> ORGANISM: Homo sapiens

<400> SEQUENCE: 326

```
Arg Ile His Glu Asp Ser Asp Ser Ala Leu Gln Leu Gln Asp Phe Tyr
1              5              10             15

Gln Glu Val Ala Asn Pro Leu Leu Thr Ala Val Thr Phe Glu Tyr Pro
               20             25             30

Ser Asn Ala Val Glu Glu Val Thr Gln Asn Asn Phe Arg Leu
        35             40             45
```

<210> SEQ ID NO 327
<211> LENGTH: 13
<212> TYPE: PRT
<213> ORGANISM: Homo sapiens

<400> SEQUENCE: 327

```
Arg Met Asn Phe Arg Pro Gly Val Leu Ser Ser Arg Gln
1              5              10
```

<210> SEQ ID NO 328
<211> LENGTH: 13
<212> TYPE: PRT
<213> ORGANISM: Homo sapiens

<400> SEQUENCE: 328

```
Arg Asn Val His Ser Ala Gly Ala Ala Gly Ser Arg Met
1              5              10
```

<210> SEQ ID NO 329
<211> LENGTH: 12
<212> TYPE: PRT
<213> ORGANISM: Homo sapiens

<400> SEQUENCE: 329

Arg Asn Val His Ser Gly Ser Thr Phe Phe Lys Tyr
1               5                   10

<210> SEQ ID NO 330
<211> LENGTH: 12
<212> TYPE: PRT
<213> ORGANISM: Homo sapiens

<400> SEQUENCE: 330

Arg Arg Leu Gly Val Tyr Glu Leu Leu Leu Lys Val
1               5                   10

<210> SEQ ID NO 331
<211> LENGTH: 10
<212> TYPE: PRT
<213> ORGANISM: Homo sapiens

<400> SEQUENCE: 331

Lys Lys Leu Glu Leu His Leu Pro Lys Phe
1               5                   10

<210> SEQ ID NO 332
<211> LENGTH: 15
<212> TYPE: PRT
<213> ORGANISM: Homo sapiens

<400> SEQUENCE: 332

Arg Glu Ile Glu Glu Val Leu Thr Pro Glu Met Leu Met Arg Trp
1               5                   10                  15

<210> SEQ ID NO 333
<211> LENGTH: 15
<212> TYPE: PRT
<213> ORGANISM: Homo sapiens

<400> SEQUENCE: 333

Lys Ala Ala Thr Gly Glu Cys Thr Ala Thr Val Gly Lys Arg Ser
1               5                   10                  15

<210> SEQ ID NO 334
<211> LENGTH: 20
<212> TYPE: PRT
<213> ORGANISM: Homo sapiens

<400> SEQUENCE: 334

Lys Leu Gly Gln Ser Leu Asp Cys Asn Ala Glu Val Tyr Val Val Pro
1               5                   10                  15

Trp Glu Lys Lys
            20

<210> SEQ ID NO 335
<211> LENGTH: 17
<212> TYPE: PRT
<213> ORGANISM: Homo sapiens

<400> SEQUENCE: 335

Lys Tyr Asn Ser Gln Asn Gln Ser Asn Asn Gln Phe Val Leu Tyr Arg
1               5                   10                  15

Ile

<210> SEQ ID NO 336

```
<211> LENGTH: 11
<212> TYPE: PRT
<213> ORGANISM: Homo sapiens

<400> SEQUENCE: 336

Arg Gln Val Val Ala Gly Leu Asn Phe Arg Ile
1               5                   10

<210> SEQ ID NO 337
<211> LENGTH: 12
<212> TYPE: PRT
<213> ORGANISM: Homo sapiens

<400> SEQUENCE: 337

Lys Asp Leu Leu Leu Pro Gln Pro Asp Leu Arg Tyr
1               5                   10

<210> SEQ ID NO 338
<211> LENGTH: 15
<212> TYPE: PRT
<213> ORGANISM: Homo sapiens

<400> SEQUENCE: 338

Arg Leu His Leu Glu Gly Asn Lys Leu Gln Val Leu Gly Lys Asp
1               5                   10                  15

<210> SEQ ID NO 339
<211> LENGTH: 20
<212> TYPE: PRT
<213> ORGANISM: Homo sapiens

<400> SEQUENCE: 339

Arg Thr Leu Asp Leu Gly Glu Asn Gln Leu Glu Thr Leu Pro Pro Asp
1               5                   10                  15

Leu Leu Arg Gly
            20

<210> SEQ ID NO 340
<211> LENGTH: 21
<212> TYPE: PRT
<213> ORGANISM: Homo sapiens

<400> SEQUENCE: 340

Lys Gly Leu Gln Tyr Ala Ala Gln Glu Gly Leu Leu Ala Leu Gln Ser
1               5                   10                  15

Glu Leu Leu Arg Ile
            20

<210> SEQ ID NO 341
<211> LENGTH: 13
<212> TYPE: PRT
<213> ORGANISM: Homo sapiens

<400> SEQUENCE: 341

Lys Leu Ala Glu Gly Phe Pro Leu Pro Leu Leu Lys Arg
1               5                   10

<210> SEQ ID NO 342
<211> LENGTH: 16
<212> TYPE: PRT
<213> ORGANISM: Homo sapiens

<400> SEQUENCE: 342

Lys Ser Leu Glu Tyr Leu Asp Leu Ser Phe Asn Gln Ile Ala Arg Leu
```

-continued

```
1               5                    10                    15

<210> SEQ ID NO 343
<211> LENGTH: 13
<212> TYPE: PRT
<213> ORGANISM: Homo sapiens

<400> SEQUENCE: 343

Arg Leu Lys Glu Asp Ala Val Ser Ala Ala Phe Lys Gly
1               5                    10

<210> SEQ ID NO 344
<211> LENGTH: 21
<212> TYPE: PRT
<213> ORGANISM: Homo sapiens

<400> SEQUENCE: 344

Arg Ile Val Phe Glu Asn Pro Asp Pro Ser Asp Gly Phe Val Leu Ile
1               5                    10                    15

Pro Asp Leu Lys Trp
            20

<210> SEQ ID NO 345
<211> LENGTH: 7
<212> TYPE: PRT
<213> ORGANISM: Homo sapiens

<400> SEQUENCE: 345

Arg Val Tyr Phe Phe Lys Gly
1               5

<210> SEQ ID NO 346
<211> LENGTH: 8
<212> TYPE: PRT
<213> ORGANISM: Homo sapiens

<400> SEQUENCE: 346

Lys Trp Phe Asp Tyr Leu Arg Glu
1               5

<210> SEQ ID NO 347
<211> LENGTH: 20
<212> TYPE: PRT
<213> ORGANISM: Homo sapiens

<400> SEQUENCE: 347

Arg Leu Thr Val Gly Ala Ala Gln Val Pro Ala Gln Leu Leu Val Gly
1               5                    10                    15

Ala Leu Arg Val
            20

<210> SEQ ID NO 348
<211> LENGTH: 18
<212> TYPE: PRT
<213> ORGANISM: Homo sapiens

<400> SEQUENCE: 348

Arg Val Ser Phe Ser Ser Pro Leu Val Ala Ile Ser Gly Val Ala Leu
1               5                    10                    15

Arg Ser

<210> SEQ ID NO 349
<211> LENGTH: 19
```

<212> TYPE: PRT
<213> ORGANISM: Homo sapiens

<400> SEQUENCE: 349

Lys Gly Ile Val Ala Ala Phe Tyr Ser Gly Pro Ser Leu Ser Asp Lys
1               5                   10                  15

Glu Lys Leu

<210> SEQ ID NO 350
<211> LENGTH: 16
<212> TYPE: PRT
<213> ORGANISM: Homo sapiens

<400> SEQUENCE: 350

Arg Trp Tyr Val Pro Val Lys Asp Leu Leu Gly Ile Tyr Glu Lys Leu
1               5                   10                  15

<210> SEQ ID NO 351
<211> LENGTH: 14
<212> TYPE: PRT
<213> ORGANISM: Homo sapiens

<400> SEQUENCE: 351

Lys Leu Gln Ser Leu Phe Asp Ser Pro Asp Phe Ser Lys Ile
1               5                   10

<210> SEQ ID NO 352
<211> LENGTH: 19
<212> TYPE: PRT
<213> ORGANISM: Homo sapiens

<400> SEQUENCE: 352

Arg Ala Leu Tyr Tyr Asp Leu Ile Ser Ser Pro Asp Ile His Gly Thr
1               5                   10                  15

Tyr Lys Glu

<210> SEQ ID NO 353
<211> LENGTH: 20
<212> TYPE: PRT
<213> ORGANISM: Homo sapiens

<400> SEQUENCE: 353

Arg Cys Leu Leu Phe Ser Phe Leu Pro Ala Ser Ser Ile Asn Asp Met
1               5                   10                  15

Glu Lys Arg Phe
            20

<210> SEQ ID NO 354
<211> LENGTH: 12
<212> TYPE: PRT
<213> ORGANISM: Homo sapiens

<400> SEQUENCE: 354

Lys Phe Gln Pro Thr Leu Leu Thr Leu Pro Arg Ile
1               5                   10

<210> SEQ ID NO 355
<211> LENGTH: 19
<212> TYPE: PRT
<213> ORGANISM: Homo sapiens

<400> SEQUENCE: 355

Lys Gly Val Thr Ser Val Ser Gln Ile Phe His Ser Pro Asp Leu Ala

-continued

```
1               5               10              15

Ile Arg Asp

<210> SEQ ID NO 356
<211> LENGTH: 18
<212> TYPE: PRT
<213> ORGANISM: Homo sapiens

<400> SEQUENCE: 356

Lys Val Ile Pro Ala Cys Leu Pro Ser Pro Asn Tyr Val Val Ala Asp
1               5               10              15

Arg Thr

<210> SEQ ID NO 357
<211> LENGTH: 12
<212> TYPE: PRT
<213> ORGANISM: Homo sapiens

<400> SEQUENCE: 357

Arg Phe Val Thr Trp Ile Glu Gly Val Met Arg Asn
1               5               10

<210> SEQ ID NO 358
<211> LENGTH: 13
<212> TYPE: PRT
<213> ORGANISM: Homo sapiens

<400> SEQUENCE: 358

Arg His Ser Ile Phe Thr Pro Glu Thr Asn Pro Arg Ala
1               5               10

<210> SEQ ID NO 359
<211> LENGTH: 17
<212> TYPE: PRT
<213> ORGANISM: Homo sapiens

<400> SEQUENCE: 359

Lys Gly Lys Glu Glu Ser Leu Asp Ser Asp Leu Tyr Ala Glu Leu Arg
1               5               10              15

Cys

<210> SEQ ID NO 360
<211> LENGTH: 17
<212> TYPE: PRT
<213> ORGANISM: Homo sapiens

<400> SEQUENCE: 360

Lys Met Val Leu Leu Glu Gln Leu Phe Leu Asp His Asn Ala Leu Arg
1               5               10              15

Gly

<210> SEQ ID NO 361
<211> LENGTH: 24
<212> TYPE: PRT
<213> ORGANISM: Homo sapiens

<400> SEQUENCE: 361

Arg Leu Val Ser Leu Asp Ser Gly Leu Leu Asn Ser Leu Gly Ala Leu
1               5               10              15

Thr Glu Leu Gln Phe His Arg Asn
        20
```

<210> SEQ ID NO 362
<211> LENGTH: 14
<212> TYPE: PRT
<213> ORGANISM: Homo sapiens

<400> SEQUENCE: 362

Lys Ala Leu Leu Ala Tyr Ala Phe Ser Leu Leu Gly Lys Gln
1               5                   10

<210> SEQ ID NO 363
<211> LENGTH: 14
<212> TYPE: PRT
<213> ORGANISM: Homo sapiens

<400> SEQUENCE: 363

Lys Asp Leu Phe His Cys Val Ser Phe Thr Leu Pro Arg Ile
1               5                   10

<210> SEQ ID NO 364
<211> LENGTH: 14
<212> TYPE: PRT
<213> ORGANISM: Homo sapiens

<400> SEQUENCE: 364

Lys Met Leu Gln Ile Thr Asn Thr Gly Phe Glu Met Lys Leu
1               5                   10

<210> SEQ ID NO 365
<211> LENGTH: 16
<212> TYPE: PRT
<213> ORGANISM: Homo sapiens

<400> SEQUENCE: 365

Arg Asn Glu Leu Ile Pro Leu Ile Tyr Leu Glu Asn Pro Arg Arg Asn
1               5                   10                  15

<210> SEQ ID NO 366
<211> LENGTH: 24
<212> TYPE: PRT
<213> ORGANISM: Homo sapiens

<400> SEQUENCE: 366

Arg Ser Tyr Ile Phe Ile Asp Glu Ala His Ile Thr Gln Ser Leu Thr
1               5                   10                  15

Trp Leu Ser Gln Met Gln Lys Asp
            20

<210> SEQ ID NO 367
<211> LENGTH: 18
<212> TYPE: PRT
<213> ORGANISM: Homo sapiens

<400> SEQUENCE: 367

Arg Ser Asp Pro Val Thr Leu Asn Leu Leu His Gly Pro Asp Leu Pro
1               5                   10                  15

Arg Ile

<210> SEQ ID NO 368
<211> LENGTH: 11
<212> TYPE: PRT
<213> ORGANISM: Homo sapiens

<400> SEQUENCE: 368

Arg Thr Leu Phe Leu Phe Gly Val Thr Lys Tyr
1               5                   10

<210> SEQ ID NO 369
<211> LENGTH: 11
<212> TYPE: PRT
<213> ORGANISM: Homo sapiens

<400> SEQUENCE: 369

Arg Ile Leu Ile Leu Pro Ser Val Thr Arg Asn
1               5                   10

<210> SEQ ID NO 370
<211> LENGTH: 13
<212> TYPE: PRT
<213> ORGANISM: Homo sapiens

<400> SEQUENCE: 370

Arg Ser Asp Pro Val Thr Leu Asn Leu Leu Pro Lys Leu
1               5                   10

<210> SEQ ID NO 371
<211> LENGTH: 8
<212> TYPE: PRT
<213> ORGANISM: Homo sapiens

<400> SEQUENCE: 371

Arg Val Leu Gln Leu Glu Lys Gln
1               5

<210> SEQ ID NO 372
<211> LENGTH: 21
<212> TYPE: PRT
<213> ORGANISM: Homo sapiens

<400> SEQUENCE: 372

Arg Val Val Ala Gln Gly Val Gly Ile Pro Glu Asp Ser Ile Phe Thr
1               5                   10                  15

Met Ala Asp Arg Gly
            20

<210> SEQ ID NO 373
<211> LENGTH: 28
<212> TYPE: PRT
<213> ORGANISM: Homo sapiens

<400> SEQUENCE: 373

Arg Leu Thr Glu Arg Glu Trp Ala Asp Glu Trp Lys His Leu Asp His
1               5                   10                  15

Ala Leu Asn Cys Ile Met Glu Met Val Glu Lys Thr
            20                  25

<210> SEQ ID NO 374
<211> LENGTH: 21
<212> TYPE: PRT
<213> ORGANISM: Homo sapiens

<400> SEQUENCE: 374

Arg Ala Leu Cys Gly Gly Asp Gly Ala Ala Ala Leu Arg Glu Pro Gly
1               5                   10                  15

Ala Gly Leu Arg Leu
            20

<210> SEQ ID NO 375
<211> LENGTH: 24
<212> TYPE: PRT
<213> ORGANISM: Homo sapiens

<400> SEQUENCE: 375

Lys Ala Leu Met Asp Leu Leu Ala Gly Lys Gly Ser Gln Gly Ser Gln
1               5                   10                  15

Ala Pro Gln Ala Leu Asp Arg Thr
            20

<210> SEQ ID NO 376
<211> LENGTH: 23
<212> TYPE: PRT
<213> ORGANISM: Homo sapiens

<400> SEQUENCE: 376

Lys Met Gly Asp His Leu Ala Leu Glu Asp Tyr Leu Thr Thr Asp Leu
1               5                   10                  15

Val Glu Thr Trp Leu Arg Asn
            20

<210> SEQ ID NO 377
<211> LENGTH: 17
<212> TYPE: PRT
<213> ORGANISM: Homo sapiens

<400> SEQUENCE: 377

Lys Ser Pro Gln Glu Leu Leu Cys Gly Ala Ser Leu Ile Ser Asp Arg
1               5                   10                  15

Trp

<210> SEQ ID NO 378
<211> LENGTH: 21
<212> TYPE: PRT
<213> ORGANISM: Homo sapiens

<400> SEQUENCE: 378

Arg Leu Ala Val Thr Thr His Gly Leu Pro Cys Leu Ala Trp Ala Ser
1               5                   10                  15

Ala Gln Ala Lys Ala
            20

<210> SEQ ID NO 379
<211> LENGTH: 21
<212> TYPE: PRT
<213> ORGANISM: Homo sapiens

<400> SEQUENCE: 379

Arg Ser Glu Gly Ser Ser Val Asn Leu Ser Pro Pro Leu Glu Gln Cys
1               5                   10                  15

Val Pro Asp Arg Gly
            20

<210> SEQ ID NO 380
<211> LENGTH: 11
<212> TYPE: PRT
<213> ORGANISM: Homo sapiens

<400> SEQUENCE: 380

Arg Ser Gly Ile Glu Cys Gln Leu Trp Arg Ser
1               5                   10

<210> SEQ ID NO 381
<211> LENGTH: 15
<212> TYPE: PRT
<213> ORGANISM: Homo sapiens

<400> SEQUENCE: 381

Arg Thr Ala Thr Ser Glu Tyr Gln Thr Phe Phe Asn Pro Arg Thr
1               5                   10                  15

<210> SEQ ID NO 382
<211> LENGTH: 19
<212> TYPE: PRT
<213> ORGANISM: Homo sapiens

<400> SEQUENCE: 382

Arg Val Thr Gly Trp Gly Asn Leu Lys Glu Thr Trp Thr Ala Asn Val
1               5                   10                  15

Gly Lys Gly

<210> SEQ ID NO 383
<211> LENGTH: 9
<212> TYPE: PRT
<213> ORGANISM: Homo sapiens

<400> SEQUENCE: 383

Arg Ile His Leu Met Ala Gly Arg Val
1               5

<210> SEQ ID NO 384
<211> LENGTH: 9
<212> TYPE: PRT
<213> ORGANISM: Homo sapiens

<400> SEQUENCE: 384

Arg Pro Ala His Pro Ala Leu Arg Leu
1               5

<210> SEQ ID NO 385
<211> LENGTH: 8
<212> TYPE: PRT
<213> ORGANISM: Homo sapiens

<400> SEQUENCE: 385

Lys Ile Ser Asn Ile Ile Lys Gln
1               5

<210> SEQ ID NO 386
<211> LENGTH: 14
<212> TYPE: PRT
<213> ORGANISM: Homo sapiens

<400> SEQUENCE: 386

Lys Met Lys Tyr Trp Gly Val Ala Ser Phe Leu Gln Lys Gly
1               5                   10

<210> SEQ ID NO 387
<211> LENGTH: 12
<212> TYPE: PRT
<213> ORGANISM: Homo sapiens

<400> SEQUENCE: 387

Arg Phe Ser Gly Thr Trp Tyr Ala Met Ala Lys Lys
1               5                   10

<210> SEQ ID NO 388
<211> LENGTH: 20
<212> TYPE: PRT
<213> ORGANISM: Homo sapiens

<400> SEQUENCE: 388

Arg Leu Leu Asn Leu Asp Gly Thr Cys Ala Asp Ser Tyr Ser Phe Val
1               5                   10                  15

Phe Ser Arg Asp
            20

<210> SEQ ID NO 389
<211> LENGTH: 27
<212> TYPE: PRT
<213> ORGANISM: Homo sapiens

<400> SEQUENCE: 389

Arg Leu Leu Asn Asn Trp Asp Val Cys Ala Asp Met Val Gly Thr Phe
1               5                   10                  15

Thr Asp Thr Glu Asp Pro Ala Lys Phe Lys Met
            20                  25

<210> SEQ ID NO 390
<211> LENGTH: 28
<212> TYPE: PRT
<213> ORGANISM: Homo sapiens

<400> SEQUENCE: 390

Arg Leu Phe Leu Gly Ala Leu Pro Gly Glu Asp Ser Ser Thr Ser Phe
1               5                   10                  15

Cys Leu Asn Gly Leu Trp Ala Gln Gly Gln Arg Leu
            20                  25

<210> SEQ ID NO 391
<211> LENGTH: 11
<212> TYPE: PRT
<213> ORGANISM: Homo sapiens

<400> SEQUENCE: 391

Lys Asp Asp Trp Phe Met Leu Gly Leu Arg Asp
1               5                   10

<210> SEQ ID NO 392
<211> LENGTH: 25
<212> TYPE: PRT
<213> ORGANISM: Homo sapiens

<400> SEQUENCE: 392

Arg Ser Cys Asp Val Glu Ser Asn Pro Gly Ile Phe Leu Pro Pro Gly
1               5                   10                  15

Thr Gln Ala Glu Phe Asn Leu Arg Gly
            20                  25

<210> SEQ ID NO 393
<211> LENGTH: 27
<212> TYPE: PRT
<213> ORGANISM: Homo sapiens

<400> SEQUENCE: 393

Arg Thr Trp Asp Pro Glu Gly Val Ile Phe Tyr Gly Asp Thr Asn Pro
1               5                   10                  15

Lys Asp Asp Trp Phe Met Leu Gly Leu Arg Asp

```
                    20                  25
```

```
<210> SEQ ID NO 394
<211> LENGTH: 26
<212> TYPE: PRT
<213> ORGANISM: Homo sapiens

<400> SEQUENCE: 394

Arg Lys Phe Cys Arg Asp Ile Gln Asp Pro Thr Gln Leu Ala Glu Met
1               5                   10                  15

Ile Phe Asn Leu Leu Leu Glu Glu Lys Arg
            20                  25

<210> SEQ ID NO 395
<211> LENGTH: 16
<212> TYPE: PRT
<213> ORGANISM: Homo sapiens

<400> SEQUENCE: 395

Arg Asn Glu Leu Ile Arg Gln Glu Lys Leu Glu Gln Leu Ala Arg Arg
1               5                   10                  15

<210> SEQ ID NO 396
<211> LENGTH: 8
<212> TYPE: PRT
<213> ORGANISM: Homo sapiens

<400> SEQUENCE: 396

Arg Lys Asn Leu Ser Glu Arg Trp
1               5

<210> SEQ ID NO 397
<211> LENGTH: 12
<212> TYPE: PRT
<213> ORGANISM: Homo sapiens

<400> SEQUENCE: 397

Arg Lys Trp Tyr Asn Leu Met Ile Gln Asn Lys Asp
1               5                   10

<210> SEQ ID NO 398
<211> LENGTH: 16
<212> TYPE: PRT
<213> ORGANISM: Homo sapiens

<400> SEQUENCE: 398

Lys Ser Arg Leu Asp Thr Leu Ala Gln Glu Val Ala Leu Leu Lys Glu
1               5                   10                  15

<210> SEQ ID NO 399
<211> LENGTH: 16
<212> TYPE: PRT
<213> ORGANISM: Homo sapiens

<400> SEQUENCE: 399

Lys Arg Leu Asp Val Asn Ala Ala Gly Ile Trp Glu Pro Lys Lys Gly
1               5                   10                  15

<210> SEQ ID NO 400
<211> LENGTH: 9
<212> TYPE: PRT
<213> ORGANISM: Homo sapiens

<400> SEQUENCE: 400
```

```
Arg Ser Ile Leu Phe Leu Gly Lys Val
1               5

<210> SEQ ID NO 401
<211> LENGTH: 28
<212> TYPE: PRT
<213> ORGANISM: Homo sapiens

<400> SEQUENCE: 401

Arg Glu Leu Ile Ser Asp Leu Glu His Arg Leu Gln Gly Ser Val Met
1               5                   10                  15

Glu Leu Leu Gln Gly Val Asp Gly Val Ile Lys Arg
            20                  25

<210> SEQ ID NO 402
<211> LENGTH: 27
<212> TYPE: PRT
<213> ORGANISM: Homo sapiens

<400> SEQUENCE: 402

Lys Glu Leu Ser Ser Phe Ile Asp Lys Gly Gln Glu Leu Cys Ala Asp
1               5                   10                  15

Tyr Ser Glu Asn Thr Phe Thr Glu Tyr Lys Lys
            20                  25

<210> SEQ ID NO 403
<211> LENGTH: 28
<212> TYPE: PRT
<213> ORGANISM: Homo sapiens

<400> SEQUENCE: 403

Lys Glu Leu Ser Ser Phe Ile Asp Lys Gly Gln Glu Leu Cys Ala Asp
1               5                   10                  15

Tyr Ser Glu Asn Thr Phe Thr Glu Tyr Lys Lys Lys
            20                  25

<210> SEQ ID NO 404
<211> LENGTH: 24
<212> TYPE: PRT
<213> ORGANISM: Homo sapiens

<400> SEQUENCE: 404

Lys Glu Val Val Ser Leu Thr Glu Ala Cys Cys Ala Glu Gly Ala Asp
1               5                   10                  15

Pro Asp Cys Tyr Asp Thr Arg Thr
            20

<210> SEQ ID NO 405
<211> LENGTH: 40
<212> TYPE: PRT
<213> ORGANISM: Homo sapiens

<400> SEQUENCE: 405

Lys Thr Ala Met Asp Val Phe Val Cys Thr Tyr Phe Met Pro Ala Ala
1               5                   10                  15

Gln Leu Pro Glu Leu Pro Asp Val Glu Leu Pro Thr Asn Lys Asp Val
            20                  25                  30

Cys Asp Pro Gly Asn Thr Lys Val
            35                  40

<210> SEQ ID NO 406
<211> LENGTH: 13
```

<212> TYPE: PRT
<213> ORGANISM: Homo sapiens

<400> SEQUENCE: 406

Arg Arg Thr His Leu Pro Glu Val Phe Leu Ser Lys Val
1               5                   10

<210> SEQ ID NO 407
<211> LENGTH: 13
<212> TYPE: PRT
<213> ORGANISM: Homo sapiens

<400> SEQUENCE: 407

Arg Val Cys Ser Gln Tyr Ala Ala Tyr Gly Glu Lys Lys
1               5                   10

<210> SEQ ID NO 408
<211> LENGTH: 20
<212> TYPE: PRT
<213> ORGANISM: Homo sapiens

<400> SEQUENCE: 408

Lys Leu Ile Arg Asp Val Trp Gly Ile Glu Gly Pro Ile Asp Ala Ala
1               5                   10                  15

Phe Thr Arg Ile
            20

<210> SEQ ID NO 409
<211> LENGTH: 17
<212> TYPE: PRT
<213> ORGANISM: Homo sapiens

<400> SEQUENCE: 409

Arg Asp Val Trp Gly Ile Glu Gly Pro Ile Asp Ala Ala Phe Thr Arg
1               5                   10                  15

Ile

<210> SEQ ID NO 410
<211> LENGTH: 9
<212> TYPE: PRT
<213> ORGANISM: Homo sapiens

<400> SEQUENCE: 410

Arg Glu Arg Val Tyr Phe Phe Lys Gly
1               5

<210> SEQ ID NO 411
<211> LENGTH: 14
<212> TYPE: PRT
<213> ORGANISM: Homo sapiens

<400> SEQUENCE: 411

Arg Phe Glu Asp Gly Val Leu Asp Pro Asp Tyr Pro Arg Asn
1               5                   10

<210> SEQ ID NO 412
<211> LENGTH: 16
<212> TYPE: PRT
<213> ORGANISM: Homo sapiens

<400> SEQUENCE: 412

Arg Ile Tyr Ile Ser Gly Met Ala Pro Arg Pro Ser Leu Ala Lys Lys
1               5                   10                  15

-continued

```
<210> SEQ ID NO 413
<211> LENGTH: 8
<212> TYPE: PRT
<213> ORGANISM: Homo sapiens

<400> SEQUENCE: 413

Lys Thr Arg Phe Leu Leu Arg Thr
1               5

<210> SEQ ID NO 414
<211> LENGTH: 23
<212> TYPE: PRT
<213> ORGANISM: Homo sapiens

<400> SEQUENCE: 414

Lys His Glu Leu Thr Asp Glu Glu Leu Gln Ser Leu Phe Thr Asn Phe
1               5                   10                  15

Ala Asn Val Val Asp Lys Cys
            20

<210> SEQ ID NO 415
<211> LENGTH: 23
<212> TYPE: PRT
<213> ORGANISM: Homo sapiens

<400> SEQUENCE: 415

Arg Asn Pro Phe Val Phe Ala Pro Thr Leu Leu Thr Val Ala Val His
1               5                   10                  15

Phe Glu Glu Val Ala Lys Ser
            20

<210> SEQ ID NO 416
<211> LENGTH: 12
<212> TYPE: PRT
<213> ORGANISM: Homo sapiens

<400> SEQUENCE: 416

Lys Ala Asp Leu Ser Gly Ile Thr Gly Ala Arg Asn
1               5                   10

<210> SEQ ID NO 417
<211> LENGTH: 17
<212> TYPE: PRT
<213> ORGANISM: Homo sapiens

<400> SEQUENCE: 417

Lys Met Glu Glu Val Glu Ala Met Leu Leu Pro Glu Thr Leu Lys Arg
1               5                   10                  15

Trp

<210> SEQ ID NO 418
<211> LENGTH: 16
<212> TYPE: PRT
<213> ORGANISM: Homo sapiens

<400> SEQUENCE: 418

Lys Trp Glu Met Pro Phe Asp Pro Gln Asp Thr His Gln Ser Arg Phe
1               5                   10                  15

<210> SEQ ID NO 419
<211> LENGTH: 20
<212> TYPE: PRT
<213> ORGANISM: Homo sapiens
```

<400> SEQUENCE: 419

Arg Leu Tyr Gly Ser Glu Ala Phe Ala Thr Asp Phe Gln Asp Ser Ala
1               5                   10                  15

Ala Ala Lys Lys
            20

<210> SEQ ID NO 420
<211> LENGTH: 14
<212> TYPE: PRT
<213> ORGANISM: Homo sapiens

<400> SEQUENCE: 420

Lys His Gln Phe Leu Leu Thr Gly Asp Thr Gln Gly Arg Tyr
1               5                   10

<210> SEQ ID NO 421
<211> LENGTH: 18
<212> TYPE: PRT
<213> ORGANISM: Homo sapiens

<400> SEQUENCE: 421

Lys Asn Gly Val Ala Gln Glu Pro Val His Leu Asp Ser Pro Ala Ile
1               5                   10                  15

Lys His

<210> SEQ ID NO 422
<211> LENGTH: 22
<212> TYPE: PRT
<213> ORGANISM: Homo sapiens

<400> SEQUENCE: 422

Lys Ser Leu Pro Ala Pro Trp Leu Ser Met Ala Pro Val Ser Trp Ile
1               5                   10                  15

Thr Pro Gly Leu Lys Thr
            20

<210> SEQ ID NO 423
<211> LENGTH: 20
<212> TYPE: PRT
<213> ORGANISM: Homo sapiens

<400> SEQUENCE: 423

Lys Val Thr Leu Thr Cys Val Ala Pro Leu Ser Gly Val Asp Phe Gln
1               5                   10                  15

Leu Arg Arg Gly
            20

<210> SEQ ID NO 424
<211> LENGTH: 11
<212> TYPE: PRT
<213> ORGANISM: Homo sapiens

<400> SEQUENCE: 424

Arg Cys Leu Ala Pro Leu Glu Gly Ala Arg Phe
1               5                   10

<210> SEQ ID NO 425
<211> LENGTH: 9
<212> TYPE: PRT
<213> ORGANISM: Homo sapiens

<400> SEQUENCE: 425

-continued

```
Arg Gly Val Thr Phe Leu Leu Arg Arg
1               5

<210> SEQ ID NO 426
<211> LENGTH: 39
<212> TYPE: PRT
<213> ORGANISM: Homo sapiens

<400> SEQUENCE: 426

Arg Leu His Asp Asn Gln Asn Gly Trp Ser Gly Asp Ser Ala Pro Val
1               5                   10                  15

Glu Leu Ile Leu Ser Asp Glu Thr Leu Pro Ala Pro Glu Phe Ser Pro
            20                  25                  30

Glu Pro Glu Ser Gly Arg Ala
        35

<210> SEQ ID NO 427
<211> LENGTH: 24
<212> TYPE: PRT
<213> ORGANISM: Homo sapiens

<400> SEQUENCE: 427

Arg Thr Pro Gly Ala Ala Ala Asn Leu Glu Leu Ile Phe Val Gly Pro
1               5                   10                  15

Gln His Ala Gly Asn Tyr Arg Cys
            20

<210> SEQ ID NO 428
<211> LENGTH: 26
<212> TYPE: PRT
<213> ORGANISM: Homo sapiens

<400> SEQUENCE: 428

Lys His Gln Met Asp Leu Val Ala Thr Leu Ser Gln Leu Gly Leu Gln
1               5                   10                  15

Glu Leu Phe Gln Ala Pro Asp Leu Arg Gly
            20                  25

<210> SEQ ID NO 429
<211> LENGTH: 13
<212> TYPE: PRT
<213> ORGANISM: Homo sapiens

<400> SEQUENCE: 429

Arg Leu Cys Gln Asp Leu Gly Pro Gly Ala Phe Arg Leu
1               5                   10

<210> SEQ ID NO 430
<211> LENGTH: 19
<212> TYPE: PRT
<213> ORGANISM: Homo sapiens

<400> SEQUENCE: 430

Arg Trp Phe Leu Leu Glu Gln Pro Glu Ile Gln Val Ala His Phe Pro
1               5                   10                  15

Phe Lys Asn

<210> SEQ ID NO 431
<211> LENGTH: 34
<212> TYPE: PRT
<213> ORGANISM: Homo sapiens
```

<400> SEQUENCE: 431

Lys Val Trp Pro Gln Gln Pro Ser Gly Glu Leu Phe Glu Ile Glu Ile
1               5                   10                  15

Asp Thr Leu Glu Thr Thr Cys His Val Leu Asp Pro Thr Pro Val Ala
            20                  25                  30

Arg Cys

<210> SEQ ID NO 432
<211> LENGTH: 22
<212> TYPE: PRT
<213> ORGANISM: Homo sapiens

<400> SEQUENCE: 432

Arg His Thr Phe Met Gly Val Val Ser Leu Gly Ser Pro Ser Gly Glu
1               5                   10                  15

Val Ser His Pro Arg Lys
            20

<210> SEQ ID NO 433
<211> LENGTH: 31
<212> TYPE: PRT
<213> ORGANISM: Homo sapiens

<400> SEQUENCE: 433

Arg Gln Pro Asn Cys Asp Asp Pro Glu Thr Glu Glu Ala Ala Leu Val
1               5                   10                  15

Ala Ile Asp Tyr Ile Asn Gln Asn Leu Pro Trp Gly Tyr Lys His
            20                  25                  30

<210> SEQ ID NO 434
<211> LENGTH: 23
<212> TYPE: PRT
<213> ORGANISM: Homo sapiens

<400> SEQUENCE: 434

Arg Thr Val Val Gln Pro Ser Val Gly Ala Ala Ala Gly Pro Val Val
1               5                   10                  15

Pro Pro Cys Pro Gly Arg Ile
            20

<210> SEQ ID NO 435
<211> LENGTH: 19
<212> TYPE: PRT
<213> ORGANISM: Homo sapiens

<400> SEQUENCE: 435

Lys Gln Pro Phe Val Gln Gly Leu Ala Leu Tyr Thr Pro Val Val Leu
1               5                   10                  15

Pro Arg Ser

<210> SEQ ID NO 436
<211> LENGTH: 13
<212> TYPE: PRT
<213> ORGANISM: Homo sapiens

<400> SEQUENCE: 436

Lys Leu Val Pro Phe Ala Thr Glu Leu His Glu Arg Leu
1               5                   10

<210> SEQ ID NO 437
<211> LENGTH: 13

-continued

```
<212> TYPE: PRT
<213> ORGANISM: Homo sapiens

<400> SEQUENCE: 437

Arg Leu Leu Pro His Ala Asn Glu Val Ser Gln Lys Ile
1               5               10

<210> SEQ ID NO 438
<211> LENGTH: 27
<212> TYPE: PRT
<213> ORGANISM: Homo sapiens

<400> SEQUENCE: 438

Arg Ser Leu Ala Pro Tyr Ala Gln Asp Thr Gln Glu Lys Leu Asn His
1               5               10              15

Gln Leu Glu Gly Leu Thr Phe Gln Met Lys Lys
            20              25

<210> SEQ ID NO 439
<211> LENGTH: 11
<212> TYPE: PRT
<213> ORGANISM: Homo sapiens

<400> SEQUENCE: 439

Lys Phe Pro Glu Val Asp Val Leu Thr Lys Tyr
1               5               10

<210> SEQ ID NO 440
<211> LENGTH: 11
<212> TYPE: PRT
<213> ORGANISM: Homo sapiens

<400> SEQUENCE: 440

Lys His Ile Asn Ile Asp Gln Phe Val Arg Lys
1               5               10

<210> SEQ ID NO 441
<211> LENGTH: 17
<212> TYPE: PRT
<213> ORGANISM: Homo sapiens

<400> SEQUENCE: 441

Lys Leu Leu Ser Gly Gly Asn Thr Leu His Leu Val Ser Thr Thr Lys
1               5               10              15

Thr

<210> SEQ ID NO 442
<211> LENGTH: 21
<212> TYPE: PRT
<213> ORGANISM: Homo sapiens

<400> SEQUENCE: 442

Lys Gln Val Phe Leu Tyr Pro Glu Lys Asp Glu Pro Thr Tyr Ile Leu
1               5               10              15

Asn Ile Lys Arg Gly
            20

<210> SEQ ID NO 443
<211> LENGTH: 10
<212> TYPE: PRT
<213> ORGANISM: Homo sapiens

<400> SEQUENCE: 443
```

```
Lys Ser Leu His Met Tyr Ala Asn Arg Leu
1               5                   10

<210> SEQ ID NO 444
<211> LENGTH: 19
<212> TYPE: PRT
<213> ORGANISM: Homo sapiens

<400> SEQUENCE: 444

Lys Ser Val Ser Asp Gly Ile Ala Ala Leu Asp Leu Asn Ala Val Ala
1               5                   10                  15

Asn Lys Ile

<210> SEQ ID NO 445
<211> LENGTH: 30
<212> TYPE: PRT
<213> ORGANISM: Homo sapiens

<400> SEQUENCE: 445

Lys Ser Val Ser Leu Pro Ser Leu Asp Pro Ala Ser Ala Lys Ile Glu
1               5                   10                  15

Gly Asn Leu Ile Phe Asp Pro Asn Asn Tyr Leu Pro Lys Glu
            20                  25                  30

<210> SEQ ID NO 446
<211> LENGTH: 13
<212> TYPE: PRT
<213> ORGANISM: Homo sapiens

<400> SEQUENCE: 446

Lys Thr Glu Val Ile Pro Pro Leu Ile Glu Asn Arg Gln
1               5                   10

<210> SEQ ID NO 447
<211> LENGTH: 12
<212> TYPE: PRT
<213> ORGANISM: Homo sapiens

<400> SEQUENCE: 447

Lys Val Leu Val Asp His Phe Gly Tyr Thr Lys Asp
1               5                   10

<210> SEQ ID NO 448
<211> LENGTH: 26
<212> TYPE: PRT
<213> ORGANISM: Homo sapiens

<400> SEQUENCE: 448

Arg Thr Ser Ser Phe Ala Leu Asn Leu Pro Thr Leu Pro Glu Val Lys
1               5                   10                  15

Phe Pro Glu Val Asp Val Leu Thr Lys Tyr
            20                  25

<210> SEQ ID NO 449
<211> LENGTH: 20
<212> TYPE: PRT
<213> ORGANISM: Homo sapiens

<400> SEQUENCE: 449

Arg Gly Trp Val Thr Asp Gly Phe Ser Ser Leu Lys Asp Tyr Trp Ser
1               5                   10                  15

Thr Val Lys Asp
            20
```

-continued

```
<210> SEQ ID NO 450
<211> LENGTH: 17
<212> TYPE: PRT
<213> ORGANISM: Homo sapiens

<400> SEQUENCE: 450

Arg Gly Glu Val Gln Ala Met Leu Gly Gln Ser Thr Glu Glu Leu Arg
1               5                   10                  15

Val

<210> SEQ ID NO 451
<211> LENGTH: 11
<212> TYPE: PRT
<213> ORGANISM: Homo sapiens

<400> SEQUENCE: 451

Arg Leu Ala Val Tyr Gln Ala Gly Ala Arg Glu
1               5                   10

<210> SEQ ID NO 452
<211> LENGTH: 11
<212> TYPE: PRT
<213> ORGANISM: Homo sapiens

<400> SEQUENCE: 452

Arg Leu Gly Pro Leu Val Glu Gln Gly Arg Val
1               5                   10

<210> SEQ ID NO 453
<211> LENGTH: 12
<212> TYPE: PRT
<213> ORGANISM: Homo sapiens

<400> SEQUENCE: 453

Lys Leu Thr Leu Thr Pro Trp Val Gly Leu Arg Lys
1               5                   10

<210> SEQ ID NO 454
<211> LENGTH: 17
<212> TYPE: PRT
<213> ORGANISM: Homo sapiens

<400> SEQUENCE: 454

Lys Phe Ile Cys Pro Leu Thr Gly Leu Trp Pro Ile Asn Thr Leu Lys
1               5                   10                  15

Cys

<210> SEQ ID NO 455
<211> LENGTH: 22
<212> TYPE: PRT
<213> ORGANISM: Homo sapiens

<400> SEQUENCE: 455

Lys Thr Phe Tyr Glu Pro Gly Glu Glu Ile Thr Tyr Ser Cys Lys Pro
1               5                   10                  15

Gly Tyr Val Ser Arg Gly
            20

<210> SEQ ID NO 456
<211> LENGTH: 27
<212> TYPE: PRT
<213> ORGANISM: Homo sapiens
```

<400> SEQUENCE: 456

Lys Met Val Val Ser Met Thr Leu Gly Leu His Pro Trp Ile Ala Asn
1               5                   10                  15

Ile Asp Asp Thr Gln Tyr Leu Ala Ala Lys Arg
            20                  25

<210> SEQ ID NO 457
<211> LENGTH: 19
<212> TYPE: PRT
<213> ORGANISM: Homo sapiens

<400> SEQUENCE: 457

Lys Val Phe Gln Tyr Ile Asp Leu His Gln Asp Glu Phe Val Gln Thr
1               5                   10                  15

Leu Lys Glu

<210> SEQ ID NO 458
<211> LENGTH: 19
<212> TYPE: PRT
<213> ORGANISM: Homo sapiens

<400> SEQUENCE: 458

Arg Thr Ser Ile Tyr Pro Phe Leu Asp Phe Met Pro Ser Pro Gln Val
1               5                   10                  15

Val Arg Trp

<210> SEQ ID NO 459
<211> LENGTH: 17
<212> TYPE: PRT
<213> ORGANISM: Homo sapiens

<400> SEQUENCE: 459

Arg Glu Leu Met Leu Gln Leu Ser Glu Phe Leu Cys Glu Glu Phe Arg
1               5                   10                  15

Asn

<210> SEQ ID NO 460
<211> LENGTH: 24
<212> TYPE: PRT
<213> ORGANISM: Homo sapiens

<400> SEQUENCE: 460

Lys Ala Glu Glu Glu His Leu Gly Ile Leu Gly Pro Gln Leu His Ala
1               5                   10                  15

Asp Val Gly Asp Lys Val Lys Ile
            20

<210> SEQ ID NO 461
<211> LENGTH: 14
<212> TYPE: PRT
<213> ORGANISM: Homo sapiens

<400> SEQUENCE: 461

Lys Ala Leu Tyr Leu Gln Tyr Thr Asp Glu Thr Phe Arg Thr
1               5                   10

<210> SEQ ID NO 462
<211> LENGTH: 28
<212> TYPE: PRT
<213> ORGANISM: Homo sapiens -continued

```
<400> SEQUENCE: 462

Lys Asp Val Asp Lys Glu Phe Tyr Leu Phe Pro Thr Val Phe Asp Glu
1               5                   10                  15

Asn Glu Ser Leu Leu Leu Glu Asp Asn Ile Arg Met
            20                  25

<210> SEQ ID NO 463
<211> LENGTH: 22
<212> TYPE: PRT
<213> ORGANISM: Homo sapiens

<400> SEQUENCE: 463

Lys His Tyr Tyr Ile Gly Ile Ile Glu Thr Thr Trp Asp Tyr Ala Ser
1               5                   10                  15

Asp His Gly Glu Lys Lys
            20

<210> SEQ ID NO 464
<211> LENGTH: 13
<212> TYPE: PRT
<213> ORGANISM: Homo sapiens

<400> SEQUENCE: 464

Arg Glu Tyr Thr Asp Ala Ser Phe Thr Asn Arg Lys Glu
1               5                   10

<210> SEQ ID NO 465
<211> LENGTH: 25
<212> TYPE: PRT
<213> ORGANISM: Homo sapiens

<400> SEQUENCE: 465

Arg His Tyr Tyr Ile Ala Ala Glu Glu Ile Ile Trp Asn Tyr Ala Pro
1               5                   10                  15

Ser Gly Ile Asp Ile Phe Thr Lys Glu
            20                  25

<210> SEQ ID NO 466
<211> LENGTH: 12
<212> TYPE: PRT
<213> ORGANISM: Homo sapiens

<400> SEQUENCE: 466

Arg Ile Tyr His Ser His Ile Asp Ala Pro Lys Asp
1               5                   10

<210> SEQ ID NO 467
<211> LENGTH: 30
<212> TYPE: PRT
<213> ORGANISM: Homo sapiens

<400> SEQUENCE: 467

Arg Gln Lys Asp Val Asp Lys Glu Phe Tyr Leu Phe Pro Thr Val Phe
1               5                   10                  15

Asp Glu Asn Glu Ser Leu Leu Leu Glu Asp Asn Ile Arg Met
            20                  25                  30

<210> SEQ ID NO 468
<211> LENGTH: 19
<212> TYPE: PRT
<213> ORGANISM: Homo sapiens

<400> SEQUENCE: 468
```

-continued

Arg Thr Tyr Tyr Ile Ala Ala Val Glu Val Glu Trp Asp Tyr Ser Pro
1                5                    10                    15

Gln Arg Glu

<210> SEQ ID NO 469
<211> LENGTH: 11
<212> TYPE: PRT
<213> ORGANISM: Homo sapiens

<400> SEQUENCE: 469

Arg Ser Ala Leu Val Leu Gln Tyr Leu Arg Val
1                5                    10

<210> SEQ ID NO 470
<211> LENGTH: 14
<212> TYPE: PRT
<213> ORGANISM: Homo sapiens

<400> SEQUENCE: 470

Lys Glu Phe Asn Pro Leu Val Ile Val Gly Leu Ser Lys Asp
1                5                    10

<210> SEQ ID NO 471
<211> LENGTH: 17
<212> TYPE: PRT
<213> ORGANISM: Homo sapiens

<400> SEQUENCE: 471

Arg Asn Pro Asp Asn Asp Ile Arg Pro Trp Cys Phe Val Leu Asn Arg
1                5                    10                    15

Asp

<210> SEQ ID NO 472
<211> LENGTH: 11
<212> TYPE: PRT
<213> ORGANISM: Homo sapiens

<400> SEQUENCE: 472

Arg Val Val Gly Gly Leu Val Ala Leu Arg Gly
1                5                    10

<210> SEQ ID NO 473
<211> LENGTH: 25
<212> TYPE: PRT
<213> ORGANISM: Homo sapiens

<400> SEQUENCE: 473

Lys Asn Ser Leu Leu Gly Met Glu Gly Ala Asn Ser Ile Phe Ser Gly
1                5                    10                    15

Phe Leu Leu Phe Pro Asp Met Glu Ala
            20                    25

<210> SEQ ID NO 474
<211> LENGTH: 16
<212> TYPE: PRT
<213> ORGANISM: Homo sapiens

<400> SEQUENCE: 474

Lys Val Pro Gly Leu Tyr Tyr Phe Thr Tyr His Ala Ser Ser Arg Gly
1                5                    10                    15

<210> SEQ ID NO 475

```
<211> LENGTH: 15
<212> TYPE: PRT
<213> ORGANISM: Homo sapiens

<400> SEQUENCE: 475

Arg Gln Thr His Gln Pro Pro Ala Pro Asn Ser Leu Ile Arg Phe
1               5                   10                  15

<210> SEQ ID NO 476
<211> LENGTH: 16
<212> TYPE: PRT
<213> ORGANISM: Homo sapiens

<400> SEQUENCE: 476

Arg Leu Pro Val Ala Asn Pro Gln Ala Cys Glu Asn Trp Leu Arg Gly
1               5                   10                  15

<210> SEQ ID NO 477
<211> LENGTH: 18
<212> TYPE: PRT
<213> ORGANISM: Homo sapiens

<400> SEQUENCE: 477

Lys Asn Gln Gly Ile Leu Glu Phe Tyr Gly Asp Asp Ile Ala Leu Leu
1               5                   10                  15

Lys Leu

<210> SEQ ID NO 478
<211> LENGTH: 16
<212> TYPE: PRT
<213> ORGANISM: Homo sapiens

<400> SEQUENCE: 478

Lys Arg Asn Asp Tyr Leu Asp Ile Tyr Ala Ile Gly Val Gly Lys Leu
1               5                   10                  15

<210> SEQ ID NO 479
<211> LENGTH: 33
<212> TYPE: PRT
<213> ORGANISM: Homo sapiens

<400> SEQUENCE: 479

Arg Gln Pro Tyr Ser Tyr Asp Phe Pro Glu Asp Val Ala Pro Ala Leu
1               5                   10                  15

Gly Thr Ser Phe Ser His Met Leu Gly Ala Thr Asn Pro Thr Gln Lys
            20                  25                  30

Thr

<210> SEQ ID NO 480
<211> LENGTH: 12
<212> TYPE: PRT
<213> ORGANISM: Homo sapiens

<400> SEQUENCE: 480

Arg Ile His Trp Glu Ser Ala Ser Leu Leu Arg Ser
1               5                   10

<210> SEQ ID NO 481
<211> LENGTH: 9
<212> TYPE: PRT
<213> ORGANISM: Homo sapiens

<400> SEQUENCE: 481
```

-continued

```
Lys Phe Ala Cys Tyr Tyr Pro Arg Val
1               5

<210> SEQ ID NO 482
<211> LENGTH: 28
<212> TYPE: PRT
<213> ORGANISM: Homo sapiens

<400> SEQUENCE: 482

Lys Leu His Leu Glu Thr Asp Ser Leu Ala Leu Val Ala Leu Gly Ala
1               5                   10                  15

Leu Asp Thr Ala Leu Tyr Ala Ala Gly Ser Lys Ser
            20                  25

<210> SEQ ID NO 483
<211> LENGTH: 14
<212> TYPE: PRT
<213> ORGANISM: Homo sapiens

<400> SEQUENCE: 483

Lys Leu Val Asn Gly Gln Ser His Ile Ser Leu Ser Lys Ala
1               5                   10

<210> SEQ ID NO 484
<211> LENGTH: 11
<212> TYPE: PRT
<213> ORGANISM: Homo sapiens

<400> SEQUENCE: 484

Lys Ser Cys Gly Leu His Gln Leu Leu Arg Gly
1               5                   10

<210> SEQ ID NO 485
<211> LENGTH: 11
<212> TYPE: PRT
<213> ORGANISM: Homo sapiens

<400> SEQUENCE: 485

Lys Tyr Val Leu Pro Asn Phe Glu Val Lys Ile
1               5                   10

<210> SEQ ID NO 486
<211> LENGTH: 21
<212> TYPE: PRT
<213> ORGANISM: Homo sapiens

<400> SEQUENCE: 486

Arg Ala Leu Glu Ile Leu Gln Glu Glu Asp Leu Ile Asp Glu Asp Asp
1               5                   10                  15

Ile Pro Val Arg Ser
            20

<210> SEQ ID NO 487
<211> LENGTH: 33
<212> TYPE: PRT
<213> ORGANISM: Homo sapiens

<400> SEQUENCE: 487

Arg Glu Cys Val Gly Phe Glu Ala Val Gln Glu Val Pro Val Gly Leu
1               5                   10                  15

Val Gln Pro Ala Ser Ala Thr Leu Tyr Asp Tyr Tyr Asn Pro Glu Arg
            20                  25                  30

Arg
```

<210> SEQ ID NO 488
<211> LENGTH: 15
<212> TYPE: PRT
<213> ORGANISM: Homo sapiens

<400> SEQUENCE: 488

Arg Glu Glu Leu Val Tyr Glu Leu Asn Pro Leu Asp His Arg Gly
1               5                   10                  15

<210> SEQ ID NO 489
<211> LENGTH: 27
<212> TYPE: PRT
<213> ORGANISM: Homo sapiens

<400> SEQUENCE: 489

Arg Ser Thr Gln Asp Thr Val Ile Ala Leu Asp Ala Leu Ser Ala Tyr
1               5                   10                  15

Trp Ile Ala Ser His Thr Thr Glu Glu Arg Gly
            20                  25

<210> SEQ ID NO 490
<211> LENGTH: 12
<212> TYPE: PRT
<213> ORGANISM: Homo sapiens

<400> SEQUENCE: 490

Arg Val Gly Asp Thr Leu Asn Leu Asn Leu Arg Ala
1               5                   10

<210> SEQ ID NO 491
<211> LENGTH: 11
<212> TYPE: PRT
<213> ORGANISM: Homo sapiens

<400> SEQUENCE: 491

Arg Val His Tyr Thr Val Cys Ile Trp Arg Asn
1               5                   10

<210> SEQ ID NO 492
<211> LENGTH: 12
<212> TYPE: PRT
<213> ORGANISM: Homo sapiens

<400> SEQUENCE: 492

Lys Lys Tyr Val Leu Pro Asn Phe Glu Val Lys Ile
1               5                   10

<210> SEQ ID NO 493
<211> LENGTH: 26
<212> TYPE: PRT
<213> ORGANISM: Homo sapiens

<400> SEQUENCE: 493

Lys Val Asp Phe Thr Leu Ser Ser Glu Arg Asp Phe Ala Leu Leu Ser
1               5                   10                  15

Leu Gln Val Pro Leu Lys Asp Ala Lys Ser
            20                  25

<210> SEQ ID NO 494
<211> LENGTH: 18
<212> TYPE: PRT
<213> ORGANISM: Homo sapiens -continued

```
<400> SEQUENCE: 494

Arg Ser Tyr Phe Pro Glu Ser Trp Leu Trp Glu Val His Leu Val Pro
1               5                   10                  15

Arg Arg

<210> SEQ ID NO 495
<211> LENGTH: 28
<212> TYPE: PRT
<213> ORGANISM: Homo sapiens

<400> SEQUENCE: 495

Arg Tyr Gly Gly Gly Phe Tyr Ser Thr Gln Asp Thr Ile Asn Ala Ile
1               5                   10                  15

Glu Gly Leu Thr Glu Tyr Ser Leu Leu Val Lys Gln
            20                  25

<210> SEQ ID NO 496
<211> LENGTH: 12
<212> TYPE: PRT
<213> ORGANISM: Homo sapiens

<400> SEQUENCE: 496

Arg His Thr Ser Leu Gly Pro Leu Glu Ala Lys Arg
1               5                   10

<210> SEQ ID NO 497
<211> LENGTH: 35
<212> TYPE: PRT
<213> ORGANISM: Homo sapiens

<400> SEQUENCE: 497

Lys Cys Gln His Glu Met Asp Gln Tyr Trp Gly Ile Gly Ser Leu Ala
1               5                   10                  15

Ser Gly Ile Asn Leu Phe Thr Asn Ser Phe Glu Gly Pro Val Leu Asp
            20                  25                  30

His Arg Tyr
        35

<210> SEQ ID NO 498
<211> LENGTH: 10
<212> TYPE: PRT
<213> ORGANISM: Homo sapiens

<400> SEQUENCE: 498

Lys Ser Gly Phe Ser Phe Gly Phe Lys Ile
1               5                   10

<210> SEQ ID NO 499
<211> LENGTH: 14
<212> TYPE: PRT
<213> ORGANISM: Homo sapiens

<400> SEQUENCE: 499

Arg Asp Thr Met Val Glu Asp Leu Val Val Leu Val Arg Gly
1               5                   10

<210> SEQ ID NO 500
<211> LENGTH: 24
<212> TYPE: PRT
<213> ORGANISM: Homo sapiens

<400> SEQUENCE: 500
```

```
Lys Ala Asn Phe Asp Ala Gln Gln Phe Ala Gly Thr Trp Leu Leu Val
1               5                   10                  15

Ala Val Gly Ser Ala Cys Arg Phe
            20

<210> SEQ ID NO 501
<211> LENGTH: 23
<212> TYPE: PRT
<213> ORGANISM: Homo sapiens

<400> SEQUENCE: 501

Arg Ala Glu Ala Thr Thr Leu His Val Ala Pro Gln Gly Thr Ala Met
1               5                   10                  15

Ala Val Ser Thr Phe Arg Lys
            20

<210> SEQ ID NO 502
<211> LENGTH: 15
<212> TYPE: PRT
<213> ORGANISM: Homo sapiens

<400> SEQUENCE: 502

Arg Asp Val Val Leu Thr Thr Thr Phe Val Asp Asp Ile Lys Ala
1               5                   10                  15

<210> SEQ ID NO 503
<211> LENGTH: 15
<212> TYPE: PRT
<213> ORGANISM: Homo sapiens

<400> SEQUENCE: 503

Arg Arg Pro Trp Asn Val Ala Ser Leu Ile Tyr Glu Thr Lys Gly
1               5                   10                  15

<210> SEQ ID NO 504
<211> LENGTH: 10
<212> TYPE: PRT
<213> ORGANISM: Homo sapiens

<400> SEQUENCE: 504

Lys Ile Ser Val Ile Arg Pro Ser Lys Gly
1               5                   10

<210> SEQ ID NO 505
<211> LENGTH: 11
<212> TYPE: PRT
<213> ORGANISM: Homo sapiens

<400> SEQUENCE: 505

Lys Val Ala Ser Tyr Gly Val Lys Pro Arg Tyr
1               5                   10

<210> SEQ ID NO 506
<211> LENGTH: 16
<212> TYPE: PRT
<213> ORGANISM: Homo sapiens

<400> SEQUENCE: 506

Arg Asp Phe His Ile Asn Leu Phe Gln Val Leu Pro Trp Leu Lys Glu
1               5                   10                  15

<210> SEQ ID NO 507
<211> LENGTH: 9
<212> TYPE: PRT
```

```
<213> ORGANISM: Homo sapiens

<400> SEQUENCE: 507

Arg Asp Leu Leu Tyr Ile Gly Lys Asp
1               5

<210> SEQ ID NO 508
<211> LENGTH: 13
<212> TYPE: PRT
<213> ORGANISM: Homo sapiens

<400> SEQUENCE: 508

Arg Leu Glu Asp Ser Val Thr Tyr His Cys Ser Arg Gly
1               5                   10

<210> SEQ ID NO 509
<211> LENGTH: 13
<212> TYPE: PRT
<213> ORGANISM: Homo sapiens

<400> SEQUENCE: 509

Arg Leu Pro Pro Thr Thr Thr Cys Gln Gln Gln Lys Glu
1               5                   10

<210> SEQ ID NO 510
<211> LENGTH: 11
<212> TYPE: PRT
<213> ORGANISM: Homo sapiens

<400> SEQUENCE: 510

Lys Cys Leu His Pro Cys Val Ile Ser Arg Glu
1               5                   10

<210> SEQ ID NO 511
<211> LENGTH: 11
<212> TYPE: PRT
<213> ORGANISM: Homo sapiens

<400> SEQUENCE: 511

Lys Ile Asp Val His Leu Val Pro Asp Arg Lys
1               5                   10

<210> SEQ ID NO 512
<211> LENGTH: 16
<212> TYPE: PRT
<213> ORGANISM: Homo sapiens

<400> SEQUENCE: 512

Lys Ser Ile Asp Val Ala Cys His Pro Gly Tyr Ala Leu Pro Lys Ala
1               5                   10                  15

<210> SEQ ID NO 513
<211> LENGTH: 25
<212> TYPE: PRT
<213> ORGANISM: Homo sapiens

<400> SEQUENCE: 513

Lys Val Ser Val Leu Cys Gln Glu Asn Tyr Leu Ile Gln Glu Gly Glu
1               5                   10                  15

Glu Ile Thr Cys Lys Asp Gly Arg Trp
            20                  25

<210> SEQ ID NO 514
<211> LENGTH: 15
```

```
<212> TYPE: PRT
<213> ORGANISM: Homo sapiens

<400> SEQUENCE: 514

Lys Trp Ser Ser Pro Pro Gln Cys Glu Gly Leu Pro Cys Lys Ser
1               5                   10                  15

<210> SEQ ID NO 515
<211> LENGTH: 12
<212> TYPE: PRT
<213> ORGANISM: Homo sapiens

<400> SEQUENCE: 515

Arg Trp Gln Ser Ile Pro Leu Cys Val Glu Lys Ile
1               5                   10

<210> SEQ ID NO 516
<211> LENGTH: 19
<212> TYPE: PRT
<213> ORGANISM: Homo sapiens

<400> SEQUENCE: 516

Arg Tyr Gln Ile Trp Thr Thr Val Val Asp Trp Ile His Pro Asp Leu
1               5                   10                  15

Lys Arg Ile

<210> SEQ ID NO 517
<211> LENGTH: 32
<212> TYPE: PRT
<213> ORGANISM: Homo sapiens

<400> SEQUENCE: 517

Lys Ala Val Leu Gln Leu Asn Glu Glu Gly Val Asp Thr Ala Gly Ser
1               5                   10                  15

Thr Gly Val Thr Leu Asn Leu Thr Ser Lys Pro Ile Ile Leu Arg Phe
            20                  25                  30

<210> SEQ ID NO 518
<211> LENGTH: 17
<212> TYPE: PRT
<213> ORGANISM: Homo sapiens

<400> SEQUENCE: 518

Arg Gly Leu Ala Ser Ala Asn Val Asp Phe Ala Phe Ser Leu Tyr Lys
1               5                   10                  15

His

<210> SEQ ID NO 519
<211> LENGTH: 22
<212> TYPE: PRT
<213> ORGANISM: Homo sapiens

<400> SEQUENCE: 519

Lys Thr Phe Pro Gly Phe Phe Ser Pro Met Leu Gly Glu Phe Val Ser
1               5                   10                  15

Glu Thr Glu Ser Arg Gly
            20

<210> SEQ ID NO 520
<211> LENGTH: 26
<212> TYPE: PRT
<213> ORGANISM: Homo sapiens
```

```
<400> SEQUENCE: 520

Lys Phe Asp Leu Val Pro Val Pro Thr Asn Leu Tyr Gly Asp Phe Phe
1               5                   10                  15

Thr Gly Asp Ala Tyr Val Ile Leu Lys Thr
            20                  25

<210> SEQ ID NO 521
<211> LENGTH: 19
<212> TYPE: PRT
<213> ORGANISM: Homo sapiens

<400> SEQUENCE: 521

Lys Gln Thr Gln Val Ser Val Leu Pro Glu Gly Gly Glu Thr Pro Leu
1               5                   10                  15

Phe Lys Gln

<210> SEQ ID NO 522
<211> LENGTH: 24
<212> TYPE: PRT
<213> ORGANISM: Homo sapiens

<400> SEQUENCE: 522

Arg Ala Gln Pro Val Gln Val Ala Glu Gly Ser Glu Pro Asp Gly Phe
1               5                   10                  15

Trp Glu Ala Leu Gly Gly Lys Ala
            20

<210> SEQ ID NO 523
<211> LENGTH: 32
<212> TYPE: PRT
<213> ORGANISM: Homo sapiens

<400> SEQUENCE: 523

Arg Ile Glu Gly Ser Asn Lys Val Pro Val Asp Pro Ala Thr Tyr Gly
1               5                   10                  15

Gln Phe Tyr Gly Gly Asp Ser Tyr Ile Ile Leu Tyr Asn Tyr Arg His
            20                  25                  30

<210> SEQ ID NO 524
<211> LENGTH: 14
<212> TYPE: PRT
<213> ORGANISM: Homo sapiens

<400> SEQUENCE: 524

Lys Phe Leu Val Gly Pro Asp Gly Ile Pro Ile Met Arg Trp
1               5                   10

<210> SEQ ID NO 525
<211> LENGTH: 17
<212> TYPE: PRT
<213> ORGANISM: Homo sapiens

<400> SEQUENCE: 525

Lys Ala Leu Pro Gln Pro Gln Asn Val Thr Ser Leu Leu Gly Cys Thr
1               5                   10                  15

His

<210> SEQ ID NO 526
<211> LENGTH: 32
<212> TYPE: PRT
<213> ORGANISM: Homo sapiens
```

-continued

```
<400> SEQUENCE: 526

Lys Ser Leu Gly Pro Asn Ser Cys Ser Ala Asn Gly Pro Gly Leu Tyr
1               5                   10                  15

Leu Ile His Gly Pro Asn Leu Tyr Cys Tyr Ser Asp Val Glu Lys Leu
            20                  25                  30

<210> SEQ ID NO 527
<211> LENGTH: 30
<212> TYPE: PRT
<213> ORGANISM: Homo sapiens

<400> SEQUENCE: 527

Arg Asp Gly Trp His Ser Trp Pro Ile Ala His Gln Trp Pro Gln Gly
1               5                   10                  15

Pro Ser Ala Val Asp Ala Ala Phe Ser Trp Glu Glu Lys Leu
            20                  25                  30

<210> SEQ ID NO 528
<211> LENGTH: 17
<212> TYPE: PRT
<213> ORGANISM: Homo sapiens

<400> SEQUENCE: 528

Arg Gly Glu Cys Gln Ala Glu Gly Val Leu Phe Phe Gln Gly Asp Arg
1               5                   10                  15

Glu

<210> SEQ ID NO 529
<211> LENGTH: 29
<212> TYPE: PRT
<213> ORGANISM: Homo sapiens

<400> SEQUENCE: 529

Arg Gly Glu Cys Gln Ala Glu Gly Val Leu Phe Phe Gln Gly Asp Arg
1               5                   10                  15

Glu Trp Phe Trp Asp Leu Ala Thr Gly Thr Met Lys Glu
            20                  25

<210> SEQ ID NO 530
<211> LENGTH: 29
<212> TYPE: PRT
<213> ORGANISM: Homo sapiens

<400> SEQUENCE: 530

Arg Leu Glu Lys Glu Val Gly Thr Pro His Gly Ile Ile Leu Asp Ser
1               5                   10                  15

Val Asp Ala Ala Phe Ile Cys Pro Gly Ser Ser Arg Leu
            20                  25

<210> SEQ ID NO 531
<211> LENGTH: 9
<212> TYPE: PRT
<213> ORGANISM: Homo sapiens

<400> SEQUENCE: 531

Arg Leu Trp Trp Leu Asp Leu Lys Ser
1               5

<210> SEQ ID NO 532
<211> LENGTH: 15
<212> TYPE: PRT
<213> ORGANISM: Homo sapiens
```

-continued

<400> SEQUENCE: 532

Arg Trp Lys Asn Phe Pro Ser Pro Val Asp Ala Ala Phe Arg Gln
1               5                   10                  15

<210> SEQ ID NO 533
<211> LENGTH: 30
<212> TYPE: PRT
<213> ORGANISM: Homo sapiens

<400> SEQUENCE: 533

Lys Asp Gln Val Asn Thr Phe Asp Asn Ile Phe Ile Ala Pro Val Gly
1               5                   10                  15

Ile Ser Thr Ala Met Gly Met Ile Ser Leu Gly Leu Lys Gly
            20                  25                  30

<210> SEQ ID NO 534
<211> LENGTH: 11
<212> TYPE: PRT
<213> ORGANISM: Homo sapiens

<400> SEQUENCE: 534

Lys Ala Asn Val Phe Val Gln Leu Pro Arg Leu
1               5                   10

<210> SEQ ID NO 535
<211> LENGTH: 16
<212> TYPE: PRT
<213> ORGANISM: Homo sapiens

<400> SEQUENCE: 535

Arg Leu Glu Ala Leu Pro Asn Ser Leu Leu Ala Pro Leu Gly Arg Leu
1               5                   10                  15

<210> SEQ ID NO 536
<211> LENGTH: 9
<212> TYPE: PRT
<213> ORGANISM: Homo sapiens

<400> SEQUENCE: 536

Arg Leu Phe Gln Gly Leu Gly Lys Leu
1               5

<210> SEQ ID NO 537
<211> LENGTH: 17
<212> TYPE: PRT
<213> ORGANISM: Homo sapiens

<400> SEQUENCE: 537

Arg Asn Leu Ile Ala Ala Val Ala Pro Gly Ala Phe Leu Gly Leu Lys
1               5                   10                  15

Ala

<210> SEQ ID NO 538
<211> LENGTH: 13
<212> TYPE: PRT
<213> ORGANISM: Homo sapiens

<400> SEQUENCE: 538

Arg Thr Phe Thr Pro Gln Pro Pro Gly Leu Glu Arg Leu
1               5                   10

<210> SEQ ID NO 539

-continued

<210> LENGTH: 14
<212> TYPE: PRT
<213> ORGANISM: Homo sapiens

<400> SEQUENCE: 539

Lys Val Thr Phe Gln Leu Thr Tyr Glu Glu Val Leu Lys Arg
1               5                  10

<210> SEQ ID NO 540
<211> LENGTH: 15
<212> TYPE: PRT
<213> ORGANISM: Homo sapiens

<400> SEQUENCE: 540

Lys Val Thr Phe Gln Leu Thr Tyr Glu Glu Val Leu Lys Arg Asn
1               5                  10                  15

<210> SEQ ID NO 541
<211> LENGTH: 39
<212> TYPE: PRT
<213> ORGANISM: Homo sapiens

<400> SEQUENCE: 541

Arg Gly Ile Glu Ile Leu Asn Gln Val Gln Glu Ser Leu Pro Glu Leu
1               5                  10                  15

Ser Asn His Ala Ser Ile Leu Ile Met Leu Thr Asp Gly Asp Pro Thr
            20                  25                  30

Glu Gly Val Thr Asp Arg Ser
        35

<210> SEQ ID NO 542
<211> LENGTH: 15
<212> TYPE: PRT
<213> ORGANISM: Homo sapiens

<400> SEQUENCE: 542

Arg Lys Ala Ala Ile Ser Gly Glu Asn Ala Gly Leu Val Arg Ala
1               5                  10                  15

<210> SEQ ID NO 543
<211> LENGTH: 27
<212> TYPE: PRT
<213> ORGANISM: Homo sapiens

<400> SEQUENCE: 543

Lys Ala Gly Glu Leu Glu Val Phe Asn Gly Tyr Phe Val His Phe Phe
1               5                  10                  15

Ala Pro Asp Asn Leu Asp Pro Ile Pro Lys Asn
            20                  25

<210> SEQ ID NO 544
<211> LENGTH: 13
<212> TYPE: PRT
<213> ORGANISM: Homo sapiens

<400> SEQUENCE: 544

Lys Phe Tyr Asn Gln Val Ser Thr Pro Leu Leu Arg Asn
1               5                  10

<210> SEQ ID NO 545
<211> LENGTH: 13
<212> TYPE: PRT
<213> ORGANISM: Homo sapiens -continued

```
<400> SEQUENCE: 545

Lys Val Gln Phe Glu Leu His Tyr Gln Glu Val Lys Trp
1               5                   10

<210> SEQ ID NO 546
<211> LENGTH: 17
<212> TYPE: PRT
<213> ORGANISM: Homo sapiens

<400> SEQUENCE: 546

Arg Glu Thr Ala Val Asp Gly Glu Leu Val Val Leu Tyr Asp Val Lys
1               5                   10                  15

Arg

<210> SEQ ID NO 547
<211> LENGTH: 9
<212> TYPE: PRT
<213> ORGANISM: Homo sapiens

<400> SEQUENCE: 547

Arg Ile Tyr Leu Gln Pro Gly Arg Leu
1               5

<210> SEQ ID NO 548
<211> LENGTH: 15
<212> TYPE: PRT
<213> ORGANISM: Homo sapiens

<400> SEQUENCE: 548

Arg Leu Trp Ala Tyr Leu Thr Ile Glu Gln Leu Leu Glu Lys Arg
1               5                   10                  15

<210> SEQ ID NO 549
<211> LENGTH: 14
<212> TYPE: PRT
<213> ORGANISM: Homo sapiens

<400> SEQUENCE: 549

Lys Ile Thr Phe Glu Leu Val Tyr Glu Glu Leu Leu Lys Arg
1               5                   10

<210> SEQ ID NO 550
<211> LENGTH: 18
<212> TYPE: PRT
<213> ORGANISM: Homo sapiens

<400> SEQUENCE: 550

Lys Leu Gln Asp Arg Gly Pro Asp Val Leu Thr Ala Thr Val Ser Gly
1               5                   10                  15

Lys Leu

<210> SEQ ID NO 551
<211> LENGTH: 29
<212> TYPE: PRT
<213> ORGANISM: Homo sapiens

<400> SEQUENCE: 551

Lys Thr Gly Leu Leu Leu Leu Ser Asp Pro Asp Lys Val Thr Ile Gly
1               5                   10                  15

Leu Leu Phe Trp Asp Gly Arg Gly Glu Gly Leu Arg Leu
                20                  25
```

-continued

```
<210> SEQ ID NO 552
<211> LENGTH: 30
<212> TYPE: PRT
<213> ORGANISM: Homo sapiens

<400> SEQUENCE: 552

Arg Ala Ile Ser Gly Gly Ser Ile Gln Ile Glu Asn Gly Tyr Phe Val
1               5                   10                  15

His Tyr Phe Ala Pro Glu Gly Leu Thr Thr Met Pro Lys Asn
            20                  25                  30

<210> SEQ ID NO 553
<211> LENGTH: 17
<212> TYPE: PRT
<213> ORGANISM: Homo sapiens

<400> SEQUENCE: 553

Arg Ala Asn Thr Val Gln Glu Ala Thr Phe Gln Met Glu Leu Pro Lys
1               5                   10                  15

Lys

<210> SEQ ID NO 554
<211> LENGTH: 35
<212> TYPE: PRT
<213> ORGANISM: Homo sapiens

<400> SEQUENCE: 554

Arg Ser Phe Ala Ala Gly Ile Gln Ala Leu Gly Gly Thr Asn Ile Asn
1               5                   10                  15

Asp Ala Met Leu Met Ala Val Gln Leu Leu Asp Ser Ser Asn Gln Glu
            20                  25                  30

Glu Arg Leu
        35

<210> SEQ ID NO 555
<211> LENGTH: 12
<212> TYPE: PRT
<213> ORGANISM: Homo sapiens

<400> SEQUENCE: 555

Arg Val Gln Gly Asn Asp His Ser Ala Thr Arg Glu
1               5                   10

<210> SEQ ID NO 556
<211> LENGTH: 15
<212> TYPE: PRT
<213> ORGANISM: Homo sapiens

<400> SEQUENCE: 556

Lys Ile Thr Phe Glu Leu Val Tyr Glu Glu Leu Leu Lys Arg Arg
1               5                   10                  15

<210> SEQ ID NO 557
<211> LENGTH: 13
<212> TYPE: PRT
<213> ORGANISM: Homo sapiens

<400> SEQUENCE: 557

Lys Val Thr Ile Gly Leu Leu Phe Trp Asp Gly Arg Gly
1               5                   10

<210> SEQ ID NO 558
<211> LENGTH: 28
```

-continued

<212> TYPE: PRT
<213> ORGANISM: Homo sapiens

<400> SEQUENCE: 558

Arg Leu Trp Ala Tyr Leu Thr Ile Gln Gln Leu Leu Glu Gln Thr Val
1               5                   10                  15

Ser Ala Ser Asp Ala Asp Gln Gln Ala Leu Arg Asn
            20                  25

<210> SEQ ID NO 559
<211> LENGTH: 23
<212> TYPE: PRT
<213> ORGANISM: Homo sapiens

<400> SEQUENCE: 559

Lys Leu Phe His Thr Asn Phe Tyr Asp Thr Val Gly Thr Ile Gln Leu
1               5                   10                  15

Ile Asn Asp His Val Lys Lys
            20

<210> SEQ ID NO 560
<211> LENGTH: 13
<212> TYPE: PRT
<213> ORGANISM: Homo sapiens

<400> SEQUENCE: 560

Lys Glu Asn Phe Leu Phe Leu Thr Pro Asp Cys Lys Ser
1               5                   10

<210> SEQ ID NO 561
<211> LENGTH: 19
<212> TYPE: PRT
<213> ORGANISM: Homo sapiens

<400> SEQUENCE: 561

Lys Ile Tyr Pro Thr Val Asn Cys Gln Pro Leu Gly Met Ile Ser Leu
1               5                   10                  15

Met Lys Arg

<210> SEQ ID NO 562
<211> LENGTH: 20
<212> TYPE: PRT
<213> ORGANISM: Homo sapiens

<400> SEQUENCE: 562

Lys Lys Ile Tyr Pro Thr Val Asn Cys Gln Pro Leu Gly Met Ile Ser
1               5                   10                  15

Leu Met Lys Arg
            20

<210> SEQ ID NO 563
<211> LENGTH: 23
<212> TYPE: PRT
<213> ORGANISM: Homo sapiens

<400> SEQUENCE: 563

Lys Ser Leu Trp Asn Gly Asp Thr Gly Glu Cys Thr Asp Asn Ala Tyr
1               5                   10                  15

Ile Asp Ile Gln Leu Arg Ile
            20

<210> SEQ ID NO 564

```
<211> LENGTH: 11
<212> TYPE: PRT
<213> ORGANISM: Homo sapiens

<400> SEQUENCE: 564

Lys Ile Leu Gly Pro Leu Ser Tyr Ser Lys Ile
1               5                   10

<210> SEQ ID NO 565
<211> LENGTH: 31
<212> TYPE: PRT
<213> ORGANISM: Homo sapiens

<400> SEQUENCE: 565

Lys Glu Tyr Gly Val Val Leu Ala Pro Asp Gly Ser Thr Val Ala Val
1               5                   10                  15

Glu Pro Leu Leu Ala Gly Leu Glu Ala Gly Leu Gln Gly Arg Arg
            20                  25                  30

<210> SEQ ID NO 566
<211> LENGTH: 34
<212> TYPE: PRT
<213> ORGANISM: Homo sapiens

<400> SEQUENCE: 566

Arg Glu Gly Lys Glu Tyr Gly Val Val Leu Ala Pro Asp Gly Ser Thr
1               5                   10                  15

Val Ala Val Glu Pro Leu Leu Ala Gly Leu Glu Ala Gly Leu Gln Gly
            20                  25                  30

Arg Arg

<210> SEQ ID NO 567
<211> LENGTH: 27
<212> TYPE: PRT
<213> ORGANISM: Homo sapiens

<400> SEQUENCE: 567

Arg Gln Asn Gly Ala Ala Leu Thr Ser Ala Ser Ile Leu Ala Gln Gln
1               5                   10                  15

Val Trp Gly Thr Leu Val Leu Leu Gln Arg Leu
            20                  25

<210> SEQ ID NO 568
<211> LENGTH: 21
<212> TYPE: PRT
<213> ORGANISM: Homo sapiens

<400> SEQUENCE: 568

Lys Ile Ala Gln Leu Pro Leu Thr Gly Ser Met Ser Ile Ile Phe Phe
1               5                   10                  15

Leu Pro Leu Lys Val
            20

<210> SEQ ID NO 569
<211> LENGTH: 32
<212> TYPE: PRT
<213> ORGANISM: Homo sapiens

<400> SEQUENCE: 569

Arg Ser Ser Thr Ser Pro Thr Thr Asn Val Leu Leu Ser Pro Leu Ser
1               5                   10                  15

Val Ala Thr Ala Leu Ser Ala Leu Ser Leu Gly Ala Glu Gln Arg Thr
```

-continued

```
              20                 25                 30

<210> SEQ ID NO 570
<211> LENGTH: 13
<212> TYPE: PRT
<213> ORGANISM: Homo sapiens

<400> SEQUENCE: 570

Lys Val Ala Glu Tyr Met Asp Trp Ile Leu Glu Lys Thr
1               5                   10

<210> SEQ ID NO 571
<211> LENGTH: 15
<212> TYPE: PRT
<213> ORGANISM: Homo sapiens

<400> SEQUENCE: 571

Arg Cys Gln Phe Phe Ser Tyr Ala Thr Gln Thr Phe His Lys Ala
1               5                   10                  15

<210> SEQ ID NO 572
<211> LENGTH: 19
<212> TYPE: PRT
<213> ORGANISM: Homo sapiens

<400> SEQUENCE: 572

Arg Cys Leu Leu Phe Ser Phe Leu Pro Ala Ser Ser Ile Asn Asp Met
1               5                   10                  15

Glu Lys Arg

<210> SEQ ID NO 573
<211> LENGTH: 14
<212> TYPE: PRT
<213> ORGANISM: Homo sapiens

<400> SEQUENCE: 573

Arg Leu Val Leu Leu Asn Ala Ile Tyr Leu Ser Ala Lys Trp
1               5                   10

<210> SEQ ID NO 574
<211> LENGTH: 16
<212> TYPE: PRT
<213> ORGANISM: Homo sapiens

<400> SEQUENCE: 574

Arg Asn Ala Leu Phe Cys Leu Glu Ser Ala Trp Asn Val Ala Lys Glu
1               5                   10                  15

<210> SEQ ID NO 575
<211> LENGTH: 18
<212> TYPE: PRT
<213> ORGANISM: Homo sapiens

<400> SEQUENCE: 575

Arg Ser Asn Pro Val Ile Leu Asn Val Leu Tyr Gly Pro Asp Leu Pro
1               5                   10                  15

Arg Ile

<210> SEQ ID NO 576
<211> LENGTH: 20
<212> TYPE: PRT
<213> ORGANISM: Homo sapiens

<400> SEQUENCE: 576
```

```
Lys Ile Ala Ile Ile Gly Ala Gly Ile Gly Gly Thr Ser Ala Ala Tyr
1               5                   10                  15

Tyr Leu Arg Gln
            20

<210> SEQ ID NO 577
<211> LENGTH: 16
<212> TYPE: PRT
<213> ORGANISM: Homo sapiens

<400> SEQUENCE: 577

Lys Trp Tyr Asn Leu Ala Ile Gly Ser Thr Cys Pro Trp Leu Lys Lys
1               5                   10                  15

<210> SEQ ID NO 578
<211> LENGTH: 13
<212> TYPE: PRT
<213> ORGANISM: Homo sapiens

<400> SEQUENCE: 578

Arg Thr Val Ala Ala Cys Asn Leu Pro Ile Val Arg Gly
1               5                   10

<210> SEQ ID NO 579
<211> LENGTH: 22
<212> TYPE: PRT
<213> ORGANISM: Homo sapiens

<400> SEQUENCE: 579

Arg Ile Val Glu Gly Ser Asp Ala Glu Ile Gly Met Ser Pro Trp Gln
1               5                   10                  15

Val Met Leu Phe Arg Lys
            20

<210> SEQ ID NO 580
<211> LENGTH: 23
<212> TYPE: PRT
<213> ORGANISM: Homo sapiens

<400> SEQUENCE: 580

Arg Arg Gln Glu Cys Ser Ile Pro Val Cys Gly Gln Asp Gln Val Thr
1               5                   10                  15

Val Ala Met Thr Pro Arg Ser
            20

<210> SEQ ID NO 581
<211> LENGTH: 19
<212> TYPE: PRT
<213> ORGANISM: Homo sapiens

<400> SEQUENCE: 581

Arg Thr Phe Gly Ser Gly Glu Ala Asp Cys Gly Leu Arg Pro Leu Phe
1               5                   10                  15

Glu Lys Lys

<210> SEQ ID NO 582
<211> LENGTH: 25
<212> TYPE: PRT
<213> ORGANISM: Homo sapiens

<400> SEQUENCE: 582

Arg Leu Leu Asn Asn Trp Asp Val Cys Ala Asp Met Val Gly Thr Phe
```

-continued

```
1               5               10              15

Thr Asp Thr Glu Asp Pro Ala Lys Phe
                20              25

<210> SEQ ID NO 583
<211> LENGTH: 12
<212> TYPE: PRT
<213> ORGANISM: Homo sapiens

<400> SEQUENCE: 583

Arg Gly Tyr Val Ile Ile Lys Pro Leu Val Trp Val
1               5               10

<210> SEQ ID NO 584
<211> LENGTH: 26
<212> TYPE: PRT
<213> ORGANISM: Homo sapiens

<400> SEQUENCE: 584

Lys Val Val Leu Ser Ser Gly Ser Gly Pro Gly Leu Asp Leu Pro Leu
1               5               10              15

Val Leu Gly Leu Pro Leu Gln Leu Lys Leu
            20              25

<210> SEQ ID NO 585
<211> LENGTH: 11
<212> TYPE: PRT
<213> ORGANISM: Homo sapiens

<400> SEQUENCE: 585

Lys Gly Phe Leu Leu Leu Ala Ser Leu Arg Gln
1               5               10

<210> SEQ ID NO 586
<211> LENGTH: 10
<212> TYPE: PRT
<213> ORGANISM: Homo sapiens

<400> SEQUENCE: 586

Lys Ala Val Leu His Ile Gly Glu Lys Gly
1               5               10

<210> SEQ ID NO 587
<211> LENGTH: 17
<212> TYPE: PRT
<213> ORGANISM: Homo sapiens

<400> SEQUENCE: 587

Lys Phe Ser Ile Ser Ala Thr Tyr Asp Leu Gly Ala Thr Leu Leu Lys
1               5               10              15

Met

<210> SEQ ID NO 588
<211> LENGTH: 17
<212> TYPE: PRT
<213> ORGANISM: Homo sapiens

<400> SEQUENCE: 588

Lys Lys Glu Leu Glu Leu Gln Ile Gly Asn Ala Leu Phe Ile Gly Lys
1               5               10              15

His
```

-continued

```
<210> SEQ ID NO 589
<211> LENGTH: 16
<212> TYPE: PRT
<213> ORGANISM: Homo sapiens

<400> SEQUENCE: 589

Lys Met Ser Ser Ile Asn Ala Asp Phe Ala Phe Asn Leu Tyr Arg Arg
1               5                   10                  15

<210> SEQ ID NO 590
<211> LENGTH: 14
<212> TYPE: PRT
<213> ORGANISM: Homo sapiens

<400> SEQUENCE: 590

Arg Leu Thr Leu Leu Ala Pro Leu Asn Ser Val Phe Lys Asp
1               5                   10

<210> SEQ ID NO 591
<211> LENGTH: 15
<212> TYPE: PRT
<213> ORGANISM: Homo sapiens

<400> SEQUENCE: 591

Arg Gly Ser Pro Ala Ile Asn Val Ala Val His Val Phe Arg Lys
1               5                   10                  15

<210> SEQ ID NO 592
<211> LENGTH: 11
<212> TYPE: PRT
<213> ORGANISM: Homo sapiens

<400> SEQUENCE: 592

Lys Met Pro Ser His Leu Met Leu Ala Arg Lys
1               5                   10

<210> SEQ ID NO 593
<211> LENGTH: 10
<212> TYPE: PRT
<213> ORGANISM: Homo sapiens

<400> SEQUENCE: 593

Lys Glu Leu Pro Glu His Thr Val Lys Leu
1               5                   10

<210> SEQ ID NO 594
<211> LENGTH: 29
<212> TYPE: PRT
<213> ORGANISM: Homo sapiens

<400> SEQUENCE: 594

Lys Glu Tyr Ala Asn Gln Phe Met Trp Glu Tyr Ser Thr Asn Tyr Gly
1               5                   10                  15

Gln Ala Pro Leu Ser Leu Leu Val Ser Tyr Thr Lys Ser
            20                  25

<210> SEQ ID NO 595
<211> LENGTH: 13
<212> TYPE: PRT
<213> ORGANISM: Homo sapiens

<400> SEQUENCE: 595

Lys His Leu Ser Leu Leu Thr Thr Leu Ser Asn Arg Val
1               5                   10
```

-continued

```
<210> SEQ ID NO 596
<211> LENGTH: 24
<212> TYPE: PRT
<213> ORGANISM: Homo sapiens

<400> SEQUENCE: 596

Lys His Gln Pro Gln Glu Phe Pro Thr Tyr Val Glu Pro Thr Asn Asp
1               5                   10                  15

Glu Ile Cys Glu Ala Phe Arg Lys
            20

<210> SEQ ID NO 597
<211> LENGTH: 28
<212> TYPE: PRT
<213> ORGANISM: Homo sapiens

<400> SEQUENCE: 597

Lys Leu Ala Gln Lys Val Pro Thr Ala Asp Leu Glu Asp Val Leu Pro
1               5                   10                  15

Leu Ala Glu Asp Ile Thr Asn Ile Leu Ser Lys Cys
            20                  25

<210> SEQ ID NO 598
<211> LENGTH: 10
<212> TYPE: PRT
<213> ORGANISM: Homo sapiens

<400> SEQUENCE: 598

Lys Leu Cys Asp Asn Leu Ser Thr Lys Asn
1               5                   10

<210> SEQ ID NO 599
<211> LENGTH: 9
<212> TYPE: PRT
<213> ORGANISM: Homo sapiens

<400> SEQUENCE: 599

Lys Leu Cys Met Ala Ala Leu Lys His
1               5

<210> SEQ ID NO 600
<211> LENGTH: 22
<212> TYPE: PRT
<213> ORGANISM: Homo sapiens

<400> SEQUENCE: 600

Lys Ser Cys Glu Ser Asn Ser Pro Phe Pro Val His Pro Gly Thr Ala
1               5                   10                  15

Glu Cys Cys Thr Lys Glu
            20

<210> SEQ ID NO 601
<211> LENGTH: 23
<212> TYPE: PRT
<213> ORGANISM: Homo sapiens

<400> SEQUENCE: 601

Lys Ser Tyr Leu Ser Met Val Gly Ser Cys Cys Thr Ser Ala Ser Pro
1               5                   10                  15

Thr Val Cys Phe Leu Lys Glu
            20
```

<210> SEQ ID NO 602
<211> LENGTH: 31
<212> TYPE: PRT
<213> ORGANISM: Homo sapiens

<400> SEQUENCE: 602

Lys Thr Ala Met Asp Val Phe Val Cys Thr Tyr Phe Met Pro Ala Ala
1               5                   10                  15

Gln Leu Pro Glu Leu Pro Asp Val Glu Leu Pro Thr Asn Lys Asp
            20                  25                  30

<210> SEQ ID NO 603
<211> LENGTH: 9
<212> TYPE: PRT
<213> ORGANISM: Homo sapiens

<400> SEQUENCE: 603

Lys Val Leu Glu Pro Thr Leu Lys Ser
1               5

<210> SEQ ID NO 604
<211> LENGTH: 17
<212> TYPE: PRT
<213> ORGANISM: Homo sapiens

<400> SEQUENCE: 604

Arg Lys Phe Pro Ser Gly Thr Phe Glu Gln Val Ser Gln Leu Val Lys
1               5                   10                  15

Glu

<210> SEQ ID NO 605
<211> LENGTH: 12
<212> TYPE: PRT
<213> ORGANISM: Homo sapiens

<400> SEQUENCE: 605

Arg Thr His Leu Pro Glu Val Phe Leu Ser Lys Val
1               5                   10

<210> SEQ ID NO 606
<211> LENGTH: 9
<212> TYPE: PRT
<213> ORGANISM: Homo sapiens

<400> SEQUENCE: 606

Arg Thr Ser Ala Leu Ser Ala Lys Ser
1               5

<210> SEQ ID NO 607
<211> LENGTH: 12
<212> TYPE: PRT
<213> ORGANISM: Homo sapiens

<400> SEQUENCE: 607

Arg Gly Gln Tyr Cys Tyr Glu Leu Asp Glu Lys Ala
1               5                   10

<210> SEQ ID NO 608
<211> LENGTH: 24
<212> TYPE: PRT
<213> ORGANISM: Homo sapiens

<400> SEQUENCE: 608

Arg Met Asp Trp Leu Val Pro Ala Thr Cys Glu Pro Ile Gln Ser Val

-continued

```
1               5                    10                   15

Phe Phe Phe Ser Gly Asp Lys Tyr
            20

<210> SEQ ID NO 609
<211> LENGTH: 9
<212> TYPE: PRT
<213> ORGANISM: Homo sapiens

<400> SEQUENCE: 609

Arg Gln Pro Gln Phe Ile Ser Arg Asp
1               5

<210> SEQ ID NO 610
<211> LENGTH: 9
<212> TYPE: PRT
<213> ORGANISM: Homo sapiens

<400> SEQUENCE: 610

Lys His Phe Gln Asn Leu Gly Lys Asp
1               5

<210> SEQ ID NO 611
<211> LENGTH: 14
<212> TYPE: PRT
<213> ORGANISM: Homo sapiens

<400> SEQUENCE: 611

Arg Arg His Pro Asp Leu Ser Ile Pro Glu Leu Leu Arg Ile
1               5                    10

<210> SEQ ID NO 612
<211> LENGTH: 13
<212> TYPE: PRT
<213> ORGANISM: Homo sapiens

<400> SEQUENCE: 612

Arg Thr Ile Asn Pro Ala Val Asp His Cys Cys Lys Thr
1               5                    10

<210> SEQ ID NO 613
<211> LENGTH: 22
<212> TYPE: PRT
<213> ORGANISM: Homo sapiens

<400> SEQUENCE: 613

Arg Asp Tyr Asn Leu Asn Asp Ile Leu Leu Gln Leu Gly Ile Glu Glu
1               5                    10                   15

Ala Phe Thr Ser Lys Ala
            20

<210> SEQ ID NO 614
<211> LENGTH: 23
<212> TYPE: PRT
<213> ORGANISM: Homo sapiens

<400> SEQUENCE: 614

Arg Gly Thr His Val Asp Leu Gly Leu Ala Ser Ala Asn Val Asp Phe
1               5                    10                   15

Ala Phe Ser Leu Tyr Lys Gln
            20

<210> SEQ ID NO 615
```

```
<211> LENGTH: 28
<212> TYPE: PRT
<213> ORGANISM: Homo sapiens

<400> SEQUENCE: 615

Lys Gly Phe Pro Ile Lys Glu Asp Phe Leu Glu Gln Ser Glu Gln Leu
1               5                   10                  15

Phe Gly Ala Lys Pro Val Ser Leu Thr Gly Lys Gln
            20                  25

<210> SEQ ID NO 616
<211> LENGTH: 20
<212> TYPE: PRT
<213> ORGANISM: Homo sapiens

<400> SEQUENCE: 616

Arg Gln Leu Thr Ser Gly Pro Asn Gln Glu Gln Val Ser Pro Leu Thr
1               5                   10                  15

Leu Leu Lys Leu
            20

<210> SEQ ID NO 617
<211> LENGTH: 26
<212> TYPE: PRT
<213> ORGANISM: Homo sapiens

<400> SEQUENCE: 617

Arg Ala Gln Leu Val Pro Leu Pro Pro Ser Thr Tyr Val Glu Phe Thr
1               5                   10                  15

Val Ser Gly Thr Asp Cys Val Ala Lys Glu
            20                  25

<210> SEQ ID NO 618
<211> LENGTH: 14
<212> TYPE: PRT
<213> ORGANISM: Homo sapiens

<400> SEQUENCE: 618

Lys Asp Pro Thr Phe Ile Pro Ala Pro Ile Gln Ala Lys Thr
1               5                   10

<210> SEQ ID NO 619
<211> LENGTH: 11
<212> TYPE: PRT
<213> ORGANISM: Homo sapiens

<400> SEQUENCE: 619

Arg Phe Met Gln Ala Val Thr Gly Trp Lys Thr
1               5                   10

<210> SEQ ID NO 620
<211> LENGTH: 12
<212> TYPE: PRT
<213> ORGANISM: Homo sapiens

<400> SEQUENCE: 620

Lys Ala Asn Arg Pro Phe Leu Val Phe Ile Arg Glu
1               5                   10

<210> SEQ ID NO 621
<211> LENGTH: 17
<212> TYPE: PRT
<213> ORGANISM: Homo sapiens
```

<400> SEQUENCE: 621

Lys Gly Asp Asp Ile Thr Met Val Leu Ile Leu Pro Lys Pro Glu Lys
1               5                   10                  15

Ser

<210> SEQ ID NO 622
<211> LENGTH: 13
<212> TYPE: PRT
<213> ORGANISM: Homo sapiens

<400> SEQUENCE: 622

Arg Asp Ile Pro Met Asn Pro Met Cys Ile Tyr Arg Ser
1               5                   10

<210> SEQ ID NO 623
<211> LENGTH: 14
<212> TYPE: PRT
<213> ORGANISM: Homo sapiens

<400> SEQUENCE: 623

Lys Lys Leu Val Pro Phe Ala Thr Glu Leu His Glu Arg Leu
1               5                   10

<210> SEQ ID NO 624
<211> LENGTH: 19
<212> TYPE: PRT
<213> ORGANISM: Homo sapiens

<400> SEQUENCE: 624

Lys Ser Leu Ala Glu Leu Gly Gly His Leu Asp Gln Gln Val Glu Glu
1               5                   10                  15

Phe Arg Arg

<210> SEQ ID NO 625
<211> LENGTH: 17
<212> TYPE: PRT
<213> ORGANISM: Homo sapiens

<400> SEQUENCE: 625

Lys Ala Leu Tyr Trp Val Asn Gly Gln Val Pro Asp Gly Val Ser Lys
1               5                   10                  15

Val

<210> SEQ ID NO 626
<211> LENGTH: 9
<212> TYPE: PRT
<213> ORGANISM: Homo sapiens

<400> SEQUENCE: 626

Lys Phe Ile Ile Pro Gly Leu Lys Leu
1               5

<210> SEQ ID NO 627
<211> LENGTH: 20
<212> TYPE: PRT
<213> ORGANISM: Homo sapiens

<400> SEQUENCE: 627

Lys Phe Ser Val Pro Ala Gly Ile Val Ile Pro Ser Phe Gln Ala Leu
1               5                   10                  15

Thr Ala Arg Phe
            20

<210> SEQ ID NO 628
<211> LENGTH: 17
<212> TYPE: PRT
<213> ORGANISM: Homo sapiens

<400> SEQUENCE: 628

Lys Ile Glu Gly Asn Leu Ile Phe Asp Pro Asn Asn Tyr Leu Pro Lys
1               5                   10                  15

Glu

<210> SEQ ID NO 629
<211> LENGTH: 28
<212> TYPE: PRT
<213> ORGANISM: Homo sapiens

<400> SEQUENCE: 629

Lys Leu Asn Asp Leu Asn Ser Val Leu Val Met Pro Thr Phe His Val
1               5                   10                  15

Pro Phe Thr Asp Leu Gln Val Pro Ser Cys Lys Leu
            20                  25

<210> SEQ ID NO 630
<211> LENGTH: 16
<212> TYPE: PRT
<213> ORGANISM: Homo sapiens

<400> SEQUENCE: 630

Lys Val Glu Leu Glu Val Pro Gln Leu Cys Ser Phe Ile Leu Lys Thr
1               5                   10                  15

<210> SEQ ID NO 631
<211> LENGTH: 18
<212> TYPE: PRT
<213> ORGANISM: Homo sapiens

<400> SEQUENCE: 631

Lys Val Asn Trp Glu Glu Glu Ala Ala Ser Gly Leu Leu Thr Ser Leu
1               5                   10                  15

Lys Asp

<210> SEQ ID NO 632
<211> LENGTH: 17
<212> TYPE: PRT
<213> ORGANISM: Homo sapiens

<400> SEQUENCE: 632

Arg Ala Thr Leu Tyr Ala Leu Ser His Ala Val Asn Asn Tyr His Lys
1               5                   10                  15

Thr

<210> SEQ ID NO 633
<211> LENGTH: 12
<212> TYPE: PRT
<213> ORGANISM: Homo sapiens

<400> SEQUENCE: 633

Arg Thr Gly Ile Ser Pro Leu Ala Leu Ile Lys Gly
1               5                   10

<210> SEQ ID NO 634
<211> LENGTH: 16

<212> TYPE: PRT
<213> ORGANISM: Homo sapiens

<400> SEQUENCE: 634

Arg Thr Leu Gln Gly Ile Pro Gln Met Ile Gly Glu Val Ile Arg Lys
1               5                   10                  15

<210> SEQ ID NO 635
<211> LENGTH: 18
<212> TYPE: PRT
<213> ORGANISM: Homo sapiens

<400> SEQUENCE: 635

Lys Asp Ala Leu Ser Ser Val Gln Glu Ser Gln Val Ala Gln Gln Ala
1               5                   10                  15

Arg Gly

<210> SEQ ID NO 636
<211> LENGTH: 15
<212> TYPE: PRT
<213> ORGANISM: Homo sapiens

<400> SEQUENCE: 636

Arg Asp Gly Trp Gln Trp Phe Trp Ser Pro Ser Thr Phe Arg Gly
1               5                   10                  15

<210> SEQ ID NO 637
<211> LENGTH: 18
<212> TYPE: PRT
<213> ORGANISM: Homo sapiens

<400> SEQUENCE: 637

Lys Val Gln Ala Ala Val Gly Thr Ser Ala Ala Pro Val Pro Ser Asp
1               5                   10                  15

Asn His

<210> SEQ ID NO 638
<211> LENGTH: 9
<212> TYPE: PRT
<213> ORGANISM: Homo sapiens

<400> SEQUENCE: 638

Arg Trp Glu Leu Ala Leu Gly Arg Phe
1               5

<210> SEQ ID NO 639
<211> LENGTH: 24
<212> TYPE: PRT
<213> ORGANISM: Homo sapiens

<400> SEQUENCE: 639

Lys Ser Asn Phe Leu Asn Cys Tyr Val Ser Gly Phe His Pro Ser Asp
1               5                   10                  15

Ile Glu Val Asp Leu Leu Lys Asn
            20

<210> SEQ ID NO 640
<211> LENGTH: 12
<212> TYPE: PRT
<213> ORGANISM: Homo sapiens

<400> SEQUENCE: 640

Arg Gly Gly His Cys Val Ala Leu Cys Thr Arg Gly

-continued

```
1               5                    10
```

```
<210> SEQ ID NO 641
<211> LENGTH: 22
<212> TYPE: PRT
<213> ORGANISM: Homo sapiens

<400> SEQUENCE: 641

Arg Leu Val Asp Phe Tyr Val Met Pro Val Val Asn Val Asp Gly Tyr
1               5                    10                  15

Asp Tyr Ser Trp Lys Lys
            20
```

```
<210> SEQ ID NO 642
<211> LENGTH: 29
<212> TYPE: PRT
<213> ORGANISM: Homo sapiens

<400> SEQUENCE: 642

Arg Tyr Thr His Gly His Gly Ser Glu Thr Leu Tyr Leu Ala Pro Gly
1               5                    10                  15

Gly Gly Asp Asp Trp Ile Tyr Asp Leu Gly Ile Lys Tyr
            20                  25
```

```
<210> SEQ ID NO 643
<211> LENGTH: 18
<212> TYPE: PRT
<213> ORGANISM: Homo sapiens

<400> SEQUENCE: 643

Lys Leu Ser Asn Asn Ala Leu Ser Gly Leu Pro Gln Gly Val Phe Gly
1               5                    10                  15

Lys Leu
```

```
<210> SEQ ID NO 644
<211> LENGTH: 29
<212> TYPE: PRT
<213> ORGANISM: Homo sapiens

<400> SEQUENCE: 644

Lys Thr Leu Asn Leu Ala Gln Asn Leu Leu Ala Gln Leu Pro Glu Glu
1               5                    10                  15

Leu Phe His Pro Leu Thr Ser Leu Gln Thr Leu Lys Leu
            20                  25
```

```
<210> SEQ ID NO 645
<211> LENGTH: 11
<212> TYPE: PRT
<213> ORGANISM: Homo sapiens

<400> SEQUENCE: 645

Arg Trp Leu Asn Val Gln Leu Ser Pro Arg Gln
1               5                    10
```

```
<210> SEQ ID NO 646
<211> LENGTH: 32
<212> TYPE: PRT
<213> ORGANISM: Homo sapiens

<400> SEQUENCE: 646

Lys Gly Asp Ser Val Val Trp Tyr Leu Phe Ser Ala Gly Asn Glu Ala
1               5                    10                  15
```

-continued

```
Asp Val His Gly Ile Tyr Phe Ser Gly Asn Thr Tyr Leu Trp Arg Gly
        20                  25                  30

<210> SEQ ID NO 647
<211> LENGTH: 12
<212> TYPE: PRT
<213> ORGANISM: Homo sapiens

<400> SEQUENCE: 647

Lys Met Tyr Tyr Ser Ala Val Asp Pro Thr Lys Asp
1               5                   10

<210> SEQ ID NO 648
<211> LENGTH: 25
<212> TYPE: PRT
<213> ORGANISM: Homo sapiens

<400> SEQUENCE: 648

Arg Gly Pro Glu Glu Glu His Leu Gly Ile Leu Gly Pro Val Ile Trp
1               5                   10                  15

Ala Glu Val Gly Asp Thr Ile Arg Val
            20                  25

<210> SEQ ID NO 649
<211> LENGTH: 39
<212> TYPE: PRT
<213> ORGANISM: Homo sapiens

<400> SEQUENCE: 649

Arg Ser Gly Ala Gly Thr Glu Asp Ser Ala Cys Ile Pro Trp Ala Tyr
1               5                   10                  15

Tyr Ser Thr Val Asp Gln Val Lys Asp Leu Tyr Ser Gly Leu Ile Gly
            20                  25                  30

Pro Leu Ile Val Cys Arg Arg
            35

<210> SEQ ID NO 650
<211> LENGTH: 13
<212> TYPE: PRT
<213> ORGANISM: Homo sapiens

<400> SEQUENCE: 650

Lys Ile Phe Phe Pro Gly Val Ser Glu Phe Gly Lys Glu
1               5                   10

<210> SEQ ID NO 651
<211> LENGTH: 23
<212> TYPE: PRT
<213> ORGANISM: Homo sapiens

<400> SEQUENCE: 651

Arg Ala Ile Leu Gln Ser Gly Ser Phe Asn Ala Pro Trp Ala Val Thr
1               5                   10                  15

Ser Leu Tyr Glu Ala Arg Asn
            20

<210> SEQ ID NO 652
<211> LENGTH: 19
<212> TYPE: PRT
<213> ORGANISM: Homo sapiens

<400> SEQUENCE: 652

Arg Val Leu Gln Gly Val Leu Pro Ala Leu Pro Gln Val Val Cys Asn
```

-continued

```
1              5              10             15

Tyr Arg Asp

<210> SEQ ID NO 653
<211> LENGTH: 16
<212> TYPE: PRT
<213> ORGANISM: Homo sapiens

<400> SEQUENCE: 653

Arg Ile Ser Leu Leu Leu Ile Glu Ser Trp Leu Glu Pro Val Arg Phe
1              5              10             15

<210> SEQ ID NO 654
<211> LENGTH: 20
<212> TYPE: PRT
<213> ORGANISM: Homo sapiens

<400> SEQUENCE: 654

Arg Leu His Glu Ala Phe Ser Pro Val Ser Tyr Gln His Asp Leu Ala
1              5              10             15

Leu Leu Arg Leu
          20

<210> SEQ ID NO 655
<211> LENGTH: 20
<212> TYPE: PRT
<213> ORGANISM: Homo sapiens

<400> SEQUENCE: 655

Arg Thr Thr Leu Ser Gly Ala Pro Cys Gln Pro Trp Ala Ser Glu Ala
1              5              10             15

Thr Tyr Arg Asn
          20

<210> SEQ ID NO 656
<211> LENGTH: 29
<212> TYPE: PRT
<213> ORGANISM: Homo sapiens

<400> SEQUENCE: 656

Lys Gly Leu Phe Gln Val Val Ser Gly Gly Met Val Leu Gln Leu Gln
1              5              10             15

Gln Gly Asp Gln Val Trp Val Glu Lys Asp Pro Lys Lys
          20             25

<210> SEQ ID NO 657
<211> LENGTH: 12
<212> TYPE: PRT
<213> ORGANISM: Homo sapiens

<400> SEQUENCE: 657

Lys Val Leu Asn Tyr Val Asp Trp Ile Lys Lys Glu
1              5              10

<210> SEQ ID NO 658
<211> LENGTH: 18
<212> TYPE: PRT
<213> ORGANISM: Homo sapiens

<400> SEQUENCE: 658

Lys Ser Asn Ala Leu Asp Ile Ile Phe Gln Thr Asp Leu Thr Gly Gln
1              5              10             15
```

-continued

```
Lys Lys

<210> SEQ ID NO 659
<211> LENGTH: 21
<212> TYPE: PRT
<213> ORGANISM: Homo sapiens

<400> SEQUENCE: 659

Lys Glu Gly Ala Ile His Arg Glu Glu Leu Val Tyr Glu Leu Asn Pro
1               5                   10                  15

Leu Asp His Arg Gly
            20

<210> SEQ ID NO 660
<211> LENGTH: 11
<212> TYPE: PRT
<213> ORGANISM: Homo sapiens

<400> SEQUENCE: 660

Lys Ile Thr Gln Val Leu His Phe Thr Lys Asp
1               5                   10

<210> SEQ ID NO 661
<211> LENGTH: 11
<212> TYPE: PRT
<213> ORGANISM: Homo sapiens

<400> SEQUENCE: 661

Lys Ser His Ala Leu Gln Leu Asn Asn Arg Gln
1               5                   10

<210> SEQ ID NO 662
<211> LENGTH: 20
<212> TYPE: PRT
<213> ORGANISM: Homo sapiens

<400> SEQUENCE: 662

Arg Ala Val Gly Ser Gly Ala Thr Phe Ser His Tyr Tyr Tyr Met Ile
1               5                   10                  15

Leu Ser Arg Gly
            20

<210> SEQ ID NO 663
<211> LENGTH: 16
<212> TYPE: PRT
<213> ORGANISM: Homo sapiens

<400> SEQUENCE: 663

Arg Glu Pro Phe Leu Ser Cys Cys Gln Phe Ala Glu Ser Leu Arg Lys
1               5                   10                  15

<210> SEQ ID NO 664
<211> LENGTH: 19
<212> TYPE: PRT
<213> ORGANISM: Homo sapiens

<400> SEQUENCE: 664

Arg Gly His Leu Phe Leu Gln Thr Asp Gln Pro Ile Tyr Asn Pro Gly
1               5                   10                  15

Gln Arg Val

<210> SEQ ID NO 665
<211> LENGTH: 15
```

```
<212> TYPE: PRT
<213> ORGANISM: Homo sapiens

<400> SEQUENCE: 665

Arg Gly Leu Glu Glu Glu Leu Gln Phe Ser Leu Gly Ser Lys Ile
1               5                   10                  15

<210> SEQ ID NO 666
<211> LENGTH: 15
<212> TYPE: PRT
<213> ORGANISM: Homo sapiens

<400> SEQUENCE: 666

Arg Gly Ser Phe Glu Phe Pro Val Gly Asp Ala Val Ser Lys Val
1               5                   10                  15

<210> SEQ ID NO 667
<211> LENGTH: 19
<212> TYPE: PRT
<213> ORGANISM: Homo sapiens

<400> SEQUENCE: 667

Arg Leu Leu Ala Thr Leu Cys Ser Ala Glu Val Cys Gln Cys Ala Glu
1               5                   10                  15

Gly Lys Cys

<210> SEQ ID NO 668
<211> LENGTH: 24
<212> TYPE: PRT
<213> ORGANISM: Homo sapiens

<400> SEQUENCE: 668

Arg Val Gln Gln Pro Asp Cys Arg Glu Pro Phe Leu Ser Cys Cys Gln
1               5                   10                  15

Phe Ala Glu Ser Leu Arg Lys Lys
            20

<210> SEQ ID NO 669
<211> LENGTH: 16
<212> TYPE: PRT
<213> ORGANISM: Homo sapiens

<400> SEQUENCE: 669

Arg Tyr Ile Tyr Gly Lys Pro Val Gln Gly Val Ala Tyr Val Arg Phe
1               5                   10                  15

<210> SEQ ID NO 670
<211> LENGTH: 13
<212> TYPE: PRT
<213> ORGANISM: Homo sapiens

<400> SEQUENCE: 670

Lys Ile Thr His Tyr Asn Tyr Leu Ile Leu Ser Lys Gly
1               5                   10

<210> SEQ ID NO 671
<211> LENGTH: 17
<212> TYPE: PRT
<213> ORGANISM: Homo sapiens

<400> SEQUENCE: 671

Arg Glu Asn Ser Leu Tyr Leu Thr Ala Phe Thr Val Ile Gly Ile Arg
1               5                   10                  15
```

-continued

```
Lys

<210> SEQ ID NO 672
<211> LENGTH: 12
<212> TYPE: PRT
<213> ORGANISM: Homo sapiens

<400> SEQUENCE: 672

Arg Lys Ala Phe Asp Ile Cys Pro Leu Val Lys Ile
1               5                   10

<210> SEQ ID NO 673
<211> LENGTH: 26
<212> TYPE: PRT
<213> ORGANISM: Homo sapiens

<400> SEQUENCE: 673

Arg Val Asp Asp Gly Val Ala Ser Phe Val Leu Asn Leu Pro Ser Gly
1               5                   10                  15

Val Thr Val Leu Glu Phe Asn Val Lys Thr
            20                  25

<210> SEQ ID NO 674
<211> LENGTH: 30
<212> TYPE: PRT
<213> ORGANISM: Homo sapiens

<400> SEQUENCE: 674

Lys Thr Phe Ser Glu Trp Leu Glu Ser Val Lys Glu Asn Pro Ala Val
1               5                   10                  15

Ile Asp Phe Glu Leu Ala Pro Ile Val Asp Leu Val Arg Asn
            20                  25                  30

<210> SEQ ID NO 675
<211> LENGTH: 33
<212> TYPE: PRT
<213> ORGANISM: Homo sapiens

<400> SEQUENCE: 675

Arg Ile Phe Asp Asp Phe Gly Thr His Tyr Phe Thr Ser Gly Ser Leu
1               5                   10                  15

Gly Gly Val Tyr Asp Leu Leu Tyr Gln Phe Ser Ser Glu Glu Leu Lys
            20                  25                  30

Asn

<210> SEQ ID NO 676
<211> LENGTH: 17
<212> TYPE: PRT
<213> ORGANISM: Homo sapiens

<400> SEQUENCE: 676

Lys Glu Leu Ser His Leu Pro Ser Leu Tyr Asp Tyr Ser Ala Tyr Arg
1               5                   10                  15

Arg

<210> SEQ ID NO 677
<211> LENGTH: 19
<212> TYPE: PRT
<213> ORGANISM: Homo sapiens

<400> SEQUENCE: 677

Arg Arg Tyr Ser Ala Trp Ala Glu Ser Val Thr Asn Leu Pro Gln Val
```

```
1               5               10              15

Ile Lys Gln

<210> SEQ ID NO 678
<211> LENGTH: 22
<212> TYPE: PRT
<213> ORGANISM: Homo sapiens

<400> SEQUENCE: 678

Lys Val Glu Pro Leu Tyr Glu Leu Val Thr Ala Thr Asp Phe Ala Tyr
1               5               10              15

Ser Ser Thr Val Arg Gln
            20

<210> SEQ ID NO 679
<211> LENGTH: 13
<212> TYPE: PRT
<213> ORGANISM: Homo sapiens

<400> SEQUENCE: 679

Arg Ser Leu Met Leu His Tyr Glu Phe Leu Gln Arg Val
1               5               10

<210> SEQ ID NO 680
<211> LENGTH: 19
<212> TYPE: PRT
<213> ORGANISM: Homo sapiens

<400> SEQUENCE: 680

Lys Tyr Gly Phe Cys Glu Ala Ala Asp Gln Phe His Val Leu Asp Glu
1               5               10              15

Val Arg Arg

<210> SEQ ID NO 681
<211> LENGTH: 10
<212> TYPE: PRT
<213> ORGANISM: Homo sapiens

<400> SEQUENCE: 681

Arg Phe Leu Gln Glu Gln Gly His Arg Ala
1               5               10

<210> SEQ ID NO 682
<211> LENGTH: 12
<212> TYPE: PRT
<213> ORGANISM: Homo sapiens

<400> SEQUENCE: 682

Arg Lys Leu Asp Gly Ile Cys Trp Gln Val Arg Gln
1               5               10

<210> SEQ ID NO 683
<211> LENGTH: 17
<212> TYPE: PRT
<213> ORGANISM: Homo sapiens

<400> SEQUENCE: 683

Arg Ser Leu Pro Val Ser Asp Ser Val Leu Ser Gly Phe Glu Gln Arg
1               5               10              15

Val

<210> SEQ ID NO 684
```

-continued

```
<211> LENGTH: 28
<212> TYPE: PRT
<213> ORGANISM: Homo sapiens

<400> SEQUENCE: 684

Arg Gly Thr Val Ile Asp Val Thr Asp Phe Val Asn Trp Ala Ser Ser
1               5                   10                  15

Ile Asn Asp Ala Pro Val Leu Ile Ser Gln Lys Leu
            20                  25

<210> SEQ ID NO 685
<211> LENGTH: 31
<212> TYPE: PRT
<213> ORGANISM: Homo sapiens

<400> SEQUENCE: 685

Lys Asn Pro Arg Glu Asp Tyr Leu Asp Val Tyr Val Phe Gly Val Gly
1               5                   10                  15

Pro Leu Val Asn Gln Val Asn Ile Asn Ala Leu Ala Ser Lys Lys
            20                  25                  30

<210> SEQ ID NO 686
<211> LENGTH: 14
<212> TYPE: PRT
<213> ORGANISM: Homo sapiens

<400> SEQUENCE: 686

Arg Gly Asp Ser Gly Gly Pro Leu Ile Val His Lys Arg Ser
1               5                   10

<210> SEQ ID NO 687
<211> LENGTH: 27
<212> TYPE: PRT
<213> ORGANISM: Homo sapiens

<400> SEQUENCE: 687

Arg His Val Ile Ile Leu Met Thr Asp Gly Leu His Asn Met Gly Gly
1               5                   10                  15

Asp Pro Ile Thr Val Ile Asp Glu Ile Arg Asp
            20                  25

<210> SEQ ID NO 688
<211> LENGTH: 32
<212> TYPE: PRT
<213> ORGANISM: Homo sapiens

<400> SEQUENCE: 688

Arg Lys Asn Pro Arg Glu Asp Tyr Leu Asp Val Tyr Val Phe Gly Val
1               5                   10                  15

Gly Pro Leu Val Asn Gln Val Asn Ile Asn Ala Leu Ala Ser Lys Lys
            20                  25                  30

<210> SEQ ID NO 689
<211> LENGTH: 13
<212> TYPE: PRT
<213> ORGANISM: Homo sapiens

<400> SEQUENCE: 689

Lys Ser Cys Asp Ile Pro Val Phe Met Asn Ala Arg Thr
1               5                   10

<210> SEQ ID NO 690
<211> LENGTH: 28
```

<212> TYPE: PRT
<213> ORGANISM: Homo sapiens

<400> SEQUENCE: 690

Lys Ser Pro Pro Glu Ile Ser His Gly Val Val Ala His Met Ser Asp
1               5                   10                  15

Ser Tyr Gln Tyr Gly Glu Glu Val Thr Tyr Lys Cys
            20                  25

<210> SEQ ID NO 691
<211> LENGTH: 21
<212> TYPE: PRT
<213> ORGANISM: Homo sapiens

<400> SEQUENCE: 691

Lys Thr Asp Cys Leu Ser Leu Pro Ser Phe Glu Asn Ala Ile Pro Met
1               5                   10                  15

Gly Glu Lys Lys Asp
            20

<210> SEQ ID NO 692
<211> LENGTH: 16
<212> TYPE: PRT
<213> ORGANISM: Homo sapiens

<400> SEQUENCE: 692

Lys Arg Ala Gln Leu Gly Asp Leu Pro Trp Gln Val Ala Ile Lys Asp
1               5                   10                  15

<210> SEQ ID NO 693
<211> LENGTH: 12
<212> TYPE: PRT
<213> ORGANISM: Homo sapiens

<400> SEQUENCE: 693

Lys Ser Leu Glu Cys Leu His Pro Gly Thr Lys Phe
1               5                   10

<210> SEQ ID NO 694
<211> LENGTH: 18
<212> TYPE: PRT
<213> ORGANISM: Homo sapiens

<400> SEQUENCE: 694

Arg Thr Met Gly Tyr Gln Asp Phe Ala Asp Val Val Cys Tyr Thr Gln
1               5                   10                  15

Lys Ala

<210> SEQ ID NO 695
<211> LENGTH: 12
<212> TYPE: PRT
<213> ORGANISM: Homo sapiens

<400> SEQUENCE: 695

Arg Glu Leu Leu Ala Leu Ile Gln Leu Glu Arg Glu
1               5                   10

<210> SEQ ID NO 696
<211> LENGTH: 20
<212> TYPE: PRT
<213> ORGANISM: Homo sapiens

<400> SEQUENCE: 696

-continued

```
Arg Val Pro Glu Ala Arg Pro Asn Ser Met Val Val Glu His Pro Glu
1               5                   10                  15

Phe Leu Lys Ala
            20

<210> SEQ ID NO 697
<211> LENGTH: 9
<212> TYPE: PRT
<213> ORGANISM: Homo sapiens

<400> SEQUENCE: 697

Arg Leu Phe Trp Glu Pro Met Lys Val
1               5

<210> SEQ ID NO 698
<211> LENGTH: 14
<212> TYPE: PRT
<213> ORGANISM: Homo sapiens

<400> SEQUENCE: 698

Arg Asp Val Arg Asp Tyr Phe Met Pro Cys Pro Gly Arg Gly
1               5                   10

<210> SEQ ID NO 699
<211> LENGTH: 23
<212> TYPE: PRT
<213> ORGANISM: Homo sapiens

<400> SEQUENCE: 699

Lys Asp Ala Leu Glu Asn Ile Asp Pro Ala Thr Gln Met Met Ile Leu
1               5                   10                  15

Asn Cys Ile Tyr Phe Lys Gly
            20

<210> SEQ ID NO 700
<211> LENGTH: 27
<212> TYPE: PRT
<213> ORGANISM: Homo sapiens

<400> SEQUENCE: 700

Lys Gly Leu Ile Lys Asp Ala Leu Glu Asn Ile Asp Pro Ala Thr Gln
1               5                   10                  15

Met Met Ile Leu Asn Cys Ile Tyr Phe Lys Gly
            20                  25

<210> SEQ ID NO 701
<211> LENGTH: 11
<212> TYPE: PRT
<213> ORGANISM: Homo sapiens

<400> SEQUENCE: 701

Lys Gln Phe Pro Ile Leu Leu Asp Phe Lys Thr
1               5                   10

<210> SEQ ID NO 702
<211> LENGTH: 12
<212> TYPE: PRT
<213> ORGANISM: Homo sapiens

<400> SEQUENCE: 702

Arg Ala Phe Trp Leu Asp Val Ser His Asn Arg Leu
1               5                   10
```

```
<210> SEQ ID NO 703
<211> LENGTH: 27
<212> TYPE: PRT
<213> ORGANISM: Homo sapiens

<400> SEQUENCE: 703

Lys Ala Asp Val Gln Ala His Gly Glu Gly Gln Glu Phe Ser Ile Thr
1               5                   10                  15

Cys Leu Val Asp Glu Glu Glu Met Lys Lys Leu
            20                  25

<210> SEQ ID NO 704
<211> LENGTH: 21
<212> TYPE: PRT
<213> ORGANISM: Homo sapiens

<400> SEQUENCE: 704

Lys Ile Leu Gly Asp Met Gln Pro Gly Asp Tyr Phe Asp Leu Val Leu
1               5                   10                  15

Phe Gly Thr Arg Val
            20

<210> SEQ ID NO 705
<211> LENGTH: 15
<212> TYPE: PRT
<213> ORGANISM: Homo sapiens

<400> SEQUENCE: 705

Lys Asn Val Val Phe Val Ile Asp Ile Ser Gly Ser Met Arg Gly
1               5                   10                  15

<210> SEQ ID NO 706
<211> LENGTH: 25
<212> TYPE: PRT
<213> ORGANISM: Homo sapiens

<400> SEQUENCE: 706

Lys Thr Ala Phe Ile Ser Asp Phe Ala Val Thr Ala Asp Gly Asn Ala
1               5                   10                  15

Phe Ile Gly Asp Ile Lys Asp Lys Val
            20                  25

<210> SEQ ID NO 707
<211> LENGTH: 12
<212> TYPE: PRT
<213> ORGANISM: Homo sapiens

<400> SEQUENCE: 707

Arg Gly His Met Leu Glu Asn His Val Glu Arg Leu
1               5                   10

<210> SEQ ID NO 708
<211> LENGTH: 15
<212> TYPE: PRT
<213> ORGANISM: Homo sapiens

<400> SEQUENCE: 708

Arg Leu Trp Ala Tyr Leu Thr Ile Gln Glu Leu Leu Ala Lys Arg
1               5                   10                  15

<210> SEQ ID NO 709
<211> LENGTH: 12
<212> TYPE: PRT
<213> ORGANISM: Homo sapiens
```

-continued

<400> SEQUENCE: 709

Arg Asn His Met Gln Tyr Glu Ile Val Ile Lys Val
1               5                   10

<210> SEQ ID NO 710
<211> LENGTH: 15
<212> TYPE: PRT
<213> ORGANISM: Homo sapiens

<400> SEQUENCE: 710

Lys Ala His Val Ser Phe Lys Pro Thr Val Ala Gln Gln Arg Ile
1               5                   10                  15

<210> SEQ ID NO 711
<211> LENGTH: 27
<212> TYPE: PRT
<213> ORGANISM: Homo sapiens

<400> SEQUENCE: 711

Lys Glu Asn Ile Gln Asp Asn Ile Ser Leu Phe Ser Leu Gly Met Gly
1               5                   10                  15

Phe Asp Val Asp Tyr Asp Phe Leu Lys Arg Leu
            20                  25

<210> SEQ ID NO 712
<211> LENGTH: 17
<212> TYPE: PRT
<213> ORGANISM: Homo sapiens

<400> SEQUENCE: 712

Lys His Leu Glu Val Asp Val Trp Val Ile Glu Pro Gln Gly Leu Arg
1               5                   10                  15

Phe

<210> SEQ ID NO 713
<211> LENGTH: 16
<212> TYPE: PRT
<213> ORGANISM: Homo sapiens

<400> SEQUENCE: 713

Lys Leu Trp Ala Tyr Leu Thr Ile Asn Gln Leu Leu Ala Glu Arg Ser
1               5                   10                  15

<210> SEQ ID NO 714
<211> LENGTH: 17
<212> TYPE: PRT
<213> ORGANISM: Homo sapiens

<400> SEQUENCE: 714

Arg Ala Glu Asp His Phe Ser Val Ile Asp Phe Asn Gln Asn Ile Arg
1               5                   10                  15

Thr

<210> SEQ ID NO 715
<211> LENGTH: 22
<212> TYPE: PRT
<213> ORGANISM: Homo sapiens

<400> SEQUENCE: 715

Arg Phe Leu His Val Pro Asp Thr Phe Glu Gly His Phe Asp Gly Val
1               5                   10                  15

```
Pro Val Ile Ser Lys Gly
          20

<210> SEQ ID NO 716
<211> LENGTH: 10
<212> TYPE: PRT
<213> ORGANISM: Homo sapiens

<400> SEQUENCE: 716

Lys Ile Leu Asp Asp Leu Ser Pro Arg Asp
1               5                   10

<210> SEQ ID NO 717
<211> LENGTH: 13
<212> TYPE: PRT
<213> ORGANISM: Homo sapiens

<400> SEQUENCE: 717

Lys Ile Pro Lys Pro Glu Ala Ser Phe Ser Pro Arg Arg
1               5                   10

<210> SEQ ID NO 718
<211> LENGTH: 18
<212> TYPE: PRT
<213> ORGANISM: Homo sapiens

<400> SEQUENCE: 718

Lys Ser Pro Glu Gln Gln Glu Thr Val Leu Asp Gly Asn Leu Ile Ile
1               5                   10                  15

Arg Tyr

<210> SEQ ID NO 719
<211> LENGTH: 31
<212> TYPE: PRT
<213> ORGANISM: Homo sapiens

<400> SEQUENCE: 719

Arg Phe Ser Ser His Val Gly Gly Thr Leu Gly Gln Phe Tyr Gln Glu
1               5                   10                  15

Val Leu Trp Gly Ser Pro Ala Ala Ser Asp Asp Gly Arg Arg Thr
          20                  25                  30

<210> SEQ ID NO 720
<211> LENGTH: 14
<212> TYPE: PRT
<213> ORGANISM: Homo sapiens

<400> SEQUENCE: 720

Arg Gly Pro Asp Val Leu Thr Ala Thr Val Ser Gly Lys Leu
1               5                   10

<210> SEQ ID NO 721
<211> LENGTH: 18
<212> TYPE: PRT
<213> ORGANISM: Homo sapiens

<400> SEQUENCE: 721

Arg Asn Met Glu Gln Phe Gln Val Ser Val Ser Val Ala Pro Asn Ala
1               5                   10                  15

Lys Ile

<210> SEQ ID NO 722
<211> LENGTH: 21
```

```
<212> TYPE: PRT
<213> ORGANISM: Homo sapiens

<400> SEQUENCE: 722

Arg Arg Leu Asp Tyr Gln Glu Gly Pro Pro Gly Val Glu Ile Ser Cys
1               5                   10                  15

Trp Ser Val Glu Leu
            20

<210> SEQ ID NO 723
<211> LENGTH: 12
<212> TYPE: PRT
<213> ORGANISM: Homo sapiens

<400> SEQUENCE: 723

Lys Ile Val Asp Leu Val Ser Glu Leu Lys Lys Asp
1               5                   10

<210> SEQ ID NO 724
<211> LENGTH: 14
<212> TYPE: PRT
<213> ORGANISM: Homo sapiens

<400> SEQUENCE: 724

Arg Val Gly Ser Ala Leu Phe Leu Ser His Asn Leu Lys Phe
1               5                   10

<210> SEQ ID NO 725
<211> LENGTH: 13
<212> TYPE: PRT
<213> ORGANISM: Homo sapiens

<400> SEQUENCE: 725

Lys Thr Val Gly Ser Asp Thr Phe Tyr Ser Phe Lys Tyr
1               5                   10

<210> SEQ ID NO 726
<211> LENGTH: 21
<212> TYPE: PRT
<213> ORGANISM: Homo sapiens

<400> SEQUENCE: 726

Arg Asp Ile Pro Thr Asn Ser Pro Glu Leu Glu Glu Thr Leu Thr His
1               5                   10                  15

Thr Ile Thr Lys Leu
            20

<210> SEQ ID NO 727
<211> LENGTH: 9
<212> TYPE: PRT
<213> ORGANISM: Homo sapiens

<400> SEQUENCE: 727

Arg Val Gln Val Val Ala Gly Lys Lys
1               5

<210> SEQ ID NO 728
<211> LENGTH: 10
<212> TYPE: PRT
<213> ORGANISM: Homo sapiens

<400> SEQUENCE: 728

Arg Phe Asn Ala Leu Gln Tyr Leu Arg Leu
1               5                   10
```

-continued

```
<210> SEQ ID NO 729
<211> LENGTH: 19
<212> TYPE: PRT
<213> ORGANISM: Homo sapiens

<400> SEQUENCE: 729

Lys Val Ile Pro Gly Pro Pro Ala Leu Thr Leu Val Pro Ala Glu Leu
1               5                   10                  15

Val Arg Ile

<210> SEQ ID NO 730
<211> LENGTH: 23
<212> TYPE: PRT
<213> ORGANISM: Homo sapiens

<400> SEQUENCE: 730

Lys Ile Thr Gly Thr Met Pro Pro Leu Pro Leu Glu Ala Thr Gly Leu
1               5                   10                  15

Ala Leu Ser Ser Leu Arg Leu
            20

<210> SEQ ID NO 731
<211> LENGTH: 17
<212> TYPE: PRT
<213> ORGANISM: Homo sapiens

<400> SEQUENCE: 731

Lys Glu Phe Thr Glu Ala Phe Leu Gly Cys Pro Ala Ile His Pro Arg
1               5                   10                  15

Cys

<210> SEQ ID NO 732
<211> LENGTH: 33
<212> TYPE: PRT
<213> ORGANISM: Homo sapiens

<400> SEQUENCE: 732

Arg Arg Val Ile Asn Leu Pro Leu Asp Ser Met Ala Ala Pro Trp Glu
1               5                   10                  15

Thr Gly Asp Thr Phe Pro Asp Val Val Ala Ile Ala Pro Asp Val Arg
            20                  25                  30

Ala

<210> SEQ ID NO 733
<211> LENGTH: 21
<212> TYPE: PRT
<213> ORGANISM: Homo sapiens

<400> SEQUENCE: 733

Arg Gly Val Phe Phe Ser Val Asn Ser Trp Thr Pro Asp Ser Met Ser
1               5                   10                  15

Phe Ile Tyr Lys Ala
            20

<210> SEQ ID NO 734
<211> LENGTH: 19
<212> TYPE: PRT
<213> ORGANISM: Homo sapiens

<400> SEQUENCE: 734
```

-continued

```
Lys Glu Ile Pro Asp Glu Ile Ser Ile Leu Leu Leu Gly Val Ala His
1               5                   10                  15

Phe Lys Gly

<210> SEQ ID NO 735
<211> LENGTH: 12
<212> TYPE: PRT
<213> ORGANISM: Homo sapiens

<400> SEQUENCE: 735

Lys Thr Val Gln Ala Val Leu Thr Val Pro Lys Leu
1               5                   10

<210> SEQ ID NO 736
<211> LENGTH: 30
<212> TYPE: PRT
<213> ORGANISM: Homo sapiens

<400> SEQUENCE: 736

Arg Ala Leu Tyr Tyr Asp Leu Ile Ser Ser Pro Asp Ile His Gly Thr
1               5                   10                  15

Tyr Lys Glu Leu Leu Asp Thr Val Thr Ala Pro Gln Lys Asn
            20                  25                  30

<210> SEQ ID NO 737
<211> LENGTH: 14
<212> TYPE: PRT
<213> ORGANISM: Homo sapiens

<400> SEQUENCE: 737

Arg Asp Thr Asp Thr Gly Ala Leu Leu Phe Ile Gly Lys Ile
1               5                   10

<210> SEQ ID NO 738
<211> LENGTH: 16
<212> TYPE: PRT
<213> ORGANISM: Homo sapiens

<400> SEQUENCE: 738

Arg Glu Leu Arg Pro Trp Cys Phe Thr Thr Asp Pro Asn Lys Arg Trp
1               5                   10                  15

<210> SEQ ID NO 739
<211> LENGTH: 23
<212> TYPE: PRT
<213> ORGANISM: Homo sapiens

<400> SEQUENCE: 739

Arg Thr Glu Cys Phe Ile Thr Gly Trp Gly Glu Thr Gln Gly Thr Phe
1               5                   10                  15

Gly Ala Gly Leu Leu Lys Glu
            20

<210> SEQ ID NO 740
<211> LENGTH: 16
<212> TYPE: PRT
<213> ORGANISM: Homo sapiens

<400> SEQUENCE: 740

Lys Gly Thr His Cys Asn Gln Val Glu Val Ile Ala Thr Leu Lys Asp
1               5                   10                  15

<210> SEQ ID NO 741
```

-continued

```
<211> LENGTH: 13
<212> TYPE: PRT
<213> ORGANISM: Homo sapiens

<400> SEQUENCE: 741

Lys Ala Val Gly Tyr Leu Ile Thr Gly Tyr Gln Arg Gln
1               5                   10

<210> SEQ ID NO 742
<211> LENGTH: 29
<212> TYPE: PRT
<213> ORGANISM: Homo sapiens

<400> SEQUENCE: 742

Arg Ala Val Asp Gln Ser Val Leu Leu Met Lys Pro Glu Ala Glu Leu
1               5                   10                  15

Ser Val Ser Ser Val Tyr Asn Leu Leu Thr Val Lys Asp
            20                  25

<210> SEQ ID NO 743
<211> LENGTH: 16
<212> TYPE: PRT
<213> ORGANISM: Homo sapiens

<400> SEQUENCE: 743

Arg Ile Gln His Pro Phe Thr Val Glu Glu Phe Val Leu Pro Lys Phe
1               5                   10                  15

<210> SEQ ID NO 744
<211> LENGTH: 15
<212> TYPE: PRT
<213> ORGANISM: Homo sapiens

<400> SEQUENCE: 744

Arg Asn Glu Leu Ile Pro Leu Ile Tyr Leu Glu Asn Pro Arg Arg
1               5                   10                  15

<210> SEQ ID NO 745
<211> LENGTH: 14
<212> TYPE: PRT
<213> ORGANISM: Homo sapiens

<400> SEQUENCE: 745

Arg Ala Phe Ile Gln Leu Trp Ala Phe Asp Ala Val Lys Gly
1               5                   10

<210> SEQ ID NO 746
<211> LENGTH: 19
<212> TYPE: PRT
<213> ORGANISM: Homo sapiens

<400> SEQUENCE: 746

Lys Gly Phe Gly Gly Leu Thr Gly Gln Ile Val Ala Ala Leu Ser Thr
1               5                   10                  15

Ala Lys Tyr

<210> SEQ ID NO 747
<211> LENGTH: 11
<212> TYPE: PRT
<213> ORGANISM: Homo sapiens

<400> SEQUENCE: 747

Lys Tyr Gly Phe Tyr Thr His Val Phe Arg Leu
1               5                   10
```

```
<210> SEQ ID NO 748
<211> LENGTH: 31
<212> TYPE: PRT
<213> ORGANISM: Homo sapiens

<400> SEQUENCE: 748

Lys Lys Asp Pro Glu Gly Leu Phe Leu Gln Asp Asn Ile Val Ala Glu
1               5                   10                  15

Phe Ser Val Asp Glu Thr Gly Gln Met Ser Ala Thr Ala Lys Gly
            20                  25                  30

<210> SEQ ID NO 749
<211> LENGTH: 24
<212> TYPE: PRT
<213> ORGANISM: Homo sapiens

<400> SEQUENCE: 749

Lys Ala Gln Trp Ala Asn Pro Phe Asp Pro Ser Lys Thr Glu Asp Ser
1               5                   10                  15

Ser Ser Phe Leu Ile Asp Lys Thr
            20

<210> SEQ ID NO 750
<211> LENGTH: 11
<212> TYPE: PRT
<213> ORGANISM: Homo sapiens

<400> SEQUENCE: 750

Lys Gly Trp Val Asp Leu Phe Val Pro Lys Phe
1               5                   10

<210> SEQ ID NO 751
<211> LENGTH: 11
<212> TYPE: PRT
<213> ORGANISM: Homo sapiens

<400> SEQUENCE: 751

Arg Ser Phe Met Leu Leu Ile Leu Glu Arg Ser
1               5                   10

<210> SEQ ID NO 752
<211> LENGTH: 22
<212> TYPE: PRT
<213> ORGANISM: Homo sapiens

<400> SEQUENCE: 752

Lys Glu Phe Ser His Leu Gly Lys Glu Asp Phe Thr Ser Leu Ser Leu
1               5                   10                  15

Val Leu Tyr Ser Arg Lys
            20

<210> SEQ ID NO 753
<211> LENGTH: 25
<212> TYPE: PRT
<213> ORGANISM: Homo sapiens

<400> SEQUENCE: 753

Lys His Gln Pro Gln Glu Phe Pro Thr Tyr Val Glu Pro Thr Asn Asp
1               5                   10                  15

Glu Ile Cys Glu Ala Phe Arg Lys Asp
            20                  25
```

-continued

```
<210> SEQ ID NO 754
<211> LENGTH: 24
<212> TYPE: PRT
<213> ORGANISM: Homo sapiens

<400> SEQUENCE: 754

Lys Val Pro Thr Ala Asp Leu Glu Asp Val Leu Pro Leu Ala Glu Asp
1               5                   10                  15

Ile Thr Asn Ile Leu Ser Lys Cys
            20

<210> SEQ ID NO 755
<211> LENGTH: 10
<212> TYPE: PRT
<213> ORGANISM: Homo sapiens

<400> SEQUENCE: 755

Lys Ala Val Arg Pro Gly Tyr Pro Lys Leu
1               5                   10

<210> SEQ ID NO 756
<211> LENGTH: 18
<212> TYPE: PRT
<213> ORGANISM: Homo sapiens

<400> SEQUENCE: 756

Lys Glu Ile Pro Ala Trp Val Pro Phe Asp Pro Ala Ala Gln Ile Thr
1               5                   10                  15

Lys Gln

<210> SEQ ID NO 757
<211> LENGTH: 12
<212> TYPE: PRT
<213> ORGANISM: Homo sapiens

<400> SEQUENCE: 757

Arg Asn Leu Ala Val Ser Gln Val Val His Lys Ala
1               5                   10

<210> SEQ ID NO 758
<211> LENGTH: 14
<212> TYPE: PRT
<213> ORGANISM: Homo sapiens

<400> SEQUENCE: 758

Lys Ala Ala Ile Ser Gly Glu Asn Ala Gly Leu Val Arg Ala
1               5                   10

<210> SEQ ID NO 759
<211> LENGTH: 23
<212> TYPE: PRT
<213> ORGANISM: Homo sapiens

<400> SEQUENCE: 759

Lys Thr Ala Phe Ile Ser Asp Phe Ala Val Thr Ala Asp Gly Asn Ala
1               5                   10                  15

Phe Ile Gly Asp Ile Lys Asp
            20

<210> SEQ ID NO 760
<211> LENGTH: 9
<212> TYPE: PRT
<213> ORGANISM: Homo sapiens
```

-continued

<400> SEQUENCE: 760

Lys Val Thr Tyr Asp Val Ser Arg Asp
1               5

<210> SEQ ID NO 761
<211> LENGTH: 12
<212> TYPE: PRT
<213> ORGANISM: Homo sapiens

<400> SEQUENCE: 761

Arg Glu Val Ala Phe Asp Leu Glu Ile Pro Lys Thr
1               5                   10

<210> SEQ ID NO 762
<211> LENGTH: 8
<212> TYPE: PRT
<213> ORGANISM: Homo sapiens

<400> SEQUENCE: 762

Lys Thr Ala Gly Leu Val Arg Ser
1               5

<210> SEQ ID NO 763
<211> LENGTH: 12
<212> TYPE: PRT
<213> ORGANISM: Homo sapiens

<400> SEQUENCE: 763

Arg Ser Leu Ala Pro Thr Ala Ala Ala Lys Arg Arg
1               5                   10

<210> SEQ ID NO 764
<211> LENGTH: 12
<212> TYPE: PRT
<213> ORGANISM: Homo sapiens

<400> SEQUENCE: 764

Lys Glu Val Ser Phe Asp Val Glu Leu Pro Lys Thr
1               5                   10

<210> SEQ ID NO 765
<211> LENGTH: 8
<212> TYPE: PRT
<213> ORGANISM: Homo sapiens

<400> SEQUENCE: 765

Lys Ile Gln Glu Asn Val Arg Asn
1               5

<210> SEQ ID NO 766
<211> LENGTH: 9
<212> TYPE: PRT
<213> ORGANISM: Homo sapiens

<400> SEQUENCE: 766

Arg Ala Leu Asp Leu Ser Leu Lys Tyr
1               5

<210> SEQ ID NO 767
<211> LENGTH: 21
<212> TYPE: PRT
<213> ORGANISM: Homo sapiens

<400> SEQUENCE: 767

Arg Leu Ile Gln Asp Ala Val Thr Gly Leu Thr Val Asn Gly Gln Ile
1                   5                   10                  15

Thr Gly Asp Lys Arg
                20

<210> SEQ ID NO 768
<211> LENGTH: 11
<212> TYPE: PRT
<213> ORGANISM: Homo sapiens

<400> SEQUENCE: 768

Lys Ser Ser Phe Val Ala Pro Leu Glu Lys Ser
1                   5                   10

<210> SEQ ID NO 769
<211> LENGTH: 13
<212> TYPE: PRT
<213> ORGANISM: Homo sapiens

<400> SEQUENCE: 769

Lys Glu Leu Leu Asp Thr Val Thr Ala Pro Gln Lys Asn
1                   5                   10

<210> SEQ ID NO 770
<211> LENGTH: 9
<212> TYPE: PRT
<213> ORGANISM: Homo sapiens

<400> SEQUENCE: 770

Lys Phe Gln Leu Pro Gly Gln Lys Leu
1                   5

<210> SEQ ID NO 771
<211> LENGTH: 27
<212> TYPE: PRT
<213> ORGANISM: Homo sapiens

<400> SEQUENCE: 771

Arg Asp Leu Tyr His Tyr Ile Thr Ser Tyr Val Val Asp Gly Glu Ile
1                   5                   10                  15

Ile Ile Tyr Gly Pro Ala Tyr Ser Gly Arg Glu
                20                  25

<210> SEQ ID NO 772
<211> LENGTH: 11
<212> TYPE: PRT
<213> ORGANISM: Homo sapiens

<400> SEQUENCE: 772

Lys Leu Phe Ile Pro Gln Ile Thr Pro Lys His
1                   5                   10

<210> SEQ ID NO 773
<211> LENGTH: 15
<212> TYPE: PRT
<213> ORGANISM: Homo sapiens

<400> SEQUENCE: 773

Asn Ser Ala Thr Gly Glu Glu Ser Ser Thr Ser Leu Thr Ile Arg
1                   5                   10                  15

<210> SEQ ID NO 774
<211> LENGTH: 18

<212> TYPE: PRT
<213> ORGANISM: Homo sapiens

<400> SEQUENCE: 774

Lys Phe Gln Gln Ser Gly Gln Asn Leu Phe Ile Pro Gln Ile Thr Thr
1               5                   10                  15

Lys His

<210> SEQ ID NO 775
<211> LENGTH: 9
<212> TYPE: PRT
<213> ORGANISM: Homo sapiens

<400> SEQUENCE: 775

Ile His Pro Ser Tyr Thr Asn Tyr Arg
1               5

<210> SEQ ID NO 776
<211> LENGTH: 8
<212> TYPE: PRT
<213> ORGANISM: Homo sapiens

<400> SEQUENCE: 776

Phe Gln Leu Ser Glu Thr Asn Arg
1               5

<210> SEQ ID NO 777
<211> LENGTH: 16
<212> TYPE: PRT
<213> ORGANISM: Homo sapiens

<400> SEQUENCE: 777

Val Ser Ala Pro Ser Gly Thr Gly His Leu Pro Gly Leu Asn Pro Leu
1               5                   10                  15

<210> SEQ ID NO 778
<211> LENGTH: 12
<212> TYPE: PRT
<213> ORGANISM: Homo sapiens

<400> SEQUENCE: 778

Glu Asp Ala Gly Ser Tyr Thr Leu His Ile Val Lys
1               5                   10

<210> SEQ ID NO 779
<211> LENGTH: 11
<212> TYPE: PRT
<213> ORGANISM: Homo sapiens

<400> SEQUENCE: 779

Arg Thr Leu Phe Ile Phe Gly Val Thr Lys Tyr
1               5                   10

<210> SEQ ID NO 780
<211> LENGTH: 18
<212> TYPE: PRT
<213> ORGANISM: Homo sapiens

<400> SEQUENCE: 780

Asn Tyr Thr Tyr Ile Trp Trp Leu Asn Gly Gln Ser Leu Pro Val Ser
1               5                   10                  15

Pro Arg

<210> SEQ ID NO 781
<211> LENGTH: 13
<212> TYPE: PRT
<213> ORGANISM: Homo sapiens

<400> SEQUENCE: 781

Gly Val Thr Gly Tyr Phe Thr Phe Asn Leu Tyr Leu Lys
1               5                   10

<210> SEQ ID NO 782
<211> LENGTH: 16
<212> TYPE: PRT
<213> ORGANISM: Homo sapiens

<400> SEQUENCE: 782

Ser Asn Pro Val Thr Leu Asn Val Leu Tyr Gly Pro Asp Leu Pro Arg
1               5                   10                  15

<210> SEQ ID NO 783
<211> LENGTH: 20
<212> TYPE: PRT
<213> ORGANISM: Homo sapiens

<400> SEQUENCE: 783

Asp Val Leu Leu Leu Val His Asn Leu Pro Gln Asn Leu Thr Gly His
1               5                   10                  15

Ile Trp Tyr Lys
            20

<210> SEQ ID NO 784
<211> LENGTH: 8
<212> TYPE: PRT
<213> ORGANISM: Homo sapiens

<400> SEQUENCE: 784

Tyr Gly Pro Ala Tyr Ser Gly Arg
1               5

<210> SEQ ID NO 785
<211> LENGTH: 8
<212> TYPE: PRT
<213> ORGANISM: Homo sapiens

<400> SEQUENCE: 785

Leu Gln Leu Ser Glu Thr Asn Arg
1               5

<210> SEQ ID NO 786
<211> LENGTH: 10
<212> TYPE: PRT
<213> ORGANISM: Homo sapiens

<400> SEQUENCE: 786

Lys Leu Phe Ile Pro Gln Ile Thr Arg Asn
1               5                   10

<210> SEQ ID NO 787
<211> LENGTH: 16
<212> TYPE: PRT
<213> ORGANISM: Homo sapiens

<400> SEQUENCE: 787

Lys Leu Pro Ile Pro Tyr Ile Thr Ile Asn Asn Leu Asn Pro Arg Glu
1               5                   10                  15

<210> SEQ ID NO 788
<211> LENGTH: 22
<212> TYPE: PRT
<213> ORGANISM: Homo sapiens

<400> SEQUENCE: 788

Ser Glu Asn Tyr Thr Tyr Ile Trp Trp Leu Asn Gly Gln Ser Leu Pro
1               5                   10                  15

Val Ser Pro Gly Val Lys
            20

<210> SEQ ID NO 789
<211> LENGTH: 9
<212> TYPE: PRT
<213> ORGANISM: Homo sapiens

<400> SEQUENCE: 789

Ile Leu Ile Leu Pro Ser Val Thr Arg
1               5

<210> SEQ ID NO 790
<211> LENGTH: 13
<212> TYPE: PRT
<213> ORGANISM: Homo sapiens

<400> SEQUENCE: 790

Lys Ala Gln Trp Ala Asn Pro Phe Asp Pro Ser Lys Thr
1               5                   10

<210> SEQ ID NO 791
<211> LENGTH: 8
<212> TYPE: PRT
<213> ORGANISM: Homo sapiens

<400> SEQUENCE: 791

Lys Phe Leu Asn Asp Val Lys Thr
1               5

<210> SEQ ID NO 792
<211> LENGTH: 12
<212> TYPE: PRT
<213> ORGANISM: Homo sapiens

<400> SEQUENCE: 792

Lys Asn Ala Leu Ala Leu Phe Val Leu Pro Lys Glu
1               5                   10

<210> SEQ ID NO 793
<211> LENGTH: 12
<212> TYPE: PRT
<213> ORGANISM: Homo sapiens

<400> SEQUENCE: 793

Arg Asp Phe Asn Gln Phe Ser Ser Gly Glu Lys Asn
1               5                   10

<210> SEQ ID NO 794
<211> LENGTH: 10
<212> TYPE: PRT
<213> ORGANISM: Homo sapiens

<400> SEQUENCE: 794

Lys Gly Tyr Gln Glu Leu Leu Glu Lys Cys
1               5                   10

-continued

```
<210> SEQ ID NO 795
<211> LENGTH: 9
<212> TYPE: PRT
<213> ORGANISM: Homo sapiens

<400> SEQUENCE: 795

Lys Gly Glu Glu Glu Leu Gln Lys Tyr
1               5

<210> SEQ ID NO 796
<211> LENGTH: 9
<212> TYPE: PRT
<213> ORGANISM: Homo sapiens

<400> SEQUENCE: 796

Lys Phe Ile Tyr Glu Ile Ala Arg Arg
1               5

<210> SEQ ID NO 797
<211> LENGTH: 17
<212> TYPE: PRT
<213> ORGANISM: Homo sapiens

<400> SEQUENCE: 797

Arg His Pro Phe Leu Tyr Ala Pro Thr Ile Leu Leu Trp Ala Ala Arg
1               5                   10                  15

Tyr

<210> SEQ ID NO 798
<211> LENGTH: 11
<212> TYPE: PRT
<213> ORGANISM: Homo sapiens

<400> SEQUENCE: 798

Arg Thr Phe Gln Ala Ile Thr Val Thr Lys Leu
1               5                   10

<210> SEQ ID NO 799
<211> LENGTH: 8
<212> TYPE: PRT
<213> ORGANISM: Homo sapiens

<400> SEQUENCE: 799

Lys Leu Thr Thr Leu Glu Arg Gly
1               5

<210> SEQ ID NO 800
<211> LENGTH: 13
<212> TYPE: PRT
<213> ORGANISM: Homo sapiens

<400> SEQUENCE: 800

Arg His Pro Gln Leu Ala Val Ser Val Ile Leu Arg Val
1               5                   10

<210> SEQ ID NO 801
<211> LENGTH: 18
<212> TYPE: PRT
<213> ORGANISM: Homo sapiens

<400> SEQUENCE: 801

Lys Leu Gly Glu Tyr Tyr Leu Gln Asn Ala Phe Leu Val Ala Tyr Thr
1               5                   10                  15
```

-continued

Lys Lys

<210> SEQ ID NO 802
<211> LENGTH: 9
<212> TYPE: PRT
<213> ORGANISM: Homo sapiens

<400> SEQUENCE: 802

Arg Ile Leu Pro Ser Val Pro Lys Asp
1               5

<210> SEQ ID NO 803
<211> LENGTH: 18
<212> TYPE: PRT
<213> ORGANISM: Homo sapiens

<400> SEQUENCE: 803

Lys Ala Glu His Pro Thr Trp Gly Asp Glu Gln Leu Phe Gln Thr Thr
1               5                   10                  15

Arg Leu

<210> SEQ ID NO 804
<211> LENGTH: 11
<212> TYPE: PRT
<213> ORGANISM: Homo sapiens

<400> SEQUENCE: 804

Arg Leu Ile Leu Ile Gly Glu Thr Ile Lys Ile
1               5                   10

<210> SEQ ID NO 805
<211> LENGTH: 10
<212> TYPE: PRT
<213> ORGANISM: Homo sapiens

<400> SEQUENCE: 805

Arg Leu Gln Pro Phe Asn Glu Tyr Arg Lys
1               5                   10

<210> SEQ ID NO 806
<211> LENGTH: 14
<212> TYPE: PRT
<213> ORGANISM: Homo sapiens

<400> SEQUENCE: 806

Glu Leu Ile Glu Glu Leu Val Asn Ile Thr Gln Asn Gln Lys
1               5                   10

<210> SEQ ID NO 807
<211> LENGTH: 19
<212> TYPE: PRT
<213> ORGANISM: Homo sapiens

<400> SEQUENCE: 807

Leu Ile Gln Asp Ala Val Thr Gly Leu Thr Val Asn Gly Gln Ile Thr
1               5                   10                  15

Gly Asp Lys

<210> SEQ ID NO 808
<211> LENGTH: 8
<212> TYPE: PRT
<213> ORGANISM: Homo sapiens -continued

```
<400> SEQUENCE: 808

Gln Ala Leu Glu Glu Phe Gln Lys
1               5

<210> SEQ ID NO 809
<211> LENGTH: 10
<212> TYPE: PRT
<213> ORGANISM: Homo sapiens

<400> SEQUENCE: 809

Asp Ala Gly Leu Ser Trp Gly Ser Ala Arg
1               5                   10

<210> SEQ ID NO 810
<211> LENGTH: 7
<212> TYPE: PRT
<213> ORGANISM: Homo sapiens

<400> SEQUENCE: 810

Val Phe Gln Phe Leu Glu Lys
1               5

<210> SEQ ID NO 811
<211> LENGTH: 7
<212> TYPE: PRT
<213> ORGANISM: Homo sapiens

<400> SEQUENCE: 811

Val Gln Thr Ala His Phe Lys
1               5

<210> SEQ ID NO 812
<211> LENGTH: 9
<212> TYPE: PRT
<213> ORGANISM: Homo sapiens

<400> SEQUENCE: 812

Ser Asp Leu Glu Val Ala His Tyr Lys
1               5

<210> SEQ ID NO 813
<211> LENGTH: 14
<212> TYPE: PRT
<213> ORGANISM: Homo sapiens

<400> SEQUENCE: 813

Val Ser Glu Ala Asp Ser Ser Asn Ala Asp Trp Val Thr Lys
1               5                   10

<210> SEQ ID NO 814
<211> LENGTH: 9
<212> TYPE: PRT
<213> ORGANISM: Homo sapiens

<400> SEQUENCE: 814

Leu Pro Asn Asn Val Leu Gln Glu Lys
1               5

<210> SEQ ID NO 815
<211> LENGTH: 10
<212> TYPE: PRT
<213> ORGANISM: Homo sapiens

<400> SEQUENCE: 815
```

-continued

```
Thr Thr Ser Asp Gly Gly Tyr Ser Phe Lys
1               5                   10

<210> SEQ ID NO 816
<211> LENGTH: 11
<212> TYPE: PRT
<213> ORGANISM: Homo sapiens

<400> SEQUENCE: 816

Tyr Glu Asn Tyr Thr Ser Ser Phe Phe Ile Arg
1               5                   10

<210> SEQ ID NO 817
<211> LENGTH: 8
<212> TYPE: PRT
<213> ORGANISM: Homo sapiens

<400> SEQUENCE: 817

Ala Val Leu His Ile Gly Glu Lys
1               5

<210> SEQ ID NO 818
<211> LENGTH: 19
<212> TYPE: PRT
<213> ORGANISM: Homo sapiens

<400> SEQUENCE: 818

Gly Leu Gln Tyr Ala Ala Gln Glu Gly Leu Leu Ala Leu Gln Ser Glu
1               5                   10                  15

Leu Leu Arg

<210> SEQ ID NO 819
<211> LENGTH: 11
<212> TYPE: PRT
<213> ORGANISM: Homo sapiens

<400> SEQUENCE: 819

Gln Leu Tyr Gly Asp Thr Gly Val Leu Gly Arg
1               5                   10

<210> SEQ ID NO 820
<211> LENGTH: 9
<212> TYPE: PRT
<213> ORGANISM: Homo sapiens

<400> SEQUENCE: 820

Glu Leu Pro Gln Ser Ile Val Tyr Lys
1               5

<210> SEQ ID NO 821
<211> LENGTH: 8
<212> TYPE: PRT
<213> ORGANISM: Homo sapiens

<400> SEQUENCE: 821

Asn Ile Gln Ser Val Asn Val Lys
1               5

<210> SEQ ID NO 822
<211> LENGTH: 16
<212> TYPE: PRT
<213> ORGANISM: Homo sapiens

<400> SEQUENCE: 822
```

```
Thr Gly Val Ala Val Asn Lys Pro Ala Glu Phe Thr Val Asp Ala Lys
1               5                   10                  15
```

<210> SEQ ID NO 823
<211> LENGTH: 21
<212> TYPE: PRT
<213> ORGANISM: Homo sapiens

<400> SEQUENCE: 823

```
His Glu Leu Thr Asp Glu Glu Leu Gln Ser Leu Phe Thr Asn Phe Ala
1               5                   10                  15

Asn Val Val Asp Lys
            20
```

<210> SEQ ID NO 824
<211> LENGTH: 23
<212> TYPE: PRT
<213> ORGANISM: Homo sapiens

<400> SEQUENCE: 824

```
Thr Glu Phe Leu Ser Asn Tyr Leu Thr Asn Val Asp Asp Ile Thr Leu
1               5                   10                  15

Val Pro Gly Thr Leu Gly Arg
            20
```

<210> SEQ ID NO 825
<211> LENGTH: 7
<212> TYPE: PRT
<213> ORGANISM: Homo sapiens

<400> SEQUENCE: 825

```
Ile Ala Ile Asp Leu Phe Lys
1               5
```

<210> SEQ ID NO 826
<211> LENGTH: 10
<212> TYPE: PRT
<213> ORGANISM: Homo sapiens

<400> SEQUENCE: 826

```
Thr Val Gln Ala Val Leu Thr Val Pro Lys
1               5                   10
```

<210> SEQ ID NO 827
<211> LENGTH: 11
<212> TYPE: PRT
<213> ORGANISM: Homo sapiens

<400> SEQUENCE: 827

```
Leu Ile Glu Asn Gly Tyr Phe His Pro Val Lys
1               5                   10
```

<210> SEQ ID NO 828
<211> LENGTH: 7
<212> TYPE: PRT
<213> ORGANISM: Homo sapiens

<400> SEQUENCE: 828

```
Phe Leu Pro Cys Glu Asn Lys
1               5
```

<210> SEQ ID NO 829
<211> LENGTH: 17
<212> TYPE: PRT

<213> ORGANISM: Homo sapiens

<400> SEQUENCE: 829

His Pro Trp Ile Val His Trp Asp Gln Leu Pro Gln Tyr Gln Leu Asn
1               5               10              15

Arg

<210> SEQ ID NO 830
<211> LENGTH: 10
<212> TYPE: PRT
<213> ORGANISM: Homo sapiens

<400> SEQUENCE: 830

Gln Gly His Asn Ser Val Phe Leu Ile Lys
1               5               10

<210> SEQ ID NO 831
<211> LENGTH: 7
<212> TYPE: PRT
<213> ORGANISM: Homo sapiens

<400> SEQUENCE: 831

His Phe Gln Asn Leu Gly Lys
1               5

<210> SEQ ID NO 832
<211> LENGTH: 16
<212> TYPE: PRT
<213> ORGANISM: Homo sapiens

<400> SEQUENCE: 832

Ile Ala Pro Gln Leu Ser Thr Glu Glu Leu Val Ser Leu Gly Glu Lys
1               5               10              15

<210> SEQ ID NO 833
<211> LENGTH: 10
<212> TYPE: PRT
<213> ORGANISM: Homo sapiens

<400> SEQUENCE: 833

Asp Ala Asp Pro Asp Thr Phe Phe Ala Lys
1               5               10

<210> SEQ ID NO 834
<211> LENGTH: 10
<212> TYPE: PRT
<213> ORGANISM: Homo sapiens

<400> SEQUENCE: 834

Val Asn His Val Thr Leu Ser Gln Pro Lys
1               5               10

<210> SEQ ID NO 835
<211> LENGTH: 10
<212> TYPE: PRT
<213> ORGANISM: Homo sapiens

<400> SEQUENCE: 835

His Tyr Gly Gly Leu Thr Gly Leu Asn Lys
1               5               10

<210> SEQ ID NO 836
<211> LENGTH: 13
<212> TYPE: PRT

-continued

```
<213> ORGANISM: Homo sapiens

<400> SEQUENCE: 836

Asn Cys Ser Phe Ser Ile Ile Tyr Pro Val Val Ile Lys
1               5                   10

<210> SEQ ID NO 837
<211> LENGTH: 22
<212> TYPE: PRT
<213> ORGANISM: Homo sapiens

<400> SEQUENCE: 837

Ala Gln Pro Val Gln Val Ala Glu Gly Ser Glu Pro Asp Gly Phe Trp
1               5                   10                  15

Glu Ala Leu Gly Gly Lys
            20

<210> SEQ ID NO 838
<211> LENGTH: 9
<212> TYPE: PRT
<213> ORGANISM: Homo sapiens

<400> SEQUENCE: 838

Leu Asp Phe His Phe Ser Ser Asp Arg
1               5

<210> SEQ ID NO 839
<211> LENGTH: 8
<212> TYPE: PRT
<213> ORGANISM: Homo sapiens

<400> SEQUENCE: 839

Thr Leu Asn Ala Tyr Asp His Arg
1               5

<210> SEQ ID NO 840
<211> LENGTH: 14
<212> TYPE: PRT
<213> ORGANISM: Homo sapiens

<400> SEQUENCE: 840

Glu Val Phe Ser Lys Pro Ile Ser Trp Glu Glu Leu Leu Gln
1               5                   10

<210> SEQ ID NO 841
<211> LENGTH: 11
<212> TYPE: PRT
<213> ORGANISM: Homo sapiens

<400> SEQUENCE: 841

Asn Phe Pro Ser Pro Val Asp Ala Ala Phe Arg
1               5                   10

<210> SEQ ID NO 842
<211> LENGTH: 9
<212> TYPE: PRT
<213> ORGANISM: Homo sapiens

<400> SEQUENCE: 842

Thr Leu Phe Ile Phe Gly Val Thr Lys
1               5

<210> SEQ ID NO 843
<211> LENGTH: 9
```

-continued

<212> TYPE: PRT
<213> ORGANISM: Homo sapiens

<400> SEQUENCE: 843

Tyr Tyr Gly Tyr Thr Gly Ala Phe Arg
1               5

<210> SEQ ID NO 844
<211> LENGTH: 7
<212> TYPE: PRT
<213> ORGANISM: Homo sapiens

<400> SEQUENCE: 844

Gln Val Phe Ala Val Gln Arg
1               5

<210> SEQ ID NO 845
<211> LENGTH: 10
<212> TYPE: PRT
<213> ORGANISM: Homo sapiens

<400> SEQUENCE: 845

Asp Phe Asn Gln Phe Ser Ser Gly Glu Lys
1               5                   10

<210> SEQ ID NO 846
<211> LENGTH: 13
<212> TYPE: PRT
<213> ORGANISM: Homo sapiens

<400> SEQUENCE: 846

Ser Val Ser Leu Pro Ser Leu Asp Pro Ala Ser Ala Lys
1               5                   10

<210> SEQ ID NO 847
<211> LENGTH: 9
<212> TYPE: PRT
<213> ORGANISM: Homo sapiens

<400> SEQUENCE: 847

Gly Asn Gly Leu Thr Trp Ala Glu Lys
1               5

<210> SEQ ID NO 848
<211> LENGTH: 22
<212> TYPE: PRT
<213> ORGANISM: Homo sapiens

<400> SEQUENCE: 848

Gly Ala Val His Val Val Val Ala Glu Thr Asp Tyr Gln Ser Phe Ala
1               5                   10                  15

Val Leu Tyr Leu Glu Arg
            20

<210> SEQ ID NO 849
<211> LENGTH: 14
<212> TYPE: PRT
<213> ORGANISM: Homo sapiens

<400> SEQUENCE: 849

Thr Ser Glu Ser Thr Gly Ser Leu Pro Ser Pro Phe Leu Arg
1               5                   10

<210> SEQ ID NO 850

```
<211> LENGTH: 12
<212> TYPE: PRT
<213> ORGANISM: Homo sapiens

<400> SEQUENCE: 850

Tyr Ile Ser Pro Asp Gln Leu Ala Asp Leu Tyr Lys
1               5                   10

<210> SEQ ID NO 851
<211> LENGTH: 10
<212> TYPE: PRT
<213> ORGANISM: Homo sapiens

<400> SEQUENCE: 851

Glu Ser Asp Thr Ser Tyr Val Ser Leu Lys
1               5                   10

<210> SEQ ID NO 852
<211> LENGTH: 8
<212> TYPE: PRT
<213> ORGANISM: Homo sapiens

<400> SEQUENCE: 852

Ile Leu Asp Asp Leu Ser Pro Arg
1               5

<210> SEQ ID NO 853
<211> LENGTH: 11
<212> TYPE: PRT
<213> ORGANISM: Homo sapiens

<400> SEQUENCE: 853

Ser Gly Val Asp Leu Ala Asp Ser Asn Gln Lys
1               5                   10

<210> SEQ ID NO 854
<211> LENGTH: 12
<212> TYPE: PRT
<213> ORGANISM: Homo sapiens

<400> SEQUENCE: 854

Asp Thr Asp Thr Gly Ala Leu Leu Phe Ile Gly Lys
1               5                   10

<210> SEQ ID NO 855
<211> LENGTH: 9
<212> TYPE: PRT
<213> ORGANISM: Homo sapiens

<400> SEQUENCE: 855

His Tyr Phe Ile Ala Ala Val Glu Arg
1               5

<210> SEQ ID NO 856
<211> LENGTH: 10
<212> TYPE: PRT
<213> ORGANISM: Homo sapiens

<400> SEQUENCE: 856

Asp Leu His Leu Ser Asp Val Phe Leu Lys
1               5                   10

<210> SEQ ID NO 857
<211> LENGTH: 12
<212> TYPE: PRT
```

-continued

<213> ORGANISM: Homo sapiens

<400> SEQUENCE: 857

Asp Pro Thr Phe Ile Pro Ala Pro Ile Gln Ala Lys
1               5                   10

<210> SEQ ID NO 858
<211> LENGTH: 7
<212> TYPE: PRT
<213> ORGANISM: Homo sapiens

<400> SEQUENCE: 858

Ala Gly Ile Thr Ile Pro Arg
1               5

<210> SEQ ID NO 859
<211> LENGTH: 9
<212> TYPE: PRT
<213> ORGANISM: Homo sapiens

<400> SEQUENCE: 859

Ile Ala Gln Tyr Tyr Tyr Thr Phe Lys
1               5

<210> SEQ ID NO 860
<211> LENGTH: 10
<212> TYPE: PRT
<213> ORGANISM: Homo sapiens

<400> SEQUENCE: 860

Tyr Asn Ser Gln Leu Leu Ser Phe Val Arg
1               5                   10

<210> SEQ ID NO 861
<211> LENGTH: 19
<212> TYPE: PRT
<213> ORGANISM: Homo sapiens

<400> SEQUENCE: 861

Ala Asn Asp Gln Tyr Leu Thr Ala Ala Ala Leu His Asn Leu Asp Glu
1               5                   10                  15

Ala Val Lys

<210> SEQ ID NO 862
<211> LENGTH: 9
<212> TYPE: PRT
<213> ORGANISM: Homo sapiens

<400> SEQUENCE: 862

Phe Gln Ser Val Phe Thr Val Thr Arg
1               5

<210> SEQ ID NO 863
<211> LENGTH: 14
<212> TYPE: PRT
<213> ORGANISM: Homo sapiens

<400> SEQUENCE: 863

Leu Gln Val Asn Thr Pro Leu Val Gly Ala Ser Leu Leu Arg
1               5                   10

<210> SEQ ID NO 864
<211> LENGTH: 12
<212> TYPE: PRT

-continued

```
<213> ORGANISM: Homo sapiens

<400> SEQUENCE: 864

Asp Glu Ile Pro His Asn Asp Ile Ala Leu Leu Lys
1               5                   10

<210> SEQ ID NO 865
<211> LENGTH: 10
<212> TYPE: PRT
<213> ORGANISM: Homo sapiens

<400> SEQUENCE: 865

His Ala Thr Leu Ser Leu Ser Ile Pro Arg
1               5                   10

<210> SEQ ID NO 866
<211> LENGTH: 10
<212> TYPE: PRT
<213> ORGANISM: Homo sapiens

<400> SEQUENCE: 866

Thr Gly Ile Ser Pro Leu Ala Leu Ile Lys
1               5                   10

<210> SEQ ID NO 867
<211> LENGTH: 7
<212> TYPE: PRT
<213> ORGANISM: Homo sapiens

<400> SEQUENCE: 867

Ile Leu Pro Ser Val Pro Lys
1               5

<210> SEQ ID NO 868
<211> LENGTH: 12
<212> TYPE: PRT
<213> ORGANISM: Homo sapiens

<400> SEQUENCE: 868

Leu Pro Ala Thr Glu Lys Pro Val Leu Leu Ser Lys
1               5                   10

<210> SEQ ID NO 869
<211> LENGTH: 11
<212> TYPE: PRT
<213> ORGANISM: Homo sapiens

<400> SEQUENCE: 869

Thr Phe Leu Thr Val Tyr Trp Thr Pro Glu Arg
1               5                   10

<210> SEQ ID NO 870
<211> LENGTH: 16
<212> TYPE: PRT
<213> ORGANISM: Homo sapiens

<400> SEQUENCE: 870

Gly Asp Thr Tyr Pro Ala Glu Leu Tyr Ile Thr Gly Ser Ile Leu Arg
1               5                   10                  15

<210> SEQ ID NO 871
<211> LENGTH: 13
<212> TYPE: PRT
<213> ORGANISM: Homo sapiens
```

```
<400> SEQUENCE: 871

Ser Leu Asp Phe Thr Glu Leu Asp Val Ala Ala Glu Lys
1               5                   10

<210> SEQ ID NO 872
<211> LENGTH: 14
<212> TYPE: PRT
<213> ORGANISM: Homo sapiens

<400> SEQUENCE: 872

Val Glu Leu Ala Pro Leu Pro Ser Trp Gln Pro Val Gly Lys
1               5                   10

<210> SEQ ID NO 873
<211> LENGTH: 7
<212> TYPE: PRT
<213> ORGANISM: Homo sapiens

<400> SEQUENCE: 873

Gly Pro Gly Glu Asp Phe Arg
1               5

<210> SEQ ID NO 874
<211> LENGTH: 9
<212> TYPE: PRT
<213> ORGANISM: Homo sapiens

<400> SEQUENCE: 874

Ile Leu Asn Ile Phe Gly Val Ile Lys
1               5

<210> SEQ ID NO 875
<211> LENGTH: 15
<212> TYPE: PRT
<213> ORGANISM: Homo sapiens

<400> SEQUENCE: 875

Ile Ser Gln Gly Glu Ala Asp Ile Asn Ile Ala Phe Tyr Gln Arg
1               5                   10                  15

<210> SEQ ID NO 876
<211> LENGTH: 8
<212> TYPE: PRT
<213> ORGANISM: Homo sapiens

<400> SEQUENCE: 876

Phe Thr Ile Thr Ala Gly Ser Lys
1               5

<210> SEQ ID NO 877
<211> LENGTH: 7
<212> TYPE: PRT
<213> ORGANISM: Homo sapiens

<400> SEQUENCE: 877

Ile Leu Asp Gly Gly Asn Lys
1               5

<210> SEQ ID NO 878
<211> LENGTH: 13
<212> TYPE: PRT
<213> ORGANISM: Homo sapiens

<400> SEQUENCE: 878
```

-continued

```
Phe Ser Leu Val Ser Gly Trp Gly Gln Leu Leu Asp Arg
1               5                   10

<210> SEQ ID NO 879
<211> LENGTH: 9
<212> TYPE: PRT
<213> ORGANISM: Homo sapiens

<400> SEQUENCE: 879

Ser Asp Gly Ala Lys Pro Gly Pro Arg
1               5

<210> SEQ ID NO 880
<211> LENGTH: 6
<212> TYPE: PRT
<213> ORGANISM: Homo sapiens

<400> SEQUENCE: 880

Gln Asp Leu Gly Trp Lys
1               5

<210> SEQ ID NO 881
<211> LENGTH: 7
<212> TYPE: PRT
<213> ORGANISM: Homo sapiens

<400> SEQUENCE: 881

Ser Ile Leu Phe Leu Gly Lys
1               5

<210> SEQ ID NO 882
<211> LENGTH: 21
<212> TYPE: PRT
<213> ORGANISM: Homo sapiens

<400> SEQUENCE: 882

Ile Glu Val Asn Glu Ser Gly Thr Val Ala Ser Ser Ser Thr Ala Val
1               5                   10                  15

Ile Val Ser Ala Arg
            20

<210> SEQ ID NO 883
<211> LENGTH: 20
<212> TYPE: PRT
<213> ORGANISM: Homo sapiens

<400> SEQUENCE: 883

Leu Leu Ala Pro Ser Asp Ser Pro Glu Trp Leu Ser Phe Asp Val Thr
1               5                   10                  15

Gly Val Val Arg
            20

<210> SEQ ID NO 884
<211> LENGTH: 8
<212> TYPE: PRT
<213> ORGANISM: Homo sapiens

<400> SEQUENCE: 884

Ile Glu Val Ile Ile Thr Leu Lys
1               5

<210> SEQ ID NO 885
<211> LENGTH: 7
<212> TYPE: PRT
```

<213> ORGANISM: Homo sapiens

<400> SEQUENCE: 885

Asp Tyr Trp Ser Thr Val Lys
1               5

<210> SEQ ID NO 886
<211> LENGTH: 12
<212> TYPE: PRT
<213> ORGANISM: Homo sapiens

<400> SEQUENCE: 886

Trp Ile Leu Thr Ala Ala His Thr Leu Tyr Pro Lys
1               5                   10

<210> SEQ ID NO 887
<211> LENGTH: 12
<212> TYPE: PRT
<213> ORGANISM: Homo sapiens

<400> SEQUENCE: 887

Ser Pro Glu Ala Glu Asp Pro Leu Gly Val Glu Arg
1               5                   10

<210> SEQ ID NO 888
<211> LENGTH: 16
<212> TYPE: PRT
<213> ORGANISM: Homo sapiens

<400> SEQUENCE: 888

Ser Gly Ala Gln Ala Thr Trp Thr Glu Leu Pro Trp Pro His Glu Lys
1               5                   10                  15

<210> SEQ ID NO 889
<211> LENGTH: 7
<212> TYPE: PRT
<213> ORGANISM: Homo sapiens

<400> SEQUENCE: 889

Tyr Ser His Tyr Asn Glu Arg
1               5

<210> SEQ ID NO 890
<211> LENGTH: 20
<212> TYPE: PRT
<213> ORGANISM: Homo sapiens

<400> SEQUENCE: 890

Glu Val Pro Leu Ser Ala Leu Thr Asn Ile Leu Ser Ala Gln Leu Ile
1               5                   10                  15

Ser His Trp Lys
            20

<210> SEQ ID NO 891
<211> LENGTH: 22
<212> TYPE: PRT
<213> ORGANISM: Homo sapiens

<400> SEQUENCE: 891

Ala Ala Leu Ala Ala Phe Asn Ala Gln Asn Asn Gly Ser Asn Phe Gln
1               5                   10                  15

Leu Glu Glu Ile Ser Arg
            20

<210> SEQ ID NO 892
<211> LENGTH: 20
<212> TYPE: PRT
<213> ORGANISM: Homo sapiens

<400> SEQUENCE: 892

Ile Val Leu Ser Leu Asp Val Pro Ile Gly Leu Leu Gln Ile Leu Leu
1               5                   10                  15

Glu Gln Ala Arg
            20

<210> SEQ ID NO 893
<211> LENGTH: 18
<212> TYPE: PRT
<213> ORGANISM: Homo sapiens

<400> SEQUENCE: 893

Glu Asn Pro Ala Val Ile Asp Phe Glu Leu Ala Pro Ile Val Asp Leu
1               5                   10                  15

Val Arg

<210> SEQ ID NO 894
<211> LENGTH: 11
<212> TYPE: PRT
<213> ORGANISM: Homo sapiens

<400> SEQUENCE: 894

Asn Val Asn Gln Ser Leu Leu Glu Leu His Lys
1               5                   10

<210> SEQ ID NO 895
<211> LENGTH: 9
<212> TYPE: PRT
<213> ORGANISM: Homo sapiens

<400> SEQUENCE: 895

Glu Ile Gly Glu Leu Tyr Leu Pro Lys
1               5

<210> SEQ ID NO 896
<211> LENGTH: 17
<212> TYPE: PRT
<213> ORGANISM: Homo sapiens

<400> SEQUENCE: 896

Asn Lys Pro Gly Val Tyr Thr Asp Val Ala Tyr Tyr Leu Ala Trp Ile
1               5                   10                  15

Arg

<210> SEQ ID NO 897
<211> LENGTH: 13
<212> TYPE: PRT
<213> ORGANISM: Homo sapiens

<400> SEQUENCE: 897

Gln Asn Tyr His Gln Asp Ser Glu Ala Ala Ile Asn Arg
1               5                   10

<210> SEQ ID NO 898
<211> LENGTH: 6
<212> TYPE: PRT
<213> ORGANISM: Homo sapiens

<400> SEQUENCE: 898

Val Thr Phe Glu Tyr Arg
1               5

<210> SEQ ID NO 899
<211> LENGTH: 9
<212> TYPE: PRT
<213> ORGANISM: Homo sapiens

<400> SEQUENCE: 899

Asp Leu Pro His Ile Thr Val Asp Arg
1               5

<210> SEQ ID NO 900
<211> LENGTH: 19
<212> TYPE: PRT
<213> ORGANISM: Homo sapiens

<400> SEQUENCE: 900

Gly Ser Leu Val Gln Ala Ser Glu Ala Asn Leu Gln Ala Ala Gln Asp
1               5                   10                  15

Phe Val Arg

<210> SEQ ID NO 901
<211> LENGTH: 5
<212> TYPE: PRT
<213> ORGANISM: Homo sapiens

<400> SEQUENCE: 901

Phe Leu Tyr His Lys
1               5

<210> SEQ ID NO 902
<211> LENGTH: 8
<212> TYPE: PRT
<213> ORGANISM: Homo sapiens

<400> SEQUENCE: 902

Leu Gln Asp Ala Gly Val Tyr Arg
1               5

<210> SEQ ID NO 903
<211> LENGTH: 8
<212> TYPE: PRT
<213> ORGANISM: Homo sapiens

<400> SEQUENCE: 903

Ile Asn Pro Ala Ser Leu Asp Lys
1               5

<210> SEQ ID NO 904
<211> LENGTH: 8
<212> TYPE: PRT
<213> ORGANISM: Homo sapiens

<400> SEQUENCE: 904

Leu Glu Glu His Tyr Glu Leu Arg
1               5

<210> SEQ ID NO 905
<211> LENGTH: 11
<212> TYPE: PRT
<213> ORGANISM: Homo sapiens

```
<400> SEQUENCE: 905

Thr Ser Asp Gln Ile His Phe Phe Phe Ala Lys
1               5                   10

<210> SEQ ID NO 906
<211> LENGTH: 11
<212> TYPE: PRT
<213> ORGANISM: Homo sapiens

<400> SEQUENCE: 906

Ala Thr Leu Ser Ala Ala Pro Ser Asn Pro Arg
1               5                   10

<210> SEQ ID NO 907
<211> LENGTH: 13
<212> TYPE: PRT
<213> ORGANISM: Homo sapiens

<400> SEQUENCE: 907

Glu Ala Asn Gln Ser Thr Leu Glu Asn Phe Leu Glu Arg
1               5                   10

<210> SEQ ID NO 908
<211> LENGTH: 14
<212> TYPE: PRT
<213> ORGANISM: Homo sapiens

<400> SEQUENCE: 908

Gly Gln Gln Pro Ala Asp Val Thr Gly Thr Ala Leu Pro Arg
1               5                   10

<210> SEQ ID NO 909
<211> LENGTH: 12
<212> TYPE: PRT
<213> ORGANISM: Homo sapiens

<400> SEQUENCE: 909

Gly Glu Val Thr Tyr Thr Thr Ser Gln Val Ser Lys
1               5                   10

<210> SEQ ID NO 910
<211> LENGTH: 11
<212> TYPE: PRT
<213> ORGANISM: Homo sapiens

<400> SEQUENCE: 910

Ser Leu Gln Ala Phe Val Ala Val Ala Ala Arg
1               5                   10

<210> SEQ ID NO 911
<211> LENGTH: 15
<212> TYPE: PRT
<213> ORGANISM: Homo sapiens

<400> SEQUENCE: 911

Gly Pro Glu Asp Gln Asp Ile Ser Ile Ser Phe Ala Trp Asp Lys
1               5                   10                  15

<210> SEQ ID NO 912
<211> LENGTH: 12
<212> TYPE: PRT
<213> ORGANISM: Homo sapiens

<400> SEQUENCE: 912
```

```
Tyr Val Val Ile Ser Gln Gly Leu Asp Lys Pro Arg
1               5                   10

<210> SEQ ID NO 913
<211> LENGTH: 15
<212> TYPE: PRT
<213> ORGANISM: Homo sapiens

<400> SEQUENCE: 913

Gly Thr Ala Glu Trp Leu Ser Phe Asp Val Thr Asp Thr Val Arg
1               5                   10                  15

<210> SEQ ID NO 914
<211> LENGTH: 19
<212> TYPE: PRT
<213> ORGANISM: Homo sapiens

<400> SEQUENCE: 914

Ala His Gln Leu Ala Ile Asp Thr Tyr Gln Glu Phe Glu Glu Thr Tyr
1               5                   10                  15

Ile Pro Lys

<210> SEQ ID NO 915
<211> LENGTH: 10
<212> TYPE: PRT
<213> ORGANISM: Homo sapiens

<400> SEQUENCE: 915

Thr Ala Val Thr Ala Asn Leu Asp Ile Arg
1               5                   10

<210> SEQ ID NO 916
<211> LENGTH: 16
<212> TYPE: PRT
<213> ORGANISM: Homo sapiens

<400> SEQUENCE: 916

Trp Ser Ala Gly Leu Thr Ser Ser Gln Val Asp Leu Tyr Ile Pro Lys
1               5                   10                  15

<210> SEQ ID NO 917
<211> LENGTH: 7
<212> TYPE: PRT
<213> ORGANISM: Homo sapiens

<400> SEQUENCE: 917

Gln Ile Asn Ser Tyr Val Lys
1               5

<210> SEQ ID NO 918
<211> LENGTH: 12
<212> TYPE: PRT
<213> ORGANISM: Homo sapiens

<400> SEQUENCE: 918

Gly Phe Gln Ala Leu Gly Asp Ala Ala Asp Ile Arg
1               5                   10

<210> SEQ ID NO 919
<211> LENGTH: 6
<212> TYPE: PRT
<213> ORGANISM: Homo sapiens

<400> SEQUENCE: 919
```

-continued

```
Asn Glu Ile Trp Tyr Arg
1               5

<210> SEQ ID NO 920
<211> LENGTH: 7
<212> TYPE: PRT
<213> ORGANISM: Homo sapiens

<400> SEQUENCE: 920

Val Leu Glu Pro Thr Leu Lys
1               5

<210> SEQ ID NO 921
<211> LENGTH: 11
<212> TYPE: PRT
<213> ORGANISM: Homo sapiens

<400> SEQUENCE: 921

Ala Leu Asn Ser Ile Ile Asp Val Tyr His Lys
1               5                   10

<210> SEQ ID NO 922
<211> LENGTH: 25
<212> TYPE: PRT
<213> ORGANISM: Homo sapiens

<400> SEQUENCE: 922

Glu Thr Pro Glu Gly Ala Glu Ala Lys Pro Trp Tyr Glu Pro Ile Tyr
1               5                   10                  15

Leu Gly Gly Val Phe Gln Leu Glu Lys
            20                  25

<210> SEQ ID NO 923
<211> LENGTH: 10
<212> TYPE: PRT
<213> ORGANISM: Homo sapiens

<400> SEQUENCE: 923

Leu Asn Ile Gly Tyr Ile Glu Asp Leu Lys
1               5                   10

<210> SEQ ID NO 924
<211> LENGTH: 10
<212> TYPE: PRT
<213> ORGANISM: Homo sapiens

<400> SEQUENCE: 924

Asp Ile Pro His Trp Leu Asn Pro Thr Arg
1               5                   10

<210> SEQ ID NO 925
<211> LENGTH: 17
<212> TYPE: PRT
<213> ORGANISM: Homo sapiens

<400> SEQUENCE: 925

Asn Glu Ile Val Phe Pro Ala Gly Ile Leu Gln Ala Pro Phe Tyr Thr
1               5                   10                  15

Arg

<210> SEQ ID NO 926
<211> LENGTH: 16
<212> TYPE: PRT
<213> ORGANISM: Homo sapiens
```

-continued

<400> SEQUENCE: 926

Ala Glu His Pro Thr Trp Gly Asp Glu Gln Leu Phe Gln Thr Thr Arg
1               5                   10                  15

<210> SEQ ID NO 927
<211> LENGTH: 14
<212> TYPE: PRT
<213> ORGANISM: Homo sapiens

<400> SEQUENCE: 927

Ser Trp Asn Glu Pro Leu Tyr His Leu Val Thr Glu Val Arg
1               5                   10

<210> SEQ ID NO 928
<211> LENGTH: 11
<212> TYPE: PRT
<213> ORGANISM: Homo sapiens

<400> SEQUENCE: 928

Ile Pro Lys Pro Glu Ala Ser Phe Ser Pro Arg
1               5                   10

<210> SEQ ID NO 929
<211> LENGTH: 11
<212> TYPE: PRT
<213> ORGANISM: Homo sapiens

<400> SEQUENCE: 929

Asp Asp Leu Tyr Val Ser Asp Ala Phe His Lys
1               5                   10

<210> SEQ ID NO 930
<211> LENGTH: 26
<212> TYPE: PRT
<213> ORGANISM: Homo sapiens

<400> SEQUENCE: 930

Gln Arg Pro Pro Asp Leu Asp Thr Ser Ser Asn Ala Val Asp Leu Leu
1               5                   10                  15

Phe Phe Thr Asp Glu Ser Gly Asp Ser Arg
            20                  25

<210> SEQ ID NO 931
<211> LENGTH: 16
<212> TYPE: PRT
<213> ORGANISM: Homo sapiens

<400> SEQUENCE: 931

Gly Gln Val Pro Glu Asn Glu Ala Asn Val Val Ile Thr Thr Leu Lys
1               5                   10                  15

<210> SEQ ID NO 932
<211> LENGTH: 18
<212> TYPE: PRT
<213> ORGANISM: Homo sapiens

<400> SEQUENCE: 932

Phe Thr Gly Ser Gln Pro Phe Gly Gln Gly Val Glu His Ala Thr Ala
1               5                   10                  15

Asn Lys

<210> SEQ ID NO 933

<211> LENGTH: 18
<212> TYPE: PRT
<213> ORGANISM: Homo sapiens

<400> SEQUENCE: 933

Leu Glu Pro Leu Tyr Ser Ala Ser Gly Pro Gly Leu Arg Pro Leu Val
1               5                   10                  15

Ile Lys

<210> SEQ ID NO 934
<211> LENGTH: 14
<212> TYPE: PRT
<213> ORGANISM: Homo sapiens

<400> SEQUENCE: 934

Ile Gln His Pro Phe Thr Val Glu Glu Phe Val Leu Pro Lys
1               5                   10

<210> SEQ ID NO 935
<211> LENGTH: 8
<212> TYPE: PRT
<213> ORGANISM: Homo sapiens

<400> SEQUENCE: 935

Thr Glu Gln Ala Ala Val Ala Arg
1               5

<210> SEQ ID NO 936
<211> LENGTH: 13
<212> TYPE: PRT
<213> ORGANISM: Homo sapiens

<400> SEQUENCE: 936

Leu Phe Tyr Ala Asp His Pro Phe Ile Phe Leu Val Arg
1               5                   10

<210> SEQ ID NO 937
<211> LENGTH: 8
<212> TYPE: PRT
<213> ORGANISM: Homo sapiens

<400> SEQUENCE: 937

Thr Ser Tyr Gln Val Tyr Ser Lys
1               5

<210> SEQ ID NO 938
<211> LENGTH: 13
<212> TYPE: PRT
<213> ORGANISM: Homo sapiens

<400> SEQUENCE: 938

Asn Val Ile Gln Ile Ser Asn Asp Leu Glu Asn Leu Arg
1               5                   10

<210> SEQ ID NO 939
<211> LENGTH: 23
<212> TYPE: PRT
<213> ORGANISM: Homo sapiens

<400> SEQUENCE: 939

Ala Phe Leu Glu Val Asn Glu Glu Gly Ser Glu Ala Ala Ala Ser Thr
1               5                   10                  15

Ala Val Val Ile Ala Gly Arg
            20

-continued

<210> SEQ ID NO 940
<211> LENGTH: 18
<212> TYPE: PRT
<213> ORGANISM: Homo sapiens

<400> SEQUENCE: 940

Leu His Glu Ala Phe Ser Pro Val Ser Tyr Gln His Asp Leu Ala Leu
1               5                   10                  15

Leu Arg

<210> SEQ ID NO 941
<211> LENGTH: 18
<212> TYPE: PRT
<213> ORGANISM: Homo sapiens

<400> SEQUENCE: 941

Gly Pro Ile Thr Ser Ala Ala Glu Leu Asn Asp Pro Gln Ser Ile Leu
1               5                   10                  15

Leu Arg

<210> SEQ ID NO 942
<211> LENGTH: 14
<212> TYPE: PRT
<213> ORGANISM: Homo sapiens

<400> SEQUENCE: 942

Ala Val Asp Ile Pro Gly Leu Glu Ala Ala Thr Pro Tyr Arg
1               5                   10

<210> SEQ ID NO 943
<211> LENGTH: 10
<212> TYPE: PRT
<213> ORGANISM: Homo sapiens

<400> SEQUENCE: 943

Val Pro Leu Ala Leu Phe Ala Leu Asn Arg
1               5                   10

<210> SEQ ID NO 944
<211> LENGTH: 9
<212> TYPE: PRT
<213> ORGANISM: Homo sapiens

<400> SEQUENCE: 944

Val Val Gly Gly Leu Val Ala Leu Arg
1               5

<210> SEQ ID NO 945
<211> LENGTH: 11
<212> TYPE: PRT
<213> ORGANISM: Homo sapiens

<400> SEQUENCE: 945

Asn His Tyr Thr Glu Ser Ile Ser Val Ala Lys
1               5                   10

<210> SEQ ID NO 946
<211> LENGTH: 24
<212> TYPE: PRT
<213> ORGANISM: Homo sapiens

<400> SEQUENCE: 946

```
Val Val Leu Ser Ser Gly Ser Gly Pro Gly Leu Asp Leu Pro Leu Val
1               5                   10                  15

Leu Gly Leu Pro Leu Gln Leu Lys
            20

<210> SEQ ID NO 947
<211> LENGTH: 22
<212> TYPE: PRT
<213> ORGANISM: Homo sapiens

<400> SEQUENCE: 947

Ala Leu Ala Leu Pro Pro Leu Gly Leu Ala Pro Leu Leu Asn Leu Trp
1               5                   10                  15

Ala Lys Pro Gln Gly Arg
            20

<210> SEQ ID NO 948
<211> LENGTH: 8
<212> TYPE: PRT
<213> ORGANISM: Homo sapiens

<400> SEQUENCE: 948

Ile Pro Ser Asn Pro Ser His Arg
1               5

<210> SEQ ID NO 949
<211> LENGTH: 15
<212> TYPE: PRT
<213> ORGANISM: Homo sapiens

<400> SEQUENCE: 949

Ala Asn Leu Ile Asn Asn Ile Phe Glu Leu Ala Gly Leu Gly Lys
1               5                   10                  15

<210> SEQ ID NO 950
<211> LENGTH: 11
<212> TYPE: PRT
<213> ORGANISM: Homo sapiens

<400> SEQUENCE: 950

Asn Glu Pro Glu Glu Thr Pro Ser Ile Glu Lys
1               5                   10

<210> SEQ ID NO 951
<211> LENGTH: 9
<212> TYPE: PRT
<213> ORGANISM: Homo sapiens

<400> SEQUENCE: 951

Val Pro Ser His Ala Val Val Ala Arg
1               5

<210> SEQ ID NO 952
<211> LENGTH: 19
<212> TYPE: PRT
<213> ORGANISM: Homo sapiens

<400> SEQUENCE: 952

Gly Gly Leu Phe Ala Asp Ile Ala Ser His Pro Trp Gln Ala Ala Ile
1               5                   10                  15

Phe Ala Lys

<210> SEQ ID NO 953
```

```
<211> LENGTH: 7
<212> TYPE: PRT
<213> ORGANISM: Homo sapiens

<400> SEQUENCE: 953

Ser Pro Gln Ala Phe Tyr Arg
1               5

<210> SEQ ID NO 954
<211> LENGTH: 19
<212> TYPE: PRT
<213> ORGANISM: Homo sapiens

<400> SEQUENCE: 954

Ser Ser Asn Asn Pro His Ser Pro Ile Val Glu Glu Phe Gln Val Pro
1               5                   10                  15

Tyr Asn Lys

<210> SEQ ID NO 955
<211> LENGTH: 10
<212> TYPE: PRT
<213> ORGANISM: Homo sapiens

<400> SEQUENCE: 955

Leu Ile Glu Ile Ala Asn His Val Asp Lys
1               5                   10

<210> SEQ ID NO 956
<211> LENGTH: 8
<212> TYPE: PRT
<213> ORGANISM: Homo sapiens

<400> SEQUENCE: 956

Gly Tyr Gln Glu Leu Leu Glu Lys
1               5

<210> SEQ ID NO 957
<211> LENGTH: 20
<212> TYPE: PRT
<213> ORGANISM: Homo sapiens

<400> SEQUENCE: 957

Ser Val Val Leu Ile Pro Leu Gly Ala Val Asp Asp Gly Glu His Ser
1               5                   10                  15

Gln Asn Glu Lys
            20

<210> SEQ ID NO 958
<211> LENGTH: 18
<212> TYPE: PRT
<213> ORGANISM: Homo sapiens

<400> SEQUENCE: 958

Ser Glu Thr Glu Ile His Gln Gly Phe Gln His Leu His Gln Leu Phe
1               5                   10                  15

Ala Lys

<210> SEQ ID NO 959
<211> LENGTH: 8
<212> TYPE: PRT
<213> ORGANISM: Homo sapiens

<400> SEQUENCE: 959
```

```
Ala Glu Ile Glu Tyr Leu Glu Lys
1               5

<210> SEQ ID NO 960
<211> LENGTH: 9
<212> TYPE: PRT
<213> ORGANISM: Homo sapiens

<400> SEQUENCE: 960

Val Gly Val Ile Ser Phe Ala Gln Lys
1               5

<210> SEQ ID NO 961
<211> LENGTH: 17
<212> TYPE: PRT
<213> ORGANISM: Homo sapiens

<400> SEQUENCE: 961

Val Phe Gln Tyr Ile Asp Leu His Gln Asp Glu Phe Val Gln Thr Leu
1               5                   10                  15

Lys

<210> SEQ ID NO 962
<211> LENGTH: 8
<212> TYPE: PRT
<213> ORGANISM: Homo sapiens

<400> SEQUENCE: 962

Val Leu Ser Ser Ile Glu Gln Lys
1               5

<210> SEQ ID NO 963
<211> LENGTH: 6
<212> TYPE: PRT
<213> ORGANISM: Homo sapiens

<400> SEQUENCE: 963

Thr Leu Pro Phe Ser Arg
1               5

<210> SEQ ID NO 964
<211> LENGTH: 16
<212> TYPE: PRT
<213> ORGANISM: Homo sapiens

<400> SEQUENCE: 964

Ala Glu Val Ile Trp Thr Ser Ser Asp His Gln Val Leu Ser Gly Lys
1               5                   10                  15

<210> SEQ ID NO 965
<211> LENGTH: 10
<212> TYPE: PRT
<213> ORGANISM: Homo sapiens

<400> SEQUENCE: 965

Tyr Trp Gly Val Ala Ser Phe Leu Gln Lys
1               5                   10

<210> SEQ ID NO 966
<211> LENGTH: 14
<212> TYPE: PRT
<213> ORGANISM: Homo sapiens

<400> SEQUENCE: 966
```

-continued

```
Ser Tyr Thr Ile Thr Gly Leu Gln Pro Gly Thr Asp Tyr Lys
1               5                   10

<210> SEQ ID NO 967
<211> LENGTH: 24
<212> TYPE: PRT
<213> ORGANISM: Homo sapiens

<400> SEQUENCE: 967

Ala Leu Asn Phe Gly Gly Ile Gly Val Val Val Gly His Glu Leu Thr
1               5                   10                  15

His Ala Phe Asp Asp Gln Gly Arg
            20

<210> SEQ ID NO 968
<211> LENGTH: 18
<212> TYPE: PRT
<213> ORGANISM: Homo sapiens

<400> SEQUENCE: 968

Ser Val Pro Val Thr Lys Pro Val Pro Val Thr Lys Pro Ile Thr Val
1               5                   10                  15

Thr Lys

<210> SEQ ID NO 969
<211> LENGTH: 7
<212> TYPE: PRT
<213> ORGANISM: Homo sapiens

<400> SEQUENCE: 969

Ile Tyr Leu Gln Pro Gly Arg
1               5

<210> SEQ ID NO 970
<211> LENGTH: 15
<212> TYPE: PRT
<213> ORGANISM: Homo sapiens

<400> SEQUENCE: 970

Glu Trp Val Ala Ile Glu Ser Asp Ser Val Gln Pro Val Pro Arg
1               5                   10                  15

<210> SEQ ID NO 971
<211> LENGTH: 25
<212> TYPE: PRT
<213> ORGANISM: Homo sapiens

<400> SEQUENCE: 971

Asp Leu Tyr His Tyr Ile Thr Ser Tyr Val Val Asp Gly Glu Ile Ile
1               5                   10                  15

Ile Tyr Gly Pro Ala Tyr Ser Gly Arg
            20              25

<210> SEQ ID NO 972
<211> LENGTH: 8
<212> TYPE: PRT
<213> ORGANISM: Homo sapiens

<400> SEQUENCE: 972

Glu Cys Glu Glu Leu Glu Glu Lys
1               5

<210> SEQ ID NO 973
```

<211> LENGTH: 8
<212> TYPE: PRT
<213> ORGANISM: Homo sapiens

<400> SEQUENCE: 973

Ser Thr Pro Ser Leu Thr Thr Lys
1               5

<210> SEQ ID NO 974
<211> LENGTH: 10
<212> TYPE: PRT
<213> ORGANISM: Homo sapiens

<400> SEQUENCE: 974

Ala Leu Leu Leu Gly Trp Val Pro Thr Arg
1               5                   10

<210> SEQ ID NO 975
<211> LENGTH: 14
<212> TYPE: PRT
<213> ORGANISM: Homo sapiens

<400> SEQUENCE: 975

Ile Ala Leu Gly Gly Leu Leu Phe Pro Ala Ser Asn Leu Arg
1               5                   10

<210> SEQ ID NO 976
<211> LENGTH: 11
<212> TYPE: PRT
<213> ORGANISM: Homo sapiens

<400> SEQUENCE: 976

Gly Tyr Val Ile Ile Lys Pro Leu Val Trp Val
1               5                   10

<210> SEQ ID NO 977
<211> LENGTH: 14
<212> TYPE: PRT
<213> ORGANISM: Homo sapiens

<400> SEQUENCE: 977

Asn Thr Gly Val Ile Ser Val Val Thr Thr Gly Leu Asp Arg
1               5                   10

<210> SEQ ID NO 978
<211> LENGTH: 10
<212> TYPE: PRT
<213> ORGANISM: Homo sapiens

<400> SEQUENCE: 978

Ser Glu Arg Pro Pro Ile Phe Glu Ile Arg
1               5                   10

<210> SEQ ID NO 979
<211> LENGTH: 25
<212> TYPE: PRT
<213> ORGANISM: Homo sapiens

<400> SEQUENCE: 979

Thr Ala His Ile Ser Gly Leu Pro Pro Ser Thr Asp Phe Ile Val Tyr
1               5                   10                  15

Leu Ser Gly Leu Ala Pro Ser Ile Arg
            20                  25

```
<210> SEQ ID NO 980
<211> LENGTH: 9
<212> TYPE: PRT
<213> ORGANISM: Homo sapiens

<400> SEQUENCE: 980

Ala Thr Asn Ala Thr Leu Asp Pro Arg
1               5

<210> SEQ ID NO 981
<211> LENGTH: 10
<212> TYPE: PRT
<213> ORGANISM: Homo sapiens

<400> SEQUENCE: 981

Gln Thr Leu Ser Trp Thr Val Thr Pro Lys
1               5                   10

<210> SEQ ID NO 982
<211> LENGTH: 9
<212> TYPE: PRT
<213> ORGANISM: Homo sapiens

<400> SEQUENCE: 982

Asp Ile Ile Lys Pro Asp Pro Pro Lys
1               5

<210> SEQ ID NO 983
<211> LENGTH: 6
<212> TYPE: PRT
<213> ORGANISM: Homo sapiens

<400> SEQUENCE: 983

His Val Val Gln Leu Arg
1               5

<210> SEQ ID NO 984
<211> LENGTH: 11
<212> TYPE: PRT
<213> ORGANISM: Homo sapiens

<400> SEQUENCE: 984

Asn Thr Val Ile Ser Val Asn Pro Ser Thr Lys
1               5                   10

<210> SEQ ID NO 985
<211> LENGTH: 7
<212> TYPE: PRT
<213> ORGANISM: Homo sapiens

<400> SEQUENCE: 985

Ile Leu Thr Pro Glu Val Arg
1               5

<210> SEQ ID NO 986
<211> LENGTH: 7
<212> TYPE: PRT
<213> ORGANISM: Homo sapiens

<400> SEQUENCE: 986

Glu Leu Ala Asn Thr Ile Lys
1               5

<210> SEQ ID NO 987
<211> LENGTH: 9
```

<212> TYPE: PRT
<213> ORGANISM: Homo sapiens

<400> SEQUENCE: 987

Leu Ser Ile Pro Gln Ile Thr Thr Lys
1               5

<210> SEQ ID NO 988
<211> LENGTH: 17
<212> TYPE: PRT
<213> ORGANISM: Homo sapiens

<400> SEQUENCE: 988

Ser Val Gln Asn Asp Ser Gln Ala Ile Ala Glu Val Leu Asn Gln Leu
1               5                   10                  15

Lys

<210> SEQ ID NO 989
<211> LENGTH: 14
<212> TYPE: PRT
<213> ORGANISM: Homo sapiens

<400> SEQUENCE: 989

Ala Leu Pro Gly Glu Gln Gln Pro Leu His Ala Leu Thr Arg
1               5                   10

<210> SEQ ID NO 990
<211> LENGTH: 18
<212> TYPE: PRT
<213> ORGANISM: Homo sapiens

<400> SEQUENCE: 990

Gly Thr Tyr Leu Tyr Asn Asp Cys Pro Gly Pro Gly Gln Asp Thr Asp
1               5                   10                  15

Cys Arg

<210> SEQ ID NO 991
<211> LENGTH: 19
<212> TYPE: PRT
<213> ORGANISM: Homo sapiens

<400> SEQUENCE: 991

Asn Asn Gln Leu Val Ala Gly Tyr Leu Gln Gly Pro Asn Val Asn Leu
1               5                   10                  15

Glu Glu Lys

<210> SEQ ID NO 992
<211> LENGTH: 8
<212> TYPE: PRT
<213> ORGANISM: Homo sapiens

<400> SEQUENCE: 992

Phe Gly Ser Asp Asp Glu Gly Arg
1               5

<210> SEQ ID NO 993
<211> LENGTH: 13
<212> TYPE: PRT
<213> ORGANISM: Homo sapiens

<400> SEQUENCE: 993

Phe Ala Thr Thr Phe Tyr Gln His Leu Ala Asp Ser Lys
1               5                   10

<210> SEQ ID NO 994
<211> LENGTH: 10
<212> TYPE: PRT
<213> ORGANISM: Homo sapiens

<400> SEQUENCE: 994

Glu Thr Leu Ala Leu Leu Ser Thr His Arg
1               5                   10

<210> SEQ ID NO 995
<211> LENGTH: 6
<212> TYPE: PRT
<213> ORGANISM: Homo sapiens

<400> SEQUENCE: 995

Thr Tyr Asn Val Asp Lys
1               5

<210> SEQ ID NO 996
<211> LENGTH: 8
<212> TYPE: PRT
<213> ORGANISM: Homo sapiens

<400> SEQUENCE: 996

Leu Phe Ile Pro Gln Ile Thr Arg
1               5

<210> SEQ ID NO 997
<211> LENGTH: 19
<212> TYPE: PRT
<213> ORGANISM: Homo sapiens

<400> SEQUENCE: 997

Asn Ala Val Val Gln Gly Leu Glu Gln Pro His Gly Leu Val Val His
1               5                   10                  15

Pro Leu Arg

<210> SEQ ID NO 998
<211> LENGTH: 10
<212> TYPE: PRT
<213> ORGANISM: Homo sapiens

<400> SEQUENCE: 998

Ala Gly Phe Ala Gly Asp Asp Ala Pro Arg
1               5                   10

<210> SEQ ID NO 999
<211> LENGTH: 9
<212> TYPE: PRT
<213> ORGANISM: Homo sapiens

<400> SEQUENCE: 999

Val Ile Ala Val Asn Glu Val Gly Arg
1               5

<210> SEQ ID NO 1000
<211> LENGTH: 10
<212> TYPE: PRT
<213> ORGANISM: Homo sapiens

<400> SEQUENCE: 1000

Ser Leu Ser Gln Gln Ile Glu Asn Ile Arg
1               5                   10

<210> SEQ ID NO 1001
<211> LENGTH: 7
<212> TYPE: PRT
<213> ORGANISM: Homo sapiens

<400> SEQUENCE: 1001

Ser Val Asp Glu Ala Leu Arg
1               5

<210> SEQ ID NO 1002
<211> LENGTH: 12
<212> TYPE: PRT
<213> ORGANISM: Homo sapiens

<400> SEQUENCE: 1002

Phe Val Phe Gly Thr Thr Pro Glu Asp Ile Leu Arg
1               5                   10

<210> SEQ ID NO 1003
<211> LENGTH: 10
<212> TYPE: PRT
<213> ORGANISM: Homo sapiens

<400> SEQUENCE: 1003

Thr Gly Tyr Tyr Phe Asp Gly Ile Ser Arg
1               5                   10

<210> SEQ ID NO 1004
<211> LENGTH: 9
<212> TYPE: PRT
<213> ORGANISM: Homo sapiens

<400> SEQUENCE: 1004

Ile Gly Lys Pro Ala Pro Asp Phe Lys
1               5

<210> SEQ ID NO 1005
<211> LENGTH: 7
<212> TYPE: PRT
<213> ORGANISM: Homo sapiens

<400> SEQUENCE: 1005

Phe Ile Val Gly Phe Thr Arg
1               5

<210> SEQ ID NO 1006
<211> LENGTH: 14
<212> TYPE: PRT
<213> ORGANISM: Homo sapiens

<400> SEQUENCE: 1006

Asp Ser Pro Val Leu Ile Asp Phe Phe Glu Asp Thr Glu Arg
1               5                   10

<210> SEQ ID NO 1007
<211> LENGTH: 13
<212> TYPE: PRT
<213> ORGANISM: Homo sapiens

<400> SEQUENCE: 1007

Val Ala Pro Gly Val Ala Asn Pro Gly Thr Pro Leu Ala
1               5                   10

```
<210> SEQ ID NO 1008
<211> LENGTH: 16
<212> TYPE: PRT
<213> ORGANISM: Homo sapiens

<400> SEQUENCE: 1008

Asn Tyr Phe Thr Ser Val Ala His Pro Asn Leu Phe Ile Ala Thr Lys
1               5                   10                  15

<210> SEQ ID NO 1009
<211> LENGTH: 9
<212> TYPE: PRT
<213> ORGANISM: Homo sapiens

<400> SEQUENCE: 1009

Asp Thr Tyr Val Ser Ser Phe Pro Arg
1               5

<210> SEQ ID NO 1010
<211> LENGTH: 9
<212> TYPE: PRT
<213> ORGANISM: Homo sapiens

<400> SEQUENCE: 1010

His Ser His Glu Ser Gln Asp Leu Arg
1               5

<210> SEQ ID NO 1011
<211> LENGTH: 16
<212> TYPE: PRT
<213> ORGANISM: Homo sapiens

<400> SEQUENCE: 1011

Val Ser Phe Ser Ser Pro Leu Val Ala Ile Ser Gly Val Ala Leu Arg
1               5                   10                  15

<210> SEQ ID NO 1012
<211> LENGTH: 7
<212> TYPE: PRT
<213> ORGANISM: Homo sapiens

<400> SEQUENCE: 1012

Trp Gly Ala Ala Pro Tyr Arg
1               5

<210> SEQ ID NO 1013
<211> LENGTH: 14
<212> TYPE: PRT
<213> ORGANISM: Homo sapiens

<400> SEQUENCE: 1013

Ala Leu Phe Leu Asp Ala Leu Gly Pro Pro Ala Val Thr Arg
1               5                   10

<210> SEQ ID NO 1014
<211> LENGTH: 9
<212> TYPE: PRT
<213> ORGANISM: Homo sapiens

<400> SEQUENCE: 1014

Ala Lys Pro Ala Leu Glu Asp Leu Arg
1               5

<210> SEQ ID NO 1015
<211> LENGTH: 8
```

```
<212> TYPE: PRT
<213> ORGANISM: Homo sapiens

<400> SEQUENCE: 1015

Val Asn Phe Thr Glu Ile Gln Lys
1               5

<210> SEQ ID NO 1016
<211> LENGTH: 17
<212> TYPE: PRT
<213> ORGANISM: Homo sapiens

<400> SEQUENCE: 1016

Gly Val Thr Ser Val Ser Gln Ile Phe His Ser Pro Asp Leu Ala Ile
1               5                   10                  15

Arg

<210> SEQ ID NO 1017
<211> LENGTH: 10
<212> TYPE: PRT
<213> ORGANISM: Homo sapiens

<400> SEQUENCE: 1017

Leu Leu Asp Ser Leu Pro Ser Asp Thr Arg
1               5                   10

<210> SEQ ID NO 1018
<211> LENGTH: 10
<212> TYPE: PRT
<213> ORGANISM: Homo sapiens

<400> SEQUENCE: 1018

Phe Gln Pro Thr Leu Leu Thr Leu Pro Arg
1               5                   10

<210> SEQ ID NO 1019
<211> LENGTH: 8
<212> TYPE: PRT
<213> ORGANISM: Homo sapiens

<400> SEQUENCE: 1019

Thr Leu Tyr Ser Ser Ser Pro Arg
1               5

<210> SEQ ID NO 1020
<211> LENGTH: 15
<212> TYPE: PRT
<213> ORGANISM: Homo sapiens

<400> SEQUENCE: 1020

Gly Asp Ser Gly Gly Ala Phe Ala Val Gln Asp Pro Asn Asp Lys
1               5                   10                  15

<210> SEQ ID NO 1021
<211> LENGTH: 6
<212> TYPE: PRT
<213> ORGANISM: Homo sapiens

<400> SEQUENCE: 1021

Leu Gln Val Leu Gly Lys
1               5

<210> SEQ ID NO 1022
<211> LENGTH: 9
```

<212> TYPE: PRT
<213> ORGANISM: Homo sapiens

<400> SEQUENCE: 1022

Leu Phe Ile Pro Gln Ile Thr Pro Lys
1               5

<210> SEQ ID NO 1023
<211> LENGTH: 13
<212> TYPE: PRT
<213> ORGANISM: Homo sapiens

<400> SEQUENCE: 1023

Ile Arg Pro His Thr Phe Thr Gly Leu Ser Gly Leu Arg
1               5                   10

<210> SEQ ID NO 1024
<211> LENGTH: 11
<212> TYPE: PRT
<213> ORGANISM: Homo sapiens

<400> SEQUENCE: 1024

Leu Ser Asn Glu Asn His Gly Ile Ala Gln Arg
1               5                   10

<210> SEQ ID NO 1025
<211> LENGTH: 9
<212> TYPE: PRT
<213> ORGANISM: Homo sapiens

<400> SEQUENCE: 1025

Leu His Lys Pro Gly Val Tyr Thr Arg
1               5

<210> SEQ ID NO 1026
<211> LENGTH: 17
<212> TYPE: PRT
<213> ORGANISM: Homo sapiens

<400> SEQUENCE: 1026

Thr Thr Ile Glu Lys Pro Val Trp Leu Gly Phe Leu Gly Pro Ile Ile
1               5                   10                  15

Lys

<210> SEQ ID NO 1027
<211> LENGTH: 10
<212> TYPE: PRT
<213> ORGANISM: Homo sapiens

<400> SEQUENCE: 1027

Thr Gln Ile Asp Ser Pro Leu Ser Gly Lys
1               5                   10

<210> SEQ ID NO 1028
<211> LENGTH: 11
<212> TYPE: PRT
<213> ORGANISM: Homo sapiens

<400> SEQUENCE: 1028

Ala Thr Trp Ser Gly Ala Val Leu Ala Gly Arg
1               5                   10

<210> SEQ ID NO 1029
<211> LENGTH: 18

```
<212> TYPE: PRT
<213> ORGANISM: Homo sapiens

<400> SEQUENCE: 1029

Val Ala Pro Glu Glu His Pro Val Leu Leu Thr Glu Ala Pro Leu Asn
1               5                   10                  15

Pro Lys

<210> SEQ ID NO 1030
<211> LENGTH: 13
<212> TYPE: PRT
<213> ORGANISM: Homo sapiens

<400> SEQUENCE: 1030

Cys Gln Cys Leu Gln Thr Leu Gln Gly Ile His Leu Lys
1               5                   10

<210> SEQ ID NO 1031
<211> LENGTH: 10
<212> TYPE: PRT
<213> ORGANISM: Homo sapiens

<400> SEQUENCE: 1031

Leu Leu Asp Phe Glu Phe Ser Ser Gly Arg
1               5                   10

<210> SEQ ID NO 1032
<211> LENGTH: 14
<212> TYPE: PRT
<213> ORGANISM: Homo sapiens

<400> SEQUENCE: 1032

Ile Leu Asn Thr Pro Asn Cys Ala Leu Gln Ile Val Ala Arg
1               5                   10

<210> SEQ ID NO 1033
<211> LENGTH: 8
<212> TYPE: PRT
<213> ORGANISM: Homo sapiens

<400> SEQUENCE: 1033

Gly Leu Phe Ile Ile Asp Gly Lys
1               5

<210> SEQ ID NO 1034
<211> LENGTH: 9
<212> TYPE: PRT
<213> ORGANISM: Homo sapiens

<400> SEQUENCE: 1034

Glu His Ser Ser Leu Ala Phe Trp Lys
1               5

<210> SEQ ID NO 1035
<211> LENGTH: 8
<212> TYPE: PRT
<213> ORGANISM: Homo sapiens

<400> SEQUENCE: 1035

Thr Phe Thr Leu Leu Asp Pro Lys
1               5

<210> SEQ ID NO 1036
<211> LENGTH: 13
```

<212> TYPE: PRT
<213> ORGANISM: Homo sapiens

<400> SEQUENCE: 1036

Ala His Gln Leu Ala Ile Asp Thr Tyr Gln Glu Phe Arg
1               5                   10

<210> SEQ ID NO 1037
<211> LENGTH: 11
<212> TYPE: PRT
<213> ORGANISM: Homo sapiens

<400> SEQUENCE: 1037

Ala Gln Glu Thr Ser Gly Glu Glu Ile Ser Lys
1               5                   10

<210> SEQ ID NO 1038
<211> LENGTH: 10
<212> TYPE: PRT
<213> ORGANISM: Homo sapiens

<400> SEQUENCE: 1038

Leu Ser Ile Thr Gly Thr Tyr Asp Leu Lys
1               5                   10

<210> SEQ ID NO 1039
<211> LENGTH: 11
<212> TYPE: PRT
<213> ORGANISM: Homo sapiens

<400> SEQUENCE: 1039

Glu Ala Leu Val Pro Leu Val Ala Asp His Lys
1               5                   10

<210> SEQ ID NO 1040
<211> LENGTH: 12
<212> TYPE: PRT
<213> ORGANISM: Homo sapiens

<400> SEQUENCE: 1040

Cys Arg Pro Ile Asn Ala Thr Leu Ala Val Glu Lys
1               5                   10

<210> SEQ ID NO 1041
<211> LENGTH: 12
<212> TYPE: PRT
<213> ORGANISM: Homo sapiens

<400> SEQUENCE: 1041

Leu Thr Leu Leu Ala Pro Leu Asn Ser Val Phe Lys
1               5                   10

<210> SEQ ID NO 1042
<211> LENGTH: 16
<212> TYPE: PRT
<213> ORGANISM: Homo sapiens

<400> SEQUENCE: 1042

Ala Asp Leu Phe Tyr Asp Val Glu Ala Leu Asp Leu Glu Ser Pro Lys
1               5                   10                  15

<210> SEQ ID NO 1043
<211> LENGTH: 10
<212> TYPE: PRT
<213> ORGANISM: Homo sapiens

<400> SEQUENCE: 1043

Arg Ile Pro Leu Asp Leu Val Pro Lys Thr
1               5                   10

<210> SEQ ID NO 1044
<211> LENGTH: 20
<212> TYPE: PRT
<213> ORGANISM: Homo sapiens

<400> SEQUENCE: 1044

Lys Glu Asn Pro Ala Val Ile Asp Phe Glu Leu Ala Pro Ile Val Asp
1               5                   10                  15

Leu Val Arg Asn
            20

<210> SEQ ID NO 1045
<211> LENGTH: 20
<212> TYPE: PRT
<213> ORGANISM: Homo sapiens

<400> SEQUENCE: 1045

Lys Tyr Asn Pro Val Val Ile Asp Phe Glu Met Gln Pro Ile His Glu
1               5                   10                  15

Val Leu Arg His
            20

<210> SEQ ID NO 1046
<211> LENGTH: 13
<212> TYPE: PRT
<213> ORGANISM: Homo sapiens

<400> SEQUENCE: 1046

Arg Gly Asp Ser Gly Gly Pro Leu Ile Val His Lys Arg
1               5                   10

<210> SEQ ID NO 1047
<211> LENGTH: 33
<212> TYPE: PRT
<213> ORGANISM: Homo sapiens

<400> SEQUENCE: 1047

Arg Val Leu Lys Asp Gln Val Asn Thr Phe Asp Asn Ile Phe Ile Ala
1               5                   10                  15

Pro Val Gly Ile Ser Thr Ala Met Gly Met Ile Ser Leu Gly Leu Lys
            20                  25                  30

Gly

<210> SEQ ID NO 1048
<211> LENGTH: 17
<212> TYPE: PRT
<213> ORGANISM: Homo sapiens

<400> SEQUENCE: 1048

Lys Pro Leu Leu Asn Asp Ser Arg Met Leu Leu Ser Pro Asp Gln Lys
1               5                   10                  15

Val

<210> SEQ ID NO 1049
<211> LENGTH: 15
<212> TYPE: PRT
<213> ORGANISM: Homo sapiens

<400> SEQUENCE: 1049

Lys Glu Asp Phe Thr Ser Leu Ser Leu Val Leu Tyr Ser Arg Lys
1               5                   10                  15

<210> SEQ ID NO 1050
<211> LENGTH: 14
<212> TYPE: PRT
<213> ORGANISM: Homo sapiens

<400> SEQUENCE: 1050

Trp Asn Phe Ala Tyr Trp Ala Ala His Gln Pro Trp Ser Arg
1               5                   10

<210> SEQ ID NO 1051
<211> LENGTH: 11
<212> TYPE: PRT
<213> ORGANISM: Homo sapiens

<400> SEQUENCE: 1051

Ser Glu Tyr Gly Ala Ala Leu Ala Trp Glu Lys
1               5                   10

<210> SEQ ID NO 1052
<211> LENGTH: 13
<212> TYPE: PRT
<213> ORGANISM: Homo sapiens

<400> SEQUENCE: 1052

Leu Trp Ala Tyr Leu Thr Ile Gln Glu Leu Leu Ala Lys
1               5                   10

<210> SEQ ID NO 1053
<211> LENGTH: 8
<212> TYPE: PRT
<213> ORGANISM: Homo sapiens

<400> SEQUENCE: 1053

Leu Leu Glu Val Pro Glu Gly Arg
1               5

<210> SEQ ID NO 1054
<211> LENGTH: 10
<212> TYPE: PRT
<213> ORGANISM: Homo sapiens

<400> SEQUENCE: 1054

Leu Thr Thr Val Asp Ile Val Thr Leu Arg
1               5                   10

<210> SEQ ID NO 1055
<211> LENGTH: 6
<212> TYPE: PRT
<213> ORGANISM: Homo sapiens

<400> SEQUENCE: 1055

Thr Leu Ala Phe Val Arg
1               5

<210> SEQ ID NO 1056
<211> LENGTH: 9
<212> TYPE: PRT
<213> ORGANISM: Homo sapiens

<400> SEQUENCE: 1056

-continued

```
Asn Ser Asp Gln Glu Ile Asp Phe Lys
1               5

<210> SEQ ID NO 1057
<211> LENGTH: 25
<212> TYPE: PRT
<213> ORGANISM: Homo sapiens

<400> SEQUENCE: 1057

Tyr His Phe Glu Ala Leu Ala Asp Thr Gly Ile Ser Ser Glu Phe Tyr
1               5                   10                  15

Asp Asn Ala Asn Asp Leu Leu Ser Lys
            20                  25

<210> SEQ ID NO 1058
<211> LENGTH: 20
<212> TYPE: PRT
<213> ORGANISM: Homo sapiens

<400> SEQUENCE: 1058

Ile Leu Leu Leu Gly Thr Ala Val Glu Ser Ala Trp Gly Asp Glu Gln
1               5                   10                  15

Ser Ala Phe Arg
            20

<210> SEQ ID NO 1059
<211> LENGTH: 6
<212> TYPE: PRT
<213> ORGANISM: Homo sapiens

<400> SEQUENCE: 1059

Tyr Asn Gln Leu Leu Arg
1               5

<210> SEQ ID NO 1060
<211> LENGTH: 14
<212> TYPE: PRT
<213> ORGANISM: Homo sapiens

<400> SEQUENCE: 1060

Val Pro Gly Leu Tyr Tyr Phe Thr Tyr His Ala Ser Ser Arg
1               5                   10

<210> SEQ ID NO 1061
<211> LENGTH: 8
<212> TYPE: PRT
<213> ORGANISM: Homo sapiens

<400> SEQUENCE: 1061

Tyr Gly Ile Glu Glu His Gly Lys
1               5

<210> SEQ ID NO 1062
<211> LENGTH: 13
<212> TYPE: PRT
<213> ORGANISM: Homo sapiens

<400> SEQUENCE: 1062

Gln Val Cys Ala Asp Pro Ser Glu Glu Trp Val Gln Lys
1               5                   10

<210> SEQ ID NO 1063
<211> LENGTH: 11
```

-continued

```
<212> TYPE: PRT
<213> ORGANISM: Homo sapiens

<400> SEQUENCE: 1063

Asp Pro Asn Gly Leu Pro Pro Glu Ala Gln Lys
1               5                   10

<210> SEQ ID NO 1064
<211> LENGTH: 8
<212> TYPE: PRT
<213> ORGANISM: Homo sapiens

<400> SEQUENCE: 1064

Glu Thr Leu Leu Gln Asp Phe Arg
1               5

<210> SEQ ID NO 1065
<211> LENGTH: 16
<212> TYPE: PRT
<213> ORGANISM: Homo sapiens

<400> SEQUENCE: 1065

Ile Ile Glu Val Glu Glu Glu Gln Glu Asp Pro Tyr Leu Asn Asp Arg
1               5                   10                  15

<210> SEQ ID NO 1066
<211> LENGTH: 7
<212> TYPE: PRT
<213> ORGANISM: Homo sapiens

<400> SEQUENCE: 1066

Glu Leu Cys Leu Asp Pro Lys
1               5

<210> SEQ ID NO 1067
<211> LENGTH: 11
<212> TYPE: PRT
<213> ORGANISM: Homo sapiens

<400> SEQUENCE: 1067

Asn Gln Ser Pro Val Leu Glu Pro Val Gly Arg
1               5                   10

<210> SEQ ID NO 1068
<211> LENGTH: 8
<212> TYPE: PRT
<213> ORGANISM: Homo sapiens

<400> SEQUENCE: 1068

Phe Phe Gln Tyr Asp Thr Trp Lys
1               5

<210> SEQ ID NO 1069
<211> LENGTH: 13
<212> TYPE: PRT
<213> ORGANISM: Homo sapiens

<400> SEQUENCE: 1069

Ser Leu Gln Asn Ala Ser Ala Ile Glu Ser Ile Leu Lys
1               5                   10

<210> SEQ ID NO 1070
<211> LENGTH: 11
<212> TYPE: PRT
<213> ORGANISM: Homo sapiens
```

<400> SEQUENCE: 1070

Leu Val Ile Phe Asp Thr Met Leu Glu Ile Lys
1               5                   10

<210> SEQ ID NO 1071
<211> LENGTH: 28
<212> TYPE: PRT
<213> ORGANISM: Homo sapiens

<400> SEQUENCE: 1071

Phe Ile Glu Asp Asn Ile Glu Tyr Ile Thr Ile Ile Ala Phe Ala Gln
1               5                   10                  15

Tyr Val Gln Glu Ala Thr Phe Glu Glu Met Glu Lys
            20                  25

<210> SEQ ID NO 1072
<211> LENGTH: 23
<212> TYPE: PRT
<213> ORGANISM: Homo sapiens

<400> SEQUENCE: 1072

Leu Lys His Glu Leu Thr Asp Glu Glu Leu Gln Ser Leu Phe Thr Asn
1               5                   10                  15

Phe Ala Asn Val Val Asp Lys
            20

<210> SEQ ID NO 1073
<211> LENGTH: 17
<212> TYPE: PRT
<213> ORGANISM: Homo sapiens

<400> SEQUENCE: 1073

Ser Asp Val Gly Phe Leu Pro Pro Phe Pro Thr Leu Asp Pro Glu Glu
1               5                   10                  15

Lys

<210> SEQ ID NO 1074
<211> LENGTH: 8
<212> TYPE: PRT
<213> ORGANISM: Homo sapiens

<400> SEQUENCE: 1074

Val Met Asn His Ile Cys Ser Lys
1               5

<210> SEQ ID NO 1075
<211> LENGTH: 13
<212> TYPE: PRT
<213> ORGANISM: Homo sapiens

<400> SEQUENCE: 1075

Glu Ser Leu Leu Asn His Phe Leu Tyr Glu Val Ala Arg
1               5                   10

<210> SEQ ID NO 1076
<211> LENGTH: 8
<212> TYPE: PRT
<213> ORGANISM: Homo sapiens

<400> SEQUENCE: 1076

Leu Cys Phe Phe Tyr Asn Lys Lys
1               5

```
<210> SEQ ID NO 1077
<211> LENGTH: 19
<212> TYPE: PRT
<213> ORGANISM: Homo sapiens

<400> SEQUENCE: 1077

Ala Val Leu Asp Val Phe Glu Glu Gly Thr Glu Ala Ser Ala Ala Thr
1               5                   10                  15

Ala Val Lys

<210> SEQ ID NO 1078
<211> LENGTH: 8
<212> TYPE: PRT
<213> ORGANISM: Homo sapiens

<400> SEQUENCE: 1078

Glu Gln Leu Ser Leu Leu Asp Arg
1               5

<210> SEQ ID NO 1079
<211> LENGTH: 14
<212> TYPE: PRT
<213> ORGANISM: Homo sapiens

<400> SEQUENCE: 1079

Glu Gln Leu Ser Leu Leu Asp Arg Phe Thr Glu Asp Ala Lys
1               5                   10

<210> SEQ ID NO 1080
<211> LENGTH: 15
<212> TYPE: PRT
<213> ORGANISM: Homo sapiens

<400> SEQUENCE: 1080

Glu Gln Leu Ser Leu Leu Asp Arg Phe Thr Glu Asp Ala Lys Arg
1               5                   10                  15

<210> SEQ ID NO 1081
<211> LENGTH: 23
<212> TYPE: PRT
<213> ORGANISM: Homo sapiens

<400> SEQUENCE: 1081

Ile Thr Asp Leu Ile Lys Asp Leu Asp Ser Gln Thr Met Met Val Leu
1               5                   10                  15

Val Asn Tyr Ile Phe Phe Lys
            20

<210> SEQ ID NO 1082
<211> LENGTH: 11
<212> TYPE: PRT
<213> ORGANISM: Homo sapiens

<400> SEQUENCE: 1082

Ile Thr Leu Leu Ser Ala Leu Val Glu Thr Arg
1               5                   10

<210> SEQ ID NO 1083
<211> LENGTH: 19
<212> TYPE: PRT
<213> ORGANISM: Homo sapiens

<400> SEQUENCE: 1083
```

-continued

```
Arg Leu Tyr Gly Ser Glu Ala Phe Ala Thr Asp Phe Gln Asp Ser Ala
1               5                   10                  15

Ala Ala Lys

<210> SEQ ID NO 1084
<211> LENGTH: 14
<212> TYPE: PRT
<213> ORGANISM: Homo sapiens

<400> SEQUENCE: 1084

Cys Glu Gly Pro Ile Pro Asp Val Thr Phe Glu Leu Leu Arg
1               5                   10

<210> SEQ ID NO 1085
<211> LENGTH: 5
<212> TYPE: PRT
<213> ORGANISM: Homo sapiens

<400> SEQUENCE: 1085

Phe Ala Leu Val Arg
1               5

<210> SEQ ID NO 1086
<211> LENGTH: 8
<212> TYPE: PRT
<213> ORGANISM: Homo sapiens

<400> SEQUENCE: 1086

Ser Pro Pro Gly Val Cys Ser Arg
1               5

<210> SEQ ID NO 1087
<211> LENGTH: 19
<212> TYPE: PRT
<213> ORGANISM: Homo sapiens

<400> SEQUENCE: 1087

Asp Ser Phe His Leu Asp Glu Gln Phe Thr Val Pro Val Glu Met Met
1               5                   10                  15

Gln Ala Arg

<210> SEQ ID NO 1088
<211> LENGTH: 7
<212> TYPE: PRT
<213> ORGANISM: Homo sapiens

<400> SEQUENCE: 1088

Cys Asn Leu Leu Ala Glu Lys
1               5

<210> SEQ ID NO 1089
<211> LENGTH: 14
<212> TYPE: PRT
<213> ORGANISM: Homo sapiens

<400> SEQUENCE: 1089

Glu His Ala Val Glu Gly Asp Cys Asp Phe Gln Leu Leu Lys
1               5                   10

<210> SEQ ID NO 1090
<211> LENGTH: 42
<212> TYPE: PRT
<213> ORGANISM: Homo sapiens
```

-continued

<400> SEQUENCE: 1090

His Thr Leu Asn Gln Ile Asp Glu Val Lys Val Trp Pro Gln Gln Pro
1               5                   10                  15

Ser Gly Glu Leu Phe Glu Ile Glu Ile Asp Thr Leu Glu Thr Thr Cys
            20                  25                  30

His Val Leu Asp Pro Thr Pro Val Ala Arg
        35                  40

<210> SEQ ID NO 1091
<211> LENGTH: 13
<212> TYPE: PRT
<213> ORGANISM: Homo sapiens

<400> SEQUENCE: 1091

Met Val Ser Gly Phe Ile Pro Leu Lys Pro Thr Val Lys
1               5                   10

<210> SEQ ID NO 1092
<211> LENGTH: 17
<212> TYPE: PRT
<213> ORGANISM: Homo sapiens

<400> SEQUENCE: 1092

Ala Phe Gln Pro Phe Phe Val Glu Leu Thr Met Pro Tyr Ser Val Ile
1               5                   10                  15

Arg

<210> SEQ ID NO 1093
<211> LENGTH: 13
<212> TYPE: PRT
<213> ORGANISM: Homo sapiens

<400> SEQUENCE: 1093

Asn Gln Gly Asn Thr Trp Leu Thr Ala Phe Val Leu Lys
1               5                   10

<210> SEQ ID NO 1094
<211> LENGTH: 12
<212> TYPE: PRT
<213> ORGANISM: Homo sapiens

<400> SEQUENCE: 1094

Ile Asp Arg Phe Met Gln Ala Val Thr Gly Trp Lys
1               5                   10

<210> SEQ ID NO 1095
<211> LENGTH: 8
<212> TYPE: PRT
<213> ORGANISM: Homo sapiens

<400> SEQUENCE: 1095

Leu Asp Thr Glu Asp Lys Leu Arg
1               5

<210> SEQ ID NO 1096
<211> LENGTH: 25
<212> TYPE: PRT
<213> ORGANISM: Homo sapiens

<400> SEQUENCE: 1096

Thr Gly Cys Ser Leu Met Gly Ala Ser Val Asp Ser Thr Leu Ala Phe
1               5                   10                  15

Asn Thr Tyr Val His Phe Gln Gly Lys
            20                      25

<210> SEQ ID NO 1097
<211> LENGTH: 14
<212> TYPE: PRT
<213> ORGANISM: Homo sapiens

<400> SEQUENCE: 1097

Ala Ala Met Val Gly Met Leu Ala Asn Phe Leu Gly Phe Arg
1               5                   10

<210> SEQ ID NO 1098
<211> LENGTH: 21
<212> TYPE: PRT
<213> ORGANISM: Homo sapiens

<400> SEQUENCE: 1098

Asn Asp Asn Asp Asn Ile Phe Leu Ser Pro Leu Ser Ile Ser Thr Ala
1               5                   10                  15

Phe Ala Met Thr Lys
            20

<210> SEQ ID NO 1099
<211> LENGTH: 22
<212> TYPE: PRT
<213> ORGANISM: Homo sapiens

<400> SEQUENCE: 1099

Ser Lys Leu Pro Gly Ile Val Ala Glu Gly Arg Asp Asp Leu Tyr Val
1               5                   10                  15

Ser Asp Ala Phe His Lys
            20

<210> SEQ ID NO 1100
<211> LENGTH: 12
<212> TYPE: PRT
<213> ORGANISM: Homo sapiens

<400> SEQUENCE: 1100

Glu Val Pro Leu Asn Thr Ile Ile Phe Met Gly Arg
1               5                   10

<210> SEQ ID NO 1101
<211> LENGTH: 34
<212> TYPE: PRT
<213> ORGANISM: Homo sapiens

<400> SEQUENCE: 1101

Phe Ala Thr Thr Phe Tyr Gln His Leu Ala Asp Ser Lys Asn Asp Asn
1               5                   10                  15

Asp Asn Ile Phe Leu Ser Pro Leu Ser Ile Ser Thr Ala Phe Ala Met
            20                  25                  30

Thr Lys

<210> SEQ ID NO 1102
<211> LENGTH: 25
<212> TYPE: PRT
<213> ORGANISM: Homo sapiens

<400> SEQUENCE: 1102

Ile Thr Asp Val Ile Pro Ser Glu Ala Ile Asn Glu Leu Thr Val Leu

-continued

```
1               5               10              15

Val Leu Val Asn Thr Ile Tyr Phe Lys
            20              25

<210> SEQ ID NO 1103
<211> LENGTH: 7
<212> TYPE: PRT
<213> ORGANISM: Homo sapiens

<400> SEQUENCE: 1103

Arg Val Trp Glu Leu Ser Lys
1               5

<210> SEQ ID NO 1104
<211> LENGTH: 28
<212> TYPE: PRT
<213> ORGANISM: Homo sapiens

<400> SEQUENCE: 1104

Val Ala Glu Gly Thr Gln Val Leu Glu Leu Pro Phe Lys Gly Asp Asp
1               5               10              15

Ile Thr Met Val Leu Ile Leu Pro Lys Pro Glu Lys
            20              25

<210> SEQ ID NO 1105
<211> LENGTH: 22
<212> TYPE: PRT
<213> ORGANISM: Homo sapiens

<400> SEQUENCE: 1105

Ala Gly Thr Glu Leu Val Asn Phe Leu Ser Tyr Phe Val Glu Leu Gly
1               5               10              15

Thr Gln Pro Ala Thr Gln
            20

<210> SEQ ID NO 1106
<211> LENGTH: 20
<212> TYPE: PRT
<213> ORGANISM: Homo sapiens

<400> SEQUENCE: 1106

Glu Pro Cys Val Glu Ser Leu Val Ser Gln Tyr Phe Gln Thr Val Thr
1               5               10              15

Asp Tyr Gly Lys
            20

<210> SEQ ID NO 1107
<211> LENGTH: 10
<212> TYPE: PRT
<213> ORGANISM: Homo sapiens

<400> SEQUENCE: 1107

Ala Leu Val Gln Gln Met Glu Gln Leu Arg
1               5               10

<210> SEQ ID NO 1108
<211> LENGTH: 17
<212> TYPE: PRT
<213> ORGANISM: Homo sapiens

<400> SEQUENCE: 1108

Leu Gly Pro His Ala Gly Asp Val Glu Gly His Leu Ser Phe Leu Glu
1               5               10              15
```

-continued

Lys

<210> SEQ ID NO 1109
<211> LENGTH: 14
<212> TYPE: PRT
<213> ORGANISM: Homo sapiens

<400> SEQUENCE: 1109

Ser Glu Leu Thr Gln Gln Leu Asn Ala Leu Phe Gln Asp Lys
1               5                   10

<210> SEQ ID NO 1110
<211> LENGTH: 18
<212> TYPE: PRT
<213> ORGANISM: Homo sapiens

<400> SEQUENCE: 1110

Ser Leu Ala Glu Leu Gly Gly His Leu Asp Gln Gln Val Glu Glu Phe
1               5                   10                  15

Arg Arg

<210> SEQ ID NO 1111
<211> LENGTH: 12
<212> TYPE: PRT
<213> ORGANISM: Homo sapiens

<400> SEQUENCE: 1111

Val Lys Ile Asp Gln Thr Val Glu Glu Leu Arg Arg
1               5                   10

<210> SEQ ID NO 1112
<211> LENGTH: 9
<212> TYPE: PRT
<213> ORGANISM: Homo sapiens

<400> SEQUENCE: 1112

Val Asn Ser Phe Phe Ser Thr Phe Lys
1               5

<210> SEQ ID NO 1113
<211> LENGTH: 16
<212> TYPE: PRT
<213> ORGANISM: Homo sapiens

<400> SEQUENCE: 1113

Ala Thr Phe Gln Thr Pro Asp Phe Ile Val Pro Leu Thr Asp Leu Arg
1               5                   10                  15

<210> SEQ ID NO 1114
<211> LENGTH: 15
<212> TYPE: PRT
<213> ORGANISM: Homo sapiens

<400> SEQUENCE: 1114

Ala Val Ser Met Pro Ser Phe Ser Ile Leu Gly Ser Asp Val Arg
1               5                   10                  15

<210> SEQ ID NO 1115
<211> LENGTH: 11
<212> TYPE: PRT
<213> ORGANISM: Homo sapiens

<400> SEQUENCE: 1115

-continued

```
Glu Gln His Leu Phe Leu Pro Phe Ser Tyr Lys
1               5                   10
```

<210> SEQ ID NO 1116
<211> LENGTH: 11
<212> TYPE: PRT
<213> ORGANISM: Homo sapiens

<400> SEQUENCE: 1116

```
Lys Ile Ile Ser Asp Tyr His Gln Gln Phe Arg
1               5                   10
```

<210> SEQ ID NO 1117
<211> LENGTH: 18
<212> TYPE: PRT
<213> ORGANISM: Homo sapiens

<400> SEQUENCE: 1117

```
Gln Val Phe Leu Tyr Pro Glu Lys Asp Glu Pro Thr Tyr Ile Leu Asn
1               5                   10                  15

Ile Lys
```

<210> SEQ ID NO 1118
<211> LENGTH: 10
<212> TYPE: PRT
<213> ORGANISM: Homo sapiens

<400> SEQUENCE: 1118

```
Ser Pro Ala Phe Thr Asp Leu His Leu Arg
1               5                   10
```

<210> SEQ ID NO 1119
<211> LENGTH: 18
<212> TYPE: PRT
<213> ORGANISM: Homo sapiens

<400> SEQUENCE: 1119

```
Thr Ile Leu Gly Thr Met Pro Ala Phe Glu Val Ser Leu Gln Ala Leu
1               5                   10                  15

Gln Lys
```

<210> SEQ ID NO 1120
<211> LENGTH: 12
<212> TYPE: PRT
<213> ORGANISM: Homo sapiens

<400> SEQUENCE: 1120

```
Val Leu Ala Asp Lys Phe Ile Ile Pro Gly Leu Lys
1               5                   10
```

<210> SEQ ID NO 1121
<211> LENGTH: 30
<212> TYPE: PRT
<213> ORGANISM: Homo sapiens

<400> SEQUENCE: 1121

```
Tyr Ser Gln Pro Glu Asp Ser Leu Ile Pro Phe Phe Glu Ile Thr Val
1               5                   10                  15

Pro Glu Ser Gln Leu Thr Val Ser Gln Phe Thr Leu Pro Lys
            20                  25                  30
```

<210> SEQ ID NO 1122
<211> LENGTH: 11

<212> TYPE: PRT
<213> ORGANISM: Homo sapiens

<400> SEQUENCE: 1122

Asp Leu Lys Val Glu Asp Ile Pro Leu Ala Arg
1               5                   10

<210> SEQ ID NO 1123
<211> LENGTH: 16
<212> TYPE: PRT
<213> ORGANISM: Homo sapiens

<400> SEQUENCE: 1123

Gly Ile Ile Ser Ala Leu Leu Val Pro Pro Glu Thr Glu Glu Ala Lys
1               5                   10                  15

<210> SEQ ID NO 1124
<211> LENGTH: 19
<212> TYPE: PRT
<213> ORGANISM: Homo sapiens

<400> SEQUENCE: 1124

Ile Leu Gly Glu Glu Leu Gly Phe Ala Ser Leu His Asp Leu Gln Leu
1               5                   10                  15

Leu Gly Lys

<210> SEQ ID NO 1125
<211> LENGTH: 24
<212> TYPE: PRT
<213> ORGANISM: Homo sapiens

<400> SEQUENCE: 1125

Leu Glu Leu Glu Leu Arg Pro Thr Gly Glu Ile Glu Gln Tyr Ser Val
1               5                   10                  15

Ser Ala Thr Tyr Glu Leu Gln Arg
                20

<210> SEQ ID NO 1126
<211> LENGTH: 15
<212> TYPE: PRT
<213> ORGANISM: Homo sapiens

<400> SEQUENCE: 1126

Asn Ile Gln Glu Tyr Leu Ser Ile Leu Thr Asp Pro Asp Gly Lys
1               5                   10                  15

<210> SEQ ID NO 1127
<211> LENGTH: 32
<212> TYPE: PRT
<213> ORGANISM: Homo sapiens

<400> SEQUENCE: 1127

Thr Phe Gln Ile Pro Gly Tyr Thr Val Pro Val Val Asn Val Glu Val
1               5                   10                  15

Ser Pro Phe Thr Ile Glu Met Ser Ala Phe Gly Tyr Val Phe Pro Lys
                20                  25                  30

<210> SEQ ID NO 1128
<211> LENGTH: 20
<212> TYPE: PRT
<213> ORGANISM: Homo sapiens

<400> SEQUENCE: 1128

-continued

```
Thr Ile Asp Gln Met Leu Asn Ser Glu Leu Gln Trp Pro Val Pro Asp
1               5                   10                  15

Ile Tyr Leu Arg
            20

<210> SEQ ID NO 1129
<211> LENGTH: 11
<212> TYPE: PRT
<213> ORGANISM: Homo sapiens

<400> SEQUENCE: 1129

Met Arg Glu Trp Phe Ser Glu Thr Phe Gln Lys
1               5                   10

<210> SEQ ID NO 1130
<211> LENGTH: 24
<212> TYPE: PRT
<213> ORGANISM: Homo sapiens

<400> SEQUENCE: 1130

Ser Thr Ala Ala Met Ser Thr Tyr Thr Gly Ile Phe Thr Asp Gln Val
1               5                   10                  15

Leu Ser Val Leu Lys Gly Glu Glu
            20

<210> SEQ ID NO 1131
<211> LENGTH: 15
<212> TYPE: PRT
<213> ORGANISM: Homo sapiens

<400> SEQUENCE: 1131

Ala Ala Thr Val Gly Ser Leu Ala Gly Gln Pro Leu Gln Glu Arg
1               5                   10                  15

<210> SEQ ID NO 1132
<211> LENGTH: 14
<212> TYPE: PRT
<213> ORGANISM: Homo sapiens

<400> SEQUENCE: 1132

Leu Lys Ser Trp Phe Glu Pro Leu Val Glu Asp Met Gln Arg
1               5                   10

<210> SEQ ID NO 1133
<211> LENGTH: 23
<212> TYPE: PRT
<213> ORGANISM: Homo sapiens

<400> SEQUENCE: 1133

Trp Val Gln Thr Leu Ser Glu Gln Val Gln Glu Glu Leu Leu Ser Ser
1               5                   10                  15

Gln Val Thr Gln Glu Leu Arg
            20

<210> SEQ ID NO 1134
<211> LENGTH: 11
<212> TYPE: PRT
<213> ORGANISM: Homo sapiens

<400> SEQUENCE: 1134

Leu Cys Gly Gly Gly Arg Trp Glu Leu Met Arg
1               5                   10
```

<210> SEQ ID NO 1135
<211> LENGTH: 6
<212> TYPE: PRT
<213> ORGANISM: Homo sapiens

<400> SEQUENCE: 1135

Leu Pro Gly Leu Leu Lys
1               5

<210> SEQ ID NO 1136
<211> LENGTH: 17
<212> TYPE: PRT
<213> ORGANISM: Homo sapiens

<400> SEQUENCE: 1136

Thr Cys Pro Lys Pro Asp Asp Leu Pro Phe Ser Thr Val Val Pro Leu
1               5                   10                  15

Lys

<210> SEQ ID NO 1137
<211> LENGTH: 14
<212> TYPE: PRT
<213> ORGANISM: Homo sapiens

<400> SEQUENCE: 1137

Val Cys Pro Phe Ala Gly Ile Leu Glu Asn Gly Ala Val Arg
1               5                   10

<210> SEQ ID NO 1138
<211> LENGTH: 13
<212> TYPE: PRT
<213> ORGANISM: Homo sapiens

<400> SEQUENCE: 1138

Leu Phe Ala Ala Phe Phe Leu Glu Met Ala Gln Leu His
1               5                   10

<210> SEQ ID NO 1139
<211> LENGTH: 10
<212> TYPE: PRT
<213> ORGANISM: Homo sapiens

<400> SEQUENCE: 1139

Ser His Leu Ile Ile Ala Gln Val Ala Lys
1               5                   10

<210> SEQ ID NO 1140
<211> LENGTH: 12
<212> TYPE: PRT
<213> ORGANISM: Homo sapiens

<400> SEQUENCE: 1140

Asn Ala Ile Trp Ile Asp Cys Gly Ile His Ala Arg
1               5                   10

<210> SEQ ID NO 1141
<211> LENGTH: 15
<212> TYPE: PRT
<213> ORGANISM: Homo sapiens

<400> SEQUENCE: 1141

Glu Ala Leu Ile Gln Phe Leu Glu Gln Val His Gln Gly Ile Lys
1               5                   10                  15

```
<210> SEQ ID NO 1142
<211> LENGTH: 15
<212> TYPE: PRT
<213> ORGANISM: Homo sapiens

<400> SEQUENCE: 1142

Leu Leu Asn Ile Gln Thr Tyr Cys Ala Gly Pro Ala Tyr Leu Lys
1               5                   10                  15

<210> SEQ ID NO 1143
<211> LENGTH: 18
<212> TYPE: PRT
<213> ORGANISM: Homo sapiens

<400> SEQUENCE: 1143

Leu Cys Glu Asn Ile Ala Gly His Leu Lys Asp Ala Gln Ile Phe Ile
1               5                   10                  15

Gln Lys

<210> SEQ ID NO 1144
<211> LENGTH: 12
<212> TYPE: PRT
<213> ORGANISM: Homo sapiens

<400> SEQUENCE: 1144

Ala Glu Thr Gly Asp Lys Val Tyr Val His Leu Lys
1               5                   10

<210> SEQ ID NO 1145
<211> LENGTH: 14
<212> TYPE: PRT
<213> ORGANISM: Homo sapiens

<400> SEQUENCE: 1145

Ala Gly Leu Gln Ala Phe Phe Gln Val Gln Glu Cys Asn Lys
1               5                   10

<210> SEQ ID NO 1146
<211> LENGTH: 14
<212> TYPE: PRT
<213> ORGANISM: Homo sapiens

<400> SEQUENCE: 1146

Asp Ile Ala Ser Gly Leu Ile Gly Pro Leu Ile Ile Cys Lys
1               5                   10

<210> SEQ ID NO 1147
<211> LENGTH: 11
<212> TYPE: PRT
<213> ORGANISM: Homo sapiens

<400> SEQUENCE: 1147

Asp Ile Phe Thr Gly Leu Ile Gly Pro Met Lys
1               5                   10

<210> SEQ ID NO 1148
<211> LENGTH: 21
<212> TYPE: PRT
<213> ORGANISM: Homo sapiens

<400> SEQUENCE: 1148

Met Tyr Tyr Ser Ala Val Asp Pro Thr Lys Asp Ile Phe Thr Gly Leu
1               5                   10                  15

Ile Gly Pro Met Lys
```

```
              20

<210> SEQ ID NO 1149
<211> LENGTH: 12
<212> TYPE: PRT
<213> ORGANISM: Homo sapiens

<400> SEQUENCE: 1149

Pro Val Trp Leu Gly Phe Leu Gly Pro Ile Ile Lys
1               5                   10

<210> SEQ ID NO 1150
<211> LENGTH: 33
<212> TYPE: PRT
<213> ORGANISM: Homo sapiens

<400> SEQUENCE: 1150

Ala Asp Asp Lys Val Tyr Pro Gly Glu Gln Tyr Thr Tyr Met Leu Leu
1               5                   10                  15

Ala Thr Glu Glu Gln Ser Pro Gly Glu Gly Asp Gly Asn Cys Val Thr
            20                  25                  30

Arg

<210> SEQ ID NO 1151
<211> LENGTH: 38
<212> TYPE: PRT
<213> ORGANISM: Homo sapiens

<400> SEQUENCE: 1151

Asp Thr Ala Asn Leu Phe Pro Gln Thr Ser Leu Thr Leu His Met Trp
1               5                   10                  15

Pro Asp Thr Glu Gly Thr Phe Asn Val Glu Cys Leu Thr Thr Asp His
            20                  25                  30

Tyr Thr Gly Gly Met Lys
            35

<210> SEQ ID NO 1152
<211> LENGTH: 19
<212> TYPE: PRT
<213> ORGANISM: Homo sapiens

<400> SEQUENCE: 1152

Phe Asn Lys Asn Asn Glu Gly Thr Tyr Tyr Ser Pro Asn Tyr Asn Pro
1               5                   10                  15

Gln Ser Arg

<210> SEQ ID NO 1153
<211> LENGTH: 35
<212> TYPE: PRT
<213> ORGANISM: Homo sapiens

<400> SEQUENCE: 1153

Ile Asp Thr Ile Asn Leu Phe Pro Ala Thr Leu Phe Asp Ala Tyr Met
1               5                   10                  15

Val Ala Gln Asn Pro Gly Glu Trp Met Leu Ser Cys Gln Asn Leu Asn
            20                  25                  30

His Leu Lys
        35

<210> SEQ ID NO 1154
<211> LENGTH: 23
```

<212> TYPE: PRT
<213> ORGANISM: Homo sapiens

<400> SEQUENCE: 1154

Lys Ala Glu Glu Glu His Leu Gly Ile Leu Gly Pro Gln Leu His Ala
1               5                   10                  15

Asp Val Gly Asp Lys Val Lys
            20

<210> SEQ ID NO 1155
<211> LENGTH: 8
<212> TYPE: PRT
<213> ORGANISM: Homo sapiens

<400> SEQUENCE: 1155

Phe Trp Thr Ser Phe Phe Pro Lys
1               5

<210> SEQ ID NO 1156
<211> LENGTH: 17
<212> TYPE: PRT
<213> ORGANISM: Homo sapiens

<400> SEQUENCE: 1156

Leu Phe Asp Ser Asp Pro Ile Thr Val Thr Val Pro Val Glu Val Ser
1               5                   10                  15

Arg

<210> SEQ ID NO 1157
<211> LENGTH: 12
<212> TYPE: PRT
<213> ORGANISM: Homo sapiens

<400> SEQUENCE: 1157

Ala Ser Ser Ile Ile Asp Glu Leu Phe Gln Asp Arg
1               5                   10

<210> SEQ ID NO 1158
<211> LENGTH: 14
<212> TYPE: PRT
<213> ORGANISM: Homo sapiens

<400> SEQUENCE: 1158

Trp Ile Val Thr Ala Ala His Cys Val Glu Thr Gly Val Lys
1               5                   10

<210> SEQ ID NO 1159
<211> LENGTH: 11
<212> TYPE: PRT
<213> ORGANISM: Homo sapiens

<400> SEQUENCE: 1159

Glu Thr Tyr Asp Phe Asp Ile Ala Val Leu Arg
1               5                   10

<210> SEQ ID NO 1160
<211> LENGTH: 17
<212> TYPE: PRT
<213> ORGANISM: Homo sapiens

<400> SEQUENCE: 1160

Val Arg Gln Leu Glu Met Glu Ile Gly Gln Leu Asn Val His Tyr Leu
1               5                   10                  15

Arg

<210> SEQ ID NO 1161
<211> LENGTH: 7
<212> TYPE: PRT
<213> ORGANISM: Homo sapiens

<400> SEQUENCE: 1161

Pro Ala Phe Ser Ala Ile Arg
1               5

<210> SEQ ID NO 1162
<211> LENGTH: 22
<212> TYPE: PRT
<213> ORGANISM: Homo sapiens

<400> SEQUENCE: 1162

Val Val Thr Phe Cys Asp Tyr Ala Tyr Asn Thr Phe Gln Val Thr Thr
1               5                   10                  15

Gly Gly Met Val Leu Lys
            20

<210> SEQ ID NO 1163
<211> LENGTH: 18
<212> TYPE: PRT
<213> ORGANISM: Homo sapiens

<400> SEQUENCE: 1163

Thr Leu Asp Glu Phe Thr Ile Ile Gln Asn Leu Gln Pro Gln Tyr Gln
1               5                   10                  15

Phe Arg

<210> SEQ ID NO 1164
<211> LENGTH: 17
<212> TYPE: PRT
<213> ORGANISM: Homo sapiens

<400> SEQUENCE: 1164

Met Asp Val Phe Ser Gln Asn Met Phe Cys Ala Gly His Pro Ser Leu
1               5                   10                  15

Lys

<210> SEQ ID NO 1165
<211> LENGTH: 21
<212> TYPE: PRT
<213> ORGANISM: Homo sapiens

<400> SEQUENCE: 1165

Phe Tyr Ala Ala Gly Leu Val Ser Trp Gly Pro Gln Cys Gly Thr Tyr
1               5                   10                  15

Gly Leu Tyr Thr Arg
            20

<210> SEQ ID NO 1166
<211> LENGTH: 9
<212> TYPE: PRT
<213> ORGANISM: Homo sapiens

<400> SEQUENCE: 1166

Gly Phe Gln Val Val Val Thr Leu Arg
1               5

-continued

```
<210> SEQ ID NO 1167
<211> LENGTH: 17
<212> TYPE: PRT
<213> ORGANISM: Homo sapiens

<400> SEQUENCE: 1167

Gly Ala Leu Ile Ser Asp Gln Trp Val Leu Thr Ala Ala His Cys Phe
1               5                   10                  15

Arg

<210> SEQ ID NO 1168
<211> LENGTH: 15
<212> TYPE: PRT
<213> ORGANISM: Homo sapiens

<400> SEQUENCE: 1168

Pro Ile Cys Leu Pro Cys Thr Met Glu Ala Asn Leu Ala Leu Arg
1               5                   10                  15

<210> SEQ ID NO 1169
<211> LENGTH: 24
<212> TYPE: PRT
<213> ORGANISM: Homo sapiens

<400> SEQUENCE: 1169

Tyr Tyr Gly Gly Gly Tyr Gly Ser Thr Gln Ala Thr Phe Met Val Phe
1               5                   10                  15

Gln Ala Leu Ala Gln Tyr Gln Lys
            20

<210> SEQ ID NO 1170
<211> LENGTH: 11
<212> TYPE: PRT
<213> ORGANISM: Homo sapiens

<400> SEQUENCE: 1170

Gly Leu Cys Val Ala Thr Pro Val Gln Leu Arg
1               5                   10

<210> SEQ ID NO 1171
<211> LENGTH: 19
<212> TYPE: PRT
<213> ORGANISM: Homo sapiens

<400> SEQUENCE: 1171

Met Arg Pro Ser Thr Asp Thr Ile Thr Val Met Val Glu Asn Ser His
1               5                   10                  15

Gly Leu Arg

<210> SEQ ID NO 1172
<211> LENGTH: 21
<212> TYPE: PRT
<213> ORGANISM: Homo sapiens

<400> SEQUENCE: 1172

Val Gly Leu Ser Gly Met Ala Ile Ala Asp Val Thr Leu Leu Ser Gly
1               5                   10                  15

Phe His Ala Leu Arg
            20

<210> SEQ ID NO 1173
<211> LENGTH: 15
<212> TYPE: PRT
```

-continued

```
<213> ORGANISM: Homo sapiens

<400> SEQUENCE: 1173

Val Leu Ser Leu Ala Gln Glu Gln Val Gly Gly Ser Pro Glu Lys
1               5                   10                  15

<210> SEQ ID NO 1174
<211> LENGTH: 13
<212> TYPE: PRT
<213> ORGANISM: Homo sapiens

<400> SEQUENCE: 1174

Glu Met Ser Gly Ser Pro Ala Ser Gly Ile Pro Val Lys
1               5                   10

<210> SEQ ID NO 1175
<211> LENGTH: 18
<212> TYPE: PRT
<213> ORGANISM: Homo sapiens

<400> SEQUENCE: 1175

Gly Cys Gly Glu Gln Thr Met Ile Tyr Leu Ala Pro Thr Leu Ala Ala
1               5                   10                  15

Ser Arg

<210> SEQ ID NO 1176
<211> LENGTH: 9
<212> TYPE: PRT
<213> ORGANISM: Homo sapiens

<400> SEQUENCE: 1176

Gly Leu Gln Asp Glu Asp Gly Tyr Arg
1               5

<210> SEQ ID NO 1177
<211> LENGTH: 11
<212> TYPE: PRT
<213> ORGANISM: Homo sapiens

<400> SEQUENCE: 1177

Gly Gln Ile Val Phe Met Asn Arg Glu Pro Lys
1               5                   10

<210> SEQ ID NO 1178
<211> LENGTH: 27
<212> TYPE: PRT
<213> ORGANISM: Homo sapiens

<400> SEQUENCE: 1178

Lys Lys Glu Val Tyr Met Pro Ser Ser Ile Phe Gln Asp Asp Phe Val
1               5                   10                  15

Ile Pro Asp Ile Ser Glu Pro Gly Thr Trp Lys
            20                  25

<210> SEQ ID NO 1179
<211> LENGTH: 6
<212> TYPE: PRT
<213> ORGANISM: Homo sapiens

<400> SEQUENCE: 1179

Leu Pro Met Ser Val Arg
1               5
```

-continued

```
<210> SEQ ID NO 1180
<211> LENGTH: 18
<212> TYPE: PRT
<213> ORGANISM: Homo sapiens

<400> SEQUENCE: 1180

Leu Thr Val Ala Ala Pro Pro Ser Gly Gly Pro Gly Phe Leu Ser Ile
1               5                   10                  15

Glu Arg

<210> SEQ ID NO 1181
<211> LENGTH: 5
<212> TYPE: PRT
<213> ORGANISM: Homo sapiens

<400> SEQUENCE: 1181

Asn Phe Leu Val Arg
1               5

<210> SEQ ID NO 1182
<211> LENGTH: 32
<212> TYPE: PRT
<213> ORGANISM: Homo sapiens

<400> SEQUENCE: 1182

Asn Gly Glu Ser Val Lys Leu His Leu Glu Thr Asp Ser Leu Ala Leu
1               5                   10                  15

Val Ala Leu Gly Ala Leu Asp Thr Ala Leu Tyr Ala Ala Gly Ser Lys
            20                  25                  30

<210> SEQ ID NO 1183
<211> LENGTH: 9
<212> TYPE: PRT
<213> ORGANISM: Homo sapiens

<400> SEQUENCE: 1183

Gln Gly Ser Phe Gln Gly Gly Phe Arg
1               5

<210> SEQ ID NO 1184
<211> LENGTH: 23
<212> TYPE: PRT
<213> ORGANISM: Homo sapiens

<400> SEQUENCE: 1184

Thr Leu Glu Ile Pro Gly Asn Ser Asp Pro Asn Met Ile Pro Asp Gly
1               5                   10                  15

Asp Phe Asn Ser Tyr Val Arg
            20

<210> SEQ ID NO 1185
<211> LENGTH: 26
<212> TYPE: PRT
<213> ORGANISM: Homo sapiens

<400> SEQUENCE: 1185

Val Thr Ala Ser Asp Pro Leu Asp Thr Leu Gly Ser Glu Gly Ala Leu
1               5                   10                  15

Ser Pro Gly Gly Val Ala Ser Leu Leu Arg
            20                  25

<210> SEQ ID NO 1186
<211> LENGTH: 16
```

```
<212> TYPE: PRT
<213> ORGANISM: Homo sapiens

<400> SEQUENCE: 1186

Tyr Leu Asp Lys Thr Glu Gln Trp Ser Thr Leu Pro Pro Glu Thr Lys
1               5                   10                  15

<210> SEQ ID NO 1187
<211> LENGTH: 30
<212> TYPE: PRT
<213> ORGANISM: Homo sapiens

<400> SEQUENCE: 1187

Ala Asp Asn Phe Leu Leu Glu Asn Thr Leu Pro Ala Gln Ser Thr Phe
1               5                   10                  15

Thr Leu Ala Ile Ser Ala Tyr Ala Leu Ser Leu Gly Asp Lys
            20                  25                  30

<210> SEQ ID NO 1188
<211> LENGTH: 16
<212> TYPE: PRT
<213> ORGANISM: Homo sapiens

<400> SEQUENCE: 1188

Ala Leu Val Glu Gly Val Asp Gln Leu Phe Thr Asp Tyr Gln Ile Lys
1               5                   10                  15

<210> SEQ ID NO 1189
<211> LENGTH: 20
<212> TYPE: PRT
<213> ORGANISM: Homo sapiens

<400> SEQUENCE: 1189

Asp Gly His Val Ile Leu Gln Leu Asn Ser Ile Pro Ser Ser Asp Phe
1               5                   10                  15

Leu Cys Val Arg
            20

<210> SEQ ID NO 1190
<211> LENGTH: 14
<212> TYPE: PRT
<213> ORGANISM: Homo sapiens

<400> SEQUENCE: 1190

Asp Val Phe Leu Glu Met Asn Ile Pro Tyr Ser Val Val Arg
1               5                   10

<210> SEQ ID NO 1191
<211> LENGTH: 13
<212> TYPE: PRT
<213> ORGANISM: Homo sapiens

<400> SEQUENCE: 1191

Glu Phe Pro Tyr Arg Ile Pro Leu Asp Leu Val Pro Lys
1               5                   10

<210> SEQ ID NO 1192
<211> LENGTH: 12
<212> TYPE: PRT
<213> ORGANISM: Homo sapiens

<400> SEQUENCE: 1192

Phe Gln Asn Ser Ala Ile Leu Thr Ile Gln Pro Lys
1               5                   10
```

<210> SEQ ID NO 1193
<211> LENGTH: 17
<212> TYPE: PRT
<213> ORGANISM: Homo sapiens

<400> SEQUENCE: 1193

Val Phe Lys Asp Val Phe Leu Glu Met Asn Ile Pro Tyr Ser Val Val
1               5                   10                  15

Arg

<210> SEQ ID NO 1194
<211> LENGTH: 19
<212> TYPE: PRT
<213> ORGANISM: Homo sapiens

<400> SEQUENCE: 1194

Thr Glu Cys Ile Lys Pro Val Val Gln Glu Val Leu Thr Ile Thr Pro
1               5                   10                  15

Phe Gln Arg

<210> SEQ ID NO 1195
<211> LENGTH: 9
<212> TYPE: PRT
<213> ORGANISM: Homo sapiens

<400> SEQUENCE: 1195

Ser Ser Gly Trp His Phe Val Val Lys
1               5

<210> SEQ ID NO 1196
<211> LENGTH: 8
<212> TYPE: PRT
<213> ORGANISM: Homo sapiens

<400> SEQUENCE: 1196

Ile Leu Pro Leu Thr Val Cys Lys
1               5

<210> SEQ ID NO 1197
<211> LENGTH: 13
<212> TYPE: PRT
<213> ORGANISM: Homo sapiens

<400> SEQUENCE: 1197

Ala Leu Asp Gln Tyr Leu Met Glu Phe Asn Ala Cys Arg
1               5                   10

<210> SEQ ID NO 1198
<211> LENGTH: 17
<212> TYPE: PRT
<213> ORGANISM: Homo sapiens

<400> SEQUENCE: 1198

Tyr Gly Phe Cys Glu Ala Ala Asp Gln Phe His Val Leu Asp Glu Val
1               5                   10                  15

Arg

<210> SEQ ID NO 1199
<211> LENGTH: 13
<212> TYPE: PRT
<213> ORGANISM: Homo sapiens -continued

```
<400> SEQUENCE: 1199

Ala Ile Glu Asp Tyr Ile Asn Glu Phe Ser Val Arg Lys
1               5                   10

<210> SEQ ID NO 1200
<211> LENGTH: 29
<212> TYPE: PRT
<213> ORGANISM: Homo sapiens

<400> SEQUENCE: 1200

Thr Ala Gly Tyr Gly Ile Asn Ile Leu Gly Met Asp Pro Leu Ser Thr
1               5                   10                  15

Pro Phe Asp Asn Glu Phe Tyr Asn Gly Leu Cys Asn Arg
            20                  25

<210> SEQ ID NO 1201
<211> LENGTH: 10
<212> TYPE: PRT
<213> ORGANISM: Homo sapiens

<400> SEQUENCE: 1201

Ala Leu Phe Val Ser Glu Glu Glu Lys Lys
1               5                   10

<210> SEQ ID NO 1202
<211> LENGTH: 8
<212> TYPE: PRT
<213> ORGANISM: Homo sapiens

<400> SEQUENCE: 1202

Cys Leu Val Asn Leu Ile Glu Lys
1               5

<210> SEQ ID NO 1203
<211> LENGTH: 16
<212> TYPE: PRT
<213> ORGANISM: Homo sapiens

<400> SEQUENCE: 1203

Glu Ala Gly Ile Pro Glu Phe Tyr Asp Tyr Asp Val Ala Leu Ile Lys
1               5                   10                  15

<210> SEQ ID NO 1204
<211> LENGTH: 18
<212> TYPE: PRT
<213> ORGANISM: Homo sapiens

<400> SEQUENCE: 1204

Tyr Gly Gln Thr Ile Arg Pro Ile Cys Leu Pro Cys Thr Glu Gly Thr
1               5                   10                  15

Thr Arg

<210> SEQ ID NO 1205
<211> LENGTH: 18
<212> TYPE: PRT
<213> ORGANISM: Homo sapiens

<400> SEQUENCE: 1205

Asp Leu Glu Ile Glu Val Val Leu Phe His Pro Asn Tyr Asn Ile Asn
1               5                   10                  15

Gly Lys
```

-continued

```
<210> SEQ ID NO 1206
<211> LENGTH: 17
<212> TYPE: PRT
<213> ORGANISM: Homo sapiens

<400> SEQUENCE: 1206

Phe Leu Cys Thr Gly Gly Val Ser Pro Tyr Ala Asp Pro Asn Thr Cys
1               5                   10                  15

Arg

<210> SEQ ID NO 1207
<211> LENGTH: 11
<212> TYPE: PRT
<213> ORGANISM: Homo sapiens

<400> SEQUENCE: 1207

Asp Gly Trp Ser Ala Gln Pro Thr Cys Ile Lys
1               5                   10

<210> SEQ ID NO 1208
<211> LENGTH: 12
<212> TYPE: PRT
<213> ORGANISM: Homo sapiens

<400> SEQUENCE: 1208

Glu Gly Trp Ile His Thr Val Cys Ile Asn Gly Arg
1               5                   10

<210> SEQ ID NO 1209
<211> LENGTH: 18
<212> TYPE: PRT
<213> ORGANISM: Homo sapiens

<400> SEQUENCE: 1209

Thr Asp Cys Leu Ser Leu Pro Ser Phe Glu Asn Ala Ile Pro Met Gly
1               5                   10                  15

Glu Lys

<210> SEQ ID NO 1210
<211> LENGTH: 18
<212> TYPE: PRT
<213> ORGANISM: Homo sapiens

<400> SEQUENCE: 1210

Asp Thr Ser Cys Val Asn Pro Pro Thr Val Gln Asn Ala Tyr Ile Val
1               5                   10                  15

Ser Arg

<210> SEQ ID NO 1211
<211> LENGTH: 11
<212> TYPE: PRT
<213> ORGANISM: Homo sapiens

<400> SEQUENCE: 1211

Cys Thr Ser Thr Gly Trp Ile Pro Ala Pro Arg
1               5                   10

<210> SEQ ID NO 1212
<211> LENGTH: 8
<212> TYPE: PRT
<213> ORGANISM: Homo sapiens

<400> SEQUENCE: 1212
```

-continued

```
Ile Ile Tyr Lys Glu Asn Glu Arg
1               5

<210> SEQ ID NO 1213
<211> LENGTH: 19
<212> TYPE: PRT
<213> ORGANISM: Homo sapiens

<400> SEQUENCE: 1213

Ile Val Ser Ser Ala Met Glu Pro Asp Arg Glu Tyr His Phe Gly Gln
1               5                   10                  15

Ala Val Arg

<210> SEQ ID NO 1214
<211> LENGTH: 12
<212> TYPE: PRT
<213> ORGANISM: Homo sapiens

<400> SEQUENCE: 1214

Cys Thr Leu Lys Pro Cys Asp Tyr Pro Asp Ile Lys
1               5                   10

<210> SEQ ID NO 1215
<211> LENGTH: 11
<212> TYPE: PRT
<213> ORGANISM: Homo sapiens

<400> SEQUENCE: 1215

Lys Gly Glu Trp Val Ala Leu Asn Pro Leu Arg
1               5                   10

<210> SEQ ID NO 1216
<211> LENGTH: 12
<212> TYPE: PRT
<213> ORGANISM: Homo sapiens

<400> SEQUENCE: 1216

Lys Gly Glu Trp Val Ala Leu Asn Pro Leu Arg Lys
1               5                   10

<210> SEQ ID NO 1217
<211> LENGTH: 10
<212> TYPE: PRT
<213> ORGANISM: Homo sapiens

<400> SEQUENCE: 1217

Arg Pro Tyr Phe Pro Val Ala Val Gly Lys
1               5                   10

<210> SEQ ID NO 1218
<211> LENGTH: 11
<212> TYPE: PRT
<213> ORGANISM: Homo sapiens

<400> SEQUENCE: 1218

Glu Ile Met Glu Asn Tyr Asn Ile Ala Leu Arg
1               5                   10

<210> SEQ ID NO 1219
<211> LENGTH: 25
<212> TYPE: PRT
<213> ORGANISM: Homo sapiens

<400> SEQUENCE: 1219
```

```
Asp Ala Ser Gly Ile Thr Cys Gly Gly Ile Tyr Ile Gly Gly Cys Trp
1               5                   10                  15

Ile Leu Thr Ala Ala His Cys Leu Arg
            20                  25
```

<210> SEQ ID NO 1220
<211> LENGTH: 14
<212> TYPE: PRT
<213> ORGANISM: Homo sapiens

<400> SEQUENCE: 1220

```
Val Ala Asn Tyr Phe Asp Trp Ile Ser Tyr His Val Gly Arg
1               5                   10
```

<210> SEQ ID NO 1221
<211> LENGTH: 22
<212> TYPE: PRT
<213> ORGANISM: Homo sapiens

<400> SEQUENCE: 1221

```
Ile Ile Phe His Glu Asn Tyr Asn Ala Gly Thr Tyr Gln Asn Asp Ile
1               5                   10                  15

Ala Leu Ile Glu Met Lys
            20
```

<210> SEQ ID NO 1222
<211> LENGTH: 16
<212> TYPE: PRT
<213> ORGANISM: Homo sapiens

<400> SEQUENCE: 1222

```
Tyr Gln Ile Trp Thr Thr Val Val Asp Trp Ile His Pro Asp Leu Lys
1               5                   10                  15
```

<210> SEQ ID NO 1223
<211> LENGTH: 6
<212> TYPE: PRT
<213> ORGANISM: Homo sapiens

<400> SEQUENCE: 1223

```
Ile Ser Asn Leu Leu Lys
1               5
```

<210> SEQ ID NO 1224
<211> LENGTH: 11
<212> TYPE: PRT
<213> ORGANISM: Homo sapiens

<400> SEQUENCE: 1224

```
His Val Leu Ala Ala Trp Ala Leu Gly Ala Lys
1               5                   10
```

<210> SEQ ID NO 1225
<211> LENGTH: 14
<212> TYPE: PRT
<213> ORGANISM: Homo sapiens

<400> SEQUENCE: 1225

```
Ala Gly Leu Arg Tyr Val Cys Leu Ala Glu Pro Ala Glu Arg
1               5                   10
```

<210> SEQ ID NO 1226
<211> LENGTH: 17
<212> TYPE: PRT

-continued

<213> ORGANISM: Homo sapiens

<400> SEQUENCE: 1226

Phe Thr Gln Leu Cys Val Lys Gly Gly Gly Gly Gly Asn Gly Ile
1               5                   10                  15

Arg

<210> SEQ ID NO 1227
<211> LENGTH: 17
<212> TYPE: PRT
<213> ORGANISM: Homo sapiens

<400> SEQUENCE: 1227

Val Gln Leu Gly Pro Tyr Gln Pro Gly Arg Pro Ala Ala Cys Asp Leu
1               5                   10                  15

Arg

<210> SEQ ID NO 1228
<211> LENGTH: 22
<212> TYPE: PRT
<213> ORGANISM: Homo sapiens

<400> SEQUENCE: 1228

Gly Gly Leu Gly Ser Leu Phe Tyr Leu Thr Leu Asp Val Leu Glu Thr
1               5                   10                  15

Asp Cys His Val Leu Arg
            20

<210> SEQ ID NO 1229
<211> LENGTH: 21
<212> TYPE: PRT
<213> ORGANISM: Homo sapiens

<400> SEQUENCE: 1229

Glu Leu Leu Ser Gln Gly Ala Thr Leu Ser Gly Trp Tyr His Leu Cys
1               5                   10                  15

Leu Pro Glu Gly Arg
            20

<210> SEQ ID NO 1230
<211> LENGTH: 14
<212> TYPE: PRT
<213> ORGANISM: Homo sapiens

<400> SEQUENCE: 1230

Lys Thr Thr Asp Met Ile Leu Asn Glu Ile Lys Gln Gly Lys
1               5                   10

<210> SEQ ID NO 1231
<211> LENGTH: 25
<212> TYPE: PRT
<213> ORGANISM: Homo sapiens

<400> SEQUENCE: 1231

Asn Trp Arg Asp Pro Asp Gln Thr Asp Gly Leu Gly Leu Ser Tyr Leu
1               5                   10                  15

Ser Ser His Ile Ala Asn Val Glu Arg
            20                  25

<210> SEQ ID NO 1232
<211> LENGTH: 27
<212> TYPE: PRT

-continued

```
<213> ORGANISM: Homo sapiens

<400> SEQUENCE: 1232

Val Glu Lys Phe Asp Leu Val Pro Val Pro Thr Asn Leu Tyr Gly Asp
1               5                   10                  15

Phe Phe Thr Gly Asp Ala Tyr Val Ile Leu Lys
            20                  25

<210> SEQ ID NO 1233
<211> LENGTH: 28
<212> TYPE: PRT
<213> ORGANISM: Homo sapiens

<400> SEQUENCE: 1233

Val Pro Phe Asp Ala Ala Thr Leu His Thr Ser Thr Ala Met Ala Ala
1               5                   10                  15

Gln His Gly Met Asp Asp Asp Gly Thr Gly Gln Lys
            20                  25

<210> SEQ ID NO 1234
<211> LENGTH: 6
<212> TYPE: PRT
<213> ORGANISM: Homo sapiens

<400> SEQUENCE: 1234

Phe Tyr Thr Phe Leu Lys
1               5

<210> SEQ ID NO 1235
<211> LENGTH: 12
<212> TYPE: PRT
<213> ORGANISM: Homo sapiens

<400> SEQUENCE: 1235

Gly Asp Lys Val Trp Val Tyr Pro Pro Glu Lys Lys
1               5                   10

<210> SEQ ID NO 1236
<211> LENGTH: 21
<212> TYPE: PRT
<213> ORGANISM: Homo sapiens

<400> SEQUENCE: 1236

Leu Leu Gln Asp Glu Phe Pro Gly Ile Pro Ser Pro Leu Asp Ala Ala
1               5                   10                  15

Val Glu Cys His Arg
            20

<210> SEQ ID NO 1237
<211> LENGTH: 25
<212> TYPE: PRT
<213> ORGANISM: Homo sapiens

<400> SEQUENCE: 1237

Ser Gly Ala Gln Ala Thr Trp Thr Glu Leu Pro Trp Pro His Glu Lys
1               5                   10                  15

Val Asp Gly Ala Leu Cys Met Glu Lys
            20                  25

<210> SEQ ID NO 1238
<211> LENGTH: 9
<212> TYPE: PRT
<213> ORGANISM: Homo sapiens
```

<400> SEQUENCE: 1238

Val Asp Gly Ala Leu Cys Met Glu Lys
1               5

<210> SEQ ID NO 1239
<211> LENGTH: 9
<212> TYPE: PRT
<213> ORGANISM: Homo sapiens

<400> SEQUENCE: 1239

Asp Tyr Phe Met Pro Cys Pro Gly Arg
1               5

<210> SEQ ID NO 1240
<211> LENGTH: 12
<212> TYPE: PRT
<213> ORGANISM: Homo sapiens

<400> SEQUENCE: 1240

Glu Trp Phe Trp Asp Leu Ala Thr Gly Thr Met Lys
1               5                   10

<210> SEQ ID NO 1241
<211> LENGTH: 30
<212> TYPE: PRT
<213> ORGANISM: Homo sapiens

<400> SEQUENCE: 1241

His Gln Gly Thr Ile Thr Val Asn Glu Glu Gly Thr Gln Ala Thr Thr
1               5                   10                  15

Val Thr Thr Val Gly Phe Met Pro Leu Ser Thr Gln Val Arg
            20                  25                  30

<210> SEQ ID NO 1242
<211> LENGTH: 11
<212> TYPE: PRT
<213> ORGANISM: Homo sapiens

<400> SEQUENCE: 1242

Tyr Glu Ile Thr Thr Ile His Asn Leu Phe Arg
1               5                   10

<210> SEQ ID NO 1243
<211> LENGTH: 7
<212> TYPE: PRT
<213> ORGANISM: Homo sapiens

<400> SEQUENCE: 1243

Leu Asn Ile Leu Asn Ala Lys
1               5

<210> SEQ ID NO 1244
<211> LENGTH: 7
<212> TYPE: PRT
<213> ORGANISM: Homo sapiens

<400> SEQUENCE: 1244

Asn Phe Gly Tyr Thr Leu Arg
1               5

<210> SEQ ID NO 1245
<211> LENGTH: 31
<212> TYPE: PRT

<213> ORGANISM: Homo sapiens

<400> SEQUENCE: 1245

Val Leu Lys Asp Gln Val Asn Thr Phe Asp Asn Ile Phe Ile Ala Pro
1               5                   10                  15

Val Gly Ile Ser Thr Ala Met Gly Met Ile Ser Leu Gly Leu Lys
            20                  25                  30

<210> SEQ ID NO 1246
<211> LENGTH: 15
<212> TYPE: PRT
<213> ORGANISM: Homo sapiens

<400> SEQUENCE: 1246

Pro Leu Leu Asn Asp Ser Arg Met Leu Leu Ser Pro Asp Gln Lys
1               5                   10                  15

<210> SEQ ID NO 1247
<211> LENGTH: 19
<212> TYPE: PRT
<213> ORGANISM: Homo sapiens

<400> SEQUENCE: 1247

Val Gln Leu Ser Pro Asp Leu Leu Ala Thr Leu Pro Glu Pro Ala Ser
1               5                   10                  15

Pro Gly Arg

<210> SEQ ID NO 1248
<211> LENGTH: 9
<212> TYPE: PRT
<213> ORGANISM: Homo sapiens

<400> SEQUENCE: 1248

Asp Gly Tyr Leu Phe Gln Leu Leu Arg
1               5

<210> SEQ ID NO 1249
<211> LENGTH: 13
<212> TYPE: PRT
<213> ORGANISM: Homo sapiens

<400> SEQUENCE: 1249

Leu Lys Pro Val Asp Gly His Cys Ala Leu Glu Ser Lys
1               5                   10

<210> SEQ ID NO 1250
<211> LENGTH: 10
<212> TYPE: PRT
<213> ORGANISM: Homo sapiens

<400> SEQUENCE: 1250

Arg Pro Gly Val Tyr Thr Gln Val Thr Lys
1               5                   10

<210> SEQ ID NO 1251
<211> LENGTH: 21
<212> TYPE: PRT
<213> ORGANISM: Homo sapiens

<400> SEQUENCE: 1251

Ala Gly Ala Asp Thr His Gly Arg Leu Leu Gln Gly Asn Ile Cys Asn
1               5                   10                  15

Asp Ala Val Thr Lys

```
            20

<210> SEQ ID NO 1252
<211> LENGTH: 14
<212> TYPE: PRT
<213> ORGANISM: Homo sapiens

<400> SEQUENCE: 1252

Lys Ile Ile Glu Lys Met Ala Thr Phe Glu Ile Asp Glu Lys
1               5                   10

<210> SEQ ID NO 1253
<211> LENGTH: 22
<212> TYPE: PRT
<213> ORGANISM: Homo sapiens

<400> SEQUENCE: 1253

Ser Phe Glu Gly Leu Gly Gln Leu Glu Val Leu Thr Leu Asp His Asn
1               5                   10                  15

Gln Leu Gln Glu Val Lys
            20

<210> SEQ ID NO 1254
<211> LENGTH: 9
<212> TYPE: PRT
<213> ORGANISM: Homo sapiens

<400> SEQUENCE: 1254

Glu Leu Ala Ala Gln Thr Ile Lys Lys
1               5

<210> SEQ ID NO 1255
<211> LENGTH: 20
<212> TYPE: PRT
<213> ORGANISM: Homo sapiens

<400> SEQUENCE: 1255

Gln Leu Val His His Phe Glu Ile Asp Val Asp Ile Phe Glu Pro Gln
1               5                   10                  15

Gly Ile Ser Lys
            20

<210> SEQ ID NO 1256
<211> LENGTH: 13
<212> TYPE: PRT
<213> ORGANISM: Homo sapiens

<400> SEQUENCE: 1256

Gln Tyr Tyr Glu Gly Ser Glu Ile Val Val Ala Gly Arg
1               5                   10

<210> SEQ ID NO 1257
<211> LENGTH: 31
<212> TYPE: PRT
<213> ORGANISM: Homo sapiens

<400> SEQUENCE: 1257

Glu Val Ala Phe Asp Leu Glu Ile Pro Lys Thr Ala Phe Ile Ser Asp
1               5                   10                  15

Phe Ala Val Thr Ala Asp Gly Asn Ala Phe Ile Gly Asp Ile Lys
            20                  25                  30

<210> SEQ ID NO 1258
```

<211> LENGTH: 28
<212> TYPE: PRT
<213> ORGANISM: Homo sapiens

<400> SEQUENCE: 1258

Gly Met Ala Asp Gln Asp Gly Leu Lys Pro Thr Ile Asp Lys Pro Ser
1               5                   10                  15

Glu Asp Ser Pro Pro Leu Glu Met Leu Gly Pro Arg
            20                  25

<210> SEQ ID NO 1259
<211> LENGTH: 39
<212> TYPE: PRT
<213> ORGANISM: Homo sapiens

<400> SEQUENCE: 1259

Phe Asp Pro Ala Lys Leu Asp Gln Ile Glu Ser Val Ile Thr Ala Thr
1               5                   10                  15

Ser Ala Asn Thr Gln Leu Val Leu Glu Thr Leu Ala Gln Met Asp Asp
            20                  25                  30

Leu Gln Asp Phe Leu Ser Lys
        35

<210> SEQ ID NO 1260
<211> LENGTH: 12
<212> TYPE: PRT
<213> ORGANISM: Homo sapiens

<400> SEQUENCE: 1260

Lys Phe Tyr Asn Gln Val Ser Thr Pro Leu Leu Arg
1               5                   10

<210> SEQ ID NO 1261
<211> LENGTH: 16
<212> TYPE: PRT
<213> ORGANISM: Homo sapiens

<400> SEQUENCE: 1261

Asn Ile Leu Phe Val Ile Asp Val Ser Gly Ser Met Trp Gly Val Lys
1               5                   10                  15

<210> SEQ ID NO 1262
<211> LENGTH: 8
<212> TYPE: PRT
<213> ORGANISM: Homo sapiens

<400> SEQUENCE: 1262

Lys Leu Gly Ser Tyr Glu His Arg
1               5

<210> SEQ ID NO 1263
<211> LENGTH: 9
<212> TYPE: PRT
<213> ORGANISM: Homo sapiens

<400> SEQUENCE: 1263

Met Ala Thr Thr Met Ile Gln Ser Lys
1               5

<210> SEQ ID NO 1264
<211> LENGTH: 28
<212> TYPE: PRT
<213> ORGANISM: Homo sapiens -continued

```
<400> SEQUENCE: 1264

Ser Ile Leu Gln Met Ser Leu Asp His His Ile Val Thr Pro Leu Thr
1               5                   10                  15

Ser Leu Val Ile Glu Asn Glu Ala Gly Asp Glu Arg
            20                  25

<210> SEQ ID NO 1265
<211> LENGTH: 10
<212> TYPE: PRT
<213> ORGANISM: Homo sapiens

<400> SEQUENCE: 1265

Thr Glu Val Asn Val Leu Pro Gly Ala Lys
1               5                   10

<210> SEQ ID NO 1266
<211> LENGTH: 8
<212> TYPE: PRT
<213> ORGANISM: Homo sapiens

<400> SEQUENCE: 1266

Asn Val Val Phe Val Ile Asp Lys
1               5

<210> SEQ ID NO 1267
<211> LENGTH: 13
<212> TYPE: PRT
<213> ORGANISM: Homo sapiens

<400> SEQUENCE: 1267

Trp Lys Glu Thr Leu Phe Ser Val Met Pro Gly Leu Lys
1               5                   10

<210> SEQ ID NO 1268
<211> LENGTH: 9
<212> TYPE: PRT
<213> ORGANISM: Homo sapiens

<400> SEQUENCE: 1268

Tyr Ile Phe His Asn Phe Met Glu Arg
1               5

<210> SEQ ID NO 1269
<211> LENGTH: 9
<212> TYPE: PRT
<213> ORGANISM: Homo sapiens

<400> SEQUENCE: 1269

Phe Ala His Thr Val Val Thr Ser Arg
1               5

<210> SEQ ID NO 1270
<211> LENGTH: 10
<212> TYPE: PRT
<213> ORGANISM: Homo sapiens

<400> SEQUENCE: 1270

Phe Lys Pro Thr Leu Ser Gln Gln Gln Lys
1               5                   10

<210> SEQ ID NO 1271
<211> LENGTH: 44
<212> TYPE: PRT
<213> ORGANISM: Homo sapiens
```

```
<400> SEQUENCE: 1271

Ile His Glu Asp Ser Asp Ser Ala Leu Gln Leu Gln Asp Phe Tyr Gln
1               5                   10                  15

Glu Val Ala Asn Pro Leu Leu Thr Ala Val Thr Phe Glu Tyr Pro Ser
            20                  25                  30

Asn Ala Val Glu Glu Val Thr Gln Asn Asn Phe Arg
        35                  40

<210> SEQ ID NO 1272
<211> LENGTH: 11
<212> TYPE: PRT
<213> ORGANISM: Homo sapiens

<400> SEQUENCE: 1272

Met Asn Phe Arg Pro Gly Val Leu Ser Ser Arg
1               5                   10

<210> SEQ ID NO 1273
<211> LENGTH: 11
<212> TYPE: PRT
<213> ORGANISM: Homo sapiens

<400> SEQUENCE: 1273

Asn Val His Ser Ala Gly Ala Ala Gly Ser Arg
1               5                   10

<210> SEQ ID NO 1274
<211> LENGTH: 10
<212> TYPE: PRT
<213> ORGANISM: Homo sapiens

<400> SEQUENCE: 1274

Asn Val His Ser Gly Ser Thr Phe Phe Lys
1               5                   10

<210> SEQ ID NO 1275
<211> LENGTH: 10
<212> TYPE: PRT
<213> ORGANISM: Homo sapiens

<400> SEQUENCE: 1275

Arg Leu Gly Val Tyr Glu Leu Leu Leu Lys
1               5                   10

<210> SEQ ID NO 1276
<211> LENGTH: 8
<212> TYPE: PRT
<213> ORGANISM: Homo sapiens

<400> SEQUENCE: 1276

Lys Leu Glu Leu His Leu Pro Lys
1               5

<210> SEQ ID NO 1277
<211> LENGTH: 13
<212> TYPE: PRT
<213> ORGANISM: Homo sapiens

<400> SEQUENCE: 1277

Glu Ile Glu Glu Val Leu Thr Pro Glu Met Leu Met Arg
1               5                   10
```

```
<210> SEQ ID NO 1278
<211> LENGTH: 13
<212> TYPE: PRT
<213> ORGANISM: Homo sapiens

<400> SEQUENCE: 1278

Ala Ala Thr Gly Glu Cys Thr Ala Thr Val Gly Lys Arg
1               5                   10

<210> SEQ ID NO 1279
<211> LENGTH: 18
<212> TYPE: PRT
<213> ORGANISM: Homo sapiens

<400> SEQUENCE: 1279

Leu Gly Gln Ser Leu Asp Cys Asn Ala Glu Val Tyr Val Val Pro Trp
1               5                   10                  15

Glu Lys

<210> SEQ ID NO 1280
<211> LENGTH: 15
<212> TYPE: PRT
<213> ORGANISM: Homo sapiens

<400> SEQUENCE: 1280

Tyr Asn Ser Gln Asn Gln Ser Asn Asn Gln Phe Val Leu Tyr Arg
1               5                   10                  15

<210> SEQ ID NO 1281
<211> LENGTH: 9
<212> TYPE: PRT
<213> ORGANISM: Homo sapiens

<400> SEQUENCE: 1281

Gln Val Val Ala Gly Leu Asn Phe Arg
1               5

<210> SEQ ID NO 1282
<211> LENGTH: 10
<212> TYPE: PRT
<213> ORGANISM: Homo sapiens

<400> SEQUENCE: 1282

Asp Leu Leu Leu Pro Gln Pro Asp Leu Arg
1               5                   10

<210> SEQ ID NO 1283
<211> LENGTH: 13
<212> TYPE: PRT
<213> ORGANISM: Homo sapiens

<400> SEQUENCE: 1283

Leu His Leu Glu Gly Asn Lys Leu Gln Val Leu Gly Lys
1               5                   10

<210> SEQ ID NO 1284
<211> LENGTH: 18
<212> TYPE: PRT
<213> ORGANISM: Homo sapiens

<400> SEQUENCE: 1284

Thr Leu Asp Leu Gly Glu Asn Gln Leu Glu Thr Leu Pro Pro Asp Leu
1               5                   10                  15

Leu Arg
```

```
<210> SEQ ID NO 1285
<211> LENGTH: 11
<212> TYPE: PRT
<213> ORGANISM: Homo sapiens

<400> SEQUENCE: 1285

Leu Ala Glu Gly Phe Pro Leu Pro Leu Leu Lys
1               5                   10

<210> SEQ ID NO 1286
<211> LENGTH: 14
<212> TYPE: PRT
<213> ORGANISM: Homo sapiens

<400> SEQUENCE: 1286

Ser Leu Glu Tyr Leu Asp Leu Ser Phe Asn Gln Ile Ala Arg
1               5                   10

<210> SEQ ID NO 1287
<211> LENGTH: 11
<212> TYPE: PRT
<213> ORGANISM: Homo sapiens

<400> SEQUENCE: 1287

Leu Lys Glu Asp Ala Val Ser Ala Ala Phe Lys
1               5                   10

<210> SEQ ID NO 1288
<211> LENGTH: 19
<212> TYPE: PRT
<213> ORGANISM: Homo sapiens

<400> SEQUENCE: 1288

Ile Val Phe Glu Asn Pro Asp Pro Ser Asp Gly Phe Val Leu Ile Pro
1               5                   10                  15

Asp Leu Lys

<210> SEQ ID NO 1289
<211> LENGTH: 5
<212> TYPE: PRT
<213> ORGANISM: Homo sapiens

<400> SEQUENCE: 1289

Val Tyr Phe Phe Lys
1               5

<210> SEQ ID NO 1290
<211> LENGTH: 6
<212> TYPE: PRT
<213> ORGANISM: Homo sapiens

<400> SEQUENCE: 1290

Trp Phe Asp Tyr Leu Arg
1               5

<210> SEQ ID NO 1291
<211> LENGTH: 18
<212> TYPE: PRT
<213> ORGANISM: Homo sapiens

<400> SEQUENCE: 1291

Leu Thr Val Gly Ala Ala Gln Val Pro Ala Gln Leu Leu Val Gly Ala
1               5                   10                  15
```

Leu Arg

<210> SEQ ID NO 1292
<211> LENGTH: 17
<212> TYPE: PRT
<213> ORGANISM: Homo sapiens

<400> SEQUENCE: 1292

Gly Ile Val Ala Ala Phe Tyr Ser Gly Pro Ser Leu Ser Asp Lys Glu
1               5                   10                  15

Lys

<210> SEQ ID NO 1293
<211> LENGTH: 14
<212> TYPE: PRT
<213> ORGANISM: Homo sapiens

<400> SEQUENCE: 1293

Trp Tyr Val Pro Val Lys Asp Leu Leu Gly Ile Tyr Glu Lys
1               5                   10

<210> SEQ ID NO 1294
<211> LENGTH: 12
<212> TYPE: PRT
<213> ORGANISM: Homo sapiens

<400> SEQUENCE: 1294

Leu Gln Ser Leu Phe Asp Ser Pro Asp Phe Ser Lys
1               5                   10

<210> SEQ ID NO 1295
<211> LENGTH: 17
<212> TYPE: PRT
<213> ORGANISM: Homo sapiens

<400> SEQUENCE: 1295

Ala Leu Tyr Tyr Asp Leu Ile Ser Ser Pro Asp Ile His Gly Thr Tyr
1               5                   10                  15

Lys

<210> SEQ ID NO 1296
<211> LENGTH: 18
<212> TYPE: PRT
<213> ORGANISM: Homo sapiens

<400> SEQUENCE: 1296

Cys Leu Leu Phe Ser Phe Leu Pro Ala Ser Ser Ile Asn Asp Met Glu
1               5                   10                  15

Lys Arg

<210> SEQ ID NO 1297
<211> LENGTH: 16
<212> TYPE: PRT
<213> ORGANISM: Homo sapiens

<400> SEQUENCE: 1297

Val Ile Pro Ala Cys Leu Pro Ser Pro Asn Tyr Val Val Ala Asp Arg
1               5                   10                  15

<210> SEQ ID NO 1298
<211> LENGTH: 10
<212> TYPE: PRT

-continued

<213> ORGANISM: Homo sapiens

<400> SEQUENCE: 1298

Phe Val Thr Trp Ile Glu Gly Val Met Arg
1               5                   10

<210> SEQ ID NO 1299
<211> LENGTH: 11
<212> TYPE: PRT
<213> ORGANISM: Homo sapiens

<400> SEQUENCE: 1299

His Ser Ile Phe Thr Pro Glu Thr Asn Pro Arg
1               5                   10

<210> SEQ ID NO 1300
<211> LENGTH: 15
<212> TYPE: PRT
<213> ORGANISM: Homo sapiens

<400> SEQUENCE: 1300

Gly Lys Glu Glu Ser Leu Asp Ser Asp Leu Tyr Ala Glu Leu Arg
1               5                   10                  15

<210> SEQ ID NO 1301
<211> LENGTH: 15
<212> TYPE: PRT
<213> ORGANISM: Homo sapiens

<400> SEQUENCE: 1301

Met Val Leu Leu Glu Gln Leu Phe Leu Asp His Asn Ala Leu Arg
1               5                   10                  15

<210> SEQ ID NO 1302
<211> LENGTH: 22
<212> TYPE: PRT
<213> ORGANISM: Homo sapiens

<400> SEQUENCE: 1302

Leu Val Ser Leu Asp Ser Gly Leu Leu Asn Ser Leu Gly Ala Leu Thr
1               5                   10                  15

Glu Leu Gln Phe His Arg
            20

<210> SEQ ID NO 1303
<211> LENGTH: 12
<212> TYPE: PRT
<213> ORGANISM: Homo sapiens

<400> SEQUENCE: 1303

Ala Leu Leu Ala Tyr Ala Phe Ser Leu Leu Gly Lys
1               5                   10

<210> SEQ ID NO 1304
<211> LENGTH: 12
<212> TYPE: PRT
<213> ORGANISM: Homo sapiens

<400> SEQUENCE: 1304

Asp Leu Phe His Cys Val Ser Phe Thr Leu Pro Arg
1               5                   10

<210> SEQ ID NO 1305
<211> LENGTH: 12

<212> TYPE: PRT
<213> ORGANISM: Homo sapiens

<400> SEQUENCE: 1305

Met Leu Gln Ile Thr Asn Thr Gly Phe Glu Met Lys
1               5                   10

<210> SEQ ID NO 1306
<211> LENGTH: 14
<212> TYPE: PRT
<213> ORGANISM: Homo sapiens

<400> SEQUENCE: 1306

Asn Glu Leu Ile Pro Leu Ile Tyr Leu Glu Asn Pro Arg Arg
1               5                   10

<210> SEQ ID NO 1307
<211> LENGTH: 22
<212> TYPE: PRT
<213> ORGANISM: Homo sapiens

<400> SEQUENCE: 1307

Ser Tyr Ile Phe Ile Asp Glu Ala His Ile Thr Gln Ser Leu Thr Trp
1               5                   10                  15

Leu Ser Gln Met Gln Lys
            20

<210> SEQ ID NO 1308
<211> LENGTH: 16
<212> TYPE: PRT
<213> ORGANISM: Homo sapiens

<400> SEQUENCE: 1308

Ser Asp Pro Val Thr Leu Asn Leu Leu His Gly Pro Asp Leu Pro Arg
1               5                   10                  15

<210> SEQ ID NO 1309
<211> LENGTH: 9
<212> TYPE: PRT
<213> ORGANISM: Homo sapiens

<400> SEQUENCE: 1309

Thr Leu Phe Leu Phe Gly Val Thr Lys
1               5

<210> SEQ ID NO 1310
<211> LENGTH: 11
<212> TYPE: PRT
<213> ORGANISM: Homo sapiens

<400> SEQUENCE: 1310

Ser Asp Pro Val Thr Leu Asn Leu Leu Pro Lys
1               5                   10

<210> SEQ ID NO 1311
<211> LENGTH: 6
<212> TYPE: PRT
<213> ORGANISM: Homo sapiens

<400> SEQUENCE: 1311

Val Leu Gln Leu Glu Lys
1               5

<210> SEQ ID NO 1312

```
<211> LENGTH: 19
<212> TYPE: PRT
<213> ORGANISM: Homo sapiens

<400> SEQUENCE: 1312

Val Val Ala Gln Gly Val Gly Ile Pro Glu Asp Ser Ile Phe Thr Met
1               5                   10                  15

Ala Asp Arg

<210> SEQ ID NO 1313
<211> LENGTH: 26
<212> TYPE: PRT
<213> ORGANISM: Homo sapiens

<400> SEQUENCE: 1313

Leu Thr Glu Arg Glu Trp Ala Asp Glu Trp Lys His Leu Asp His Ala
1               5                   10                  15

Leu Asn Cys Ile Met Glu Met Val Glu Lys
            20                  25

<210> SEQ ID NO 1314
<211> LENGTH: 19
<212> TYPE: PRT
<213> ORGANISM: Homo sapiens

<400> SEQUENCE: 1314

Ala Leu Cys Gly Gly Asp Gly Ala Ala Ala Leu Arg Glu Pro Gly Ala
1               5                   10                  15

Gly Leu Arg

<210> SEQ ID NO 1315
<211> LENGTH: 22
<212> TYPE: PRT
<213> ORGANISM: Homo sapiens

<400> SEQUENCE: 1315

Ala Leu Met Asp Leu Leu Ala Gly Lys Gly Ser Gln Gly Ser Gln Ala
1               5                   10                  15

Pro Gln Ala Leu Asp Arg
            20

<210> SEQ ID NO 1316
<211> LENGTH: 21
<212> TYPE: PRT
<213> ORGANISM: Homo sapiens

<400> SEQUENCE: 1316

Met Gly Asp His Leu Ala Leu Glu Asp Tyr Leu Thr Thr Asp Leu Val
1               5                   10                  15

Glu Thr Trp Leu Arg
            20

<210> SEQ ID NO 1317
<211> LENGTH: 15
<212> TYPE: PRT
<213> ORGANISM: Homo sapiens

<400> SEQUENCE: 1317

Ser Pro Gln Glu Leu Leu Cys Gly Ala Ser Leu Ile Ser Asp Arg
1               5                   10                  15

<210> SEQ ID NO 1318
```

```
<211> LENGTH: 19
<212> TYPE: PRT
<213> ORGANISM: Homo sapiens

<400> SEQUENCE: 1318

Leu Ala Val Thr Thr His Gly Leu Pro Cys Leu Ala Trp Ala Ser Ala
1               5                   10                  15

Gln Ala Lys

<210> SEQ ID NO 1319
<211> LENGTH: 19
<212> TYPE: PRT
<213> ORGANISM: Homo sapiens

<400> SEQUENCE: 1319

Ser Glu Gly Ser Ser Val Asn Leu Ser Pro Pro Leu Glu Gln Cys Val
1               5                   10                  15

Pro Asp Arg

<210> SEQ ID NO 1320
<211> LENGTH: 9
<212> TYPE: PRT
<213> ORGANISM: Homo sapiens

<400> SEQUENCE: 1320

Ser Gly Ile Glu Cys Gln Leu Trp Arg
1               5

<210> SEQ ID NO 1321
<211> LENGTH: 17
<212> TYPE: PRT
<213> ORGANISM: Homo sapiens

<400> SEQUENCE: 1321

Val Thr Gly Trp Gly Asn Leu Lys Glu Thr Trp Thr Ala Asn Val Gly
1               5                   10                  15

Lys

<210> SEQ ID NO 1322
<211> LENGTH: 7
<212> TYPE: PRT
<213> ORGANISM: Homo sapiens

<400> SEQUENCE: 1322

Ile His Leu Met Ala Gly Arg
1               5

<210> SEQ ID NO 1323
<211> LENGTH: 7
<212> TYPE: PRT
<213> ORGANISM: Homo sapiens

<400> SEQUENCE: 1323

Pro Ala His Pro Ala Leu Arg
1               5

<210> SEQ ID NO 1324
<211> LENGTH: 6
<212> TYPE: PRT
<213> ORGANISM: Homo sapiens

<400> SEQUENCE: 1324

Ile Ser Asn Ile Ile Lys
```

```
1               5
```

```
<210> SEQ ID NO 1325
<211> LENGTH: 12
<212> TYPE: PRT
<213> ORGANISM: Homo sapiens

<400> SEQUENCE: 1325

Met Lys Tyr Trp Gly Val Ala Ser Phe Leu Gln Lys
1               5                   10

<210> SEQ ID NO 1326
<211> LENGTH: 10
<212> TYPE: PRT
<213> ORGANISM: Homo sapiens

<400> SEQUENCE: 1326

Phe Ser Gly Thr Trp Tyr Ala Met Ala Lys
1               5                   10

<210> SEQ ID NO 1327
<211> LENGTH: 18
<212> TYPE: PRT
<213> ORGANISM: Homo sapiens

<400> SEQUENCE: 1327

Leu Leu Asn Leu Asp Gly Thr Cys Ala Asp Ser Tyr Ser Phe Val Phe
1               5                   10                  15

Ser Arg

<210> SEQ ID NO 1328
<211> LENGTH: 25
<212> TYPE: PRT
<213> ORGANISM: Homo sapiens

<400> SEQUENCE: 1328

Leu Leu Asn Asn Trp Asp Val Cys Ala Asp Met Val Gly Thr Phe Thr
1               5                   10                  15

Asp Thr Glu Asp Pro Ala Lys Phe Lys
            20                  25

<210> SEQ ID NO 1329
<211> LENGTH: 26
<212> TYPE: PRT
<213> ORGANISM: Homo sapiens

<400> SEQUENCE: 1329

Leu Phe Leu Gly Ala Leu Pro Gly Glu Asp Ser Ser Thr Ser Phe Cys
1               5                   10                  15

Leu Asn Gly Leu Trp Ala Gln Gly Gln Arg
            20                  25

<210> SEQ ID NO 1330
<211> LENGTH: 9
<212> TYPE: PRT
<213> ORGANISM: Homo sapiens

<400> SEQUENCE: 1330

Asp Asp Trp Phe Met Leu Gly Leu Arg
1               5

<210> SEQ ID NO 1331
<211> LENGTH: 23
```

<212> TYPE: PRT
<213> ORGANISM: Homo sapiens

<400> SEQUENCE: 1331

Ser Cys Asp Val Glu Ser Asn Pro Gly Ile Phe Leu Pro Pro Gly Thr
1               5                   10                  15

Gln Ala Glu Phe Asn Leu Arg
            20

<210> SEQ ID NO 1332
<211> LENGTH: 25
<212> TYPE: PRT
<213> ORGANISM: Homo sapiens

<400> SEQUENCE: 1332

Thr Trp Asp Pro Glu Gly Val Ile Phe Tyr Gly Asp Thr Asn Pro Lys
1               5                   10                  15

Asp Asp Trp Phe Met Leu Gly Leu Arg
            20                  25

<210> SEQ ID NO 1333
<211> LENGTH: 24
<212> TYPE: PRT
<213> ORGANISM: Homo sapiens

<400> SEQUENCE: 1333

Lys Phe Cys Arg Asp Ile Gln Asp Pro Thr Gln Leu Ala Glu Met Ile
1               5                   10                  15

Phe Asn Leu Leu Leu Glu Glu Lys
            20

<210> SEQ ID NO 1334
<211> LENGTH: 14
<212> TYPE: PRT
<213> ORGANISM: Homo sapiens

<400> SEQUENCE: 1334

Asn Glu Leu Ile Arg Gln Glu Lys Leu Glu Gln Leu Ala Arg
1               5                   10

<210> SEQ ID NO 1335
<211> LENGTH: 6
<212> TYPE: PRT
<213> ORGANISM: Homo sapiens

<400> SEQUENCE: 1335

Lys Asn Leu Ser Glu Arg
1               5

<210> SEQ ID NO 1336
<211> LENGTH: 10
<212> TYPE: PRT
<213> ORGANISM: Homo sapiens

<400> SEQUENCE: 1336

Lys Trp Tyr Asn Leu Met Ile Gln Asn Lys
1               5                   10

<210> SEQ ID NO 1337
<211> LENGTH: 14
<212> TYPE: PRT
<213> ORGANISM: Homo sapiens

<400> SEQUENCE: 1337

Ser Arg Leu Asp Thr Leu Ala Gln Glu Val Ala Leu Leu Lys
1               5                    10

<210> SEQ ID NO 1338
<211> LENGTH: 14
<212> TYPE: PRT
<213> ORGANISM: Homo sapiens

<400> SEQUENCE: 1338

Arg Leu Asp Val Asn Ala Ala Gly Ile Trp Glu Pro Lys Lys
1               5                    10

<210> SEQ ID NO 1339
<211> LENGTH: 26
<212> TYPE: PRT
<213> ORGANISM: Homo sapiens

<400> SEQUENCE: 1339

Glu Leu Ile Ser Asp Leu Glu His Arg Leu Gln Gly Ser Val Met Glu
1               5                    10                  15

Leu Leu Gln Gly Val Asp Gly Val Ile Lys
            20                  25

<210> SEQ ID NO 1340
<211> LENGTH: 13
<212> TYPE: PRT
<213> ORGANISM: Homo sapiens

<400> SEQUENCE: 1340

Glu Asp Phe Thr Ser Leu Ser Leu Val Leu Tyr Ser Arg
1               5                    10

<210> SEQ ID NO 1341
<211> LENGTH: 25
<212> TYPE: PRT
<213> ORGANISM: Homo sapiens

<400> SEQUENCE: 1341

Glu Leu Ser Ser Phe Ile Asp Lys Gly Gln Glu Leu Cys Ala Asp Tyr
1               5                    10                  15

Ser Glu Asn Thr Phe Thr Glu Tyr Lys
            20                  25

<210> SEQ ID NO 1342
<211> LENGTH: 26
<212> TYPE: PRT
<213> ORGANISM: Homo sapiens

<400> SEQUENCE: 1342

Glu Leu Ser Ser Phe Ile Asp Lys Gly Gln Glu Leu Cys Ala Asp Tyr
1               5                    10                  15

Ser Glu Asn Thr Phe Thr Glu Tyr Lys Lys
            20                  25

<210> SEQ ID NO 1343
<211> LENGTH: 22
<212> TYPE: PRT
<213> ORGANISM: Homo sapiens

<400> SEQUENCE: 1343

Glu Val Val Ser Leu Thr Glu Ala Cys Cys Ala Glu Gly Ala Asp Pro
1               5                    10                  15

-continued

```
Asp Cys Tyr Asp Thr Arg
        20

<210> SEQ ID NO 1344
<211> LENGTH: 38
<212> TYPE: PRT
<213> ORGANISM: Homo sapiens

<400> SEQUENCE: 1344

Thr Ala Met Asp Val Phe Val Cys Thr Tyr Phe Met Pro Ala Ala Gln
1               5                   10                  15

Leu Pro Glu Leu Pro Asp Val Glu Leu Pro Thr Asn Lys Asp Val Cys
            20                  25                  30

Asp Pro Gly Asn Thr Lys
        35

<210> SEQ ID NO 1345
<211> LENGTH: 11
<212> TYPE: PRT
<213> ORGANISM: Homo sapiens

<400> SEQUENCE: 1345

Arg Thr His Leu Pro Glu Val Phe Leu Ser Lys
1               5                   10

<210> SEQ ID NO 1346
<211> LENGTH: 11
<212> TYPE: PRT
<213> ORGANISM: Homo sapiens

<400> SEQUENCE: 1346

Val Cys Ser Gln Tyr Ala Ala Tyr Gly Glu Lys
1               5                   10

<210> SEQ ID NO 1347
<211> LENGTH: 18
<212> TYPE: PRT
<213> ORGANISM: Homo sapiens

<400> SEQUENCE: 1347

Leu Ile Arg Asp Val Trp Gly Ile Glu Gly Pro Ile Asp Ala Ala Phe
1               5                   10                  15

Thr Arg

<210> SEQ ID NO 1348
<211> LENGTH: 15
<212> TYPE: PRT
<213> ORGANISM: Homo sapiens

<400> SEQUENCE: 1348

Asp Val Trp Gly Ile Glu Gly Pro Ile Asp Ala Ala Phe Thr Arg
1               5                   10                  15

<210> SEQ ID NO 1349
<211> LENGTH: 7
<212> TYPE: PRT
<213> ORGANISM: Homo sapiens

<400> SEQUENCE: 1349

Glu Arg Val Tyr Phe Phe Lys
1               5

<210> SEQ ID NO 1350
```

```
<211> LENGTH: 12
<212> TYPE: PRT
<213> ORGANISM: Homo sapiens

<400> SEQUENCE: 1350

Phe Glu Asp Gly Val Leu Asp Pro Asp Tyr Pro Arg
1               5               10

<210> SEQ ID NO 1351
<211> LENGTH: 14
<212> TYPE: PRT
<213> ORGANISM: Homo sapiens

<400> SEQUENCE: 1351

Ile Tyr Ile Ser Gly Met Ala Pro Arg Pro Ser Leu Ala Lys
1               5               10

<210> SEQ ID NO 1352
<211> LENGTH: 6
<212> TYPE: PRT
<213> ORGANISM: Homo sapiens

<400> SEQUENCE: 1352

Thr Arg Phe Leu Leu Arg
1               5

<210> SEQ ID NO 1353
<211> LENGTH: 21
<212> TYPE: PRT
<213> ORGANISM: Homo sapiens

<400> SEQUENCE: 1353

Asn Pro Phe Val Phe Ala Pro Thr Leu Leu Thr Val Ala Val His Phe
1               5               10                  15

Glu Glu Val Ala Lys
            20

<210> SEQ ID NO 1354
<211> LENGTH: 10
<212> TYPE: PRT
<213> ORGANISM: Homo sapiens

<400> SEQUENCE: 1354

Ala Asp Leu Ser Gly Ile Thr Gly Ala Arg
1               5               10

<210> SEQ ID NO 1355
<211> LENGTH: 15
<212> TYPE: PRT
<213> ORGANISM: Homo sapiens

<400> SEQUENCE: 1355

Met Glu Glu Val Glu Ala Met Leu Leu Pro Glu Thr Leu Lys Arg
1               5               10                  15

<210> SEQ ID NO 1356
<211> LENGTH: 14
<212> TYPE: PRT
<213> ORGANISM: Homo sapiens

<400> SEQUENCE: 1356

Trp Glu Met Pro Phe Asp Pro Gln Asp Thr His Gln Ser Arg
1               5               10
```

-continued

```
<210> SEQ ID NO 1357
<211> LENGTH: 18
<212> TYPE: PRT
<213> ORGANISM: Homo sapiens

<400> SEQUENCE: 1357

Leu Tyr Gly Ser Glu Ala Phe Ala Thr Asp Phe Gln Asp Ser Ala Ala
1               5                   10                  15

Ala Lys

<210> SEQ ID NO 1358
<211> LENGTH: 12
<212> TYPE: PRT
<213> ORGANISM: Homo sapiens

<400> SEQUENCE: 1358

His Gln Phe Leu Leu Thr Gly Asp Thr Gln Gly Arg
1               5                   10

<210> SEQ ID NO 1359
<211> LENGTH: 16
<212> TYPE: PRT
<213> ORGANISM: Homo sapiens

<400> SEQUENCE: 1359

Asn Gly Val Ala Gln Glu Pro Val His Leu Asp Ser Pro Ala Ile Lys
1               5                   10                  15

<210> SEQ ID NO 1360
<211> LENGTH: 20
<212> TYPE: PRT
<213> ORGANISM: Homo sapiens

<400> SEQUENCE: 1360

Ser Leu Pro Ala Pro Trp Leu Ser Met Ala Pro Val Ser Trp Ile Thr
1               5                   10                  15

Pro Gly Leu Lys
            20

<210> SEQ ID NO 1361
<211> LENGTH: 18
<212> TYPE: PRT
<213> ORGANISM: Homo sapiens

<400> SEQUENCE: 1361

Val Thr Leu Thr Cys Val Ala Pro Leu Ser Gly Val Asp Phe Gln Leu
1               5                   10                  15

Arg Arg

<210> SEQ ID NO 1362
<211> LENGTH: 9
<212> TYPE: PRT
<213> ORGANISM: Homo sapiens

<400> SEQUENCE: 1362

Cys Leu Ala Pro Leu Glu Gly Ala Arg
1               5

<210> SEQ ID NO 1363
<211> LENGTH: 7
<212> TYPE: PRT
<213> ORGANISM: Homo sapiens

<400> SEQUENCE: 1363
```

Gly Val Thr Phe Leu Leu Arg
1               5

<210> SEQ ID NO 1364
<211> LENGTH: 37
<212> TYPE: PRT
<213> ORGANISM: Homo sapiens

<400> SEQUENCE: 1364

Leu His Asp Asn Gln Asn Gly Trp Ser Gly Asp Ser Ala Pro Val Glu
1               5                   10                  15

Leu Ile Leu Ser Asp Glu Thr Leu Pro Ala Pro Glu Phe Ser Pro Glu
            20                  25                  30

Pro Glu Ser Gly Arg
        35

<210> SEQ ID NO 1365
<211> LENGTH: 22
<212> TYPE: PRT
<213> ORGANISM: Homo sapiens

<400> SEQUENCE: 1365

Thr Pro Gly Ala Ala Ala Asn Leu Glu Leu Ile Phe Val Gly Pro Gln
1               5                   10                  15

His Ala Gly Asn Tyr Arg
            20

<210> SEQ ID NO 1366
<211> LENGTH: 24
<212> TYPE: PRT
<213> ORGANISM: Homo sapiens

<400> SEQUENCE: 1366

His Gln Met Asp Leu Val Ala Thr Leu Ser Gln Leu Gly Leu Gln Glu
1               5                   10                  15

Leu Phe Gln Ala Pro Asp Leu Arg
            20

<210> SEQ ID NO 1367
<211> LENGTH: 11
<212> TYPE: PRT
<213> ORGANISM: Homo sapiens

<400> SEQUENCE: 1367

Leu Cys Gln Asp Leu Gly Pro Gly Ala Phe Arg
1               5                   10

<210> SEQ ID NO 1368
<211> LENGTH: 17
<212> TYPE: PRT
<213> ORGANISM: Homo sapiens

<400> SEQUENCE: 1368

Trp Phe Leu Leu Glu Gln Pro Glu Ile Gln Val Ala His Phe Pro Phe
1               5                   10                  15

Lys

<210> SEQ ID NO 1369
<211> LENGTH: 32
<212> TYPE: PRT
<213> ORGANISM: Homo sapiens

<400> SEQUENCE: 1369

Val Trp Pro Gln Gln Pro Ser Gly Glu Leu Phe Glu Ile Glu Ile Asp
1               5                   10                  15

Thr Leu Glu Thr Thr Cys His Val Leu Asp Pro Thr Pro Val Ala Arg
            20                  25                  30

<210> SEQ ID NO 1370
<211> LENGTH: 20
<212> TYPE: PRT
<213> ORGANISM: Homo sapiens

<400> SEQUENCE: 1370

His Thr Phe Met Gly Val Val Ser Leu Gly Ser Pro Ser Gly Glu Val
1               5                   10                  15

Ser His Pro Arg
            20

<210> SEQ ID NO 1371
<211> LENGTH: 29
<212> TYPE: PRT
<213> ORGANISM: Homo sapiens

<400> SEQUENCE: 1371

Gln Pro Asn Cys Asp Asp Pro Glu Thr Glu Glu Ala Ala Leu Val Ala
1               5                   10                  15

Ile Asp Tyr Ile Asn Gln Asn Leu Pro Trp Gly Tyr Lys
            20                  25

<210> SEQ ID NO 1372
<211> LENGTH: 21
<212> TYPE: PRT
<213> ORGANISM: Homo sapiens

<400> SEQUENCE: 1372

Thr Val Val Gln Pro Ser Val Gly Ala Ala Ala Gly Pro Val Val Pro
1               5                   10                  15

Pro Cys Pro Gly Arg
            20

<210> SEQ ID NO 1373
<211> LENGTH: 17
<212> TYPE: PRT
<213> ORGANISM: Homo sapiens

<400> SEQUENCE: 1373

Gln Pro Phe Val Gln Gly Leu Ala Leu Tyr Thr Pro Val Val Leu Pro
1               5                   10                  15

Arg

<210> SEQ ID NO 1374
<211> LENGTH: 11
<212> TYPE: PRT
<213> ORGANISM: Homo sapiens

<400> SEQUENCE: 1374

Leu Val Pro Phe Ala Thr Glu Leu His Glu Arg
1               5                   10

<210> SEQ ID NO 1375
<211> LENGTH: 11
<212> TYPE: PRT
<213> ORGANISM: Homo sapiens

<400> SEQUENCE: 1375

Leu Leu Pro His Ala Asn Glu Val Ser Gln Lys
1               5                   10

<210> SEQ ID NO 1376
<211> LENGTH: 25
<212> TYPE: PRT
<213> ORGANISM: Homo sapiens

<400> SEQUENCE: 1376

Ser Leu Ala Pro Tyr Ala Gln Asp Thr Gln Glu Lys Leu Asn His Gln
1               5                   10                  15

Leu Glu Gly Leu Thr Phe Gln Met Lys
            20                  25

<210> SEQ ID NO 1377
<211> LENGTH: 9
<212> TYPE: PRT
<213> ORGANISM: Homo sapiens

<400> SEQUENCE: 1377

Phe Pro Glu Val Asp Val Leu Thr Lys
1               5

<210> SEQ ID NO 1378
<211> LENGTH: 9
<212> TYPE: PRT
<213> ORGANISM: Homo sapiens

<400> SEQUENCE: 1378

His Ile Asn Ile Asp Gln Phe Val Arg
1               5

<210> SEQ ID NO 1379
<211> LENGTH: 15
<212> TYPE: PRT
<213> ORGANISM: Homo sapiens

<400> SEQUENCE: 1379

Leu Leu Ser Gly Gly Asn Thr Leu His Leu Val Ser Thr Thr Lys
1               5                   10                  15

<210> SEQ ID NO 1380
<211> LENGTH: 19
<212> TYPE: PRT
<213> ORGANISM: Homo sapiens

<400> SEQUENCE: 1380

Gln Val Phe Leu Tyr Pro Glu Lys Asp Glu Pro Thr Tyr Ile Leu Asn
1               5                   10                  15

Ile Lys Arg

<210> SEQ ID NO 1381
<211> LENGTH: 8
<212> TYPE: PRT
<213> ORGANISM: Homo sapiens

<400> SEQUENCE: 1381

Ser Leu His Met Tyr Ala Asn Arg
1               5

<210> SEQ ID NO 1382

-continued

```
<211> LENGTH: 17
<212> TYPE: PRT
<213> ORGANISM: Homo sapiens

<400> SEQUENCE: 1382

Ser Val Ser Asp Gly Ile Ala Ala Leu Asp Leu Asn Ala Val Ala Asn
1               5                   10                  15

Lys

<210> SEQ ID NO 1383
<211> LENGTH: 28
<212> TYPE: PRT
<213> ORGANISM: Homo sapiens

<400> SEQUENCE: 1383

Ser Val Ser Leu Pro Ser Leu Asp Pro Ala Ser Ala Lys Ile Glu Gly
1               5                   10                  15

Asn Leu Ile Phe Asp Pro Asn Asn Tyr Leu Pro Lys
            20                  25

<210> SEQ ID NO 1384
<211> LENGTH: 11
<212> TYPE: PRT
<213> ORGANISM: Homo sapiens

<400> SEQUENCE: 1384

Thr Glu Val Ile Pro Pro Leu Ile Glu Asn Arg
1               5                   10

<210> SEQ ID NO 1385
<211> LENGTH: 10
<212> TYPE: PRT
<213> ORGANISM: Homo sapiens

<400> SEQUENCE: 1385

Val Leu Val Asp His Phe Gly Tyr Thr Lys
1               5                   10

<210> SEQ ID NO 1386
<211> LENGTH: 24
<212> TYPE: PRT
<213> ORGANISM: Homo sapiens

<400> SEQUENCE: 1386

Thr Ser Ser Phe Ala Leu Asn Leu Pro Thr Leu Pro Glu Val Lys Phe
1               5                   10                  15

Pro Glu Val Asp Val Leu Thr Lys
            20

<210> SEQ ID NO 1387
<211> LENGTH: 18
<212> TYPE: PRT
<213> ORGANISM: Homo sapiens

<400> SEQUENCE: 1387

Gly Trp Val Thr Asp Gly Phe Ser Ser Leu Lys Asp Tyr Trp Ser Thr
1               5                   10                  15

Val Lys

<210> SEQ ID NO 1388
<211> LENGTH: 15
<212> TYPE: PRT
<213> ORGANISM: Homo sapiens
```

-continued

<400> SEQUENCE: 1388

```
Gly Glu Val Gln Ala Met Leu Gly Gln Ser Thr Glu Glu Leu Arg
1               5                   10                  15
```

<210> SEQ ID NO 1389
<211> LENGTH: 9
<212> TYPE: PRT
<213> ORGANISM: Homo sapiens

<400> SEQUENCE: 1389

```
Leu Ala Val Tyr Gln Ala Gly Ala Arg
1               5
```

<210> SEQ ID NO 1390
<211> LENGTH: 9
<212> TYPE: PRT
<213> ORGANISM: Homo sapiens

<400> SEQUENCE: 1390

```
Leu Gly Pro Leu Val Glu Gln Gly Arg
1               5
```

<210> SEQ ID NO 1391
<211> LENGTH: 10
<212> TYPE: PRT
<213> ORGANISM: Homo sapiens

<400> SEQUENCE: 1391

```
Leu Thr Leu Thr Pro Trp Val Gly Leu Arg
1               5                   10
```

<210> SEQ ID NO 1392
<211> LENGTH: 15
<212> TYPE: PRT
<213> ORGANISM: Homo sapiens

<400> SEQUENCE: 1392

```
Phe Ile Cys Pro Leu Thr Gly Leu Trp Pro Ile Asn Thr Leu Lys
1               5                   10                  15
```

<210> SEQ ID NO 1393
<211> LENGTH: 20
<212> TYPE: PRT
<213> ORGANISM: Homo sapiens

<400> SEQUENCE: 1393

```
Thr Phe Tyr Glu Pro Gly Glu Glu Ile Thr Tyr Ser Cys Lys Pro Gly
1               5                   10                  15

Tyr Val Ser Arg
            20
```

<210> SEQ ID NO 1394
<211> LENGTH: 25
<212> TYPE: PRT
<213> ORGANISM: Homo sapiens

<400> SEQUENCE: 1394

```
Met Val Val Ser Met Thr Leu Gly Leu His Pro Trp Ile Ala Asn Ile
1               5                   10                  15

Asp Asp Thr Gln Tyr Leu Ala Ala Lys
            20                  25
```

-continued

```
<210> SEQ ID NO 1395
<211> LENGTH: 17
<212> TYPE: PRT
<213> ORGANISM: Homo sapiens

<400> SEQUENCE: 1395

Thr Ser Ile Tyr Pro Phe Leu Asp Phe Met Pro Ser Pro Gln Val Val
1               5                   10                  15

Arg

<210> SEQ ID NO 1396
<211> LENGTH: 15
<212> TYPE: PRT
<213> ORGANISM: Homo sapiens

<400> SEQUENCE: 1396

Glu Leu Met Leu Gln Leu Ser Glu Phe Leu Cys Glu Glu Phe Arg
1               5                   10                  15

<210> SEQ ID NO 1397
<211> LENGTH: 22
<212> TYPE: PRT
<213> ORGANISM: Homo sapiens

<400> SEQUENCE: 1397

Ala Glu Glu Glu His Leu Gly Ile Leu Gly Pro Gln Leu His Ala Asp
1               5                   10                  15

Val Gly Asp Lys Val Lys
            20

<210> SEQ ID NO 1398
<211> LENGTH: 12
<212> TYPE: PRT
<213> ORGANISM: Homo sapiens

<400> SEQUENCE: 1398

Ala Leu Tyr Leu Gln Tyr Thr Asp Glu Thr Phe Arg
1               5                   10

<210> SEQ ID NO 1399
<211> LENGTH: 26
<212> TYPE: PRT
<213> ORGANISM: Homo sapiens

<400> SEQUENCE: 1399

Asp Val Asp Lys Glu Phe Tyr Leu Phe Pro Thr Val Phe Asp Glu Asn
1               5                   10                  15

Glu Ser Leu Leu Leu Glu Asp Asn Ile Arg
            20                  25

<210> SEQ ID NO 1400
<211> LENGTH: 20
<212> TYPE: PRT
<213> ORGANISM: Homo sapiens

<400> SEQUENCE: 1400

His Tyr Tyr Ile Gly Ile Ile Glu Thr Thr Trp Asp Tyr Ala Ser Asp
1               5                   10                  15

His Gly Glu Lys
            20

<210> SEQ ID NO 1401
<211> LENGTH: 11
```

-continued

```
<212> TYPE: PRT
<213> ORGANISM: Homo sapiens

<400> SEQUENCE: 1401

Glu Tyr Thr Asp Ala Ser Phe Thr Asn Arg Lys
1               5                   10

<210> SEQ ID NO 1402
<211> LENGTH: 23
<212> TYPE: PRT
<213> ORGANISM: Homo sapiens

<400> SEQUENCE: 1402

His Tyr Tyr Ile Ala Ala Glu Glu Ile Ile Trp Asn Tyr Ala Pro Ser
1               5                   10                  15

Gly Ile Asp Ile Phe Thr Lys
            20

<210> SEQ ID NO 1403
<211> LENGTH: 10
<212> TYPE: PRT
<213> ORGANISM: Homo sapiens

<400> SEQUENCE: 1403

Ile Tyr His Ser His Ile Asp Ala Pro Lys
1               5                   10

<210> SEQ ID NO 1404
<211> LENGTH: 28
<212> TYPE: PRT
<213> ORGANISM: Homo sapiens

<400> SEQUENCE: 1404

Gln Lys Asp Val Asp Lys Glu Phe Tyr Leu Phe Pro Thr Val Phe Asp
1               5                   10                  15

Glu Asn Glu Ser Leu Leu Leu Glu Asp Asn Ile Arg
            20                  25

<210> SEQ ID NO 1405
<211> LENGTH: 17
<212> TYPE: PRT
<213> ORGANISM: Homo sapiens

<400> SEQUENCE: 1405

Thr Tyr Tyr Ile Ala Ala Val Glu Val Glu Trp Asp Tyr Ser Pro Gln
1               5                   10                  15

Arg

<210> SEQ ID NO 1406
<211> LENGTH: 9
<212> TYPE: PRT
<213> ORGANISM: Homo sapiens

<400> SEQUENCE: 1406

Ser Ala Leu Val Leu Gln Tyr Leu Arg
1               5

<210> SEQ ID NO 1407
<211> LENGTH: 12
<212> TYPE: PRT
<213> ORGANISM: Homo sapiens

<400> SEQUENCE: 1407
```

-continued

```
Glu Phe Asn Pro Leu Val Ile Val Gly Leu Ser Lys
1               5                   10

<210> SEQ ID NO 1408
<211> LENGTH: 15
<212> TYPE: PRT
<213> ORGANISM: Homo sapiens

<400> SEQUENCE: 1408

Asn Pro Asp Asn Asp Ile Arg Pro Trp Cys Phe Val Leu Asn Arg
1               5                   10                  15

<210> SEQ ID NO 1409
<211> LENGTH: 24
<212> TYPE: PRT
<213> ORGANISM: Homo sapiens

<400> SEQUENCE: 1409

Asn Ser Leu Leu Gly Met Glu Gly Ala Asn Ser Ile Phe Ser Gly Phe
1               5                   10                  15

Leu Leu Phe Pro Asp Met Glu Ala
            20

<210> SEQ ID NO 1410
<211> LENGTH: 13
<212> TYPE: PRT
<213> ORGANISM: Homo sapiens

<400> SEQUENCE: 1410

Gln Thr His Gln Pro Pro Ala Pro Asn Ser Leu Ile Arg
1               5                   10

<210> SEQ ID NO 1411
<211> LENGTH: 14
<212> TYPE: PRT
<213> ORGANISM: Homo sapiens

<400> SEQUENCE: 1411

Leu Pro Val Ala Asn Pro Gln Ala Cys Glu Asn Trp Leu Arg
1               5                   10

<210> SEQ ID NO 1412
<211> LENGTH: 16
<212> TYPE: PRT
<213> ORGANISM: Homo sapiens

<400> SEQUENCE: 1412

Asn Gln Gly Ile Leu Glu Phe Tyr Gly Asp Asp Ile Ala Leu Leu Lys
1               5                   10                  15

<210> SEQ ID NO 1413
<211> LENGTH: 14
<212> TYPE: PRT
<213> ORGANISM: Homo sapiens

<400> SEQUENCE: 1413

Arg Asn Asp Tyr Leu Asp Ile Tyr Ala Ile Gly Val Gly Lys
1               5                   10

<210> SEQ ID NO 1414
<211> LENGTH: 31
<212> TYPE: PRT
<213> ORGANISM: Homo sapiens

<400> SEQUENCE: 1414
```

-continued

```
Gln Pro Tyr Ser Tyr Asp Phe Pro Glu Asp Val Ala Pro Ala Leu Gly
1               5                   10                  15

Thr Ser Phe Ser His Met Leu Gly Ala Thr Asn Pro Thr Gln Lys
            20                  25                  30

<210> SEQ ID NO 1415
<211> LENGTH: 10
<212> TYPE: PRT
<213> ORGANISM: Homo sapiens

<400> SEQUENCE: 1415

Ile His Trp Glu Ser Ala Ser Leu Leu Arg
1               5                   10

<210> SEQ ID NO 1416
<211> LENGTH: 7
<212> TYPE: PRT
<213> ORGANISM: Homo sapiens

<400> SEQUENCE: 1416

Phe Ala Cys Tyr Tyr Pro Arg
1               5

<210> SEQ ID NO 1417
<211> LENGTH: 26
<212> TYPE: PRT
<213> ORGANISM: Homo sapiens

<400> SEQUENCE: 1417

Leu His Leu Glu Thr Asp Ser Leu Ala Leu Val Ala Leu Gly Ala Leu
1               5                   10                  15

Asp Thr Ala Leu Tyr Ala Ala Gly Ser Lys
            20                  25

<210> SEQ ID NO 1418
<211> LENGTH: 12
<212> TYPE: PRT
<213> ORGANISM: Homo sapiens

<400> SEQUENCE: 1418

Leu Val Asn Gly Gln Ser His Ile Ser Leu Ser Lys
1               5                   10

<210> SEQ ID NO 1419
<211> LENGTH: 9
<212> TYPE: PRT
<213> ORGANISM: Homo sapiens

<400> SEQUENCE: 1419

Ser Cys Gly Leu His Gln Leu Leu Arg
1               5

<210> SEQ ID NO 1420
<211> LENGTH: 9
<212> TYPE: PRT
<213> ORGANISM: Homo sapiens

<400> SEQUENCE: 1420

Tyr Val Leu Pro Asn Phe Glu Val Lys
1               5

<210> SEQ ID NO 1421
<211> LENGTH: 19
```

<212> TYPE: PRT
<213> ORGANISM: Homo sapiens

<400> SEQUENCE: 1421

Ala Leu Glu Ile Leu Gln Glu Glu Asp Leu Ile Asp Glu Asp Ile
1               5                   10                  15

Pro Val Arg

<210> SEQ ID NO 1422
<211> LENGTH: 31
<212> TYPE: PRT
<213> ORGANISM: Homo sapiens

<400> SEQUENCE: 1422

Glu Cys Val Gly Phe Glu Ala Val Gln Glu Val Pro Val Gly Leu Val
1               5                   10                  15

Gln Pro Ala Ser Ala Thr Leu Tyr Asp Tyr Tyr Asn Pro Glu Arg
            20                  25                  30

<210> SEQ ID NO 1423
<211> LENGTH: 13
<212> TYPE: PRT
<213> ORGANISM: Homo sapiens

<400> SEQUENCE: 1423

Glu Glu Leu Val Tyr Glu Leu Asn Pro Leu Asp His Arg
1               5                   10

<210> SEQ ID NO 1424
<211> LENGTH: 25
<212> TYPE: PRT
<213> ORGANISM: Homo sapiens

<400> SEQUENCE: 1424

Ser Thr Gln Asp Thr Val Ile Ala Leu Asp Ala Leu Ser Ala Tyr Trp
1               5                   10                  15

Ile Ala Ser His Thr Thr Glu Glu Arg
            20                  25

<210> SEQ ID NO 1425
<211> LENGTH: 10
<212> TYPE: PRT
<213> ORGANISM: Homo sapiens

<400> SEQUENCE: 1425

Val Gly Asp Thr Leu Asn Leu Asn Leu Arg
1               5                   10

<210> SEQ ID NO 1426
<211> LENGTH: 9
<212> TYPE: PRT
<213> ORGANISM: Homo sapiens

<400> SEQUENCE: 1426

Val His Tyr Thr Val Cys Ile Trp Arg
1               5

<210> SEQ ID NO 1427
<211> LENGTH: 10
<212> TYPE: PRT
<213> ORGANISM: Homo sapiens

<400> SEQUENCE: 1427

-continued

```
Lys Tyr Val Leu Pro Asn Phe Glu Val Lys
1               5                   10

<210> SEQ ID NO 1428
<211> LENGTH: 24
<212> TYPE: PRT
<213> ORGANISM: Homo sapiens

<400> SEQUENCE: 1428

Val Asp Phe Thr Leu Ser Ser Glu Arg Asp Phe Ala Leu Leu Ser Leu
1               5                   10                  15

Gln Val Pro Leu Lys Asp Ala Lys
            20

<210> SEQ ID NO 1429
<211> LENGTH: 8
<212> TYPE: PRT
<213> ORGANISM: Homo sapiens

<400> SEQUENCE: 1429

Ile Pro Leu Asp Leu Val Pro Lys
1               5

<210> SEQ ID NO 1430
<211> LENGTH: 16
<212> TYPE: PRT
<213> ORGANISM: Homo sapiens

<400> SEQUENCE: 1430

Ser Tyr Phe Pro Glu Ser Trp Leu Trp Glu Val His Leu Val Pro Arg
1               5                   10                  15

<210> SEQ ID NO 1431
<211> LENGTH: 26
<212> TYPE: PRT
<213> ORGANISM: Homo sapiens

<400> SEQUENCE: 1431

Tyr Gly Gly Gly Phe Tyr Ser Thr Gln Asp Thr Ile Asn Ala Ile Glu
1               5                   10                  15

Gly Leu Thr Glu Tyr Ser Leu Leu Val Lys
            20                  25

<210> SEQ ID NO 1432
<211> LENGTH: 18
<212> TYPE: PRT
<213> ORGANISM: Homo sapiens

<400> SEQUENCE: 1432

Tyr Asn Pro Val Val Ile Asp Phe Glu Met Gln Pro Ile His Glu Val
1               5                   10                  15

Leu Arg

<210> SEQ ID NO 1433
<211> LENGTH: 10
<212> TYPE: PRT
<213> ORGANISM: Homo sapiens

<400> SEQUENCE: 1433

His Thr Ser Leu Gly Pro Leu Glu Ala Lys
1               5                   10

<210> SEQ ID NO 1434
```

```
<211> LENGTH: 33
<212> TYPE: PRT
<213> ORGANISM: Homo sapiens

<400> SEQUENCE: 1434

Cys Gln His Glu Met Asp Gln Tyr Trp Gly Ile Gly Ser Leu Ala Ser
1               5                   10                  15

Gly Ile Asn Leu Phe Thr Asn Ser Phe Glu Gly Pro Val Leu Asp His
            20                  25                  30

Arg

<210> SEQ ID NO 1435
<211> LENGTH: 12
<212> TYPE: PRT
<213> ORGANISM: Homo sapiens

<400> SEQUENCE: 1435

Asp Thr Met Val Glu Asp Leu Val Val Leu Val Arg
1               5                   10

<210> SEQ ID NO 1436
<211> LENGTH: 22
<212> TYPE: PRT
<213> ORGANISM: Homo sapiens

<400> SEQUENCE: 1436

Ala Asn Phe Asp Ala Gln Gln Phe Ala Gly Thr Trp Leu Leu Val Ala
1               5                   10                  15

Val Gly Ser Ala Cys Arg
            20

<210> SEQ ID NO 1437
<211> LENGTH: 21
<212> TYPE: PRT
<213> ORGANISM: Homo sapiens

<400> SEQUENCE: 1437

Ala Glu Ala Thr Thr Leu His Val Ala Pro Gln Gly Thr Ala Met Ala
1               5                   10                  15

Val Ser Thr Phe Arg
            20

<210> SEQ ID NO 1438
<211> LENGTH: 13
<212> TYPE: PRT
<213> ORGANISM: Homo sapiens

<400> SEQUENCE: 1438

Asp Val Val Leu Thr Thr Thr Phe Val Asp Asp Ile Lys
1               5                   10

<210> SEQ ID NO 1439
<211> LENGTH: 13
<212> TYPE: PRT
<213> ORGANISM: Homo sapiens

<400> SEQUENCE: 1439

Arg Pro Trp Asn Val Ala Ser Leu Ile Tyr Glu Thr Lys
1               5                   10

<210> SEQ ID NO 1440
<211> LENGTH: 8
<212> TYPE: PRT
```

<213> ORGANISM: Homo sapiens

<400> SEQUENCE: 1440

Ile Ser Val Ile Arg Pro Ser Lys
1               5

<210> SEQ ID NO 1441
<211> LENGTH: 9
<212> TYPE: PRT
<213> ORGANISM: Homo sapiens

<400> SEQUENCE: 1441

Val Ala Ser Tyr Gly Val Lys Pro Arg
1               5

<210> SEQ ID NO 1442
<211> LENGTH: 7
<212> TYPE: PRT
<213> ORGANISM: Homo sapiens

<400> SEQUENCE: 1442

Asp Leu Leu Tyr Ile Gly Lys
1               5

<210> SEQ ID NO 1443
<211> LENGTH: 11
<212> TYPE: PRT
<213> ORGANISM: Homo sapiens

<400> SEQUENCE: 1443

Gly Asp Ser Gly Gly Pro Leu Ile Val His Lys
1               5                   10

<210> SEQ ID NO 1444
<211> LENGTH: 11
<212> TYPE: PRT
<213> ORGANISM: Homo sapiens

<400> SEQUENCE: 1444

Leu Glu Asp Ser Val Thr Tyr His Cys Ser Arg
1               5                   10

<210> SEQ ID NO 1445
<211> LENGTH: 11
<212> TYPE: PRT
<213> ORGANISM: Homo sapiens

<400> SEQUENCE: 1445

Leu Pro Pro Thr Thr Thr Cys Gln Gln Gln Lys
1               5                   10

<210> SEQ ID NO 1446
<211> LENGTH: 9
<212> TYPE: PRT
<213> ORGANISM: Homo sapiens

<400> SEQUENCE: 1446

Cys Leu His Pro Cys Val Ile Ser Arg
1               5

<210> SEQ ID NO 1447
<211> LENGTH: 9
<212> TYPE: PRT
<213> ORGANISM: Homo sapiens

<400> SEQUENCE: 1447

Ile Asp Val His Leu Val Pro Asp Arg
1               5

<210> SEQ ID NO 1448
<211> LENGTH: 14
<212> TYPE: PRT
<213> ORGANISM: Homo sapiens

<400> SEQUENCE: 1448

Ser Ile Asp Val Ala Cys His Pro Gly Tyr Ala Leu Pro Lys
1               5                   10

<210> SEQ ID NO 1449
<211> LENGTH: 23
<212> TYPE: PRT
<213> ORGANISM: Homo sapiens

<400> SEQUENCE: 1449

Val Ser Val Leu Cys Gln Glu Asn Tyr Leu Ile Gln Glu Gly Glu Glu
1               5                   10                  15

Ile Thr Cys Lys Asp Gly Arg
            20

<210> SEQ ID NO 1450
<211> LENGTH: 13
<212> TYPE: PRT
<213> ORGANISM: Homo sapiens

<400> SEQUENCE: 1450

Trp Ser Ser Pro Pro Gln Cys Glu Gly Leu Pro Cys Lys
1               5                   10

<210> SEQ ID NO 1451
<211> LENGTH: 10
<212> TYPE: PRT
<213> ORGANISM: Homo sapiens

<400> SEQUENCE: 1451

Trp Gln Ser Ile Pro Leu Cys Val Glu Lys
1               5                   10

<210> SEQ ID NO 1452
<211> LENGTH: 17
<212> TYPE: PRT
<213> ORGANISM: Homo sapiens

<400> SEQUENCE: 1452

Tyr Gln Ile Trp Thr Thr Val Val Asp Trp Ile His Pro Asp Leu Lys
1               5                   10                  15

Arg

<210> SEQ ID NO 1453
<211> LENGTH: 30
<212> TYPE: PRT
<213> ORGANISM: Homo sapiens

<400> SEQUENCE: 1453

Ala Val Leu Gln Leu Asn Glu Glu Gly Val Asp Thr Ala Gly Ser Thr
1               5                   10                  15

Gly Val Thr Leu Asn Leu Thr Ser Lys Pro Ile Ile Leu Arg
            20                  25                  30

-continued

<210> SEQ ID NO 1454
<211> LENGTH: 15
<212> TYPE: PRT
<213> ORGANISM: Homo sapiens

<400> SEQUENCE: 1454

Gly Leu Ala Ser Ala Asn Val Asp Phe Ala Phe Ser Leu Tyr Lys
1               5                   10                  15

<210> SEQ ID NO 1455
<211> LENGTH: 20
<212> TYPE: PRT
<213> ORGANISM: Homo sapiens

<400> SEQUENCE: 1455

Thr Phe Pro Gly Phe Phe Ser Pro Met Leu Gly Glu Phe Val Ser Glu
1               5                   10                  15

Thr Glu Ser Arg
            20

<210> SEQ ID NO 1456
<211> LENGTH: 24
<212> TYPE: PRT
<213> ORGANISM: Homo sapiens

<400> SEQUENCE: 1456

Phe Asp Leu Val Pro Val Pro Thr Asn Leu Tyr Gly Asp Phe Phe Thr
1               5                   10                  15

Gly Asp Ala Tyr Val Ile Leu Lys
            20

<210> SEQ ID NO 1457
<211> LENGTH: 17
<212> TYPE: PRT
<213> ORGANISM: Homo sapiens

<400> SEQUENCE: 1457

Gln Thr Gln Val Ser Val Leu Pro Glu Gly Gly Glu Thr Pro Leu Phe
1               5                   10                  15

Lys

<210> SEQ ID NO 1458
<211> LENGTH: 30
<212> TYPE: PRT
<213> ORGANISM: Homo sapiens

<400> SEQUENCE: 1458

Ile Glu Gly Ser Asn Lys Val Pro Val Asp Pro Ala Thr Tyr Gly Gln
1               5                   10                  15

Phe Tyr Gly Gly Asp Ser Tyr Ile Ile Leu Tyr Asn Tyr Arg
            20                  25                  30

<210> SEQ ID NO 1459
<211> LENGTH: 12
<212> TYPE: PRT
<213> ORGANISM: Homo sapiens

<400> SEQUENCE: 1459

Phe Leu Val Gly Pro Asp Gly Ile Pro Ile Met Arg
1               5                   10

<210> SEQ ID NO 1460

<211> LENGTH: 16
<212> TYPE: PRT
<213> ORGANISM: Homo sapiens

<400> SEQUENCE: 1460

Ala Leu Pro Gln Pro Gln Asn Val Thr Ser Leu Leu Gly Cys Thr His
1               5                   10                  15

<210> SEQ ID NO 1461
<211> LENGTH: 30
<212> TYPE: PRT
<213> ORGANISM: Homo sapiens

<400> SEQUENCE: 1461

Ser Leu Gly Pro Asn Ser Cys Ser Ala Asn Gly Pro Gly Leu Tyr Leu
1               5                   10                  15

Ile His Gly Pro Asn Leu Tyr Cys Tyr Ser Asp Val Glu Lys
            20                  25                  30

<210> SEQ ID NO 1462
<211> LENGTH: 28
<212> TYPE: PRT
<213> ORGANISM: Homo sapiens

<400> SEQUENCE: 1462

Asp Gly Trp His Ser Trp Pro Ile Ala His Gln Trp Pro Gln Gly Pro
1               5                   10                  15

Ser Ala Val Asp Ala Ala Phe Ser Trp Glu Glu Lys
            20                  25

<210> SEQ ID NO 1463
<211> LENGTH: 15
<212> TYPE: PRT
<213> ORGANISM: Homo sapiens

<400> SEQUENCE: 1463

Gly Glu Cys Gln Ala Glu Gly Val Leu Phe Phe Gln Gly Asp Arg
1               5                   10                  15

<210> SEQ ID NO 1464
<211> LENGTH: 27
<212> TYPE: PRT
<213> ORGANISM: Homo sapiens

<400> SEQUENCE: 1464

Gly Glu Cys Gln Ala Glu Gly Val Leu Phe Phe Gln Gly Asp Arg Glu
1               5                   10                  15

Trp Phe Trp Asp Leu Ala Thr Gly Thr Met Lys
            20                  25

<210> SEQ ID NO 1465
<211> LENGTH: 27
<212> TYPE: PRT
<213> ORGANISM: Homo sapiens

<400> SEQUENCE: 1465

Leu Glu Lys Glu Val Gly Thr Pro His Gly Ile Ile Leu Asp Ser Val
1               5                   10                  15

Asp Ala Ala Phe Ile Cys Pro Gly Ser Ser Arg
            20                  25

<210> SEQ ID NO 1466
<211> LENGTH: 7

```
<212> TYPE: PRT
<213> ORGANISM: Homo sapiens

<400> SEQUENCE: 1466

Leu Trp Trp Leu Asp Leu Lys
1               5

<210> SEQ ID NO 1467
<211> LENGTH: 13
<212> TYPE: PRT
<213> ORGANISM: Homo sapiens

<400> SEQUENCE: 1467

Trp Lys Asn Phe Pro Ser Pro Val Asp Ala Ala Phe Arg
1               5                   10

<210> SEQ ID NO 1468
<211> LENGTH: 28
<212> TYPE: PRT
<213> ORGANISM: Homo sapiens

<400> SEQUENCE: 1468

Asp Gln Val Asn Thr Phe Asp Asn Ile Phe Ile Ala Pro Val Gly Ile
1               5                   10                  15

Ser Thr Ala Met Gly Met Ile Ser Leu Gly Leu Lys
            20                  25

<210> SEQ ID NO 1469
<211> LENGTH: 9
<212> TYPE: PRT
<213> ORGANISM: Homo sapiens

<400> SEQUENCE: 1469

Ala Asn Val Phe Val Gln Leu Pro Arg
1               5

<210> SEQ ID NO 1470
<211> LENGTH: 14
<212> TYPE: PRT
<213> ORGANISM: Homo sapiens

<400> SEQUENCE: 1470

Leu Glu Ala Leu Pro Asn Ser Leu Leu Ala Pro Leu Gly Arg
1               5                   10

<210> SEQ ID NO 1471
<211> LENGTH: 7
<212> TYPE: PRT
<213> ORGANISM: Homo sapiens

<400> SEQUENCE: 1471

Leu Phe Gln Gly Leu Gly Lys
1               5

<210> SEQ ID NO 1472
<211> LENGTH: 15
<212> TYPE: PRT
<213> ORGANISM: Homo sapiens

<400> SEQUENCE: 1472

Asn Leu Ile Ala Ala Val Ala Pro Gly Ala Phe Leu Gly Leu Lys
1               5                   10                  15

<210> SEQ ID NO 1473
```

-continued

```
<211> LENGTH: 11
<212> TYPE: PRT
<213> ORGANISM: Homo sapiens

<400> SEQUENCE: 1473

Thr Phe Thr Pro Gln Pro Pro Gly Leu Glu Arg
1               5                   10

<210> SEQ ID NO 1474
<211> LENGTH: 12
<212> TYPE: PRT
<213> ORGANISM: Homo sapiens

<400> SEQUENCE: 1474

Val Thr Phe Gln Leu Thr Tyr Glu Glu Val Leu Lys
1               5                   10

<210> SEQ ID NO 1475
<211> LENGTH: 13
<212> TYPE: PRT
<213> ORGANISM: Homo sapiens

<400> SEQUENCE: 1475

Val Thr Phe Gln Leu Thr Tyr Glu Glu Val Leu Lys Arg
1               5                   10

<210> SEQ ID NO 1476
<211> LENGTH: 37
<212> TYPE: PRT
<213> ORGANISM: Homo sapiens

<400> SEQUENCE: 1476

Gly Ile Glu Ile Leu Asn Gln Val Gln Glu Ser Leu Pro Glu Leu Ser
1               5                   10                  15

Asn His Ala Ser Ile Leu Ile Met Leu Thr Asp Gly Asp Pro Thr Glu
            20                  25                  30

Gly Val Thr Asp Arg
            35

<210> SEQ ID NO 1477
<211> LENGTH: 13
<212> TYPE: PRT
<213> ORGANISM: Homo sapiens

<400> SEQUENCE: 1477

Lys Ala Ala Ile Ser Gly Glu Asn Ala Gly Leu Val Arg
1               5                   10

<210> SEQ ID NO 1478
<211> LENGTH: 25
<212> TYPE: PRT
<213> ORGANISM: Homo sapiens

<400> SEQUENCE: 1478

Ala Gly Glu Leu Glu Val Phe Asn Gly Tyr Phe Val His Phe Phe Ala
1               5                   10                  15

Pro Asp Asn Leu Asp Pro Ile Pro Lys
            20                  25

<210> SEQ ID NO 1479
<211> LENGTH: 11
<212> TYPE: PRT
<213> ORGANISM: Homo sapiens
```

-continued

<400> SEQUENCE: 1479

Phe Tyr Asn Gln Val Ser Thr Pro Leu Leu Arg
1               5                   10

<210> SEQ ID NO 1480
<211> LENGTH: 11
<212> TYPE: PRT
<213> ORGANISM: Homo sapiens

<400> SEQUENCE: 1480

Val Gln Phe Glu Leu His Tyr Gln Glu Val Lys
1               5                   10

<210> SEQ ID NO 1481
<211> LENGTH: 15
<212> TYPE: PRT
<213> ORGANISM: Homo sapiens

<400> SEQUENCE: 1481

Glu Thr Ala Val Asp Gly Glu Leu Val Val Leu Tyr Asp Val Lys
1               5                   10                  15

<210> SEQ ID NO 1482
<211> LENGTH: 13
<212> TYPE: PRT
<213> ORGANISM: Homo sapiens

<400> SEQUENCE: 1482

Leu Trp Ala Tyr Leu Thr Ile Glu Gln Leu Leu Glu Lys
1               5                   10

<210> SEQ ID NO 1483
<211> LENGTH: 12
<212> TYPE: PRT
<213> ORGANISM: Homo sapiens

<400> SEQUENCE: 1483

Ile Thr Phe Glu Leu Val Tyr Glu Glu Leu Leu Lys
1               5                   10

<210> SEQ ID NO 1484
<211> LENGTH: 16
<212> TYPE: PRT
<213> ORGANISM: Homo sapiens

<400> SEQUENCE: 1484

Leu Gln Asp Arg Gly Pro Asp Val Leu Thr Ala Thr Val Ser Gly Lys
1               5                   10                  15

<210> SEQ ID NO 1485
<211> LENGTH: 27
<212> TYPE: PRT
<213> ORGANISM: Homo sapiens

<400> SEQUENCE: 1485

Thr Gly Leu Leu Leu Leu Ser Asp Pro Asp Lys Val Thr Ile Gly Leu
1               5                   10                  15

Leu Phe Trp Asp Gly Arg Gly Glu Gly Leu Arg
            20                  25

<210> SEQ ID NO 1486
<211> LENGTH: 28
<212> TYPE: PRT
<213> ORGANISM: Homo sapiens

<400> SEQUENCE: 1486

Ala Ile Ser Gly Gly Ser Ile Gln Ile Glu Asn Gly Tyr Phe Val His
1               5                   10                  15

Tyr Phe Ala Pro Glu Gly Leu Thr Thr Met Pro Lys
            20                  25

<210> SEQ ID NO 1487
<211> LENGTH: 15
<212> TYPE: PRT
<213> ORGANISM: Homo sapiens

<400> SEQUENCE: 1487

Ala Asn Thr Val Gln Glu Ala Thr Phe Gln Met Glu Leu Pro Lys
1               5                   10                  15

<210> SEQ ID NO 1488
<211> LENGTH: 33
<212> TYPE: PRT
<213> ORGANISM: Homo sapiens

<400> SEQUENCE: 1488

Ser Phe Ala Ala Gly Ile Gln Ala Leu Gly Gly Thr Asn Ile Asn Asp
1               5                   10                  15

Ala Met Leu Met Ala Val Gln Leu Leu Asp Ser Ser Asn Gln Glu Glu
            20                  25                  30

Arg

<210> SEQ ID NO 1489
<211> LENGTH: 10
<212> TYPE: PRT
<213> ORGANISM: Homo sapiens

<400> SEQUENCE: 1489

Val Gln Gly Asn Asp His Ser Ala Thr Arg
1               5                   10

<210> SEQ ID NO 1490
<211> LENGTH: 13
<212> TYPE: PRT
<213> ORGANISM: Homo sapiens

<400> SEQUENCE: 1490

Ile Thr Phe Glu Leu Val Tyr Glu Glu Leu Leu Lys Arg
1               5                   10

<210> SEQ ID NO 1491
<211> LENGTH: 11
<212> TYPE: PRT
<213> ORGANISM: Homo sapiens

<400> SEQUENCE: 1491

Val Thr Ile Gly Leu Leu Phe Trp Asp Gly Arg
1               5                   10

<210> SEQ ID NO 1492
<211> LENGTH: 26
<212> TYPE: PRT
<213> ORGANISM: Homo sapiens

<400> SEQUENCE: 1492

Leu Trp Ala Tyr Leu Thr Ile Gln Gln Leu Leu Glu Gln Thr Val Ser
1               5                   10                  15

-continued

```
Ala Ser Asp Ala Asp Gln Gln Ala Leu Arg
            20                  25

<210> SEQ ID NO 1493
<211> LENGTH: 21
<212> TYPE: PRT
<213> ORGANISM: Homo sapiens

<400> SEQUENCE: 1493

Leu Phe His Thr Asn Phe Tyr Asp Thr Val Gly Thr Ile Gln Leu Ile
1               5                   10                  15

Asn Asp His Val Lys
            20

<210> SEQ ID NO 1494
<211> LENGTH: 11
<212> TYPE: PRT
<213> ORGANISM: Homo sapiens

<400> SEQUENCE: 1494

Glu Asn Phe Leu Phe Leu Thr Pro Asp Cys Lys
1               5                   10

<210> SEQ ID NO 1495
<211> LENGTH: 17
<212> TYPE: PRT
<213> ORGANISM: Homo sapiens

<400> SEQUENCE: 1495

Ile Tyr Pro Thr Val Asn Cys Gln Pro Leu Gly Met Ile Ser Leu Met
1               5                   10                  15

Lys

<210> SEQ ID NO 1496
<211> LENGTH: 18
<212> TYPE: PRT
<213> ORGANISM: Homo sapiens

<400> SEQUENCE: 1496

Lys Ile Tyr Pro Thr Val Asn Cys Gln Pro Leu Gly Met Ile Ser Leu
1               5                   10                  15

Met Lys

<210> SEQ ID NO 1497
<211> LENGTH: 21
<212> TYPE: PRT
<213> ORGANISM: Homo sapiens

<400> SEQUENCE: 1497

Ser Leu Trp Asn Gly Asp Thr Gly Glu Cys Thr Asp Asn Ala Tyr Ile
1               5                   10                  15

Asp Ile Gln Leu Arg
            20

<210> SEQ ID NO 1498
<211> LENGTH: 9
<212> TYPE: PRT
<213> ORGANISM: Homo sapiens

<400> SEQUENCE: 1498

Ile Leu Gly Pro Leu Ser Tyr Ser Lys
1               5
```

-continued

<210> SEQ ID NO 1499
<211> LENGTH: 29
<212> TYPE: PRT
<213> ORGANISM: Homo sapiens

<400> SEQUENCE: 1499

Glu Tyr Gly Val Val Leu Ala Pro Asp Gly Ser Thr Val Ala Val Glu
1               5                   10                  15

Pro Leu Leu Ala Gly Leu Glu Ala Gly Leu Gln Gly Arg
            20                  25

<210> SEQ ID NO 1500
<211> LENGTH: 32
<212> TYPE: PRT
<213> ORGANISM: Homo sapiens

<400> SEQUENCE: 1500

Glu Gly Lys Glu Tyr Gly Val Val Leu Ala Pro Asp Gly Ser Thr Val
1               5                   10                  15

Ala Val Glu Pro Leu Leu Ala Gly Leu Glu Ala Gly Leu Gln Gly Arg
            20                  25                  30

<210> SEQ ID NO 1501
<211> LENGTH: 25
<212> TYPE: PRT
<213> ORGANISM: Homo sapiens

<400> SEQUENCE: 1501

Gln Asn Gly Ala Ala Leu Thr Ser Ala Ser Ile Leu Ala Gln Gln Val
1               5                   10                  15

Trp Gly Thr Leu Val Leu Leu Gln Arg
            20                  25

<210> SEQ ID NO 1502
<211> LENGTH: 19
<212> TYPE: PRT
<213> ORGANISM: Homo sapiens

<400> SEQUENCE: 1502

Ile Ala Gln Leu Pro Leu Thr Gly Ser Met Ser Ile Ile Phe Phe Leu
1               5                   10                  15

Pro Leu Lys

<210> SEQ ID NO 1503
<211> LENGTH: 30
<212> TYPE: PRT
<213> ORGANISM: Homo sapiens

<400> SEQUENCE: 1503

Ser Ser Thr Ser Pro Thr Thr Asn Val Leu Leu Ser Pro Leu Ser Val
1               5                   10                  15

Ala Thr Ala Leu Ser Ala Leu Ser Leu Gly Ala Glu Gln Arg
            20                  25                  30

<210> SEQ ID NO 1504
<211> LENGTH: 11
<212> TYPE: PRT
<213> ORGANISM: Homo sapiens

<400> SEQUENCE: 1504

Val Ala Glu Tyr Met Asp Trp Ile Leu Glu Lys

-continued

```
1               5               10
```

```
<210> SEQ ID NO 1505
<211> LENGTH: 13
<212> TYPE: PRT
<213> ORGANISM: Homo sapiens

<400> SEQUENCE: 1505

Cys Gln Phe Phe Ser Tyr Ala Thr Gln Thr Phe His Lys
1               5               10

<210> SEQ ID NO 1506
<211> LENGTH: 17
<212> TYPE: PRT
<213> ORGANISM: Homo sapiens

<400> SEQUENCE: 1506

Cys Leu Leu Phe Ser Phe Leu Pro Ala Ser Ser Ile Asn Asp Met Glu
1               5               10                  15

Lys

<210> SEQ ID NO 1507
<211> LENGTH: 12
<212> TYPE: PRT
<213> ORGANISM: Homo sapiens

<400> SEQUENCE: 1507

Leu Val Leu Leu Asn Ala Ile Tyr Leu Ser Ala Lys
1               5               10

<210> SEQ ID NO 1508
<211> LENGTH: 14
<212> TYPE: PRT
<213> ORGANISM: Homo sapiens

<400> SEQUENCE: 1508

Asn Ala Leu Phe Cys Leu Glu Ser Ala Trp Asn Val Ala Lys
1               5               10

<210> SEQ ID NO 1509
<211> LENGTH: 16
<212> TYPE: PRT
<213> ORGANISM: Homo sapiens

<400> SEQUENCE: 1509

Ser Asn Pro Val Ile Leu Asn Val Leu Tyr Gly Pro Asp Leu Pro Arg
1               5               10                  15

<210> SEQ ID NO 1510
<211> LENGTH: 18
<212> TYPE: PRT
<213> ORGANISM: Homo sapiens

<400> SEQUENCE: 1510

Ile Ala Ile Ile Gly Ala Gly Ile Gly Gly Thr Ser Ala Ala Tyr Tyr
1               5               10                  15

Leu Arg

<210> SEQ ID NO 1511
<211> LENGTH: 14
<212> TYPE: PRT
<213> ORGANISM: Homo sapiens

<400> SEQUENCE: 1511
```

-continued

```
Trp Tyr Asn Leu Ala Ile Gly Ser Thr Cys Pro Trp Leu Lys
1               5               10

<210> SEQ ID NO 1512
<211> LENGTH: 11
<212> TYPE: PRT
<213> ORGANISM: Homo sapiens

<400> SEQUENCE: 1512

Thr Val Ala Ala Cys Asn Leu Pro Ile Val Arg
1               5               10

<210> SEQ ID NO 1513
<211> LENGTH: 20
<212> TYPE: PRT
<213> ORGANISM: Homo sapiens

<400> SEQUENCE: 1513

Ile Val Glu Gly Ser Asp Ala Glu Ile Gly Met Ser Pro Trp Gln Val
1               5               10                  15

Met Leu Phe Arg
            20

<210> SEQ ID NO 1514
<211> LENGTH: 21
<212> TYPE: PRT
<213> ORGANISM: Homo sapiens

<400> SEQUENCE: 1514

Arg Gln Glu Cys Ser Ile Pro Val Cys Gly Gln Asp Gln Val Thr Val
1               5               10                  15

Ala Met Thr Pro Arg
            20

<210> SEQ ID NO 1515
<211> LENGTH: 17
<212> TYPE: PRT
<213> ORGANISM: Homo sapiens

<400> SEQUENCE: 1515

Thr Phe Gly Ser Gly Glu Ala Asp Cys Gly Leu Arg Pro Leu Phe Glu
1               5               10                  15

Lys

<210> SEQ ID NO 1516
<211> LENGTH: 23
<212> TYPE: PRT
<213> ORGANISM: Homo sapiens

<400> SEQUENCE: 1516

Leu Leu Asn Asn Trp Asp Val Cys Ala Asp Met Val Gly Thr Phe Thr
1               5               10                  15

Asp Thr Glu Asp Pro Ala Lys
            20

<210> SEQ ID NO 1517
<211> LENGTH: 9
<212> TYPE: PRT
<213> ORGANISM: Homo sapiens

<400> SEQUENCE: 1517

Gly Phe Leu Leu Leu Ala Ser Leu Arg
```

-continued

```
1               5
```

```
<210> SEQ ID NO 1518
<211> LENGTH: 15
<212> TYPE: PRT
<213> ORGANISM: Homo sapiens

<400> SEQUENCE: 1518

Phe Ser Ile Ser Ala Thr Tyr Asp Leu Gly Ala Thr Leu Leu Lys
1               5                   10                  15

<210> SEQ ID NO 1519
<211> LENGTH: 15
<212> TYPE: PRT
<213> ORGANISM: Homo sapiens

<400> SEQUENCE: 1519

Lys Glu Leu Glu Leu Gln Ile Gly Asn Ala Leu Phe Ile Gly Lys
1               5                   10                  15

<210> SEQ ID NO 1520
<211> LENGTH: 14
<212> TYPE: PRT
<213> ORGANISM: Homo sapiens

<400> SEQUENCE: 1520

Met Ser Ser Ile Asn Ala Asp Phe Ala Phe Asn Leu Tyr Arg
1               5                   10

<210> SEQ ID NO 1521
<211> LENGTH: 13
<212> TYPE: PRT
<213> ORGANISM: Homo sapiens

<400> SEQUENCE: 1521

Gly Ser Pro Ala Ile Asn Val Ala Val His Val Phe Arg
1               5                   10

<210> SEQ ID NO 1522
<211> LENGTH: 9
<212> TYPE: PRT
<213> ORGANISM: Homo sapiens

<400> SEQUENCE: 1522

Met Pro Ser His Leu Met Leu Ala Arg
1               5

<210> SEQ ID NO 1523
<211> LENGTH: 27
<212> TYPE: PRT
<213> ORGANISM: Homo sapiens

<400> SEQUENCE: 1523

Glu Tyr Ala Asn Gln Phe Met Trp Glu Tyr Ser Thr Asn Tyr Gly Gln
1               5                   10                  15

Ala Pro Leu Ser Leu Leu Val Ser Tyr Thr Lys
            20                  25

<210> SEQ ID NO 1524
<211> LENGTH: 22
<212> TYPE: PRT
<213> ORGANISM: Homo sapiens

<400> SEQUENCE: 1524
```

-continued

```
His Gln Pro Gln Glu Phe Pro Thr Tyr Val Glu Pro Thr Asn Asp Glu
1               5                   10                  15

Ile Cys Glu Ala Phe Arg
            20

<210> SEQ ID NO 1525
<211> LENGTH: 26
<212> TYPE: PRT
<213> ORGANISM: Homo sapiens

<400> SEQUENCE: 1525

Leu Ala Gln Lys Val Pro Thr Ala Asp Leu Glu Asp Val Leu Pro Leu
1               5                   10                  15

Ala Glu Asp Ile Thr Asn Ile Leu Ser Lys
            20                  25

<210> SEQ ID NO 1526
<211> LENGTH: 8
<212> TYPE: PRT
<213> ORGANISM: Homo sapiens

<400> SEQUENCE: 1526

Leu Cys Asp Asn Leu Ser Thr Lys
1               5

<210> SEQ ID NO 1527
<211> LENGTH: 7
<212> TYPE: PRT
<213> ORGANISM: Homo sapiens

<400> SEQUENCE: 1527

Leu Cys Met Ala Ala Leu Lys
1               5

<210> SEQ ID NO 1528
<211> LENGTH: 20
<212> TYPE: PRT
<213> ORGANISM: Homo sapiens

<400> SEQUENCE: 1528

Ser Cys Glu Ser Asn Ser Pro Phe Pro Val His Pro Gly Thr Ala Glu
1               5                   10                  15

Cys Cys Thr Lys
            20

<210> SEQ ID NO 1529
<211> LENGTH: 21
<212> TYPE: PRT
<213> ORGANISM: Homo sapiens

<400> SEQUENCE: 1529

Ser Tyr Leu Ser Met Val Gly Ser Cys Cys Thr Ser Ala Ser Pro Thr
1               5                   10                  15

Val Cys Phe Leu Lys
            20

<210> SEQ ID NO 1530
<211> LENGTH: 29
<212> TYPE: PRT
<213> ORGANISM: Homo sapiens

<400> SEQUENCE: 1530

Thr Ala Met Asp Val Phe Val Cys Thr Tyr Phe Met Pro Ala Ala Gln
```

-continued

```
1               5               10              15

Leu Pro Glu Leu Pro Asp Val Glu Leu Pro Thr Asn Lys
            20              25
```

<210> SEQ ID NO 1531
<211> LENGTH: 15
<212> TYPE: PRT
<213> ORGANISM: Homo sapiens

<400> SEQUENCE: 1531

```
Lys Phe Pro Ser Gly Thr Phe Glu Gln Val Ser Gln Leu Val Lys
1               5               10              15
```

<210> SEQ ID NO 1532
<211> LENGTH: 10
<212> TYPE: PRT
<213> ORGANISM: Homo sapiens

<400> SEQUENCE: 1532

```
Thr His Leu Pro Glu Val Phe Leu Ser Lys
1               5               10
```

<210> SEQ ID NO 1533
<211> LENGTH: 7
<212> TYPE: PRT
<213> ORGANISM: Homo sapiens

<400> SEQUENCE: 1533

```
Thr Ser Ala Leu Ser Ala Lys
1               5
```

<210> SEQ ID NO 1534
<211> LENGTH: 10
<212> TYPE: PRT
<213> ORGANISM: Homo sapiens

<400> SEQUENCE: 1534

```
Gly Gln Tyr Cys Tyr Glu Leu Asp Glu Lys
1               5               10
```

<210> SEQ ID NO 1535
<211> LENGTH: 22
<212> TYPE: PRT
<213> ORGANISM: Homo sapiens

<400> SEQUENCE: 1535

```
Met Asp Trp Leu Val Pro Ala Thr Cys Glu Pro Ile Gln Ser Val Phe
1               5               10              15

Phe Phe Ser Gly Asp Lys
            20
```

<210> SEQ ID NO 1536
<211> LENGTH: 7
<212> TYPE: PRT
<213> ORGANISM: Homo sapiens

<400> SEQUENCE: 1536

```
Gln Pro Gln Phe Ile Ser Arg
1               5
```

<210> SEQ ID NO 1537
<211> LENGTH: 12
<212> TYPE: PRT
<213> ORGANISM: Homo sapiens

<400> SEQUENCE: 1537

Arg His Pro Asp Leu Ser Ile Pro Glu Leu Leu Arg
1               5                   10

<210> SEQ ID NO 1538
<211> LENGTH: 11
<212> TYPE: PRT
<213> ORGANISM: Homo sapiens

<400> SEQUENCE: 1538

Thr Ile Asn Pro Ala Val Asp His Cys Cys Lys
1               5                   10

<210> SEQ ID NO 1539
<211> LENGTH: 20
<212> TYPE: PRT
<213> ORGANISM: Homo sapiens

<400> SEQUENCE: 1539

Asp Tyr Asn Leu Asn Asp Ile Leu Leu Gln Leu Gly Ile Glu Glu Ala
1               5                   10                  15

Phe Thr Ser Lys
            20

<210> SEQ ID NO 1540
<211> LENGTH: 21
<212> TYPE: PRT
<213> ORGANISM: Homo sapiens

<400> SEQUENCE: 1540

Gly Thr His Val Asp Leu Gly Leu Ala Ser Ala Asn Val Asp Phe Ala
1               5                   10                  15

Phe Ser Leu Tyr Lys
            20

<210> SEQ ID NO 1541
<211> LENGTH: 26
<212> TYPE: PRT
<213> ORGANISM: Homo sapiens

<400> SEQUENCE: 1541

Gly Phe Pro Ile Lys Glu Asp Phe Leu Glu Gln Ser Glu Gln Leu Phe
1               5                   10                  15

Gly Ala Lys Pro Val Ser Leu Thr Gly Lys
            20                  25

<210> SEQ ID NO 1542
<211> LENGTH: 18
<212> TYPE: PRT
<213> ORGANISM: Homo sapiens

<400> SEQUENCE: 1542

Gln Leu Thr Ser Gly Pro Asn Gln Glu Gln Val Ser Pro Leu Thr Leu
1               5                   10                  15

Leu Lys

<210> SEQ ID NO 1543
<211> LENGTH: 24
<212> TYPE: PRT
<213> ORGANISM: Homo sapiens

<400> SEQUENCE: 1543

-continued

```
Ala Gln Leu Val Pro Leu Pro Pro Ser Thr Tyr Val Glu Phe Thr Val
1               5               10                  15

Ser Gly Thr Asp Cys Val Ala Lys
            20

<210> SEQ ID NO 1544
<211> LENGTH: 9
<212> TYPE: PRT
<213> ORGANISM: Homo sapiens

<400> SEQUENCE: 1544

Phe Met Gln Ala Val Thr Gly Trp Lys
1               5

<210> SEQ ID NO 1545
<211> LENGTH: 15
<212> TYPE: PRT
<213> ORGANISM: Homo sapiens

<400> SEQUENCE: 1545

Gly Asp Asp Ile Thr Met Val Leu Ile Leu Pro Lys Pro Glu Lys
1               5               10                  15

<210> SEQ ID NO 1546
<211> LENGTH: 11
<212> TYPE: PRT
<213> ORGANISM: Homo sapiens

<400> SEQUENCE: 1546

Asp Ile Pro Met Asn Pro Met Cys Ile Tyr Arg
1               5               10

<210> SEQ ID NO 1547
<211> LENGTH: 12
<212> TYPE: PRT
<213> ORGANISM: Homo sapiens

<400> SEQUENCE: 1547

Lys Leu Val Pro Phe Ala Thr Glu Leu His Glu Arg
1               5               10

<210> SEQ ID NO 1548
<211> LENGTH: 17
<212> TYPE: PRT
<213> ORGANISM: Homo sapiens

<400> SEQUENCE: 1548

Ser Leu Ala Glu Leu Gly Gly His Leu Asp Gln Gln Val Glu Glu Phe
1               5               10                  15

Arg

<210> SEQ ID NO 1549
<211> LENGTH: 15
<212> TYPE: PRT
<213> ORGANISM: Homo sapiens

<400> SEQUENCE: 1549

Ala Leu Tyr Trp Val Asn Gly Gln Val Pro Asp Gly Val Ser Lys
1               5               10                  15

<210> SEQ ID NO 1550
<211> LENGTH: 7
<212> TYPE: PRT
```

```
<213> ORGANISM: Homo sapiens

<400> SEQUENCE: 1550

Phe Ile Ile Pro Gly Leu Lys
1               5

<210> SEQ ID NO 1551
<211> LENGTH: 18
<212> TYPE: PRT
<213> ORGANISM: Homo sapiens

<400> SEQUENCE: 1551

Phe Ser Val Pro Ala Gly Ile Val Ile Pro Ser Phe Gln Ala Leu Thr
1               5                   10                  15

Ala Arg

<210> SEQ ID NO 1552
<211> LENGTH: 26
<212> TYPE: PRT
<213> ORGANISM: Homo sapiens

<400> SEQUENCE: 1552

Leu Asn Asp Leu Asn Ser Val Leu Val Met Pro Thr Phe His Val Pro
1               5                   10                  15

Phe Thr Asp Leu Gln Val Pro Ser Cys Lys
            20                  25

<210> SEQ ID NO 1553
<211> LENGTH: 14
<212> TYPE: PRT
<213> ORGANISM: Homo sapiens

<400> SEQUENCE: 1553

Val Glu Leu Glu Val Pro Gln Leu Cys Ser Phe Ile Leu Lys
1               5                   10

<210> SEQ ID NO 1554
<211> LENGTH: 16
<212> TYPE: PRT
<213> ORGANISM: Homo sapiens

<400> SEQUENCE: 1554

Val Asn Trp Glu Glu Glu Ala Ala Ser Gly Leu Leu Thr Ser Leu Lys
1               5                   10                  15

<210> SEQ ID NO 1555
<211> LENGTH: 15
<212> TYPE: PRT
<213> ORGANISM: Homo sapiens

<400> SEQUENCE: 1555

Ala Thr Leu Tyr Ala Leu Ser His Ala Val Asn Asn Tyr His Lys
1               5                   10                  15

<210> SEQ ID NO 1556
<211> LENGTH: 14
<212> TYPE: PRT
<213> ORGANISM: Homo sapiens

<400> SEQUENCE: 1556

Thr Leu Gln Gly Ile Pro Gln Met Ile Gly Glu Val Ile Arg
1               5                   10
```

<210> SEQ ID NO 1557
<211> LENGTH: 13
<212> TYPE: PRT
<213> ORGANISM: Homo sapiens

<400> SEQUENCE: 1557

Asp Gly Trp Gln Trp Phe Trp Ser Pro Ser Thr Phe Arg
1               5                   10

<210> SEQ ID NO 1558
<211> LENGTH: 17
<212> TYPE: PRT
<213> ORGANISM: Homo sapiens

<400> SEQUENCE: 1558

Val Gln Ala Ala Val Gly Thr Ser Ala Ala Pro Val Pro Ser Asp Asn
1               5                   10                  15

His

<210> SEQ ID NO 1559
<211> LENGTH: 7
<212> TYPE: PRT
<213> ORGANISM: Homo sapiens

<400> SEQUENCE: 1559

Trp Glu Leu Ala Leu Gly Arg
1               5

<210> SEQ ID NO 1560
<211> LENGTH: 22
<212> TYPE: PRT
<213> ORGANISM: Homo sapiens

<400> SEQUENCE: 1560

Ser Asn Phe Leu Asn Cys Tyr Val Ser Gly Phe His Pro Ser Asp Ile
1               5                   10                  15

Glu Val Asp Leu Leu Lys
            20

<210> SEQ ID NO 1561
<211> LENGTH: 10
<212> TYPE: PRT
<213> ORGANISM: Homo sapiens

<400> SEQUENCE: 1561

Gly Gly His Cys Val Ala Leu Cys Thr Arg
1               5                   10

<210> SEQ ID NO 1562
<211> LENGTH: 20
<212> TYPE: PRT
<213> ORGANISM: Homo sapiens

<400> SEQUENCE: 1562

Leu Val Asp Phe Tyr Val Met Pro Val Val Asn Val Asp Gly Tyr Asp
1               5                   10                  15

Tyr Ser Trp Lys
            20

<210> SEQ ID NO 1563
<211> LENGTH: 27
<212> TYPE: PRT
<213> ORGANISM: Homo sapiens

```
<400> SEQUENCE: 1563

Tyr Thr His Gly His Gly Ser Glu Thr Leu Tyr Leu Ala Pro Gly Gly
1               5                   10                  15

Gly Asp Asp Trp Ile Tyr Asp Leu Gly Ile Lys
            20                  25

<210> SEQ ID NO 1564
<211> LENGTH: 16
<212> TYPE: PRT
<213> ORGANISM: Homo sapiens

<400> SEQUENCE: 1564

Leu Ser Asn Asn Ala Leu Ser Gly Leu Pro Gln Gly Val Phe Gly Lys
1               5                   10                  15

<210> SEQ ID NO 1565
<211> LENGTH: 27
<212> TYPE: PRT
<213> ORGANISM: Homo sapiens

<400> SEQUENCE: 1565

Thr Leu Asn Leu Ala Gln Asn Leu Leu Ala Gln Leu Pro Glu Glu Leu
1               5                   10                  15

Phe His Pro Leu Thr Ser Leu Gln Thr Leu Lys
            20                  25

<210> SEQ ID NO 1566
<211> LENGTH: 9
<212> TYPE: PRT
<213> ORGANISM: Homo sapiens

<400> SEQUENCE: 1566

Trp Leu Asn Val Gln Leu Ser Pro Arg
1               5

<210> SEQ ID NO 1567
<211> LENGTH: 30
<212> TYPE: PRT
<213> ORGANISM: Homo sapiens

<400> SEQUENCE: 1567

Gly Asp Ser Val Val Trp Tyr Leu Phe Ser Ala Gly Asn Glu Ala Asp
1               5                   10                  15

Val His Gly Ile Tyr Phe Ser Gly Asn Thr Tyr Leu Trp Arg
            20                  25                  30

<210> SEQ ID NO 1568
<211> LENGTH: 10
<212> TYPE: PRT
<213> ORGANISM: Homo sapiens

<400> SEQUENCE: 1568

Met Tyr Tyr Ser Ala Val Asp Pro Thr Lys
1               5                   10

<210> SEQ ID NO 1569
<211> LENGTH: 23
<212> TYPE: PRT
<213> ORGANISM: Homo sapiens

<400> SEQUENCE: 1569

Gly Pro Glu Glu Glu His Leu Gly Ile Leu Gly Pro Val Ile Trp Ala
1               5                   10                  15
```

-continued

```
Glu Val Gly Asp Thr Ile Arg
          20

<210> SEQ ID NO 1570
<211> LENGTH: 37
<212> TYPE: PRT
<213> ORGANISM: Homo sapiens

<400> SEQUENCE: 1570

Ser Gly Ala Gly Thr Glu Asp Ser Ala Cys Ile Pro Trp Ala Tyr Tyr
1               5                   10                  15

Ser Thr Val Asp Gln Val Lys Asp Leu Tyr Ser Gly Leu Ile Gly Pro
          20                  25                  30

Leu Ile Val Cys Arg
        35

<210> SEQ ID NO 1571
<211> LENGTH: 11
<212> TYPE: PRT
<213> ORGANISM: Homo sapiens

<400> SEQUENCE: 1571

Ile Phe Phe Pro Gly Val Ser Glu Phe Gly Lys
1               5                   10

<210> SEQ ID NO 1572
<211> LENGTH: 21
<212> TYPE: PRT
<213> ORGANISM: Homo sapiens

<400> SEQUENCE: 1572

Ala Ile Leu Gln Ser Gly Ser Phe Asn Ala Pro Trp Ala Val Thr Ser
1               5                   10                  15

Leu Tyr Glu Ala Arg
          20

<210> SEQ ID NO 1573
<211> LENGTH: 17
<212> TYPE: PRT
<213> ORGANISM: Homo sapiens

<400> SEQUENCE: 1573

Val Leu Gln Gly Val Leu Pro Ala Leu Pro Gln Val Val Cys Asn Tyr
1               5                   10                  15

Arg

<210> SEQ ID NO 1574
<211> LENGTH: 18
<212> TYPE: PRT
<213> ORGANISM: Homo sapiens

<400> SEQUENCE: 1574

Thr Thr Leu Ser Gly Ala Pro Cys Gln Pro Trp Ala Ser Glu Ala Thr
1               5                   10                  15

Tyr Arg

<210> SEQ ID NO 1575
<211> LENGTH: 27
<212> TYPE: PRT
<213> ORGANISM: Homo sapiens

<400> SEQUENCE: 1575
```

-continued

```
Gly Leu Phe Gln Val Val Ser Gly Gly Met Val Leu Gln Leu Gln Gln
1               5                   10                  15

Gly Asp Gln Val Trp Val Glu Lys Asp Pro Lys
            20                  25

<210> SEQ ID NO 1576
<211> LENGTH: 10
<212> TYPE: PRT
<213> ORGANISM: Homo sapiens

<400> SEQUENCE: 1576

Val Leu Asn Tyr Val Asp Trp Ile Lys Lys
1               5                   10

<210> SEQ ID NO 1577
<211> LENGTH: 16
<212> TYPE: PRT
<213> ORGANISM: Homo sapiens

<400> SEQUENCE: 1577

Ser Asn Ala Leu Asp Ile Ile Phe Gln Thr Asp Leu Thr Gly Gln Lys
1               5                   10                  15

<210> SEQ ID NO 1578
<211> LENGTH: 19
<212> TYPE: PRT
<213> ORGANISM: Homo sapiens

<400> SEQUENCE: 1578

Glu Gly Ala Ile His Arg Glu Glu Leu Val Tyr Glu Leu Asn Pro Leu
1               5                   10                  15

Asp His Arg

<210> SEQ ID NO 1579
<211> LENGTH: 9
<212> TYPE: PRT
<213> ORGANISM: Homo sapiens

<400> SEQUENCE: 1579

Ile Thr Gln Val Leu His Phe Thr Lys
1               5

<210> SEQ ID NO 1580
<211> LENGTH: 9
<212> TYPE: PRT
<213> ORGANISM: Homo sapiens

<400> SEQUENCE: 1580

Ser His Ala Leu Gln Leu Asn Asn Arg
1               5

<210> SEQ ID NO 1581
<211> LENGTH: 18
<212> TYPE: PRT
<213> ORGANISM: Homo sapiens

<400> SEQUENCE: 1581

Ala Val Gly Ser Gly Ala Thr Phe Ser His Tyr Tyr Tyr Met Ile Leu
1               5                   10                  15

Ser Arg

<210> SEQ ID NO 1582
```

-continued

```
<211> LENGTH: 14
<212> TYPE: PRT
<213> ORGANISM: Homo sapiens

<400> SEQUENCE: 1582

Glu Pro Phe Leu Ser Cys Cys Gln Phe Ala Glu Ser Leu Arg
1               5                   10

<210> SEQ ID NO 1583
<211> LENGTH: 17
<212> TYPE: PRT
<213> ORGANISM: Homo sapiens

<400> SEQUENCE: 1583

Gly His Leu Phe Leu Gln Thr Asp Gln Pro Ile Tyr Asn Pro Gly Gln
1               5                   10                  15

Arg

<210> SEQ ID NO 1584
<211> LENGTH: 13
<212> TYPE: PRT
<213> ORGANISM: Homo sapiens

<400> SEQUENCE: 1584

Gly Leu Glu Glu Glu Leu Gln Phe Ser Leu Gly Ser Lys
1               5                   10

<210> SEQ ID NO 1585
<211> LENGTH: 13
<212> TYPE: PRT
<213> ORGANISM: Homo sapiens

<400> SEQUENCE: 1585

Gly Ser Phe Glu Phe Pro Val Gly Asp Ala Val Ser Lys
1               5                   10

<210> SEQ ID NO 1586
<211> LENGTH: 17
<212> TYPE: PRT
<213> ORGANISM: Homo sapiens

<400> SEQUENCE: 1586

Leu Leu Ala Thr Leu Cys Ser Ala Glu Val Cys Gln Cys Ala Glu Gly
1               5                   10                  15

Lys

<210> SEQ ID NO 1587
<211> LENGTH: 22
<212> TYPE: PRT
<213> ORGANISM: Homo sapiens

<400> SEQUENCE: 1587

Val Gln Gln Pro Asp Cys Arg Glu Pro Phe Leu Ser Cys Cys Gln Phe
1               5                   10                  15

Ala Glu Ser Leu Arg Lys
            20

<210> SEQ ID NO 1588
<211> LENGTH: 14
<212> TYPE: PRT
<213> ORGANISM: Homo sapiens

<400> SEQUENCE: 1588
```

-continued

```
Tyr Ile Tyr Gly Lys Pro Val Gln Gly Val Ala Tyr Val Arg
1               5                   10

<210> SEQ ID NO 1589
<211> LENGTH: 11
<212> TYPE: PRT
<213> ORGANISM: Homo sapiens

<400> SEQUENCE: 1589

Ile Thr His Tyr Asn Tyr Leu Ile Leu Ser Lys
1               5                   10

<210> SEQ ID NO 1590
<211> LENGTH: 15
<212> TYPE: PRT
<213> ORGANISM: Homo sapiens

<400> SEQUENCE: 1590

Glu Asn Ser Leu Tyr Leu Thr Ala Phe Thr Val Ile Gly Ile Arg
1               5                   10                  15

<210> SEQ ID NO 1591
<211> LENGTH: 10
<212> TYPE: PRT
<213> ORGANISM: Homo sapiens

<400> SEQUENCE: 1591

Lys Ala Phe Asp Ile Cys Pro Leu Val Lys
1               5                   10

<210> SEQ ID NO 1592
<211> LENGTH: 24
<212> TYPE: PRT
<213> ORGANISM: Homo sapiens

<400> SEQUENCE: 1592

Val Asp Asp Gly Val Ala Ser Phe Val Leu Asn Leu Pro Ser Gly Val
1               5                   10                  15

Thr Val Leu Glu Phe Asn Val Lys
            20

<210> SEQ ID NO 1593
<211> LENGTH: 28
<212> TYPE: PRT
<213> ORGANISM: Homo sapiens

<400> SEQUENCE: 1593

Thr Phe Ser Glu Trp Leu Glu Ser Val Lys Glu Asn Pro Ala Val Ile
1               5                   10                  15

Asp Phe Glu Leu Ala Pro Ile Val Asp Leu Val Arg
            20                  25

<210> SEQ ID NO 1594
<211> LENGTH: 31
<212> TYPE: PRT
<213> ORGANISM: Homo sapiens

<400> SEQUENCE: 1594

Ile Phe Asp Asp Phe Gly Thr His Tyr Phe Thr Ser Gly Ser Leu Gly
1               5                   10                  15

Gly Val Tyr Asp Leu Leu Tyr Gln Phe Ser Ser Glu Glu Leu Lys
            20                  25                  30
```

<210> SEQ ID NO 1595
<211> LENGTH: 15
<212> TYPE: PRT
<213> ORGANISM: Homo sapiens

<400> SEQUENCE: 1595

Glu Leu Ser His Leu Pro Ser Leu Tyr Asp Tyr Ser Ala Tyr Arg
1               5                   10                  15

<210> SEQ ID NO 1596
<211> LENGTH: 17
<212> TYPE: PRT
<213> ORGANISM: Homo sapiens

<400> SEQUENCE: 1596

Arg Tyr Ser Ala Trp Ala Glu Ser Val Thr Asn Leu Pro Gln Val Ile
1               5                   10                  15

Lys

<210> SEQ ID NO 1597
<211> LENGTH: 11
<212> TYPE: PRT
<213> ORGANISM: Homo sapiens

<400> SEQUENCE: 1597

Ser Leu Met Leu His Tyr Glu Phe Leu Gln Arg
1               5                   10

<210> SEQ ID NO 1598
<211> LENGTH: 18
<212> TYPE: PRT
<213> ORGANISM: Homo sapiens

<400> SEQUENCE: 1598

Tyr Gly Phe Cys Glu Ala Ala Asp Gln Phe His Val Leu Asp Glu Val
1               5                   10                  15

Arg Arg

<210> SEQ ID NO 1599
<211> LENGTH: 10
<212> TYPE: PRT
<213> ORGANISM: Homo sapiens

<400> SEQUENCE: 1599

Lys Leu Asp Gly Ile Cys Trp Gln Val Arg
1               5                   10

<210> SEQ ID NO 1600
<211> LENGTH: 26
<212> TYPE: PRT
<213> ORGANISM: Homo sapiens

<400> SEQUENCE: 1600

Gly Thr Val Ile Asp Val Thr Asp Phe Val Asn Trp Ala Ser Ser Ile
1               5                   10                  15

Asn Asp Ala Pro Val Leu Ile Ser Gln Lys
            20                  25

<210> SEQ ID NO 1601
<211> LENGTH: 29
<212> TYPE: PRT
<213> ORGANISM: Homo sapiens

<400> SEQUENCE: 1601

-continued

```
Asn Pro Arg Glu Asp Tyr Leu Asp Val Tyr Val Phe Gly Val Gly Pro
1               5                   10                  15

Leu Val Asn Gln Val Asn Ile Asn Ala Leu Ala Ser Lys
            20                  25

<210> SEQ ID NO 1602
<211> LENGTH: 12
<212> TYPE: PRT
<213> ORGANISM: Homo sapiens

<400> SEQUENCE: 1602

Gly Asp Ser Gly Gly Pro Leu Ile Val His Lys Arg
1               5                   10

<210> SEQ ID NO 1603
<211> LENGTH: 25
<212> TYPE: PRT
<213> ORGANISM: Homo sapiens

<400> SEQUENCE: 1603

His Val Ile Ile Leu Met Thr Asp Gly Leu His Asn Met Gly Gly Asp
1               5                   10                  15

Pro Ile Thr Val Ile Asp Glu Ile Arg
            20                  25

<210> SEQ ID NO 1604
<211> LENGTH: 30
<212> TYPE: PRT
<213> ORGANISM: Homo sapiens

<400> SEQUENCE: 1604

Lys Asn Pro Arg Glu Asp Tyr Leu Asp Val Tyr Val Phe Gly Val Gly
1               5                   10                  15

Pro Leu Val Asn Gln Val Asn Ile Asn Ala Leu Ala Ser Lys
            20                  25                  30

<210> SEQ ID NO 1605
<211> LENGTH: 11
<212> TYPE: PRT
<213> ORGANISM: Homo sapiens

<400> SEQUENCE: 1605

Ser Cys Asp Ile Pro Val Phe Met Asn Ala Arg
1               5                   10

<210> SEQ ID NO 1606
<211> LENGTH: 26
<212> TYPE: PRT
<213> ORGANISM: Homo sapiens

<400> SEQUENCE: 1606

Ser Pro Pro Glu Ile Ser His Gly Val Val Ala His Met Ser Asp Ser
1               5                   10                  15

Tyr Gln Tyr Gly Glu Glu Val Thr Tyr Lys
            20                  25

<210> SEQ ID NO 1607
<211> LENGTH: 19
<212> TYPE: PRT
<213> ORGANISM: Homo sapiens

<400> SEQUENCE: 1607
```

-continued

```
Thr Asp Cys Leu Ser Leu Pro Ser Phe Glu Asn Ala Ile Pro Met Gly
1               5                   10                  15

Glu Lys Lys

<210> SEQ ID NO 1608
<211> LENGTH: 14
<212> TYPE: PRT
<213> ORGANISM: Homo sapiens

<400> SEQUENCE: 1608

Arg Ala Gln Leu Gly Asp Leu Pro Trp Gln Val Ala Ile Lys
1               5                   10

<210> SEQ ID NO 1609
<211> LENGTH: 10
<212> TYPE: PRT
<213> ORGANISM: Homo sapiens

<400> SEQUENCE: 1609

Ser Leu Glu Cys Leu His Pro Gly Thr Lys
1               5                   10

<210> SEQ ID NO 1610
<211> LENGTH: 16
<212> TYPE: PRT
<213> ORGANISM: Homo sapiens

<400> SEQUENCE: 1610

Thr Met Gly Tyr Gln Asp Phe Ala Asp Val Val Cys Tyr Thr Gln Lys
1               5                   10                  15

<210> SEQ ID NO 1611
<211> LENGTH: 10
<212> TYPE: PRT
<213> ORGANISM: Homo sapiens

<400> SEQUENCE: 1611

Glu Leu Leu Ala Leu Ile Gln Leu Glu Arg
1               5                   10

<210> SEQ ID NO 1612
<211> LENGTH: 18
<212> TYPE: PRT
<213> ORGANISM: Homo sapiens

<400> SEQUENCE: 1612

Val Pro Glu Ala Arg Pro Asn Ser Met Val Val Glu His Pro Glu Phe
1               5                   10                  15

Leu Lys

<210> SEQ ID NO 1613
<211> LENGTH: 7
<212> TYPE: PRT
<213> ORGANISM: Homo sapiens

<400> SEQUENCE: 1613

Leu Phe Trp Glu Pro Met Lys
1               5

<210> SEQ ID NO 1614
<211> LENGTH: 12
<212> TYPE: PRT
<213> ORGANISM: Homo sapiens
```

-continued

```
<400> SEQUENCE: 1614

Asp Val Arg Asp Tyr Phe Met Pro Cys Pro Gly Arg
1               5                   10

<210> SEQ ID NO 1615
<211> LENGTH: 21
<212> TYPE: PRT
<213> ORGANISM: Homo sapiens

<400> SEQUENCE: 1615

Asp Ala Leu Glu Asn Ile Asp Pro Ala Thr Gln Met Met Ile Leu Asn
1               5                   10                  15

Cys Ile Tyr Phe Lys
            20

<210> SEQ ID NO 1616
<211> LENGTH: 25
<212> TYPE: PRT
<213> ORGANISM: Homo sapiens

<400> SEQUENCE: 1616

Gly Leu Ile Lys Asp Ala Leu Glu Asn Ile Asp Pro Ala Thr Gln Met
1               5                   10                  15

Met Ile Leu Asn Cys Ile Tyr Phe Lys
            20                  25

<210> SEQ ID NO 1617
<211> LENGTH: 9
<212> TYPE: PRT
<213> ORGANISM: Homo sapiens

<400> SEQUENCE: 1617

Gln Phe Pro Ile Leu Leu Asp Phe Lys
1               5

<210> SEQ ID NO 1618
<211> LENGTH: 10
<212> TYPE: PRT
<213> ORGANISM: Homo sapiens

<400> SEQUENCE: 1618

Ala Phe Trp Leu Asp Val Ser His Asn Arg
1               5                   10

<210> SEQ ID NO 1619
<211> LENGTH: 25
<212> TYPE: PRT
<213> ORGANISM: Homo sapiens

<400> SEQUENCE: 1619

Ala Asp Val Gln Ala His Gly Glu Gly Gln Glu Phe Ser Ile Thr Cys
1               5                   10                  15

Leu Val Asp Glu Glu Glu Met Lys Lys
            20                  25

<210> SEQ ID NO 1620
<211> LENGTH: 19
<212> TYPE: PRT
<213> ORGANISM: Homo sapiens

<400> SEQUENCE: 1620

Ile Leu Gly Asp Met Gln Pro Gly Asp Tyr Phe Asp Leu Val Leu Phe
1               5                   10                  15
```

Gly Thr Arg

<210> SEQ ID NO 1621
<211> LENGTH: 13
<212> TYPE: PRT
<213> ORGANISM: Homo sapiens

<400> SEQUENCE: 1621

Asn Val Val Phe Val Ile Asp Ile Ser Gly Ser Met Arg
1               5                   10

<210> SEQ ID NO 1622
<211> LENGTH: 23
<212> TYPE: PRT
<213> ORGANISM: Homo sapiens

<400> SEQUENCE: 1622

Thr Ala Phe Ile Ser Asp Phe Ala Val Thr Ala Asp Gly Asn Ala Phe
1               5                   10                  15

Ile Gly Asp Ile Lys Asp Lys
            20

<210> SEQ ID NO 1623
<211> LENGTH: 10
<212> TYPE: PRT
<213> ORGANISM: Homo sapiens

<400> SEQUENCE: 1623

Gly His Met Leu Glu Asn His Val Glu Arg
1               5                   10

<210> SEQ ID NO 1624
<211> LENGTH: 10
<212> TYPE: PRT
<213> ORGANISM: Homo sapiens

<400> SEQUENCE: 1624

Asn His Met Gln Tyr Glu Ile Val Ile Lys
1               5                   10

<210> SEQ ID NO 1625
<211> LENGTH: 13
<212> TYPE: PRT
<213> ORGANISM: Homo sapiens

<400> SEQUENCE: 1625

Ala His Val Ser Phe Lys Pro Thr Val Ala Gln Gln Arg
1               5                   10

<210> SEQ ID NO 1626
<211> LENGTH: 25
<212> TYPE: PRT
<213> ORGANISM: Homo sapiens

<400> SEQUENCE: 1626

Glu Asn Ile Gln Asp Asn Ile Ser Leu Phe Ser Leu Gly Met Gly Phe
1               5                   10                  15

Asp Val Asp Tyr Asp Phe Leu Lys Arg
            20                  25

<210> SEQ ID NO 1627
<211> LENGTH: 15
<212> TYPE: PRT

-continued

<213> ORGANISM: Homo sapiens

<400> SEQUENCE: 1627

His Leu Glu Val Asp Val Trp Val Ile Glu Pro Gln Gly Leu Arg
1               5                   10                  15

<210> SEQ ID NO 1628
<211> LENGTH: 14
<212> TYPE: PRT
<213> ORGANISM: Homo sapiens

<400> SEQUENCE: 1628

Leu Trp Ala Tyr Leu Thr Ile Asn Gln Leu Leu Ala Glu Arg
1               5                   10

<210> SEQ ID NO 1629
<211> LENGTH: 15
<212> TYPE: PRT
<213> ORGANISM: Homo sapiens

<400> SEQUENCE: 1629

Ala Glu Asp His Phe Ser Val Ile Asp Phe Asn Gln Asn Ile Arg
1               5                   10                  15

<210> SEQ ID NO 1630
<211> LENGTH: 20
<212> TYPE: PRT
<213> ORGANISM: Homo sapiens

<400> SEQUENCE: 1630

Phe Leu His Val Pro Asp Thr Phe Glu Gly His Phe Asp Gly Val Pro
1               5                   10                  15

Val Ile Ser Lys
            20

<210> SEQ ID NO 1631
<211> LENGTH: 29
<212> TYPE: PRT
<213> ORGANISM: Homo sapiens

<400> SEQUENCE: 1631

Phe Ser Ser His Val Gly Gly Thr Leu Gly Gln Phe Tyr Gln Glu Val
1               5                   10                  15

Leu Trp Gly Ser Pro Ala Ala Ser Asp Asp Gly Arg Arg
            20                  25

<210> SEQ ID NO 1632
<211> LENGTH: 12
<212> TYPE: PRT
<213> ORGANISM: Homo sapiens

<400> SEQUENCE: 1632

Gly Pro Asp Val Leu Thr Ala Thr Val Ser Gly Lys
1               5                   10

<210> SEQ ID NO 1633
<211> LENGTH: 16
<212> TYPE: PRT
<213> ORGANISM: Homo sapiens

<400> SEQUENCE: 1633

Asn Met Glu Gln Phe Gln Val Ser Val Ser Val Ala Pro Asn Ala Lys
1               5                   10                  15

```
<210> SEQ ID NO 1634
<211> LENGTH: 20
<212> TYPE: PRT
<213> ORGANISM: Homo sapiens

<400> SEQUENCE: 1634

Arg Leu Asp Tyr Gln Glu Gly Pro Pro Gly Val Glu Ile Ser Cys Trp
1               5                   10                  15

Ser Val Glu Leu
            20

<210> SEQ ID NO 1635
<211> LENGTH: 10
<212> TYPE: PRT
<213> ORGANISM: Homo sapiens

<400> SEQUENCE: 1635

Ile Val Asp Leu Val Ser Glu Leu Lys Lys
1               5                   10

<210> SEQ ID NO 1636
<211> LENGTH: 12
<212> TYPE: PRT
<213> ORGANISM: Homo sapiens

<400> SEQUENCE: 1636

Val Gly Ser Ala Leu Phe Leu Ser His Asn Leu Lys
1               5                   10

<210> SEQ ID NO 1637
<211> LENGTH: 11
<212> TYPE: PRT
<213> ORGANISM: Homo sapiens

<400> SEQUENCE: 1637

Thr Val Gly Ser Asp Thr Phe Tyr Ser Phe Lys
1               5                   10

<210> SEQ ID NO 1638
<211> LENGTH: 19
<212> TYPE: PRT
<213> ORGANISM: Homo sapiens

<400> SEQUENCE: 1638

Asp Ile Pro Thr Asn Ser Pro Glu Leu Glu Glu Thr Leu Thr His Thr
1               5                   10                  15

Ile Thr Lys

<210> SEQ ID NO 1639
<211> LENGTH: 7
<212> TYPE: PRT
<213> ORGANISM: Homo sapiens

<400> SEQUENCE: 1639

Val Gln Val Val Ala Gly Lys
1               5

<210> SEQ ID NO 1640
<211> LENGTH: 8
<212> TYPE: PRT
<213> ORGANISM: Homo sapiens

<400> SEQUENCE: 1640
```

```
Phe Asn Ala Leu Gln Tyr Leu Arg
1               5

<210> SEQ ID NO 1641
<211> LENGTH: 17
<212> TYPE: PRT
<213> ORGANISM: Homo sapiens

<400> SEQUENCE: 1641

Val Ile Pro Gly Pro Pro Ala Leu Thr Leu Val Pro Ala Glu Leu Val
1               5                   10                  15

Arg

<210> SEQ ID NO 1642
<211> LENGTH: 21
<212> TYPE: PRT
<213> ORGANISM: Homo sapiens

<400> SEQUENCE: 1642

Ile Thr Gly Thr Met Pro Pro Leu Pro Leu Glu Ala Thr Gly Leu Ala
1               5                   10                  15

Leu Ser Ser Leu Arg
            20

<210> SEQ ID NO 1643
<211> LENGTH: 15
<212> TYPE: PRT
<213> ORGANISM: Homo sapiens

<400> SEQUENCE: 1643

Glu Phe Thr Glu Ala Phe Leu Gly Cys Pro Ala Ile His Pro Arg
1               5                   10                  15

<210> SEQ ID NO 1644
<211> LENGTH: 31
<212> TYPE: PRT
<213> ORGANISM: Homo sapiens

<400> SEQUENCE: 1644

Arg Val Ile Asn Leu Pro Leu Asp Ser Met Ala Ala Pro Trp Glu Thr
1               5                   10                  15

Gly Asp Thr Phe Pro Asp Val Val Ala Ile Ala Pro Asp Val Arg
            20                  25                  30

<210> SEQ ID NO 1645
<211> LENGTH: 19
<212> TYPE: PRT
<213> ORGANISM: Homo sapiens

<400> SEQUENCE: 1645

Gly Val Phe Phe Ser Val Asn Ser Trp Thr Pro Asp Ser Met Ser Phe
1               5                   10                  15

Ile Tyr Lys

<210> SEQ ID NO 1646
<211> LENGTH: 17
<212> TYPE: PRT
<213> ORGANISM: Homo sapiens

<400> SEQUENCE: 1646

Glu Ile Pro Asp Glu Ile Ser Ile Leu Leu Leu Gly Val Ala His Phe
1               5                   10                  15
```

-continued

Lys

```
<210> SEQ ID NO 1647
<211> LENGTH: 28
<212> TYPE: PRT
<213> ORGANISM: Homo sapiens

<400> SEQUENCE: 1647

Ala Leu Tyr Tyr Asp Leu Ile Ser Ser Pro Asp Ile His Gly Thr Tyr
1               5                   10                  15

Lys Glu Leu Leu Asp Thr Val Thr Ala Pro Gln Lys
            20                  25

<210> SEQ ID NO 1648
<211> LENGTH: 14
<212> TYPE: PRT
<213> ORGANISM: Homo sapiens

<400> SEQUENCE: 1648

Glu Leu Arg Pro Trp Cys Phe Thr Thr Asp Pro Asn Lys Arg
1               5                   10

<210> SEQ ID NO 1649
<211> LENGTH: 21
<212> TYPE: PRT
<213> ORGANISM: Homo sapiens

<400> SEQUENCE: 1649

Thr Glu Cys Phe Ile Thr Gly Trp Gly Glu Thr Gln Gly Thr Phe Gly
1               5                   10                  15

Ala Gly Leu Leu Lys
            20

<210> SEQ ID NO 1650
<211> LENGTH: 14
<212> TYPE: PRT
<213> ORGANISM: Homo sapiens

<400> SEQUENCE: 1650

Gly Thr His Cys Asn Gln Val Glu Val Ile Ala Thr Leu Lys
1               5                   10

<210> SEQ ID NO 1651
<211> LENGTH: 27
<212> TYPE: PRT
<213> ORGANISM: Homo sapiens

<400> SEQUENCE: 1651

Ala Val Asp Gln Ser Val Leu Leu Met Lys Pro Glu Ala Glu Leu Ser
1               5                   10                  15

Val Ser Ser Val Tyr Asn Leu Leu Thr Val Lys
            20                  25

<210> SEQ ID NO 1652
<211> LENGTH: 13
<212> TYPE: PRT
<213> ORGANISM: Homo sapiens

<400> SEQUENCE: 1652

Asn Glu Leu Ile Pro Leu Ile Tyr Leu Glu Asn Pro Arg
1               5                   10

<210> SEQ ID NO 1653
```

```
<211> LENGTH: 17
<212> TYPE: PRT
<213> ORGANISM: Homo sapiens

<400> SEQUENCE: 1653

Gly Phe Gly Gly Leu Thr Gly Gln Ile Val Ala Ala Leu Ser Thr Ala
1               5                   10                  15

Lys

<210> SEQ ID NO 1654
<211> LENGTH: 29
<212> TYPE: PRT
<213> ORGANISM: Homo sapiens

<400> SEQUENCE: 1654

Lys Asp Pro Glu Gly Leu Phe Leu Gln Asp Asn Ile Val Ala Glu Phe
1               5                   10                  15

Ser Val Asp Glu Thr Gly Gln Met Ser Ala Thr Ala Lys
            20                  25

<210> SEQ ID NO 1655
<211> LENGTH: 22
<212> TYPE: PRT
<213> ORGANISM: Homo sapiens

<400> SEQUENCE: 1655

Ala Gln Trp Ala Asn Pro Phe Asp Pro Ser Lys Thr Glu Asp Ser Ser
1               5                   10                  15

Ser Phe Leu Ile Asp Lys
            20

<210> SEQ ID NO 1656
<211> LENGTH: 9
<212> TYPE: PRT
<213> ORGANISM: Homo sapiens

<400> SEQUENCE: 1656

Gly Trp Val Asp Leu Phe Val Pro Lys
1               5

<210> SEQ ID NO 1657
<211> LENGTH: 9
<212> TYPE: PRT
<213> ORGANISM: Homo sapiens

<400> SEQUENCE: 1657

Ser Phe Met Leu Leu Ile Leu Glu Arg
1               5

<210> SEQ ID NO 1658
<211> LENGTH: 20
<212> TYPE: PRT
<213> ORGANISM: Homo sapiens

<400> SEQUENCE: 1658

Glu Phe Ser His Leu Gly Lys Glu Asp Phe Thr Ser Leu Ser Leu Val
1               5                   10                  15

Leu Tyr Ser Arg
            20

<210> SEQ ID NO 1659
<211> LENGTH: 23
<212> TYPE: PRT
```

-continued

```
<213> ORGANISM: Homo sapiens

<400> SEQUENCE: 1659

His Gln Pro Gln Glu Phe Pro Thr Tyr Val Glu Pro Thr Asn Asp Glu
1               5                   10                  15

Ile Cys Glu Ala Phe Arg Lys
            20

<210> SEQ ID NO 1660
<211> LENGTH: 22
<212> TYPE: PRT
<213> ORGANISM: Homo sapiens

<400> SEQUENCE: 1660

Val Pro Thr Ala Asp Leu Glu Asp Val Leu Pro Leu Ala Glu Asp Ile
1               5                   10                  15

Thr Asn Ile Leu Ser Lys
            20

<210> SEQ ID NO 1661
<211> LENGTH: 8
<212> TYPE: PRT
<213> ORGANISM: Homo sapiens

<400> SEQUENCE: 1661

Ala Val Arg Pro Gly Tyr Pro Lys
1               5

<210> SEQ ID NO 1662
<211> LENGTH: 16
<212> TYPE: PRT
<213> ORGANISM: Homo sapiens

<400> SEQUENCE: 1662

Glu Ile Pro Ala Trp Val Pro Phe Asp Pro Ala Ala Gln Ile Thr Lys
1               5                   10                  15

<210> SEQ ID NO 1663
<211> LENGTH: 10
<212> TYPE: PRT
<213> ORGANISM: Homo sapiens

<400> SEQUENCE: 1663

Asn Leu Ala Val Ser Gln Val Val His Lys
1               5                   10

<210> SEQ ID NO 1664
<211> LENGTH: 12
<212> TYPE: PRT
<213> ORGANISM: Homo sapiens

<400> SEQUENCE: 1664

Ala Ala Ile Ser Gly Glu Asn Ala Gly Leu Val Arg
1               5                   10

<210> SEQ ID NO 1665
<211> LENGTH: 21
<212> TYPE: PRT
<213> ORGANISM: Homo sapiens

<400> SEQUENCE: 1665

Thr Ala Phe Ile Ser Asp Phe Ala Val Thr Ala Asp Gly Asn Ala Phe
1               5                   10                  15
```

```
Ile Gly Asp Ile Lys
            20

<210> SEQ ID NO 1666
<211> LENGTH: 7
<212> TYPE: PRT
<213> ORGANISM: Homo sapiens

<400> SEQUENCE: 1666

Val Thr Tyr Asp Val Ser Arg
1               5

<210> SEQ ID NO 1667
<211> LENGTH: 10
<212> TYPE: PRT
<213> ORGANISM: Homo sapiens

<400> SEQUENCE: 1667

Glu Val Ala Phe Asp Leu Glu Ile Pro Lys
1               5                   10

<210> SEQ ID NO 1668
<211> LENGTH: 6
<212> TYPE: PRT
<213> ORGANISM: Homo sapiens

<400> SEQUENCE: 1668

Thr Ala Gly Leu Val Arg
1               5

<210> SEQ ID NO 1669
<211> LENGTH: 10
<212> TYPE: PRT
<213> ORGANISM: Homo sapiens

<400> SEQUENCE: 1669

Ser Leu Ala Pro Thr Ala Ala Ala Lys Arg
1               5                   10

<210> SEQ ID NO 1670
<211> LENGTH: 10
<212> TYPE: PRT
<213> ORGANISM: Homo sapiens

<400> SEQUENCE: 1670

Glu Val Ser Phe Asp Val Glu Leu Pro Lys
1               5                   10

<210> SEQ ID NO 1671
<211> LENGTH: 6
<212> TYPE: PRT
<213> ORGANISM: Homo sapiens

<400> SEQUENCE: 1671

Ile Gln Glu Asn Val Arg
1               5

<210> SEQ ID NO 1672
<211> LENGTH: 9
<212> TYPE: PRT
<213> ORGANISM: Homo sapiens

<400> SEQUENCE: 1672

Ser Ser Phe Val Ala Pro Leu Glu Lys
1               5
```

-continued

```
<210> SEQ ID NO 1673
<211> LENGTH: 11
<212> TYPE: PRT
<213> ORGANISM: Homo sapiens

<400> SEQUENCE: 1673

Glu Leu Leu Asp Thr Val Thr Ala Pro Gln Lys
1               5               10

<210> SEQ ID NO 1674
<211> LENGTH: 16
<212> TYPE: PRT
<213> ORGANISM: Homo sapiens

<400> SEQUENCE: 1674

Phe Gln Gln Ser Gly Gln Asn Leu Phe Ile Pro Gln Ile Thr Thr Lys
1               5               10                  15

<210> SEQ ID NO 1675
<211> LENGTH: 14
<212> TYPE: PRT
<213> ORGANISM: Homo sapiens

<400> SEQUENCE: 1675

Leu Pro Ile Pro Tyr Ile Thr Ile Asn Asn Leu Asn Pro Arg
1               5               10

<210> SEQ ID NO 1676
<211> LENGTH: 11
<212> TYPE: PRT
<213> ORGANISM: Homo sapiens

<400> SEQUENCE: 1676

Ala Gln Trp Ala Asn Pro Phe Asp Pro Ser Lys
1               5               10

<210> SEQ ID NO 1677
<211> LENGTH: 6
<212> TYPE: PRT
<213> ORGANISM: Homo sapiens

<400> SEQUENCE: 1677

Phe Leu Asn Asp Val Lys
1               5

<210> SEQ ID NO 1678
<211> LENGTH: 10
<212> TYPE: PRT
<213> ORGANISM: Homo sapiens

<400> SEQUENCE: 1678

Asn Ala Leu Ala Leu Phe Val Leu Pro Lys
1               5               10

<210> SEQ ID NO 1679
<211> LENGTH: 7
<212> TYPE: PRT
<213> ORGANISM: Homo sapiens

<400> SEQUENCE: 1679

Gly Glu Glu Glu Leu Gln Lys
1               5
```

<210> SEQ ID NO 1680
<211> LENGTH: 7
<212> TYPE: PRT
<213> ORGANISM: Homo sapiens

<400> SEQUENCE: 1680

Phe Ile Tyr Glu Ile Ala Arg
1               5

<210> SEQ ID NO 1681
<211> LENGTH: 15
<212> TYPE: PRT
<213> ORGANISM: Homo sapiens

<400> SEQUENCE: 1681

His Pro Phe Leu Tyr Ala Pro Thr Ile Leu Leu Trp Ala Ala Arg
1               5                   10                  15

<210> SEQ ID NO 1682
<211> LENGTH: 9
<212> TYPE: PRT
<213> ORGANISM: Homo sapiens

<400> SEQUENCE: 1682

Thr Phe Gln Ala Ile Thr Val Thr Lys
1               5

<210> SEQ ID NO 1683
<211> LENGTH: 6
<212> TYPE: PRT
<213> ORGANISM: Homo sapiens

<400> SEQUENCE: 1683

Leu Thr Thr Leu Glu Arg
1               5

<210> SEQ ID NO 1684
<211> LENGTH: 11
<212> TYPE: PRT
<213> ORGANISM: Homo sapiens

<400> SEQUENCE: 1684

His Pro Gln Leu Ala Val Ser Val Ile Leu Arg
1               5                   10

<210> SEQ ID NO 1685
<211> LENGTH: 16
<212> TYPE: PRT
<213> ORGANISM: Homo sapiens

<400> SEQUENCE: 1685

Leu Gly Glu Tyr Tyr Leu Gln Asn Ala Phe Leu Val Ala Tyr Thr Lys
1               5                   10                  15

<210> SEQ ID NO 1686
<211> LENGTH: 9
<212> TYPE: PRT
<213> ORGANISM: Homo sapiens

<400> SEQUENCE: 1686

Leu Ile Leu Ile Gly Glu Thr Ile Lys
1               5

<210> SEQ ID NO 1687
<211> LENGTH: 8

-continued

```
<212> TYPE: PRT
<213> ORGANISM: Homo sapiens

<400> SEQUENCE: 1687

Leu Gln Pro Phe Asn Glu Tyr Arg
1               5
```